US009789508B2

(12) United States Patent
Baumgartner et al.

(10) Patent No.: US 9,789,508 B2
(45) Date of Patent: Oct. 17, 2017

(54) AEROSOL EXTRACTION APPARATUS

(71) Applicants: Paul Baumgartner, Port St. Lucie, FL (US); Jonathan J. Ricciardi, Wausau, WI (US)

(72) Inventors: Paul Baumgartner, Port St. Lucie, FL (US); Jonathan J. Ricciardi, Wausau, WI (US)

( * ) Notice: Subject to any disclaimer, the term of this patent is extended or adjusted under 35 U.S.C. 154(b) by 0 days.

(21) Appl. No.: 15/351,724

(22) Filed: Nov. 15, 2016

(65) Prior Publication Data
US 2017/0066003 A1 Mar. 9, 2017

Related U.S. Application Data

(60) Continuation of application No. 15/080,376, filed on Mar. 24, 2016, now Pat. No. 9,551,996, which is a (Continued)

(51) Int. Cl.
| | |
|---|---|
| *B05B 17/06* | (2006.01) |
| *A61L 9/12* | (2006.01) |
| *A61L 9/14* | (2006.01) |
| *A61L 2/22* | (2006.01) |
| *G01F 23/00* | (2006.01) |

(Continued)

(52) U.S. Cl.
CPC ............ *B05B 17/0607* (2013.01); *A61L 2/22* (2013.01); *A61L 2/24* (2013.01); *A61L 9/122* (2013.01); *A61L 9/14* (2013.01); *G01F 23/00* (2013.01); *G01F 23/30* (2013.01); *G01K 7/02* (2013.01); *G05B 15/02* (2013.01); *G05D 7/0629* (2013.01); *A61L 2202/14* (2013.01); *A61L 2202/15* (2013.01)

(58) Field of Classification Search
CPC . B05B 17/06; B05B 17/0607; B05B 17/0615; B05B 17/063; B05B 17/0653; A61L 2/22; A61L 9/12; A61L 9/122; A61L 9/14; A61L 2202/14; A61L 2202/15
See application file for complete search history.

(56) References Cited

U.S. PATENT DOCUMENTS 3,561,444 A 2/1971 Boucher
3,901,443 A * 8/1975 Mitsui ................ B05B 17/0615 239/102.2

(Continued)

*Primary Examiner* — Darren W Gorman
(74) *Attorney, Agent, or Firm* — Donald J. Ersler

(57) ABSTRACT

An ultrasonic aerosol generation apparatus preferably includes an aerosol generation case, a case cover, at least one outlet pipe, an air feed manifold, at least one, transducer, transducer power supply, and microprocessor based controller. The aerosol generation case preferably includes a fluid reservoir and a transducer chamber. The case cover is attached to a top of the aerosol generation case. Each outlet pipe preferably includes an outer base tube, an inner tube and an exhaust tube. The at least one outlet pipe is attached to the case cover over the at least one transducer. The air feed manifold includes an inlet tube, a supply tube and at least one exhaust pipe tube. The supply tube communicates with the transducer chamber and the at least one exhaust pipe communicates with the at least one outlet pipe. The microprocessor based controller is used to monitor, power, and/or control, the above mentioned components.

14 Claims, 142 Drawing Sheets

Related U.S. Application Data continuation of application No. 14/247,893, filed on Apr. 8, 2014, now abandoned, which is a division of application No. 13/716,245, filed on Dec. 17, 2012, now abandoned, which is a continuation of application No. 13/425,478, filed on Mar. 21, 2012, now Pat. No. 8,382,008, which is a continuation of application No. 12/816,986, filed on Jun. 16, 2010, now Pat. No. 8,177,142, which is a continuation of application No. 12/114,454, filed on May 2, 2008, now Pat. No. 7,871,016, which is a continuation of application No. 11/509,332, filed on Aug. 24, 2006, now Pat. No. 7,641,130.

(60) Provisional application No. 60/711,858, filed on Aug. 26, 2005, provisional application No. 61/295,869, filed on Jan. 18, 2010, provisional application No. 60/915,524, filed on May 2, 2007.

(51) Int. Cl.
  *G01K 7/02* (2006.01)
  *G05B 15/02* (2006.01)
  *G05D 7/06* (2006.01)
  *A61L 2/24* (2006.01)
  *G01F 23/30* (2006.01)

(56) References Cited

U.S. PATENT DOCUMENTS

| | | | |
|---|---|---|---|
| 4,257,989 A * | 3/1981 | Nishikawa | B01J 47/14 |
| | | | 210/282 |
| 4,366,125 A | 12/1982 | Kodera et al. | |
| 5,173,274 A * | 12/1992 | Owen | B01J 19/10 |
| | | | 239/102.2 |
| 5,878,355 A | 3/1999 | Berg et al. | |
| 5,922,247 A * | 7/1999 | Shoham | B05B 17/0615 |
| | | | 239/102.2 |
| 5,925,966 A | 7/1999 | Riftin et al. | |
| 6,102,992 A | 8/2000 | Berg et al. | |
| 6,402,046 B1 * | 6/2002 | Loser | A61M 15/0085 |
| | | | 128/200.16 |
| 7,641,130 B2 | 1/2010 | Ricciardi et al. | |
| 7,871,016 B2 | 1/2011 | Ricciardi et al. | |
| 8,196,604 B1 | 6/2012 | Ricciardi et al. | |
| 8,382,008 B1 | 2/2013 | Riccardi et al. | |
| 2010/0233020 A1 * | 9/2010 | Klaassen | A61L 2/208 |
| | | | 422/20 |

\* cited by examiner

AEROSOL EXTRACTION APPARATUS

CROSS-REFERENCE TO RELATED APPLICATIONS

This application is a continuation-in-part of application Ser. No. 15/080,376, filed on Mar. 24, 2016, which is a continuation-in-part of application Ser. No. 14/247,893, filed on Apr. 8, 2014, which claims the benefit of divisional application Ser. No. 13/716,245, filed on Dec. 17, 2012, which claims the benefit of continuation-in-part application Ser. No. 13/425,478, filed on Mar. 21, 2012, which claims the benefit of U.S. Non-provisional application Ser. No. 12/816,986, filed on Jun. 16, 2010, which claims the benefit of U.S. Provisional Application Ser. No. 61/295,869, filed Jan. 18, 2010, and as a continuation-in-part of U.S. Non-Provisional patent application Ser. No. 12/114,454, filed on May 2, 2008, now U.S. Pat. No. 7,871,016, which claims the benefit of both U.S. Provisional Patent Application Ser. No. 60/915,524, filed on May 2, 2007, and as a continuation-in-part from U.S. patent application Ser. No. 11/509,332, filed on Aug. 24, 2006, now U.S. Pat. No. 7,641,130, which claims the benefit of U.S. Provisional Patent Application Ser. No. 60/711,858, filed on Aug. 26, 2005 and all of the above patent documents are expressly incorporated herein by reference in their entirety. U.S. Pat. No. 8,196,604 and patent application Ser. No. 13/494,824 are hereby incorporated into this patent application by reference in their entirety.

TECHNICAL FIELD OF THE INVENTION

The present invention relates to improved apparatuses and methods for the generation and application of an ultrasonically generated aerosol for uses including but not limited to the sanitization, detoxification, disinfection, high-level disinfection, or sterilization of one or more areas and the surfaces in those areas, as well as the delivery of other types of liquid agents, for various purposes to one or more areas, and without limitation, the surfaces in those area(s). The present invention includes, but it is not limited to, a new and improved ultrasonic aerosol generation apparatus, which is able to generate and/or deploy greater volumes of disinfecting aerosol than that of the prior art.

BACKGROUND OF THE INVENTION

The apparatus described in U.S. Pat. No. 4,366,125, which is incorporated herein by reference in its entirety, including any references cited therein, generates a hydrogen peroxide mist by an ultrasonic wave vibrator. The mist adheres to the surface of materials being sterilized and is then irradiated with ultraviolet-ray lamps. U.S. Pat. Nos. 5,878,355 and 6,102,992, each of which is incorporated herein by reference in its entirety, including any references cited therein, disclose a method and device for decontamination of a contaminated process area whereby a fine aerosol of an encapsulant is generated to encapsulate contaminants within a contaminated environment. The aerosol is generated by one or more ultrasonic transducers located below the surface of a reservoir containing a liquid. The output of the transducers is focused to either a point and/or directed toward an area near the surface of the liquid to cause a surface disturbance, which results in the formation of an aerosol from the liquid. The transducers used in these apparatuses are made from lead-zirconate-titanate-four (PZT-4) or other piezoelectric materials. This material is coated with a conductive coating (electrode material) that enables an electrical signal to energize the transducer and causes it to emit high frequency pressure (energy).

While operating these prior art apparatuses and similar apparatuses, it has been found that certain liquids, especially acidic solutions, chemically react with the electrode materials of the transducers that generate the aerosol. The result is a noticeable deterioration of both the transducers and their performance. For example, acidic solutions of hydrogen peroxide and peroxyacetic acid have caused noticeable deterioration of the transducers within minutes of operation.

An attempt was made to prevent transducer degradation by coating the face of the transducers with a thin coating of different materials. None of these efforts have been successful. For example, U.S. Pat. No. 4,109,863, which is incorporated herein by reference in its entirety, including any references cited therein, discloses similar findings. The protective coating on the transducer deteriorated to a point where the transducer failed to be energized. It was initially believed that this deterioration was caused by transducer induced cavitation within the tank; however, the aforementioned coatings were also shown to fail in simple immersion tests, conducted over time in an acidic solution, with unpowered transducers. For example, laboratory work indicated that PZT material coated with an electroless nickel plating, or a glaze, were both found to be incompatible with a 4% solution of hydrogen peroxide and peroxyacetic acid, after being exposed to the solution for two weeks at 160° F.

In addition, it was found that various materials used to construct the transducer housing and assembly experienced deterioration after being subjected to a simulated long-term exposure to an acid solution of hydrogen peroxide and peroxyacetic acid. This was observed with an accelerated aging test. This test consisted of placing components constructed of various material types in vessels containing the hydrogen peroxide and peroxyacetic acid solution and subjecting them to increased temperature over a course of time. Without being limited to the theory, this test is based on the theory recognized in the art that at higher temperatures chemical or physical reactions will proceed faster due to the increased probability that two molecules will collide and chemically react.

Without being limited to a particular mechanism, method, or chemical, it is believed that chemically reactive liquids are necessary in sterilization processes to contact contaminants including but not limited to toxins, bacteria, virus, fungus, and spores (both fungal and bacterial), prions or protein structures, within a target area(s) either killing the bacteria, fungus, or spores, neutralizing or destroying toxins, or rendering a protein structure incapable of replication or otherwise interfering with the target's cellular physiology. These chemically reactive liquids may be provided as an aerosol. For example, U.S. Pat. No. 4,512,951, which is incorporated herein by reference in its entirety, including any references cited therein, teaches using hydrogen peroxide to sterilize medical devices by condensing hydrogen peroxide-water vapors to deposit a film of liquid on the devices. The liquid film is then evaporated.

While the prior art attempted to coat the transducer with a protective substance, there were problems with these coatings. U.S. Pat. Nos. 3,729,138; 4,109,863; and 4,976,259, each of which is incorporated herein by reference in its entirety, including any references cited therein, teach that the optimum thickness of a glass barrier, which may be used as a protective plate and/or cover, on a transducer should be any multiple of one-half (½) the wavelength of the transmitted pressure (energy). The thicknesses of protective barriers have been calculated using wave transmission theories and their respective mathematical formulas known to those skilled in the art. It is estimated that twenty percent (20%) of the energy emitted from the transducers is being transmitted into the liquid beyond the protective barrier. The prior art does not include techniques for further increasing the energy emitted from the transducer with a protective plate and/or cover.

U.S. Pat. Nos. 3,433,461; 3,729,138; 4,109,863; and 4,976,259, each of which is incorporated herein by reference in its entirety, including any references cited therein, teach that an effective thickness of a protective barrier material "interfaced with" a transducer can be approximately any multiple of one-half (½) the wavelength of the transmitted pressure (energy) from the transducer. Prior art has taught that barriers having a thickness equal to or about one-half (½) wavelength constructed from non-conductive and/or insulating type materials like glass, could be effectively coupled with an ultrasonic transducer for generating aerosol, as long as they included a special design consideration for cooling the transducer, or the transducer was separated from the glass barrier with a layer of liquid. U.S. Pat. No. 3,433,461 teaches utilizing a 1.5 inch diameter transducer bonded to a metal barrier that is a one-half wavelength thick. A problem associated with using metal barriers is corrosion, which was acknowledged in U.S. Pat. No. 3,729,138. In addition, U.S. Pat. No. 3,433,461 discloses that heat has a detrimental effect associated with the operation of a transducer and that a metal barrier interfaced with a transducer permitted the use of much higher driving powers than in prior art devices, since it provided more heat dissipation. Further, the driving power supplied to the transducers is limited by the heat dissipation in the device, which is a function, in each case, of the total area of the generator.

According to U.S. Pat. No. 4,976,259, an attempt was made to bond a glass barrier to a piezoelectric crystal with an adhesive, but such an attempt did not improve on the prior art and resulted in a major loss of acoustic coupling of the ultrasonic energy into the glass cover as the adhesive bond deteriorated. The deterioration was due to high localized temperatures caused by reflected energy resulting from mismatched acoustical impedances.

The prior art does not currently include commercially effective techniques for constructing and operating a high frequency and high power aerosol producing transducer assembly consisting of one or more transducers bonded or adhered to a protective barrier constructed from non-metallic and/or insulative type materials, such as glass, with a thickness that is not one-half (½) of a wavelength. Furthermore, the prior art does not currently include high frequency and high power aerosol producing glass barrier and transducer assemblies that are capable of operating without additional liquid layers or liquid cooling means incorporated into the transducer assembly design.

Therefore, the need for a protective barrier for the aerosol producing transducer that is highly resistant to degradation caused by chemically reactive solutions exists. The protective barrier should withstand the heat generated by a transducer and should function effectively with the transducer to produce a fine aerosol at high output levels (which requires high energy emitted by the transducer). This heat is due to the high frequency and energy that is needed to achieve a high output of aerosolized liquid per hour with the aerosol droplets being less than about 10 microns in size. In general, within the effective frequency band, the higher the power at the effective aerosol producing frequencies, the larger the quantity of aerosol produced; and the higher the effective frequency the smaller the droplet size in the aerosol.

The complete and assured sanitization, disinfection, high-level disinfection, or sterilization of devices, tools, machinery, or other objects or surfaces, within enclosed or unenclosed targeted areas or surfaces, related to industries including, but not limited to, health care, food production, medical device or products, clean rooms, and pharmaceutical, has always been a challenge in terms of overall effectiveness, processing time, cost, and engineering tradeoffs. In addition, the applied agents must have limited toxicity, be reasonably safe, as well as non-harmful to the materials or substances to which they are applied.

The prior art has extensively taught that relatively quick disinfection and sterilization of surfaces can be achieved by exposing them to an aerosol of a disinfectant/sterilizing agent created by ultrasonic nebulization. The apparatus described in U.S. Pat. No. 4,366,125 (Kodera et al., 1980), which is incorporated herein by reference in its entirety, including any references cited therein, generates a hydrogen peroxide mist by an ultrasonic waves vibrator. The aqueous hydrogen peroxide is heated as it travels from a tank into a basin (col. 4, line 6-8) where it is turned into a fog or mist as the surface of the germicidal liquid in the basin is acted upon by ultrasonic waves. The fog or mist will adhere to the surface of materials being sterilized or disinfected. The surface is then irradiated with ultraviolet-ray lamps.

G.B. Patent No. 1,128,245, (Rosdahl et al., 1968) which is incorporated herein by reference in its entirety, including any references cited therein, describes a device for disinfecting apparatuses and instruments, including medical instruments. This apparatus also generates a mist of disinfectant, including hydrogen peroxide, by means of an ultrasonic aerosol generator. According to Rosdahl et al., this patent was "primarily adapted for the disinfection of small medical instruments such as scalpels, tongs, syringes, or the like, positioned on a grid in a container" (pg. 3 col. 23-30). However, another separate intended use for a second described apparatus was to disinfect the interior surfaces of objects such as hollow tubing used for "breathing apparatuses" and "heart lung machines" (pg. 1 line 30-36 and pg 2 line 95-101). Rosdahl et al. also taught the use of the germicidal fogging technology to disinfect rooms, apartments and the like (pg. 2 col. 28-30). The pressurized air in Rosdahl et al. is supplied by way of a fan etc. or carrier gas, (pg. 2 line 48-49) and is used to move the generated aerosol as well as to dry objects placed within the enclosed area of the described apparatus. Rosdahl et al. also incorporated "a heating element in the flow path of the carrier gas, to increase drying efficiency" (pg. 3 line 123-127).

Ultrasonic nebulizers have a unique advantage in that they can create aerosol droplets less than 10 microns in size depending on the power and frequency used in their operation. The small size of the droplets enables them to penetrate small cracks and crevices and to behave like a gas due to Brownian movement and diffusion. In addition, the dense cloud of small droplets is able to form a very thin coating or film over surfaces. The thin coating or film of disinfectant or sterilization agent is able to dry much faster than coatings created by aerosols consisting of larger diameter droplets. It is also theorized that even partial contact of the aerosol droplets with the targeted contaminate(s), can contribute to the overall efficacy of the process. U.S. Pat. No. 4,366,125, (Kodera et al., 1980) taught that heated H2O2 was more efficacious than H2O2 used at room temperature (col. 1, line 19-25). In other words, (Kodera et al., 1980) taught that the efficacious nature of a liquid agent can be increased as it is heated to temperatures higher than ambient temperature. This is desired, without limitation, in the present invention. The text entitled, "Aerosol Technology" by William C. Hinds (1982), which is incorporated herein by reference in its entirety, including any references cited therein, also taught that the size of the aerosol particles produced by ultrasounic means is not only affected by the frequency of the transducer operation, but also by the surface tension and density of the liquid as shown by the following mathematical expression (page 382):

$$CMD = ((y)/(pL)(f^2))^{1/3}$$  Equation 1:

where: CMD=particle size produced; y=surface tension; pL=liquid density; and f=frequency It is commonly known that heating a liquid to point less than its boiling point will reduce its surface tension. Therefore, according to Equation 1 above, a direct relationship was established by William C. Hinds (1982) where one skilled in the art can ascertain that the higher the temperature of the liquid, the lower the liquid's surface tension, which will result in smaller sized aerosol particles. This principal is incorporated without limitation, in the present invention. William C. Hinds (1982) also taught in the same text that smaller diameter particles demonstrate characteristics such as but not limited to, a lower settling velocity, a higher diffusion coefficient, and a higher Brownian displacement (movement), which is desired, without limitation, in the present invention. William C. Hinds (1982) further taught that ultrasonic aerosol generating transducers can heat the surrounding liquid (page 382). This is also desired in the present invention.

Despite the plethora of advancements shown in the current art, limitations exist in many areas that reduce the effectiveness or viability of the ultrasonic aerosol generator technology in actual commercial applications. The methods and apparatuses of the present invention address the need for an ultrasonic aerosol generator that is, without limitation: (a) designed so that the apparatus can be quickly and easily set up and operated in a reproducible manner on uneven or angled surfaces(s), (b) designed so that the transducers can quickly heat the liquid and liquid surface above and/or around them, (c) designed to prevent or limit dust and debris contamination inside the pressurized air channels or pipes of the apparatus or in the tank in which one or more transducer(s) are located, (d) designed so that if a valve of a liquid storage, holding tank, or reservoir, breaks the tank(s) or reservoir(s) in which the transducer(s) is located is not flooded, (e) designed so that excess, leaked, or spilled liquid can be transferred to a separate containment tank or basin from sources such as but not limited to the fill pipe(s), blower housing(s), internal catch pan(s), transducer tank(s) or basin(s), (f) designed so that the liquid in the tank in which the transducers are located does not drop below the minimum or exceed the maximum operating temperature for that liquid or particular process, coupled with one or more sensor(s) that can determine when an effective or sufficient amount of aerosol has been applied or administered to the targeted area and/or surfaces, (g) designed so that a partially empty apparatus can be easily and effectively refilled, (h) designed to prevent expired liquid that has been added or is otherwise available to the apparatus from being administered by or deployed from the apparatus, (i) designed so that the stream of aerosol deployed from the apparatus can be simultaneously delivered to one or more separate areas.

It is obvious to those skilled in the art that an apparatus can automatically shut down if an insufficient amount of inventory or product is available with which to complete its defined operational cycle. This activity is also mentioned in French Patent No. FR2860721 (Schwal et al.), which is incorporated herein by reference in its entirety, including any references cited therein. This patent claims the use, by any aerosol generator, of single-use liquid refill/fill cartridges that are associated with specific identifiers, and a reader integrated into the aerosol generator apparatus that can read the said identifiers, all of which is dependently combined with a system of defined steps to establish a set process whereby the apparatus will not generate aerosol if there are any non-conformances related to the entire process, and each cycle of use is terminated with a recording of various information pertaining to the process as a whole. However, according to patent No. FR2860721, the apparatus only notifies the operator if an insufficient liquid quantity is available (pg. 6 line 15-25 and pg. 10 line 10-25) and when it is necessary to replace a filler cartridge (pg. 10 line 15-25).

Patent No. FR2860721, does not teach or describe an aerosol generator apparatus that can communicate, by any means, to the apparatus operator the quantity of liquid or at least the exact minimum quantity of liquid, expressed in units of measurement, that is necessary to add or make available to the apparatus so that it may successfully complete its desired or chosen operational time or run cycle. The methods and apparatuses of the present invention address the need to provide this information.

French Patent No. FR2860721 also fails to address the issue of preventing the apparatus from using expired or outdated liquid that is available to the apparatus from, without limitation, one or more tanks or reservoirs inside or attached to the apparatus that have been fed, supplied, or filled by a refill/fill cartridge or other means. This is critical since some liquid agents have a defined period of time of efficacious use once they have undergone, without limitation, dilution from a concentrate or exposure to air. The methods and apparatuses of the present invention address the need to prevent the use or deployment of a liquid agent that is available to the apparatus, but has expired, is unusable, or undesired.

The need for an ultrasonic aerosol generator that can be positioned and operated from within the area in which the aerosol is being dispersed so as to, without limitation, eliminate or reduce the effects of increased air pressure within the targeted area and operate without damage to its internal and external structures and components is also addressed in the present invention and includes, without limitation, methods and apparatuses such as: (a) means for cooling the various motors, electronics, and other components; (b) properly housing various motors, electronics, and other components to prevent their exposure to the environment surrounding the apparatus; (c) the remote control of and remote communication with the apparatus; (d) preventing any parts of the apparatus that are exposed to the aerosol from becoming higher in temperature than the temperature of the atmosphere surrounding the apparatus.

There is also a continued need in the market place to increase efficacy and effectiveness from the aerosol and the process of its administration, as well as a system that offers shortened cycle times. The present invention addresses these issues. One such means in the present invention is the utilization of thermal forces and their resultant effects, by cooling or decreasing the temperature of the objects, the atmosphere in which they reside, or the targeted area for the administration of an aerosol as well any surfaces in that area, before the administration of the aerosol to the targeted area or surfaces. Prior art has taught the step of cooling an enclosed area and its surfaces before the administration of a hydrogen peroxide disinfectant, however the hydrogen peroxide was first vaporized into a gaseous state before its administration, and the cooling step was intended to condense the vaporized hydrogen peroxide gas out of the atmosphere in which it was administered and onto the intended surfaces, as taught in U.S. Pat. No. 4,512,951 (Koubek et al., 1983), which is incorporated herein by reference in its entirety, including any references cited therein. More specifically, Koubek et al., teaches a method of sterilization where a liquid of aqueous hydrogen peroxide is vaporized, and the uniformly vaporized mixed hydrogen peroxide-water vapors are delivered into an evacuated sterilizer chamber. The articles to be sterilized are cooled if necessary prior to the introduction of the vapor (or are cooled by the evacuation of air from the sterilizing zone) to a temperature below the dew point of the entering vapors and the condensing vapor deposits a film of liquid on all such cool surfaces (col 2, line 40-51). Koubek et al., also mentions in Claim 2 that the result of vaporization was a mixed "gaseous vapor" consisting of hydrogen peroxide and water vapor free of solid contaminants.

U.S. Pat. No. 4,952,370 (Cummings et al., 1988), which is incorporated herein by reference in its entirety, including any references cited therein, teaches a similar method of sterilization where a liquid of aqueous hydrogen peroxide is also vaporized into a gaseous state before its administration into an evacuated sterilizer chamber. However, Cummings et al., teaches improvements to the art where the hydrogen peroxide-water vapor is applied under vacuum to surfaces that are below 10 degree centigrade, or surfaces in an environment that are both below 10 degree centigrade and above 10 degree centigrade. The cold surfaces mentioned in Cummings et al., were not cooled to accentuate or enhance the process, but were surfaces of components that were inherently cold for their own operational purposes. This is mentioned in sections such as (col 2, line 4-9), (col 2, line 29-33), and (col 4, line 67 to col 5, line 2).

U.S. Patent Application No. 2005/0042130 A1 (Lin et al., 2003), which is incorporated herein by reference in its entirety, including any references cited therein, claims the use of an applied vacuum to move an ultrasonically derived aerosol, consisting of a sterilant, throughout the area of an enclosed chamber. The use of various vacuum pressures below atmospheric pressure was also mentioned as well as the possibility that vacuum pressures lower than 5 torr lower than atmospheric pressure would likely "enhance the results", and that using a vacuum pressure low enough to vaporize the sterilant generally enhances sterilization (pg. 2, paragraph 28). However, Lin et al, was silent with respect to how the lower vacuum pressures would "enhance the results" other than any enhancement that vaporization of the aerosol might bring. Lin et al, was also silent with respect to the amount of time that is needed to elapse between lowering the pressure within the enclosed chamber and the application of an aerosol, in order to obtain the needed or desired level of efficacy. (Lin et al., 2003) was silent with respect to cooling any surfaces within the sterilization chamber or applying the aerosol to any cooled surfaces.

It is important to note that Lin et al, did not mention any process or method to heat the liquid of the aerosol or cool the surfaces in the sterilization chamber before or during the delivery of the aerosol, or any means to incur condensation if the liquid was vaporized. In fact, the 5 torr negative pressure that was used by Lin et al. to generate their findings was reported to be sufficient enough to disperse the mist within the sterilization chamber (pg. 2, paragraph 28), but was never mentioned to have cooled the surfaces within the sterilization chamber or to have that intended effect.

In addition, it is important to note that the cooling of a targeted environment(s) and/or the surfaces contained therein addressed by the present invention is intended, without limitation, for a completely different application and purpose. The present invention utilizes the principals of aerosol behavior to increase the performance of the process of the present invention, and not the condensation of a gas as taught in the prior art. This is further addressed in the present invention.

By comparison, the current invention utilizes, without limitation, the cooling of the targeted environment(s) and its surfaces to enhance the performance and efficacy of the aerosol administration process and not to condense a gas as taught by the prior art. The methods and apparatuses of the present invention also address the need to apply an aerosol to surfaces that are without limitation, difficult, impossible, time consuming, or not cost effective to enclose.

U.S. Pat. No. 7,641,130 to Ricciardi et al., discloses methods and apparatus for optimizing aerosol generation with ultrasonic transducers.

Accordingly, there is a clearly felt need in the art for an ultrasonic aerosol generation apparatus, which is able to generate greater volumes of disinfecting aerosol than that of the prior art. The present invention also combines the ability to generate and deploy larger amounts of small diameter aerosol, with a combination of apparatus parts that can constitute a smaller overall package, when compared with the prior art.

U.S. Pat. Nos. 3,561,444, 7,871,016, 7,641,130, 8,196,604, and U.S. patent application Ser. No. 13/494,824, and U.S. patent application Ser. No. 13/277,750 "Methods & Apparatuses For Applying Agents To Objects", are hereby incorporated into this patent application by reference in their entirety, including any references cited therein.

SUMMARY OF THE INVENTION

In view of the need for improvements in the current art, the present invention includes improved apparatuses and methods for the generation and application of an ultrasonically generated aerosol for uses including, but not limited to, the sanitization, disinfection, high-level disinfection, or sterilization of one or more areas and the surfaces in those areas, as well as the delivery of other types of liquid agents, for various purposes, to one or more areas, and the surfaces found therein.

It is preferred, without limitation, that the aerosol is generated within the apparatus and administered into a targeted area and/or onto targeted surfaces by pressurized air or the movement of air or gas. The generated aerosol can be of various sizes, mass concentration or density, and number concentration. It is preferred without limitation that the aerosol is a submicron droplet fog or aerosol of an anti-pathogen, toxin, fungal, sterilization, disinfection, or sporicidal agent(s) or mixtures thereof (herein collectively "agent(s)"). However, any liquid agent(s) may be used in the present invention for various purposes. The fog or aerosol can, without limitation, consist substantially of ten micron to submicron size aerosolized droplets. It is preferred, without limitation, that the aerosol has a higher rather than lower mass concentration or density of droplets. It is also preferred, without limitation, that the aerosol has a higher rather than lower number concentration of droplets.

The apparatus and methods described in the present invention can pertain to any ultrasonic aerosol producing apparatus. They can also pertain to an aerosol producing apparatus as described in the present invention. This apparatus, briefly described, has one or more piezoelectric transducers that are operated in parallel or series. The transducers are submerged in one or more tanks or reservoirs, and cause a surface disturbance, which results in the formation of an aerosol of the liquid in the tanks or reservoir(s). The one or more tanks or reservoirs in which the transducers are located can be connected to one or more additional tanks or reservoirs that hold the liquid agent. The liquid level in the tank(s) or reservoir(s) in which the transducers are located is controlled by one or more valves which are actuated when the liquid level drops to a certain level causing the valves to open and allows additional liquid to flow in. The tanks or reservoirs also have a means to sense if they are under or overfilled, and can cause the apparatus to shut down if this occurs. The tank(s) or reservoir(s) in which the transducers are located, can be positioned in a chamber that can have a flow of pressurized air/gas, or can be constructed in such a way so that pressurized air/gas can flow through or over them. The pressurized air/gas is intended to move the generated aerosol from the apparatus to the targeted areas or surfaces. The pressurized air/gas can be supplied from sources such as, but not limited to, one or more, fan(s), blower(s), or supply of pressurized air or gas. The apparatus in the present invention can be operated either from inside or outside of the targeted area.

An apparatus and method of an embodiment of the present invention, briefly summarized, comprises constructing the apparatus so that the aerosol producing transducer(s) and/or their liquid facing surfaces, are able to, without limitation, automatically align themselves with, match the angle of, or remain level with, the surface of the liquid above them. This allows the apparatus to be quickly and easily set up and operated, in a reproducible manner, on uneven or angled surfaces. It also eliminates, without limitation, the need to operate the apparatus on level surfaces. This embodiment includes placing, positioning, or mounting the transducers to or with a gimbal or other similar means known in the art, where the transducers are located at an effective range or depth below the surface of the liquid during their operation. However, it is preferred without limitation that the transducer(s) and their associated parts and housing(s) are designed so that they can be suspended, positioned, held, or maintained, in numerous ways at an effective range or depth below the surface of the liquid during their operation. Without being limited, the transducer(s) and their housing(s) can be suspended, positioned, held, or maintained, at an effective range or depth below the surface of the liquid from an object or component that is floating on the surface of the liquid, partially submerged in the liquid, or completely submerged in the liquid.

An apparatus and method of an embodiment of the present invention, briefly summarized, comprises interfacing the transducer(s) with a protective barrier that is ground and polished on one or more sides. Polishing the side of the barrier that interfaces with the liquid in the reservoir(s) offers advantages including, but not limited to, ease of cleaning, increased resistance to mineral or foreign object debris deposition or buildup, efficient and effective movement of liquid off of the barrier. In addition, polishing the side of the barrier that interfaces with the adhesive and transducer(s), offers advantages including, but not limited to, reduced variability in adhesive thickness due to diminished variability in the protective barrier's surface features, which can without limitation, reduce variability in transmission related issues.

An apparatus and method of an embodiment of the present invention, briefly summarized, comprises constructing the enclosing glass plate to have approximately a thickness of about ¼ the wavelength in glass or other material forming the barrier of the transmitted pressure wave generated by the transducer at the natural resonant frequency of the transducer. When the barrier thickness has been calculated, the transducer can be operated at an operational frequency up to 60% percent greater than the natural resonant frequency to achieve a much more efficient operation for the transducer in forming the aerosol. Alternatively, the thickness of the barrier can be varied from the optimal thickness in the range of −0.010 inches to +0.024 inches to increase the efficiency of operation of the transducer. Further, it has been found that the glass or other material barrier thickness may be increased to around various odd multiples of ¼ wavelength and still operate effectively to provide a high volume small aerosol particle output.

An apparatus and method of an embodiment of the present invention, briefly summarized, comprises enclosing or encircling aerosol producing transducers with one or more wall(s) or barrier(s), that can be, without limitation, continuous or discontinuous, sealed, partially sealed, or unsealed, of various heights including, but not limited to, above the surface of the liquid above the transducers. The purpose of the wall(s) or barrier(s) is to contain the liquid above and around the transducers and use the heat from the transducers to heat that liquid above and around the transducers, and without limitation, the liquid surface above the transducers. The wall(s) or barrier(s) can be perforated or have holes or notches in various orientations or locations in order to allow liquid of various temperatures to flow in and out of the enclosed or encircled areas.

An apparatus and method of an embodiment of the present invention, briefly summarized, comprises filtering the pressurized air before it enters the apparatus, or at least before entering the aerosol generation chamber. Without limitation, it is preferred that one or more filter(s) is located where the air is drawn or pulled into the apparatus by a blower or fan. The filter(s) can be located either on the inside or outside of the apparatus. The addition of one or more filter(s) prevents or limits dust and debris contamination inside the pressurized air channels or pipes of the apparatus or in the tank or area in which the transducer(s) are located. Various types of filters can be used in the present invention and is dependent on the application. The filter(s), are not used in any configuration(s) or application(s) where aerosol is pulled or pushed from the area in which it was administered, back through the aerosol generator and filtered before it is exhausted out from the targeted or treated area.

An apparatus and method of an embodiment of the present invention, briefly summarized, comprises connecting one or more tanks between the main tank(s) in which the liquid is stored in the apparatus, and the tank(s) in which the transducer(s) are located, and without limitation, each of the aforementioned tanks have one or more inline valve(s) or float valve(s) that controls the flow of liquid. Without limitation, these connecting tank(s) and valve(s) system(s) act as a check or failsafe mechanism to ensure that the tank(s) or basin(s) in which the transducer(s) are located is not over filled or flooded.

An apparatus and method of an embodiment of the present invention, briefly summarized, comprises connecting, without limitation, the fill pipe(s) or their spill over tray(s) or basin(s), blower or fan housing(s), internal catch pan(s) or basin(s), transducer tank(s) or basin(s), to one or more liquid containment tank(s). Without limitation, the liquid containment tank(s) are designed to collect excess, spilled, leaked, gathered, or coalesced liquid. This collection system can be connected to the pipe(s) and valve(s) used to drain the apparatus, or it can also have its own drain pipe(s) and valve(s).

An apparatus and method of an embodiment of the present invention, briefly summarized, comprises the incorporation of a means to control or prevent the temperature of the liquid in the tank or basin in which the transducer(s) are located from exceeding the maximum desired, established, or required operating temperature for that liquid or particular process. The prior art has taught that the transducers impart heat into the liquid during their operation. The air that is used to transfer the aerosol from the basin or tank in which the transducer(s) are located to the targeted area(s), can function as a heat removal system. However this pressurized air flow can only remove a certain or calculated number of BTUs or watts of heat due to factors including, but not limited to, the surface area of the liquid in the basin or tank, and the volume and velocity of air that moves over that surface area. If more heat is imparted into the liquid than is removed or dissipated over time, the temperature of the liquid will continue to rise. The means to control or prevent the temperature of the liquid in the tank(s) or basin(s) in which the transducers are located from exceeding the aforementioned maximum desired, established, or required operating temperature, includes without limitation, pumping or otherwise moving the liquid that is in the basin(s) or tank(s) in which the transducer(s) are located, or any other liquid that could possibly have contact with that liquid, through one or more heat exchanger, cooling fins, cooling plate, cooling block, chiller, chilling or cooling apparatus, or other means to remove heat from the liquid. Without limitation, the liquid from the basin(s) or tank(s) in which the transducer(s) are located, can be pumped or moved through one or more cooling fins, chill block, or heat exchanger that is located in the path of the pressurized air that is used to move the generated aerosol out from the apparatus.

An apparatus and method of an embodiment of the present invention, briefly summarized, comprises the remote control of and communication with the apparatus in the present invention. This improvement in the present invention offers many advantages such as, but not limited to, reducing or eliminating the chance of the operator having an accidental exposure to the aerosol from an apparatus that is operated from within the same environment in which the aerosol is applied. The remote control of and communication with the apparatus can be accomplished by means such as, but not limited to, any radio frequency, any light frequency, or directly or indirectly connected wires, or any combination of the said means. Various information, data, and commands can be communicated between the apparatus and a separate means to send and receive information, data, or commands.

An apparatus and method of an embodiment of the present invention, briefly summarized, comprises the apparatus having one or more sensors or the communication with one or more sensors to determine when an effective or sufficient amount of aerosol has been applied to the targeted area and/or surfaces. The sensor(s) consists of a means of varying intensity to project one or more beams of light or a light source, and one or more means to sense the beam(s) of light or light source(s) and indicate its absence or presence. Without limitation, the means to sense the light can vary widely in its sensitivity, and can indicate the presence or absence of the beam or light with a signal such as but not limited to any electrical, fiber optic, or radio frequency signal. It is preferred, without limitation, the sensor consists of a laser and a photoelectric sensor. The means to sense the beam of light communicates with a programmable logic circuit, computer, control mechanism or device, or other electronics that control or operate the apparatus (herein called "PLC"), and the presence or absence of a signal or communication causes or results in the apparatus to take actions or undergo activities, such as but not limited to, ceasing the production of aerosol, ceasing the operation of the blower or fan, or even shutting down. It is the intent of the present invention to generate and deliver aerosol into an area until a sufficient amount or density of aerosol is present which will, disrupt, diminish, or completely prevent, the light, beams of light, or light source, from reaching the means to sense the light. The amount of this applied aerosol can vary depending on the application.

An apparatus and method of an embodiment of the present invention, briefly summarized, comprises the apparatus alerting or communicating with the operator if he/she programs the apparatus or otherwise undertakes an activity that would cause the apparatus to operate and generate aerosol for a specific period of time or to fill a specific volume of space with aerosol, and there is an insufficient amount of liquid available in or available to the apparatus for the chosen operating time or volume of space to fill with aerosol, and communicating to the operator the quantity of liquid or at least the exact minimum quantity of liquid, expressed in units of measurement, that is necessary to add or make available to the apparatus so that it may successfully complete its desired or chosen operational time or run cycle. The actual number of needed fill/refill cartridges can also be communicated to the operator. This embodiment includes without limitation, the apparatus having the ability to sense or detect the liquid level or amount of liquid available to the apparatus, or calculating the total amount of liquid available in one or more reservoir(s) that are, without limitation, inside, attached, or otherwise connected to the apparatus. In addition, the means to alert and communicate information to the operator can include but is not limited to any alphanumeric image shown on a screen, monitor, or human-machine-interface (herein called "HMI"), any graphic-user-interface (GUI) shown on a screen, monitor, or human-machine-interface (HMI), lights, lights with associated text, voice commands or directions, or any audible signal.

An apparatus and method of an embodiment of the present invention, briefly summarized, comprises the apparatus having the ability to prevent the liquid agent from being dispersed, that is available to the apparatus from, without limitation, one or more tanks or reservoirs inside, attached, or connected, to the apparatus, which has exceeded its time or date of expiration, exceeded the time or date in which it can be efficaciously used, or has reached a point of time or date where it has degraded or aged to a point where its use is unacceptable. This embodiment does not encompass refill/fill cartridges. The apparatus in this embodiment possesses a means known in the art for measuring, comparing, calculating, or otherwise keeping track of the time between when the apparatus is initially charged or filled with the liquid agent, or the last purge of the apparatus of undesired or unusable liquid, and when the time has been reached when that liquid agent cannot be used and must be disposed of. Once the usable time for the liquid agent has expired, the apparatus can prevent the liquid agent from being dispersed with means including, but is not limited to, using a programmable logic circuit (PLC), control mechanism or device, or other electronics that control or operate the apparatus, to take action(s) that result in stopping the apparatus from generating aerosol. In addition, the apparatus can alert or communicate to the operator that the liquid agent has expired. The means to alert and communicate information to the operator can include but is not limited to any alphanumeric image shown on a screen, monitor, or human-machine-interface (HMI), any graphic-user-interface (GUI) shown on a screen, monitor, or human-machine-interface (HMI), lights, lights with associated text, voice commands or directions, any audible signal.

An apparatus and method of an embodiment of the present invention, briefly summarized, addresses the cooling of components that can heat up inside of the apparatus when it is being operated in areas such as, but not limited to, the area in which the aerosol is being applied. This situation presents engineering challenges because as the apparatus is operated, its components such as, but not limited to, motors or electronics heat up over time. They cannot be cooled by blowing air from outside of the apparatus past or onto them to remove heat if they are in an aerosol filled environment. This air would contain the administered aerosol and be wet. This condition could pose a risk for unwanted chemical reactions with the components depending on the chemical agent that is present in the aerosol. In one part of this embodiment, the electronics that are used to operate or power the transducer(s) are located in a sealed enclosure and cooled with a means that transfers the heat generated from the electronics into a pressurized air stream. It is preferred, without limitation, that this pressurized air stream is the same air stream that is used to move the generated aerosol out of the apparatus. This helps, without limitation, to minimize the total amperage that is utilized or needed for proper or effective function of the apparatus, which is a critical issue with regard to aerosol generators of this complexity. The one or more heat transfer point(s) can be located before or after the fan(s) or blower(s) that create the pressurized air stream. It is also preferred, without limitation, that the heat generated from the electronics is transferred in various ways known in the art to a heat sink that has fins or other cooling enhancements also known in the art, and the heat sink is positioned in the pressurized air stream. In another part of this embodiment, the components other than the electronics that are used to operate or power the transducer(s), including but not limited to motors or electronics, or the atmosphere in their enclosure(s), are also cooled with a means that transfers the heat generated from the components into a pressurized air stream.

An apparatus and method of an embodiment of the present invention, briefly summarized, comprises constructing the apparatus in a way that prevents any exterior parts of the apparatus that are exposed to the aerosol from becoming higher in temperature than the temperature of the atmosphere surrounding the apparatus. Generally speaking, this is important because aerosol particles experience a force in the direction of decreasing temperature. This embodiment is applicable and especially beneficial for applications where the apparatus is operated from within the same environment in which the aerosol is applied, and it is desired or required that all of the exterior surfaces of the apparatus have interaction or contact with the administered aerosol. Without this improvement to the current art, the exterior surfaces of the apparatus could become warmer in temperature than the surrounding atmosphere and repel the aerosol, which would prevent the exterior surfaces from having interaction or contact with the administered aerosol if it is desired or required. The apparatus can be constructed in ways that include, but are not limited to, enclosing the components or parts that can heat up in a sealed enclosure and then placing that enclosure inside of another closure that is sealed or unsealed, or insulating the outer skin of the apparatus.

An apparatus and method of an embodiment of the present invention, briefly summarized, comprises cooling or decreasing the temperature of the objects, the atmosphere in which they reside, or the targeted area for the administration of an aerosol as well any surfaces in that area with refrigerated or chilled air, before the administration of the aerosol to the targeted area or surfaces. This cooling activity or process enables the present invention to utilize the principals of aerosol behavior to increase the efficacy or performance of the process of the present invention. Aerosol particles experience a force in the direction of decreasing temperature. By decreasing the surface temperature of the targeted surfaces, the administered aerosol, and especially an aerosol where the liquid was heated, is drawn towards the cooled surfaces in the targeted area or environment where they interact, interface, or coat the said surfaces with the liquid agent.

An apparatus and method of an embodiment of the present invention, briefly summarized, comprises utilizing a means to administer the mixture of aerosol and gas or air that is ejected or moved out of the apparatus to one or more separate enclosed rooms or areas. This embodiment does not encompass applications where the areas are within the same room, since this is already known in the art. The said means can include but is not limited to connecting one or more tubes to the apparatus, or splitting the flow from these tube(s) so that they can connect, interface, or otherwise empty into the one or more separate enclosed areas. The said means can also have a means to close off the flow of the air/gas and aerosol to one or more of the said tube(s).

An apparatus and method of an embodiment of the present invention, briefly summarized, comprises designing the apparatus so that the electronics that operate or energize the transducer(s) may be able to adjust the frequency or frequency range of the signal that is sent to the transducer(s) multiple times during the lifespan of the transducer(s) so that the transducer(s) are able to be consistently operated at a frequency or within frequency range in which the they are able to have an effective or functional output and/or operate at their maximum performance or aerosol output.

An apparatus and method of an embodiment of the present invention, briefly summarized, comprises connecting, interfacing, or attaching, the aerosol generating apparatus in the present invention to one or more sealed, semi-sealed, or semi-open enclosures or areas. The enclosure(s) has at least five distinguishing features: a) the enclosure(s) is designed to fit over or under various things such as, but not limited to, equipment, objects, or architectural features, etc., b) any walls can have various openings through which any objects may be moved or accessed, c) the enclosure can hang from hooks or other means of attachment that connect to the ceiling or other locations of the area in which the enclosure(s) is located, d) the floors of the enclosure(s) can be constructed with or utilize a surface design or accessory(s) so as to reduce any potential for slip hazards inside the enclosure(s), e) the enclosure can be interfaced with one or means for fire suppression inside or outside of the enclosure.

An apparatus and method of an embodiment of the present invention, briefly summarized, comprises administering an aerosol into an enclosed area where the floor of that enclosed area is removed, and the surface(s) which the walls of the enclosed area interfaces forms the floor of the enclosed area. This interface can be fully sealed, semi sealed, or unsealed. In addition, one or more holes for access to the enclosed area can also be present in the walls of the enclosed area and the holes can be covered in a matter so that they are sealed or semi-sealed closed, or they can be open and unsealed.

An apparatus and method of an embodiment of the present invention, briefly summarized, comprises the incorporation of a means to add or remove one or more sources of weight or mass from various locations on any of the floated parts of the apparatus including, but not limited to, transducer housing(s), the buoyant objects or components, and/or any of the parts that are directly or indirectly connected to the buoyant objects or components, in order to position or maintain the position of each of the transducer(s) and/or their housing(s) at an effective range or depth below the surface of the liquid.

An apparatus and method of an embodiment of the present invention, briefly summarized, comprises without limitation, allowing the buoyant objects or components, and/or any of the parts that are directly or indirectly connected to the buoyant objects or components, as well as the transducers and their housing(s), to freely float in any tank(s) or reservoir(s), where the only anchor point(s) for these parts is the location where the transducer electrical cable(s) and any tubing through which they travel connect either directly or indirectly to the walls of the tank(s) or reservoir(s).

An apparatus and method of an embodiment of the present invention, briefly summarized, comprises locating the inlet for the inbound air opposite from the air outlet of the fog tank or reservoir in which the transducers are located, and directing or moving the inbound air downward into the one or more reservoir(s) in which the transducer(s) are located. This is coupled with locating one or more openings of various sizes and shapes in the roof of the reservoir opposite from the air outlet. This means can reduce the number of larger droplets in the exiting air stream.

An apparatus and method of an embodiment of the present invention, briefly summarized, comprises using one or more means to distribute the inbound air to more than one location in the fog tank(s) or reservoir(s) for purposes including, but not limited to eliminating or diminishing any, uneven airflow, uneven air distribution, turbulent air, or vortices, within the interior air space of the fog tank or reservoir. This means to move the air can also be perforated in various orientations with one or more orifices of various sizes and shapes.

An apparatus and method of an embodiment of the present invention, briefly summarized, comprises reducing the feet per second output of the air exiting from the fog tank(s) or reservoir(s) in which the transducers are located, or otherwise the aerosol generating apparatus, any time near the end of the aerosol generation and delivery cycle. This procedure will promote faster accumulation of the aerosol cloud in the immediate vicinity of the aerosol generating apparatus.

An apparatus and method of an embodiment of the present invention, briefly summarized, comprises equipping the aerosol generating apparatus with one or more sensors to determine when an effective or sufficient amount of aerosol has been applied to the targeted area and/or its targeted surfaces. The sensor(s) may be directly or indirectly attached to the apparatus, or they may be remotely located in any location where the aerosol is applied or administered. The sensor(s) can be positioned in any orientation and communicate with the aerosol generating apparatus in various ways such as, but not limited to, radio, sound, fiber optics, or wires, all in a manner known to those skilled in the art.

An apparatus and method of an embodiment of the present invention, briefly summarized, comprises the operation of a means to dehumidify the area in which the aerosol was administered, any time after the aerosol deployment cycle has finished, or the aerosol generating apparatus was shut down for any reason(s). In one embodiment, a dehumidifier is used as an independent apparatus "not" connected to the aerosol generating apparatus. It may be remotely controlled or programmed by the operator all in a manner all known to those skilled in the art. In another embodiment, an independent dehumidifier is used, but in this particular embodiment it is controlled by, and electrically connected to, the aerosol generating apparatus. The operation of the dehumidifying apparatus is controlled by the software or computer program that operates or controls the aerosol generating apparatus. In an additional embodiment, the means to dehumidify the area in which the aerosol was administered, is enhanced so that it contains one or more filter media to filter the aerosol before, during, or after it passes over the chill coils.

Filtering the deployed aerosol was initially demonstrated by the inventors of the present invention in a public area at the Richland, Wash. Municipal Airport on Oct. 9, 2003. Staff from Washington State University, observed aerosol created by the aerosol generating apparatus described in the present invention, pass through a long tortuous path created with 150 feet of six inch diameter flex ducting, that terminated with various filter media including a HEPA filter and a furnace filter. This same system was used to dehumidify and dry the system of ductwork, after the aerosol was deployed.

In an embodiment, the dehumidifier can also incorporate a means to receive any type of signal from various sources including, but not limited to, the aerosol generating apparatus, or any means for remote control, to not only signal the dehumidifier to dehumidify a targeted area or environment, but also to complete or terminate the dehumidification process by moving, switching, or directing the air flow through a separate filter, such as, but not limited to, an activated carbon filter, or any filter that can remove various gases or vapor(s) from the treated area(s).

An apparatus and method of an embodiment of the present invention, briefly summarized, comprises the construction and use of a means to effectively cover and/or seal the various types of vents that can be found in treated areas including, but not limited to, inbound and outbound air vents for a building HVAC system. These air vents are commonly found in facilities such as, hospitals, schools, clinics, factories, laboratories, and clean rooms. Many times these vents have one or more protruding metal geometries, which makes sealing the vents difficult or impossible with current means. In addition, sealing these vents can be time consuming as well as dangerous because ladders are often necessitated to reach the ceiling mounted vents. The improved means to effectively cover or seal the various types of vents, consists of parts such as but not limited to, a vent cover with sealing material to seal it to the vent or any surrounding or connected areas or materials, any pole which can, without limitation, be adjusted or modified for length, and a means to directly or indirectly connect the pole to the vent cover. In another embodiment, the pole with adjustable length can be constructed so that its one or more ends that are opposite from the vent cover has a means to swivel or articulate so that the base(s) of the pole can articulate at any angle with the floor or any other surface that it contacts. In an additional embodiment, any surfaces of the end(s) of the pole that is compressed or pushed down onto any surface that results in the compression of the vent cover or its seal material can be, without limitation, formed from, coated with, adhered with, or consist of any absorbent material. This material can be, without limitation, treated or saturated with any liquid, at any time, consisting of any anti-pathogen, toxin, fungal, sterilization, disinfection, or sporicidal agent(s) or mixtures thereof (herein collectively "agent(s)"). However, any liquid agent(s) may be used in the present invention for various purposes.

An apparatus and method of an embodiment of the present invention, briefly summarized, comprises modifying a magnetic vent cover so that it has one or more attachment points where a means, such as, but not limited to, rope, cord, thread, wire, cable, twine, tube, or hose, can be attached to the vent cover so that it may be easily removed from a ceiling or ceiling vent eliminating the need to use a ladder. The magnetic vent cover is known to those skilled in the art, and is commonly found in the form of a flexible sheet that is embedded with one or magnets, or coated or laminated with one or more magnetic materials.

An apparatus and method of an embodiment of the present invention, briefly summarized, comprises the utilization of one or more means or holder to prop or hold any items such as, but not limited to, any hose(s), wire(s), cord(s) that are present in the area in which the aerosol is administered or lead to or from the aerosol generator(s), so that they are prevented from touching or contacting any floor or surface on which the holder is placed. The use of the holder(s) helps to reduce or eliminate an incomplete treatment or administration of the aerosol to all of the desired or needed surfaces in a targeted area. The holder(s) can, without limitation, have absorbent material placed between the holder and any surface(s) on which the holder is placed or interfaces. Absorbent material can also, without limitation, be placed between the holder(s) and any object(s) that it holds or supports. The absorbent material may, without limitation, be soaked, saturated, or contacted with any liquid or substance for various purposes before, during, or after the holder is interfaced with an object(s) or placed on a surface(s) or floor.

An apparatus and method of an embodiment of the present invention, briefly summarized, comprises without limitation, the construction and use of a means to isolate or maintain one or more wheels, tracks, or other means for providing movement (herein collectively "wheel(s)"), that are directly or indirectly connected to the aerosol generating apparatus or any aerosol or vapor generating apparatus, so that they are in direct or indirect contact with one or more materials (herein collectively "absorbent material(s)") that can hold, contain, or absorb, without limitation, any liquid, (a) mixture or solids suspended in any liquid, (b) solution, (c) medication, (d) organisms suspended in any liquid, (e) anti-pathogen/toxin/fungal/sporicidal agent(s) or substance(s), (herein collectively "agent(s)"), and prohibit the wheel(s) from directly touching any floor or other surface that it would otherwise come in contact with when it is moved, stopped, or held in a static or semi-static position. Furthermore, the absorbent material in this embodiment is treated with any liquid agent, in various ways known to those skilled in the art, and enables, without limitation, wheel surfaces and surfaces under the wheel to be treated or come in contact with the intended or applied agent(s). The implementation of this means improves the art, and can ensure, without limitation, that any surfaces under or associated with any wheels, tracks, or other supporting structures, are sterilized, sanitized, disinfected, high level disinfected, decontaminated, or otherwise treated with any agent(s) for any intended effect.

An apparatus and method of an embodiment of the present invention, briefly summarized, comprises without limitation, filtering any liquid utilized, processed, or located in the apparatus, in one of more locations, as well as anywhere along the path of any circulating or moving liquid in the apparatus. Furthermore, the aerosol generating device may be designed so that all pipes, filters, pumps, and valves may all be positioned and plumbed so that when the apparatus is drained, all of these components and plumbing may be fully emptied of any liquid.

An apparatus and method of an embodiment of the present invention, briefly summarized, comprises without limitation, the design and/or plumbing of any housing, conduit, or cover, for any blower, fan, or other source of pressurized air, so that it can be drained of any accumulated liquid that may reside inside. The liquid can be drained to any location or ports in the apparatus in a manner known to those skilled in the art.

An apparatus and method of an embodiment of the present invention, briefly summarized, comprises without limitation, the design of a sealed or semi-sealed tank or reservoir in which any aerosol is generated, where one or more pipe(s), tube(s), hose(s), or other enclosed means for transporting the generated aerosol (herein collectively "fog tube(s)") out of the fog tank, protrudes into the fog tank or reservoir from the exterior of the machine, fog tank, or reservoir, and the orifice or open end of each fog tube is located approximately above and/or to the side, of each transducer, or other type of aerosol emanating device. The effectiveness of the fog tubes(s) diminishes at a distance greater than three (3) inches from the surface of the liquid under which the transducer(s) is located, or the source of the generated aerosol. Performance and effectiveness is also impacted by the length of the fog tube(s). A visually noticeable and desired behavior and consistency of the deployed aerosol is observed when these fog tube(s) are utilized. The deployed aerosol appears visually lighter, and it appears to float longer in the air, supporting the theory that this design enhancement enables the apparatus to deploy aerosol droplets with a smaller average size.

An apparatus and method of an embodiment of the present invention, briefly summarized, comprises without limitation, the design of the air outlet of the fog tank or reservoir, so that it has a door or cover that can, without limitation, be effectively sealed closed or opened. This door can be mounted, removed, or attached, all in a manner known to those skilled in the art. This improvement can, without limitation, reduce or eliminate any vapor emanating from the apparatus when it is moved or sitting idle.

An apparatus and method of an embodiment of the present invention, briefly summarized, comprises without limitation, the design of the apparatus and its software so that the programmable logic circuit (PLC) and/or HMI shall keep a record of the time between purges of the liquid agent(s) in the apparatus to ensure that expired agents are not utilized by preventing the operation of the apparatus. The apparatus can, without limitation, be prevented from or cease to function until the apparatus is drained and replenished with fresh liquid after it has expired or reached a point where it loses efficaciousness, or at a minimum prompting the operator though the use of an HMI that the liquid or agent in the apparatus has expired. This can help maintain quality control and quality assurance for the apparatus and its processes in a manner known to those skilled in the art.

An apparatus and method of an embodiment of the present invention, briefly summarized, comprises without limitation, the positioning of one or more sensors to determine when an effective or sufficient amount of aerosol has been applied to the targeted area and/or surfaces, near the ceiling of the area in which the aerosol or agent is deployed. The sensor(s) can be, without limitation, mounted on any pole, tripod, or connected anywhere to any structure or apparatus. Furthermore, the sensor(s) mounted near the ceiling can work in tandem with similar sensor(s) located near approximately ground level. This is important since aerosol behavior can be impacted by various attributes such as, but not limited to, the temperature of the deployed aerosol, and the temperature of the atmosphere in the area in which the aerosol is deployed. This embodiment further improves the art to account for these different operating scenarios.

An apparatus and method of an embodiment of the present invention, briefly summarized, comprises without limitation, the incorporation and use of a device that includes one or more of any housing or area (herein collectively "blade housing(s)") that holds, without limitation, a plurality of any paddle(s), blade(s), or other moving surface(s) (herein collectively "paddle(s)"), that are otherwise moved, rotated, or spun. This device is intended to cause aerosol particles to impact against, without limitation, any of the paddle(s) and/or any of the interior surfaces of the blade housing(s), resulting in the removal of aerosol from the air. It is preferred, without limitation, that one or more paddles attached to a movable shaft are positioned in front of each inlet and outlet for each blade housing(s). It is even more preferred, without limitation, that these paddles are mounted to a common shaft in different angles or orientations to create a more tortuous path for the air/gas and aerosol as it moves through the blade housing(s).

This device can improve the effectiveness and efficiency that is needed to remove various amounts of aerosol from any air or gas when it is necessary or desired to do so. This device can, without limitation, function independently, or be installed within any airflow of any apparatus, such as, but not limited to any aerosol generating apparatus, or any dehumidification apparatus.

An apparatus and method of an embodiment of the present invention, briefly summarized, comprises improvements to the art as taught by U.S. Patent and U.S. application Ser. No. 09/855,546 Morneault et al., Ser. No. 10/671,837 Morneault et al., and U.S. Pat. No. 7,045,096 B2 to D'Ottone, which are incorporated herein by reference in its entirety, including any references cited therein. The prior art and the improvements that they teach, as well as these new improvements can, without limitation, be incorporated into the present invention in order to help reduce or eliminate any odors at the end of a treatment cycle from any aerosol or vapor generating apparatus.

In the first part of this embodiment, one or more of any ultraviolet (UV) light sources of any wavelength can be, without limitation, contained in one or more of any enclosure connected to any air or gas stream, and the enclosure(s) can be of any size, shape, or made from any materials. Furthermore, at least one, but preferably all of the walls, ceilings, and floor, of the enclosure are, without limitation, lined with mirrors. The mirrors can help to increase the effectiveness and efficiency of the process of treating the air or gas that is moved through the enclosure, as greater amounts of the emitted light is bounced back or redirected from the mirrored surfaces and into the enclosure space.

In the second part of this embodiment, the processed air or gas can be, without limitation, channeled or moved through one or more tortuous path(s) or complex maze(s) of mirrored channels populated with one or more of any ultraviolet light sources positioned in various areas of the channels. This torturous path or complex maze serves various purposes including, but not limited to, increasing the amount of UV light exposure to the processed air or gas.

In the third part of this embodiment, the flow air or gas can be, without limitation, disrupted with various means, such as but not limited to baffles to cause a turbulent flow of air or gas at various locations within the enclosure in which the UV light sources are located, including, but not limited to, near the source(s) of UV light, or between the sources of UV light.

In the fourth part of this embodiment, the UV light lamps or bulbs, can not only be installed so that they are vertical and offset to the direction of the air or gas flow as taught by Morneault et al, in U.S. application Ser. No. 10/671,837, (paragraphs 19-20) but they may also, without limitation, be located in any angled orientations relative to the direction of the air or gas flow, and they can also be offset to one another as well. This can also help to increase the efficiency of the process as, without limitation, the UV light contacts the air or gas, first as the emitted UV light is redirected by the mirrors, and then again as the air or gas flows closer and then past the UV light source(s). The UV light source(s) can also be installed horizontally and offset, to the direction of the air or gas flow. This can, without limitation, be combined with the mirrored surfaces of the UV light source enclosure previously mentioned above.

In the fifth part of this embodiment, one or more of any UV light source(s) can be, without limitation, positioned anywhere in the air or gas stream of a dehumidifying apparatus. In addition any air or gas, from any area treated by any aerosol or vapor generating apparatus, can be processed or treated with any UV light source and/or any dehumidifier, at any time or during any stage of any treatment cycle, for any period of time, to reduce or eliminate any unwanted or undesired odors. The treated air or gas can, without limitation, contain any concentration of any aerosol or gas that contains any applied agent(s) in any concentration. The dehumidifier and UV light source(s) can, without limitation, be operated at the same time, or at different times.

In the sixth part of this embodiment, any aerosol generator can, without limitation, incorporate the use of one or more of any UV light source(s), and/or any dehumidification technology, anywhere in its design. The dehumidifier and UV light source(s) can, without limitation, be operated at the same time, or at different times. Any air or gas, from any area treated by any aerosol or vapor generating apparatus, with any liquid agent(s) can also be processed or treated with any UV light source and/or any dehumidifier, at any time and for any duration, or during any stage of any treatment cycle to reduce or eliminate any unwanted or undesired odors in the treated area.

In the seventh part of this embodiment, the UV light source(s) can, without limitation, be combined with any aerosol or vapor generating apparatus that emits an aerosol or vapor containing one or more of, in any concentration, hydrogen peroxide, peroxyacetic acid (PAA), or any other aqueous solutions or agent(s) that are acidic, or any combinations thereof. This embodiment can also, without limitation, be combined with the use of a dehumidification technology. According to U.S. Pat. No. 7,045,096 B2 to D'Ottone, a high relative humidity (RH) increases the effectiveness of the invention as water droplets can deliver concentrated solutions of hydroxyl free radicals throughout the area in which it is employed ('096 patent, line 56). This effect can be, without limitation, enhanced in the present invention, as the dense cloud of very small aerosol droplets and vapor that is suspended in the air or gas in the treated area(s), is pulled into the enclosure or area that houses the UV light source(s) and is treated by the UV light and then deployed back into the treated area(s). This may, without limitation, be more enhanced when the aerosol or vapor droplets are less than ten (10) micron in size. This may, without limitation, be even more enhanced when the droplets are generated with ultrasonic processes, which are known to emit large amounts of aerosol droplets less than five (5) microns in diameter.

The use of any dehumidifier that is, without limitation, directly or indirectly connected to one or more UV light source(s) can also add an additional synergistic effect by reducing the relative humidity of the air or gas stream that is presented to the UV light source(s) after one or more passes of the same air or gas from the treated area(s). This may be beneficial as it may, without limitation, be possible to initially inundate the UV light source(s) with limiting conditions such as, but not limited to, too much humidity, or too much aerosol, which could wet the UV light source(s) under certain conditions known to those skilled in the art, and their performance or efficiency of the UV light source(s), such as in eliminating bacteria in the air or gas stream, could be decreased. In addition, according to U.S. Pat. No. 7,045,096 B2 to D'Ottone, to reduce the rate at which the ozone spontaneously decomposes into oxygen it is preferable, if possible, to lower the temperature of the inside of the enclosure ('096 patent, lines 48-51), where the UV light source(s) are located. The UV light source(s) can, without limitation, be located in close proximity to, in the same enclosure as, or effectively near, any chill coil(s), cooling tube(s), or cooling surface(s), associated with any dehumidifier designs known to those skilled in the art, to help reduce the temperature of the air or gas near the UV light source(s) to an effective temperature between 0-70 degree Centigrade, and more preferably near 0-15 degree Centigrade.

According to U.S. application Ser. No. 10/671,837 by Morneault et al, (paragraph 8), "A variation of photocatalytic oxidation, dubbed Advanced Photocatalytic Oxidation (APO) is defined by the complementary utilization of any ozone, hydrogen peroxide, or reactive material surfaces such as titanium dioxide in tandem with UV energy, and is deemed to yield higher oxidation performance, but it comes with the higher costs to operate and bulkiness to the apparatus." This effect can also, without limitation, be enhanced in the present invention, as the aqueous aerosol or vapor, containing any amount of hydrogen peroxide or peroxyacetic acid (PAA), is pulled into the enclosure or area that houses the UV light source(s), from the treated area(s), and is treated by the UV light. The aqueous aerosol or vapor in the present invention is unique because it provides the benefit of inherently providing the needed substance(s) to yield higher oxidation performance without any additional cost, bulkiness, or complexity to the apparatus. This synergism may also, without limitation, be accomplished with any other aerosols consisting of any other agent(s) that can have the same or similar effect.

The combination of one or more of these various technologies such as, but not limited to, any enclosed UV light source(s), dehumidification, and any aqueous aerosol generator or vapor generator, technologies, especially when combined with the use of any aerosol containing any hydrogen peroxide and/or peroxyacetic acid (PAA), can without limitation, create an enhanced synergy that can be used for a quicker process to not only decontaminate, sanitize, disinfect, or sterilize, a targeted area and various surfaces within the targeted area, but to also quickly reduce or eliminate odors or smells in the targeted area that results from these activities. This can, without limitation, be especially important when using agent(s) that contain ingredients such as, but not limited to, peroxyacetic acid (PAA). This synergy, can also, without limitation, be even more enhanced when acidic agent(s) are deployed into a targeted area and treated by the UV light source(s). This can translate to quicker overall cycle or turn over times for a treated space.

An apparatus and method of an embodiment of the present invention, briefly summarized, comprises using any combination of sensors, programmable logic circuit (PLC), computer software, algorithms, or other automated means known to those skilled in the art, to automatically adjust and modify the timing sequences and time periods of various steps of the operational cycle performed by any aerosol generating apparatus or any ancillary equipment, at any time, to account for various attributes such as, but not limited to, the total volume of the treated space, temperature of the air or gas in the treated space, the relative humidity level in the treated space, the dew point in the treated space, and the atmospheric pressure in the treated space. In addition, the operator of the apparatus can, without limitation, manually enter into the apparatus one or more values such as, but not limited to, the volume of the room or treated space, or the desired operational time for any of the various steps of any operation cycle.

An apparatus and method of an embodiment of the present invention, briefly summarized, comprises the aerosol generator conducting or carrying out, without limitation, the following operational steps or sequences. One or more of the following steps can also, without limitation, be bypassed either temporarily or permanently per the desires or needs of the operator. Each step can vary for any length of time for any reason known to those skilled in the art. In addition the time between each step can also vary for any length of time for any reason. The first step is aerosol generation and deployment into the one or more targeted area(s). This step includes, without limitation, the additional step of heating the liquid that will be aerosolized to any preset temperature. The second step provides a dwell time to allow the aerosol and any vapor component to have efficacious contact with any targeted surfaces and/or area(s). The third step is dehumidification. Dehumidification can be achieved in various ways known to those skilled in the art. Dehumidification can also, without limitation, include operating any spinning paddles or blades as mentioned in the present invention, and this can be operated with our without any other dehumidification device(s) or methodologies. The fourth step is deodorization. This is achieved by using one or more UV light source(s) as described in the present invention. The fifth step is filtering the air with one or more of any filter(s) to remove any amount of any unwanted gases or vapor. Furthermore, the aerosol generating apparatus may stop all other steps and enter into or start the dehumidification step at any time for any reason. The dehumidification step may be started for reasons including, but not limited to, the apparatus or operator has detected a fault with any part or operation of the apparatus or any other ancillary equipment, an emergency stop has been actuated, or the operator has chosen to abort or stop the function of the apparatus. Finally, the operator of the apparatus can, without limitation, manually operate the dehumidification step or deodorization step either any time before the aerosol generating apparatus has started to generate and deploy any aerosol, or any time after the entire operational cycle is complete.

An apparatus and method of an embodiment of the present invention, briefly summarized, comprises the construction and use of one or more means to effectively cover, plug, and/or seal any space(s) or gap(s) that can be present near or at the bottom of any door or set of doors when they are closed. These space(s) or gap(s) can also occur even when seals are attached to the bottom of a door(s). These spaces(s) or gap(s) can, without limitation, leak any applied aerosol depending on various variables known in the art, when a room or space is treated.

Various door seals are used in the present art to prevent drafts from emanating from under doors. However, the present invention improves the current art, by designing and constructing an enhanced door seal that it not only effectively seals the door, but it also insures that various surfaces such as, but not limited to, the surfaces of the door and door seal that are in contact with each other, as well as any floor, door frame, or flooring material, have sufficient exposure to any applied agent(s) so they may be sterilized, sanitized, disinfected, high level disinfected, or decontaminated.

An apparatus and method of an embodiment of the present invention, briefly summarized, comprises without limitation, moving or pumping any quantity of air or gas from any area treated with any agent(s), in the form of an aerosol, through a liquid contained in one or more tank(s) or reservoir(s). The liquid is any substance that can, without limitation, neutralize, degrade, or remove, any odors or vapor from the processed air or gas. The liquid can also, without limitation, neutralize or degrade any liquid agent(s) that the aerosol may contain. The air or gas can be, without limitation, recirculated one or more times before it returned to the treated area or any other designated space.

An optimized and miniaturized aerosol generator preferably includes a transducer plate, at least one transducer, a level float, a fluid container, at least one aerosol output member and an air input member. At least one transducer counterbore is formed in the transducer plate to retain the at least one transducer. The fluid container includes a float chamber and an aerosol chamber. An air input hole is formed through a top of the fluid container to receive the air input member. At least one output hole is formed through a top of the fluid container to receive the at least one aerosol output member. A sealing gasket is placed between a top of the transducer plate and a bottom of the fluid container to prevent leakage of aerosol solution in the fluid container. At least one solution passage is preferably cut through a middle rib of the sealing gasket. The level float is contained in the float chamber. The aerosol solution is pumped into the float chamber through a solution input port. The aerosol flows through the solution passage into the aerosol chamber. Air is pumped into the aerosol chamber through the air input member. A transducer driver powers the at least one transducer. The at least one transducer vibrates and produces an aerosol, which exits the at least one aerosol output member.

The present invention includes improved apparatuses and methods for the generation, extraction, and application, of an ultrasonically generated aerosol for uses including, but not limited to, the sanitization, disinfection, high-level disinfection, and/or sterilization, of one or more areas and the surfaces in those areas, as well as the delivery of other types of liquid agents, for various purposes, to one or more areas, and the surfaces found therein.

The present invention provides an ultrasonic aerosol generation apparatus, that is able to offer improvements including, but not limited to, generating and deploying greater volumes of disinfecting aerosol, than that of the prior art. The present invention can also be designed in a manner so that it offers a smaller package with a greater total output, than the prior art.

It is preferred, without limitation, that the aerosol is generated within the apparatus and administered into at least one targeted area(s) and/or onto targeted surfaces, by pressurized air or the movement of any air or gas to remove the generated aerosol from the aerosol generating apparatus. The aerosol that is produced, can be of any, sizes, mass concentration or density, and number concentration. It is preferred without limitation that the aerosol is a submicron droplet fog or aerosol of an anti-pathogen, toxin, fungal, sterilization, disinfection, or sporicidal agent(s) or mixtures thereof (herein collectively "agent(s)"). However, any suitable liquid agent(s) may also be used in the present invention for various purposes such as, but not limited to, the delivery of any medication(s) to any part of any, plant, organism, animal, and/or human being.

According to an embodiment, and without limitation, the liquid that is aerosolized can be, but is not limited to one or more of any, chemical, compound, mixture, or substance, which is a liquid, preferably a solution, and may optionally include but is not limited to any, water, medicines, pharmaceutical or medical products, enzymes, fertilizers, pesticides, fuels, chemical neutralizers, and/or anti-pathogen/toxin/fungal/sporicidal agents, substances, combinations thereof, and the like.

According to a preferred embodiment, and without limitation, a preferred liquid is any suitable PAA or peroxyacetic acid, or any suitable hydrogen peroxide combined with any suitable peroxyacetic acid in an aqueous solution, which can be effective in sanitization, disinfection, high-level disinfection, and/or sterilization, and other applications, preferably approximately between 0.1-40% hydrogen peroxide combined with approximately 0.1-40% peroxyacetic acid in solution, more preferably approximately 0.88% hydrogen peroxide combined with approximately 0.18% peroxyacetic acid in an aqueous solution. Other liquids that may also be used include, but are not limited to, any chlorine dioxide in any solution and/or ozone in any solution.

Without limitation, the generated and deployed fog or aerosol can include any sized aerosol droplets, preferably including substantially of about ten micron to submicron or less sized aerosolized droplets. It is preferred, without limitation, that the aerosol has a higher rather than lower mass concentration or density of droplets. It is also preferred, without limitation, that the aerosol has a higher rather than lower number concentration of droplets.

The apparatus and methods described in the present invention can pertain to any ultrasonic aerosol producing apparatus. They can also pertain to any aerosol producing apparatus as described in the present invention. This apparatus, briefly described, has one or more piezoelectric transducers that are operated in parallel or series. The transducers are submerged in one or more of any suitable and effective tanks or reservoirs, and cause a surface disturbance, which results in the formation of an aerosol of the liquid in the tanks or reservoir(s).

According to an embodiment, and without being limited, one or more of any, ultrasonic aerosol generating apparatus, transducer, transducer design, transducer construction, transducer assembly, and means to hold or mount any transducer inside any tank or reservoir, may be used in the present invention. It is preferred, without limitation, that the transducers are bonded to any effective barrier material such as, but not limited to any glass. It is more preferred without limitation, that the transducer(s) are combined with a protective barrier, all in a manner disclosed in U.S. Pat. No. 7,641,130 (Ricciardi et al.).

The transducer(s) may be operated or driven with various combinations of power, watts, volts peak to peak, and/or frequencies, that result in the generation of an effective amount of aerosolized liquid output. It is preferred, without limitation, that at least an effective combination of attributes such as, but not limited to any, power, watts, volts peak to peak, and/or frequency, is utilized.

Examples of electronic equipment and methods for operating or driving the transducer(s) are discussed in U.S. Pat. Nos. 5,878,355 and 6,102,992 (both of which are incorporated herein by reference in their entirety, including any references cited therein). U.S. Pat. No. 5,925,966, which is incorporated herein by reference in its entirety, including any references cited therein, also provides details of the hardware necessary to operate the transducer(s). Additional electronic equipment, tolerances, and methods for operating or driving the transducer(s) known in the art may also be used. A variable frequency oscillator or signal generator is used to generate a high frequency wave, preferably a sine or square wave.

According to an embodiment, and without limitation, a preferred oscillator is a digital function generator/counter capable of producing sine, square, triangle, pulse and ramp waves. A preferred oscillator has an adjustable frequency range from about 0.025 MHz to about 12 MHz, and may be set or designed for a particular need or requirement. It preferably, and without limitation, has variable output amplitude from 5 mV to 20 Vp-p (Volts peak to peak) being delivered to the amplifier, variable symmetry/duty cycle from 5% to 95% in the ramp or pulse mode, continuous or externally controlled outputs. This signal can then be optionally amplified using a power amplifier to increase the power to the optimum aerosol producing power. The volts peak to peak is a measure of power that is supplied to the transducer(s). A direct current (D.C.) offset between −10 v to +10 v can be added to any of the output waveforms.

In one embodiment, and without being limited, the amplifier is a solid-state amplifier that provides up to 2500 watts of linear power with low harmonic and intermodulation distortion and peak to peak voltages of about 20 volts to about 300 volts; however the number of watts could also be increased in order to provide enough power to drive a desired number of transducers and the peak to peak voltages could also be increased, preferably approximately at least about 100 watts of linear power per transducer(s) with about 190 to about 230 Vp-p.

The amplified signal from the amplifier is used to operate or drive one or a plurality of transducer(s), where in an embodiment each transducer(s) is operated at a frequency range between about 0.025 MHz to about 10 MHz or higher, preferably between about 0.5 MHz to about 2.5 MHz, more preferably between about 1.2 MHz and about 2.2 MHz. Moreover, in such an embodiment each transducer(s) has a resonant frequency between about 0.025 and about 10.0 MHz or higher. The operating frequency is the frequency at which the transducer(s) is being driven or operated.

One or more transducers are located in at least one tank or reservoir. It is preferred, without limitation, that at least one transducer is located in each tank or reservoir. It is more preferred, without limitation, that two transducers are located in each tank or reservoir. Without limitation, the output of the transducer(s) may be focused and/or directed to a point and/or any area or location near and/or at the surface of the liquid in a reservoir to cause a surface disturbance, which results in the formation of an aerosol of the liquid in the reservoir. Without being limited, the aerosol can then be blown or otherwise moved with pressurized air/gas(s) out of the tank or reservoir(s), and into one or more targeted areas or chambers.

It was found that the geyser and accompanying aerosol plume that is ultrasonically generated in the tank(s) or reservoir(s) by a transducer (herein called "aerosol plume"), can be any suitable size, and can be adjusted to change in any effective size, shape, width, circumference, length, width, and/or height (Herein called "aerosol plume shape"), when the transducer is operated with one or more of any effective combination(s) of various range(s) of power and frequency, and even more so when operated within the most effective combination of ranges of power and frequency. It is preferred, without limitation, that the one or more transducers are at least operated with an effective combination of power and frequency. Without being limited, one major engineering problem presented was how to extract, remove, and deploy, as many of the "smaller" and/or effective aerosol droplets that are generated, as possible, especially, and without limitation, when encountering a geyser and aerosol plume that is near its maximum possible aerosol plume shape and aerosol plume density. The present invention is and improvement over the prior art by providing multiple enhancements to improve the production and extraction of the ultrasonically generated aerosol plume.

In one embodiment of the present invention, the extraction and removal of the aerosol generated above the surface of the liquid in the tank(s) or reservoir(s) is improved. In the first aspect of this embodiment, and without limitation, this is accomplished by providing at least one source of pressurized air/gas(s) or flow of air/gas(s) at one or more of any effective locations along the path of the evacuated, moving, evacuating, and/or extracted, aerosol, after it has left the tank and/or reservoir, where the ultrasonically created liquid surface disturbance(s) and/or aerosol is generated. It is preferred, without limitation, that this source of pressurized air/gas(s) or flow of air/gas(s) at one or more of any effective locations along the path of the evacuated, moving, evacuating, and/or extracted, aerosol, is in addition to any supply of pressurized air/gas(s) or flow of air/gas(s) that is supplied into the tank and/or reservoir, where the ultrasonically created liquid surface disturbance(s) and/or aerosol is generated.

Without limitation, and as another part of this first aspect of this embodiment, it is preferred, without limitation, that the one or more tank(s) and/or reservoir(s), where the one or more ultrasonically created liquid surface disturbance(s) is generated, and the at least one additional source(s) of pressurized air/gas(s) or flow of air/gas(s) located at one or more of any effective locations along the path of the evacuated, moving, evacuating, and/or extracted, aerosol, after it has left the tank(s) and/or reservoir(s), where the ultrasonically created liquid surface disturbance(s) is generated, are at least provided with any suitable source of pressurized air/gas(s) or flow of air/gas(s) that is, without limitation, common, separate, and/or independent, and more preferably, a shared source of pressurized air/gas(s) or flow of air/gas(s). Without limitation, the one or more source(s) of pressurized air/gas(s) or flow of air/gas(s) can be any suitable, air pump, fan, and/or blower. It is preferred, without limitation, that the air/gas that is supplied to the aerosol generating apparatus and/or one or more of any of its parts such as, but not limited to any of its, tank(s), reservoir(s), tube(s), conduit(s), pipe(s), chamber(s), and/or cavity(s), where the aerosol (a) can travel, (b) is created, or (c) can be present at any time, can be supplied at any effective velocity and/or volume measurement, preferably between at least 1-1000 cubic feet per minute, more preferably between about 50-700 cubic feet per minute, and even more preferably, between about 100-650 cubic feet per minute, and very preferably between about 350-500 cubic feet per minute. Without limitation, one or more, or even various, parts of the aerosol generating apparatus may be supplied with any air/gas that has identical, similar, and/or different, characteristics or attributes, preferably that are at least effective.

In a second aspect of this embodiment, and without limitation, the at least one ultrasonically generated aerosol plume(s) and/or geyser(s) is initially formed, and has its base, in at least one tank or reservoir, but is then able to rise and/or flow into at least one of any suitable, tube, conduit, pipe, chamber, and/or cavity, that either directly or indirectly expels the aerosol from the aerosol generating apparatus, and/or preferably directly or indirectly connects with one or more of any suitable and additional, sealed component, tube, conduit, and pipe, to provide at least an effective path to exhaust or expel the generated aerosol from the aerosol generating apparatus. The one or more of any suitable, tube, conduit, pipe, chamber, and/or cavity, can have any effective, design, construct, and/or attributes such as, but not limited to any, length, geometry, width, height, shape, diameter, and internal shape and/or geometry(s). It is preferred, without limitation, that at least one of any suitable tube, conduit, pipe, chamber, and/or cavity, is allocated to and located above, only one ultrasonically generated aerosol plume(s) and/or geyser(s).

Without limitation, and as another part of this second aspect of this embodiment, the at least one of any suitable, tube, conduit, pipe, chamber, and/or cavity, that either expels the aerosol from the aerosol generating apparatus, and/or preferably connects directly or indirectly with one or more of any additional sealed component, tube, conduit, and pipe, to provide an effective path to exhaust or expel the generated aerosol from the aerosol generating apparatus, is effectively positioned adjacent to, and preferably over and/or around, the at least one ultrasonically generated aerosol plume(s) and/or geyser(s), and its one or more of any effective orifice(s), is at least positioned at any effective height or distance over the surface of the liquid where the one or more ultrasonically created liquid surface disturbance(s) is generated.

Without limitation, and as still another part of this second aspect of this embodiment, and more specifically, at least an open end of the at least one of any suitable, tube, conduit, pipe, chamber, and/or cavity, and/or at least an effectively sized orifice of any suitable, pipe or conduit, that can also, without limitation, connect to any cavity(s) or chamber(s), at any effective location(s), can be effectively positioned around and/or over the one or more ultrasonically generated aerosol plume(s) and/or geyser(s), and one or more of any effective source of pressurized air may be located at one or more of any effective locations along the height or length of the ultrasonically generated aerosol plume(s) and/or geyser(s), preferably, and without limitation, outside of the tank and/or reservoir, where the ultrasonically created liquid surface disturbance is generated.

In a third aspect of this embodiment, and without limitation, the said at least one of any suitable, tube, conduit, pipe, and/or cavity, that directly or indirectly connects with the tank and/or reservoir, where the ultrasonically created liquid surface disturbance is generated, can have dimensions or at least can develop and change dimensions and/or is shaped or changes shape, so that a connected or disconnected chamber or cavity that is formed can have a greater volume and/or shape area than any pipe or conduit connecting to it. It is preferred, without limitation, that the said chamber or cavity is suitably sized to allow the geyser(s) and/or aerosol plume(s) that is ultrasonically generated, to enter and/or expand both laterally and/or in height. It is also preferred, without limitation, that the said expansion chamber, space, or area, and/or any other encompassing conduit or pipe, that the geyser(s) and/or aerosol plume(s) can enter and/or be present in, is at least suitably sized, and is of any suitable, length(s), geometry(s), width(s), height(s), diameter(s), and/or shape(s), to provide effective aerosol plume expansion in one or more of any dimensions and/or axis. The geyser(s) and/or aerosol plume(s) expansion space or area can be any effective size, height, width, length, shape, and/or geometry. It is further preferred, without limitation, that the said geyser(s) and/or aerosol plume(s) expansion space or area has at least a larger diameter or width when compared to any of its entry and/or exit orifice(s), and/or any other connecting tube(s), conduit(s), and pipe(s), used to supply and/or evacuate the aerosol from the said geyser and/or aerosol plume expansion space or area. It is even further preferred, without limitation, that at least one source of suitable pressurized air/gas(s) or flow of air/gas(s) is supplied to the said cavity or chamber, and/or tube(s), conduit(s), and pipe(s), at one or more of any suitable location(s). It is very preferred, without limitation, that the at least one source of any suitable pressurized air/gas(s) or flow of air/gas(s), is supplied at least approximately or even entirely around the periphery at one or more of any location(s) of the one or more aerosol plume(s) and/or geyser(s) within the at least one of any, tube, conduit, pipe, chamber, and/or cavity, at one or more of any effective locations.

In a fourth aspect of this embodiment, and without limitation, one or more of any air/gas(s) flow experiences a decrease in pressure and/or decrease in velocity, as it flows from the tank(s) and/or reservoir(s), where the ultrasonically created liquid surface disturbance is generated, into any expanded space or larger diameter cavity (when compared to pipe or conduit that feeds it) that is formed around the geyser(s) and/or aerosol plume(s) that is ultrasonically created.

In a fifth aspect of this embodiment, and without limitation, the flow of air/gas that is supplied to the tank(s) and/or reservoir(s), where the ultrasonically created liquid surface disturbance(s) is generated, can be balanced, proportioned, or put within any ratio or proportion, preferably at least any effective ratio or proportion, with any of one or more flow(s) of air/gas that is supplied to the one or more additional source(s) of pressurized air/gas(s) or flow of air/gas(s), such as, but not limited to any, exhaust supply hole(s), along the path of the evacuated, moving, evacuating, and/or extracted, aerosol, after it has left the tank and/or reservoir, where the ultrasonically created liquid surface disturbance is generated. These various flows of air/gas, including any air/gas that is supplied to any chamber where the aerosol is generated, can be adjusted for various attributes including, but not limited to any, air/gas velocity (ie: meters per second), air/gas volume (ie: cubic feet per minute), location(s), interior dimensions of any components the air/gas flows through, and volume and/or density of any aerosol that is created. Without being limited, it is preferred that these various sources and/or flows of any air/gas are adjusted for any effective aerosol output from the aerosol generating apparatus, and even more preferred for maximum aerosol output from the aerosol generating apparatus.

In a sixth aspect of this embodiment, and without limitation, the flow of any air/gas exiting the exhaust supply holes, and/or the air/gas pressure that is established within or at locations such as, but not limited to any, exhaust supply holes, and inner air chamber, is effective and/or is at least at an effective amount or level, where an effective amount of the aerosol that is produced, preferably all of the aerosol that is produced, is able to be evacuated and moved out of the aerosol generation apparatus, and more preferably that the generated aerosol is not able to flow back into locations such as, but not limited to any exhaust supply holes and any inner air chamber(s).

In another embodiment of the present invention, one or more interior surfaces within the tank(s) and/or reservoir(s), where the ultrasonically created liquid surface disturbance is generated, can be protected by one or more of any suitable metallic guards or barriers, where the metallic guards or barriers are effectively located between one or more transducer(s) and one or more of any tank and/or reservoir wall(s). Without limitation, the one or more of said metallic guards or barriers can provide various advantages such as, but not limited to, protecting the one or more surfaces inside of the tank(s) or reservoir(s) from the energy and/or pressure waves emitted by the transducers. It has been found that without the guards in place, wall damage can occur over time, especially when they are constructed from polymer. Any effective space can be maintained between the walls of the tank or reservoir and the metallic guards or barriers. In one part of this embodiment, and without limitation, at least the walls of the tank(s) or reservoir(s) are protected by one or more of these metallic guards or barriers.

Without limitation, the present invention can be further summarized as the following. The ultrasonic aerosol generation apparatus (aerosol generation apparatus) preferably includes at least one aerosol generation case, at least one case cover plate, at least one outlet pipe, at least one air/gas feed manifold, at least one ultrasonic transducers, at least one transducer power supply, and at least one microprocessor based controller. The aerosol generation case preferably includes at least one fluid reservoir, at least one transducer fluid supply chamber and/or fluid holding sump, and at least one transducer chamber. Preferably, the fluid reservoir is formed adjacent one side of the aerosol generation case and the transducer chamber is formed adjacent an opposing side of the aerosol generation case. The transducer fluid supply chamber is formed in the transducer chamber and below a bottom of the transducer chamber. A fluid passage is formed through a bottom of the fluid reservoir to substantially a bottom of the transducer fluid supply chamber. The case cover plate is attached to a top of the aerosol generation case.

Each outlet pipe preferably includes at least one outer base tube, at least one inner tube, and at least one exhaust tube. The outer base tube preferably includes at least one input base portion and at least one outlet base portion. The input and output base portions include a base tube portion, a conical tube portion and a body tube portion. The base tube portion extends from a smaller outer perimeter end of the conical input portion and the body tube portion extends from an opposing end of the conical tube portion. A bottom of the inner tube is concentrically located effectively close to and/or near to an inside surface of the conical tube portion of the input base portion. The body tube portions of the input and output base portions are attached to each other with adhesive, sonic welding or any other suitable process. The exhaust tube is directly secured and/or indirectly connected to an output of the base portion of the outlet base portion. At least one aerosol hole is formed through a top of the case cover plate over a center of each transducer. The base tube portion of the input base portion is attached to the case cover plate, concentric with the aerosol hole.

The air feed manifold can include, without limitation, at least one of any, suitable pipe(s), tubing, or conduit(s), that can supply at least any effective amount, flow rate, flow velocity, and/or volume, of any air/gas and/or air gas supply, to one or more of any locations and/or parts of the aerosol generator apparatus such as, but not limited to any, inlet manifold, supply manifold, inlet tube, transducer chamber supply tube, plate hole, transducer chamber, exhaust supply hole tube, exhaust supply hole, and inner air chamber.

It is preferred, without limitation, that at least one inlet tube is able to supply pressurized air/gas and/or an effective flow of air/gas to the one or more of any exhaust supply hole(s) effectively located in the one or more outlet pipe(s).

It is also preferred, without limitation, that at least one inlet tube (63) is able to supply pressurized air/gas and/or an effective flow of air/gas to the one or more of any plate holes effectively connected to the one or more transducer chamber(s).

It is more preferred, without limitation, that at least one inlet tube suitably connects either directly or indirectly to both the at least one chamber tube end, transducer chamber supply tube, and the at least one exhaust supply tube, and exhaust hole supply tube, and the air flow from the at least one vertical air connector tube(s) splits and is able to connect with the one or more exhaust supply hole(s) that are effectively located in each of the at least two outlet pipes that connect to a shared transducer chamber.

Without limitation, various parts and components such as, but not limited to the at least one, air feed manifold, inlet manifold, transducer chamber supply tube, and supply manifold, can extend from a distal end of the inlet tube. At least one plate hole is formed through a top of the case cover plate over substantially a center of a transducer fluid supply chamber. The chamber tube end and/or a distal end of a transducer chamber supply tube, is concentrically secured over the at least one plate hole. At least one exhaust supply hole is formed through at least one of the body tube portions of the at least one input and outlet base portions. A distal end of one or more of any, exhaust supply tube(s), exhaust hole supply tube, and/or supply tube end, is concentrically secured over the one or more exhaust supply hole(s). At least one vent hole is formed through the case cover plate over the fluid reservoir. A vent tube is secured to the vent hole with a hose nipple or the like. It is preferred, without limitation, that the vent tube is directly or indirectly vented to the atmosphere surrounding the outside of the aerosol generating machine. One or more transducer counter bore(s) is preferably formed in a bottom of each transducer chamber to receive one or more of any effective transducer, transducer housing, transducer assembly, and/or sealed transducer assembly or housing. Each transducer, transducer housing, transducer assembly, and/or sealed transducer assembly or housing is effectively secured, and/or sealed to, and/or sealed in, and/or sealed around, the transducer counterbore(s). A suitable source of electrical power is connected to each transducer. A distal end of the inlet tube is connected to one or more of any source of any effective air flow or pressurized air, such as, but not limited to any, air pump, fan, and/or blower.

Without limitation, one or more liquid level sensor hole(s) is formed through the case cover plate, preferably over the fluid reservoir. At least one liquid level sensor is suitably attached to a top of the case cover plate over the one or more liquid level sensor hole(s) to determine one or more of any liquid level(s) in the fluid reservoir and/or the chamber in which the aerosol is generated and/or the transducer(s) are located.

Without being limited, the liquid level sensor(s) includes at least one, but preferably at least two or more, stainless steel pins that are mounted to an insulating material and protrude into the fluid within the chamber. It is preferred, without limitation, that the longest pin is preferably used as the reference pin. It is also preferred, without limitation, that the reference pin contacts the fluid first as the chamber is filled with liquid. Without limitation, the "sensor pins" and/or "reference pins" can be machined to a point, and at specific lengths as desired to sense various levels of fluid in the chamber and/or the connecting transducer chamber. Without being limited, it is preferred that the various pins are mounted in a non-conductive material to avoid any unintentional current flow between them.

Without limitation, a suitable voltage can be applied between the reference rod and the sensor pin(s) through a voltage divider network. When the fluid reaches the sensor pin(s), it can conduct a small amount of current from the sensor pin(s) to the reference pin. This current causes the voltage to drop in the voltage divider which is then sensed by a highly sensitive comparator circuit whose output is then switched to indicate the conduction of current on that particular sensor pin. As soon as the fluid is no longer contacting the sensor rod, the current stops, causing the comparator output to switch back to the non-conduction state. The comparator output is then used by the microcontroller to make appropriate decisions regarding the liquid levels as required.

A tube nipple is threaded through any wall or cover, preferably the side wall of the fluid reservoir. One end of a fill tube is secured to the tube nipple and a distal end of the fill tube is attached to an output of any suitable liquid valve and an input of the liquid valve is attached to any suitable source of liquid that is to be fed into the transducer chamber. At least one heater element is threaded through a side wall of the transducer fluid supply chamber, preferably near a bottom thereof. At least one supply chamber thermocouple or at least any suitable temperature sensing device, is threaded through a side wall of the transducer fluid supply chamber, in one or more of any effective location(s). Without limitation, at least one transducer thermocouple can also be threaded through a side wall of the transducer chamber in one or more of any effective location(s).

Without being limited, at least one microprocessor based controller is preferably used to monitor and/or power various components, including, but not limited to, the components described in the following description. At least one fluid reservoir is filled with liquid through at least one liquid valve. The liquid is preferably gravity fed to the liquid valve. The liquid is heated by the heater element to a temperature at least above 80° F., preferably between 90° F.-150° F., and more preferable between about 110° degree F.-130° degree F. The temperature of the liquid is measured with the supply chamber thermocouple and/or the transducer thermocouple. The at least one transducer is powered by the transducer power supply. An aerosol is generated by ultrasonic vibration of the piezoelectric transducer. Any suitable air/gas can be blown, pumped, and/or flowed, into locations such as, but not limited to any, transducer chamber, and/or any inner air chamber formed between the outer base tube and the inner tube.

Accordingly, it is an object of the present invention to provide an aerosol generation apparatus, which is able to generate greater volumes of disinfecting aerosol than that of the prior art. It is also another object of the present invention to provide an aerosol generation apparatus, which is contained in a smaller package than that of the prior art.

It is a further object of the present invention to provide an aerosol generation apparatus, which extracts a greater number of aerosol droplets, more preferably and without limitation, sub-micron aerosol droplets, from an ultrasonically produced disinfectant plume without the droplets coalescing.

These and additional objects, advantages, features and benefits of the present invention will become apparent from the following specification. Furthermore, numerous other features, aspects and advantages of the present invention will be made apparent from the following detailed description taken together with the drawing figures.

BRIEF DESCRIPTION OF THE DRAWINGS

The methods and devices for the present invention, is best understood with reference to the following detailed description of the invention and the drawings in which:

FIG. 106-B is an optimized and miniaturized aerosol generator, showing more fully showing an air outlet pipes located within an air inlet pipe according to the present invention;

FIG. 117-B is a schematic view of an optimized and miniaturized aerosol generator connected to a shared fan and blower according to the present invention.

FIG. 118 is an exploded perspective view of an aerosol compartment and a liquid level sensor compartment created by a removable barrier of an optimized and miniaturized aerosol generator according to the present invention.

FIG. 119 is a schematic side view of an aerosol deposit sensor positioned in an area targeted for aerosol deposition and/or deployment, showing the deposited aerosol droplets located on an insulator material as well as between, and effectively connecting, various conductors of an aerosol deposit sensor, according to the present invention.

FIG. 120 is a schematic side view of an aerosol deposit sensor positioned in an area targeted for aerosol deposition and/or deployment, showing a liquid film that is formed by the deposited of aerosol droplets on an insulator material as well as between, and effectively connecting, various conductors of an aerosol deposit sensor, according to the present invention.

FIG. 121 is a schematic side view of an aerosol deposit sensor positioned in an area targeted for aerosol deposition and/or deployment, showing various contact surface(s) and insulator material(s), that are located between the various conductors of an aerosol deposit sensor, according to the present invention.

FIG. 122 is a schematic view of an aerosol deposit sensor, showing an insulator material, conductors, wires, and various channels, where the various channels connect with one another of an aerosol deposit sensor, according to the present invention.

FIG. 123 is a schematic view of an aerosol deposit sensor, showing insulator material(s), conductors, wires, and various channels, where the various channels connect with one another, and one or more circuit paths may be established with the various conductors and wires utilized of an aerosol deposit sensor, according to the present invention.

FIG. 124 is a schematic view of an aerosol deposit sensor, showing insulator material(s), conductors, and wires, and one or more circuit paths established with the various conductors and the wires utilized of an aerosol deposit sensor, according to the present invention.

FIG. 125 is a schematic view of an aerosol deposit sensor, showing insulator material(s), conductors, wires, and a conductivity sensor of an aerosol deposit sensor, according to the present invention.

FIG. 126 is a schematic view of an aerosol deposit sensor, showing insulator material(s), conductors, and wires, where at least one circuit path may be established with the various conductors and wires utilized, and the various wires suitably connect with a remote PLC of an aerosol deposit sensor, according to the present invention.

FIG. 127 is a schematic view of an aerosol deposit sensor, showing insulator material(s), conductive path(s), conductors, wires, an amplifier, and conductivity sensor(s) of an aerosol deposit sensor, according to the present invention.

FIG. 128 is a schematic view of an aerosol deposit sensor, showing insulator material(s), conductive paths, conductors, and wires and the various wires are connected to a remote PLC of an aerosol deposit sensor, according to the present invention.

FIG. 129 is a schematic top view of an aerosol deposit sensor, showing insulator material(s), and at least two conductors opposed to one another of an aerosol deposit sensor, according to the present invention.

Figure 130:
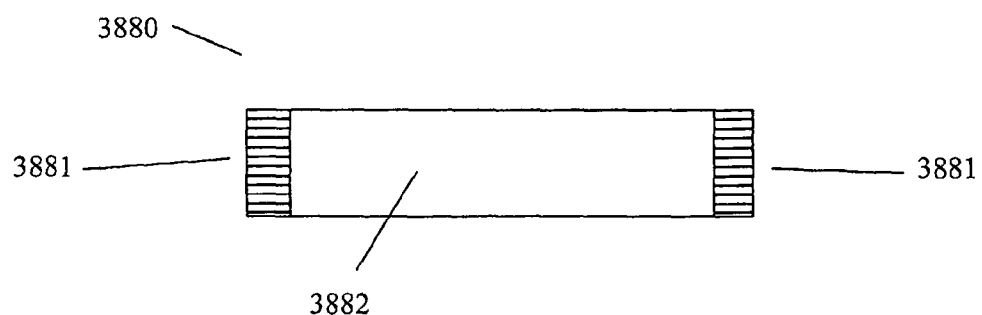

FIG. 130 is a schematic top view of an aerosol deposit sensor, showing the insulator material(s), and at least two conductors that are opposed to one another in a parallel configuration of an aerosol deposit sensor, according to the present invention.

Figure 131:
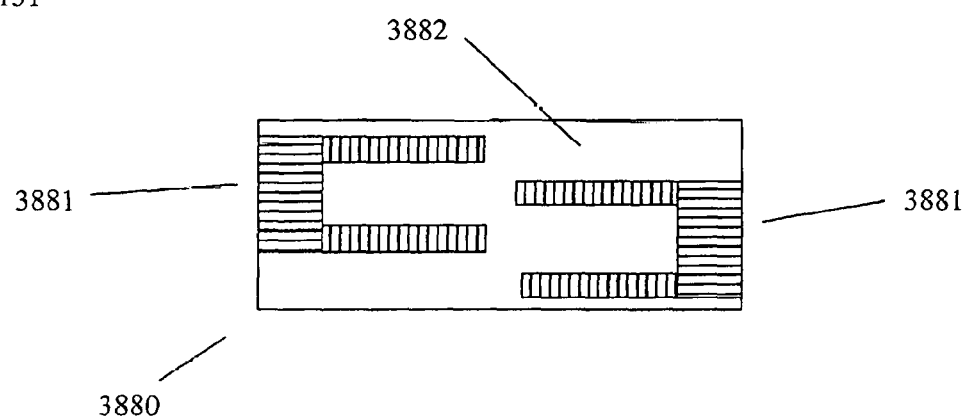

FIG. 131 is a schematic top view of an aerosol deposit sensor, showing insulator material(s), and at least two conductors that are opposed to one another, each including complex geometries and offset positioning of an aerosol deposit sensor, according to the present invention.

Figure 132:
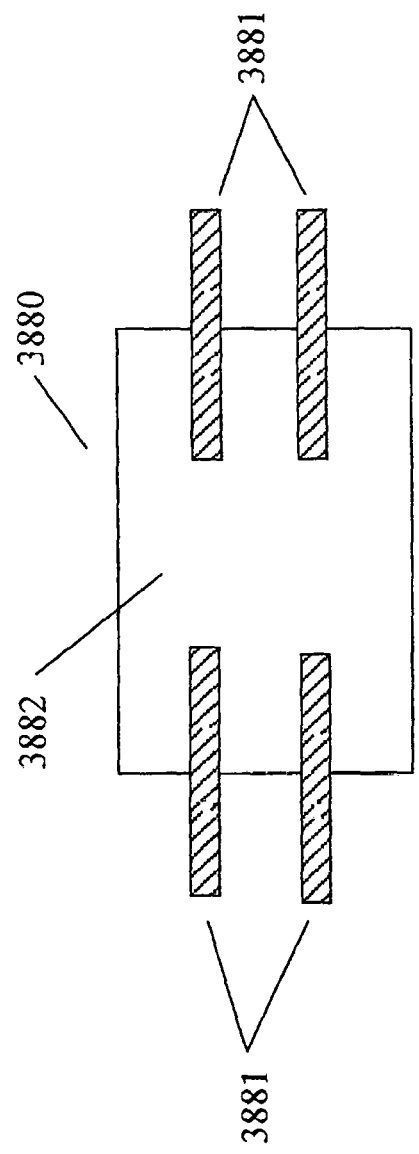

FIG. 132 is a schematic top view of an aerosol deposit sensor, showing insulator material(s), and at least four conductors that are opposed to one another of an aerosol deposit sensor, according to the present invention.

Figure 133:
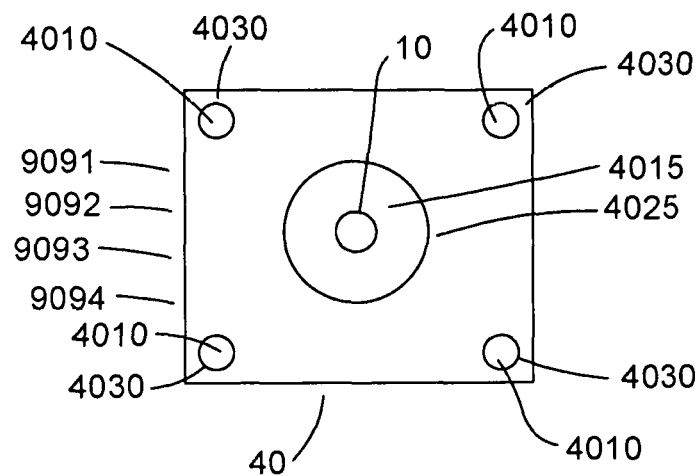

FIG. 133 is a schematic top view of a reservoir including a transducer, where an air outlet pipe is centered above thereof and one or more airflow inlets is located around the transducer, according to the present invention.

Figure 134:
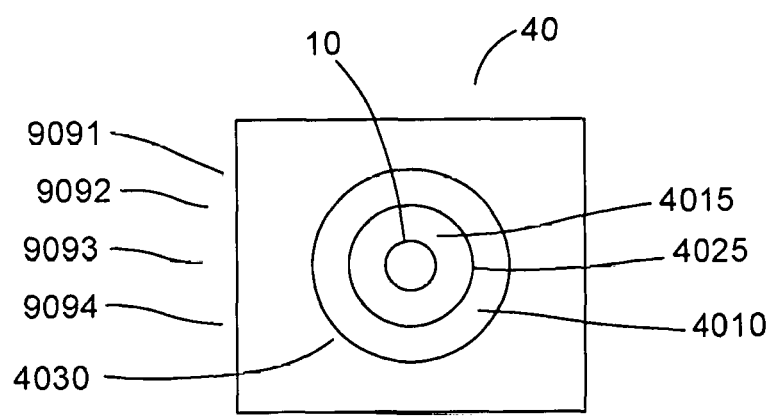

FIG. 134 is a schematic top view of a reservoir including a transducer, where an air outlet pipe and airflow inlet are centered around the transducer, according to the present invention.

Figure 135:
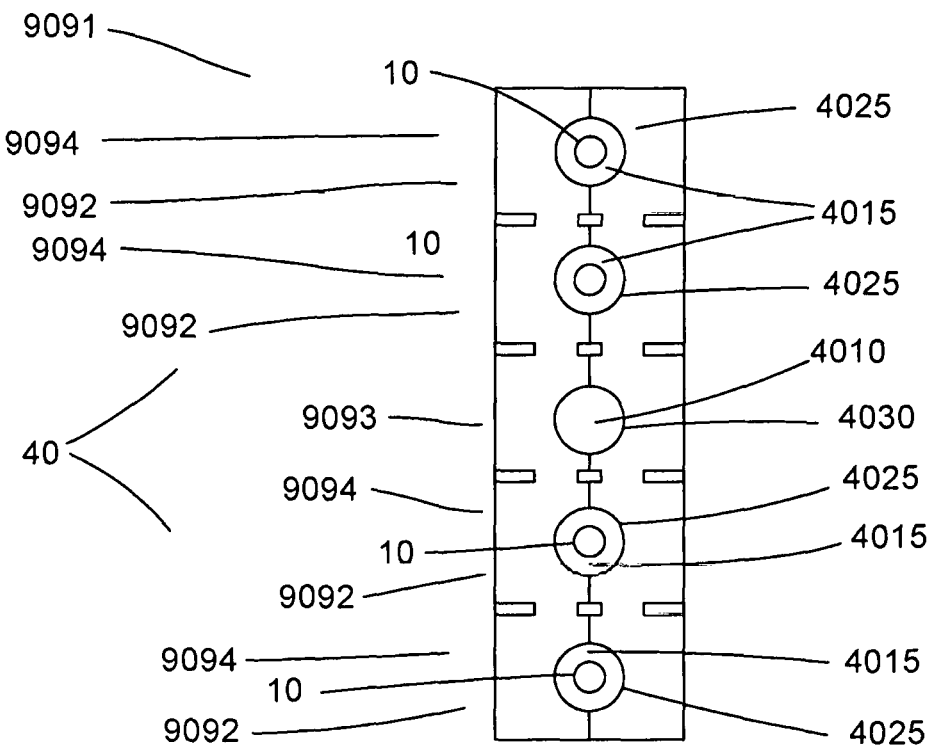

FIG. 135 is a schematic top view of a reservoir including five reservoir building segments, where all of the reservoir building segments include a transducer and at least one airflow outlet, except the center most reservoir building segment, and the center most reservoir building segment includes at least one airflow inlet, according to the present invention.

Figure 136:
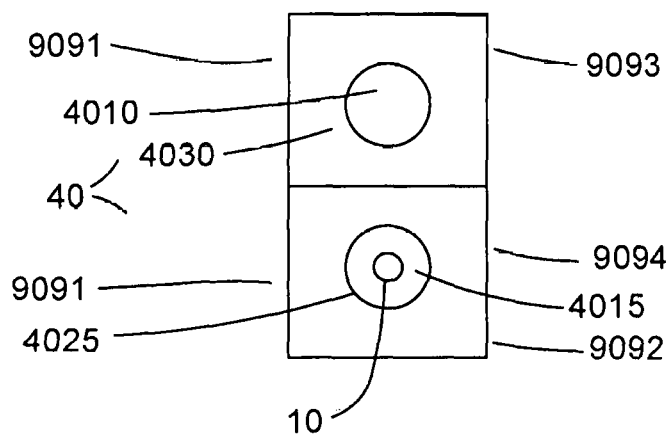

FIG. 136 is a schematic top view of a reservoir including two reservoir building segments, where the first reservoir building segment includes a transducer and at least one airflow outlet and a second reservoir building segment includes at least one airflow inlet, according to the present invention.

Figure 137:
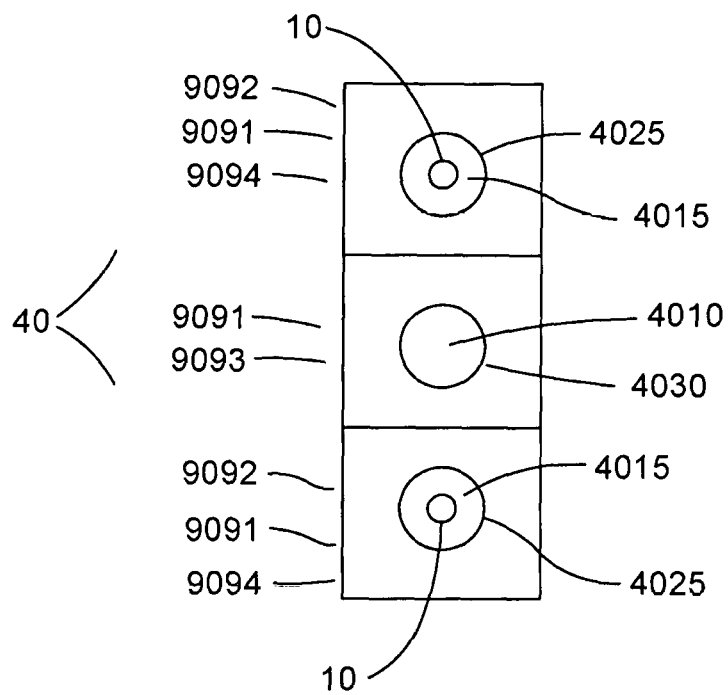

FIG. 137 is a schematic top view of a reservoir including three reservoir building segments, where all of the reservoir building segments include a transducer and at least one airflow outlet, except the center reservoir building segment, and the center reservoir building segment includes at least one airflow inlet, according to the present invention.

Figure 138:
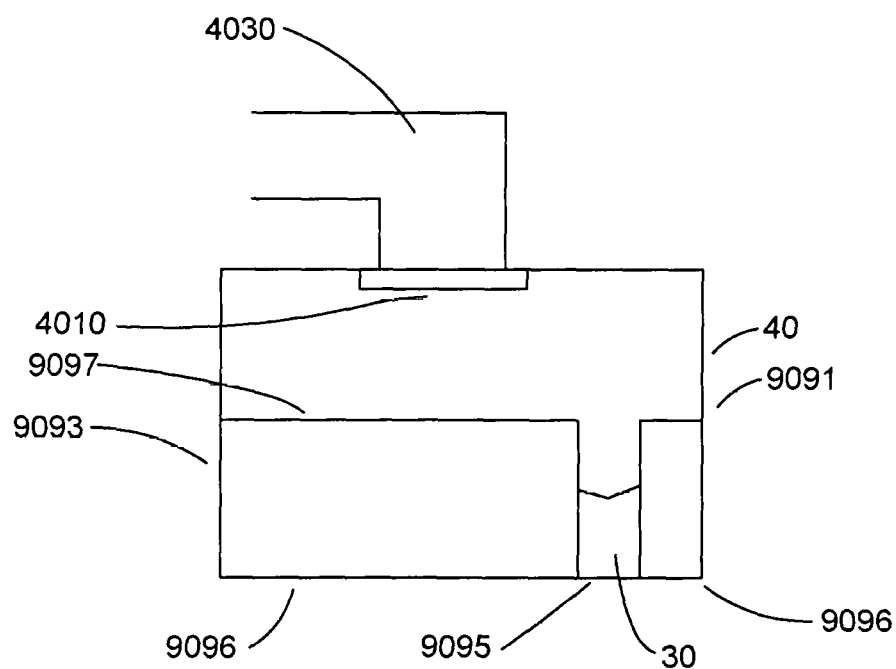

FIG. 138 is a schematic side view of a reservoir including the side view of a reservoir building segment, where the reservoir building segment includes at least one reservoir shelf centered under the airflow inlet, according to the present invention.

Figure 139:
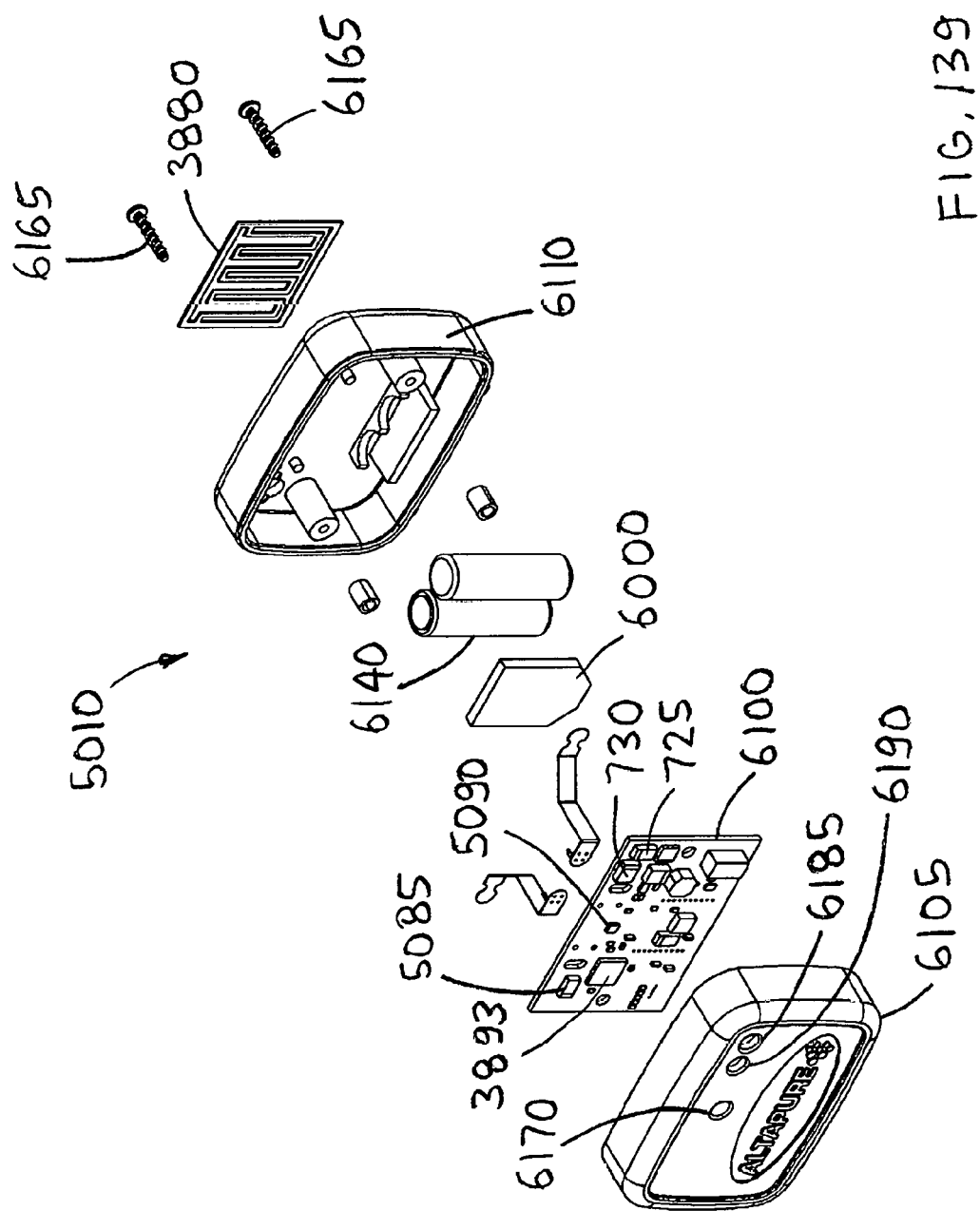

FIG. 139 is an exploded perspective view of a remote aerosol sensor, according to the present invention.

Figure 140:
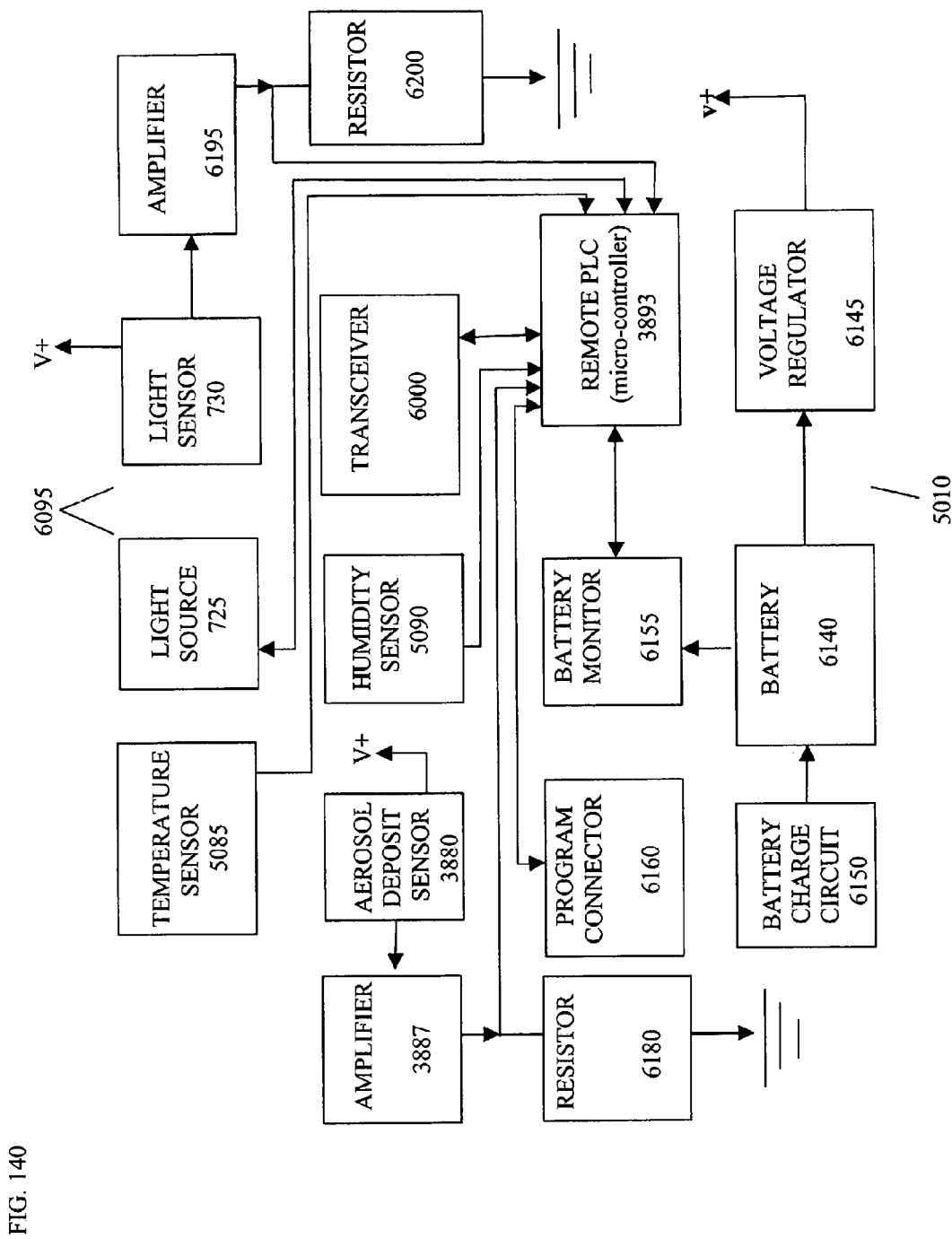

FIG. 140 is a schematic diagram of a remote aerosol sensor including voltage amplifiers, according to the present invention.

Figure 141:
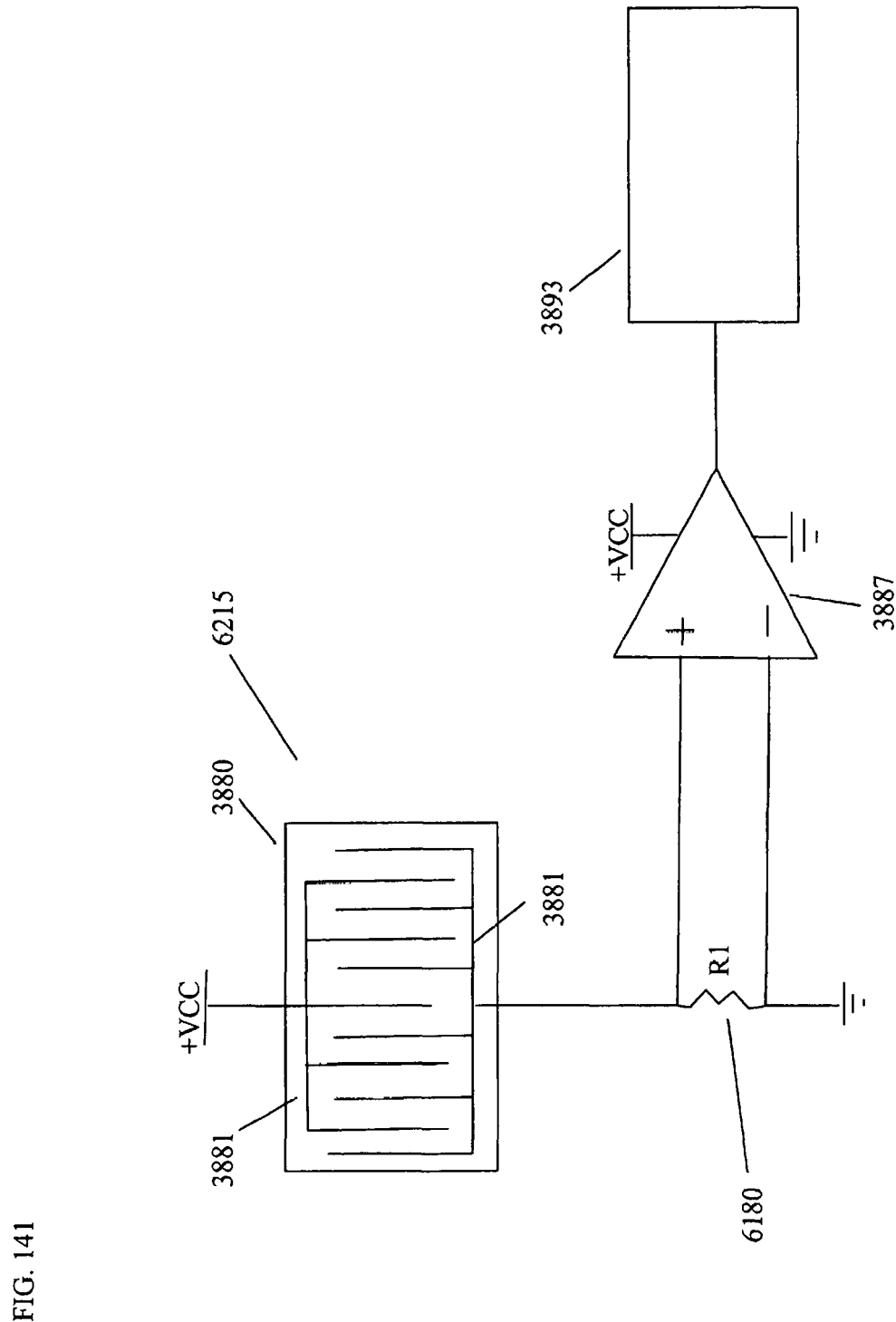

FIG. 141 is a schematic diagram of an amplifier circuit for a remote aerosol sensor, according to the present invention.

Figure 142:
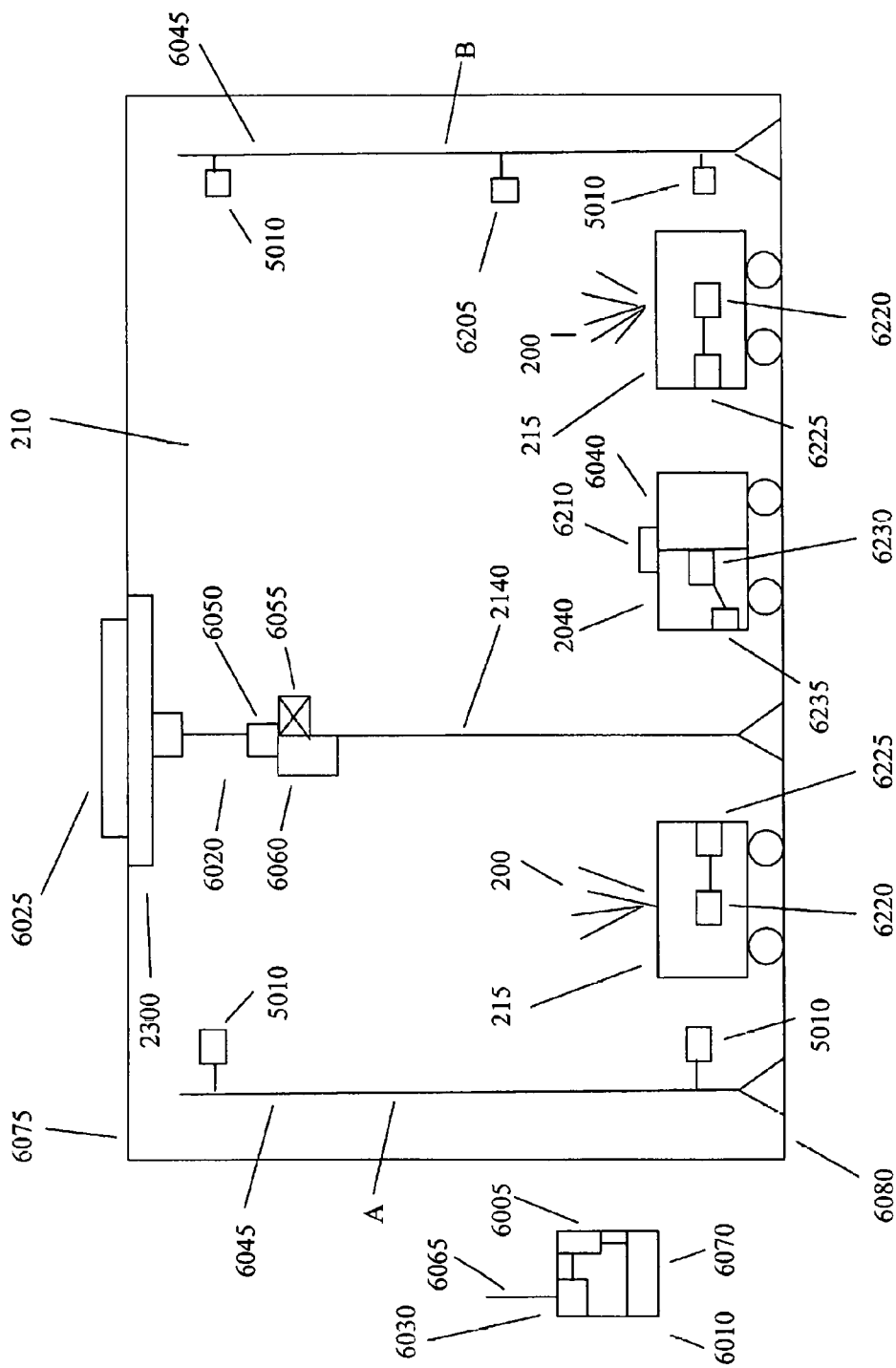

FIG. 142 is a schematic diagram showing a plurality of remote aerosol sensors and other components in an enclosed space and a remote control device outside the enclosed space, according to the present invention.

Figure 143:
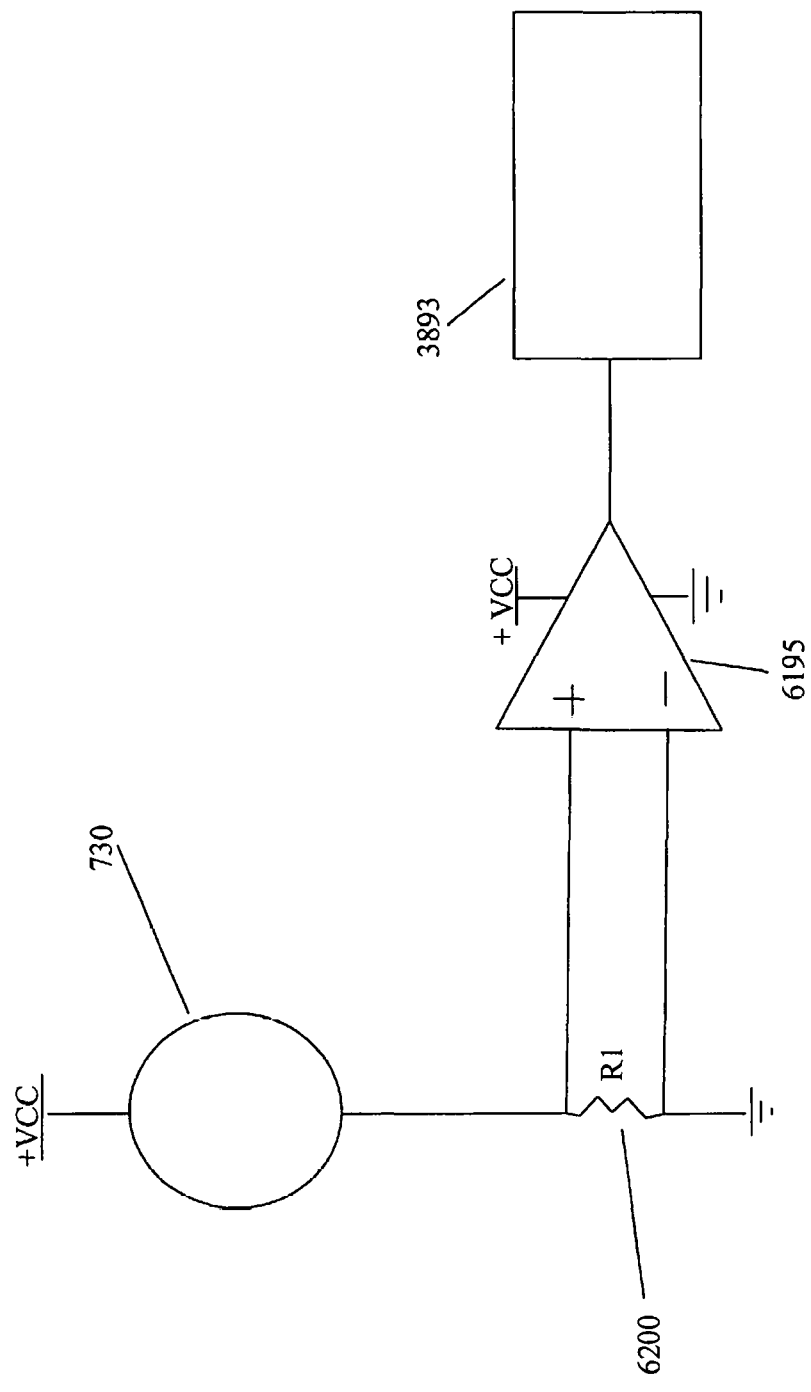

FIG. 143 is a schematic diagram of an amplifier circuit for a light sensor, according to the present invention.

Figure 144:
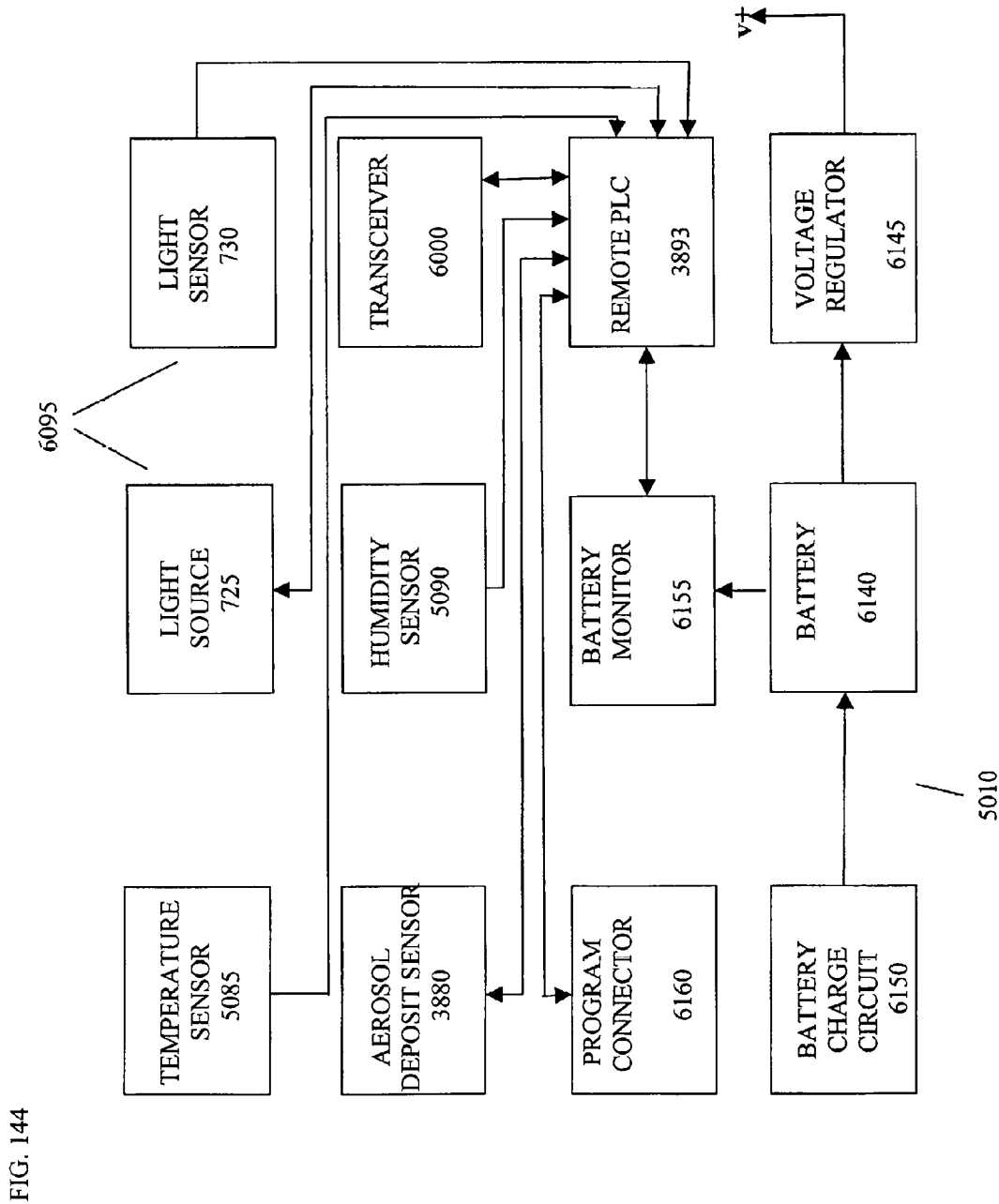

FIG. 144 is a schematic diagram of a remote aerosol sensor, according to the present invention.

Figure 145:
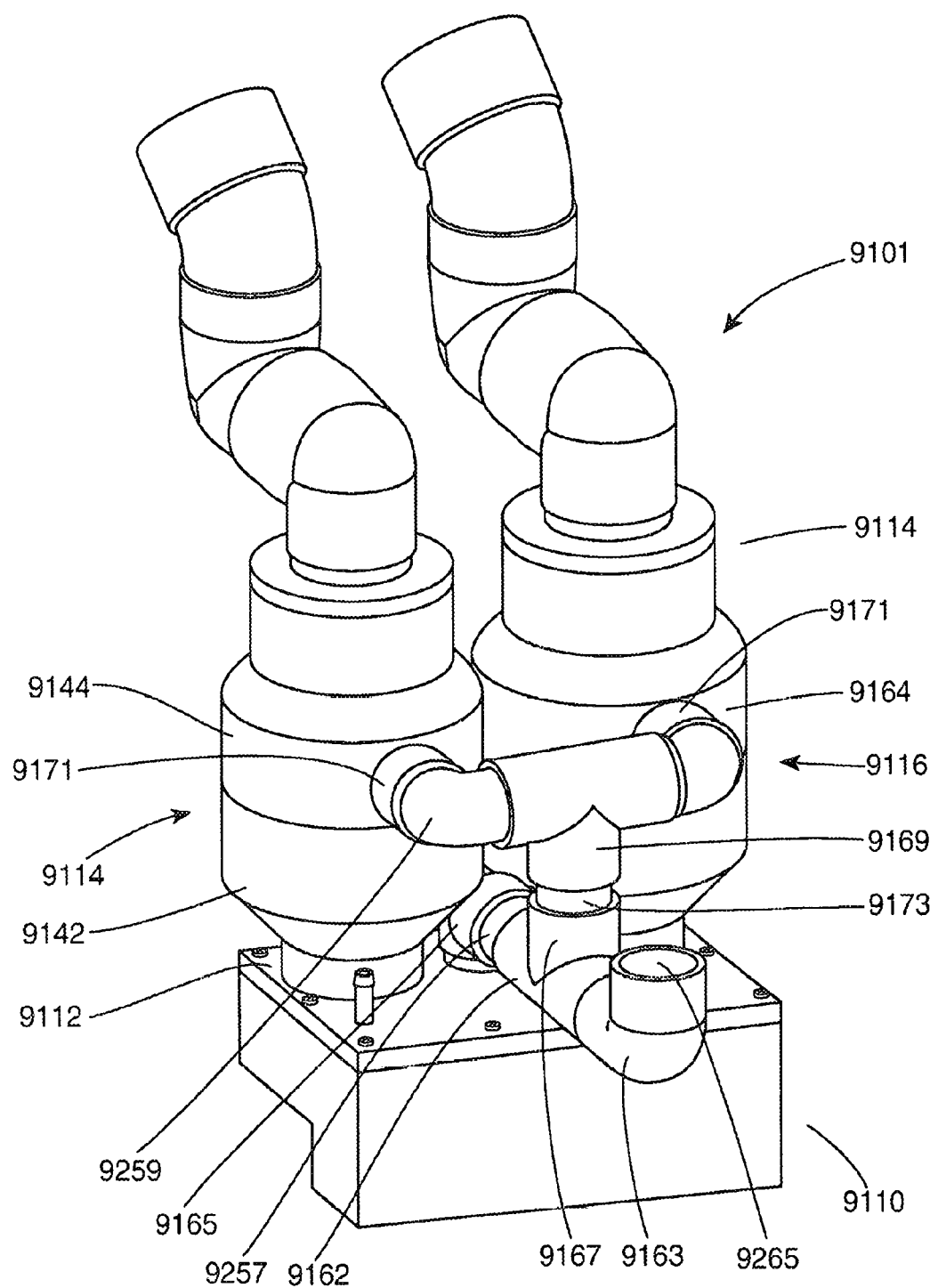

FIG. 145 is a perspective view of an aerosol generation apparatus in accordance with the present invention.

Figure 146:
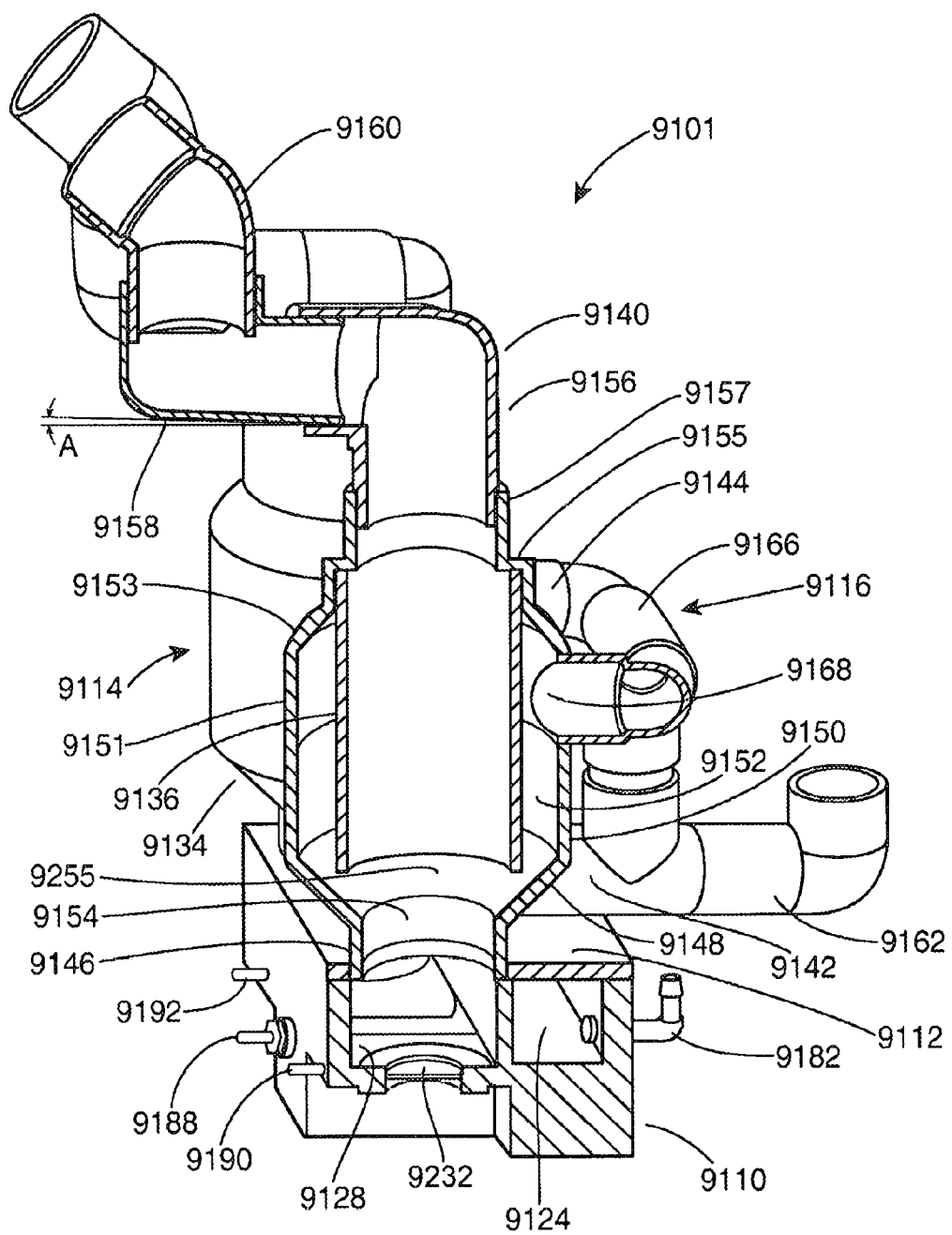

FIG. 146 is a perspective cross sectional view cut through one of the transducer chamber of an aerosol generation apparatus in accordance with the present invention.

Figure 147:
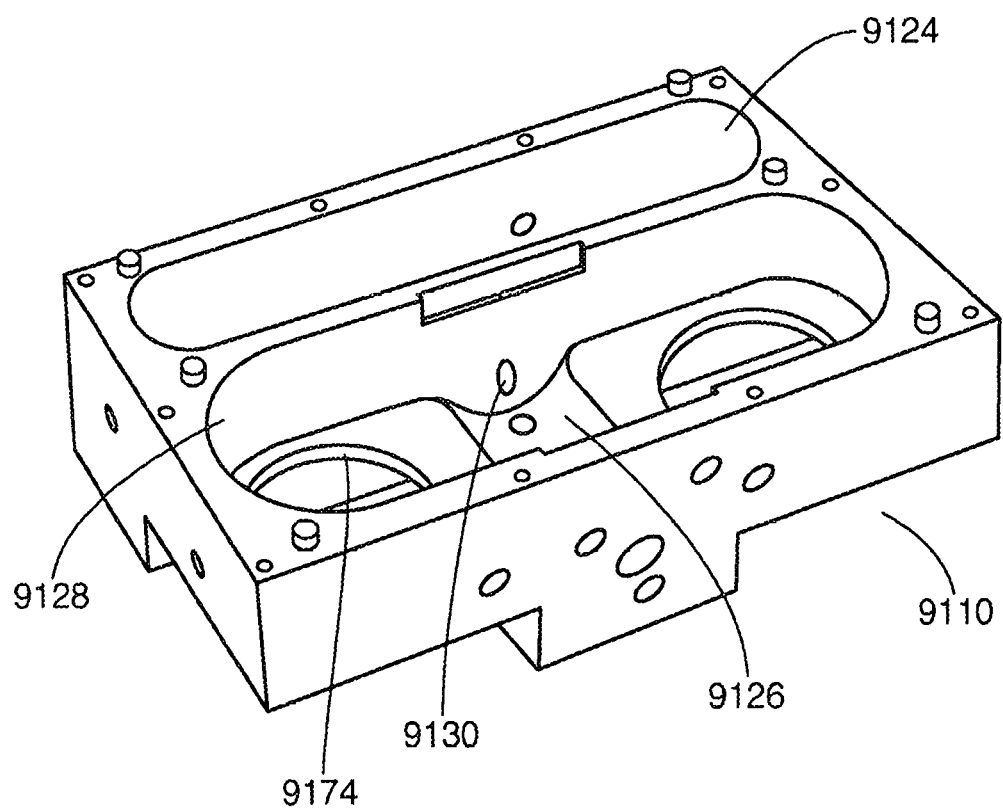

FIG. 147 is a perspective top view of an aerosol generation case of an aerosol generation apparatus in accordance with the present invention.

Figure 148:
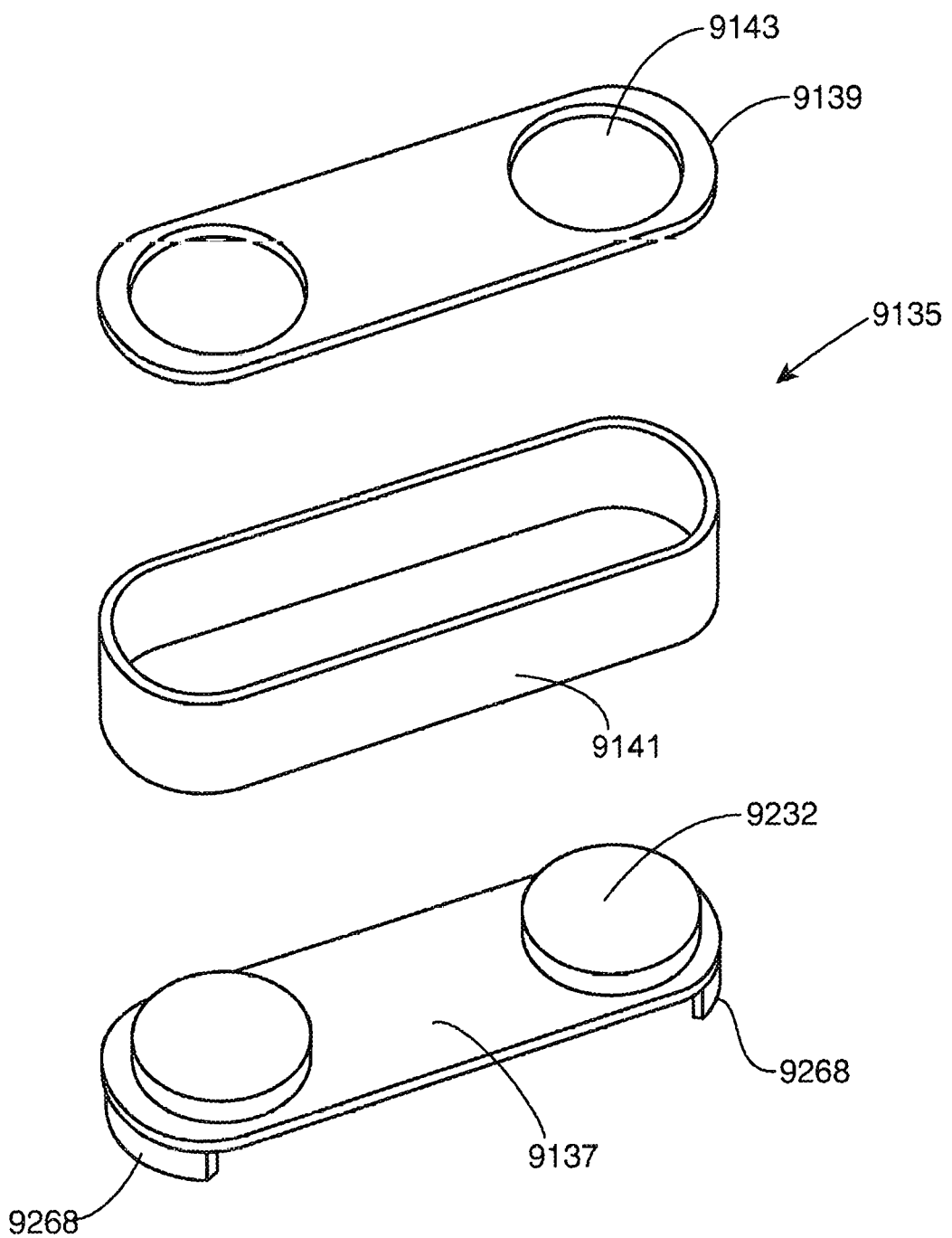

FIG. 148 is a partially exploded perspective view of a transducer chamber shield for protecting an aerosol generation case from damage due to acoustic energy generated two transducers contained in the transducer chamber in accordance with the present invention.

Figure 149:
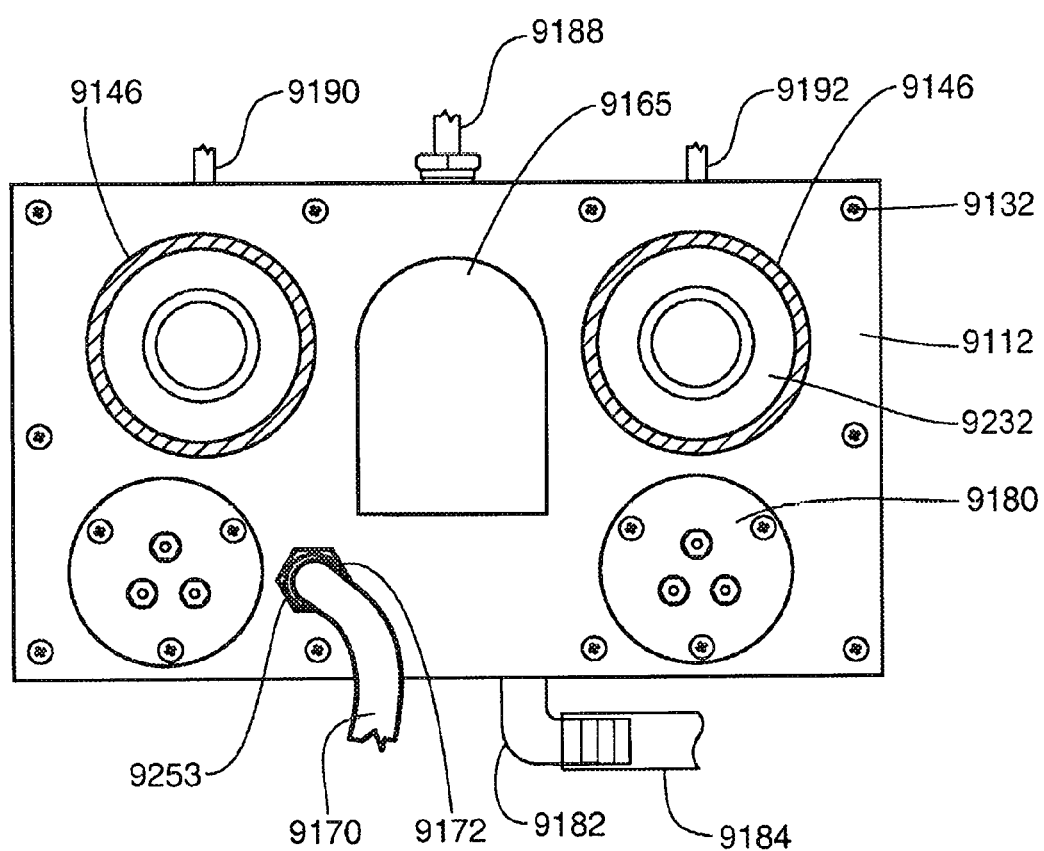

FIG. 149 is a top view of an aerosol generation case with case cover plate attached to a top thereof and with two outlet pipes cut-off at a bottom thereof of an ultrasonic aerosol generation apparatus in accordance with the present invention.

Figure 150:
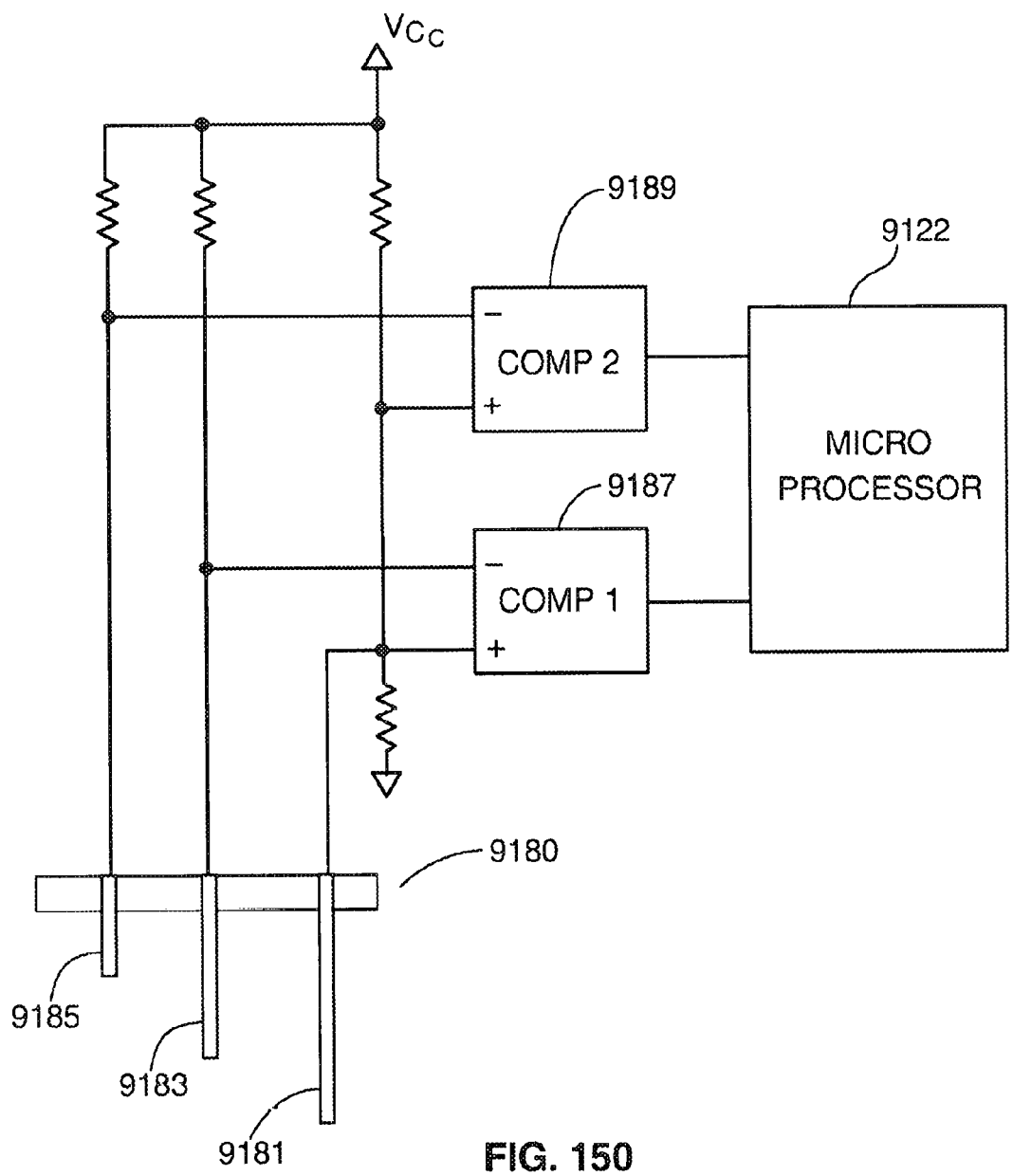

FIG. 150 is an electrical schematic of a liquid level sensor of an aerosol generation case in accordance with the present invention.

Figure 151:
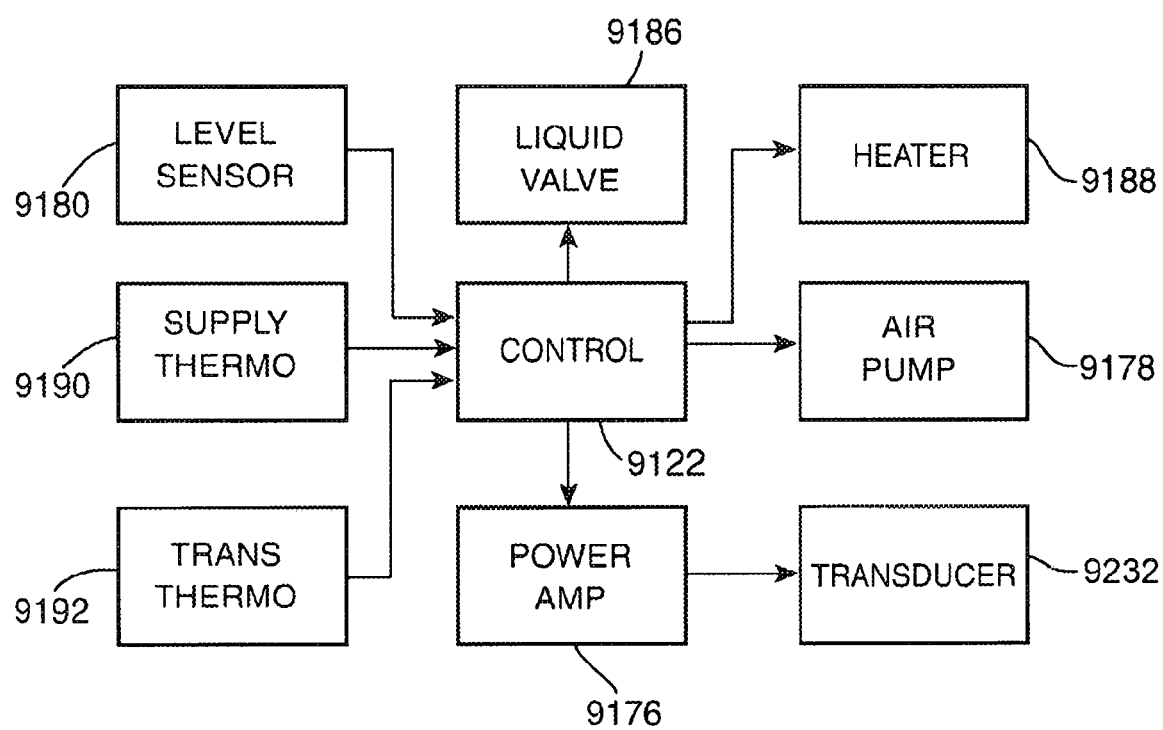

FIG. 151 is a schematic diagram of an aerosol generation apparatus in accordance with the present invention.

Figure 152:
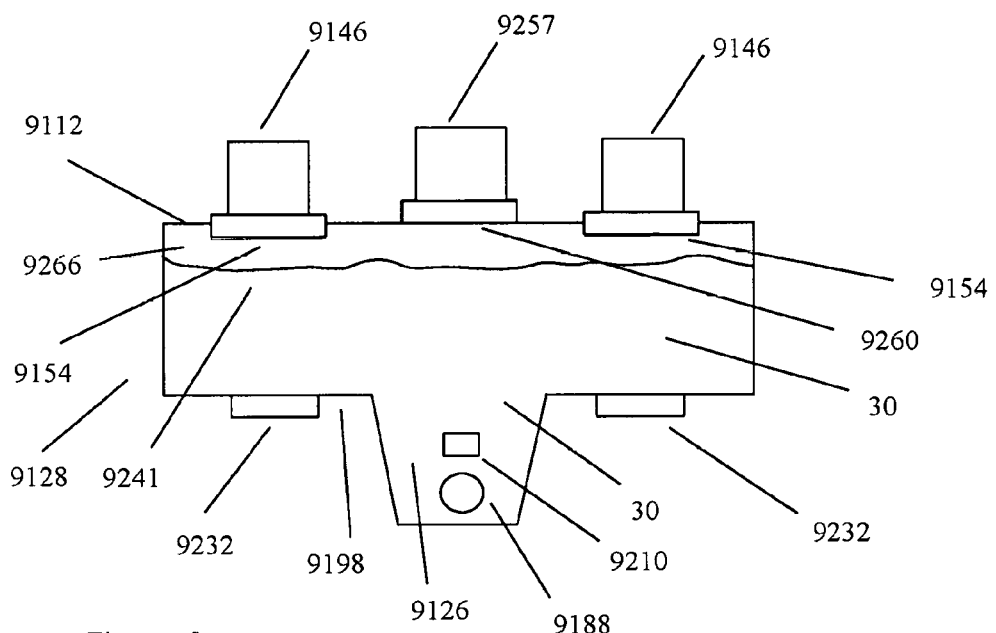

FIG. 152 is a front cross sectional view of a transducer chamber of an aerosol generation apparatus in accordance with the present invention.

Figure 153:
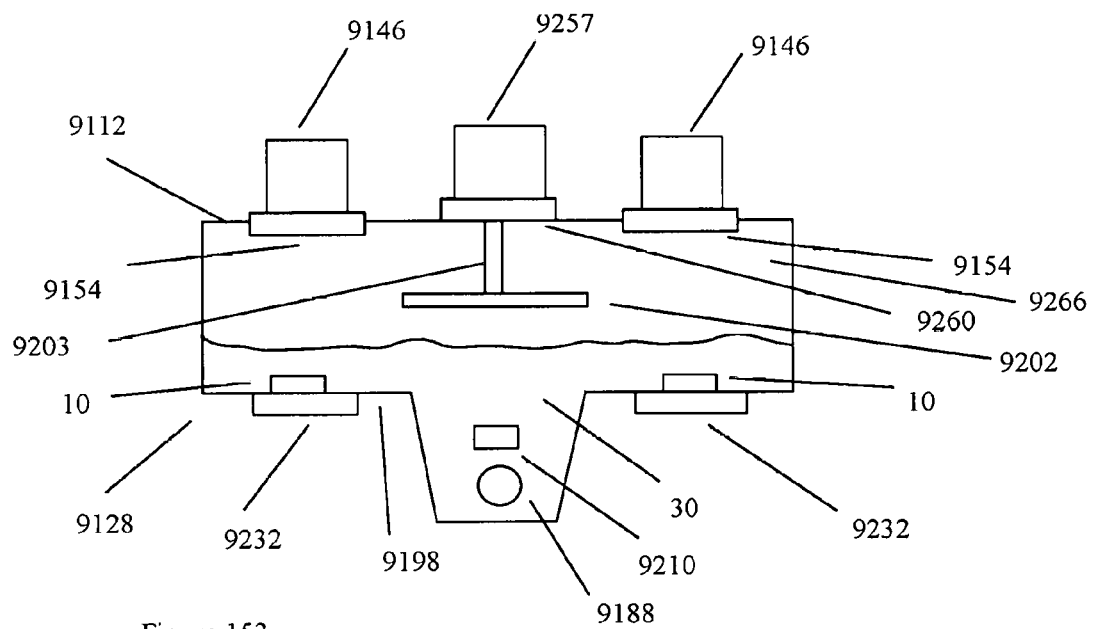

FIG. 153 is a front cross sectional view of a transducer chamber with a deflector bracket of an aerosol generation apparatus in accordance with the present invention.

Figure 154:
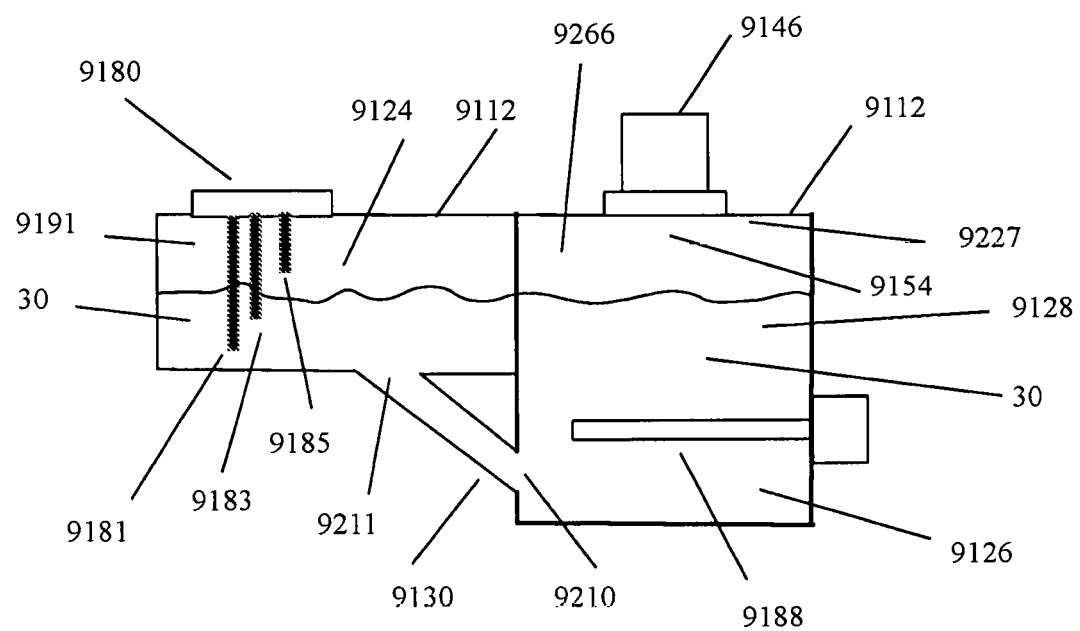

FIG. 154 is a side cross sectional view of a transducer chamber with a liquid level sensor of an aerosol generation apparatus in accordance with the present invention.

Figure 155:
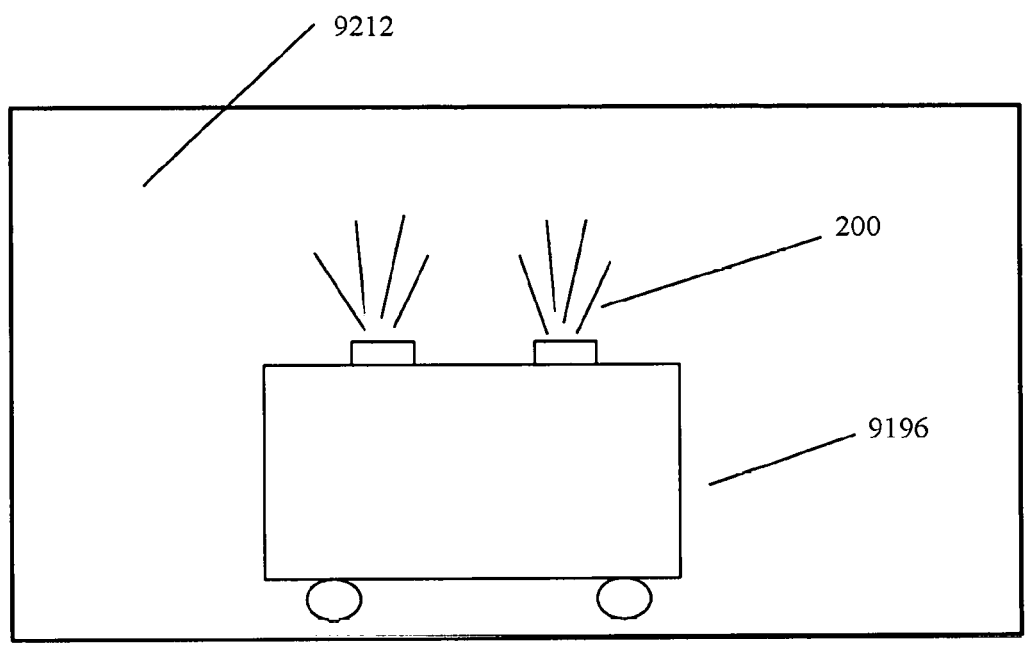

FIG. 155 is a schematic diagram of an aerosol generation apparatus inside an enclosure in accordance with the present invention.

Figure 156:
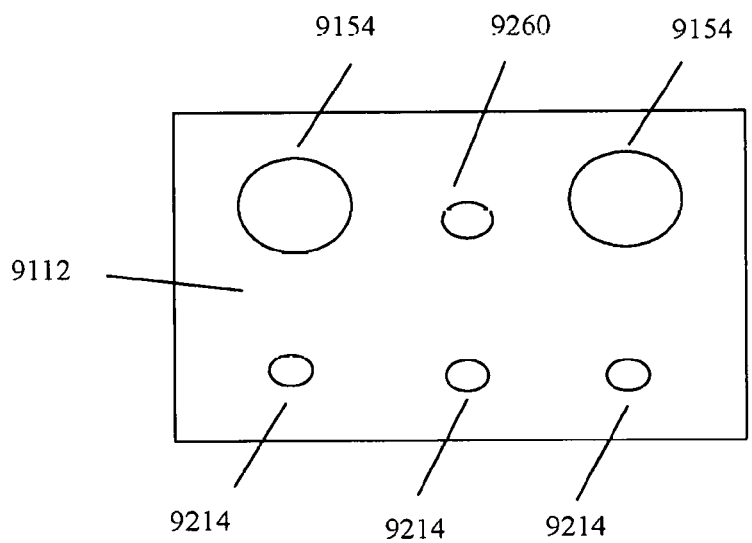

FIG. 156 is a top view of a case cover plate of an aerosol generation apparatus in accordance with the present invention.

Figure 157:
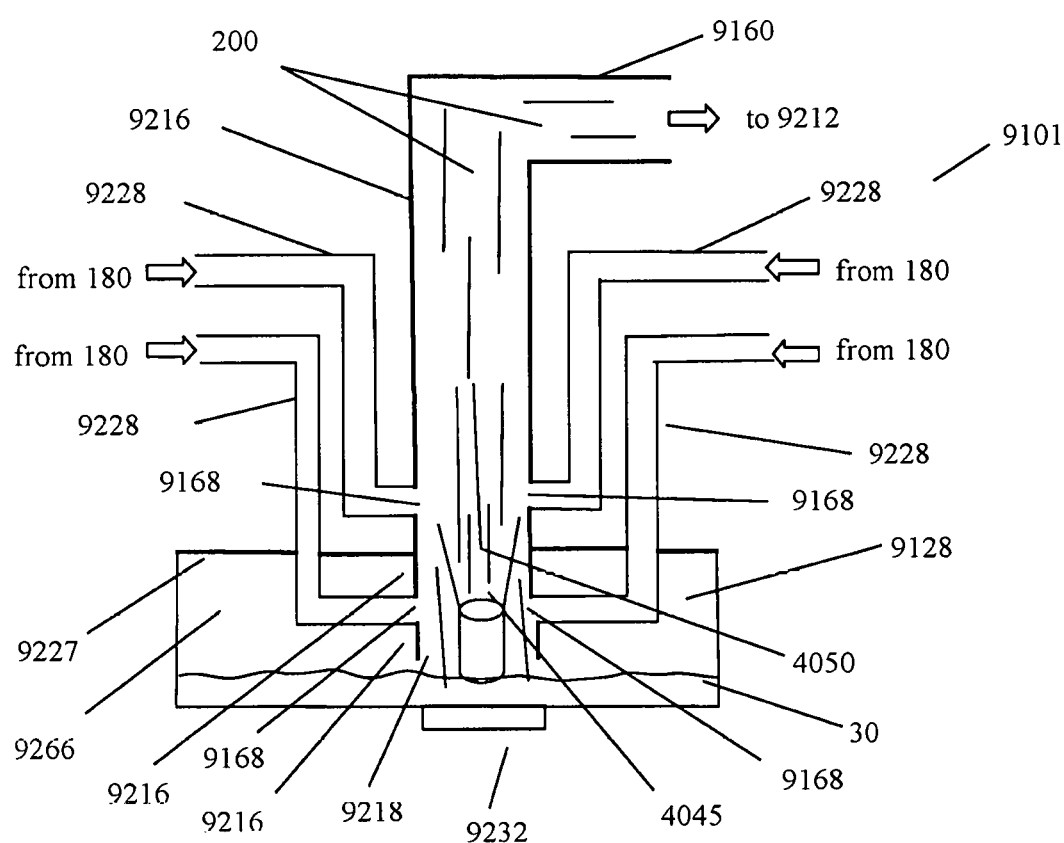

FIG. 157 is a cross sectional schematic diagram an aerosol generation apparatus in accordance with the present invention.

Figure 158:
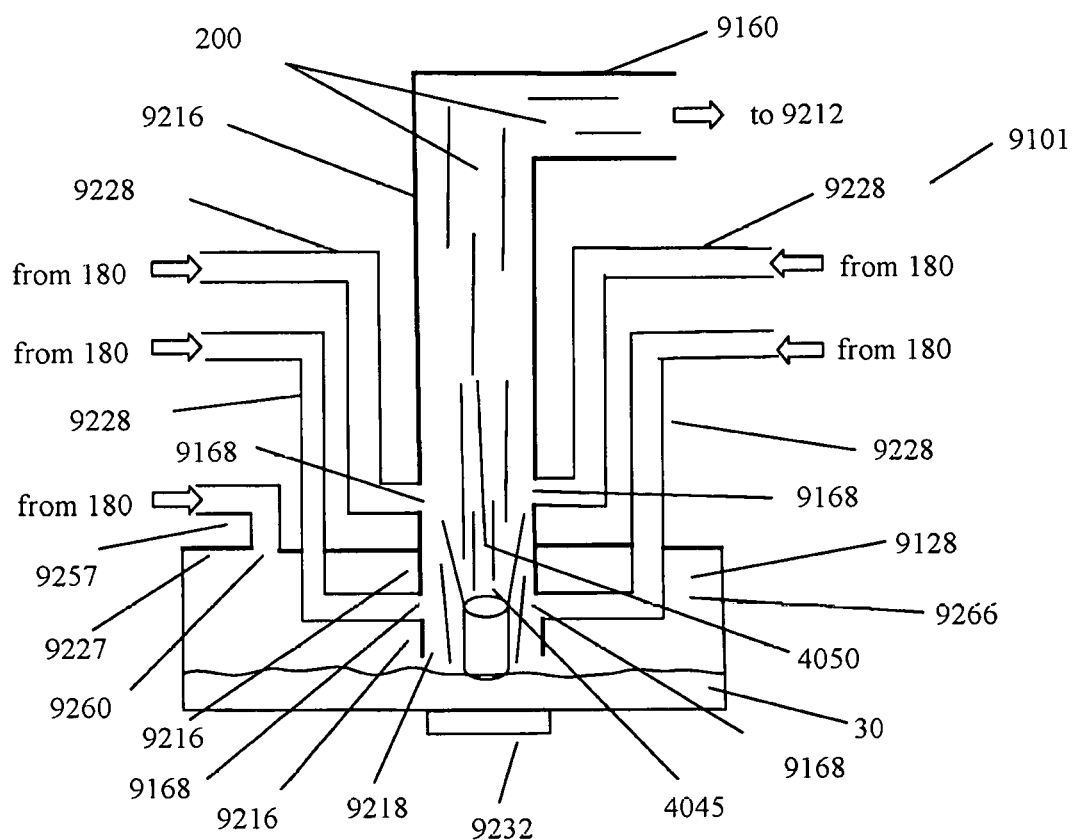

FIG. 158 is a cross sectional schematic diagram an aerosol generation apparatus with a gas input into a transducer chamber in accordance with the present invention.

Figure 159:
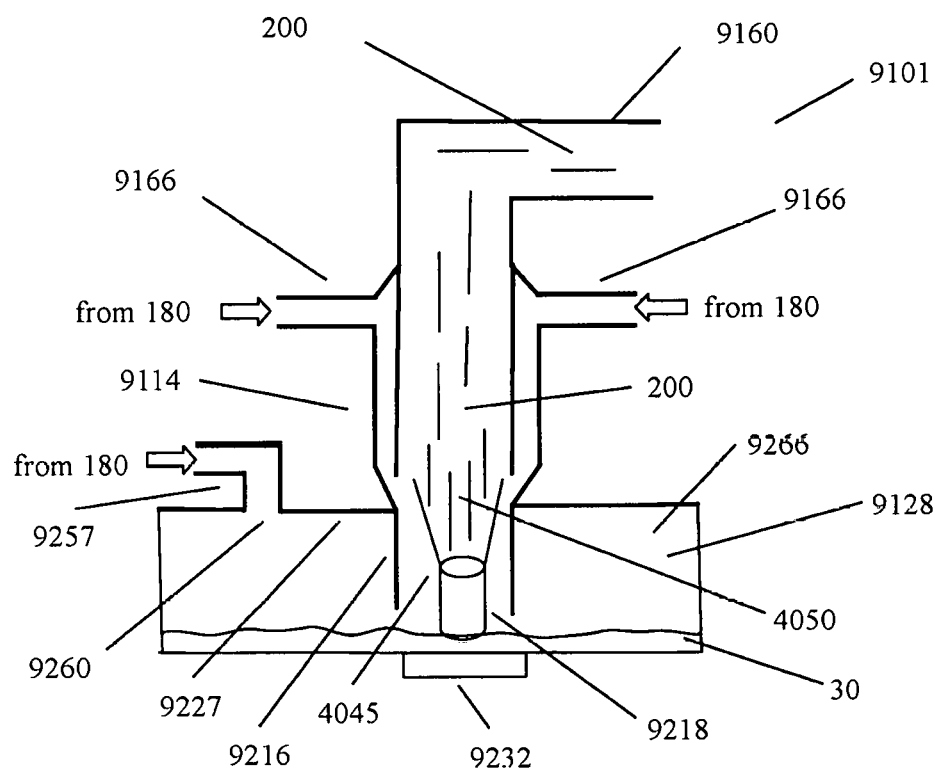

FIG. 159 is a cross sectional schematic diagram an aerosol generation apparatus with an outlet pipe having an inner air chamber in accordance with the present invention.

Figure 160:
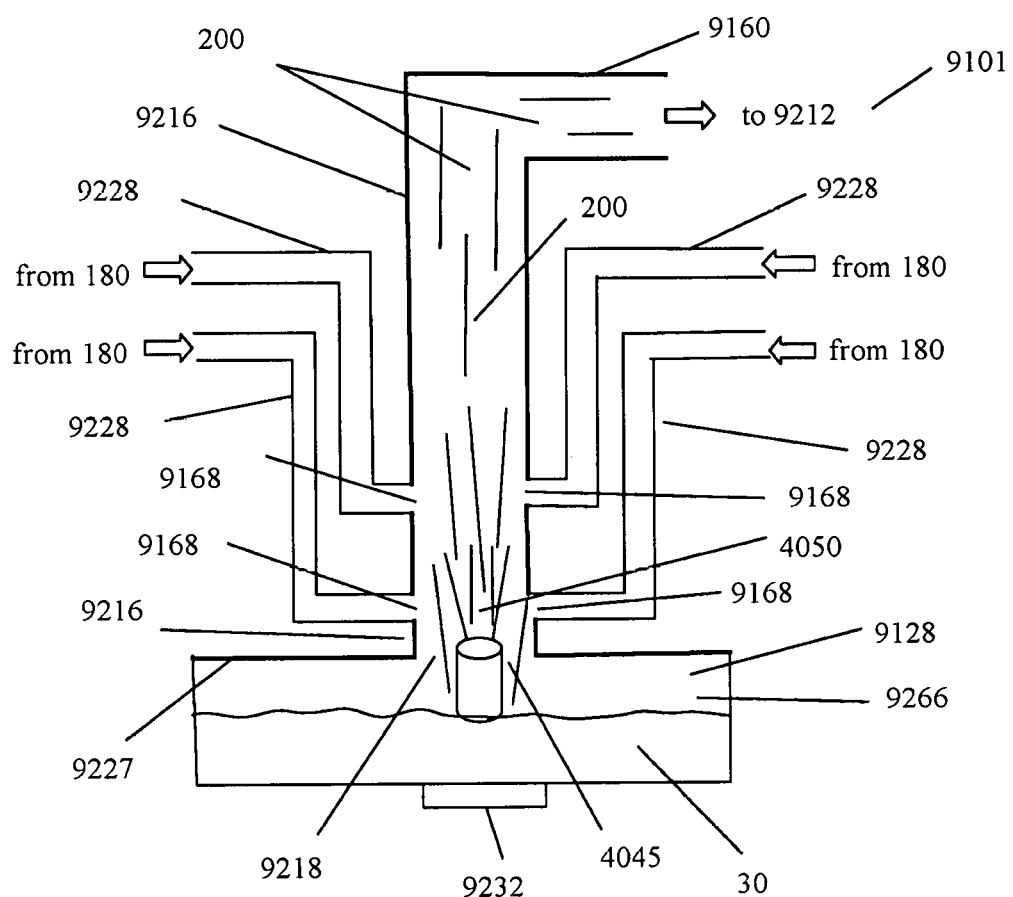

FIG. 160 is a cross sectional schematic diagram an aerosol generation apparatus without a chamber gas supply in accordance with the present invention.

Figure 161:
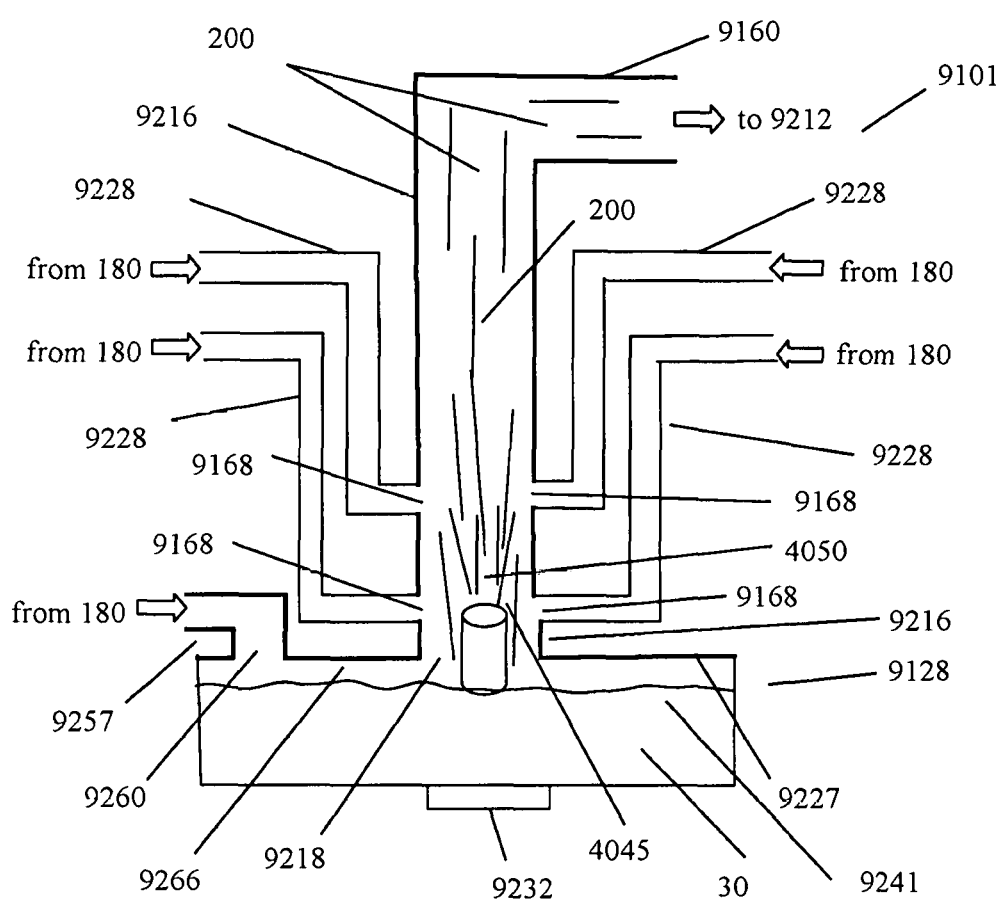

FIG. 161 is a cross sectional schematic diagram an aerosol generation apparatus with a chamber gas supply in accordance with the present invention.

Figure 162:
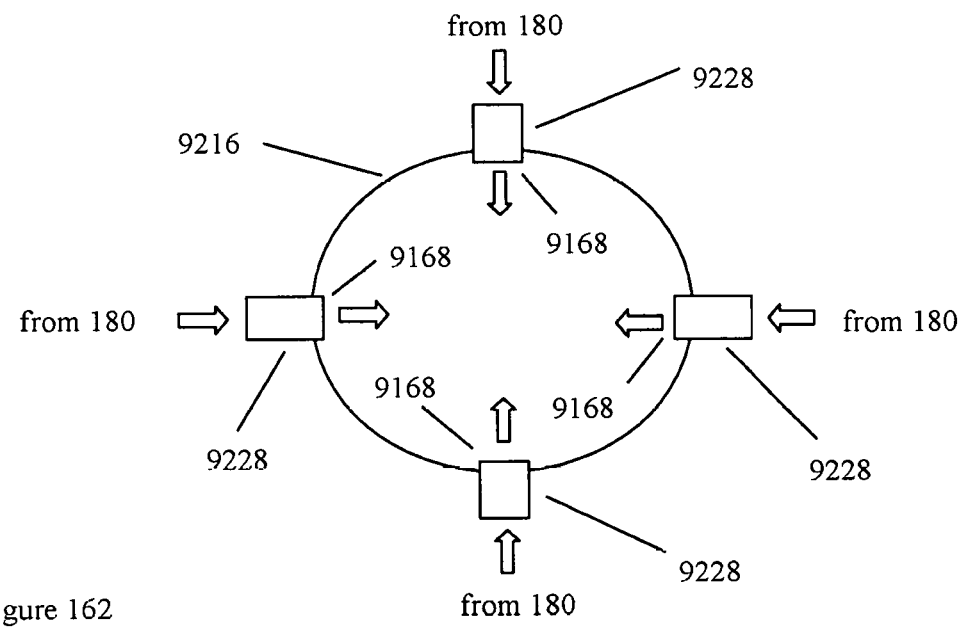

FIG. 162 is a cross sectional schematic diagram of an alternative gas tube of an aerosol generation apparatus in accordance with the present invention.

Figure 163:
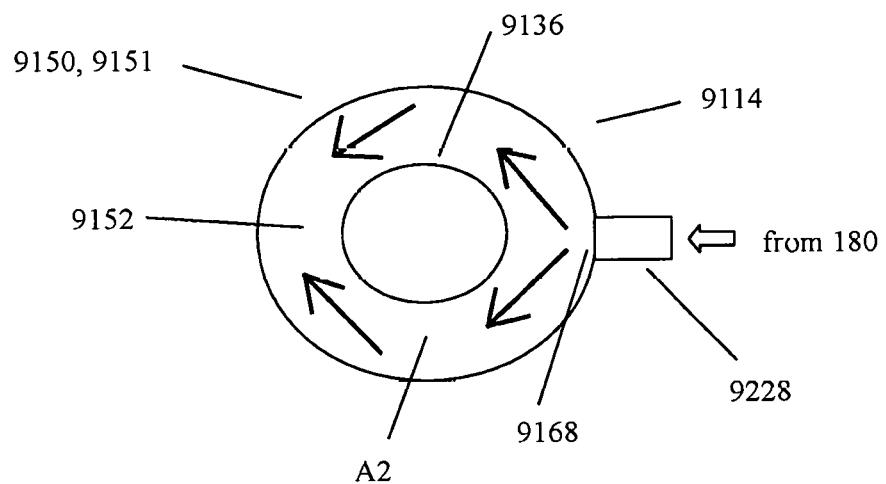

FIG. 163 is a cross sectional schematic diagram of an outlet pipe having an inner air chamber of an aerosol generation apparatus in accordance with the present invention.

Figure 164:
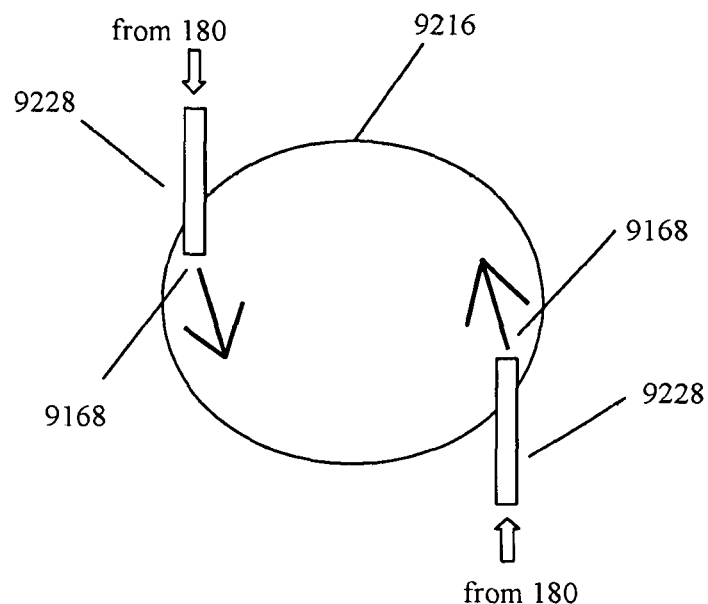

FIG. 164 is a cross sectional schematic diagram of an alternative gas tube with gas input substantially tangent to a side wall thereof of an aerosol generation apparatus in accordance with the present invention.

Figure 165:
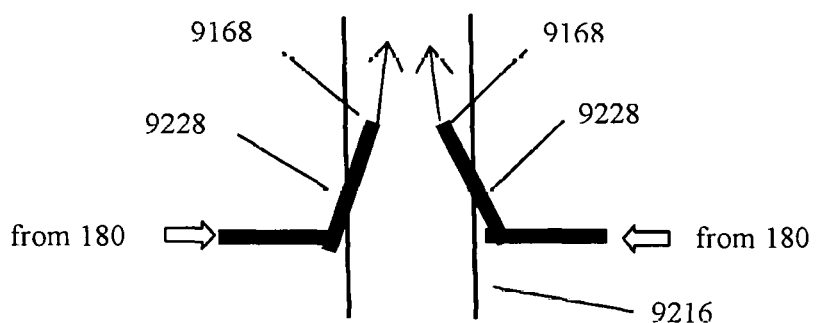

FIG. 165 is a cross sectional schematic diagram of an alternative gas tube with gas input at an acute angle from a side wall thereof of an aerosol generation apparatus in accordance with the present invention.

Figure 166:
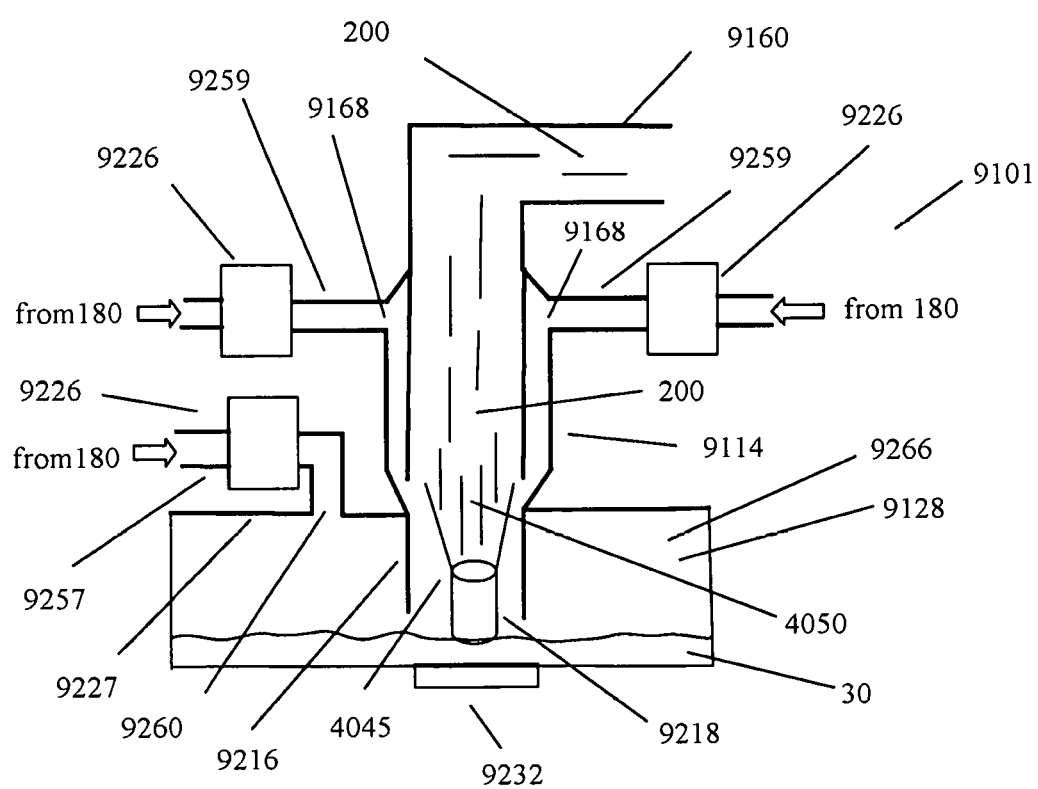

FIG. 166 is a cross sectional schematic diagram an aerosol generation apparatus with an outlet pipe having an inner air chamber and air control valves controlling gas input into the outlet pipe in accordance with the present invention.

Figure 167:
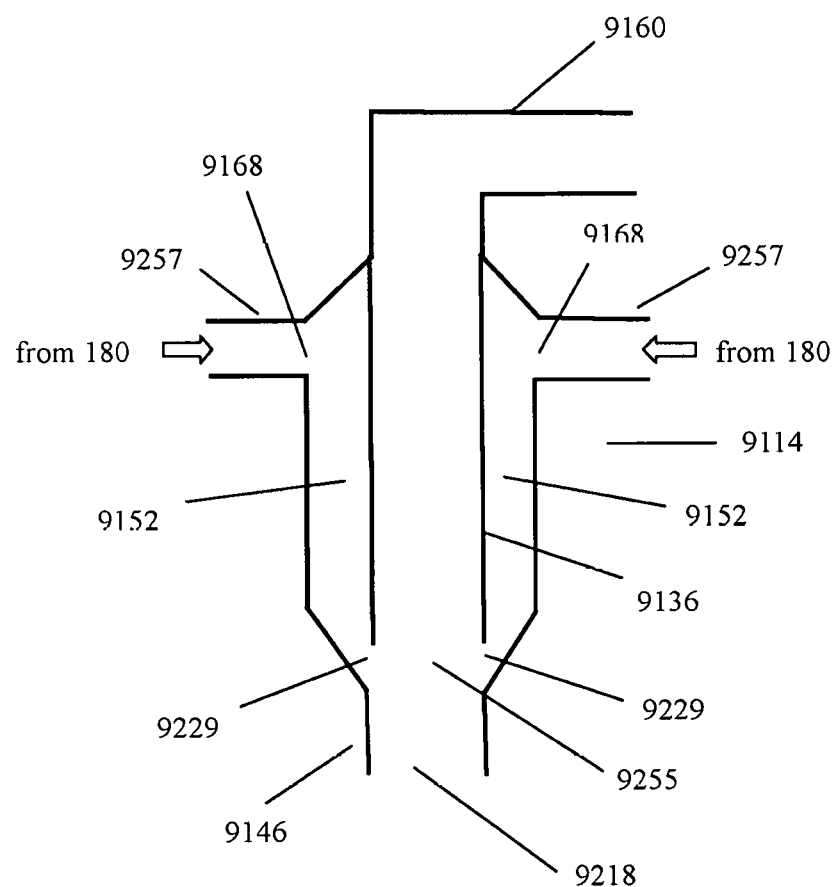

FIG. 167 is a cross sectional schematic diagram an outlet pipe with an inner air chamber illustrating a outlet air gap of an aerosol generation apparatus in accordance with the present invention.

Figure 168:
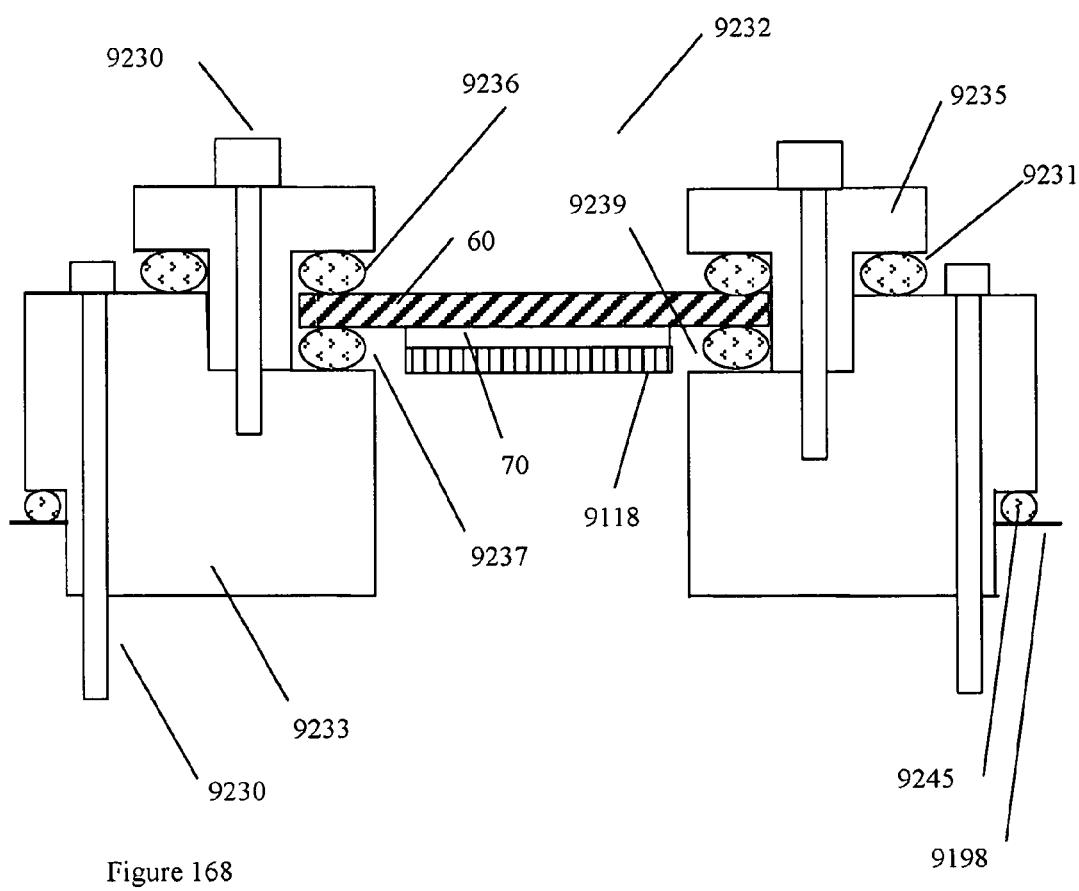

FIG. 168 is a cross sectional view of a transducer assembly of an aerosol generation apparatus in accordance with the present invention.

Figure 169:
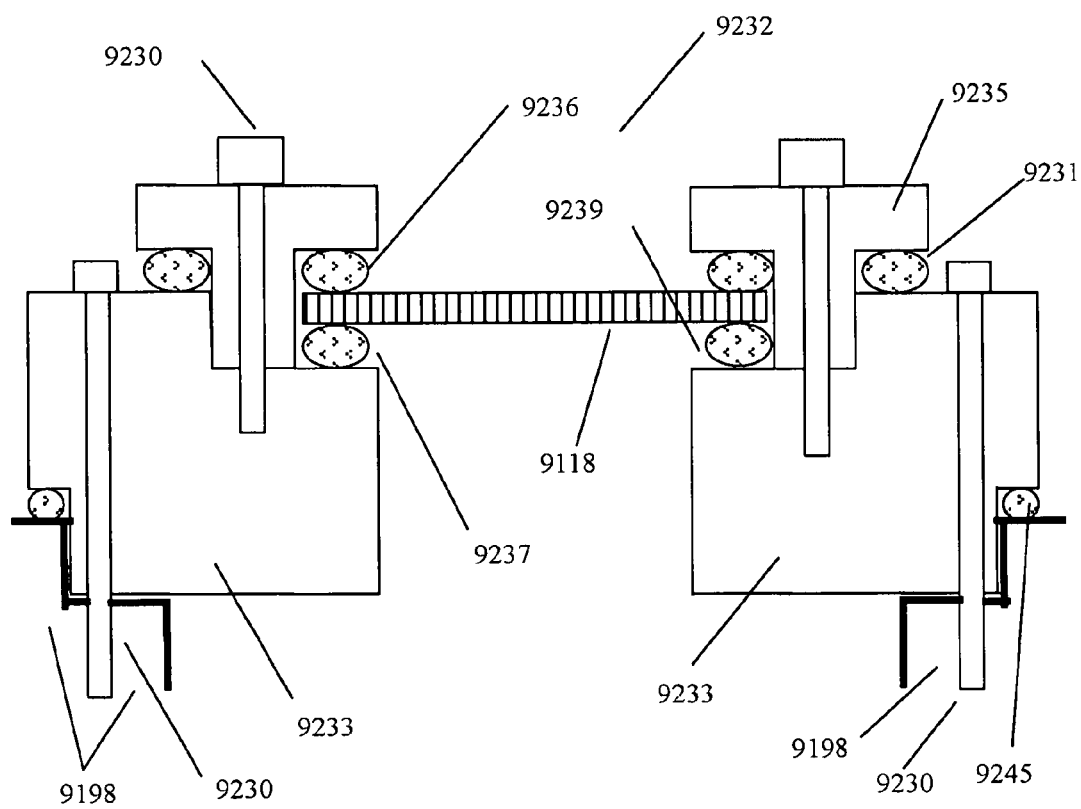

FIG. 169 is a cross sectional view of an alternative embodiment of a transducer assembly of an aerosol generation apparatus in accordance with the present invention.

Figure 170:
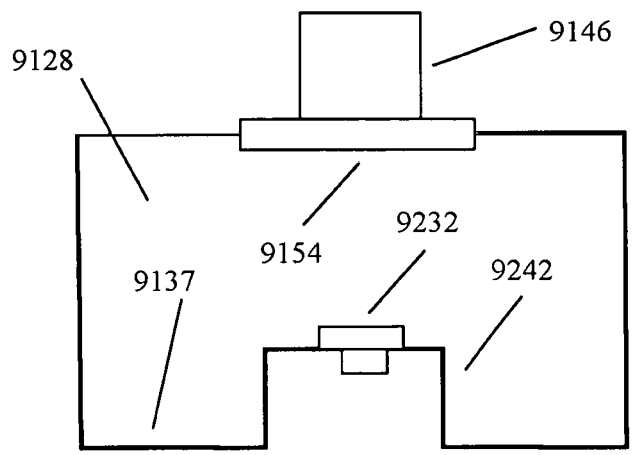

FIG. 170 is a cross sectional view of an alternative embodiment of a transducer chamber of an aerosol generation apparatus in accordance with the present invention.

Figure 171A:
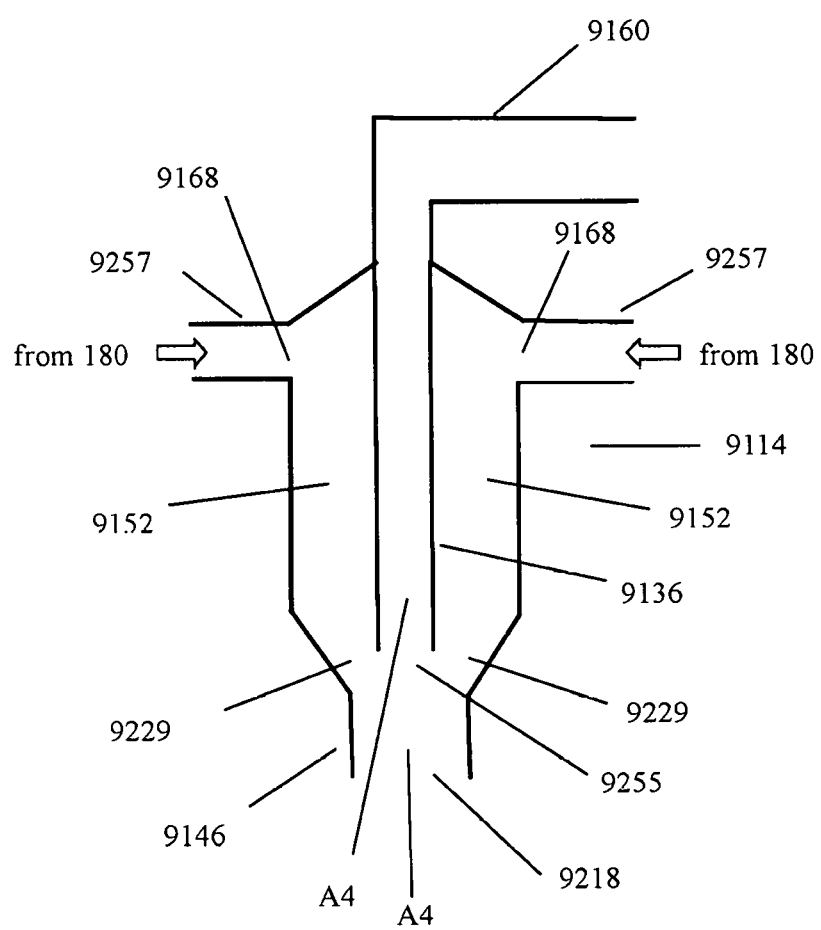

FIG. 171A is a cross sectional view of an outlet pipe having a small sized perimeter relative to an outlet base portion of an aerosol generation apparatus in accordance with the present invention.

Figure 171B:
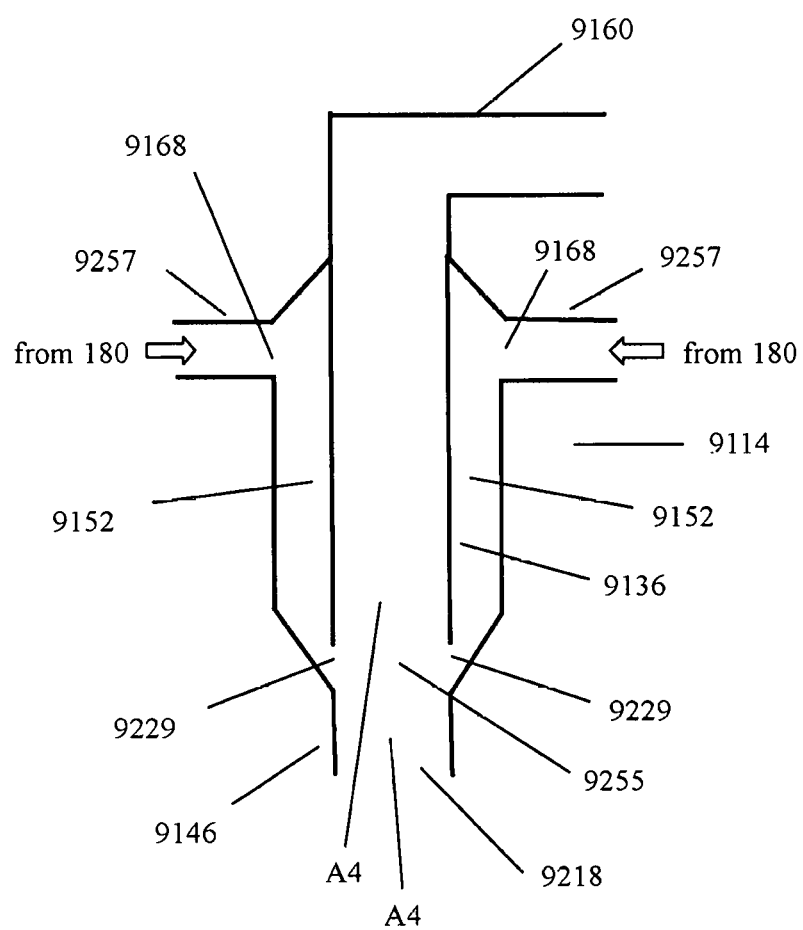

FIG. 171B is a cross sectional view of an outlet pipe having a medium sized perimeter relative to an outlet base portion of an aerosol generation apparatus in accordance with the present invention.

Figure 171C:
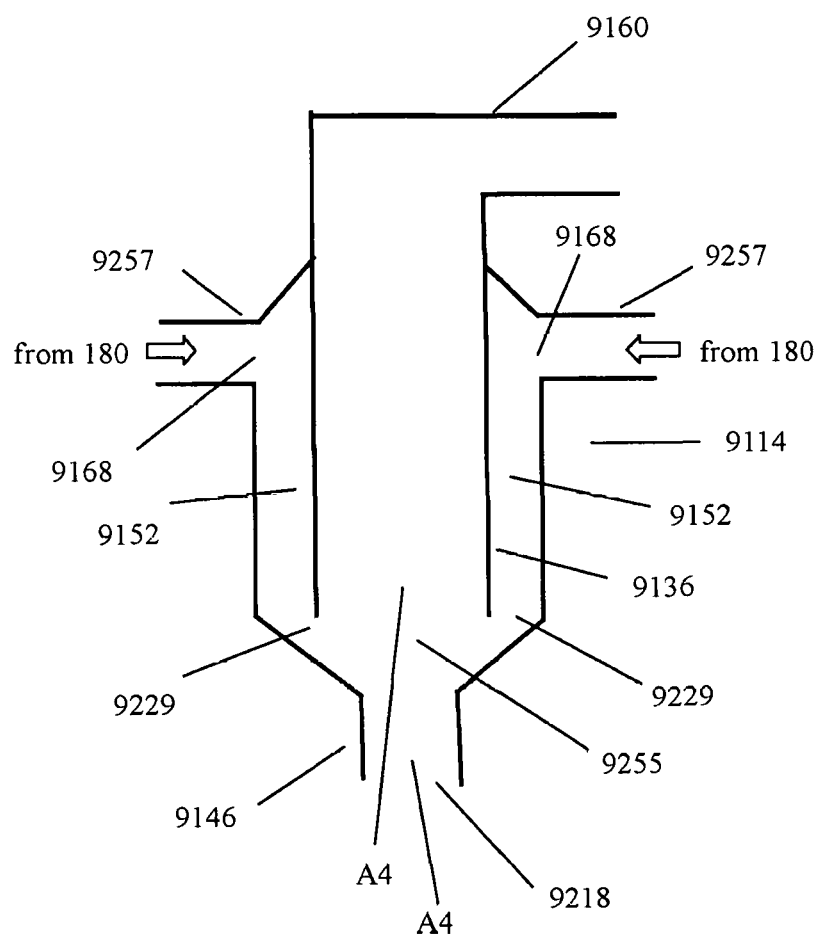

FIG. 171C is a cross sectional view of an outlet pipe having a large sized perimeter relative to an outlet base portion of an aerosol generation apparatus in accordance with the present invention.

DETAILED DESCRIPTION OF THE PREFERRED EMBODIMENTS

Detailed references to the embodiments of the invention, are illustrated in the accompanying drawings that serve as examples. While the invention will be described in conjunction with the embodiments, it is understood that they are not intended to limit the invention to those embodiments. On the contrary, the invention is intended to cover alternatives, modifications, and equivalents, which may be included within the spirit and scope of the invention as defined by the appended claims.

As illustrated in FIGS. 1-5B, an embodiment of the invention includes a method and apparatus for protecting and enhancing the performance of one or more aerosol generating ultrasonic transducer(s) (10) by adhering one or more protective barrier(s) (60) to a transducer(s) (10). Unless otherwise stated, adhering in this specification includes, but is not limited to adhering, coupling, gluing, attaching, cementing, cohering, fastening, pasting, depositing, applying, melting onto or melting together, and chemically, thermally, or physically bonding. According to an embodiment the transducer(s) (10) may be made of a piezoelectric material, preferably a lead-zirconate-titanate (PZT) material, and more preferably lead-zirconate-titanate-four (PZT-4). According to an embodiment, the protective barrier (60) may be any material that has an effective or high chemical resistance to a liquid (30); however any material that has an effective coefficient of conductivity for pressure (energy) could also be used. Further, the protective barrier (60) may be a pane, sheet, or plate, and may be made of materials such as glass, ceramic, or a polymer. According to an embodiment, the thickness of the protective barrier(s) (60) can range from about 0.001 inches to about 0.125 inches, wherein the thickness is not equal to or about n/2 of a wavelength of sound or pressure (energy), preferably in the form of a wave, generated by the transducer(s) (10) at a frequency, wherein n is any integer. In an embodiment, the liquid (30) may be, but is not limited to one or more of any chemical, compound, mixture, or substance, which is a liquid, preferably a solution, and may optionally include but is not limited to any, water, medicines, pharmaceutical or medical products, enzymes, fertilizers, pesticides, fuels, chemical neutralizers, or anti-pathogen/toxin/fungal/sporicidal agents, substances, combinations thereof, and the like. According to an embodiment, the liquid (30) may also be heated to achieve a desired aerosol (200) output.

According to an embodiment, a protective barrier (60) is adhered to the side of the transducer(s) 10 that faces the liquid (30), preferably hydrogen peroxide and peroxyacetic acid in solution, to separate the transducer(s) (10) from the liquid (30). In an embodiment, the protective barrier (60) is quartz glass and is adhered to the transducer(s) (10) by an adhesive (70) whose performance is unaffected and/or not adversely affected by heat. No liquid or other medium, other than the adhesive (70) (and optionally, a conductive coating (50)), is necessary between the transducer(s) (10) and the protective barrier (60) for the transducer(s) (10) to function properly. According to an embodiment, the thickness of the protective barrier (60) ranges from about 0.001 inches to about 0.125 inches, wherein the thickness is not equal to or about n/2 of a wavelength of pressure generated by the transducer(s) (10) at a frequency between about 0.025 MHz and about 10 MHz, wherein n is any integer, preferably a thickness between about 0.026 inches and about 0.070 inches at a frequency between about 0.5 MHz and about 2.5 MHz, more preferably a thickness between about 0.030 inches and about 0.060 inches at a frequency between about 1.2 MHz and about 2.2 MHz, and even more preferably a thickness between about 0.029 inches and about 0.042 inches at a frequency between about 1.2 MHz and about 2.2 MHz.

Figure 1:
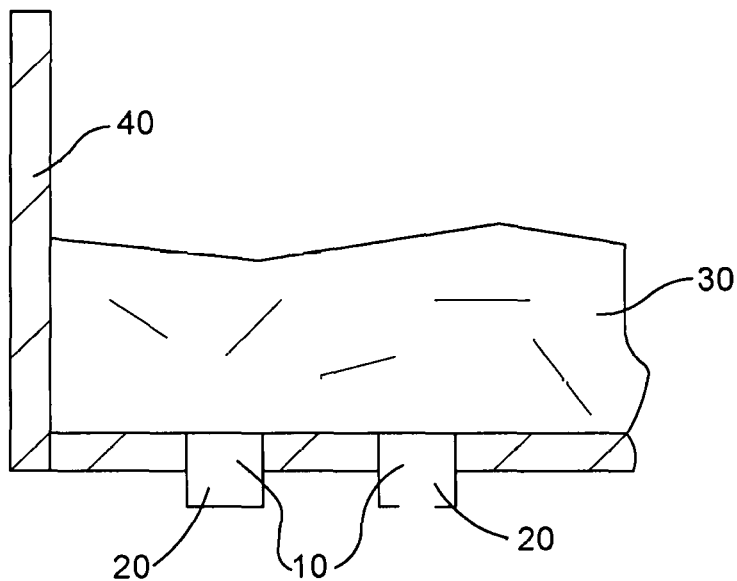
FIG. 1 is a schematic view of an embodiment of a reservoir where one or more aerosol generating ultrasonic transducers are located below the surface of a liquid held within the reservoir.
Figure 2:
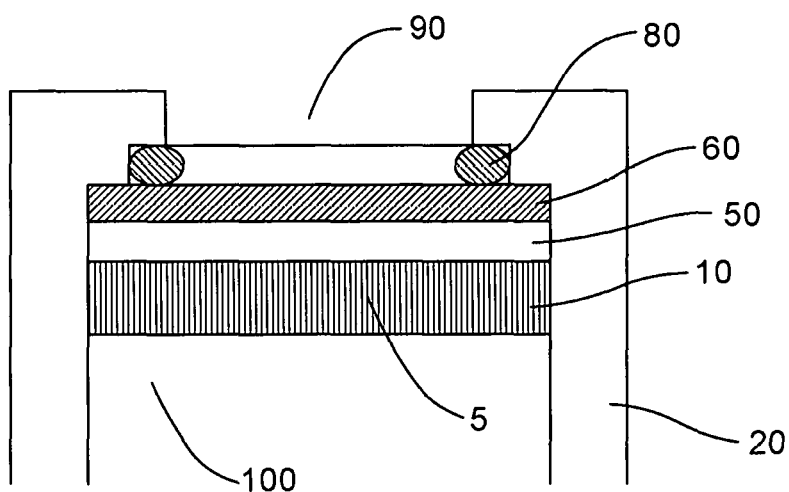
FIG. 2 is a schematic view of an embodiment of a transducer assembly comprising a housing, a transducer, and a protective O-ring interface, wherein a protective barrier is applied to the side of a transducer that faces a liquid.

Referring to FIGS. 1 and 2, an embodiment of the invention includes one or more aerosol generating ultrasonic transducer(s) (10) (and their housings (20), if utilized) located below the surface of a solution, fluid, or liquid (herein collectively "liquid") (30) in a reservoir (40). According to an embodiment, the liquid (30) can be, but is not limited to one or more of any chemical, compound, mixture, or substance, which is a liquid, preferably a solution, and may optionally include but is not limited to any, water, medicines, pharmaceutical or medical products, enzymes, fertilizers, pesticides, fuels, chemical neutralizers, or anti-pathogen/toxin/fungal/sporicidal agents, substances, combinations thereof, and the like.

According to a preferred embodiment, a preferred liquid (30) is hydrogen peroxide and peroxyacetic acid in an aqueous solution, which may be effective in sanitization, disinfection, high-level disinfection, and sterilization, and other applications, preferably approximately 2.2% hydrogen peroxide and approximately 0.45% peroxyacetic acid in solution, more preferably approximately 1% hydrogen peroxide and approximately 0.25% peroxyacetic acid in an aqueous solution. Other liquids (30) that may be used include, but are not limited to chlorine dioxide in solution and ozone in solution.

The tank or reservoir (40) may be made of any suitable material that is not affected by the chemical action of the liquid (30). Suitable materials of the reservoir (40) may include PVC, polypropylene, and stainless steel, but other suitable materials may be used. The aerosol (200) generated by operation of the transducer(s) (10) forms above the surface of the liquid (30) in the reservoir (40) and may be transferred from the reservoir (40) to the space to be treated by a blower (180) or other source of pressurized air, as will be described in greater detail below.

The output of the protected transducer(s) (10) may be focused or directed to a point and/or an area near the surface of the liquid (30) to cause a surface disturbance, which results in the formation of an aerosol (200) of the liquid (30) in the reservoir (40). The aerosol (200) is then blown or otherwise moved with pressurized air, into one or more targeted areas or chambers.

According to an embodiment, the transducer(s) (10) may be made of a piezoelectric material, preferably a lead-zirconate-titanate (PZT) material, and more preferably lead-zirconate-titanate-four (PZT-4). With reference to FIG. 2, the transducer(s) (10) is coated with a conductive coating (50) that enables an electrical signal to energize or drive the transducer(s) (10) causing it to emit pressure (energy) of a desired character. When a protective barrier (60) is adhered or otherwise coupled to a transducer(s) (10) it is understood to mean herein that a conductive coating (50) may exist between the protective barrier (60) and the transducer(s) (10). According to an embodiment, some or all of the conductive coating (50) may be removed from the back of the transducer(s) (10) to allow it to receive the radio frequency (RF) output from the amplifier. Moreover, according to an embodiment, an electrically conductive material (i.e., metal wire, conductive tab or spring, etc.) interfaces or is connected to the conductive coating (50) on the transducer(s) (10), and is then either electrically grounded or electrically connected back to the power amplifier to complete the circuit. This circuit is not polarity sensitive. The electrically conductive material can be attached in their reverse manner.

According to an embodiment, the transducer(s) (10) may be manufactured into various shapes and sizes according to a desired application, preferably circular in shape. Also, according to an embodiment, the transducer(s) (10) may have a diameter of various lengths, preferably about one (1) inch. By using a protective barrier (60) of the present invention, the transducer(s) (10) may have a smaller diameter and smaller surface area than that taught in the prior art without the problems of overheating and/or failing during operation, the need for a cooling mechanism to prevent the transducer(s) (10) from overheating and/or failing, and/or putting space between the protective barrier (60) and the transducer(s) (10) and/or filling that space with various cooling fluids.

Examples of electronic equipment and methods for operating or driving the transducer(s) (10) are discussed in U.S. Pat. Nos. 5,878,355 and 6,102,992 (both of which are incorporated herein by reference in its entirety, including any references cited therein). U.S. Pat. No. 5,925,966, which is incorporated herein by reference in its entirety, including any references cited therein, also provides details of the hardware necessary to operate the transducer(s) (10). Additional electronic equipment, tolerances, and methods for operating or driving the transducer(s) (10) known in the art may also be used. A variable frequency oscillator or signal generator is used to generate a high frequency wave, preferably a sine or square wave.

According to an embodiment, a preferred oscillator is a digital function generator/counter capable of producing sine, square, triangle, pulse and ramp waves. A preferred oscillator has an adjustable frequency range from about 0.025 MHz to about 12 MHz, and may be set or designed for a particular need or requirement. It preferably has variable output amplitude from 5 mV to 20 Vp-p (Volts peak to peak) being delivered to the amplifier, variable symmetry/duty cycle from 5% to 95% in the ramp or pulse mode, continuous or externally controlled outputs. This signal can then be optionally amplified using a power amplifier to increase the power to the optimum aerosol producing power. The volts peak to peak is a measure of power that is supplied to the transducer(s) (10). A direct current (D.C.) offset between −10 v to +10 v can be added to any of the output waveforms.

In one embodiment, the amplifier is a solid-state amplifier that provides up to 2500 watts of linear power with low harmonic and intermodulation distortion and peak to peak voltages of about 20 volts to about 300 volts; however the number of watts could also be increased in order to provide enough power to drive a desired number of transducers and the peak to peak voltages could also be increased, preferably about 100 watts of linear power per transducer(s) (10) with about 190 to about 230 Vp-p.

The amplified signal from the amplifier is used to operate or drive one or a plurality of transducer(s) (10), where in an embodiment each transducer(s) (10) is operated at a frequency range between about 0.025 MHz to about 10 MHz or higher, preferably between about 0.5 MHz to about 2.5 MHz, more preferably between about 1.2 MHz and about 2.2 MHz. Moreover, in such an embodiment each transducer(s) (10) has a resonant frequency between about 0.025 and about 10.0 MHz or higher. The operating frequency is the frequency at which the transducer(s) (10) is being driven or operated. The resonant frequency is the frequency of the transducer(s) (10), unloaded in air, without being adhered to the protective barrier (60) or other parts of the transducer assembly (100).

Optionally, in one embodiment, the conductive coating (50) may be applied to the entirety of the surface of each transducer(s) (10) so that it can be energized. According to an embodiment, some or all of the conductive coating (50) may be removed from the side (5) that faces away from the liquid (30) in the reservoir (40). The side (5) of the transducer(s) (10) is also the side that receives the radio frequency (RF) output from the amplifier. According to an embodiment, an electrically conductive material (i.e., metal wire, conductive tab or spring, etc.) interfaces or is connected to the conductive coating (50) on the transducer(s) (10), and is then either electrically grounded or electrically connected back to the power amplifier to complete the circuit. This circuit is not polarity sensitive. The electrically conductive material can be attached in their reverse manner.

The transducer(s) (10) is protected from chemical interaction with a liquid (30), as well as any erosion that could be caused by cavitation, by utilizing a protective barrier (60). In an embodiment, referring to FIG. 2, applying a protective barrier (60) onto the side of the transducer(s) (10) that faces the liquid (30); where the protective barrier (60) is first heated to a pliable or molten state and then applied to the transducer(s) (10). In another embodiment, referring to FIG. 3, adhering, or bonding the surface of one or more transducer(s) (10) that faces the liquid (30) with a protective barrier (60). According to an embodiment, the protective barrier (60) may be a pane or plate, and/or be made of materials such as glass, ceramic, or a polymer. Preferably the protective barrier (60) is a sheet of quartz glass. The material of a protective barrier (60) should have an effective or high chemical resistance to the liquid (30) used. The thickness of a protective barrier (60) is held to specific tolerances. In one embodiment, an adhesive, cement, epoxy, or bonding agent/compound, etc. (herein, collectively "adhesive" (70)), whose performance is unaffected and/or not adversely affected by heat, is utilized for adhering, or otherwise connecting a protective barrier (60) with a transducer(s) (10). An interface and/or connection between a protective barrier (60) and a transducer(s) (10) may also be established by other means known to those skilled in the art. Further, no liquid or other medium, other than the adhesive (70) (and optionally, a conductive coating (50)), is necessary between a transducer(s) (10) and a protective barrier (60) for the transducer(s) (10) to function properly. According to an embodiment, glass was chosen due to attributes including, but not limited to its physical and/or mechanical properties, and ability to withstand the heat generated by a transducer(s) (10) and its general ability to withstand chemical attack. The technique of adhering a transducer to a glass barrier material is taught in U.S. Pat. Nos. 4,109,863; 3,433,461; 3,729,138; and 4,976,259, each of which is incorporated herein by reference in its entirety, including the references cited therein.

According to a preferred embodiment, a transducer(s) (10) and/or a transducer assembly (100) are placed in a chemically resistant housing (20) or other chemically resistant means to hold, holdfast, secure, and/or protect the transducer(s) (10). Certain metals and plastics have demonstrated high chemical resistance to various liquids. A chemical resistant seal or O-ring (herein "O-ring") (80) serves as a seal between the transducer assembly (100), and the liquid (30) in the reservoir (40). According to an embodiment, the O-ring (80) may be made of any chemically resistant material depending upon the composition of the liquid (30) utilized, preferably Viton®. The preferred material has the highest chemical resistance to the liquid used.

In each of the embodiments shown in FIGS. 2-5, the transducer assembly (100), including the transducer(s) (10) and the protective barrier (60), is enclosed or packaged in, assembled with, or coupled with, a housing (20). According to an embodiment, the housing (20) may be a hermetically or non-hermetically sealed or unsealed housing, or other hermetically or non-hermetically sealed or unsealed means to hold, holdfast, secure, and/or protect transducer(s) 10, that is either interfaced with the reservoir (40), or mounted to or in the reservoir (40), or positioned within the reservoir (40), or preferably coupled or attached to the bottom wall of the reservoir (40). According to an embodiment, a sealed interface exists between the protective barrier (60) and/or the housing (20) or means to hold, holdfast, secure, and/or protect the transducer(s) (10).

Figure 3:
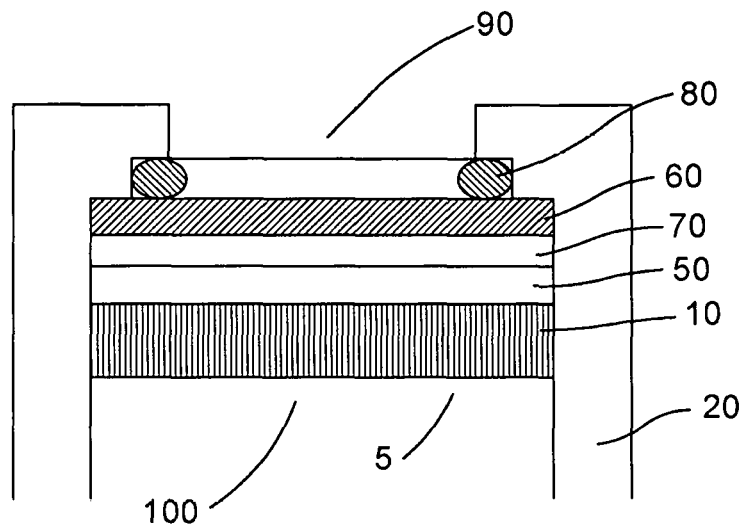
FIG. 3 is a schematic view of an embodiment of a transducer assembly comprising a housing, a transducer coupled with a protective barrier such as a pane, plate, or sheet of glass or other material, and a protective interface above the protective barrier.
Figure 4:
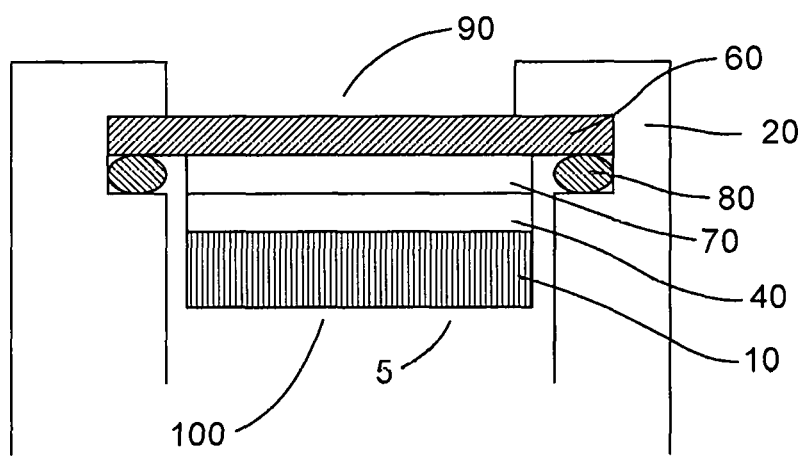
FIG. 4 is a schematic view of an embodiment of a transducer assembly comprising a housing, a transducer coupled with a protective barrier, and a protective seal below the protective barrier.

In one embodiment, see FIGS. 2 and 3, the O-ring seal (80) seals the interface between the protective barrier (60) and the open upper end (90) of the housing (20). In FIG. 4, the O-ring seal (80) is positioned below the protective barrier (60).

Figure 5A:
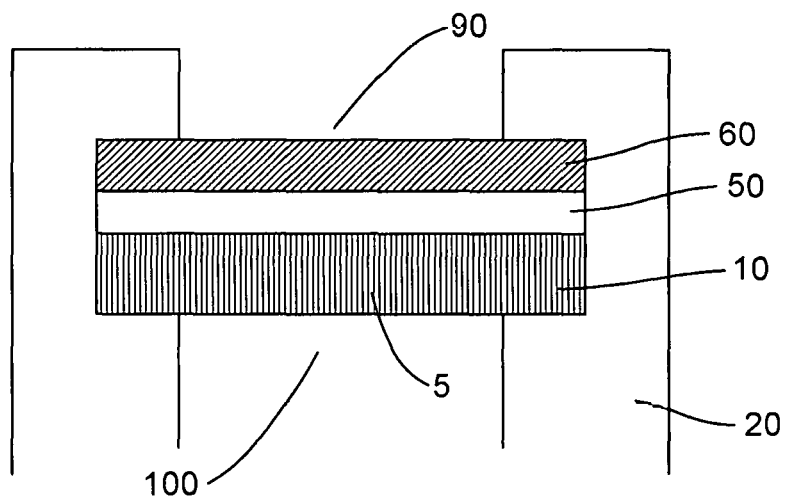
FIGS. 5a and b are a schematic views of embodiments of a transducer assembly according to the present invention.
Figure 5B:
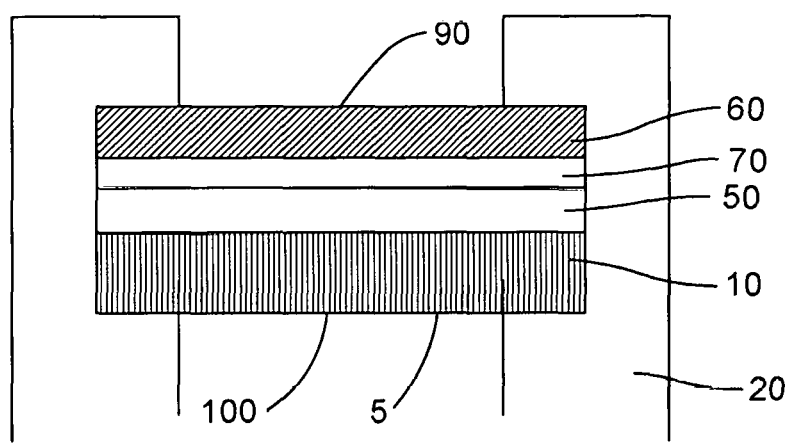
Figure 6:
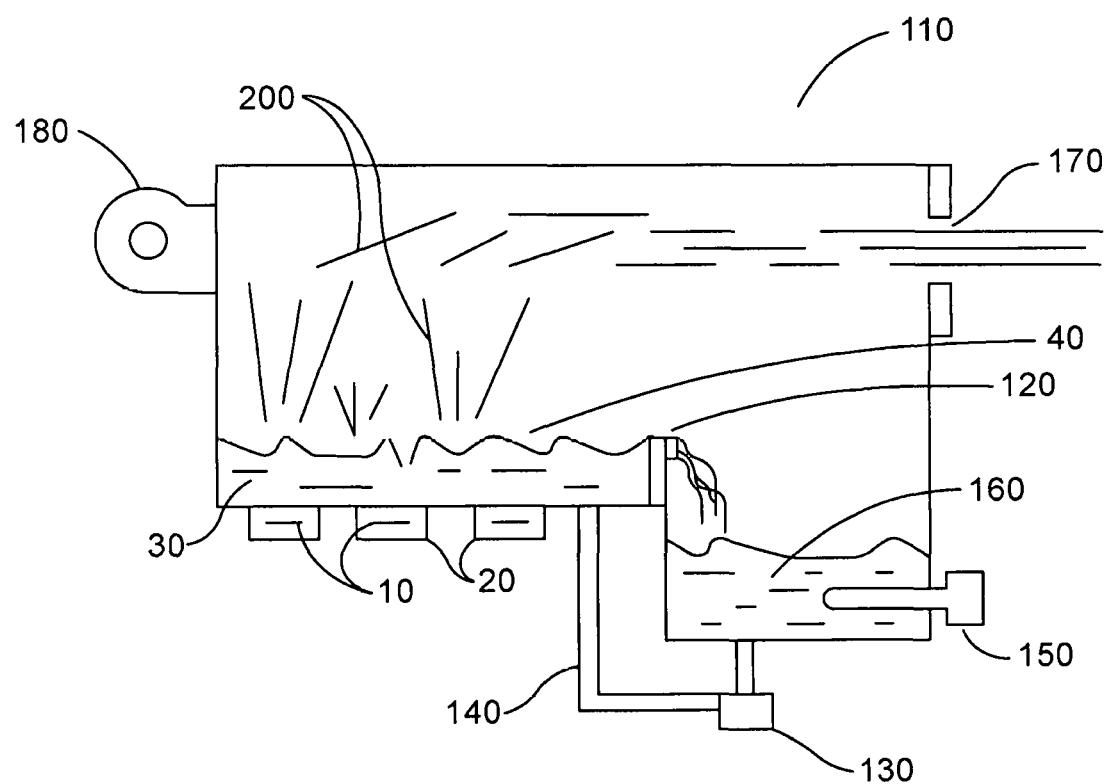
FIG. 6 is a schematic view of an embodiment of an aerosol generator according to the present invention.

In FIGS. 5a and 5b, the transducer(s) 10 and the protective barrier (60), where the protective barrier (60) is formed and/or assembled by method (1) or (2), is molded, thermoformed, cemented, adhered, or otherwise interfaced with/to the reservoir (40), or the housing (20) or other means to hold, holdfast, secure, and/or protect the transducer(s) (10), which establishes an effective seal between the interfacing materials. Other methods known in the art can also be used to establish this interface. In an another embodiment, the surfaces within the reservoir (40), or other surfaces to which the transducer assembly (100) is coupled, interfaced, connected, or mounted, may also act or function as the housing (20) and FIGS. 2-4 are also applicable in this capacity. Finally, a sealed interface may also exist between the housing (20) or the means to hold, holdfast, secure, and/or protect the transducer(s) (10), and a wall of the reservoir (40), or other surface(s) with which it interfaces.

According to an embodiment, it is preferred that with both protective barrier (60) methods (1) and (2), when glass is used, the glass type used may be of any acid and/or alkaline resistant glass such as, for example, quartz, or Type I (borosilicate glass or Pyrex) or Type II glass as defined by the United States Pharmacopoeia. The protective barrier (60) may be any chemically resistant material. Preferably, the protective barrier (60) has a high chemical resistance to the liquid (30) used.

The selection of a material for either of the two protective barrier (60) assemblies and methods is further determined by the material's impedance properties according to known wave transmission theories. In other words, some materials are better at transmitting pressure (energy) than others. This correlates directly with the efficiency and effectiveness of the transducer(s) (10) and is represented by the maximum amount of aerosol (200) generated by the aerosol generating system (110) per unit of time. In order to maximize the energy transfer into the liquid (30), transmission coefficients for various protective barrier (60) materials are calculated by means of known mathematical formulas pertaining to the various theories of wave transmission known to those of skill in the art. The transmission coefficients are calculated and then compared and the highest transmission coefficient is chosen. Generally, the higher the energy transmitted through the protective barrier (60), the higher the aerosol (200) output. In addition, the higher the frequency, the smaller the particles. According to an embodiment, good wave transmission is achieved through the use of a quartz glass or a borosilicate glass protective barrier (60).

The thickness of the material of the protective barrier (60) is another factor that influences the efficiency and effectiveness of the transducer(s) (10) or the total amount of or size of aerosol (200) the transducer(s) (10) is able to generate. This relates to the fact that operational frequencies will dictate selected glass thicknesses, thinner glass being selected with higher frequencies. These higher operational frequencies produce smaller droplet sizes. In the first protective barrier method, the protective barrier (60) is either formed or applied to the proper thickness. If the thickness of the protective barrier (60) is not within specifications, the protective barrier (60) may be further processed or machined to achieve the proper thickness. The second protective barrier method involves adhering, or otherwise connecting the protective barrier (60), which may be processed or machined to the proper thickness, with the transducer(s) (10). In both methods, the thickness of the protective barrier (60) is controlled to tight tolerances in order to control its transmission coefficient.

It was thought in the prior art that the optimum protective barrier thickness was equal to or about one-half (½) or any multiple of one-half (½) of the wavelength of the transmitted pressure (energy) wave. According to the prior art, at this thickness, the protective barrier material looks acoustically invisible and roughly twenty percent (20%) of the energy emitted from the transducers is being transmitted into the liquid beyond the protective barrier.

However, according to an embodiment of the present invention, it has been found that the transmission of energy through a material can be further optimized or enhanced if the thickness of that material, is between about 0.001 inches and about 0.125 inches, wherein the thickness is not n/2 or about n/2 of the wavelength of a transmitted pressure (energy) that is generated by the transducer(s) (10), wherein n is any integer. Without being limited to the mechanism, it is believed that roughly seventy percent (70%) of the energy emitted from the transducer(s) (10) may be transmitted into the liquid (30) beyond the protective barrier (60) with the thicknesses of the present invention, which is significantly higher than the 20% emitted from the protective barrier (60) with a prior art thickness of one-half (½) or any multiple of ½ the wavelength. Without being limited to the mechanism of action, the material of the protective barrier (60) may actually maximize the transmission coefficient of the pressure (energy) and thus increase the efficiency and effectiveness of the aerosol (200) output of the transducer(s) (10), in addition to protecting the electrode material. A preferred material of the protective barrier (60) may be glass, more preferably quartz glass.

Based upon an embodiment, the invention gave rise to unexpected results, including, but not limited to a significant increase in aerosol (200) output, smaller aerosol (200) particle size, and more energy being transferred to the liquid (30). Additionally, in an embodiment of the apparatus and methods of protecting a transducer(s) (10), a cooling system to prevent the transducer(s) (10) from burning or otherwise failing at various operating frequencies is not necessary. For example, U.S. Pat. No. 4,109,863, which is incorporated herein by reference in its entirety, including the references cited therein, requires a means for circulating a fluid over the transducer and glass for cooling and stabilizing a transducer. However, according to U.S. Pat. No. 4,976,259, this method has the undesirable effect of acoustically dampening the back side of the transducer which reduces the efficiency of the nebulizer system.

When calculating the optimum thickness of the protective barrier (60) in an embodiment of the present invention, the following are considered: (1) operating frequency; (2) the specific natural frequency of the transducer(s) (10); (3) the type of protective barrier (60) material; (4) the thickness of the protective barrier (60); (5) optionally, a suitable adhesive/bonding agent (70); and (6) an acceptable and optimum level of aerosol (200) by sweeping the transducer assembly (100) with a range of frequencies and power to find the desired aerosol (200) output.

According to an embodiment, once the transducer assembly (100) is assembled it can be operated at a range of frequencies. The thickness of the protective barrier (60) may range depending upon the operating frequency of the transducer(s) (10). According to an embodiment, the thickness of the protective barrier (60) ranges from about 0.001 inches to about 0.125 inches, wherein the thickness is not equal to or about n/2 of the wavelength of pressure (energy) generated by the transducer(s) (10) at a frequency between about 0.025 MHz and about 10 MHz, wherein n is any integer, preferably a thickness between about 0.026 inches and about 0.070 inches at a frequency between about 0.5 MHz and about 2.5 MHz, more preferably a thickness between about 0.030 inches and about 0.060 inches at a frequency between about 1.2 MHz and about 2.2 MHz, and even more preferably a thickness between about 0.029 inches and about 0.042 inches at a frequency between about 1.2 MHz and about 2.2 MHz.

Empirical testing for hydrogen peroxide and peroxyacetic acid in solution; and water determined that the transducer(s) (10) generated the greatest amount of aerosol (200) when the liquid (30) above them was maintained at a temperature above about 80° F., preferably about 105° F. This is most likely due to the reduction of the surface tension of the liquid (30) as its temperature increases.

According to an embodiment, the liquid (30) may not have to be at least 80° F. for effective performance in certain circumstances where high aerosol output is not necessary, or the liquid already has a low enough surface tension to achieve a desired result. Further, according to an embodiment, any variations in the temperature may be made to optimize the aerosol (200) output based upon the type of liquid (30) used and the results desired by the user.

According to an embodiment, a protective barrier (60) for an aerosol (200) producing transducer(s) (10) has a thickness between about 0.001 inches and 0.125 inches, wherein the thickness is other than equal to or about n/2 of the wavelength of the transmitted pressure (energy) waves that are generated by the transducer(s) (10), wherein n is any integer. Thus, the thickness of the protective barrier (60) as described above permits the transducer(s) (10) to operate effectively to provide a high volume small aerosol (200) particle output, which is preferred, or any other desired output without the need for space between the transducer(s) (10) and the protective barrier (60) or a cooling mechanism.

Most preferably, in accordance with one aspect of the present invention, it has been found that the transmission of energy through a material can also be optimized if the thickness of that material, in this case glass, is about one quarter (¼) or any multiple of one quarter (¼) of the wavelength of the transmitted pressure waves generated at the natural resonant frequency of the transducer. The barrier material in this case will not only look acoustically invisible but will also maximize the transmission coefficient of the pressure waves and thus increase the efficiency and effectiveness of the transducer's aerosol output. The gain in power transmission for a particular transducer can, without limitation, increase from approximately 20%, for a barrier sized at one half (½) of the wavelength of the transmitted pressure waves generated by the transducer at the natural resonant frequency of the transducer, to approximately 71% for a barrier sized at one quarter (¼) of the wavelength of the transmitted pressure waves generated by the same transducer at the natural resonant frequency of that transducer.

Testing was conducted in the laboratory to determine what glass thickness when adhered to the transducer would generate the maximum amount of aerosol. Transducers with an adhered quartz glass thickness of 0.096 inch and 0.125 inch were tested first, and both suffered damage when the heat from operating the transducer burned the epoxy, which is used to adhere the glass to the transducer. This was evidence that a thinner glass material was needed in order to, without limitation, more effectively transmit the energy and heat produced by the transducer into the liquid above the glass. A quartz glass barrier of about ¼ wave length of the propagated pressure wave for a 1.5 Mhz transducer, or 0.036 inch, was manufactured, and its output greatly exceeded the target of 800 milliliters of aerosolized liquid per hour with an average output of 1500 milliliters per hour, as shown in the data in Table 1, along with data illustrating the effectiveness of barriers having other thicknesses with the 1.5 Mhz transducer.

TABLE 1

Experimental Data

| Frequency (Mhz) | Wavelength | Protective Barrier Thickness (inches) | Aerosol Results: Output Observations/Volumes (ml/hr) |
|---|---|---|---|
| 1.87 | 0.311 | 0.036 | 2138 ml per hr |
| 1.85 | 0.308 | 0.036 | 1769 ml per hr |
| 1.86 | 0.309 | 0.036 | 2064 ml per hr |
| 1.89 | 0.314 | 0.036 | 1622 ml per hr |
| 1.89 | 0.314 | 0.036 | 1843 ml per hr |
| 1.88 | 0.313 | 0.036 | 0 ml per hr; transducer burned |
| 1.90 | 0.316 | 0.036 | 1460 ml per hr |
| 1.84 | 0.306 | 0.036 | 1695 ml per hr |
| 1.85 | 0.308 | 0.036 | 1500 ml per hr |
| 1.86 | 0.309 | 0.036 | 1825 ml per hr |
| 1.89 | 0.314 | 0.036 | 1870 ml per hr |
| 1.90 | 0.316 | 0.036 | 1550 ml per hr |
| 1.90 | 0.316 | 0.036 | 1550 ml per hr |
| 2.11 | 0.283 | 0.029 | Est. <500 ml per hr |
| 1.83 | 0.338 | 0.040 | 1971 ml per hr |
| 1.81 | 0.334 | 0.040 | 2138 ml per hr |
| 1.83 | 0.338 | 0.040 | 2005 ml per hr |
| 1.68 | 0.388 | 0.050 | 1769 ml per hr |
| 1.91 | 0.847 | 0.096 | 0 ml per hr; transducer burned |
| 1.58 | 0.912 | 0.125 | 0 ml per hr |
| 1.59 | 0.918 | 0.125 | 0 ml per hr |
| 1.88 | 0.313 | 0.036 | 0 ml per hr; transducer burned |
| 1.90 | 0.316 | 0.036 | 1900 ml per hr; amplifier issue - ran hot |
| 1.80 | 0.299 | 0.036 | 0 ml per hr; transducer burned |
| 1.82 | 0.303 | 0.036 | 0 ml per hr; lens may have been cracked |
| 1.71 | 0.355 | 0.045 | 0 ml per hr |
| 1.74 | 0.362 | 0.045 | 0 ml per hr |

As a result of this testing, it has recently been determined that the transducer incorporating the barrier provides the best results when the thickness is calculated as a multiple of about n/4 of the wavelength of the natural resonant frequency (unloaded in air) of the transducer. The transducer including the barrier having this calculated thickness must also be operated at an operational frequency that is greater than the natural resonant frequency of the transducer by between about 4% and about 60% of the natural resonant frequency of the transducer. This calculation of the barrier thickness and the resulting operational frequency to optimize the aerosol generation by the transducer can be utilized for transducers having natural resonant frequencies in the range of 0.5 Mhz to 8.0 Mhz.

Further empirical testing in the laboratory for a particular transducer also determined that the actual effective range of glass thickness for aerosol output of a transducer having a natural resonant frequency of 1.5 Mhz was minus 0.010 inches and plus 0.024 inches, from 0.036 inches, or the calculated barrier thickness of one quarter (¼) of the wavelength of the transmitted pressure waves from the 1.5 Mhz transducer. It was also found that this asymmetrical range is, without limitation, strongly correlated with the admittance vs. frequency sweeps for transducers with glass barriers of this type. These sweeps include, but are not limited to, showing two distinct and separate peaks or amplitudes that both exhibit a curve that has a pronounced or sharp drop to the right of each amplitude. Thus, the operation and effectiveness of the aerosol generator including the transducer (10) including the barrier (60) can also be increased by utilizing a barrier having a thickness in this range above and below the calculated barrier thickness at approximately n/4 for the wavelength of the transducer at its natural resonant frequency.

Also, empirical testing determined that the transducers generated the greatest amount of aerosol when the liquid above them was maintained at a temperature above 80 degree Fahrenheit. This is most likely due to the reduction of the liquid's surface tension as its temperature increases.

Therefore, in the present invention the optimum glass barrier thickness for the aerosol producing transducer, is approximately one quarter (¼) or approximately any multiple of one quarter (e.g., 0.5/4, ¼, 1.5/4, 2.5/4, ¾, 3.5/4, 5/4 . . . or n/4 where n=about any odd number, or the result of any mathematical operation) but not equal or about equal to any multiple of n/2 of the wavelength of the transmitted pressure waves from the transducer as calculated by the formula:

$$\lambda(\text{wavelength}) = \frac{c(\text{speed of sound in the selected material})}{f(\text{natural resonance frequency})}$$

when the transducer is operated at an operation frequency of up to 60% above, preferably between 4% and 60% above, more preferably between 9% and 50% above or about 10% to about 45% above, and most preferably between about 18% and 27% above the natural resonant frequency of the transducer.

Additionally, the transducer can be constructed with a barrier within a range of minus 0.010 inches (−0.010 inches) and plus 0.024 inches (+0.024 inches) from the calculated optimum barrier thickness, where the n/4 multiple of the wavelength is not equal to or approximately equal to any multiple of one half (½) of a wavelength. These methods in their entirety can be used with any transducer with a natural resonant frequency, unloaded in air, between 0.5 MHz to 8.0 MHz.

Specifically, maximum aerosol output is achieved with a glass thickness within the range of minus (−) 0.010 inches and plus (+) 0.024 inches, from the optimum thickness calculated as the multiple of n/4 of the wavelength of the transmitted pressure waves, with this multiple more preferably being a multiple where n=an odd number (i.e., 1, 3, 5, 7, 9, etc.) and where n/4 is not equal to any multiple of n/2. More preferably, n is from 1 to 9. In a particularly preferred embodiment, the calculated glass barrier thickness is 0.036 inches (0.036−0.010 to 0.036+0.024 inches).

In a preferred embodiment, the transducers utilized with the barriers having these thicknesses have a natural resonant frequency, unloaded in air, between 1.25 to 1.65 MHz and their operating frequency range in liquid is between 1.71 to 2.00 MHz.

In one embodiment, the liquid depth above the transducers can range from 0.5 to 5.0 inches. In addition the liquid in the tank above the transducers should be maintained at a temperature of 80 degree Fahrenheit or greater in order to maximize the amount of aerosol that is generated.

When utilizing a barrier (60) having a thickness in this calculated range, the transmission of energy from the transducer (10) through the barrier (60) to the liquid (30) is increased from around 20% to around 70%. This increased transmission percentage greatly reduces the degradation of the bond formed by the adhesive (70) binding the barrier (60) to the transducer (10), allowing the adhesive (70) to hold the barrier (60) in place during operation of the transducer (10).

According to an embodiment, many depths of the liquid (30) above the transducer(s) (10) may be used; preferably the depth of the liquid (30) above the transducer(s) (10) is from about 0.25 inches to about 8.0 inches, and more preferably a depth of about 1.25 inches. However, it may be possible to operate the invention at levels below 0.25 inches if lower power and/or frequencies are used. Moreover, according to an embodiment, the liquid (30) may be maintained at any temperature necessary to achieve the desired results based upon the preferences of the user or the type of liquid used. Preferably any liquid (30), such as peroxyacetic acid and hydrogen peroxide, in the reservoir (40) may be maintained at a temperature of about 80° F. or greater in order to maximize the amount of aerosol (200) that is generated. However, the temperature of the liquid (30) may vary depending upon such parameters as the desired aerosol (200) output, the type of liquid (30) used, and the surface tension of the liquid (30).

Referring to FIGS. 6-15, there are shown embodiments of an aerosol generator (110) according to the present invention. The reservoir (40) contains a volume of liquid (30), the level of which is controlled by a dam (or weir gate) (120) operatively associated with a supply pump (130) and a supply line (140) to maintain the level of the liquid (30) at a preferred level above the transducer(s) (10) mounted on the bottom wall of the reservoir (40). The transducer(s) (10) may be individually mounted in separate housings (20), as shown in one of the embodiments of FIGS. 2-4, or they may all be coupled to a common protective barrier (60) wall and appropriately sealed from contact with the liquid (30). It has been found that efficiency of aerosol (200) generation is enhanced by heating the liquid (30) to at least 20° F. above ambient, preferably to at least about 80° F.; however the temperature may vary depending upon the type of liquid (30) used. A heater element (150) is coupled with a liquid supply sump (160) to control the temperature of the liquid (30). The aerosolized liquid (200) is delivered to the space to be treated via an exit orifice (170) of the aerosol generator (110) to which suitable piping (not shown) may be attached for delivery. A blower (180), fan, or other source of pressurized air generates the air flow necessary to deliver the aerosol (200), all in a manner well-known in the art.

According to an embodiment, the transducer(s) (10) and the protective barrier (60) may be sized to provide an optimized resonant frequency that is operative when driven or operated at an operating frequency in the range of about 0.5 MHz to about 2.5 MHz. This large range is due to the appearance of two separate operating ranges that are apparently unique to the transducer assembly (100). For example, using a transducer(s) (10) having a resonant frequency of about 1.40 MHz to about 1.48 MHz with a protective barrier (60) thickness of about 0.036 inches, driven at an operating frequency ranging from about 1.78 MHz to about 1.98 MHz will most commonly show a maximized aerosol (200) output of at least about 1,000 ml per hour of the liquid (30). A second effective operating frequency with lower output is noted at about 1.2 MHz. According to an embodiment, for certain applications where the volume of the space to be treated is small, an output of at least 1,000 ml/hr may not be necessary. In such a situation, the transducer(s) (10) may be operated or driven with various combinations of power or volts peak to peak, and frequencies that result in the generation of lower aerosolized (200) liquid output. For example, in the treatment of a space the size of about a small glove box or the like, an output of 10 ml/hr or less may be adequate.

The apparatus and methods of the present invention may yield aerosol (200) droplets of various sizes. According to an embodiment, they may yield aerosol (200) droplets with a defined size distribution of mostly less than about one (1) microns in diameter, without being limited to a mechanism it is believed this allows the droplets to behave more like a gas with respect to Brownian movement and diffusion. The size of the aerosol (200) droplets may be adjusted upward or downward according to the desired results. The small aerosol (200) droplet size enables the drops to penetrate small cracks and crevices, and apply very thin films on surfaces. In addition, the aerosol (200) may effectively reach and disinfect areas of contamination and areas of otherwise limited accessibility. Any means to create an aerosol (200) with droplets less than about 10 microns in size could be used in the present invention. Larger particles will by their nature cause less penetration and decrease the effectiveness for many but not all possible application. Thus, the present invention may generate predominantly submicron size droplets or sizes may be controlled for a desired result. According to an embodiment, the average particle size may range from less than one micron to about 10 microns, preferably less than about 5 microns, more preferably less than one micron, and even more preferably about 0.68 microns.

According to an embodiment, multiple transducer(s) (10) are typically used to provide an output volume of aerosolized liquid (200) sufficient to rapidly treat a large enclosed space. In such a case, the transducer(s) (10) may be mounted individually, or a plurality of transducer(s) (10) may be coupled to a single protective barrier (60), with one or more of the protective barrier (60) being coupled, mounted on or in a reservoir (40), or positioned within a reservoir (40) with an appropriate coupling device. Multiple transducer(s) (10) may be coupled to a single protective barrier (60) at varying distances apart, preferably between at least about 0.25 inches apart, more preferably about 0.75 inches apart.

Figure 7:
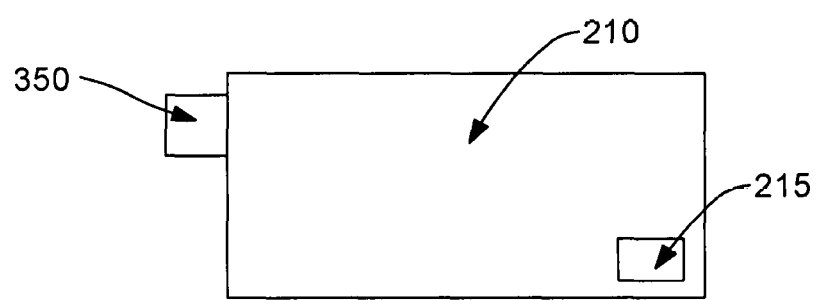
FIG. 7 is a schematic view of an embodiment of a targeted area(s) for administering the aerosol from the aerosol generating apparatus.
Figure 8:
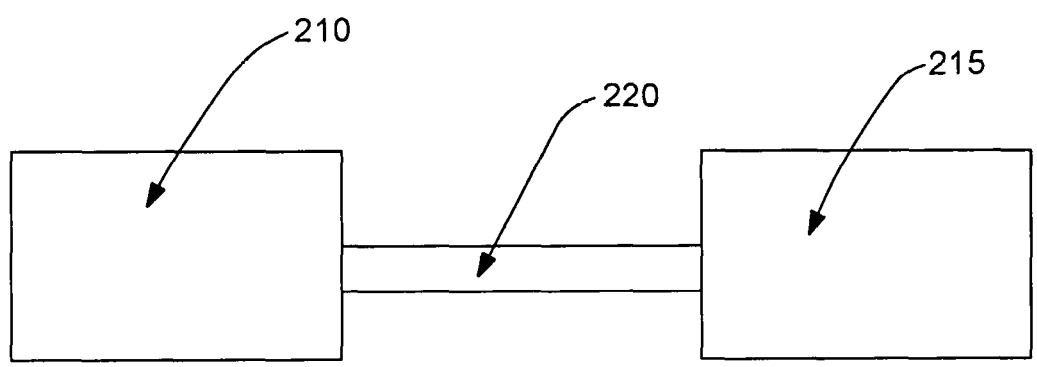
FIG. 8 is a schematic view of an embodiment of an aerosol generating apparatus connected to a targeted area(s) with a pipe through which aerosol can be administered.
Figure 9:
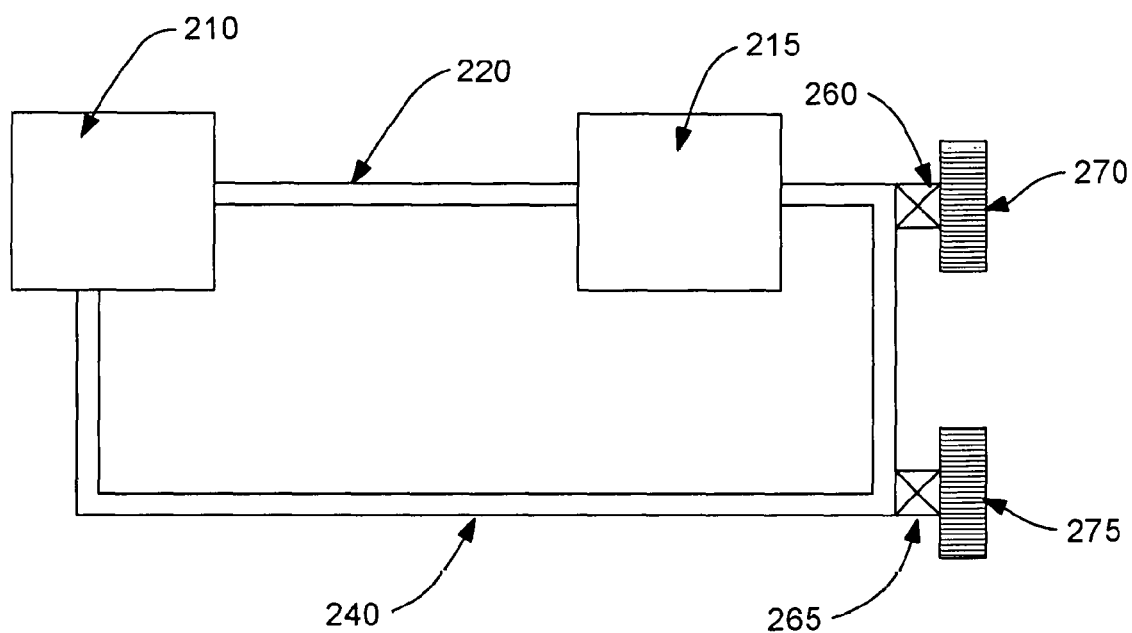
FIG. 9 is a schematic view of an embodiment of an aerosol generating apparatus connected to the targeted area(s) in a closed loop system.

The present invention includes apparatuses and methods related to the generation and delivery or application of an aerosol (200) of liquid (30) that is created with ultrasound or piezoelectric transducers (10), for a wide range of uses including but not limited to: (a) the sanitization, disinfection, high-level disinfection, or sterilization of one or more areas and the surfaces in those areas, (b) the delivery of other types of liquid (30) in the form of an aerosol (200) for various purposes, such as, but not limited to, the application of pesticides, moisture, medication, particles, or nano sized or smaller machines, to one or more areas and surfaces within those area(s). The attributes of the area to which the aerosol (200) is delivered or applied can vary and can include, but is not limited to: spaces that are open, enclosed, semi-enclosed, unsealed, sealed, or partially sealed. It is preferred, without limitation, that the area in which the aerosol is administered in the present invention is enclosed and effectively sealed to prevent the leakage of the aerosol from the enclosed area. Referring initially to FIGS. 7-9, the apparatus (215) can be operated either outside, partially inside and partially outside, or within the area in which the aerosol is deployed or administered.

Preferably and without limitation, an aerosol (200) of a liquid is first generated and/or administered in or into the intended or targeted area (210). This area can also, without limitation, contain one or more objects and surfaces. The aerosol (200) may have various mass concentrations, which is the mass of particulate matter in a unit volume of aerosol. The number concentration of the aerosol (200) may also vary. The number concentration is the number of particles per unit volume of aerosol. It is preferred without limitation, that the aerosol (200) has a higher rather than lower mass concentration of droplets. It is preferred without limitation, that the aerosol (200) has a higher rather than lower number concentration of droplets. The aerosol (200) droplets may be of various sizes. The aerosol may be created from any liquid containing one or more chemical(s) of any kind, or a combination of liquids each containing one or more of any kind of chemical(s).

According to an embodiment, it is preferred, without limitation, that the aerosol (200) is a ten micron to submicron size droplet. The fog or aerosol can, without limitation, consist substantially of submicron aerosolized droplets. The fog or aerosol can, without limitation, have characteristics that include but are not limited to (1) a faster anti-pathogen, toxin, fungal, sterilization, disinfection, or sporicidal effect than the non-aerosolized liquid; (2) the ability to penetrate and disinfect, high-level disinfect or sterilize, areas and surfaces where aerosols comprised of droplets greater than two microns may not work; (3) resists coalescence and condensation typical of larger size droplets; and/or (4) dense packing of small particles provides an unprecedented droplet surface area per volume of gas.

The apparatus and methods described in the present invention can pertain to any aerosol generator or aerosol generator that uses ultrasound or piezoelectric transducers (10). They may also pertain to an aerosol producing apparatus as described in the present invention, including the specifics of the present invention hereto mentioned. This apparatus is further described with the attributes discussed below. Referring to FIGS. 11-13, 16-32 and 35-36, which shows the preferred apparatus (215) in the present invention, the apparatus (215) generates aerosol (200) by operating one or more piezoelectric transducers (10), in parallel or series. One or more amplifiers (230) may be used. It is preferred, without limitation, that the transducer(s) (10) receive signal or power from at least one amplifier(s) (230), and that multiple transducers are operated in parallel. One or more transducers (10) are located under the surface of the liquid (30) in one or more reservoirs, chambers, basins, or tanks (40) (herein referred to as reservoir(s)) at an effective depth and orientation. The reservoir(s) (40) may be made from any material that is compatible, and suitable for use with the liquid (30). The aerosol (200) generated by operation of the transducer(s) (10) forms above the surface of the liquid (30) in the reservoir(s) (40) and may be transferred from the reservoir(s) (40) to one or more targeted area(s) or chamber(s) by one or more fan(s) or blower(s) or other source of pressurized air or gas (herein referred to as blower(s)) (180).

The air and aerosol (200) can, without limitation, flow from the aerosol generator (110) to the one or more targeted area(s) (210) through one or more pipe(s) (220). It is preferred, without limitation, that only one reservoir (40) in which the transducer(s) are located is utilized in the apparatus (215) of the present invention. The reservoir(s) (40) can be, without limitation, unenclosed, semi-enclosed, or enclosed. It is preferred, without limitation that an enclosed reservoir(s) is utilized, and is built in a manner known in the art so that air from a fan or blower can flow through it and carry the generated aerosol out of the reservoir and away from the apparatus (215).

The air and aerosol can flow through a zig-zag path or be directed around one or more baffle plates (250), positioned anywhere in the path of the air/aerosol as it moves from the reservoirs in which the transducers are located to the exterior of the apparatus (215). The use of the aforementioned baffle plate(s) is taught at (col. 4, line 18-22) of U.S. Pat. No. 4,366,125 (Kodera et al., 1980), which is incorporated herein by reference in its entirety, including any references cited therein.

If needed or desired, the apparatus (215) in the present invention can be connected in a closed loop or system as shown in FIG. 9, to the targeted area(s) or chamber(s) (210), as taught at (pg. 3 col. 23-34) of G.B. Patent No. 1,128,245, (Rosdahl et al., 1968), which is incorporated herein by reference in its entirety, including any references cited therein. The air and aerosol (200) discharged from the apparatus (215) in the present invention, can be delivered with one or more pipe(s) or conduit(s) (220). The air and aerosol (200) may also be recirculated through one or more return pipe(s) or conduit(s) (240) from the targeted area(s) or chamber(s) (210), back to the air/gas intake(s) (255) for the fan(s) or blower(s) (180). Throughout the present invention, the terms "pipe", "pipes", or "piping" includes pipes, ducts, conduits, tunnels, and the like. In addition, the aforementioned closed loop or system can have, without limitation, one or more air/gas valve(s) (260) that can allow non-filtered or filtered inbound air/gas into the said closed loop or system, as well as one or more air/gas valve(s) (265) that can allow non-filtered or filtered inbound air/gas out of the said closed loop or system. The air/gas that is supplied via the inbound air/gas valve(s) (260) can be supplied, without limitation, from the atmosphere surrounding the apparatus (215) and the air/gas that passes through the outbound air/gas valve can be, without limitation, vented into the atmosphere surrounding the apparatus (215). The filter(s) (265) can be or consist of any filter design, material, or other effective means for the intended application. The filter or its application can include, without limitation, what is taught in U.S. Pat. No. 4,512,951 (Koubek et al., 1983), and incorporated herein by reference in its entirety, including any references cited therein. The said air/gas valves (260) or (265) can, without limitation, be electronically or electrically opened and closed in a manner known to those skilled in the art, and can be positioned or interfaced in numerous places in the closed loop or system. The outbound air or aerosol can, without limitation, be filtered with one or more filters (270) to prevent any employees or operators from being exposed to any vented aerosol, and to comply with any worker safety or environmental safety guidelines or regulations.

The liquid capacity of the reservoir(s) (40) in which the transducer(s) (10) are located can vary, but the liquid level is at least at a suitable depth or level so that the transducer(s) (10) can effectively and safely operate. The reservoir(s) (40) in which the transducer(s) (10) are located is connected to one or more tanks(s) (280) that are connected and feed liquid to the reservoir(s) (40). The tank(s) (280) that feeds or supplies the liquid (30) can be of any size, geometry, shape, and capacity, and may be made from any material that is compatible, and suitable for use with the liquid (30). The tank(s) (280) may be non-ventilated, or ventilated in one or more places in a way know to those skilled in the art, and the means to ventilate the tank(s) (280) can incorporate a suitable filter. The filter(s) are any suitable filter for the intended application, and are known to those skilled in the art. It is preferred, without limitation, that the apparatus (215) in the present invention has only one tank (280) that feeds or supplies liquid to the reservoir (40) in which the transducer(s) (10) are located. However, a means known to those skilled in the art can be provided so that additional tanks (280) can be attached to or interfaced with the apparatus (215) and feed liquid to either the main feed or supply tank (280) or the reservoir(s) (40) in which the transducers (10) are located.

The one or more tank(s) (280), that feeds or supplies the liquid (30) to the reservoir(s) (40) in which the transducer(s) (10) are located, can be filled in various ways, including, but not limited to, directly pouring a liquid that is either mixed or unmixed into one or more feed interface(s) (285) or pipe(s) (295) that are connected to the said tank(s) (280). Without limitation, the feed interface(s) (285) or pipe(s) (295) orifices can have: (a) a funnel or be shaped like a funnel to make pouring the liquid (30) into the feed interface(s) (285) or pipe(s) orifices (295) easier, (b) a tray or bowl located under or around the outer edges of the feed interface(s) (285) or pipe(s) orifices (295) to catch any spilled liquid (30) in a manner known in the art. Without limitation, the apparatus (215) in the present invention can also be designed and constructed, in a manner that is known to those skilled in the art, so that it can interface with one or more disposable or reusable containers or cartridges (herein referred to as "cartridge", "cartridges", or "cartridge(s)") (290) used to supply, fill, or refill the apparatus (215) with liquid (30). Without being limited, the cartridges (290) and apparatus (215) can be designed in a manner known in the art, so that only unique, special, or proprietary cartridges (290) may be used. The means to interface the cartridge(s)s with the apparatus (215) so that the liquid is effectively and safely transferred from the cartridges (290) into the said reservoir(s) (40), is known to those skilled in the art.

The reservoir(s) (40) in which the transducer(s) (10) are located can also have one or more valves (300) that can, without limitation, control the flow of liquid (30) from the tank(s) (280) that feed or supply the said reservoir(s) (40). Without limitation, the valve(s) (300) can be connected to one or more sensor(s) (305) or PLC(s) (315) which are known to those skilled in the art, that can cause the valve(s) (300) to close or open and allow liquid (30) to flow into the reservoir(s) (40) in which the transducer(s) (10) are located when the liquid (30) level or depth in the reservoir(s) (40) reaches a specified level. The depth or level of the liquid (30) causing the valve (300) to open can vary. The sensor (305) can include, but is not limited to a float switch. The valve (300) can include, but is not limited to, a solenoid valve. However, it is preferred in the present invention that at least one float-valve is used, which consists of a valve (300) that is mechanically or electrically opened or closed by the movement of a float which acts as the sensor (305).

The reservoir(s) (40) in which the transducer(s) (10) are located, can have one or more float switch(s) or other sensor(s) (305) that can cause the apparatus (215), the PLC, (315), HMI (320), or any other parts or components, to enter a fault/error mode or completely shut down if the depth of the liquid (30) exceeds a certain specified depth or level. The float switch or other sensor(s) (305) is actuated and communicates or is connected to suitable circuitry, all in a way known to those skilled in the art, to cause the apparatus (215), the PLC, (315), HMI (320), or any other parts or components to shut down or enter a fault or error mode when the depth or level of liquid (30) exceeds a specified depth. The positioning of the float switch(s) or other sensor(s) (305) can vary inside the reservoir(s) (40). It is preferred in the present invention that at least one float switch (305) is utilized for this purpose.

A float switch or other liquid level sensor(s) (305) can also be used to detect and communicate or is connected to suitable circuitry, all in a way known to those skilled in the art, to cause the apparatus (215), the PLC, (315), HMI (320), or any other parts or components to shut down or enter a fault or error mode when the depth or level of liquid (30) drops below a certain point or depth in the reservoir(s) (40) in which the transducer(s) (10) are located. This can, without limitation, prevent the liquid (30) in the reservoir(s) (40) from dropping to an ineffective or unsafe depth or level. This condition may occur from situations including, but not limited to, a valve (300) that is stuck closed from a tank (280) that supplies the liquid, or a leaking tank. The positioning of the float switch(s) or other sensor(s) (305) can vary inside the reservoir(s) (40). It is preferred in the present invention that at least one float switch or liquid level sensor (305) is utilized for this purpose.

The fan or blower (180), or other source of pressurized air or gas, may also be constructed from any suitable material that is not affected by the chemical action of the liquid (30). Suitable materials may include PVC, polypropylene, and stainless steel, but other suitable materials may also be used. The blower(s) can either push or pull the air or gas, as well as aerosol, through, or across, the chamber, reservoir, or other area in which the aerosol is generated to remove it from the apparatus (215). The blower(s) (180) or other source of pressurized air or gas can move any quantity of air at any speed sufficient for the intended application. The blower(s) (180) can also be chosen, without limitation, to meet the following variables that include, but are not limited to: (a) the quantity of aerosol that is being generated, (b) the amount of surface disruption that it might create and its effect on aerosol production, (c) the desired quantity of aerosol that is evacuated from the apparatus (215), (d) the geometry and volume of the targeted area, (e) the geometry and volume of any conduit or piping that may be used to deliver the aerosol, (f) the manner and effectiveness in which the targeted area is sealed, (g) and uniformity of the aerosol (200) deployment or administration in or into the targeted area. Without limitation, the blower(s) (180) can be controlled by the PLC (315) in a manner known in the art.

Certain applications will require lower airflows, while other applications will require higher airflows. It is preferred, without limitation, that the blower (180) used in the present invention is a centrifugal fan or blower and that it is constructed using polypropylene for a housing and impeller, and 316L stainless steel for its drive shaft. It is further preferred, without limitation, that the fan or blower (180) pushes air/gas and aerosol out of the chamber, reservoir, or other area in which the aerosol is generated. The housing or enclosure for the blower(s) (180) can be plumbed to remove any excess liquid that may collect as the blower is operated. It is preferred, without limitation, that the housing or enclosure for the blower(s) (180) is plumbed in the present invention.

According to the prior art established by U.S. Pat. No. 4,366,125 (Kodera et al., 1980), and the book titled, "Aerosol Technology" by William C. Hinds (1982), the liquid (30) utilized in the present invention can be heated by using three different means, or a combination of one or more of the three different means. First, the liquid (30) can be heated inside the reservoir(s) (40) in which the transducers (10) are located, by utilizing one or more means to provide heat (150) that is either in direct contact with the liquid or interface with the walls of the reservoir(s) (40), or both. Second, the liquid (30) in the reservoir(s) in which the transducer(s) (10) are located can also be heated by circulating it through one or more means to heat (310) the liquid, and back into the reservoir(s) (40). Third, the liquid can be heated as it flows from one or more tank(s) (280), that feeds or supplies the liquid (30) to the reservoir(s) (40) in which the transducers (10) are located.

In addition, and without limitation, the one or more valves (300) that control the flow of the liquid (30) can be electrically or electronically signaled to open, close, or semi-open, in a manner known in the art. A pump or other means (130) can move the liquid (30) intermittently or can continuously circulate the liquid (30) from the reservoir(s) (40) in which the transducers (10) are located, back to the aforementioned tank(s) that feeds or supplies the liquid (30) to the reservoir(s) (40). Without being limited, the valves (300) in this situation can be maintained in a semi-open or open position unless signaled or caused by some other means including, but not limited to, an electrical signal from an electronic controller or programmable logic circuit (315), to close, for various reasons including, but not limited to, a pump (130) failure that would cause the reservoir(s) (40) in which the transducers (10) are located to overflow.

It is preferred, without limitation, that one or more means (150) for heating the liquid (30) is located inside or partially inside the reservoir(s) (40) in which the transducers (10) are located, and is installed into or interfaced with the said reservoir(s) (40) in a way that is known to those skilled in the art. It is further preferred, without limitation, that the said means for heating (150) the liquid (30) is a cartridge heater.

The three aforementioned means to heat the liquid (30) are known to those skilled in the art, and are sufficiently designed and built for their intended purpose, and may be constructed from any material that is compatible, and suitable for use with the liquid (30). Properly heating the liquid (30) to the desired, or efficacious temperature can involve issues such as, but not limited to, the type of heater(s) that would be effective, the number of heater(s) used, the heat output of each heater, the duration and timing of operation for each heater, the intensity of the heat generated, the materials of construction, and are known to those skilled in the art. In addition, the pump or other means (130) used to circulate the liquid (30) provides the necessary flow rate or pumping capacity, which can vary, for the intended application and may be constructed from any material that is compatible, and suitable for use with the liquid (30).

Figure 10:
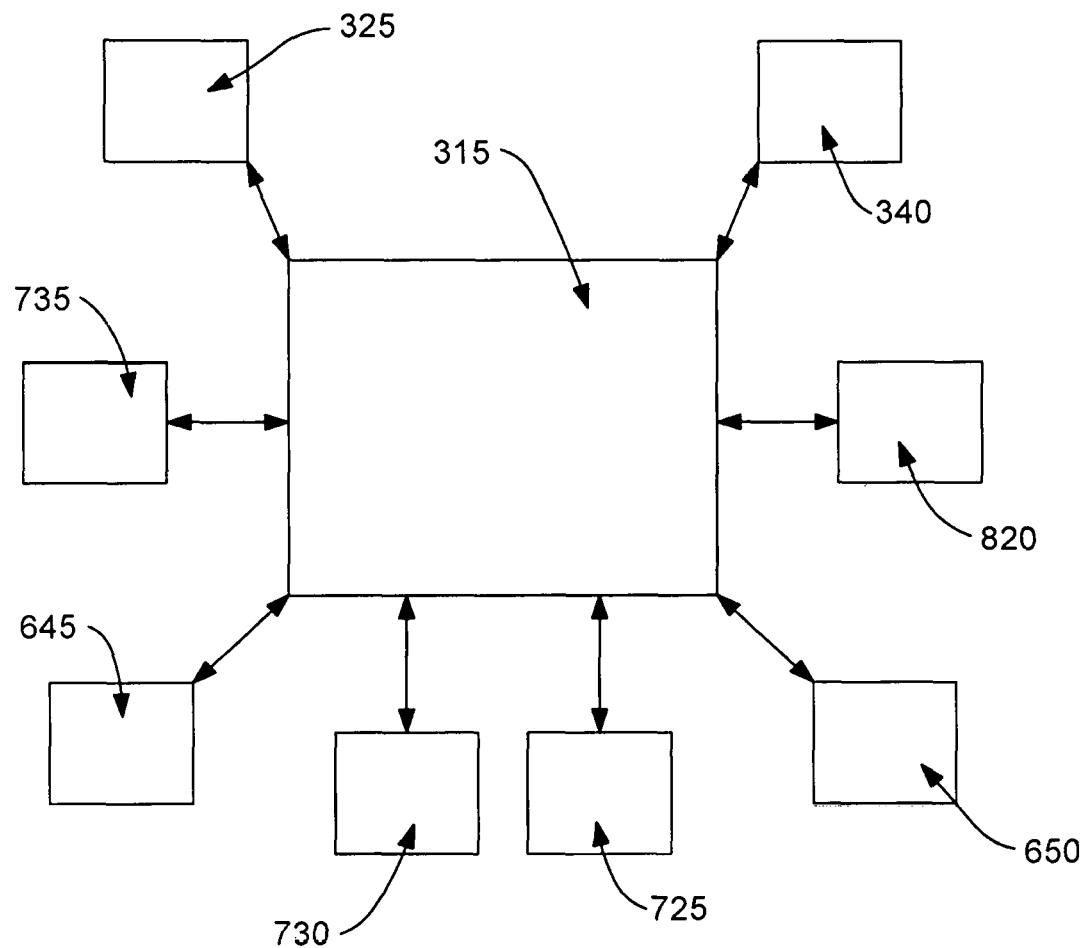
FIG. 10 is a schematic view of an embodiment of a PLC connected to various components of the aerosol generating apparatus.
Figure 11:
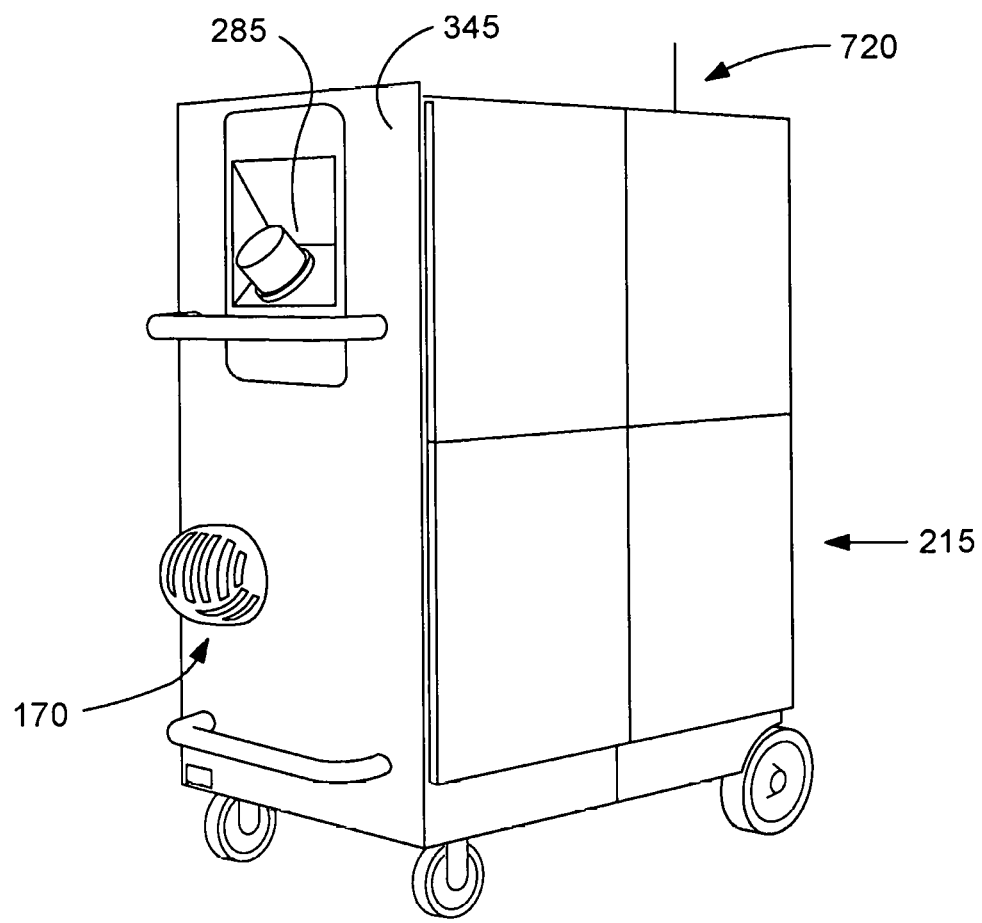
FIG. 11 is an isometric view of an embodiment of an aerosol generating apparatus according to the present invention.
Figure 12:
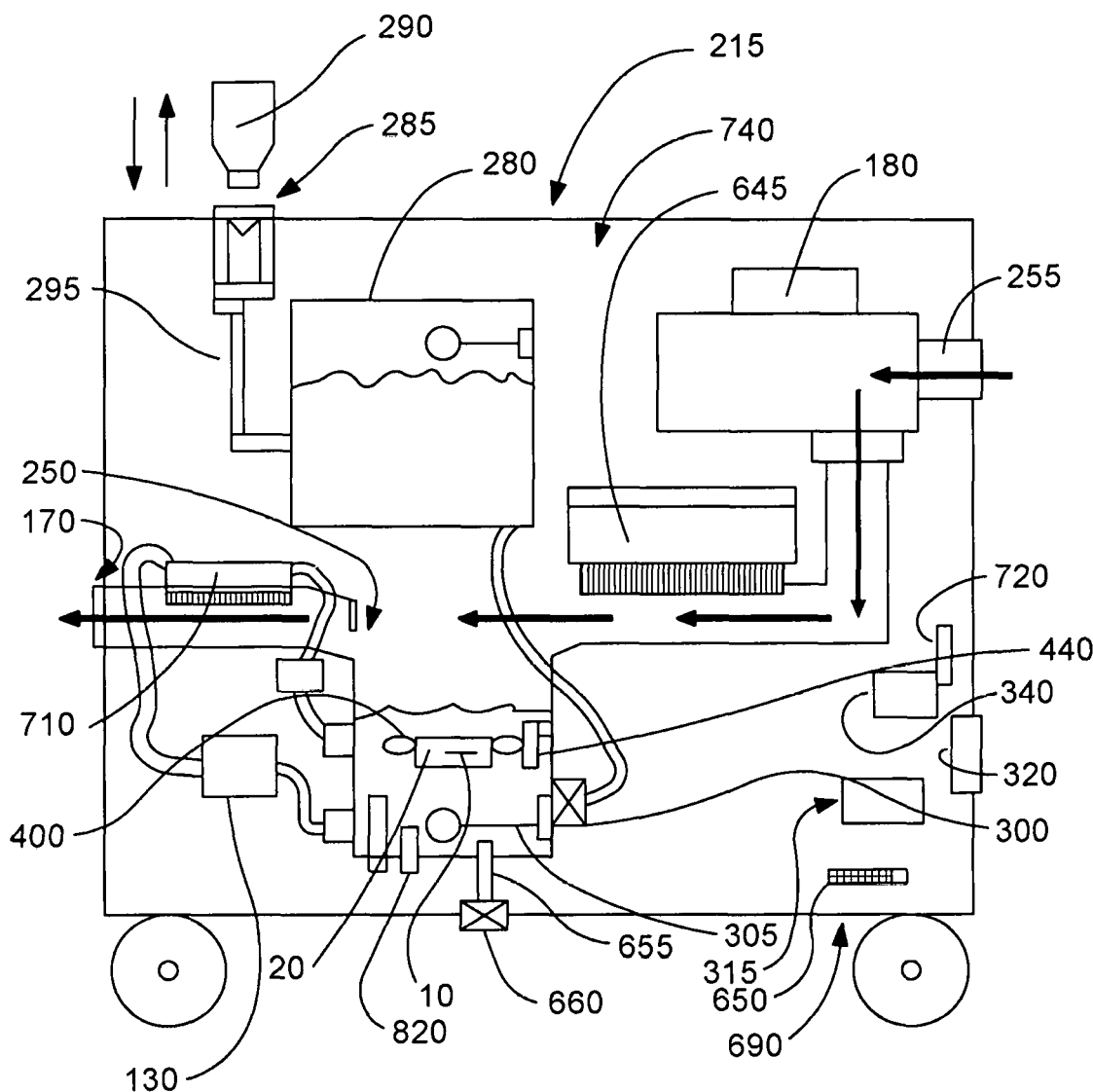
FIG. 12 is a schematic view of an embodiment of an aerosol generating apparatus according to the present invention.
Figure 13:
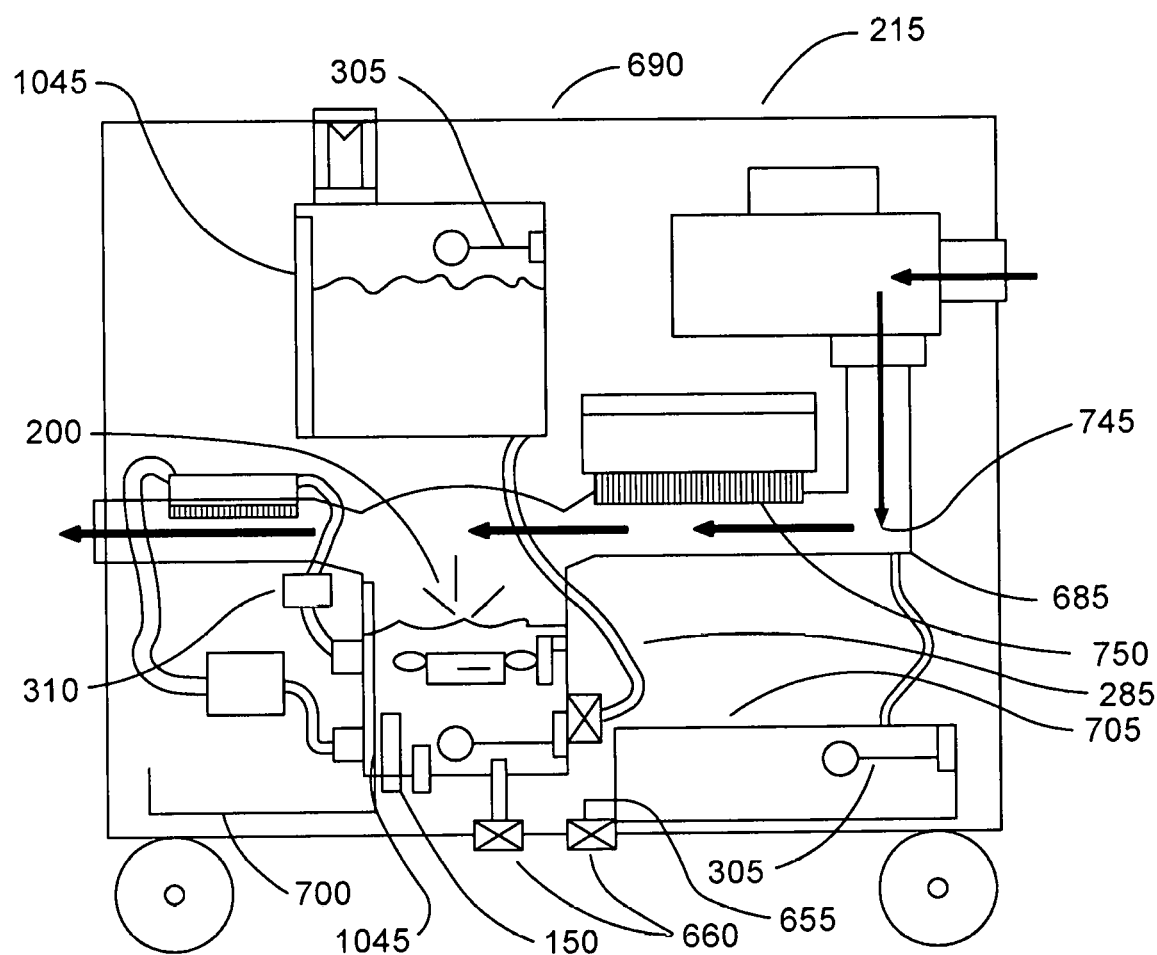
FIG. 13 is a schematic view of an embodiment of an aerosol generating apparatus according to the present invention.
Figure 14:
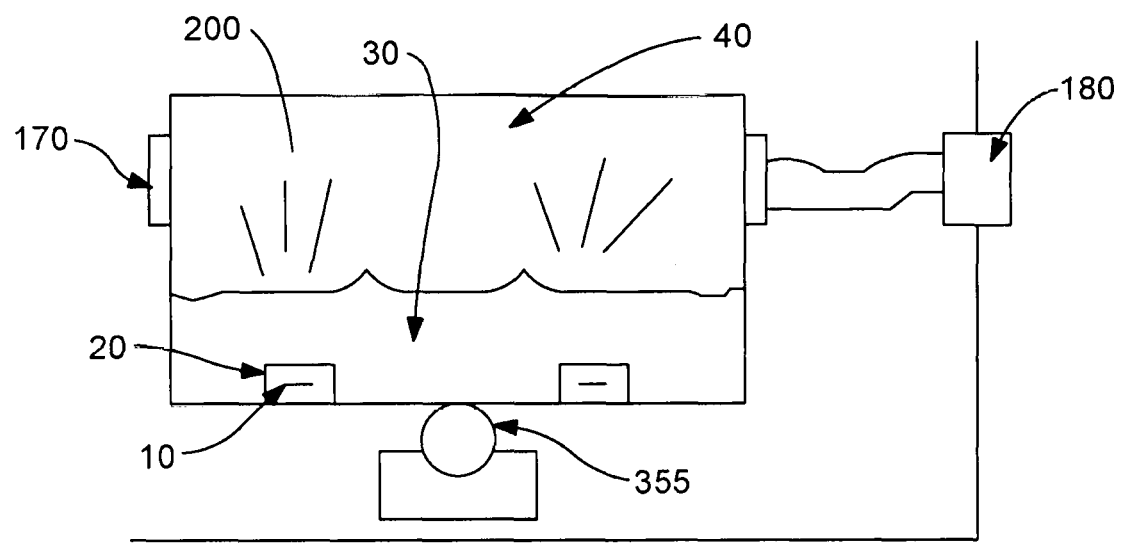
FIG. 14 is a schematic view of an embodiment of aerosol generating transducers attached to a reservoir that is connected to a means that can enable the transducers and/or their liquid facing surfaces to match the angle of or remain aligned with, the surface of the liquid above them.
Figure 15:
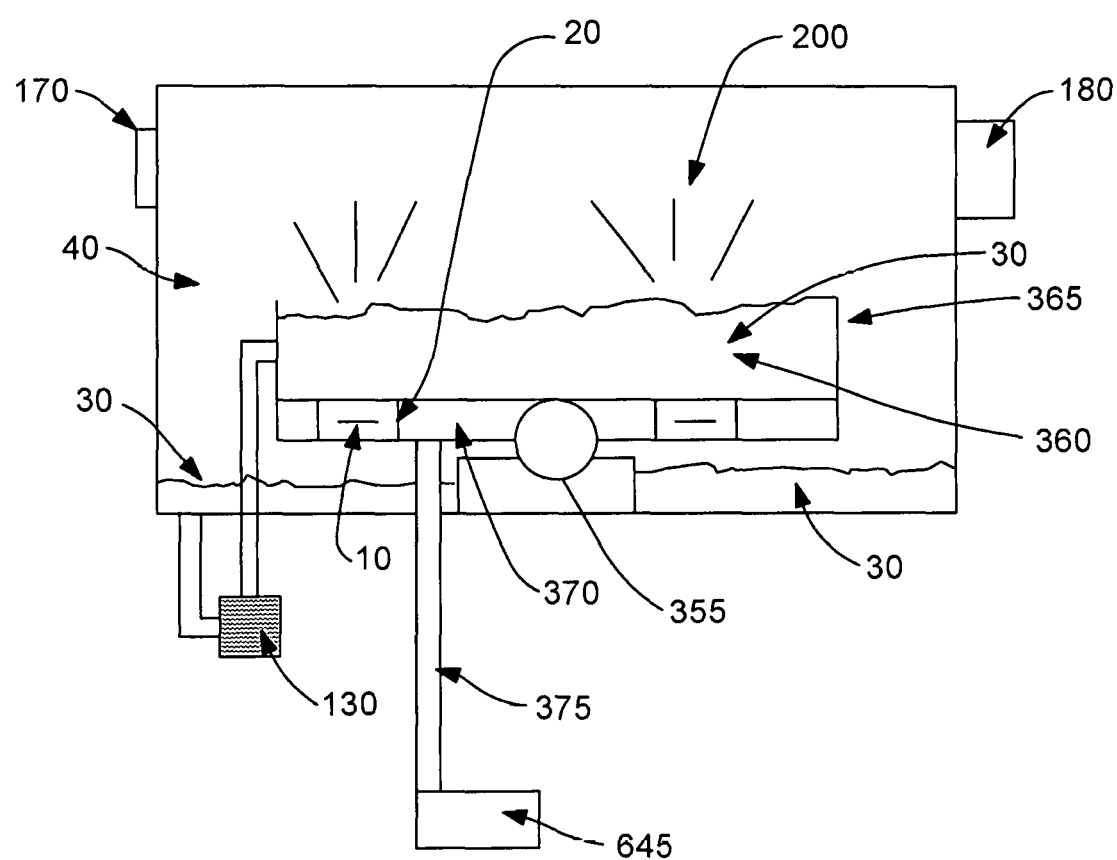
FIG. 15 is a schematic view of an embodiment of aerosol generating transducers attached to a secondary reservoir inside of a main reservoir and that is connected to a means that can enable the transducers and/or their liquid facing surfaces to match the angle of or remain aligned with, the surface of the liquid above them.
Figure 16:
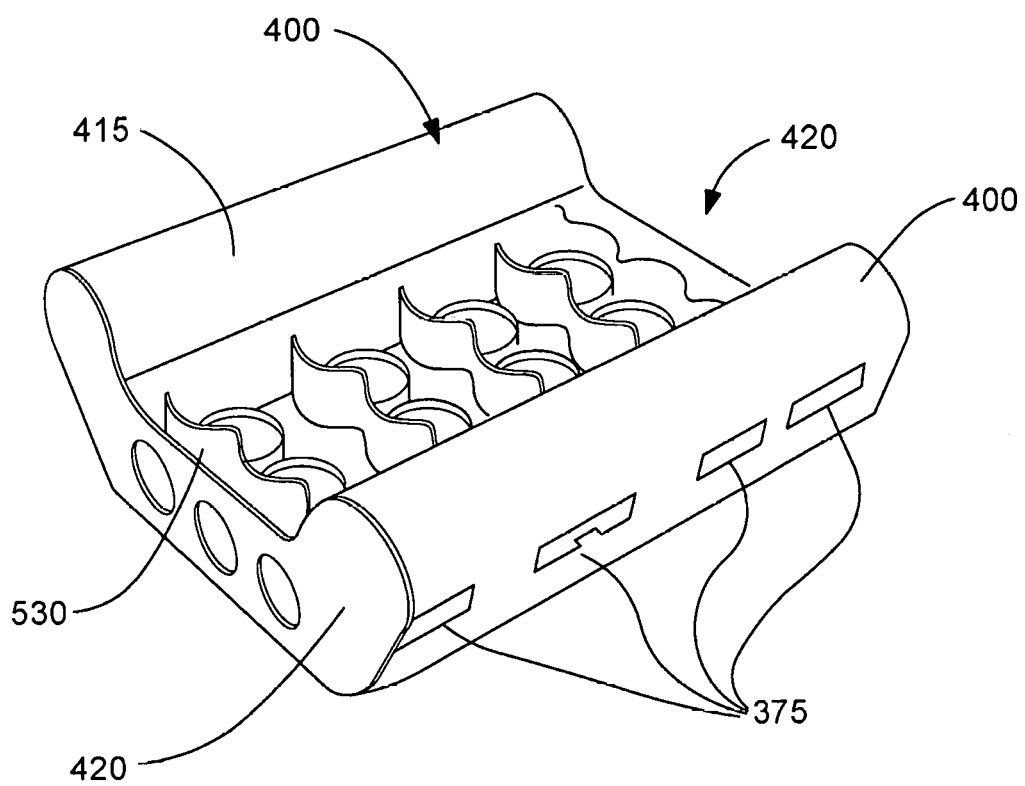
FIG. 16 is an isometric view of an embodiment of multiple transducers interfaced with multiple housings, and the housings are attached to multiple buoyant objects.
Figure 17:
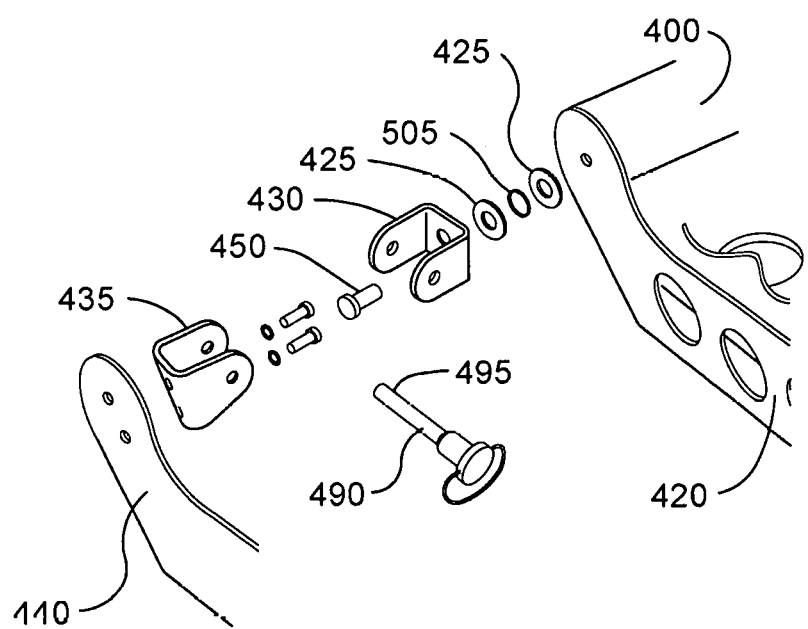
FIG. 17 is a partially broken away, exploded isometric view of an embodiment of more than one clevis assembly that allows various ranges of motion for various parts and components such as, the transducers, housings, and buoyant objects according to the present invention.
Figure 18:
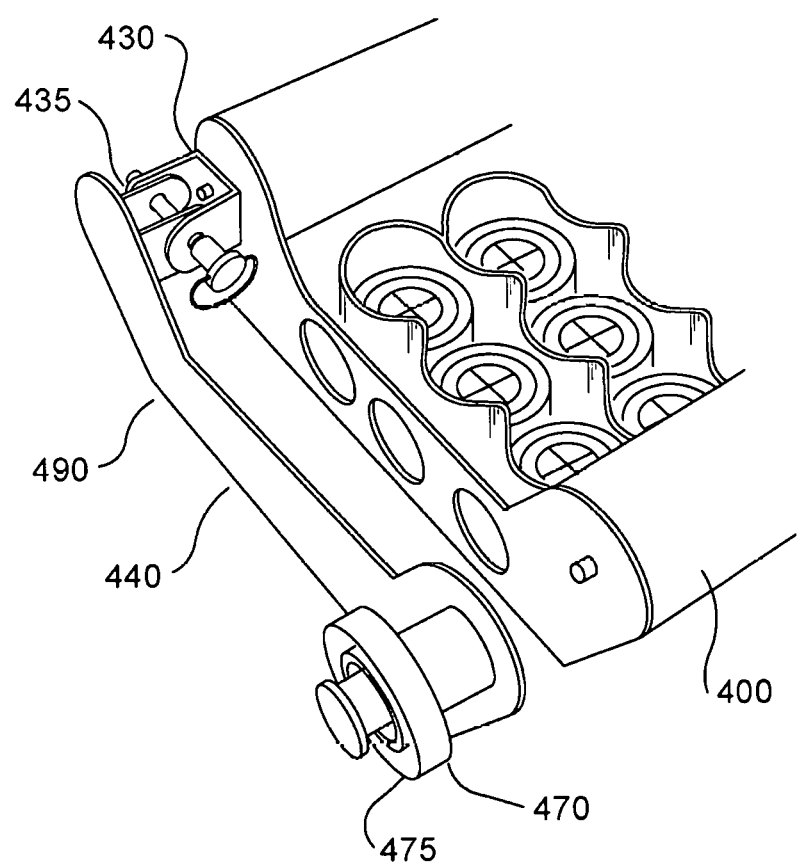
FIG. 18 is a partially broken away isometric view of an embodiment of the pivot arm assembly that allows various ranges of motion for various parts and components such as, the transducers, housings, and buoyant objects, according to the present invention.
Figure 19:
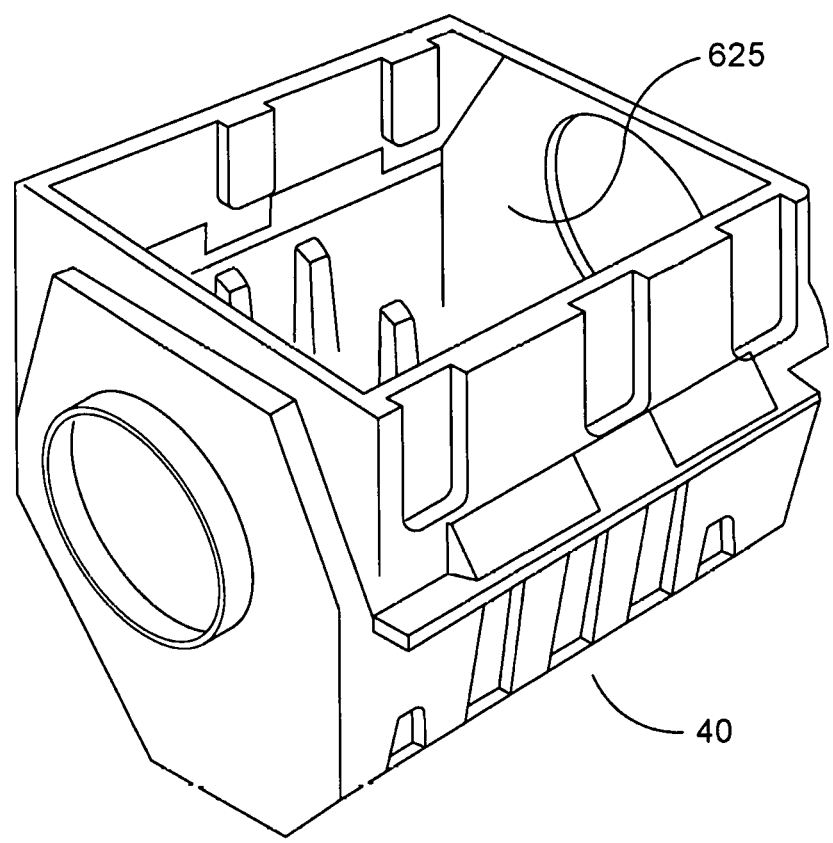
FIG. 19 is a schematic view of an embodiment of the reservoir in which the transducers are located according to the present invention.
Figure 20:
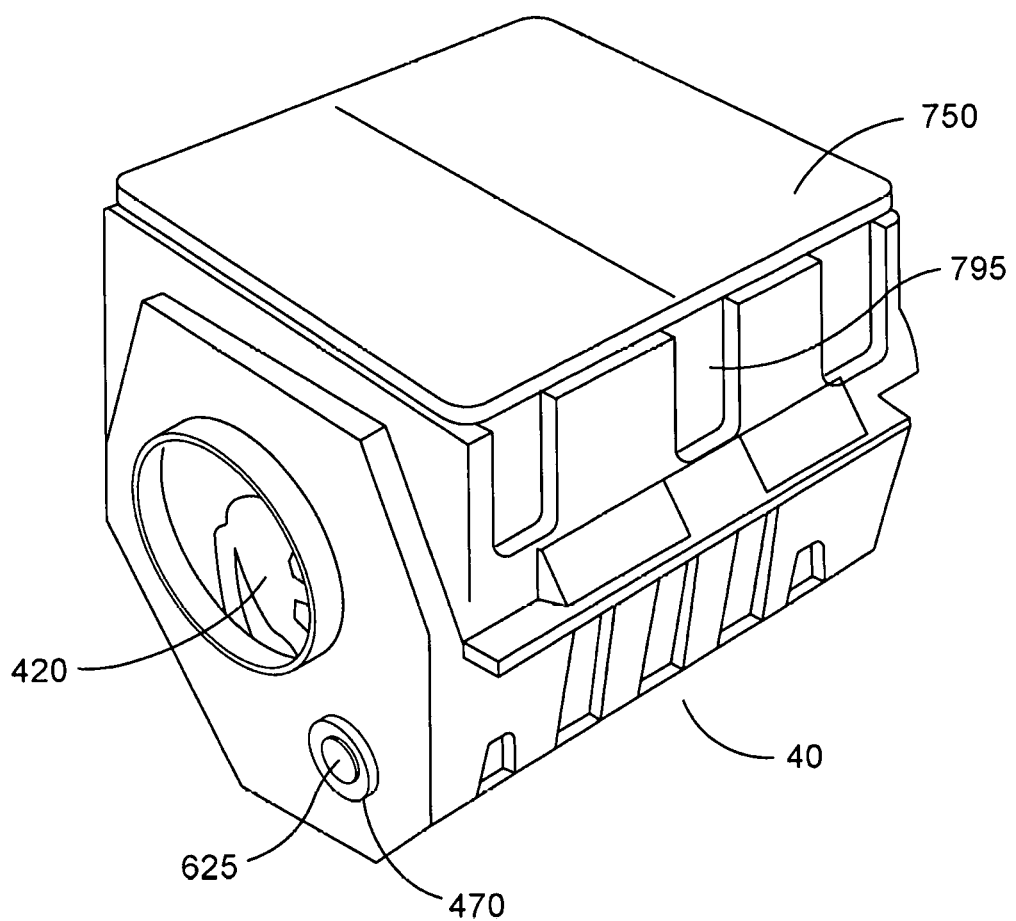
FIG. 20 is an isometric view of an embodiment of a heat sink interfacing with the reservoir in which the transducers are located with the cooling fins of the heat sink effectively positioned within the air stream that passes through the reservoir, in addition a hole which interfaces with the pivot arm is positioned within the wall of the reservoir.
Figure 21:
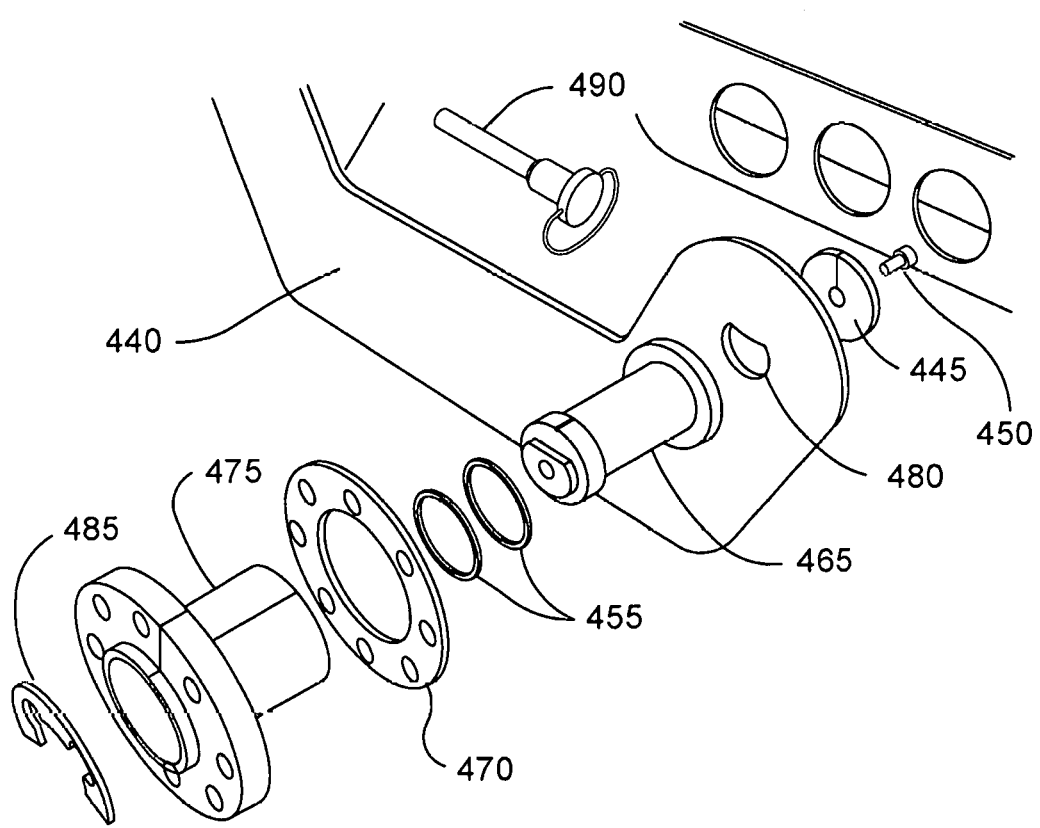
FIG. 21 is a partially broken away, exploded isometric view of an embodiment of the pivot arm assembly that consists of various parts and components according to the present invention.
Figure 22:
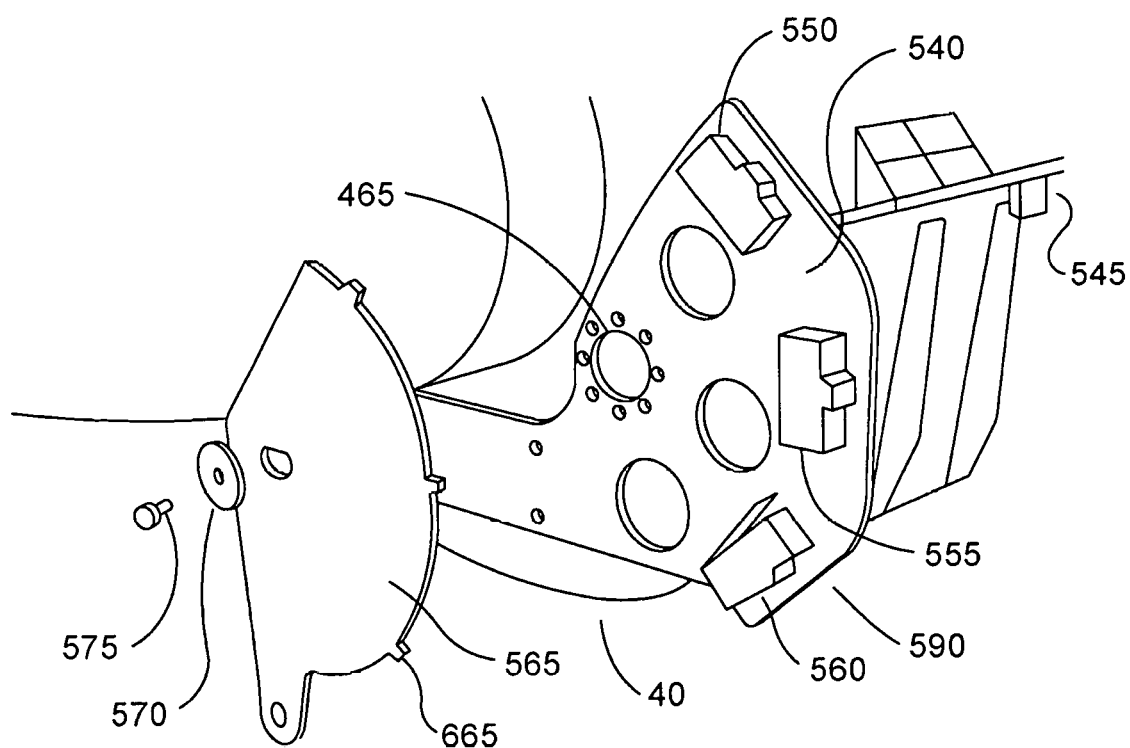
FIG. 22 is a partially broken away, exploded isometric view of an embodiment of the means used to actuate the various switches to communicate any information or status related to the reservoir or within the reservoir to the PLC, and consists of components such as, switches, switch actuator plate, protrusions, torque tube, and base plate.
Figure 23:
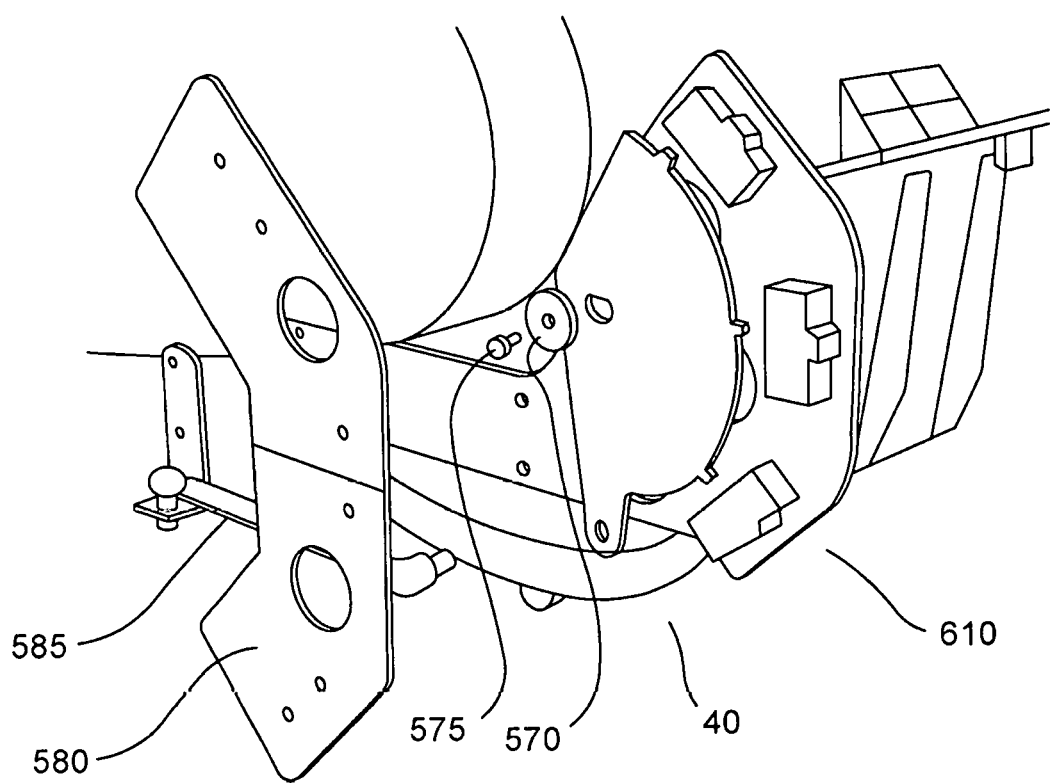
FIG. 23 is a partially broken away, exploded isometric view of an embodiment of the means used to actuate the various switches to communicate any information or status related to the reservoir or within the reservoir to the PLC, and consists of components such as, switches, switch actuator plate, protrusions, torque tube, base plate, cover plate, and hydraulic dampener.
Figure 24:
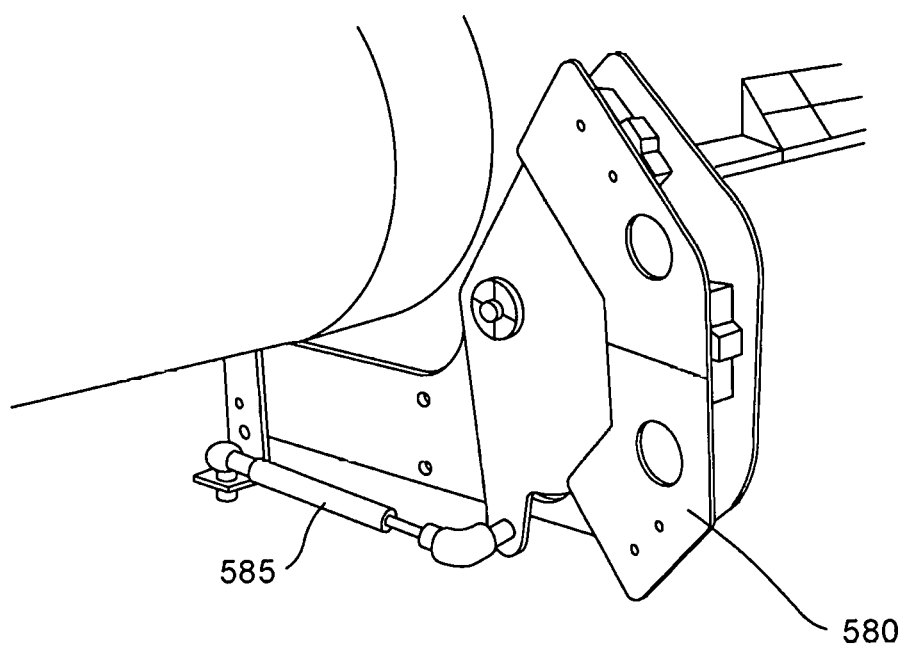
FIG. 24 is a partially broken away isometric view of an embodiment of the means used to actuate the various switches to communicate any information or status related to the reservoir or within the reservoir to the PLC, and consists of components such as, switches, switch actuator plate, protrusions, torque tube, base plate, cover plate, and hydraulic dampener.
Figure 25:
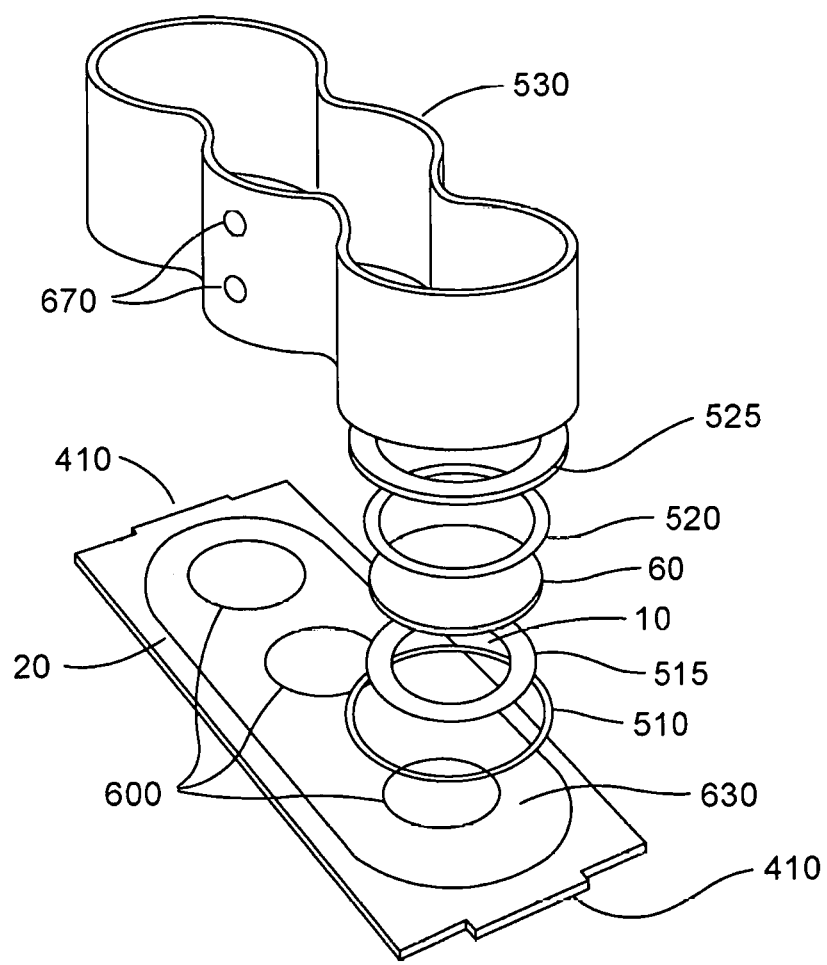
FIG. 25 is an exploded isometric view of an embodiment of an enhanced design for interfacing one or more transducers or transducer assemblies with their housing, consisting of various features, parts, and components according to the present invention.
Figure 26:
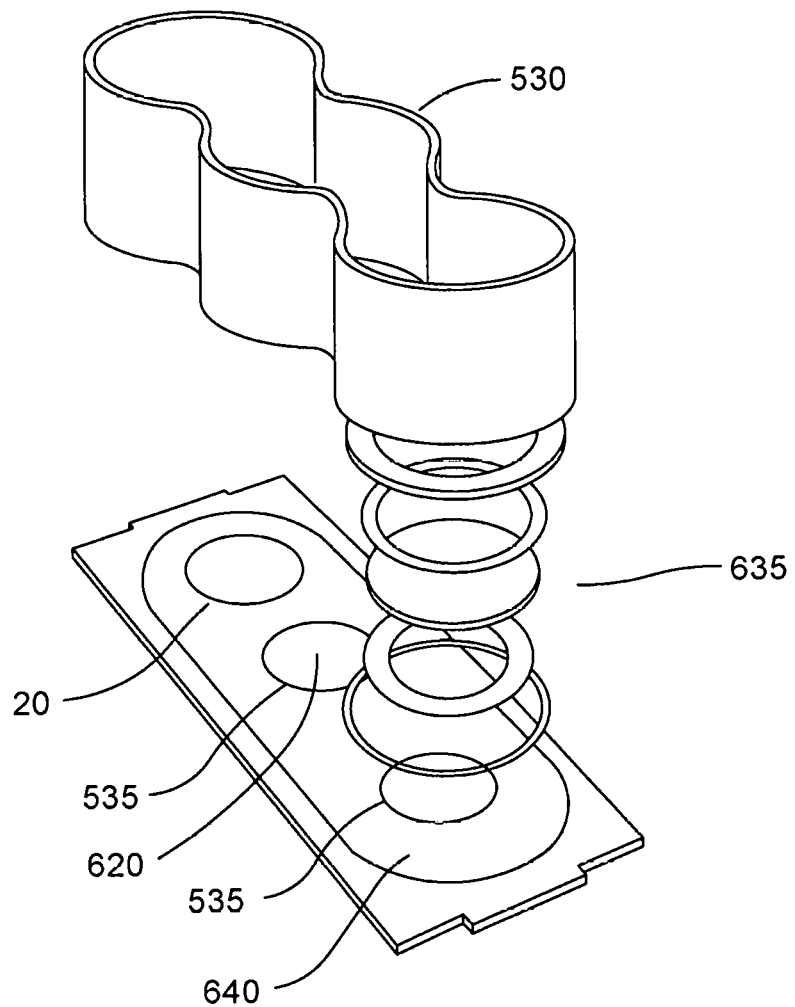
FIG. 26 is an exploded isometric view of an embodiment of an enhanced design for interfacing one or more transducers or transducer assemblies with their housing, consisting of various features, parts, and components according to the present invention.
Figure 27:
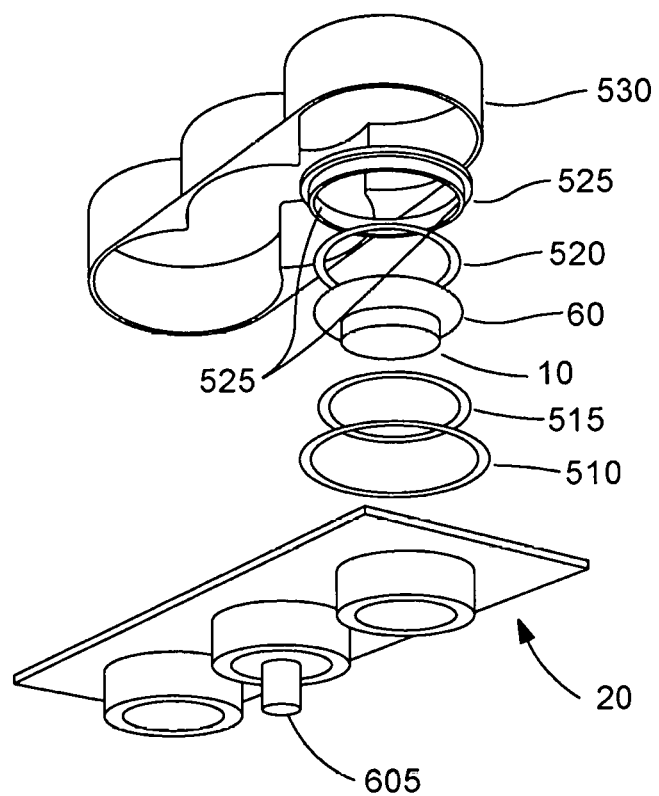
FIG. 27 is an isometric view of an embodiment of an enhanced design for interfacing one or more transducers with their housing, consisting of various features, parts, and components according to the present invention.
Figure 28:
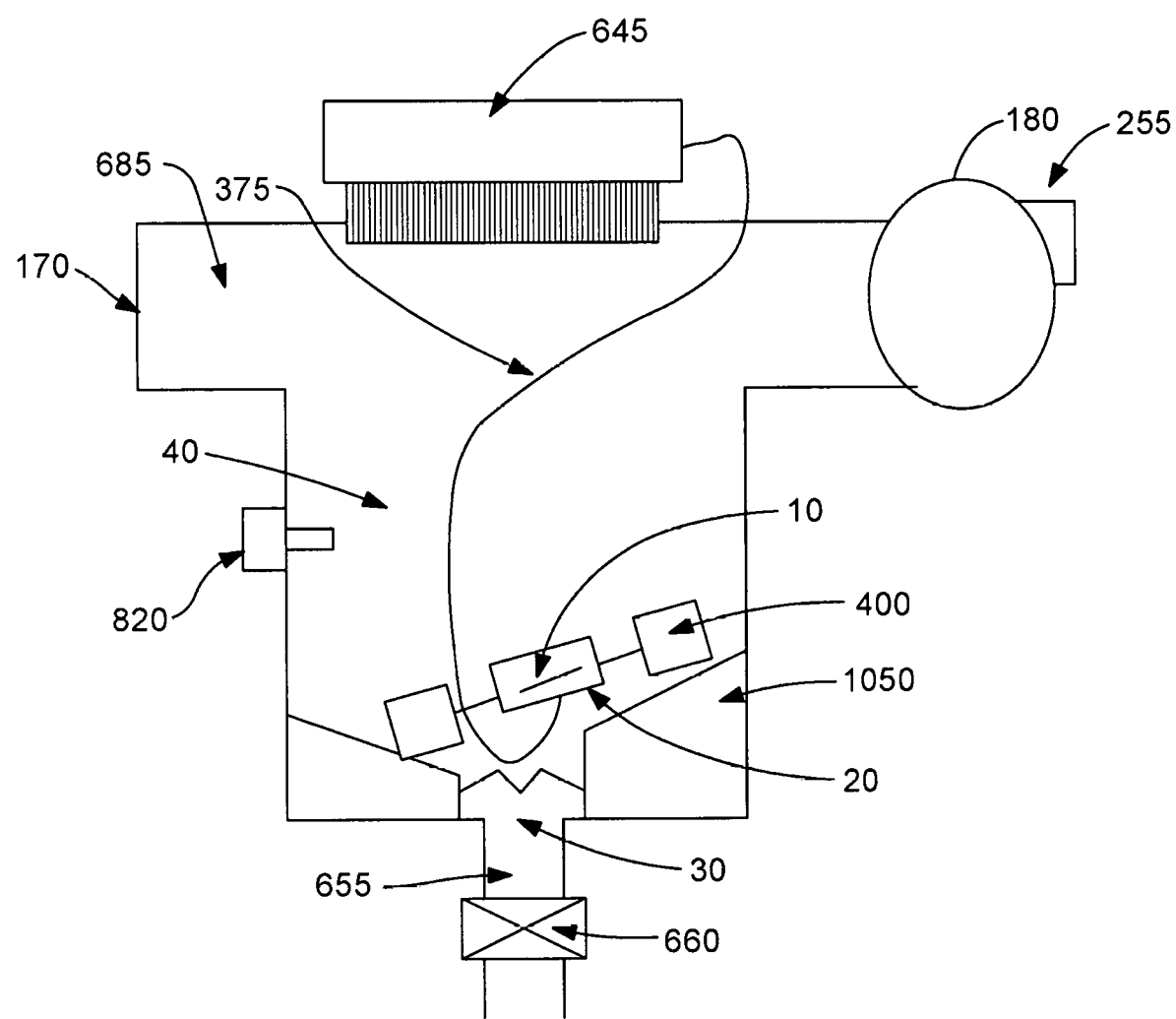
FIG. 28 is a schematic view of an embodiment of a means for the transducer housing, buoyant objects, or other parts and components to interact with any means so that the transducers or transducer assemblies are angled when the liquid in the reservoir is at a specified level or is drained.
Figure 29:
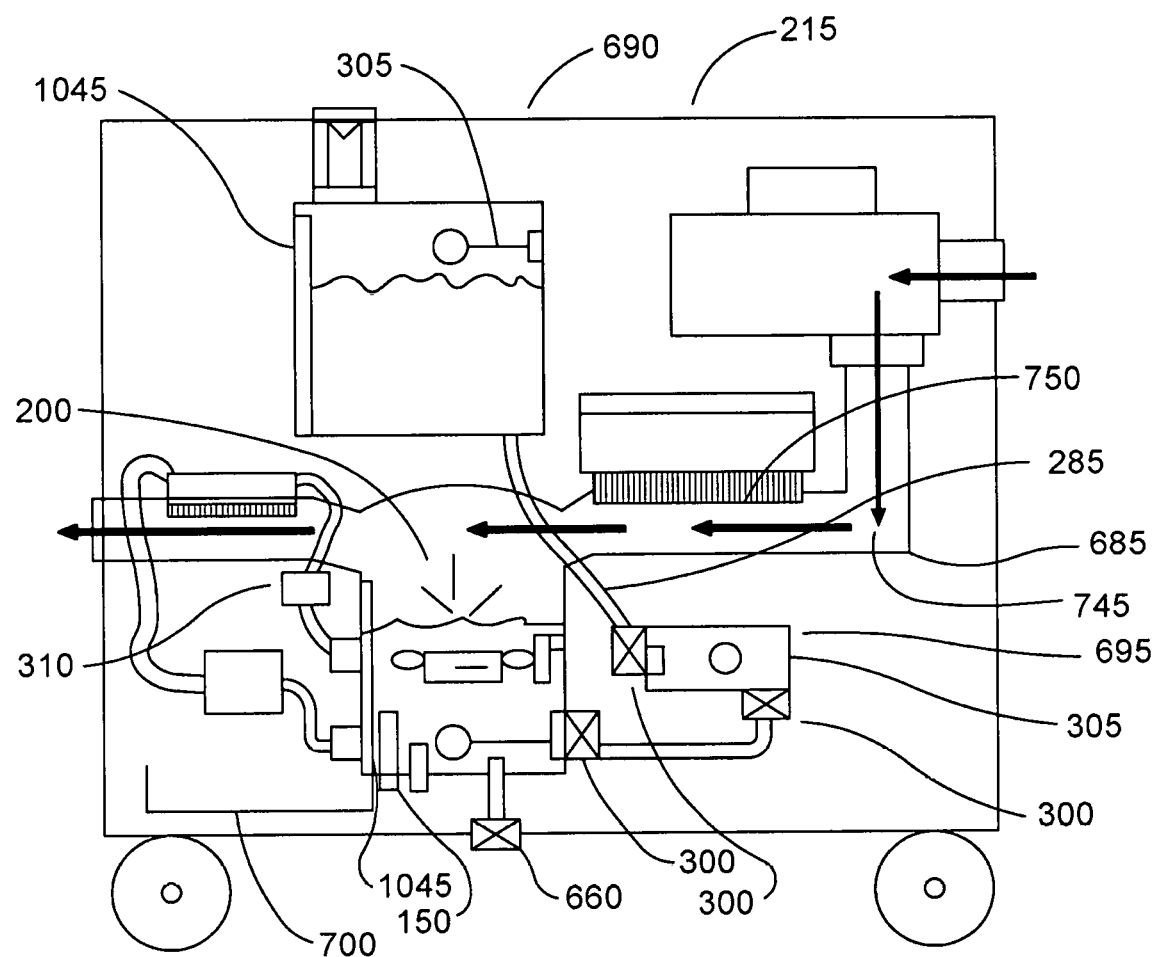
FIG. 29 is a schematic view of an embodiment of an aerosol generating apparatus according to the present invention.
Figure 30:
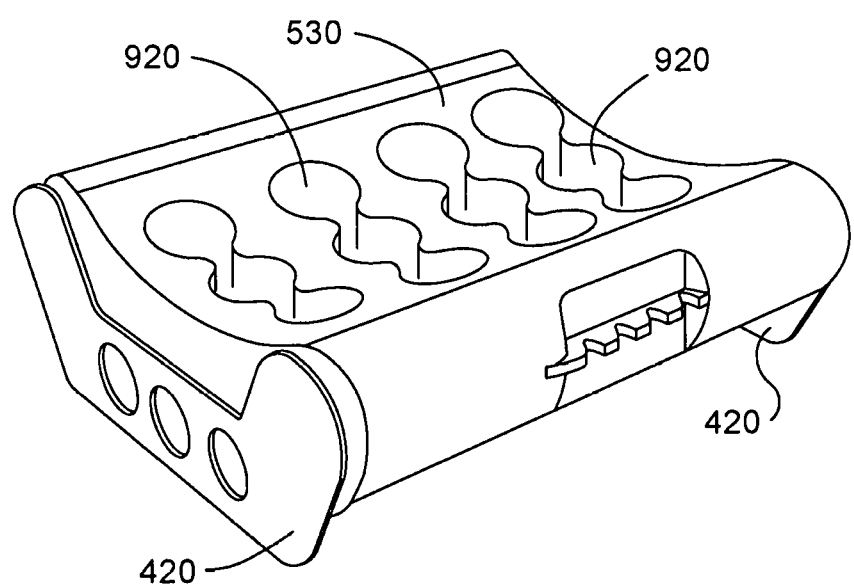
FIG. 30 is an isometric view of an embodiment of a buoyant object interfaced with multiple transducer assemblies and end plates, according to the present invention.
Figure 31:
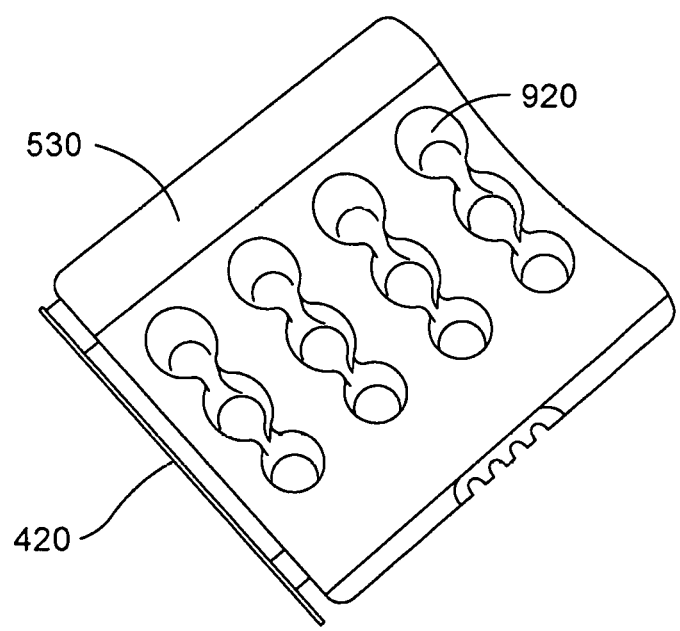
FIG. 31 is a top plan view of an embodiment of a buoyant object interfaced with multiple transducer assemblies and end plates, according to the present invention.
Figure 32:
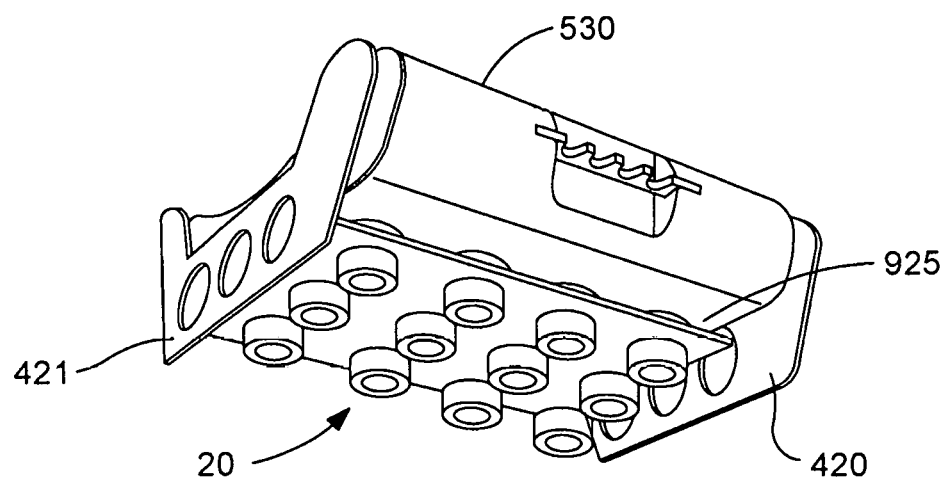
FIG. 32 is an isometric view of an embodiment of a buoyant object interfaced with multiple transducer assemblies and end plates, and spaces or gaps exist, especially above the transducers, between the housing and the buoyant object that is positioned above the transducers, according to the present invention.

As best shown in FIG. 10, the apparatus (215) in the present invention can be controlled, without limitation, by one or more programmable logic circuit(s) (PLC) or other suitable circuitry, computer, controller, electrical system, micro-controller, or electronics (herein called "PLC or PLC(s)") (315), and related software and program(s), known to those skilled in the art. Without limitation, one or more human machine interface(s) (HMI), screen, or other means to interact with the operator (herein called "HMI or HMI(s)") (320), and related software and program(s), known to those skilled in the art, can be used, without limitation, to convey information as well as allow the operator to set parameters or enter commands. The PLC (315) and HMI (320) can be configured or programmed to enable the operator to, without limitation, enter information into the HMI (320) or PLC (315), program the HMI (320) or PLC (315), or execute command(s). The HMI (320) or PLC (315) can also provide a means, without limitation, for the operator to choose a specific volume or area for the apparatus (215) to administer or deploy the generated aerosol, or choose a specific aerosol deployment time. The HMI (320) or PLC (315) can be programmed to associate one or more values for volumes or areas chosen by the operator with specific aerosol deployment time(s). The menus, software, and programming for the HMI (320) or PLC (315) can be customized for each customer's needs and may include, without limitation, providing the operator with one or more menus that presents a plurality of room numbers or other attributes that the operator can choose, and each room number or attribute is associated with operational parameters and variables such as, but not limited to, liquid temperature(s), volume of the room or targeted area, and the total cycle time that the apparatus (215) would need to operate in order to efficaciously and effectively deploy the aerosol into the chosen room or targeted area. In addition, and without limitation, the HMI (320) or PLC (315) can have a provision in its program(s) or software to change the operational parameters that effect the performance of the apparatus (215) or process due to temperature and humidity values that are either reported to the HMI (320) or PLC (315) by the operator or by automated means known to those skilled in the art. The PLC (315) can, without limitation, include any PID, PID tuning, or PID auto tuning, functions, attributes, or activities. The PLC (315) can, without limitation, control and maintain the temperature of any liquid (30) to any desired or necessary temperature in any reservoir(s), including, but not limited to, the reservoir(s) (40) in which the transducers (10) are located. Without limitation, the PLC (315) can control liquid (30) temperature, by controlling one or more part(s) and component(s) of the apparatus (215) such as, but not limited to any: (a) blower(s), (b) valve(s), (c) heater(s), (d) pump(s), (e) amplifier(s) or other means to power or control the transducer(s) (10), or (f) any means used to cool the liquid (30). Without limitation, the PLC (315) can control liquid (30) temperature, by controlling or communicating with one or more part(s) and component(s) of the apparatus (215) such as, but not limited to any: (a) any thermostat or temperature controlling device (b) blower(s), (c) valve(s), (d) heater(s), (e) pump(s), (f) amplifier(s) or other means to power or control the transducer(s) (10), or (g) any means used to cool the liquid (30).

The PLC (315) can also, without limitation, send or receive or detect any signal, current, or other modes of communication, or their absence, from various components or parts of the apparatus (215) or components or parts related to effective operation of the apparatus (215). These signals, current, or other modes of communication, or their absence, can without limitation, be used by the PLC (315) to, control the apparatus (215) or its components and functions, or monitor the function or status of components or parts of the apparatus (215). Without limitation, the signals, current, or other modes of communication, or their absence, sent by the PLC or to the PLC, can result from the direct or indirect connection and communication of the PLC (315) with components such as, but not limited to, any: (a) current sensor(s) (325), (b) liquid level sensor(s) (305), (c) electronics that power, operate, or control, the transducer(s) (10) (herein referred to as "drive electronics") (645), (d) air/gas temperature sensing thermocouple(s) (650) or other means to sense air/gas temperature, (e) liquid temperature sensing thermocouple(s) (820) or other means to sense liquid temperature, (f) humidity sensor(s) (335), (g) valve(s) (300) (660) that control the flow of liquid, (h) valve(s) (260) (265) (210) (815) (775) that control the flow of any air/gas or aerosol that can flow into or out of a targeted area, (i) wireless transceiver(s) (340) or other signal transmitter(s)/receiver(s).

One or more air/gas temperature sensor(s) (650) can be placed in various locations inside or outside of the apparatus(s) (215). It is preferred, without limitation, that at least one air/gas temperature sensor is positioned in any enclosure or NEMA or IP rated sealed enclosure (345) that has the potential for its internal atmosphere (740) to increase in temperature due to the operation of the apparatus(s) (215). The PLC(s) (315) can, without limitation, use the input from any sensors including, but not limited to, liquid temperature, air/gas temperature, or any other temperature sensor(s), to control activities such as, but not limited to, heating of any liquid and any related activities (30), cooling of any liquid and any related activities (30), or cooling of any part(s), component(s), or atmosphere(s) (740) in any enclosed space(s) found in the apparatus(s) (215) and any related activities. Any valve(s) utilized in the present invention can also, without limitation, be manually controlled and operated, or electronically controlled and operated by one or more PLC(s) (315) in a manner known to those skilled in the art. It is preferred, without limitation, that any electrically or electronically controlled valve(s) that can be utilized for various purposes and at various locations, are solenoid valve(s).

The drive electronics (645) can include, but is not limited to, the following parts or components: (a) one or more power supply(s), (b) one or more signal or waveform generator(s) (herein referred to as "signal generator(s)") (c) one or more amplifier(s), or (d) other electronic equipment, components, parts, and methods for operating or driving the transducer(s) (10) known in the art may also be used. In addition, one or more sensors or means (1045) for determining the liquid level or the amount of liquid in the reservoir(s) (40) in which the transducers (10) are located or in the tank(s) (280) that feeds or supplies liquid (30) to the said reservoir(s) (40), can also be connected or communicate with the PLC (315), in a manner known in the art, and can enable the PLC (315) to determine if a sufficient quantity of liquid is available for any application time or volume of space chosen by the operator.

More specifically, the various signals, current, or other modes of communication, or their absence, received or detected by the PLC (315) can be used, without limitation to determine if the apparatus is functioning or operating within acceptable operational parameters. If the apparatus (215) is not operating within acceptable operational parameters, the PLC (315) can shut down, without limitation, the aerosol generation activity, any blower(s) (180), any means to heat the liquid (30), any means to cool the liquid (30), or any fluid pumps (130). The PLC (315) can also cause the apparatus (215) to shut down and enter a fault or error mode if the apparatus (215) is not functioning or operating within acceptable parameters. These can include, without limitation, the apparatus (215) shutting down all components and displaying a fault or error message on the HMI (320) communicating the source of the fault or error. Faults or errors can result from sources or situations including, but not limited to, insufficient liquid (30) availability to start or complete a cycle, failure to heat the liquid (30) to effective temperatures, overheating of the liquid (30) or components, failure of one or more components evidenced by the lack of current detected by a current sensor, under filling or over filling of the tank(s) (280) or reservoir(s) (40), failure of any drive electronics (645), failure of a transceiver(s) (340). If the apparatus (215) is not functioning or operating within acceptable operational parameters, the PLC (315) can also cause the apparatus (215) to emit an audible as well as visual warning. Without limitation, an audible as well as visual signal can also be communicated to the operator after the apparatus (215) has successfully completed administering the aerosol. The HMI (320) can be located inside, outside, or partially inside and outside of the apparatus (215).

At the end of the operational cycle, or upon a premature shut down of the apparatus (215) due to a failure of the apparatus (215) to function or operate within acceptable operational parameters, the apparatus (215) can create a record or report that can include, but is not limited to, whether or not there were any faults or errors during operation, the source of any faults or errors if they transpired, the lowest and highest recorded liquid (30) temperature that is in the reservoir(s) (40), the total time the aerosol was administered, the date and time the cycle was started, the date and time the cycle was completed, the room number or name if applicable, operator descriptor. The record or report may be stored, without limitation, in the memory of the PLC (315) or HMI (320), or on removable memory media, or other means known to those skilled in the art. The record or data may also be made available for printing or download via a USB port or other means known to those skilled in the art.

The PLC (315) can, without limitation, operate, energize, shut down, suspend, idle, or deactivate, one or more parts or components including, but not limited to any, (a) heater(s), (b) pump(s), (c) transceiver(s), (d) blower(s), (e) valve(s), (f) HMI(s), or (g) drive electronics, numerous times of various duration during the operation of the apparatus (215). This is particularly useful in situations that include, but are not limited to: (a) an insufficient amount of power is available to the apparatus(s) (215) to operate one or more of its parts or components simultaneously, necessitating that one or more parts and components such as, but not limited to, the blower(s) (180) and/or drive electronics (645) are temporarily idled, shut down, turned off, or suspended, to provide or make sufficient power available to the heater(s) (150) or (310), or other parts and components, (b) an insufficient amount of power is available to the apparatus(s) (215) to operate one or more of its parts or components simultaneously, necessitating that one or more parts and components such as, but not limited to, the heater(s) (150) or (310) is temporarily idled, shut down, turned off, or suspended, to provide or make sufficient power available to the drive electronics (645), or other parts or components.

The apparatus (215) can be designed, without limitation, so that all of the components or parts are mounted inside the skin or covering of the machine. For applications where the apparatus (215) is operated from within the area in which the aerosol is deployed or administered, the components or parts can be housed inside a suitable and effective NEMA or IP rated enclosure (345) that can keep any liquid, aerosol, or humidity from reaching or contacting any parts or components, and is accomplished in a manner known to those skilled in the art. The components can be independently or collectively housed in the aforementioned enclosure(s). The exterior or outside walls (755) (the term "wall(s)" can also refer to ceilings and floors in the present invention) of the apparatus (215) can, without limitation, form the NEMA or IP rated enclosure.

The apparatus (215) can, without limitation, be designed so that it can be mobile and easy to move. Without being limited, the apparatus (215) can have features including, but not limited to, a robust frame, robust wheels, bumpers, multiple grab and hoist points, and other design features known to those skilled in the art for designing a mobile apparatus (215) that can be of variable weight and size. The apparatus (215) may be constructed from any material that is compatible, and suitable for use with the liquid (30).

Without limitation, the administered or applied aerosol (200) can be removed from the area(s) in which it is applied during or after the application of the aerosol and can be accomplished with various means know to those skilled in the art. It is preferred, without limitation, that one or more ventilation or exhaust blower(s) (350) be used to pull or push air or gas and aerosol (200) out of the area(s) (210) in which the aerosol is administered or deployed. The said ventilation or exhaust blower(s) (350) can be controlled with one or more PLC(s) either not connected or connected directly or indirectly to the PLC(s) (315) of the apparatus of the present invention. The ventilation or exhaust blower(s) (350) can move any quantity of air/gas at any speed, but should have effective attributes and design for the intended application, all which is known by those skilled in the art. Anything that is removed from the area(s) (210) with the ventilation or exhaust blower(s) (350) can be done so in a manner known to those skilled in the art.

The ventilation or exhaust blower(s) (350) can also be used to bring fresh air into the area(s) in which the aerosol is applied either during or after the administration or deployment of the aerosol. The air or gas that is either removed or brought into the process area(s) can be accomplished in a manner known to those skilled in the art. The blower(s) (350) and related parts may be constructed from any material that is compatible, and suitable for use with the liquid (30).

The liquid (30) in any tank(s) or reservoir(s) (40) can be removed from the apparatus via one or more drain (655) in a manner known in the art. The movement of any liquid (30) out of the apparatus (215) can be controlled with one or more valve(s) (660). It is preferred, without limitation, that the valve(s) (660) is a solenoid valve and can communicate or send signal to one or more PLC(s) (315).

According to an embodiment, the apparatus is designed and constructed so that the aerosol producing transducer(s) (10) and/or their liquid facing surfaces or the surfaces from which there is aerosol-producing output, are able to match the angle of or remain level or parallel with, the surface of the liquid (30) above them. This is made possible by means including, but not limited to, a float assembly that holds, houses, or otherwise positions the transducers, and a gimbaled or articulating arm or holding assembly, as best shown in FIGS. 16-32. This embodiment is important for reasons including, but not limited to, the need to cover the transducers (10) with an effective amount or depth of liquid (30) to prevent the transducers (10) from being damaged due to being covered with an insufficient amount or depth of liquid (30), or to prevent the transducers (10) from being damaged by being operated without liquid above them. (30). This embodiment permits the present invention to be operated on or interfaced with surfaces that are without limitation, flat, semi-angled, angled, sloped, not sloped, or have various orientations. This embodiment does not claim, or attempt to claim, leveling the apparatus (215) by utilizing height adjustable legs or wheels that extend from the apparatus (215) and interface with a floor(s), a table top(s), or other surface(s) on which the apparatus (215) is placed or otherwise resting on, since this feature is taught in (col. 8, line 42-51) by U.S. Pat. No. 5,878,355 (Berg et al. 1996), and in (col. 8, line 50-58) by U.S. Pat. No. 6,102,992 (Berg et al. 1998). This embodiment includes interfacing, connecting, positioning, placing, or mounting, the transducers (10) to a means, or a material or object that is connected to a means, that can enable the transducer(s) (10) and/or their liquid facing surfaces or the surfaces from which there is aerosol-producing output, to match the angle of or remain aligned, level, or parallel with, the surface of the liquid (30) above them.

Figure 51:
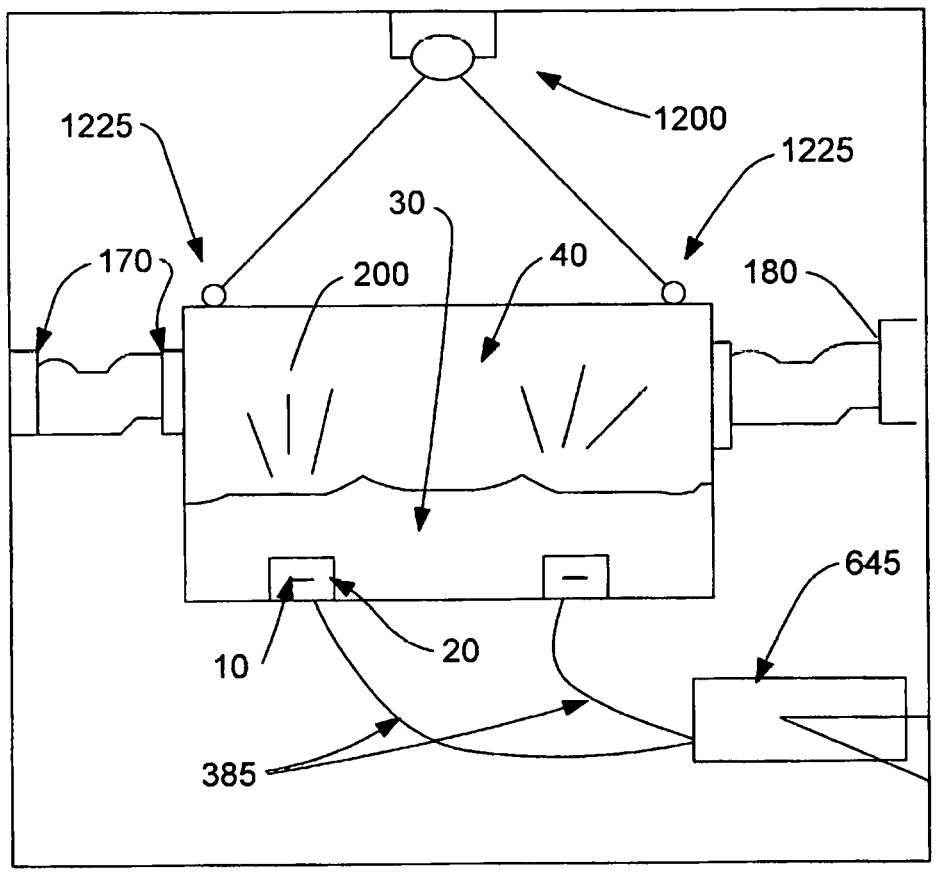
FIG. 51 is a schematic view of an embodiment of the aerosol generator that suspends the tank or reservoir including the transducers from a vertically-elevated support surface.

The first aspect of this embodiment includes, without limitation, mounting, interfacing, or connecting the aerosol generating transducers (10) to a reservoir (40) or into a reservoir (40), or to a means such as, but not limited to, one or more float(s) or float assembly(s) positioned or located in a reservoir (40), and the transducers (10) or reservoir(s) (40) is interfaced, connected, positioned, placed, or mounted, to a means (355), or a material or object that is connected to a means, that can enable the transducer(s) (10) and/or their liquid (30) facing surfaces or the surfaces from which there is aerosol (200) producing output, to match the angle of or remain aligned, level, or parallel with, the surface of the liquid (30) above them. The said means can include, but is not limited to, a ball joint, gimbal, or other means known to those skilled in the art. The components are designed and assembled in a manner known to those skilled in the art, but at least, without limitation, addresses design and assembly issues such that design considerations or variables like center of gravity and balance of the total system are sufficiently addressed and results in an effective apparatus (215). The transducers (10) in this first aspect can be, without limitation, mounted or interfaced with the reservoir(s) (40) through openings in the reservoir(s) in a way that is known to those skilled in the art, or they can be mounted, interfaced, or connected to the reservoir(s) either inside or outside of the reservoir. Without limitation, the reservoir(s) (40) can be fixed in position, free floated, or allowed to freely move. Without limitation, the reservoir(s) (40) can be enclosed, not enclosed, or semi-enclosed, so that air/gas can flow through it and carry the generated aerosol (200) away from the apparatus (215). The said means can also include, but is not limited to, hanging or suspending the entire nebulizing apparatus(s), or at least one or more of the reservoirs (40) in which the aerosol (200) is generated, from any means that would allow them to be freely hung or suspended in air or in a liquid, and have an effective free range of motion so that the transducer(s) (10) are covered with a sufficient or effective amount of liquid (30). It is preferred, without limitation, that if more than one transducer (10) is utilized, they are not only effectively covered with liquid, but that they are covered with an equal depth or amount of liquid (30). This may, without limitation, include suspending or hanging the entire nebulizing apparatus(s) or one or more of the reservoir(s) (40) in which the aerosol (200) is generated, from one or more of any pivot point, swivel, ball joint, gimbal, or other means known to those skilled in the art (1200), as shown in FIG. 51. The one or more attachment points that enable the entire nebulizing apparatus(s), reservoir(s), or chambers to be suspended or hung, are effectively positioned. The means to hang (1200) the reservoir(s) (40) or chambers may also, without limitation, attach to one or more of any pivot point, swivel, ball joint, gimbal, or other similar means known to those skilled in the art (1225), that may also be effectively connected or otherwise directly or indirectly attached to the entire nebulizing apparatus(s), or reservoir(s) (40). The nebulizing apparatus(s), reservoir(s) (40), or any related parts or components in the present invention may be attached to any material or components including, but not limited to, wiring, tubing, piping, or conduits, and they may be, without limitation, flexible. They may also, without limitation, have sufficient flexibility to enable the entire nebulizing apparatus(s) or reservoir(s) (40) to freely hang, suspend, or have an effective free range of motion.

The second aspect of this embodiment includes, without limitation, placing one or more reservoir(s) (herein referred to as "secondary reservoir(s)") (360) inside of another reservoir(s) (herein referred to as "primary reservoir(s)") (40). Transducer(s) (10) are mounted or interfaced to or with the secondary reservoir(s) (360) in a way that is effective and is known in the art, or they can be mounted, interfaced, or connected to the secondary reservoir(s) (360) either inside or outside of that reservoir(s) (360), in a way that is effective and known to those skilled in the art. The secondary reservoir(s) (360) may also be interfaced, connected, positioned, placed, or mounted, to a means (355), or a material or object that is connected to a means, that can enable the transducer(s) (10) and/or their liquid facing surfaces or the surfaces from which there is aerosol (200) producing output, to match the angle of or remain aligned, level, or parallel with, the surface of the liquid (30) above them. The said means can include, but is not limited to a spherical ball joint or gimbal. Without limitation, the secondary reservoir(s) (40) can be free floated or allowed to freely move. Again, the components are designed and assembled in a manner known to those skilled in the art, but at least, without limitation, addresses design and assembly issues such that the center of gravity and balance of the total system are effectively or sufficiently accommodated.

Liquid (30) from the primary reservoir(s) (40) may be pumped into the secondary reservoir(s) (360) in various ways and fill the secondary reservoir(s) (360) so that it an effective depth or amount of liquid (30) is maintained. The walls (365) of the secondary reservoir(s) (360) can be of various heights, including, but not limited to, a height that allows the liquid (30) in the secondary reservoir(s) (360) to attain at least an effective depth. More specifically, the effective liquid (30) depth in the secondary reservoir(s) (360) may be attained by means including, but not limited to, positioning one or more openings or notches in the walls (365) of the secondary reservoir(s) (360) so that a sufficient amount of liquid (30) is able to drain out into the primary reservoir(s) (40) to maintain an effective depth of liquid in the secondary reservoir(s) (360). However, it is preferred, without limitation, that the walls (365) of the secondary reservoir(s) (360) are of a height so that the liquid (30) crests and spills over the walls (365) and back into the primary reservoir(s) (40), to ensure that an effective depth of liquid (30) is maintained. The height of the walls (365) of the secondary reservoir(s) (360) can also be adjusted to compensate for any drain holes that may be present to ensure that the secondary reservoir(s) (360) may effectively drain into the primary reservoir(s) (40) once the apparatus (215) has shut down.

Without limitation, the secondary reservoir(s) (360) can be designed so that a hermitically sealed area or compartment(s) (370) with a sufficient airspace known to those skilled in the art, can connect to or is extended from at least the floor or bottom of the secondary reservoir(s) (360), or even its walls (365), to facilitate the mounting or interface of the transducers (10) and provide an environment where the transducers (10) can safely and effectively operate. Without limitation, the hermitically sealed compartment(s) (370) can extend with flexible wall material and interface with the floor, bottom, or wall(s), of the primary reservoir(s) (40), or even extend through the floor, bottom, or wall(s), of the primary reservoir(s) (40). The flexible wall material is sufficiently flexible to allow the secondary reservoir(s) (360) to effectively move. However, it is preferred without limitation that flexible tubing (375) connect the aforementioned hermitically sealed compartment(s) (370) with any airspace in which the drive electronics (645) or amplifier(s) (230) is located. Wiring from the drive electronics (645) or amplifier(s) (230) can travel through this tubing to the transducer(s) (10). The secondary reservoir(s) (360) and related components, hermitically sealed area(s) or compartment(s) (370), flexible wall material, and tubing, are constructed from any material that is compatible, and suitable for use with the liquid (30). The secondary reservoir(s) (360) can also have sensor(s) to determine if the liquid (30) is either above or below what is desired or needed. In addition, any reference made in the present invention, to any reservoir(s) (40) in which the transducer(s) (10) are located, can also apply to the reservoir(s) (360) and (40) referenced in this second aspect of the embodiment.

The third aspect of this embodiment is preferred, and it includes, without limitation, locating or suspending one or more transducer(s) (10), their wiring, and housing(s) (20), where the housing (20) can be shared or used independently with the one or more transducer(s) (10), with the transducer(s) (10) being independently, interchangeably or collectively mounted to the housing (20), and other associated circuitry, parts and components, (herein referred to as "transducer assembly(s)") (100), at an effective orientation, depth, or distance below the surface of the liquid (30) in the reservoir(s) (40) during their operation. The transducer(s) (10) are a part of the transducer assembly(s) (100) and the transducer assembly(s) (100) may consist of one or more transducers (10). The transducer assembly(s) (100) consists of one or more transducer(s) (10) and their related parts, which are hermitically sealed in a housing (100). One or more transducers (10) and its associated parts may be located in or with a housing (20). There are numerous ways to effectively locate, position, or suspend the transducer assembly(s) (100) in the liquid (30) and includes, but is not limited to locating or suspending the transducer assembly(s) (100) at an effective distance, range, or depth, below the surface of the liquid (30), from one or more, wire(s), cable(s), tube(s), conduit(s), beam(s), or other means, that interfaces with or is attached to various locations, including, but not limited to, the walls or roof of the reservoir(s) (40), or secondary reservoir(s) (360) if it is used, or the walls or roof of the targeted area or sterilization chamber (210). The wire(s) (385) that connects from the transducer(s) (10) or transducer assembly(s) (100) to any drive electronics (645) or amplifier(s) (230) that sends signal to or operates the transducer(s) (10), can be, without limitation, protected from the liquid (30) or aerosol (200) in various ways including, but not limited to, placing, positioning, or running the wire(s) (385) inside or through tubing, pipes, conduit, beams, or other means to contain or embed the wire(s) (375)

(herein referred to as "tubing"), and keep the wire(s) (385) separated from any aerosol (200) or any liquid (30). The tubing (375) may be constructed from any material that is compatible and suitable for use with the liquid (30). The wire(s) (385) may also be constructed from any material that is compatible, and suitable for use with the liquid (30). It is even more preferred that flexible tubing (375) connect the hermitically sealed transducer assembly(s) (100) with any airspace, that is hermitically or not hermitically sealed, in which the drive electronics (645) or amplifier(s) (230) is located. The flexible tubing (375) can also, without limitation, connect the environments of the transducer assembly(s) (100) and the drive electronics (645) or amplifier(s) (230) in a manner that is effective and safe, and known to those skilled in the art.

It is also preferred, without limitation, that the said tubing (375) or wire(s) (385) can connect with a suitable, effective, and usable, interface at various locations underneath the transducer assembly(s) (100). The wire(s) (385) and tubing (375) can also connect at other locations of the transducer assembly(s) (100) and in various ways known to those skilled in the art. It is further preferred that the wire(s) (385) or tubing (375) connects or interfaces with the underside of the transducer assembly(s) (100) with a watertight seal in a manner known to those skilled in the art. The wire(s) (385) or tubing (375) and wire(s) (385) can then travel through the wall(s) of the transducers assembly(s) (100) into its interior and connect to the transducer(s) (10). Without limitation, any clamp (390) made of a material that is compatible with the liquid (30), can help to create an effective seal between the tubing (375), and the housing (20) or transducer assembly(s) (100). It is even further preferred, without limitation, that the interface of the wire(s) (385) or tubing (375) with the transducer assembly(s) (100) is effectively or hermitically sealed from at least the inside of the transducer assembly(s) (100) with a means that includes, but is not limited to any, caulk, glue, sealant, or other means known to those skilled in the art, that is compatible and suitable for use with the liquid (30).

It is also preferred, without limitation, that the transducer(s) (10) or transducer assembly(s) (100), is located or suspended at an effective distance, range, or depth, below the surface of the liquid (30) by being directly or indirectly attached to or suspended from, without limitation, one or more buoyant object(s) (400), an interconnection or system of buoyant object(s) (400), or one or more components or parts that are connected or interconnected to one or more buoyant object(s) (400), where the said buoyant object(s) (400): (a) has buoyancy or neutral buoyancy but is completely submerged in the liquid (30), (b) has the ability to float partially submerged in the liquid (30), or (c) have the ability to float on the surface of the liquid (30). Without limitation, the transducer assembly(s) (100) can also be designed so that it can independently, have buoyancy or neutral buoyancy but is completely submerged in the liquid (30), have the ability to float partially submerged in the liquid (30), or have the ability to float on the surface of the liquid (30).

The transducer assembly(s) (100) and the said buoyant object(s) (400) can be designed to rise and fall in the reservoir(s) (40) to match any fluctuations in the depth of the liquid (30) in the reservoir(s) (40) so that an effective orientation and effective depth or distance below the surface of the liquid (30) in the reservoir(s) (40) is constantly maintained during the operation of the transducer(s) (10). It is also preferred, without limitation, that the transducer assembly(s) (100), as well as buoyant object(s) (400) if they are used, in the preferred aspect, be maintained in the proper, designated, or desired position(s), in an X-Y-Z coordinate plane or desired area(s) in the reservoir(s) (40), especially if the liquid (30) level fluctuates. This can be accomplished, without limitation, by connecting the transducer assembly(s) (100) or buoyant object(s) (400) with one or more control arm(s) (440) or other means, which is directly or indirectly connected to or interfaced with the walls, floors, roof, or any surfaces, of the reservoir(s) (40). The control arm(s) (440) or other means can, without limitation, be connected to any buoyant object (400). It is further preferred, without limitation that the control arm(s) (440) be designed in a manner known to those skilled in the art, so it can pivot or move in various directions or orientations. The control arm(s) (440) can also, without limitation, have one or more additional means to allow the transducer assembly(s) to freely pivot or move in various directions or orientations, and without limitation, directly or indirectly interface with the transducer assembly(s) (100). The control arm(s) (440) can be designed to keep the transducer assembly(s) (100) from inadvertently contacting any walls or surfaces of the reservoir(s) (40). The various components and parts that interface with the transducer housing(s) (20), or assist in holding or positioning the transducer housing(s) (20), are constructed from any material that is compatible and suitable for use with the liquid (30).

The control arm(s) (405) or other similar means, can also, without limitation, incorporate sensors into their design or the design of direct or indirectly connected parts and components, or in the design of the walls or ceiling of the reservoir(s) (40) so that the apparatus (215) will shut down or enter a fault or error mode if the control arm(s) (405) or related parts or components rises beyond a predetermined point due to a rise in the depth of the liquid (30) in the reservoir(s) (40), or drops below a predetermined point due to a drop in the depth of the liquid (30) in the reservoir. The type of sensors and their incorporation into the design of the apparatus (215), as well as their communication with the PLC (315) can vary. The various components utilized in this embodiment can be, without limitation, designed and assembled to address issues such as center of gravity and balance of the total system.

It is more preferred, without limitation, that one or more transducer assembly(s) (100) are effectively positioned within the reservoir(s) (40) using a combination of one or more, but not limited to, the following features or attributes: First, the transducer housing(s) (20) is located between or connected to one or more buoyant object(s) (400) of various size, shape, material, and buoyancy. Second, one or more spring clip(s) (415) are attached or connected to each buoyant object(s) (400) and interface, hold, or support the transducer housing(s) (20). Other means may also be used to connect or interface the transducer housing(s) (20) with the buoyant object(s) (400). The spring clip(s) (415) can interface with the transducer housing(s) (20) in various ways. It is preferred, without limitation, that one or more protrusions (410) from the transducer housing(s) (20) engage one or more trough(s), hole(s), or grove(s) of any shape and size present in the spring clip(s) (415). This supports or holds the transducer assembly(s) (100). Third, one or more end plates (420) connect with the buoyant object(s) (400). Fourth, one or more buoyant object(s) (400) or end plate(s) (420) connects with a spacer washer (425), which is connected to a wave washer (505) that also connects with another spacer washer (425). Fifth, a rotating clevis (430) connects to the spacer washer (425) furthest from the buoyant object(s) (400) or end plate(s) (420). Sixth, a shoulder bolt (500)

connects with the rotating clevis (430), spacer washer (425), wave washer (505), another spacer washer (425), and end plate(s) (420) or buoyant object(s) (400). Seventh, the interface or connection of the shoulder bolt (500), spacer washers (425), and the wave washer (505), enables the transducer housing(s) (20) and buoyant object(s) (400) to have a free range of motion about the longitudinal axis of the shoulder bolt (500).

Eighth, a second clevis (435) is attached or connected to a pivot arm (herein referred to as "control arm") (440). The second clevis (435) can either move or be fixed in position. Ninth, the second clevis (435) can move by being connected or attached to the control arm (440) in the same manner that the rotating clevis (430) connects to the buoyant object(s) (400) or end plate(s) (420). Tenth, it is preferred, without limitation, that the fixed clevis (435) is held in place to the control arm (440) with bolts or screws. Eleventh, the fixed clevis (435) and rotating clevis (430) are connected and held together with a bolt, pin, or quick release pin (herein referred to as "pin") (490). The pin (490) can have a locking mechanism (495). Twelfth, the interface of the fixed clevis (435), rotating clevis (430), and pin (490), enable the transducer housing(s) (20) to have a free range of motion about the longitudinal axis of the pin (490).

Thirteenth, the control arm (440) has a hole (480) into or through which a torque tube (465) is positioned or connected. Fourteenth, the torque tube (465) interfaces with a washer (445) and bolt (450) from the interior side of the reservoir (40). Fifteenth, the torque tube (465) can have one or more notches or grooves located at any effective location where at least one, but preferably two or more o-rings (455) are seated. Sixteenth, the flange plate (470) fits over and interfaces with the bearing (475). Both the o-rings (455) and flange plate (470) are made of any suitable, effective, and chemically compatible material, and their hardness can vary. Seventeenth, the bearing (475) fits over and interfaces with the torque tube (465). Eighteenth, it is preferred, without limitation, that the torque tube (465) and bearing (475) are interfaced by inserting the torque tube (465) through a pivot hole (625) in the wall of the reservoir(s) (40), from the interior side of the reservoir(s) (40), and inserting the bearing (475) into the same hole (625) from outside of the reservoir(s) (40). Nineteenth, it is further preferred, without limitation, that the flange plate (470) interfaces with the bearing (475) outside of the reservoir(s) (40). Twentieth, the retaining spring plate (485) interfaces with the bearing (475). Twenty-first, the bearing (475) can also, without limitation, be connected or attached to the control arm (440), and the torque tube (465) and bearing (475) can be interfaced by inserting the bearing (475) and related components, through a hole (625) in the wall of the reservoir(s) (40), from the interior side of the reservoir(s) (40), and inserting the torque tube (465) and related components, into the same hole (480) from outside of the reservoir(s) (40). In this situation, the flange plate (470) would interface with the bearing (475) inside of the reservoir(s) (40).

Twenty-second, one or more control arm(s) (440) and any direct or indirectly connected parts or components can be used. The control arm(s) may have any range, angle, or degree of motion or movement. It is preferred, without limitation, that the control arm(s) (440) can have up to thirteen degrees in vertical, arc, or semi-vertical motion. Twenty-third, in essence, the control arm(s) (440) is connected to a torsional tube (445) that transfers motion from the inside of the reservoir(s) (40) through the reservoir(s) (40) walls, to the switch actuator plate (565).

Twenty-fourth, one or more switch actuator plates (565) is interfaced with the torsional tube (445) or bearing (475) and is located at the exterior of the reservoir(s) (40). It is preferred, without limitation, that the switch actuator plate(s) (565) is interfaced with the torsional tube (445). Twenty-fifth, the movement of the control arm(s) (440) directly or indirectly causes the switch actuator plate(s) (565) to move. Twenty-sixth, the switch actuator plate(s) (565) is designed so that its movement causes the actuation of one or more various switch(s) (590). The switch actuator plate(s) (565) can be of many different shapes, sizes, and geometries. Twenty-seventh, any type and number of switch(s) (590) may be used to indicate or communicate any condition(s) or situation(s) in the reservoir(s) (40). Twenty-eighth, the switch(s) (590) may be located anywhere around, in front of, or at any effective proximity to the switch actuator plate(s) (565). It is preferred, without limitation, that the switch actuator plate(s) (565) has one or more protrusion(s), groove(s), or indentation(s) (665), which can interface with and contact or actuate one or more switch(s) (590). Twenty-ninth, one or more switch(s) (590) are interfaced with or connected to one or more base plate(s) (540) which is interfaced with the exterior wall(s) of the reservoir(s) (40) or other surfaces. Thirtieth, the position and meaning of each switch (590) connected to a base plate(s) (540) can vary and be interchanged. It is preferred, without limitation, that three switches (590) are used to indicate or communicate to the PLC(s) (315) the various liquid levels in the reservoir(s) (40). The first switch is the tank full switch (550). Without limitation, the interaction or lack of interaction of the switch actuator plate(s) (565) with this switch (550) can indicate or communicate to the PLC(s) (315) that the liquid (30) level in the reservoir(s) (40) is at or above a designated or specified level. This can, without limitation, cause one or more valves (300) that control the flow of liquid (30) into the reservoir(s) (40) to close. The second switch is the tank refill switch (555). Without limitation, the interaction or lack of interaction of the switch actuator plate(s) (565) with this switch (555) can indicate or communicate to the PLC(s) (315) that the liquid (30) level in the reservoir(s) (40) is at or below a designated or specified level and the reservoir(s) (40) needs refilling. This can, without limitation, cause one or more valves (300) that control the flow of liquid (30) into the reservoir(s) (40) to open or semi-open. The third switch is the tank low level switch (560). Without limitation, the interaction or lack of interaction of the switch actuator plate(s) (565) with this switch (560) can indicate or communicate to the PLC(s) (315) that the liquid (30) level in the reservoir(s) (40) is at or below a designated or specified level. This can, without limitation, cause various components of the apparatus (215) to shut down such as, but not limited to any, pump(s) (130), blower(s) (180), heater(s) (150) or (310), or any drive electronics (645) or amplifier(s) (230).

Thirty-first, one or more cover plate(s) (580) fit over the switch(s) (590). The cover plate(s) can, without limitation, provide rigidity to the various connected components (610) and prevent damage to the switches (590) resulting from possible contact with any objects. The cover plate(s) (580) can also prevent certain shock hazards as well as act as a passive terminal protection for the various switch(s) (590).

Thirty-second, one or more hydraulic dampener(s) are connected to the switch actuator plate(s) (565) or any other components that directly or indirectly connect to the transducer assembly(s) (100), buoyant objects (400), or control/control arm (440). The hydraulic dampener(s) (585) is a push or pull hydraulic mechanism whose design and function is known in the art. The hydraulic dampener(s) (585) can, without limitation, dampen any rotation or movement of the control arm (440), transducer housing(s) (20), switch actuator plate (565), or other related components, resulting from any shock and vibration that the apparatus (215) may encounter.

It is further preferred, without limitation, that an enhanced design for interfacing one or more transducer(s) (10) with one or more housing(s) (20) in various and modifiable configurations is utilized in the present invention. This design includes, without limitation, the following features. First, each housing (20) that is utilized is constructed so that it has one or more space(s) or recess(s) (600) that interface with one or more transducer(s) (10) as desired. The housing(s) may be made of any suitable material that is not affected by the chemical action of the liquid (30). Suitable materials for the housing(s) (20) may include PVC, polypropylene, and stainless steel, but other suitable materials may be used. It is preferred without limitation that the housing(s) (20) is made from stainless steel. It is preferred, without limitation, that three spaces or recesses (600) are utilized per transducer housing (20), and the center space or recess (620) connects with the other spaces or recesses (600) through one or more hole(s), opening(s), pipe(s), channel(s), or conduit(s) (herein referred to as "holes") (535). The wire(s) (385) that connect the amplifier(s) (230) to the transducer(s) (10), enter the housing(s) (20) through one or more hole(s), opening(s), pipe(s), channel(s), or conduit(s) (605) located anywhere on the side of the housing (20) that faces opposite from the surface of the liquid (30) in the reservoir(s) (40). The wire(s) (385) can, without limitation, enter the center space(s) or recess(s) (620) and travel through the hole(s) (535) to connect with their respective transducer(s) (10). The wire(s) (385) connect with the transducer(s) in a manner known to those skilled in the art.

Each space(s) or recess(s) (600) or their surrounding surfaces (640) can interface with one or more o-rings (635). It is preferred, without limitation, that each space(s) or recess(s) (600) interfaces directly or indirectly with at least three different o-rings and various other parts or components. The first o-ring is the secondary o-ring (515), and it interfaces with a concentric shelf (630) that is built into each space or recess (600). The second is the outside o-ring (510), and it interfaces with the outside circumference of the compression ring (525). Without limitation, any surface of each housing (20) can have groves or indentations of various construction in which the o-rings can be seated, and the groves are designed and constructed in a manner known to those skilled in the art. The transducer (10) is interfaced or adhered to the barrier (60). It is preferred, without limitation, that the barrier (60) is constructed from glass. The barrier (60) is interfaced with, seated into, or nested on top of the secondary o-ring (515). The third o-ring is the primary o-ring (520), and it interfaces with the liquid (30) facing side of the barrier (60) and any of the inside surfaces (525) of the compression ring (525). The compression ring (525) can be constructed from any suitable material that is not affected by the chemical action of the liquid (30). Suitable materials of the compression ring (525) may include PVC, polypropylene, and stainless steel, but other suitable materials may be used. It is preferred, without limitation that the compression ring (525) is made from stainless steel. Any o-rings, including the secondary o-ring (515), outside o-ring (510), and primary o-ring (520), can have any cross section shape, or hardness, and are constructed from any suitable material that is not affected by the chemical action of the liquid (30). It is preferred, without limitation, that the primary o-ring (520) and secondary o-ring (515) have a double seal cross-section shape, and the outside o-ring (510) has a round cross-section shape, and these various o-rings are constructed from Viton material. The various components, except for the transducer (10) and barrier (60) are assembled and compressed together to form a watertight seal in various ways known to those skilled in the art. Without limitation, tub walls (530) may also interface with any housing(s) (20).

The control arm(s) (405), transducer assembly(s) (100), reservoir(s) (40), and other related component(s), can be designed, so that when the reservoir(s) (40) is drained, the buoyant object(s) (400), transducer assembly(s) (100), control arm(s) (405), or other connected parts or components will move down into or onto, one or more of any means to sufficiently and effectively prop, position, stabilize, or hold, the buoyant object(s) (400), transducer assembly(s) (100), control arm(s) (405), or other connected parts or components, at any angle or orientation, within the reservoir(s) (40). This may include, without limitation, any mechanism(s), apparatus(s), structure(s), inset mold(s), nest(s), groove(s), indentation(s), or protrusion(s) (herein referred to as "structure") (1050) that can, interface with the buoyant object(s) (400), transducer assembly(s) (100), control arm(s) (405), or other connected parts or components, or without limitation, partially, generally, roughly, or exactly, mirror or generally mirror, at least a sufficient amount of the contours or geometry of the buoyant object(s) (400), transducer assembly(s) (100), control arm(s) (405), or other connected parts or components, to be effective. The said mold(s), inset(s), nest(s), groove(s), indentation(s), or other structures can be designed to drain if necessary or when desired, in a manner known to those skilled in the art. When the reservoir(s) (40) is drained the buoyant object(s) (400), transducer assembly(s) (100), control arm(s) (405), or other connected parts or components, can rest, without limitation, at any angle or orientation to provide an angle that is steep enough for any deposited liquid to move off or drain from any surfaces of the transducer assembly(s) (100), including any surfaces above or interfaced with the transducers(s) (10), into the reservoir(s)'s (40) drain(s) (655).

According to an embodiment, the protective barrier (60) that interfaces with the transducer(s) (10) can be polished on one or more sides. When a protective barrier (60) is ground to a specific thickness, its ground sides may have an appearance or characteristics that can include, but is not limited to, unpolished, rough, hazy, or frosted due to the grinding process. This is, without limitation, especially true with protective barriers (60) that are constructed from any type of glass that is ground. The prior art has taught the use of protective barriers (60), including glass, in U.S. Pat. No. 3,433,461 (Scarpa et al.), U.S. Pat. No. 3,729,138 (Tysk), U.S. Pat. No. 4,109,863 (Olson et al.), and U.S. Pat. No. 4,976,259 (Higson et al.), which are incorporated herein by reference in their entirety, including any references cited therein. However, the prior art is silent with respect to the use of a polished barrier(s). It can be assumed that the protective barriers (60) mentioned in the prior art were ground to their specific thicknesses but not polished after being ground. Polishing the liquid side of the protective barrier (60) can, without limitation: (a) reduce or eliminate the texture or surface features that can catch or hold undesirable foreign objects or debris, (b) provide a surface that easier to clean and/or be more effectively cleaned, (c) reduce the amount of texture or surface features that may promote the build up of mineral deposits, (d) promote easier movement of liquid (30), foreign objects, or debris, off of the protective barrier (60) surface(s) when the reservoir(s) (40)

is emptied. Polishing the side of the protective barrier (60) that is not in contact with the liquid can, without limitation: (a) reduce surface variability on the side of the protective barrier (60) that interfaces with any adhesive (70), which can reduce the variability in the thickness of the adhesive (70) between the protective barrier (60) and transducer(s) (10) which may in turn, without being limited, reduce variability in certain energy transmission characteristics or other transmission related issues. An unpolished protective barrier (60) surface that interfaces with an adhesive (70) can enhance the bonding between the protective barrier (60) and the transducer(s) (10) for reasons known to those skilled in the art. The protective barrier (60) in the present invention can, without limitation, be polished or unpolished on both the liquid (30) and transducer (10) facing sides. However, it is preferred, without limitation, that the protective barrier (60) is polished on the side that faces the liquid (30) and remain unpolished on the side that faces the transducer(s) (10). Polishing in this embodiment can vary in ways including, but not limited to its, depth, completeness, precision, quality, and accuracy.

According to an embodiment, the apparatus can be designed and constructed so that more than one aerosol producing transducer (10) is surrounded, enclosed, or encircled by one or more walls or barriers (herein referred to as "tub walls") (530). However, if only one transducer (10) is used in the present invention, it may also be surrounded, enclosed, or encircled by one or more tub walls (530). This embodiment should not be confused with what is taught in U.S. Pat. No. 5,300,260 (Keshet et al., 1993) in (col. 3, line 15-21) and (col. 3, line 50-51), which is incorporated herein by reference in its entirety, including any references cited therein. Keshet et al., taught the positioning of baffles between each aerosol producing transducer as a means to suppress waves. The tub walls (530) in this embodiment are not positioned between individual transducers (10) so as to not conflict with U.S. Pat. No. 5,300,260. The performance of the transducers (10) in the present invention was found in the laboratory not to be adversely effected by waves created by neighboring, or even closely positioned transducers (10). The art taught by Keshet et al. is inapplicable to the present invention. The walls (10) in the present invention are intended to contain the liquid (30) above and around the transducers (10) and use the heat generated by the transducer(s) (10) to heat the liquid (30) above and around the transducer(s) (10), as well as the liquid (30) at the liquid (30) surface above the transducers (10). This embodiment may, without limitation, eliminate the need for any additional means to heat the liquid in certain circumstances known to those skilled in the art. This embodiment utilizes teachings from the book titled, "Aerosol Technology" by William C. Hinds (1982), which is incorporated herein by reference in its entirety, including any references cited therein, where it is taught that ultrasonic aerosol generating transducers can heat the surrounding liquid (page 382). This embodiment can without limitation, offer the added benefit of enabling the transducers (10) to quickly heat the surrounding liquid (30) and liquid (30) surface above them. The tub walls (530) can also, without limitation, be designed or modified in a manner known to those skilled in the art so that the liquid (30) contained within the tub walls (530) is able to reach or experience an effective exchange with the surrounding liquid (30) outside of the tub walls (530), so that the liquid (30) within the tub walls (530) is not able to either exceed a given temperature or drop below a given temperature. Without limitation, the tub walls (530) can be continuous or non-continuous, and they can have one or more openings (670) of various size, shape, and in various locations. The tub walls (530) can, without limitation, be sealed or partially sealed, interfaced or not interfaced, interlocked either tightly or loosely, or be unsealed. The tub walls (530) can without limitation, interface completely or intermittently, or not interface, with the surfaces of the transducer assembly(s) (100) or the housing (20), and the height of the tub walls (530) can also vary. Any gap or distance (925) may exist between the tub walls (530) and any surfaces of the transducer assembly(s) (100) or the housing (20). It is preferred without limitation, that the tub walls (530) extend to an effective height above the surface of the liquid (30). Without being limited, one or more notches can also be cut into the top of the walls and can be of various size, shape, and in various locations. The tub walls (530) and associated parts may be constructed from any material that is compatible, and suitable for use with the liquid (30). The tub wall(s) (530) can also be designed and constructed to perform the same function(s) as the buoyant object(s) (400), or share any of the same features of the buoyant object(s) (400). The tub wall(s) (530) can, without limitation, have any density, buoyancy, air space, thickness, size, shape, and can be injection or blow molded. Without limitation, the tub wall(s) can be directly or indirectly positioned or interfaced anywhere with and in any orientation to the transducer assembly(s) (100) or housing(s) (20). The tub wall(s) (530) can have any number of vertical or angled voids, holes or openings (herein referred to as "openings") (920) above the transducer(s) (10) or transducer assembly(s) (100). The openings (920) can, without limitation, allow any emitted pressure (energy) resulting from the operation of the transducer(s) (10), to reach the surface of the liquid (30) in the reservoir(s) (40). The openings (920) can be any size, shape, or have any angle or cant.

According to an embodiment shown in FIGS. 53 and 36, the apparatus can be designed and constructed so that air/gas that surrounds the apparatus (215) or outside air/gas that is pulled into the apparatus (215) for purposes including, without limitation, removing the aerosol (200) that is generated by the transducer(s) (10), from the apparatus (215) and into the intended or targeted area (210), is filtered before it enters the apparatus (215), or at least before the air/gas reaches the aerosol generation chamber (40). One or more filters (675) of various kinds and function, may be used, but should be at least sufficient for the intended amount or degree of filtering that is desired or needed, and the correct filter (675) that is used for a specific application is known to those skilled in the art. It is preferred, without limitation that the filter(s) (675) is located at any location where the air/gas is drawn or pulled into the apparatus (215) by a blower or fan or other means (180) to move the air/gas or aerosol (200). It can be located either on the inside or outside of the apparatus (215) and sufficiently interfaced with the apparatus (215) in a manner that is known to those skilled in the art. The filter(s) (675) can, without limitation, prevent or limit dust or debris contamination inside of, on, or in: (a) any liquid (30), (b) any pipe(s) (685) that are used to construct the aerosol generating apparatus (215) through which the air/gas is moved, (c) the fan or blower or other source of pressurized air (180), (d) the chamber (40) in which the transducer(s) (10) are located, or (e) the introduction of various types of contaminates into the intended or targeted area (210) in which the aerosol (200) is deployed. The filter(s) (535) are not used in any configuration(s) or application(s) involving a "closed loop system" where the air/gas or aerosol (200) that is deployed from the apparatus (215) is then recirculated back to the apparatus (215) through one or more return conduit(s) or pipe(s) (240). This avoids any conflict with: (a) (col. 3, line 19-24), (col. 11, line 14-17) and (claim #21) of U.S. Pat. No. 5,878,355 (Berg et al. 1996), and (b) (col. 3 line 26-31), (col. 11, line 20-23) and (claim #8) of U.S. Pat. No. 6,102,992 (Berg et al. 1998), both of which are incorporated herein by reference in its entirety, including any references cited therein. The filter(s) (675) can be, without limitation, disposable. One or more protective covers (680) may also be directly or indirectly connected to the filters (535). The protective covers (680) may be positioned, or installed anywhere in the air/gas stream before the air/gas enters the filter(s). One or more protective cover(s) (680) may also be integrated into any external walls (755) of the apparatus and may be constructed from any material that is compatible, and suitable for use with the liquid (30).

According to an embodiment, the apparatus (215) can be designed and constructed so that one or more tank(s) (herein referred to as "intermediate tank(s)") (695), are connected between the one or more tank(s) (280) in which liquid (30) is stored and the reservoir(s) (40) they feed or supply, in which transducer(s) (10) are located. The intermediate tank(s) (280) can, without limitation, perform the function of a check or failsafe device or design, and prevent the reservoir(s) (40) in which the transducers (10) are located from being overfilled with liquid (30) if one or more valve(s) (300) from the tank(s) (280) that feed or supplies the reservoir(s) (40) fail in an open or semi-open position. The intermediate tanks (695) can have one or more of various types of valves (300) that include, but are not limited to, float valves, or solenoid valves. The valve(s) (300) can control the flow of either inbound or outbound liquid (30). The said valve(s) (300) can, without limitation, be actuated by a PLC (315), or by one or more sensor(s) (305) located in the intermediate tank(s) (695) or reservoir(s) (40) in which the transducer(s) (10) are located, and is accomplished in a manner known in the art. The valve(s) (300) are also installed, and connected to a PLC (315), if applicable, in a manner known to those skilled in the art. The valve(s), immediate tank(s), and associated parts may be constructed from any material that is compatible, and suitable for use with the liquid (30).

According to an embodiment, the apparatus (215) can be designed and constructed so that one or more liquid containment tank(s) (705) is connected to various parts, components, or areas of the apparatus including, but not limited to, the fill pipe(s) (295), blower or fan housing(s) (180), internal catch pan(s) or basin(s) (700), reservoir(s) (40) in which the transducers (10) are located, or pressurized air pipe(s) or conduit(s) (685). Without limitation, the aforementioned liquid containment tank(s) (705) is designed to collect excess, spilled, leaked, coalesced, or other undesired liquid (30). It can be connected to the main drain (655) and valve (660) used to drain the apparatus, or it can have its own drain pipe and valve. The positioning of the liquid containment tank(s) (705) as well as its shape and capacity can vary. A liquid level sensor (305) may be used to detect the presence of any liquid (30) or the depth of the liquid (30) in the containment tank(s) (705). The said liquid level sensor (305) may communicate with a PLC (315) and cause the apparatus to shut down or enter a fault or error mode if the if the liquid level (30) exceeds a defined depth. The liquid containment tank(s) (705) and associated parts may be constructed from any material that is compatible, and suitable for use with the liquid (30). Without limitation, any pipe(s) (685) carrying inbound or outbound air or aerosol, as well as the blower(s) (180) and the pipe(s) (685) that connect it to the reservoir(s) (40) in which the transducers (10) are located, can be canted or angled back toward the reservoir(s) (40) in which the transducer(s) (10) are located to carry out various functions such as, but not limited to, helping collect any liquid (30) from those areas.

According to an embodiment, the apparatus can be designed and constructed so that it has one or more means to control the temperature of the liquid (30) in the various reservoir(s), which includes, but is not limited to, preventing the temperature of the liquid (30) in the reservoir(s) (40) in which the transducers (10) are located, from exceeding the maximum desired, established, or required operating temperature for that liquid (30) or particular process in which the liquid (30) is being used.

As previously discussed, the prior art has taught the heating of the liquid (30) in various ways including, but not limited to, heating the liquid (30) from the heat that is imparted into the liquid (30) during the operation of the transducers (10). It is obvious to one skilled in the art, that the air or gas that is used to remove the generated aerosol (200) from the reservoir(s) (40) in which the transducers (10) are located, can contribute to the removal of heat from the liquid (30). However, this pressurized air/gas flow can only remove a certain quantity of heat and is affected by factors including, but not limited to, the surface area of the liquid (30) in the reservoir(s) (40), and the volume and velocity of air/gas that moves over that surface area. If more heat is imparted into the liquid (30) than is removed over time, the liquid (30) will continue to rise in temperature.

The means to control or prevent the temperature of the liquid (30) in the reservoir(s) (40) in which the transducers (10) are located, from exceeding the aforementioned maximum desired, established, or required operating temperature, includes without limitation, a means to cool the liquid (30) by pumping or otherwise moving the liquid (30) that is in the reservoir(s) (40) in which the transducer(s) (10) are located, or any other liquid (30) that could possibly have contact with the liquid (30) in the reservoir(s) (40) in which the transducer(s) (10) are located, through a heat exchanger, cooling fins, cooling plate, cooling block, chiller, chilling or cooling apparatus, or other means known in the art (710), to remove heat from the liquid (30). It is preferred that this means includes pumping or moving the liquid (30) from the reservoir(s) (40) in which the transducers (10) are located, through cooling fins, chill block, or heat exchanger that is located in the path of the pressurized air/gas that is used to move the generated aerosol (200) away from the apparatus. The means to cool the liquid (30) can also interface or directly interface with the reservoir(s) (40) in which the transducers (10) are located and can include, but is not limited to, the interface or insertion of chill coil(s) or chill block(s) directly into the reservoir(s) (40) in which the transducers (10) are located. The means mentioned in this embodiment to cool the liquid (30) and associated parts may be constructed from any material that is compatible, and suitable for use with the liquid (30). The PLC(s) (315) can monitor the temperature of the liquid (30) in the reservoir(s) (40) with input from one or more liquid temperature sensing device(s) (820). The PLC(s) (315) can activate whatever means necessary to start, maintain, or stop any liquid (30) cooling activities or actions, to maintain any desired or necessary temperature.

An additional aspect of this embodiment includes, without limitation, insulating the reservoir(s) (40) in which the transducer(s) (10) are located, in various ways including, but not limited to, interfacing or applying any type of insulation material (760) to any surfaces of the reservoir(s) (40), or using a double wall construction (765) for the reservoir (40)

where the said walls are separated with a layer of air, or other means known to those skilled in the art. Without limitation, insulating the reservoir(s) (40) can be useful in environments where it is important to increase heating efficiency or capacity and diminish heat loss from the system.

Figure 33:
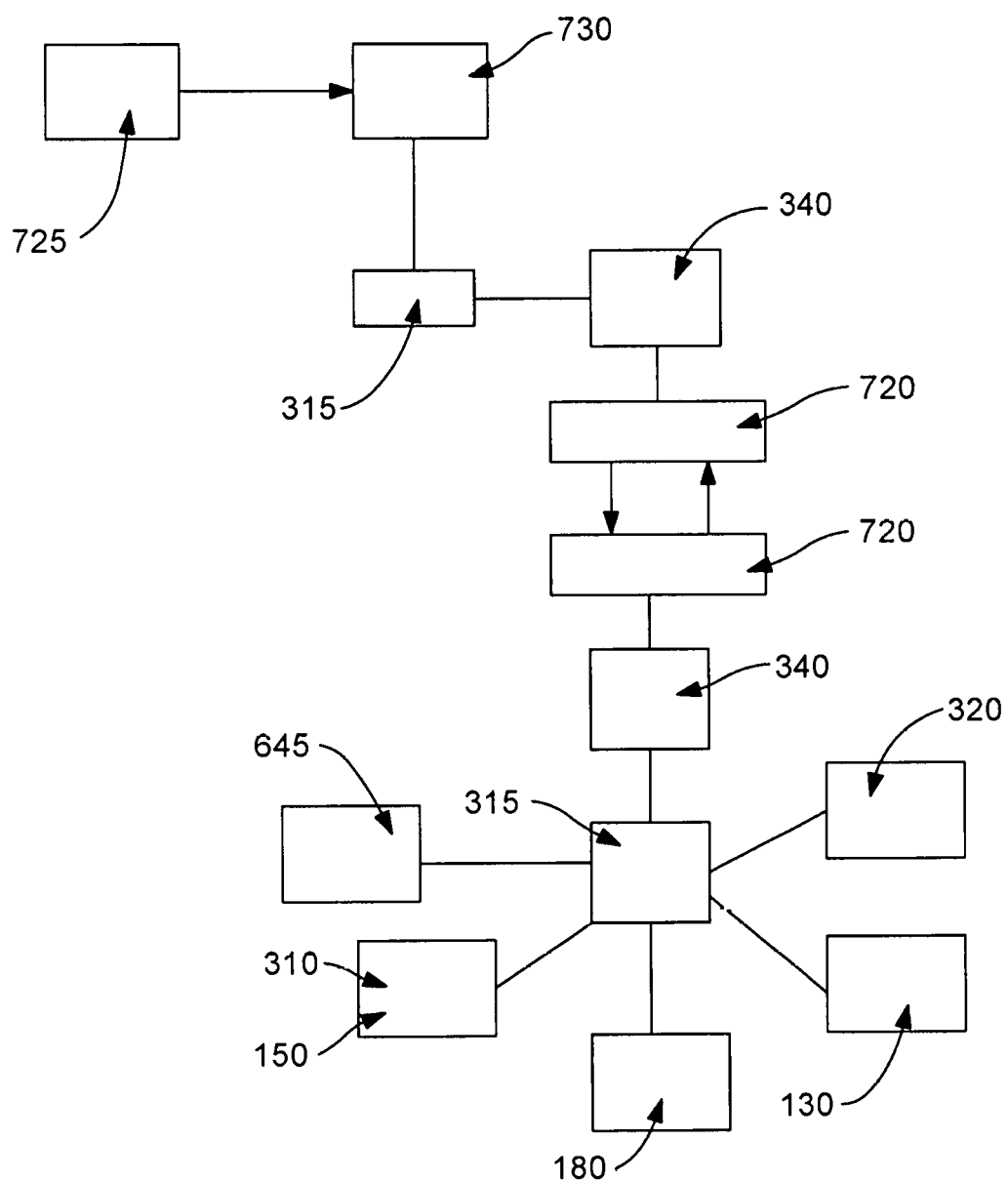
FIG. 33 is a schematic view of an embodiment of a light source and light sensor that communicates with a PLC that communicates with various parts and components of an aerosol generating apparatus, according to the present invention.
Figure 34:
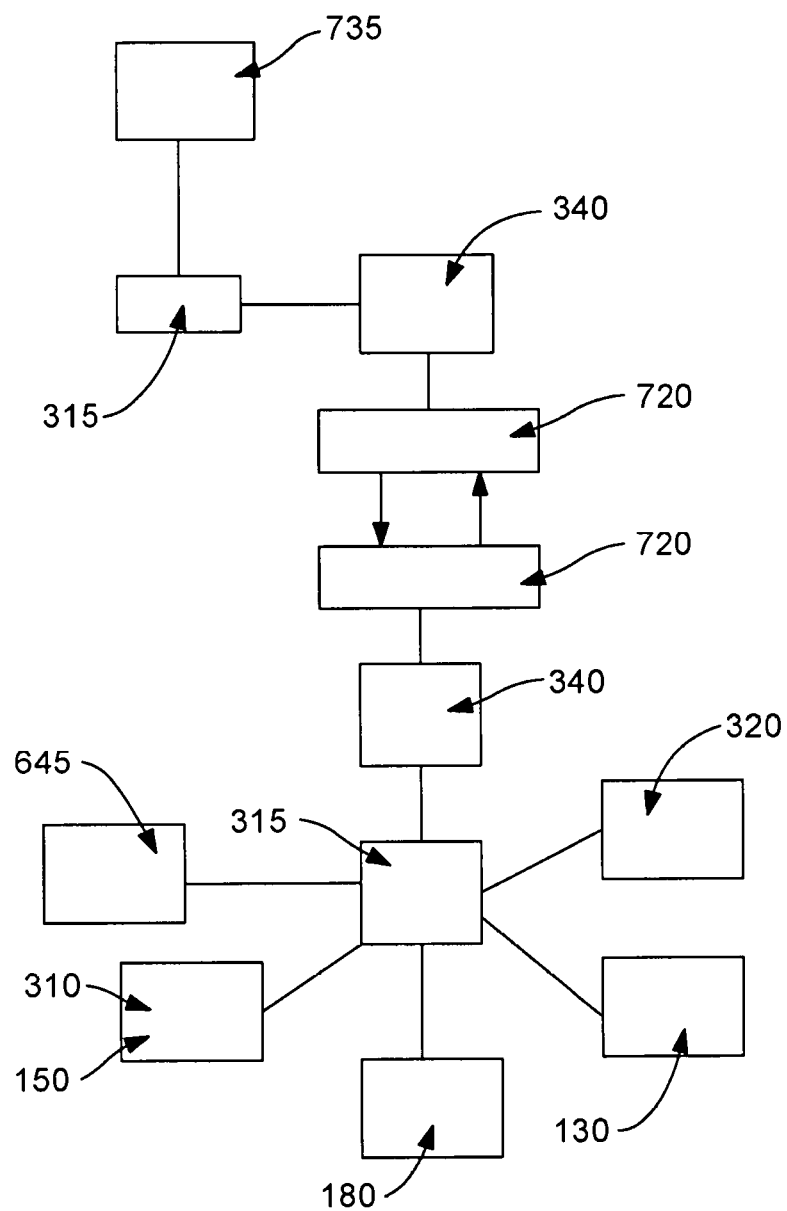
FIG. 34 is a schematic view of an embodiment of a relative humidity sensor that communicates with a PLC that communicates with a transceiver that communicates with various parts and components of an aerosol generating apparatus, according to the present invention.
Figure 35:
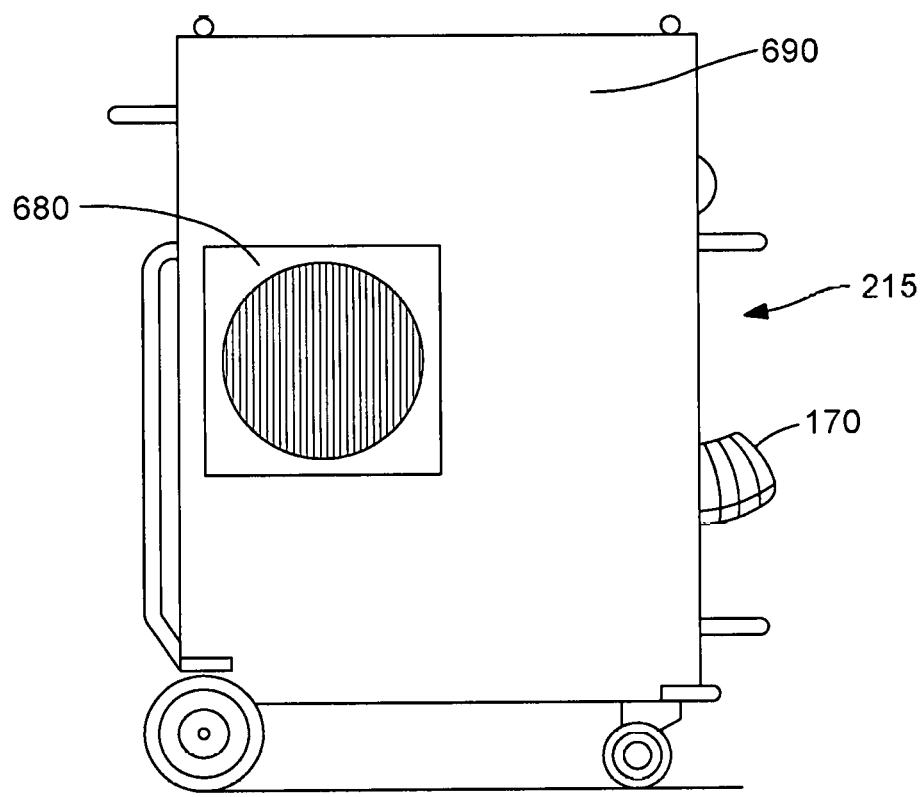
FIG. 35 is a side plan view of an embodiment of an aerosol generating apparatus according to the present invention.
Figure 36:
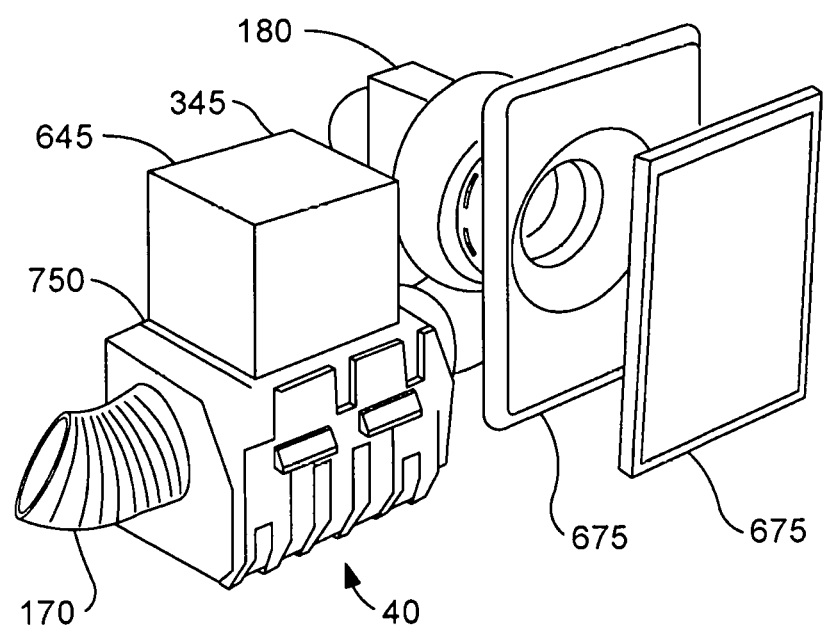
FIG. 36 is a partially broken away, exploded isometric view of an embodiment of various parts and components of the aerosol generating apparatus such as, filters, blower, pipes, reservoir, drive electronics and exit orifice, according to the present invention.
Figure 37:
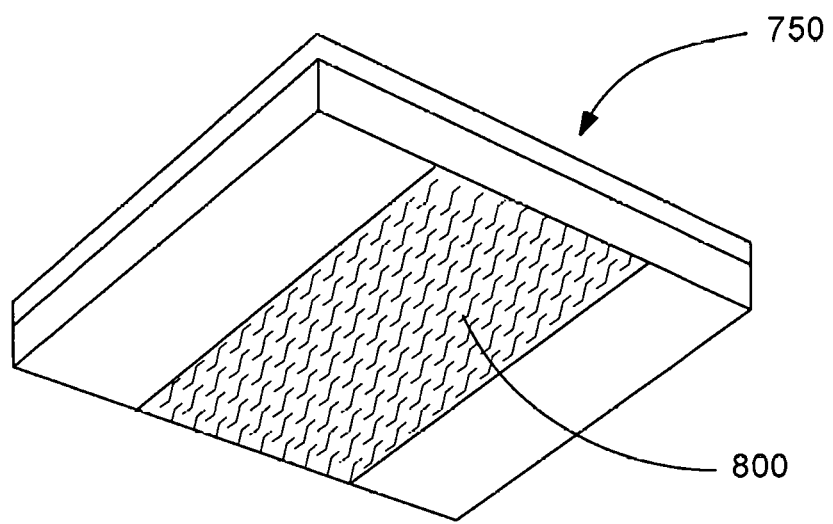
FIG. 37 is an isometric view of an embodiment of a heat sink that interfaces with parts and components such as, the drive electronics and a reservoir, according to the present invention.
Figure 38:
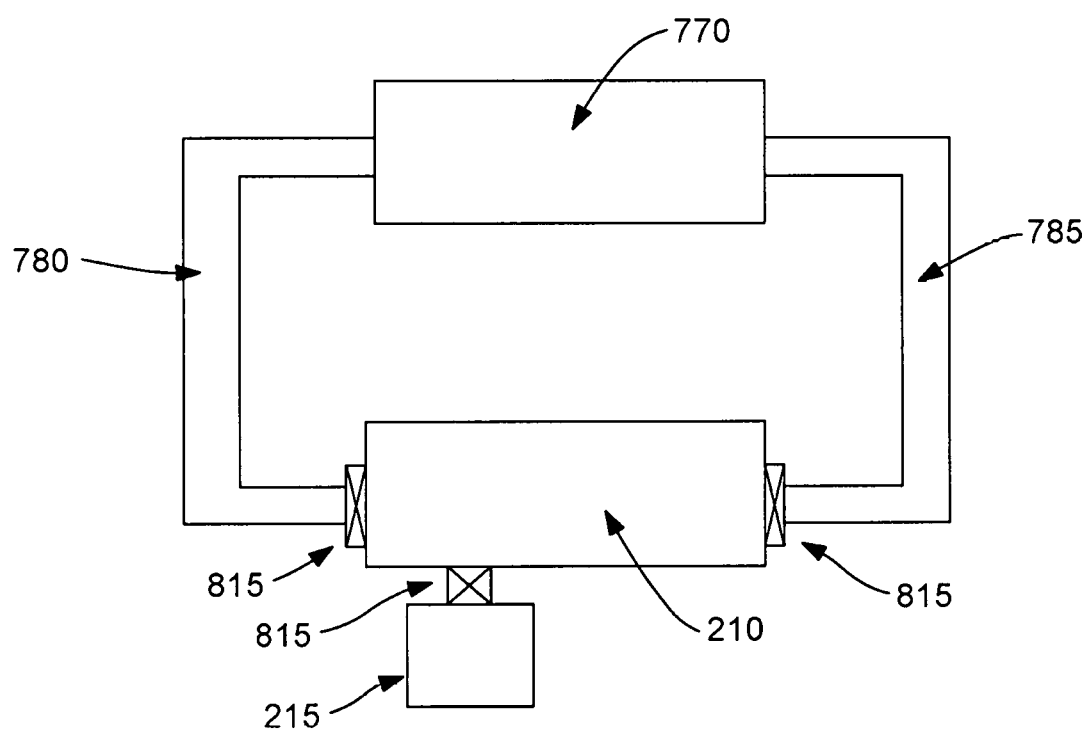
FIG. 38 is a schematic view of an embodiment of a means to decrease the temperature of the atmosphere and surfaces in the targeted area(s) consisting of generating, moving, and recirculating cooled or chilled air into the targeted area(s), as well as the interface of valves with the targeted area(s), according to the present invention.
Figure 39:
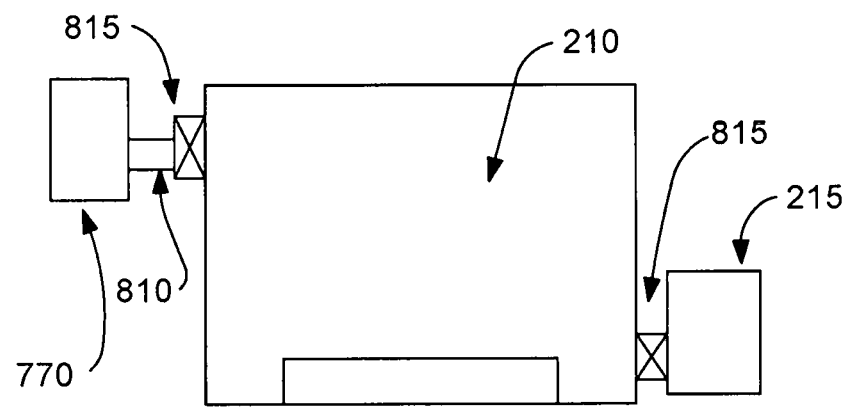
FIG. 39 is a schematic view of an embodiment of a means to decrease the temperature of the atmosphere and surfaces in the targeted area(s) consisting of generating, and moving, cooled or chilled air into the targeted area(s), as well as the interface of a valve before or at the entrance to the targeted area(s), according to the present invention.
Figure 40:
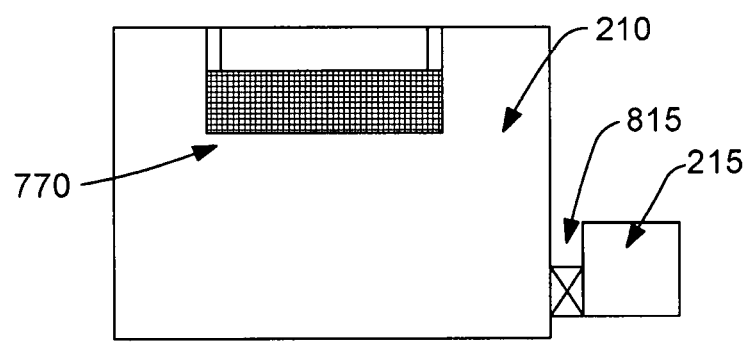
FIG. 40 is a schematic view of an embodiment of a means to decrease the temperature of the atmosphere and surfaces in the targeted area(s) consisting of generating, cooled or chilled air inside the targeted area(s), according to the present invention.
Figure 41:
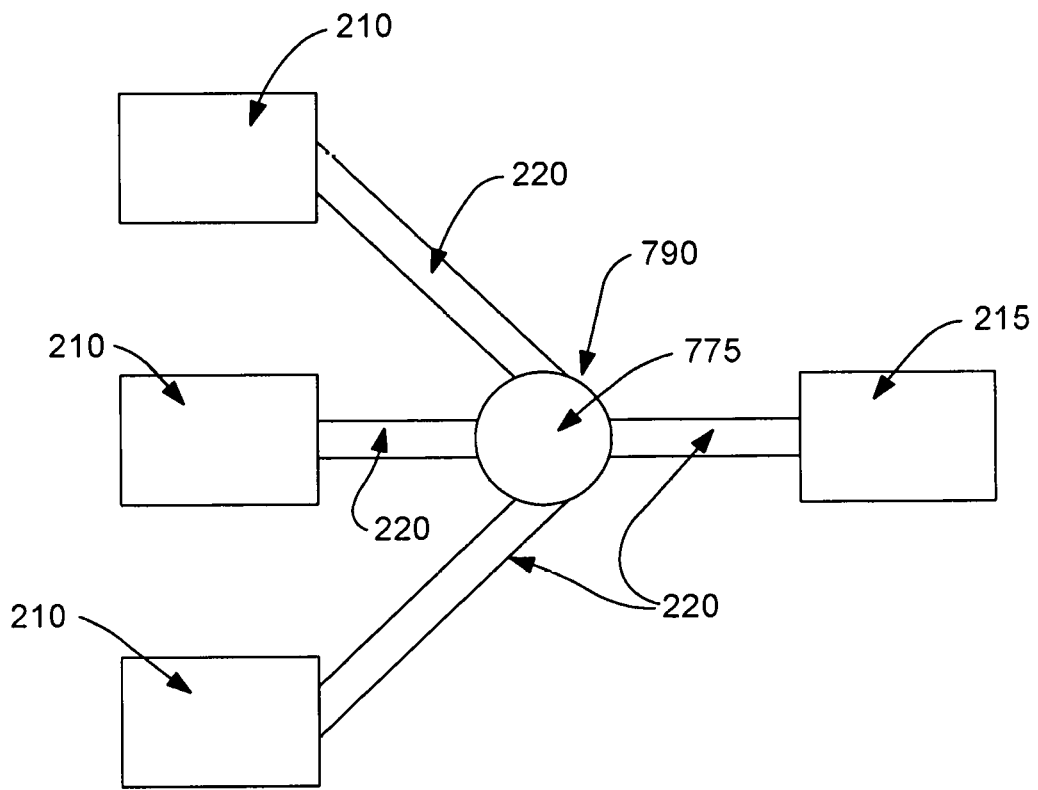
FIG. 41 is a schematic view of an embodiment of a means to divert air/gas and aerosol emanating from the aerosol generating apparatus, to multiple separate enclosed targeted areas, and consists of parts and components such as a pipe junction and valve, according to the present invention.
Figure 42:
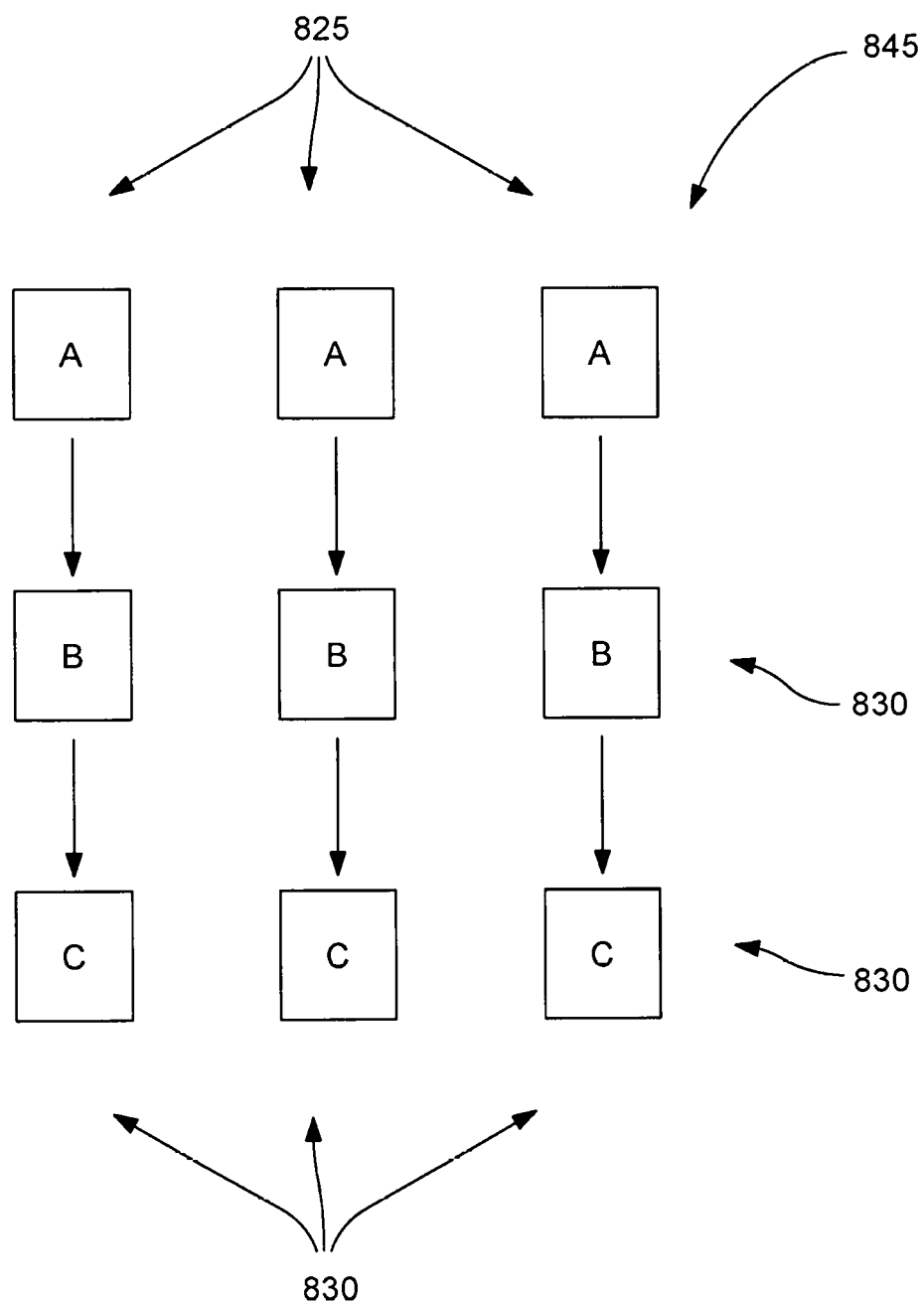
FIG. 42 is a schematic view of an embodiment of a means to compensate for any shifting of transducer frequencies, where a crystal is initially used to generate one specific frequency or specific frequency range for a transducer(s), and is then switched to a different crystal that is used to generate another specific frequency or specific frequency range for the transducer(s), and this can be performed multiple times for a plurality of transducers, according to the present invention.
Figure 43:
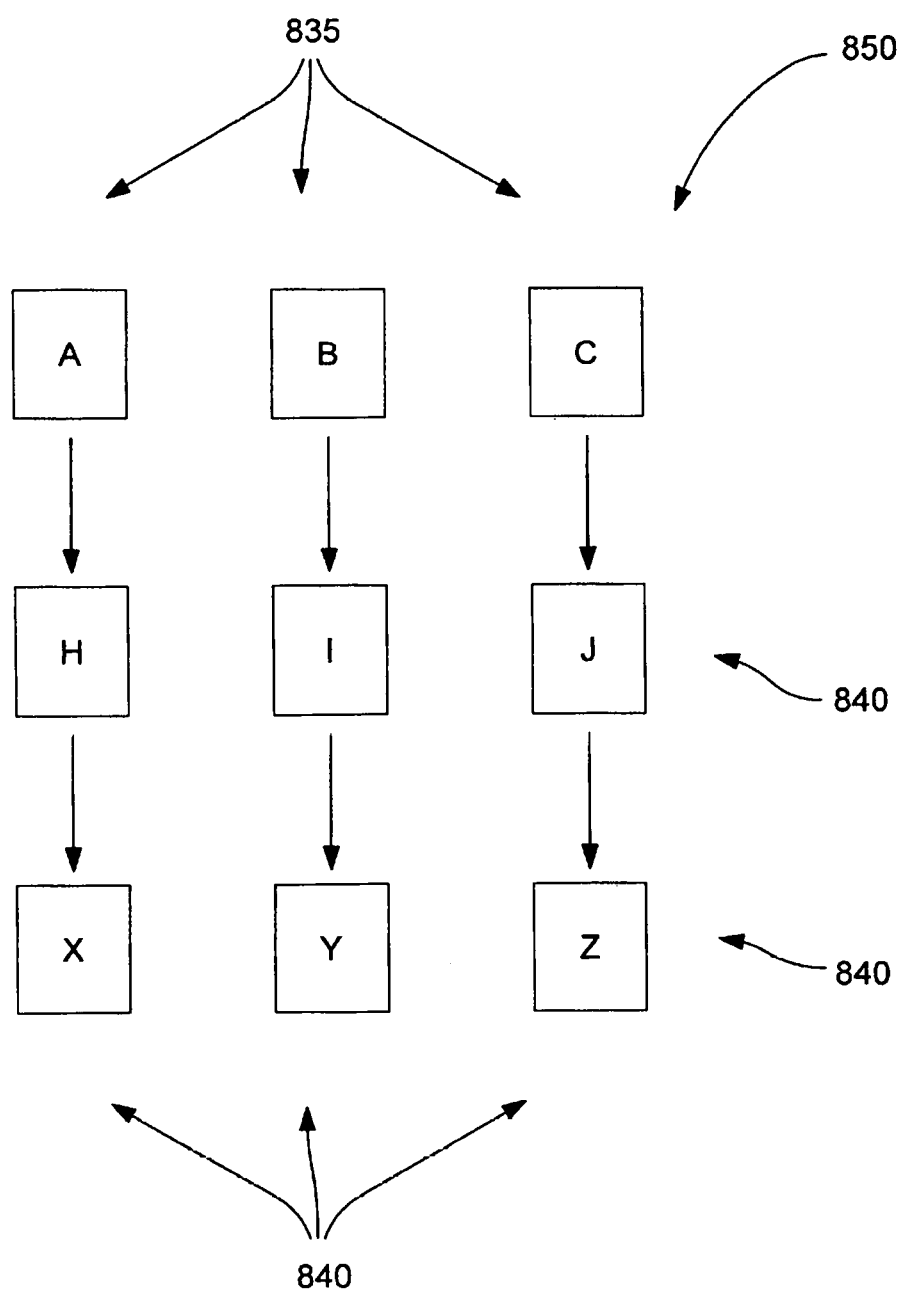
FIG. 43 is a schematic view of an embodiment of a means to compensate for any shifting of transducer frequencies, where a signal generator is initially used to generate one specific frequency or specific frequency range for a transducer(s), and is then switched to a different signal generator that is used to generate another specific frequency or specific frequency range for the transducer(s), and this can be performed multiple times for a plurality of transducers, according to the present invention.
Figure 44:
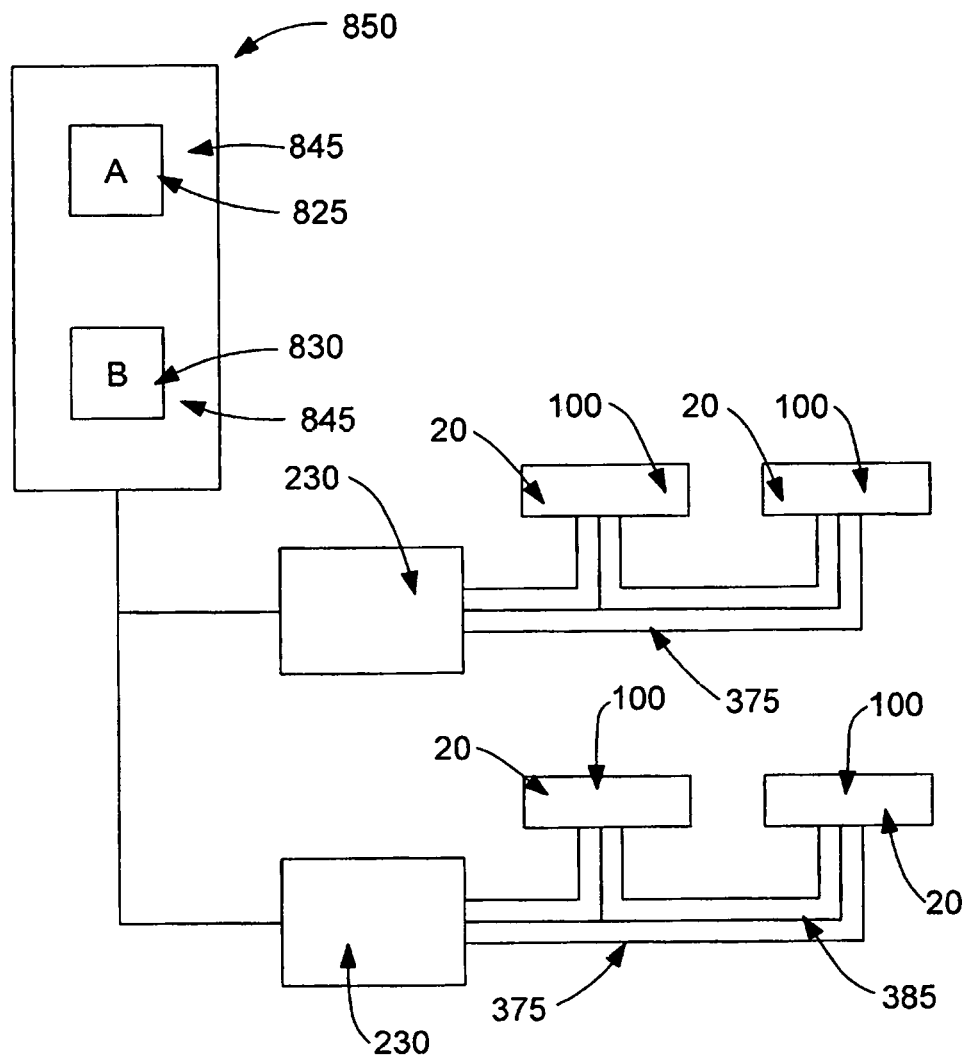
FIG. 44 is a schematic view of an embodiment of a means to compensate for any shifting of transducer frequencies, where a crystal that is a part or component of a signal generator is initially used to generate one specific frequency or specific frequency range for a transducer(s), is then switched to a different crystal that is a part or component of the same signal generator, and is used to generate another specific frequency or specific frequency range for the transducer(s), and the signal generated from the activated crystal is sent via the signal generator to an amplifier(s) that is connected to one or more transducers, according to the present invention.
Figure 45:
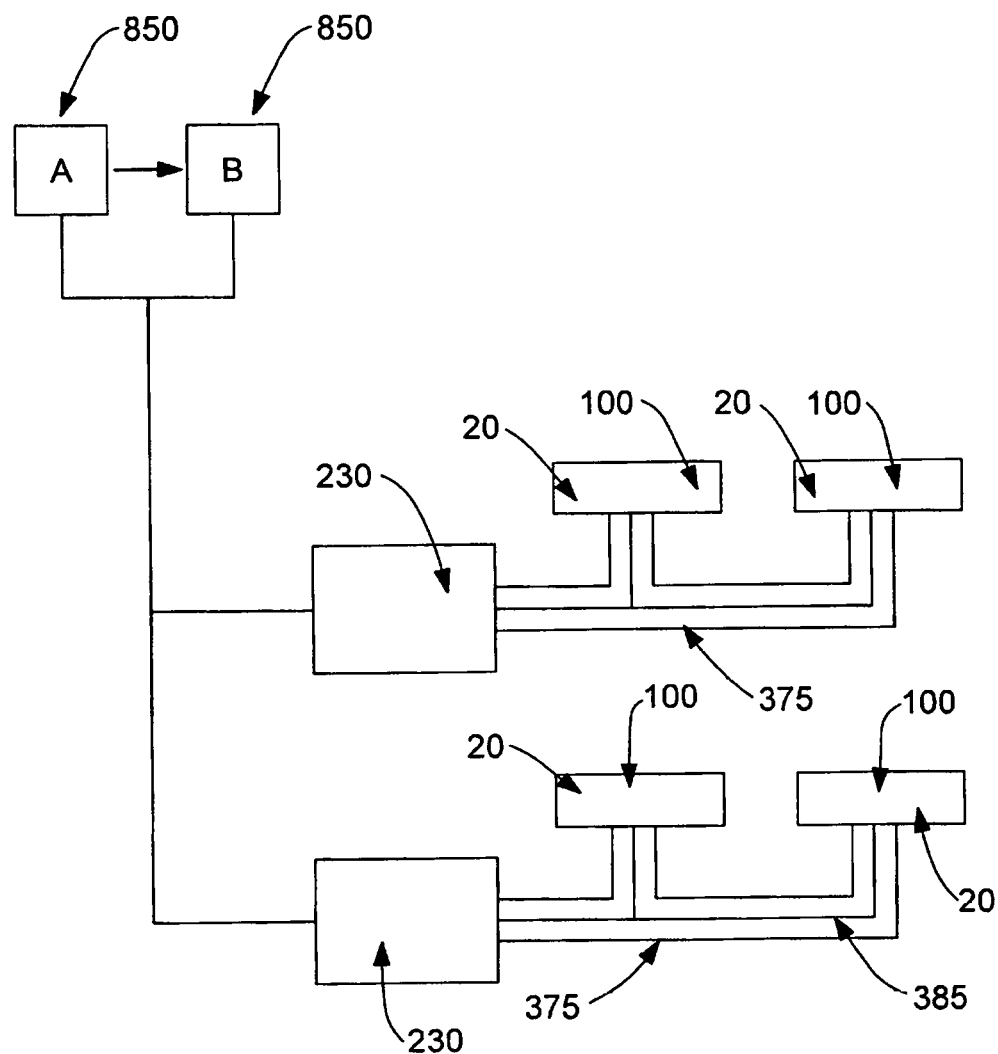
FIG. 45 is a schematic view of an embodiment of a means to compensate for any shifting of transducer frequencies, where a signal generator is initially used to generate one specific frequency or specific frequency range for a transducer(s), is then switched to a different signal generator, that is used to generate another specific frequency or specific frequency range for the transducer(s), and the signal generated from the activated signal generator is sent to an amplifier(s) that is connected to one or more transducers, according to the present invention.

According to an embodiment illustrated in FIGS. 33 and 34, the apparatus can be designed and constructed so that it can be remotely communicated with and controlled, by anyone or any means. Without being limited, one or more PLC(s) (315) that control one or more parts of the apparatus can also communicate with or be controlled by any other apparatus and their PLC(s). More specifically, and without limitation, the remote control and communication with the apparatus can be accomplished by means such as, but not limited to, any radio frequency or amplitude, any electrical frequency or amplitude, any light frequency or amplitude, any digital or analog data packet, or by any directly or indirectly connected wire(s), which includes fiber optic wire(s), or any combination of the of the said means. Without limitation, any data, commands, or information can be sent and received by the apparatus and communicated between the apparatus and one or more additional means to send and receive any data, commands, or information. Commands, can include, but are not limited to, a command for the apparatus to start or to end an aerosol generation or deployment cycle. Communicated information or data can include, but is not limited to, the apparatus communicating its current operational status or condition, as well as liquid (30) level and temperature. It is preferred, without limitation, that the apparatus communicates by using one or more radio transceiver(s) (340) that is connected to one or more PLC(s) (315), that is connected to one or more HMI(s) (320), and communicates with one or more remote radio transceiver(s) (315) that is connected to one or more remote PLC(s) (315) which are attached to one or more remote HMI(s) (320) or other parts or components. The one or more antenna(s) (720) connected to the radio transceiver(s) (340), can be located anywhere on or in the apparatus (215), and can be constructed from various materials. The antenna(s) (720) and any related parts may be constructed from any material that is compatible, and suitable for use with the liquid (30). It is preferred, without limitation, that the radio transceiver(s) (340) and antenna(s) (720) be located within any NEMA or IP rated or hermetically sealed container(s) (345) that is constructed from polymer that is compatible, and suitable for use with the liquid (30). Within this embodiment, and without limitation, a plurality of apparatuses, including, but not limited to, apparatuses that are similar in process, or apparatuses that are similar or identical to the apparatus (215) of the present invention, can operate in the same, connected, or shared volume of space, and communicate information including, but not limited to their condition or status of their systems or the apparatus in general, to all of these apparatuses, so that if one apparatus has a problem, or enters into a fault or error condition or state, all of the other apparatuses can also shut down, or at least relay the incident to one or more remote PLC(s) (315), HMI(s) (320) which the operator can monitor. This embodiment also offers many advantages including, but not limited to, reducing or eliminating the chance of accidental exposure to the aerosol (200) from an apparatus (215) that is operating within the same environment (210) in which the aerosol (200) is applied.

According to an embodiment, and without limitation, the apparatus (215) can be designed and constructed so that it has one or more sensors (3530), or the means for indirect or direct communication with one or more sensor(s) (3530), or one or more PLC(s) (315) which are connected to one or more sensor(s) (3530), to determine if an effective or sufficient amount of aerosol (200) has been applied to the targeted area (210) and/or surfaces.

In the first aspect of this embodiment, each sensor (3530) can, without limitation, consist of at least two parts including, but not limited to, a light source (725) and a light sensor (730), known to those skilled in the art. The light source (725) and light sensor (730) can be directly or indirectly connected, or they can be placed or positioned independent from one another. The distance between the light source (725) and light sensor (730) can be any distance, but should be at least an effective distance. The light source (725) and light sensor (730) can be, without limitation, separated by a distance of one (1) foot or less. However, it is preferred, without limitation, that the light source (725) and light sensor (730) are at separated by a distance of one (1) foot or more. It is more preferred, without limitation, that the light source (725) and light sensor (730) are separated by a distance of two (2) feet or more. It is even more preferred, without limitation, that the light source (725) and light sensor (730) are separated by a distance of four (4) feet or more. Without being limited, any effective light source (725) and any effective light sensor (730), known in the art, may be utilized in the present invention. Each sensor(s) can, without limitation, consist of at least one of any effective laser, of any power or class type, for a light source (725), and at least one of any photoelectric sensor, of any type and sensitivity (730), for a light sensor (730). The one or more light source(s) (725) and one or more light sensor(s) (730) that are utilized can be, without limitation, configured or positioned so that the light sensor(s) (730) receives light in various ways such as, but not limited to, directly from one or more light source(s) (725), indirectly from one or more light source(s) (725), or from any reflected light that is generated from one or more light sources(s) (725). Any light that is reflected back to the one or more light sensor(s) after being generated by any light source(s) (7225) may reflect off of one or more of any surface(s) or substance(s) such as, but not limited to any, aerosol (200), reflecting surface(s), or mirrored surface(s). The aerosol (200) may be of any effective density and size. Without being limited, the one or more light source(s) (725) and light sensor(s) (730) may be positioned in any effective direction, angle, orientation, configuration, or position. If light from one or more reflected surface(s) is utilized, the one or more surface(s) from which the light is reflected back to the light sensor(s) (730) can be, without limitation, positioned at any effective distance and any effective orientation or angle from the one or more light sensor(s) (730) and the one or more light source(s) (725). The reflective surface(s) may be, without limitation, any suitable size and shape.

The emitted light or energy, or light source (725) can have, without limitation, any traits or attributes including, but not limited to, any: (a) intensity(s), (b) brightness, (c) period(s), (d) frequency(s), type of light(s), and (e) wavelength(s). The one or more light source(s) (725) and light sensor(s) (730) can, without limitation, be controlled and/or communicate with one or more of any digital, electronic, or analog, controller(s) such as, but not limited to, any PLC. The means to sense the light (730) can, without limitation, vary widely in its sensitivity and ability to sense any kind of light consisting of any traits or attributes including, but not limited to, any: (a) intensity(s), (b) brightness, (c) period(s), (d) frequency(s), type of light(s), and (e) wavelength(s). The means to sense the light (730) can also have various capabilities known in the art, including, without limitation, the ability to have any adjustable sensitivity and trigger level(s), or the ability to communicate with a PLC(s) (315) or other components. The light sensor(s) (730) can, without limitation, indicate to or communicate with any PLC(s) (315) if or when it either receives or ceases to receive any trait or attribute pertaining to light such as, but not limited to, any desired or set level of light stimulus or light intensity. The said communication can be accomplished in various ways known in the art. It is preferred, without limitation, that the PLC(s) (315) is indicated or receives information about the status of any light generated by the light sensor(s) (730), in various ways including, but not limited to any, electrical signal, level or intensity of any electrical signal, or lack of any electrical signal(s) from the light sensor(s) (730). This communication can, without limitation, result in various actions or combination of actions, such as, but not limited to: (a) shutting down any drive electronics (645) or amplifier(s) (230), (b) shutting down any blower (180) or flow of pressurized air, or (c) shutting down any apparatus (215).

Without limitation, an effective or sufficient amount of administered aerosol (200) in this embodiment is indicated by its causing any, disruption, diminishment, decrease, or cessation, of the light that is emitted from the light source(s) (725), before it reaches any light sensor (730). The effective, sufficient amount, or specified quantity, of administered aerosol (200) can vary for any intended or unintended reasons or designs, and the trigger or sensitivity levels for the light sensor(s) (730) can, without limitation, be varied, calibrated, or adjusted, to any amount or level of light disruption, for each situation or any level of aerosol that is equated with an efficacious outcome.

In the second aspect of this embodiment one or more of the sensor(s) (3530) can, without limitation, sense or measure any relative humidity level or humidity level, in a manner known to those skilled in the art. Without being limited, the humidity sensor(s) (4090) can have various capabilities and attributes including, without limitation, varying sensitivity, the ability to have any adjustable trigger level(s), and/or the ability to be controlled and/or communicate with one or more of any digital, electronic, or analog, controller(s) such as, but not limited to, any PLC. The humidity sensor(s) (4090) can, without limitation, indicate or communicate to any PLC(s) (315) any relative humidity data it collects, which can be accomplished in a manner known to those skilled in the art. The relative humidity sensor(s) (4090) can also, without limitation, receive or send any signal of any kind, to or from any other components. It is preferred, without limitation, that the PLC(s) (315) is indicated or receives information about the status of any humidity that is detected in the targeted area (210), in various ways including, but not limited to, receiving any, electrical signal, level or intensity of any electrical signal, or lack of any electrical signal(s) from the humidity sensor(s) (4090). This communication can, without limitation, result in various actions or combination of actions, such as, but not limited to: (a) shutting down any drive electronics (645) or amplifier(s) (230), (b) shutting down any blower (180) or flow of pressurized air, or (c) shutting down any apparatus (215).

Also, without limitation, one or more of any PLC(s) (315) can be programmed to have delays of various length of time after receiving any, data, communication, or signal, to initiate actions such as, but not limited to: (a) shutting down any drive electronics (645) or amplifier(s) (230), (b) shutting down any blower(s) (180) or flow of pressurized air, or (c) shutting down one or more of any apparatus(s) (215), after receiving any signal(s), data, or communication from any sensor(s) such as the light sensor (730) and/or the relative humidity sensor(s) (4090) or any other related components or sensor(s).

According to an embodiment, the apparatus can be designed and constructed so that it can without limitation, measure, determine, or sense, the amount of liquid (30) that is in any tank or reservoir. Without limitation, this information or data may be used, in concert with or without a PLC (315), to: (a) communicate to the operator whether there is either a sufficient or insufficient amount of liquid (30) to execute a chosen operational cycle time, (b) communicate to the operator whether there is either a sufficient or insufficient amount of liquid (30) to execute an operational cycle time associated with a specific volume of space or other attribute(s) chosen by the operator, (c) communicate to the operator the quantity of liquid (30) or at least the minimum quantity of liquid (30), expressed in units of measure, which may be necessary to add or make available to the apparatus so that it may effectively or successfully complete a chosen or desired operational cycle. It is preferred, without limitation, that the units of measure in the present invention include, but are not limited to, any liquid (30) volume quantities expressed in, standard units of measure, imperial units of measure, English units of measure, units of measure according to the metric system, or units of measure according to System International (SI) units. French Patent No. FR2860721 (Schwal et al.), which is incorporated herein by reference in its entirety, including any references cited therein, taught that a fogging apparatus can notify the operator if an insufficient liquid (30) quantity is available (pg. 6 line 15-25 and pg. 10 line 10-25) and when it is necessary to replace a cartridge (290) (pg. 10 line 15-25). However, FR2860721 (Schwal et al.), only mentioned that an indication would be made by the fogging apparatus to the operator to replace an interfaced cartridge (290) (pg. 10 line 15-25), or additional possibly interfaced cartridges (290) (pg. 7 line 3-10), but it was silent with respect to the apparatus itself determining the amount of liquid (30) that is needed to properly or effectively fill the apparatus, and communicating the exact number of a plurality of cartridges (290) that may be needed to fill the apparatus with liquid (30) either partially or to full capacity so that it can successfully and effectively complete a predetermined operational cycle. Therefore, it is more preferred, without limitation, that the units of measure communicated can also include more than one or a plurality of cartridges (290) with a known quantity of liquid (30) that is needed to provide the apparatus with a sufficient quantity of liquid (30) for it to effectively or successfully complete its operational cycle time. It is even more preferred, without limitation, that the units of measure include, any units of measure, including any number of cartridges (290) as long as it is a plurality of cartridges. The apparatus can, without limitation, communicate to the operator the minimum quantity of liquid (30) needed to complete an operational cycle, as well as the quantity of liquid (30) that would be needed to fill the apparatus to capacity. Again, the quantity of liquid (30) may be expressed in any units of measure including, but not limited to, the number of cartridges (290). Information or data can be communicated to or from the apparatus with any means known to those skilled in the art including, but not limited to, human-machine-interface(s) (HMI) (320), terminal(s), remote terminal(s), any button(s) and associated light(s), screen(s), or audible signal(s). The apparatus can, without limitation, require the operator to acknowledge one or more prompts to add a certain amount of liquid (30) or a certain number of cartridges (290) as well as one or more prompts to verify if the action was undertaken. This can be accomplished with an HMI (320) or other means known to those skilled in the art. More specifically, this embodiment includes without limitation, the apparatus having the ability to sense, detect, or determine, with one or more sensor(s) or other effective means, any: (a) liquid (30) level, (b) liquid (30) depth, or (c) amount of liquid (30) in any tank(s), reservoir(s) (40), or other places where liquid (30) is held and available to the apparatus, and communicate that information to a PLC(s) (315). This may be accomplished in a manner known to those skilled in the art. It is preferred, without limitation, that one or more float sensor(s) (305), which can be located in various locations in the apparatus, be utilized for this purpose. They can be constructed from any material that is compatible, and suitable for use with the liquid (30), and their use and configuration are known to those skilled in the art. Any data, information, or signals, can be sent from the said means to sense, detect, or determine the liquid (30) level, liquid (30) depth, or amount of liquid (30) available, and can be sent or communicated, without limitation, to various places or means including, but not limited to, one or more PLC(s) (315) or HMI(s) (320). The PLC(s) (315) or HMI(s) (320) can be programmed in a manner known in the art to use the inbound information, data, or communication to control or interact with the apparatus, as well as communicate information to or from the operator. The PLC(s) (315) can, without limitation, be programmed so that the apparatus (215) will enter into a fault or error condition, or shut down one or more functions, and communicate an audible or visual signal to the operator, as well as communicate with any other PLC(s) (315), if the apparatus receives a command to operate for a certain amount of time or apply aerosol (200) to a certain volume and the PLC(s) (315) determines that an insufficient amount of liquid (30) is available.

According to an embodiment, the apparatus (215) can be designed and constructed so that it will not, without limitation, generate, create, or deploy aerosol (200), when the liquid (30) that is in or available to the reservoir(s) (40) in which the transducer(s) (10) are located cannot be used, administered, or deployed, for reasons including but not limited to: (a) the fluid (30) has exceeded the time or date within which it can be efficaciously used, or (b) the fluid (30) has reached a point in time or date where it has degraded or aged to a point where its use or application would be ineffective, unaccepted, unauthorized, or illegal. The present embodiment does not encompass what is taught in French Patent No. FR2860721 (Schwal et al.), which is incorporated herein by reference in its entirety, including any references cited therein. That patent includes placing or fitting a container(s) or cartridge(s) (290) of single use that is filled with the liquid (30) to be fogged or diffused, on or with an aerosol (200) dispensing device, and reading an identifier on the said container(s) with a reader (pg. 2, line 33-36) to determine its year/date (pg. 9 line 15-20) and suspending the operation of the apparatus if there is nonconformance, or in other words, the identifier(s) is determined to be associated with a container(s) that has expired. However, this embodiment, without limitation, also encompasses the liquid (30) that is in any cartridge(s) (290) (FIG. 12) that interfaces with the apparatus after the cartridge(s) (290) has been read and its use is approved, and the cartridge(s) (290) is opened or its seal is compromised, allowing the liquid (30) to be used or made available to the apparatus. This is important for reasons including, but not limited to, the liquid (30) can have a certain shelf life or period of effectiveness while in a closed container/cartridge (290), but once the container/cartridge (290) is opened, and exposed to its surrounding environment, or diluted, the shelf life or effective period of use is diminished or shortened. This can, without limitation, necessitate the monitoring, measuring, tracking, calculating, comparing, (herein "measuring"), the time that the liquid (30) can be utilized in the present invention until it cannot be used for various reasons known to those skilled in the art. Measuring the time that the liquid (30) can or cannot be used or its useful lifespan, can be accomplished by using a PLC(s) (315), or other mechanism or device known to those skilled in the art. The apparatus (215) in this embodiment can possesses various means to determine the useful lifespan of a liquid (30) or the length of time a liquid (30) can be effectively utilized by the apparatus, and such means may include, but is not limited to, the following or combination of the following: (a) measuring the time between when an empty apparatus (215) is initially filled with liquid (30) and the time when it should be drained of the liquid (30), which is preferred in this embodiment, (b) measuring the time between when the apparatus (215) was last drained of liquid (30) and when it should be drained again, (c) measuring the time between when an empty apparatus (215) is interfaced with the first cartridge(s) (290) to begin filling the apparatus with liquid (30) and the time when it should be drained of the liquid (30). Draining the liquid (30) in these instances pertains to draining all of the liquid (30) from the apparatus (215). This embodiment includes without limitation, the apparatus (215) having the ability to sense, detect, interpret, or determine, with one or more sensor(s) known to those skilled in the art, various activities, status, or conditions such as, but are not limited to, (a) the interface of one or more cartridge(s) (290) or other means to hold liquid (30), with the apparatus (215), (b) the liquid (30) level(s) in any reservoir(s) (40), (c) the opening or closing, or any position or state, of one or more valve(s) (660) to empty the apparatus of any liquid (30) that could be used to generate aerosol (200), (d) the movement or presence of any liquid (30), object, or mechanism, resulting from the emptying of the apparatus (215). The sensor(s) can communicate information with a PLC(s) (315) in a manner known in the art, and the PLC(s) (315) can use that information to help determine the length of time the liquid (30) may be utilized until it must be drained or discarded. The PLC(s) (315) can be programmed to accomplish these tasks in a manner known to those skilled in the art. The PLC(s) (315) can, without limitation, be programmed so that the apparatus will enter into a fault or error condition, or shut down one or more functions, and communicate an audible or visual signal to the operator, as well as communicate with other PLC(s), if a period of time has elapsed where the liquid (30) should have been fully drained but was not. This feature prevents the use of liquid (30) that has, without limitation, exceeded its usefulness for various reasons known to those skilled in the art. All communication between either the PLC(s) or the operator can transpire in a manner known in the art. In addition, any information or data can be communicated to or from the apparatus (215) by means such as, but not limited to, any human-machine-interface (HMI) (320), any terminal and its images, any buttons, any buttons and associated lights, any voice command(s) and directions, or any audible signal. The apparatus (215) can, without limitation, also require the operator to acknowledge any error or fault messages, apparatus status queries, or if any action was taken by the operator. The proper, necessary or effective period of time in which the liquid (30) can be used before it needs to be fully drained, is entered into the PLC'(s)' (315) programming in a manner known to those skilled in the art.

According to an embodiment illustrated in FIGS. 12, 13, 20, 29 and 37, the apparatus (215) can be designed and constructed so that any of its part(s), component(s) or space(s) that will increase in temperature from the operation of the apparatus (215) may be cooled, or any heat that is generated by one or more part(s) or component(s) or any related part(s) can be removed or displaced from the apparatus (215) either collectively or individually. The apparatus (215) in the present invention can be operated from various locations including, but not limited to, within the same area (210) in which the aerosol (200) is administered or applied. The operation of the apparatus (215) in an environment in which the aerosol (200) is applied can introduce various engineering challenges, including, but not limited to, cooling the aforementioned part(s) or component(s) and their related part(s), or surrounding atmosphere(s) (740) in a way that does not: (a) damage the apparatus, (b) damage any part(s) or component(s) of the apparatus (215), or (c) introduce a safety hazard. Cooling the aforementioned part(s) or component(s) and their related part(s), or surrounding atmosphere(s) (740) while utilizing as little or no amperage as possible is also, without limitation, another engineering challenge addressed in the current invention. Without limitation, many component(s) of the apparatus (215), including but not limited to, any electrical or electronic parts, may not be cooled by aerosol (200) laden air from outside of the apparatus (215). Aerosol (200) laden air/gas may cause electrical problems, electrical hazards, or cause damage to the apparatus (215) or its component(s) or part(s).

Without being limited, the various component(s) or part(s) of the apparatus (215) including, but not limited to any, electrical system(s), drive electronic(s) (645), blower(s) (180), pump(s) (130), or other part(s) or component(s) of the apparatus (215), and their related part(s), can be located in various ways including, but not limited to, locating the components individually or collectively in an enclosure(s) (345) that is impervious to things such as, but not limited to, humidity, dust, liquid, and aerosol. In addition, and without limitation, the atmosphere or various component(s) or part(s) of the apparatus (215) including, but not limited to any, electrical system(s), drive electronic(s) (645), blower(s) (180), pump(s) (130), or other part(s) or component(s) of the apparatus (215), and their related part(s), inside of the enclosure(s) (345), can be directly or indirectly cooled by means known to those skilled in the art. This means for cooling can include, but is not limited to, the use of, circulated coolant liquid, or refrigerated air. Any heat that is generated in the creation of the refrigerated air or that is removed from the enclosure(s) (345), the atmosphere inside of the enclosure(s) (345), or any part(s) or component(s) inside of the enclosure(s) (345), can be transferred to any air stream or direct to the atmosphere surrounding the apparatus (215).

Without limitation, the PLC(s) (315) can monitor the temperature of any surface(s) or atmosphere(s) (740) within the apparatus (215) with input from one or more of any temperature sensing devices or air/gas temperature sensing device(s) (650). The PLC(s) (315) can activate whatever means necessary to start, maintain, or stop any cooling activities or actions for any part(s), component(s), or atmosphere(s) of the apparatus (215), to maintain any desired or necessary temperature.

It is preferred, without limitation that the heat is transferred to an air/gas stream and this air/gas stream is the same air/gas stream (745) that is used to move the generated aerosol (200) out of the apparatus (215). The heat can be transferred to the air/gas stream (745) in one or more locations of the apparatus (215) including, but not limited to, inside any reservoir(s) (40), or inside any pipe(s) (685) before or after the blower(s) (180) that create the air/gas stream (745) that moves the aerosol (200) from the apparatus (215). It is also preferred, without limitation, that the heat generated by the various component(s) or part(s), especially any drive electronics (645) that operate the transducer(s) (10), be transferred to one or more heat sink(s) (750) having one or more fin(s) or other means known in the art to enhance cooling. Without limitation, the heat sink(s) can also interface and transfer heat from any coolant liquid or circulated coolant liquid that is used to cool any part(s), component(s), or atmosphere in a manner known in the art. The heat sink(s) (750) can be positioned anywhere in the air stream (745), before or after the blower(s) (180), so that at least the fin(s) or other cooling enhancement(s) (800) is placed or positioned in the air stream (745). The interface between any heat sinks or other means to transmit heat into the air stream (745) can be sealed in a manner known in the art. It is also preferred without limitation, that the heat sink(s) (750) that interfaces with the drive electronics (645) is interfaced with the top of the reservoir(s) (40) in which the transducers(s) (10) is located, and the heat sink(s) (750) is effectively positioned and sealed in place with one or more clasps (795). Without limitation, the various part(s) and component(s) of the apparatus (215) can interface with any heat sink(s) (750) in any orientation(s), layout(s), and with any methods known to those skilled in the art.

According to an embodiment, the apparatus (215) can be designed and constructed so that any of its exterior skin, walls, or surfaces (755) that can be exposed to the administered or deployed aerosol (200), are prevented from becoming warmer in temperature than the temperature of the atmosphere surrounding the apparatus or other surfaces surrounding the apparatus (215). This is important considering the potential operating environments of the apparatus (215). The book entitled, "Aerosol Technology" by William C. Hinds (1982), which is incorporated herein by reference in its entirety, including any references cited therein, teaches that, "When a temperature gradient is established in a gas, the aerosol particles in that gas experience a force in the direction of decreasing temperature. The motion of the aerosol particle that results from this force is called thermophoresis (page 153)." William C. Hinds (1982), also taught, "The earliest studies of thermophoresis were empirical studies of the dust-free layer observed around a heated object, such as a metal rod immersed in smoke. The smoke particles appear to be repelled by the heated object and form a particle free layer usually less than 1 mm thick, with a well-defined boundary (page 153)." This embodiment is advantageous for reasons including, but not limited to, it can prevent the aerosol (200) from being repelled from the exterior skin, walls, or surfaces (755) of the apparatus (215) in situations where the apparatus (215) is operating within the area (210) in which the aerosol (200) is administered or deployed and where it is needed or required that the exterior skin, walls, or surfaces (755) of the apparatus have contact with the aerosol (200). This embodiment includes, without limitation, constructing the apparatus (215) so that the exterior skin, walls, or surfaces (755) of the apparatus (215) are insulated from heat in various ways, including, but not limited to, applying one or more layers of insulating material (760) to the inside or outside of the exterior skin, walls, or surfaces (755) of the apparatus (215), constructing the exterior skin, walls, or surfaces (755) of the apparatus (215) so that they are double walled with a layer of insulation (765), including air/gas, in the middle of the said walls, or enclosing the components or parts that can increase in temperature, inside a sealed, insulated, or both insulated and sealed, enclosure, and then placing that enclosure inside of another sealed or unsealed enclosure that can also be insulated or not insulated.

According to an embodiment, object(s), the atmosphere(s) in which they reside, or any surfaces in the area targeted (210) for the administration or deployment of an aerosol (200), can be cooled or have their/its temperature decreased, before, or during the time when, the aerosol (200) is administered. This embodiment should not be confused with what was taught by U.S. Pat. No. 4,512,951 (Koubek at al., 1983), which is incorporated herein by reference in its entirety, including any references cited therein. Koubek et al., 1983, taught a method of sterilization where a liquid of aqueous hydrogen peroxide is vaporized, and the uniformly vaporized mixed hydrogen peroxide-water vapors are delivered into an evacuated sterilizer chamber, and the articles to be sterilized are cooled prior to the introduction of the vapor (or are cooled by the evacuation of air from the sterilizing zone) to a temperature below the dew point of the entering vapors. The condensing vapor deposits a film of liquid on all such cool surfaces (col 2, line 40-51). Koubek et al., 1983, also mentions in claim 2 that the result of vaporization was a mixed "gaseous vapor" consisting of hydrogen peroxide and water vapor free of solid contaminants. The present embodiment is intended for a completely different application and purpose since it is related to using principals of aerosol (200) behavior to, without limitation, increase the efficacy or performance of the process of the present invention, and not the condensation of a gas as taught in the prior art.

Basic principles applied in this embodiment are taught in the book entitled, "Aerosol Technology" by William C. Hinds (1982), which is incorporated herein by reference in its entirety, including any references cited therein. Without limitation, the cooling of the said object(s), surfaces, or environment or atmosphere, within the targeted area (210), in the present invention, can accentuate the performance or efficacy of the aerosol (200) generated by the apparatus (215) in the present invention. In addition, and without being limited to a mechanism or method, the aforementioned principles taught by William C. Hinds (1982), show that the efficacy, efficiency, and performance of the process in the present invention can be further increased by introducing an aerosol (200), consisting of a heated liquid (30), into an environment or targeted area(s) (210) with cooled surfaces.

The cooling of object(s), surface(s), space(s), environment(s), or atmosphere(s), within a targeted area(s) (210), can be accomplished with any means except by decreasing the pressure or pulling a vacuum on an enclosed area that is sufficient enough to decrease the temperature of the surfaces or atmosphere within that enclosed area. Creating a vacuum in an enclosed area and applying an aerosol was taught in the prior art by U.S. Patent Application No. 2005/0042130 A1 (Lin et al., 2003). However, Lin et al., was silent with respect to cooling any surfaces within the sterilization chamber or targeted area, and only mentioned the vaporization of the applied aerosol as being any enhancement or advantage that further vacuum past 5 torr would provide (pg. 2 paragraph 28). The vacuum utilized by Lin et al., (pg. 2 paragraph 28) to obtain data, was intended to move the aerosol through the sterilization chamber. In addition, using a vacuum to cool object(s), surfaces, or environment or atmosphere, within an enclosed area, would not be desired in this embodiment due to the complexity and expense involved in designing a chamber for the necessary vacuum and the expense of acquiring the necessary pump, which is all known to those skilled in the art. It is desired that another means for cooling object(s), surfaces, or environment or atmosphere, within a targeted area(s) (210), other than utilizing a vacuum, be utilized.

As shown in FIGS. 38-41, it is preferred, without limitation, that the targeted area(s) (210)) and its atmosphere, environment, objects, or any of the surfaces within the targeted area(s) (210), be cooled with air or gas that is cooled or chilled in a manner known to those skilled in the art. It is further preferred that the air or gas is cooled or chilled with one or more chill coils or refrigerated air systems (770) that are known to those skilled in the art. The means (770) to chill or cool the air or gas can be, without limitation, attached to the apparatus (215) in the present invention, be separate from the apparatus (215) and connect with one or more pipe(s) (810) or outbound cooled air pipe(s) (780) or inbound air pipe(s) (785) that connect with the targeted area(s) (210), or it can be part of or positioned anywhere within the space(s) or targeted area(s) (210) to be treated, and it can be controlled by one or more PLC(s) (315) or remote PLC(s). Without limitation, any pipe(s) that lead to (780) or from (785) the source of the refrigerated or cooled air can be separated from the targeted area (210) with one or more valve(s) (815) that can be controlled by one or more PLC(s) (315) or remote PLC(s). Without limitation, one or more valve(s) (815) may also be positioned at any location between the location where the administered air/gas or aerosol enters any pipe(s) (780) (785) or targeted area(s) (210) and the aerosol generating apparatus (215), and can be controlled by one or more PLC(s) (315) or remote PLC(s). The said valve(s) (815)(775), pipe(s) (220), or other related part(s) or component(s) can all be constructed from any material that is compatible, and suitable for use with the liquid (30). Without limitation, the amount or duration of air or gas that is flowed into or recirculated through the targeted area(s) (210), the locations that the air or gas is flowed into our out of the targeted area(s) (210), the temperature of the air or gas, as well as the temperature of the surfaces within the targeted area(s) (210) can vary depending on variables such as, but not limited to, the application, the level of performance that is desired, desired application time, as well as the volume of the targeted area(s) (210). Without limitation, the temperature of the atmosphere, surfaces, or space(s) in the targeted area(s) (210) can be cooled to at least nine degrees Fahrenheit below the temperature of the applied liquid (30). It is preferred, without limitation, that the temperature of the atmosphere, surfaces, or space(s) in the targeted area(s) (210) be cooled to at least nine to twenty-five degrees Fahrenheit below the temperature of the applied liquid (30). However, it is more preferred, without limitation, that the temperature of the atmosphere, surfaces, or space(s) in the targeted area(s) (210) be cooled to at least forty degrees Fahrenheit or lower. It is further preferred, without limitation, that the temperature of the atmosphere, surfaces, or space(s) in the targeted area(s) (210) be cooled to at least thirty-two degrees Fahrenheit or lower. The temperature of the applied liquid (30) of which the aerosol (200) is created or the temperature to which the aerosol (200) is heated with other means, can also vary. It is also preferred, without limitation, that the aerosol (200) is administered or deployed into an environment or targeted area(s) (210) where all heat emanating lights and/or machinery are turned off before or during the administering or deployment of the aerosol (200).

According to an embodiment, the apparatus (215) can be designed and constructed so that it can administer the generated aerosol (200) to a plurality of separate enclosed targeted areas (210). This can be accomplished, without limitation, through the use of one or more pipes (220) that emanate from or connect to the apparatus (215) and administer the aerosol (200) to the said enclosed areas (210). The flow of air or gas and aerosol (200) that emanates from the apparatus (215) may also, without limitation, be split various times, with one or more, or to one or more pipes (220), and the various pipes (220) can interface, or connect with one or more enclosed areas (210) in which the piped air/gas and aerosol (200) is administered. The one or more pipes (220) that emanate from the apparatus (215) can connect with one or more valve(s) (775) that can open or close one or more pipe(s) (220) that can be connected to one or more pipe(s) (220) or pipe junction(s) (790). The valve(s) (775) can be electronically opened or closed by one or more PLC(s) (315) connected to the apparatus (215), or one or more control PLC(s) external to the apparatus (215), all in a manner known to those skilled in the art. The said valve(s) (775), pipe(s) (220), or other related part(s) or component(s) can all be constructed from any material that is compatible, and suitable for use with the liquid (30). This embodiment does not encompass any configuration(s) or application(s) where the plurality of targeted areas (210) or areas where the aerosol (200) is deployed is within the same room, since this is already known to those skilled in the art. This embodiment may, without limitation, be used with any anti-pathogen/toxin/fungal/sporicidal agent(s) or substance(s) that may be in the form including but not limited to any liquid, gas, vapor, plasma, or aerosol, which is generated, delivered, moved, or administered, by any means.

According to an embodiment, the apparatus (215) can, without limitation, be designed and constructed so that the drive electronics (645), or any part of the drive electronics (645) that includes, but is not limited to, one or more signal generator(s), that emit or send electrical signal (herein referred to as "signal" or "signals") to energize the transducer(s) (10), causing it to emit pressure (energy) of a desired character, can have the capability to emit or send various defined signal or signal range(s) for various defined period(s) of time during the lifespan of the transducer(s) (10) in order to, without limitation, continue to operate or energize the transducer(s) (10) at a frequency or within a frequency range in which the transducer(s) (10) are able to have an effective or functional output and/or operate at a frequency or in a frequency range where the transducer(s) (10) are able to operate at or within a range close to or at their maximum performance or aerosol (200) output. It is preferred, without limitation, that this embodiment pertains only to the new aerosol producing transducers (10) taught or claimed in co-owned and co-pending U.S. patent application Ser. No. 11/915,524 titled "Method And Apparatus For Optimizing Aerosol Generation With Ultrasonic Transducers". However, it is more preferred, without limitation, that this embodiment pertain not only to the aerosol (200) producing transducers (10) taught in co-owned and co-pending U.S. patent application Ser. No. 11/915,524 titled "Method And Apparatus For Optimizing Aerosol Generation With Ultrasonic Transducers", but also to other transducers (10) intended for aerosol (200) production, except for those that operate at the resonant frequency of the transducer (10). It is even more preferred, without limitation, that this embodiment pertains not only to the aerosol (200) producing transducers taught in co-owned and co-pending U.S. patent application Ser. No. 11/915,524 titled "Method And Apparatus For Optimizing Aerosol Generation With Ultrasonic Transducers", but also to other transducers (10) intended for aerosol (200) production, except for those that operate at or near the resonant frequency of the transducer (10). The aforementioned exclusions to the preferences are needed since the current art, without limitation, encompasses the operation of a transducer (10) at its resonant frequency, as well as the design of the drive electronics (645) or ancillary components to sense any changes in the resonant frequency of the transducer (10), and to automatically adjust the frequency of the signal to the transducer (10) by way of the drive electronics (645) in order to compensate for, or match the transducer's (10) resonant frequency change. However, the prior art does not address the adjustment of the signal output from the drive electronics (645) to an aerosol (200) producing transducer (10) that has an effective or optimum operational frequency(s) above or below its resonant frequency that changes over time. One reason for this includes, without limitation, the complexity or difficulty to detect the optimum or effective operating frequency(s) for a transducer (10) at frequencies outside of the resonant frequency of a transducer (10), especially as it changes. This can be appreciated by those skilled in the art.

Aerosol (200) producing transducer(s) (10) in the present invention can have, without limitation, one or more frequency(s), group(s) of frequencies, or frequency range(s) in which they produce an aerosol (200) that can be characterized as effective, functional, or productive. The transducer(s) (10) utilized in the present invention can, without limitation, operate at one or more specific frequency(s), group(s) of frequencies, or frequency range(s), where the transducer(s) (10) are able to generate a greater amount of aerosol when compared to other frequency(s), group(s) of frequencies, or frequency range(s). Furthermore, the transducer(s) (10) utilized in the present invention can, without limitation, have or exhibit one or more specific frequency(s), group(s) of frequencies, or frequency range(s), where the transducer(s) (10) are able to generate not only an effective or functional output of aerosol (200), but generate the maximum amount of aerosol (200) or close to the maximum amount of aerosol (200) for each transducer(s) (10). Without limitation, for any frequency(s), group(s) of frequencies, or frequency range(s), where the transducer(s) (10) produce an effective, functional, or even maximum amount of aerosol (200) that is effective or functional, the aerosol output will decrease as the frequency of the signal sent to the transducer(s) (10) either increases or decreases from these established frequency(s), group(s) of frequencies, or frequency range(s).

Without being limited, any transducer (10) utilized in the present invention, may exhibit or have one or more additional frequency range(s) that encompasses the frequency(s), group(s) of frequencies, or frequency range(s) that will produce an effective, functional, or even maximum amount of aerosol. The magnitude of this frequency range can vary greatly, however, it is preferred without limitation, that this frequency range be within at least plus or minus 0.03 MHz (+/−0.03 MHz) from the frequency where the transducer(s) (10) generates the maximum amount of aerosol (200) or close to the maximum amount of aerosol (200) for a particular group of frequencies or frequency range, and is surrounded by frequency(s), group(s) of frequencies, or frequency range(s), where the transducer(s) (10) do not produce an effective or functional aerosol (200) output. It is more preferred, without limitation, that this frequency range is within at least plus or minus 0.05 MHz (+/−0.05 MHz) from the frequency where the transducer(s) (10) are able to generate the maximum amount of aerosol (200) or close to the maximum amount of aerosol (200) for a particular frequency, group of frequencies or frequency range, and is surrounded by frequency(s), group(s) of frequencies, or frequency range(s), where the transducer(s) (10) do not produce an effective or functional aerosol (200) output. It is even more preferred, without limitation, that this frequency range is within at least plus or minus (+/−0.08 MHz) from the frequency that the transducer(s) (10) are able to generate the maximum amount of aerosol (200) or close to the maximum amount of aerosol (200) for a particular frequency, group of frequencies, or frequency range, and is surrounded by frequency(s), group(s) of frequencies, or frequency range(s), where the transducer(s) (10) do not produce an effective or functional aerosol (200) output.

It has been observed, without limitation, that the transducer(s) (10) in the present invention, can have multiple, separate, or independent, frequency(s), group(s) of frequencies, or frequency range(s), where the transducer(s) (10) are able to generate an effective, functional, or productive aerosol (200) output. In addition, and without limitation, it has been further observed that in between these frequency(s), group(s) of frequencies, or frequency range(s), the transducer(s) (10) do not produce an effective or functional amount of aerosol (200).

It is important to note that the frequency or frequency range(s) in which the transducer(s) (10) produces either the maximum amount of aerosol (200) and/or an effective or functional amount of aerosol (200) can, without limitation, vary, and that it can be at or close to the resonant frequency of the transducer(s) (10) or anywhere above or below the resonant frequency of the transducer(s) (10). Resonant frequency can refer in this embodiment to either the resonant frequency of a free unmounted transducer(s) (10) or a transducer(s) (10) that has been mounted or assembled.

The resonant frequency of a transducer(s) (10) can, without limitation, increase due to age or other variables known to those skilled in the art. The nature of this change in resonant frequency can vary depending on variables known to those skilled in the art. As the resonant frequency of the transducer(s) (10) increases, the frequency range(s) in which the transducer(s) (10) would produce either the maximum amount of aerosol (200) and/or an effective or functional amount of aerosol (200) can, without limitation, also increase.

Referring now to FIGS. 42-45, the drive electronics (645), or any part of the drive electronics (645) that includes, but is not limited to, one or more signal generator(s) or ancillary components, used in the present invention can, without limitation, compensate for this shift or increase in frequency, and continue to operate the transducer(s) (10) at a frequency or frequency range where they produce either the maximum amount of aerosol (200) and/or an effective or functional amount of aerosol (200). This does not pertain to the prior art that encompasses the operation of a transducer (10) at its resonant frequency, as well as the design of the drive electronics (645) or ancillary components to sense any changes in the resonant frequency of the transducer (10), and to automatically adjust the frequency of the signal to the transducer (10) by the drive electronics (645) in order to compensate for, or match the transducer's (10) resonant frequency change. However, due to, without limitation, the complexities or limitations involved with this mode of operation or its successful execution or implementation, the following techniques can also be applied to aerosol (200) producing transducer(s) (10) that operates at or near its resonant frequency. This may be accomplished in ways including, but not limited to: (a) switching from one or more crystal(s) (825) that is initially used to generate one specific frequency or specific frequency range, to one or more different crystal(s) (830) that is used to generate other specific frequency(s) or specific frequency range(s). This can, without limitation, occur numerous times, for various durations of time, over a period of time; or (b) switching from one or more signal generator(s) (835) that is initially used to generate one specific frequency or specific frequency range, to one or more different signal generator(s) (840) that is used to generate other specific frequency(s) or specific frequency range(s). This can, without limitation, occur numerous times, for various durations of time, over a period of time. Without limitation, this switching from one or more crystal(s) or signal generator(s) to another can also be performed multiple times or in multiple series with one or a plurality of crystal(s) or signal generator(s) with any frequency or frequency range output. Also, and without limitation, if a plurality of crystal(s) or signal generator(s) is initially used, they as well as any subsequent set of crystal(s) or signal generator(s) that are utilized may have any, similar, different, identical, approximately identical, frequency or frequency range output. Each of the one or more crystal(s) or signal generator(s) can, without limitation, be utilized to emit or send either a specific frequency, or a range of frequency(s) that is amplified by one or more amplifier(s) (230), drive electronics (645), or other electronics known in the art, and is used to power or operate one or more transducer(s) (10), all in a manner known to those skilled in the art. It is preferred, without limitation, that the crystal(s) (845) is a direct or indirect part(s) or component(s) of the signal generator(s) (850). Each crystal(s) or signal generator(s) is, of a type, design, and construction, known to those skilled in the art. Any type of crystal(s) (845) or signal generator(s) (850) can be used that is effective. However, it is preferred, without limitation, that the crystal(s) (845) is made from quartz and resonates at a frequency that can be used by a signal generator(s) (850) to create a waveform(s) that is then amplified by an amplifier (230), drive electronics (645) or other electronics known in the art, to operate or energize the transducer(s) (10) at a frequency where the one or more transducer(s) (10) can produce either the maximum amount of aerosol (200) and/or an effective or functional amount of aerosol (200); or (c) utilizing, one or more of, without limitation, drive electronics (645), signal generator(s) (850), or other component(s) or circuit board, that has the means, ability, or capacity, to electronically produce the various frequency(s) or frequency range(s) that are needed or desired, and is known to those skilled in the art. It is preferred, without limitation, that these electronics or circuitry has the ability or capacity to be programmed so that various frequencies or frequency ranges may be created or generated, for various durations of time, over a period of time.

The specific resonant frequency(s) for a free unmounted transducer(s) (10) or a transducer(s) (10) that has been mounted or assembled, as well as the specific frequency(s) or frequency range(s) in which the transducer(s) (10) produce either the maximum amount of aerosol (200) and/or an effective or functional amount of aerosol (200), can be determined, planned, calculated, plotted, or projected, over time, in a manner known to those skilled in the art.

This data can be used, without limitation, to program one or more components such as, but not limited to, a signal generator or other related components, or PLC(s) (315) which is, without limitation, either a dedicated part of the signal generator(s) (850), amplifier(s) (230), drive electronics (645), or other components that are used to generate and send signal to energize the transducer(s) (10), or the PLC(s) (315) that is used to control and operate the apparatus in the present invention, to cause the switching from a crystal(s) (845) or signal generator(s) (850) to another in order to operate the transducer(s) (10) at a frequency or frequency range where they produce either the maximum amount of aerosol (200) and/or an effective or functional amount of aerosol (200).

Figure 46:
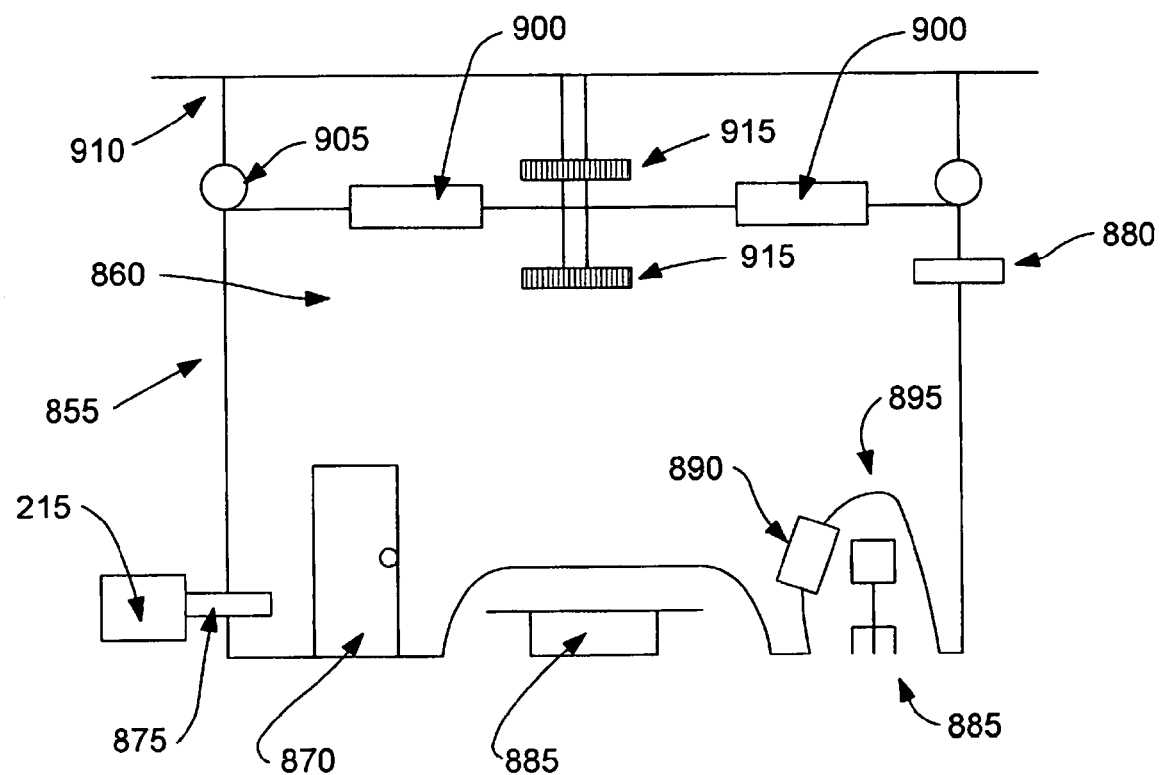
FIG. 46 is a schematic view of an embodiment of an enclosure that is connected to an aerosol generating apparatus, the enclosure having various features, parts, and components, according to the present invention.

As shown in FIG. 46, according to an embodiment, the aerosol (200) generating apparatus (215) in the present invention, can be, without limitation, connected, interfaced, or attached, to one or more sealed, semi-sealed, or semi-open, enclosure(s) or areas (herein referred to as "target enclosure(s)") (855), that is erected, established, constructed, or positioned at any place or within any area that is, without limitation, enclosed, not enclosed, semi-enclosed, sealed, semi-sealed, or unsealed. The said target enclosure(s) (855) can be without limitation, any size, shape, or dimension, and constructed of any material, and can be designed to be disposable or so that it can undergo multiple cycles of having the aerosol (200) applied to the interior of the target enclosure(s) (855) during, after, or both during and after, the use of the interior space of the enclosure(s) (860). The target enclosure(s) (855) can, without limitation, be designed in a manner known in the art so that they can be connected, interconnected, or interfaced, with one or more target enclosures(s) (855). The target enclosure(s) (855) can, without limitation, be supported with a frame that is designed and interfaced with the target enclosure(s) (855) in a manner known to those skilled in the art. Without being limited, the target enclosure(s) (855) can also have one or more doors (870) of various sizes, shapes, and locations, through which objects and people can pass through, and can be designed to be opened, closed, and effectively sealed multiple times in a manner known in the art. Without limitation, the door (870) can be designed and function as an airlock. It is preferred, without limitation, that the enclosure has at least one door (870). The target enclosure(s) (855) can be made from any material. However, it is preferred, without limitation, that the material is at least transparent or translucent. The target enclosure(s) (855) can have one or more inbound air/gas ports (875) or outbound air/gas ports (880) interfaced anywhere with the target enclosure (855), through which air and aerosol (200) may be administered or exhausted. The said ports may connect, in a manner known to those skilled in the art, to one or more aerosol generator(s) (215).

The target enclosure(s) (855) in this embodiment can have at least, but is not limited to, six features that distinguish it from chambers, tents, or bags, which have been used or have been proposed in the prior art. First, any wall(s), floor(s), or ceiling(s), of the target enclosure(s) (855) can be, without limitation, pre-formed, pre-constructed, pre-laminated, pre-seam sealed, or pre-molded, so that the chamber can effectively or functionally follow or fit over or under one or more of any, object(s), fixture(s), architectural feature(s), or equipment or fixture(s) such as, but not limited to, exam tables, x-ray equipment, anesthesia equipment, heart rate monitors, cardiopulmonary equipment, operating room theatre lights, laboratory equipment, or industrial equipment (Herein referred to as "structure(s)" (885). Second, any wall(s), floor(s), or ceiling(s), of the target enclosure(s) (855), including any material (895) that fits over the said objects, fixtures, architectural features, or equipment or fixtures (885), can, without limitation, have various openings (890) of various shapes, sizes, and locations, to allow a person to access, without limitation, any objects, various human machine interfaces, tools, or move any objects in and out of the target enclosure(s) (855). The openings (890) can also have a means so that they can be opened, closed, and effectively sealed multiple times. The openings may be designed or function as an airlock. Third, any wall(s), ceiling(s), or floor(s), of the target enclosure (855) may have one or more holes or openings of any size, shape, or dimension, and be interfaced with one or more of any plastic or glass panels, panes, or pieces (herein referred to as "panels") (900) of any size, shape, or dimension. The panels can be effectively interfaced and sealed with or into the wall(s), ceiling(s), or floor(s), of the target enclosure (855) in a manner known in the art. Any openings (890) may also interface with any plastic or glass panels (900), and the interface can be effectively sealed in a manner known in the art. The plastic or glass panels (900) can, without limitation, offer to: (a) allow light into the target enclosure(s) (855) in situations where the wall(s), floors, or ceiling(s) of the target enclosure (855) are opaque, (b) improve light transmittance or the quality of light that is transmitted into the target enclosure(s) (855), (c) decrease any diffraction of light entering the target enclosure(s) (855). Fourth, the target enclosure(s) (855) can utilize, without limitation, any means known in the art to connect, interface, hang, or suspend the target enclosure(s) (855) within the area in which it is placed, so that the target enclosure(s) (855) is erected or positioned so that its interior space (860) can be effectively or efficiently used. It is preferred without limitation, that the ceiling(s) of the target enclosure(s) (855) is suspended from at least one hook(s) (905) or other means of attachment that is effectively connected or attached to the ceiling (910) or other location(s) in the area in which the target enclosure(s) (855) is located. The various components and designs utilized for this purpose are known those skilled in the art. Fifth, the target enclosure(s) (855) can, without limitation, be constructed with or utilize any means known to those skilled in the art so that the floor(s) of the target enclosure(s) (855) do not present a slip hazard for any people working inside the target enclosure(s) (855). It is preferred, without limitation, that the floor(s) of the target enclosure (855) be textured to reduce any potential slip hazards. Sixth, the target enclosure(s) (855) can, without limitation, be interfaced with one or more means for fire suppression (915) outside or within the target enclosure(s) (855), and can be designed and built for this feature in a manner known in the art. In addition, the components and materials utilized in this embodiment are constructed from any material that is compatible, and suitable for use with the liquid (30), and may also be fireproof or fire resistant. This embodiment may, without limitation, be used with any anti-pathogen/toxin/fungal/sporicidal agent(s) or substance(s) that may be in the form including but not limited to any liquid, gas, vapor, plasma, or aerosol, which is generated, delivered, moved, or administered, by any means.

Figure 47:
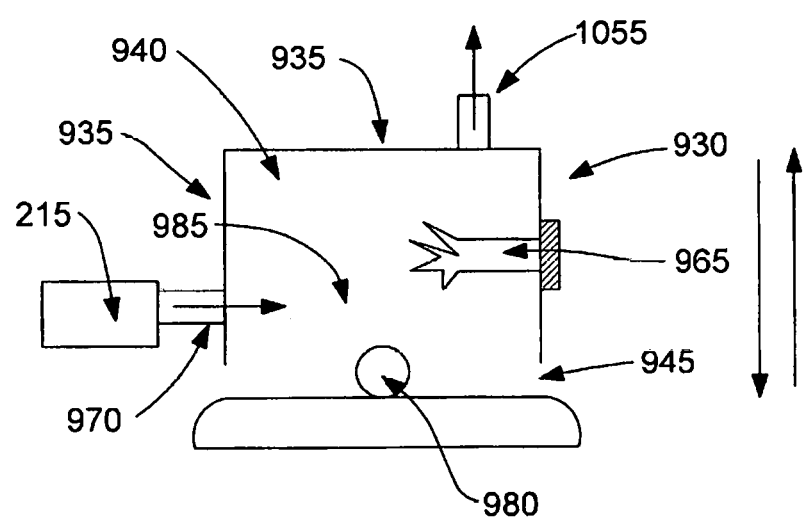
FIG. 47 is a schematic view of an embodiment of an enclosure that is connected to an aerosol generating apparatus, where the surfaces that it interfaces with effectively forms a missing wall, and the enclosure can have various features, parts, and components such as a glove sealed to the wall of the enclosure, according to the present invention.
Figure 48:
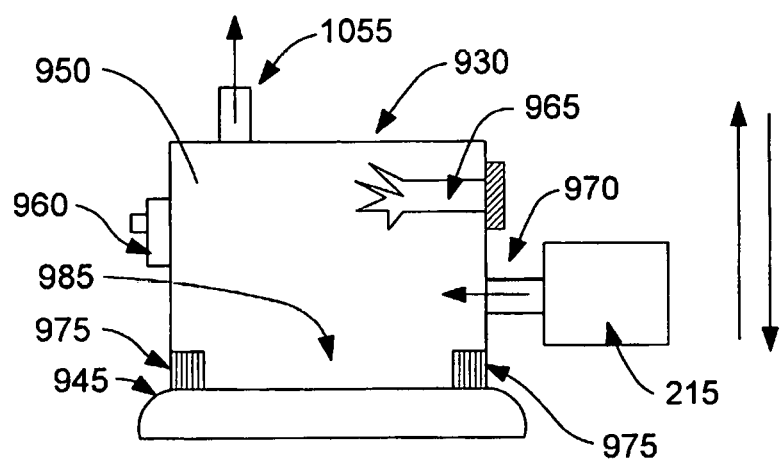
FIG. 48 is a schematic view of an embodiment of an enclosure that is connected to an aerosol generating apparatus, where the surfaces that it interfaces with effectively forms a missing wall, and the enclosure can have various features, parts, and components such as a glove sealed to the wall of the enclosure, seal material that connects with the enclosure and any surfaces with which the enclosure interfaces, according to the present invention.
Figure 49:
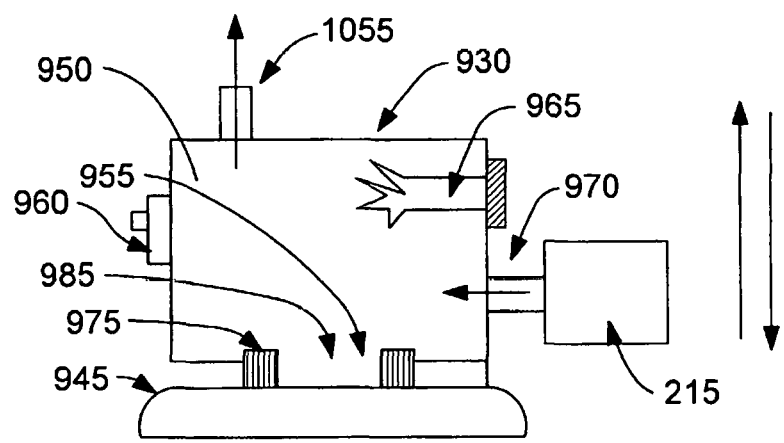
FIG. 49 is a schematic view of an embodiment of an enclosure that is connected to an aerosol generating apparatus, where the surfaces that it interfaces with effectively forms a missing wall, effectively covers or seals a hole, and the enclosure can have various features, parts, and components such as a glove sealed to the wall of the enclosure, seal material that connects with the enclosure and any surfaces with which the enclosure interfaces, and an airlock or access door, according to the present invention.

Looking now at FIGS. 47-49, according to an embodiment, the aerosol (200) generating apparatus (215) in the present invention, can be, without limitation, connected, interfaced, or attached, to one or more specially designed enclosure(s) (herein referred to as "application enclosure(s)") (930) that consists of, one or more wall(s) (935) that form one or more semi-enclosed or unenclosed area(s) (940) and where, without limitation, the interface, connection, or attachment, of any part of these wall(s) (935) with any surface(s) (945), forms one or more enclosed area(s) (950). The one or more wall(s) (935) of the application enclosure(s) (930) may also have one or more openings or holes (herein referred to as hole(s)) (955) of any size, shape, or dimension, and the interface of these hole(s) (955) with any surface(s) (945), forms one or more enclosed area(s)

(950). The wall(s) (935) of the application enclosure(s) (930) can be, without limitation, constructed from any, stainless steel, metal, glass, cellulose, cloth, gauze, polyolefin, polymer, natural or manufactured fibers or materials that may be coated or uncoated, combinations of these materials, or other materials known to those skilled in the art. The wall(s) (935) of the application enclosure(s) (930) can be, without limitation, flexible, rigid, semi-rigid, opaque, translucent, or transparent.

The enclosed area(s) formed by the interface or contact of the said wall(s) (935) or hole(s) (955) with any surface(s) (945) can be, without limitation, sealed, fully sealed, semi-sealed, or unsealed, in a manner known to those skilled in the art. Any material that can form or create an effective seal or interface (herein referred to as "seal material") (975) can also be, without limitation, glued, cemented, molded, laminated, adhered, or otherwise attached, to any part of the wall(s) (935) or hole(s) (955) that can come in contact with any surface(s) (945). Without limitation, the seal material (975) can be porous, permeable, semi-permeable, or impermeable, rigid, semi-rigid, or flexible, and can be constructed from materials including, but not limited to any, stainless steel, steel, glass, cellulose, cloth, gauze, polyolefin, polymer, natural or manufactured fibers or materials that may be coated or uncoated, combinations of these materials, or other materials known to those skilled in the art. The seal material (975) or parts of the seal material (975) may also, without limitation, have absorbent characteristics to improve its efficacy. The seal material (975) or wall(s) (935) can have, without limitation, various thicknesses, as well as lengths or heights, or it may even be designed to have the ability to vary its length(s), height(s), or thickness(es), in a manner that is known to those skilled in the art. The walls(s) (935) of the application enclosure(s) (930) can be constructed from the seal material (975).

In addition, the application enclosure(s) (930) can have, without limitation, one or more port(s), opening(s), or airlock(s) (960) of various sizes and shapes, which can be effectively sealed closed, or be in an open, semi-sealed, or unsealed state, in a manner known to those skilled in the art. The enclosure may also, without limitation, have one or more gloves (965) attached to any of the port(s), opening(s), or airlock(s) (960) and be hermitically sealed to the application enclosure(s) (930), all in a manner known to those skilled in the art. This can, without limitation, allow an operator to handle any object(s) in the application enclosure(s) (930) without being exposed to anything in the application enclosure(s) (930) or introducing anything into the application enclosure(s) (930).

The application enclosure(s) (930) can have one or more port(s) (970) at various locations through which inbound air/gas and aerosol, or filtered inbound air/gas from outside of the application enclosure(s) (930), can be administered or moved into the application enclosure(s) (930). The application enclosure(s) (930) can also have one or more port(s) (1055) at various locations through which outbound air/gas or aerosol, can move out of the application enclosure(s) (930). Without limitation, any outbound air/gas or air/gas that is laden with aerosol can be filtered at any port (1055) or at any location after it has been removed from the application enclosure (930), with any means known to those skilled in the art. The application enclosure(s) (930) can have various uses, including, but not limited to, being interfaced, strapped, positioned, or placed, over, with, or onto one or more object(s) or substance(s) (980), or targeted surfaces (985), at any angle or orientation, in order to apply an aerosol (200) onto the various surfaces. This embodiment may, without limitation, be used with any anti-pathogen/toxin/fungal/sporicidal agent(s) or substance(s) that may be in the form including but not limited to any liquid, gas, vapor, plasma, or aerosol, which is generated, delivered, moved, or administered, by any means.

According to an embodiment, any objects or items such as, but not limited to, hose(s), wire(s), pipe(s), or cord(s) (herein referred to as "cord(s)") (990), which are present in the targeted area(s) (210) in which the aerosol (200) is administered or deployed, can be, without limitation, held, lifted, or supported, by one or more holder(s) (995), that prevents the cord(s) (990) from touching or contacting the floor or surface(s) (1000) on which the holder(s) (995) are placed, but can also insure that all of the surfaces of the cord(s) (990) which interact with or contact the holder(s) (995) can also have contact, without limitation, with the same liquid (30) that is aerosolized or deployed by the apparatus in the present invention. Without limitation, surfaces that contact one another are often difficult to reach or contact with an administered aerosol (200) or other deployed substance(s), and this embodiment, without further limitation, helps to reduce or eliminate an incomplete treatment or administration of the aerosol (200), or other treatment product(s), to all of the desired or needed surfaces in a targeted area (210). In addition, the holder(s) (995) may also be used with any other chemical or agent delivery systems or apparatuses that can deliver any, without limitation, chemical(s), agent(s), or compound(s) in the form including, but not limited to, any aerosol(s), gas(s), or vapor(s), for various purposes.

Figure 50:
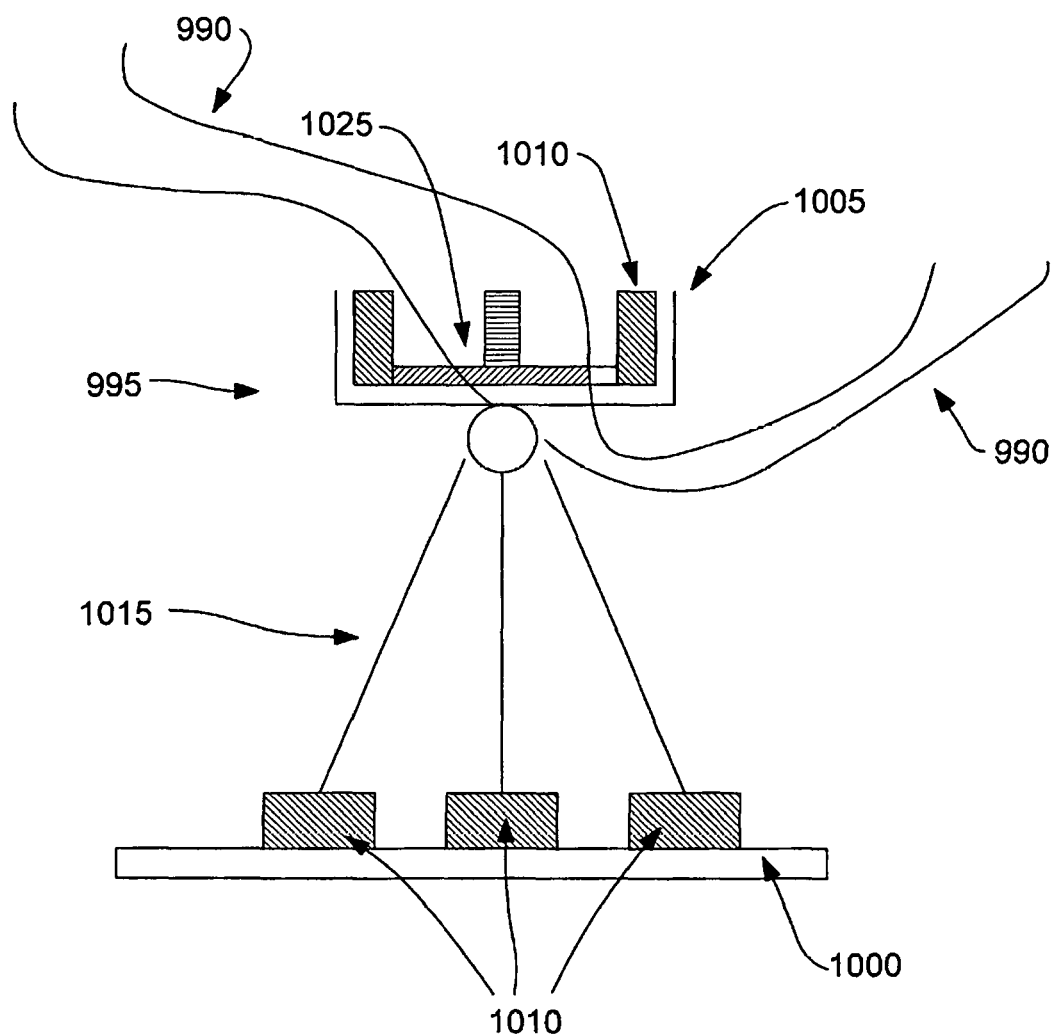
FIG. 50 is a schematic view of an embodiment of a holder that interfaces with one or a plurality of objects, and the said holder incorporates absorbent material that is positioned between the holder and any surfaces with which it interfaces including the said objects it holds and any surface on which it is placed.

Without limitation, the said holder(s) (995), as shown in FIG. 50, can consist of at least, but not limited to, the following components: (a) one or more cradle(s) or other means (herein referred to as "cradle(s)") (1005), to hold or support the cord(s) (990), (b) absorbent material(s) (1010) that is interfaced, attached, or connected to the cradle(s) (1005), (c) one or more legs or supports (1010) that extend from or are interfaced or attached to the cradle(s) (1005) or part(s) connected to the cradle(s) (1005), (d) absorbent material(s) (1010) that is interfaced, attached, applied, or connected in such a way so that it is positioned between any parts or components of the holder(s) (995) and any surfaces (1000) on which the holder(s) (995) is placed or interfaces with. Without limitation, the one or more legs or supports (1015) that extend from or are directly or indirectly interfaced or attached to the cradle(s) (1005), can be of various number and lengths, and can be designed in a manner known to those skilled in the art.

The cradle(s) (1005) or absorbent material(s) (1010) can have one or more slot(s) or a rippled shape of one or more ripple(s) (1025) so that one or more cord(s) (990) can nest or lay in or interface with the cradle(s) (1005) or absorbent material(s) (1010). The holder(s) (995) is designed and constructed in a manner known to those skilled in the art so that the cord(s) (990) cannot easily twist, fall, or move out of the cradle(s) (1005) or absorbent material(s) (1010). An absorbent material(s) (1010) is interfaced, attached, applied, or connected to the cradle(s) (1005) or holder(s) (995) in various ways known to those skilled in the art. The cradle(s) (1005) can also be constructed from any absorbent material (1010). The cradle(s) (1005) and absorbent material(s) (1010) can also be designed so that either the absorbent material(s) (1010) or even the cradle(s) (1005) can be disposable. The one or more legs or supports (1015) can also be constructed from any absorbent material (1010). The interface, attachment, application, or connection, of any absorbent material(s) (1010) to the one or more legs or supports (1015) can be accomplished in various ways known to those skilled in the art.

The absorbent material(s) (1010) that is utilized, can be made of any absorbent materials, or combinations of absorbent materials, including, but not limited to, gauze, cellulose, any sponge like material, or any material with absorbent qualities that is known to those skilled in the art. The absorbent material(s) (1010) is of a sufficient quality, thickness, density, size, shape, construction, consistency, and design, to complete its task at least once in an effective manner.

Any of the absorbent material(s) (1010) can also, without limitation, be soaked, saturated, or contacted, with any desired chemical, compound, agent, additive, or otherwise liquid (30), that would be used for various purposes. It is preferred, without limitation, that this is performed before the cord(s) (990) are interfaced or positioned in or on the cradle(s) (1005) or absorbent material(s) (1010), or the holder(s) (995) are placed on any floor or surface(s) (1000). This can, without limitation, further increase the probability that all surfaces of the cord(s) (990), holder(s) (995), or surface(s) (1000) on which the holder(s) (995) is placed, have contact with the aforementioned chemical, compound, agent, additive, or otherwise liquid (30). It is preferred, without limitation that the absorbent material(s) (1010) is saturated with the same liquid (30) that is generated into aerosol (200) in the present invention. This same absorbent material(s) (1010) can also be positioned under the wheels of the aerosol generating apparatus(s) (215). Any parts or components utilized to construct the holder(s) can be constructed from any material that is compatible, and suitable for use with the liquid (30). This embodiment may, without limitation, be used with any anti-pathogen/toxin/fungal/sporicidal agent(s) or substance(s) that may be in the form including but not limited to any liquid, gas, vapor, plasma, or aerosol, which is generated, delivered, moved, or administered, by any means.

Figure 56:
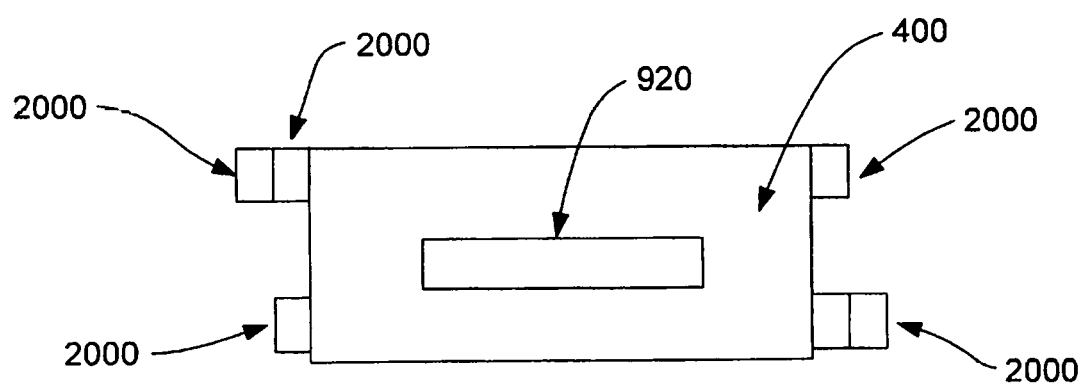
FIG. 56 is a schematic view of a buoyant object and weights that is disposed in the generator of FIG. 52.
Figure 57:
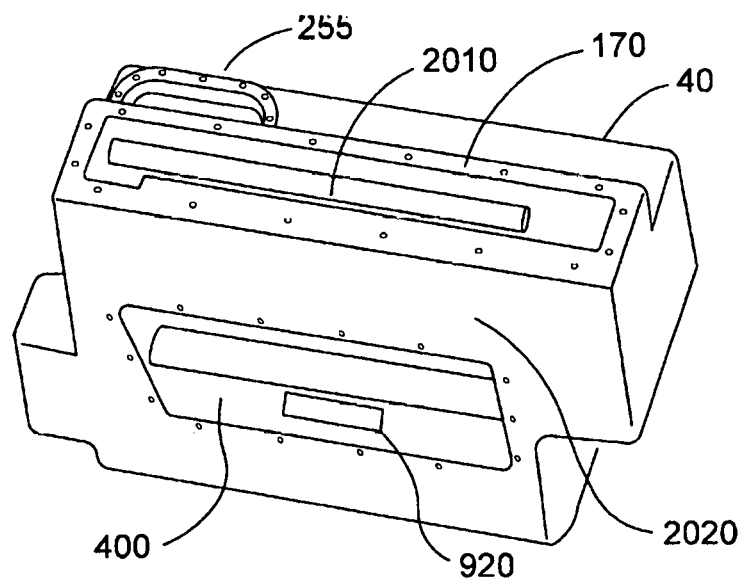
FIG. 57 is an isometric view of the tank of FIG. 56.

According to embodiments, as best shown in FIGS. 56-57, the apparatus (215) can, without limitation, be designed and constructed so weight or mass can be added or removed from any parts or components in order to maintain a specific level of liquid (30), or at least an effective amount of liquid (30), that covers all of the aerosol producing transducer(s) (10). Weight or mass (2000) can be can be added or removed from any parts that are directly or indirectly connected to any of the buoyant object(s) (400), or the transducer assembly(s) (100) themselves. It is preferred, without limitation, that the weight or mass (2000) takes the form of one or more stainless steel weights (2000) that are attached to the buoyant object(s) (400) in a manner known to those skilled in the art, and the various weight(s) (2000) are added to numerous positions or locations on the buoyant object(s) (400) in order to maintain a specific and/or effective liquid level (30) above each of the one or more aerosol producing transducer(s) (10).

Figure 64:
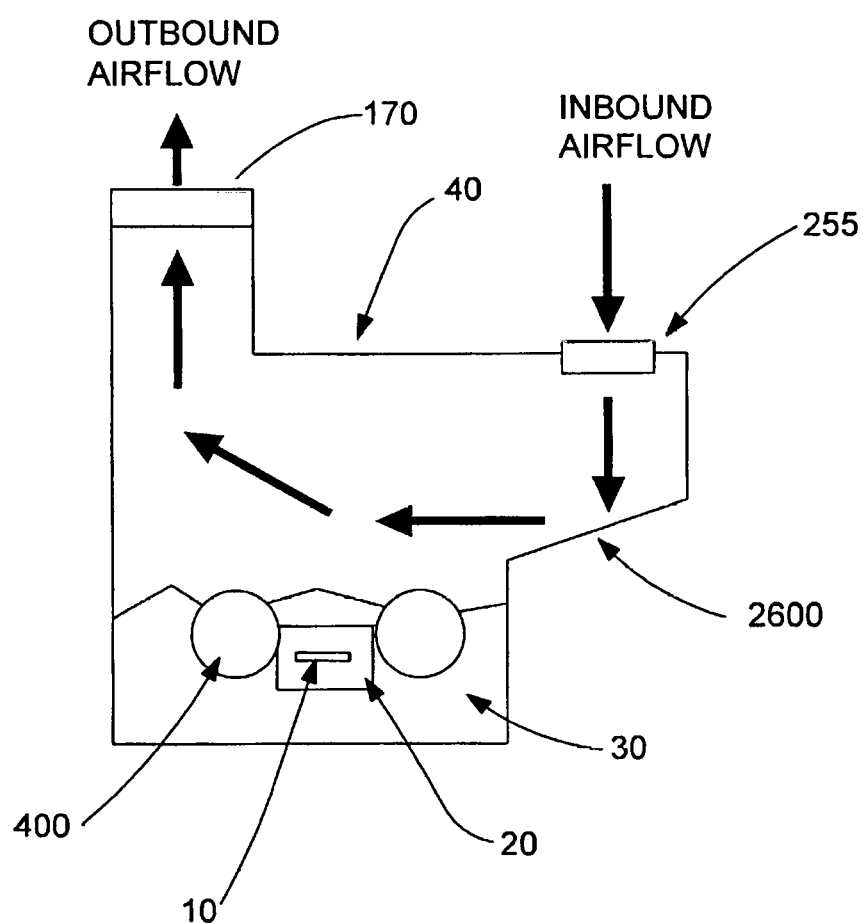
FIG. 64 is a schematic view of an embodiment of the generator of FIG. 52 including an air flow distribution shelf.

According to an embodiment shown in FIG. 64, the apparatus (215) can, without limitation, be designed and constructed so that the one or more buoyant object(s) (400), or even the transducer assembly(s) (100) themselves may freely float within the liquid (30) in the reservoir (40). It is preferred, without limitation, the one or more transducer assembly(s) (100) is attached to only one buoyant object (400) and the transducers are centered in connecting holes (920) cut in the buoyant object (400). The buoyant object (400), and one or more transducer assembly(s) (100) are connected to any wall of the reservoir (40). It is preferred, without limitation, that the one or more pieces of flexible tubing (375) that contains the wiring from the drive electronics (645) or amplifier(s) (230), emanates from a common wall of the reservoir (40), and connects to the side of each respective transducer housing (20) in order to power the one or more of the aerosol producing transducer(s) (10).

Figure 58:
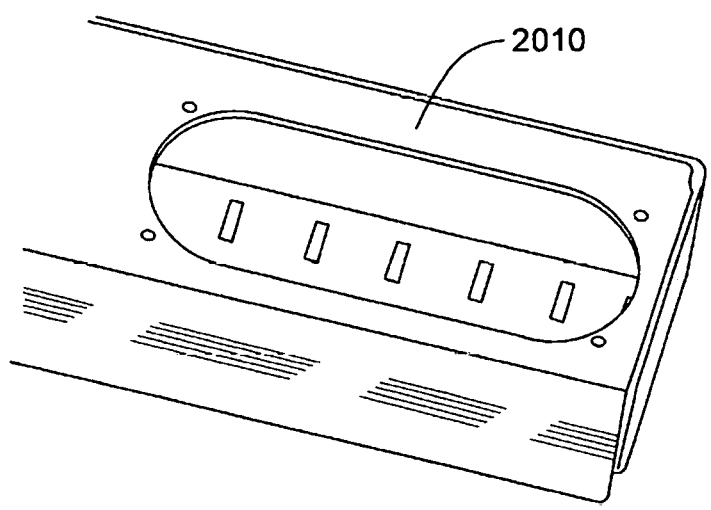
FIG. 58 is an isometric view of an airflow distribution channel for the tank of FIG. 57.
Figure 59:
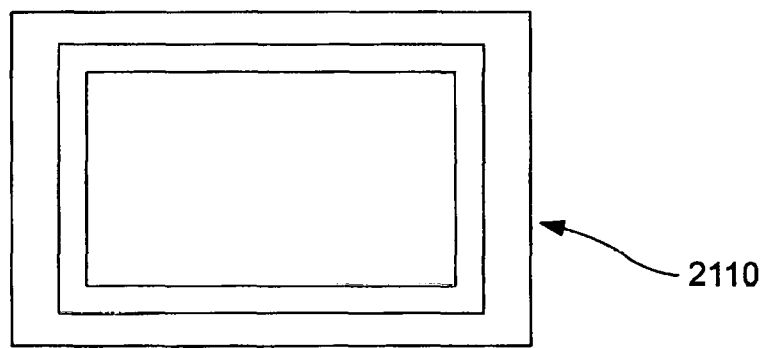
FIG. 59 is a bottom plan view of a wall vent.

According to an embodiment shown in FIGS. 57-58, the apparatus (215) can, without limitation, be designed and constructed so that air, or any combination of gas(s), enters the fog tank or reservoir (40) through one or more inlets or intake orifices (255), located opposite from the one or more air outlets, exit orifices, or openings (170) that are located on the top, roof, or ceiling of the reservoir (40). It is preferred, without limitation, that the one or more air outlets, exit orifices, or openings (170), consists of only one opening and the air outlet is formed or positioned at the end of a chimney (2020). Both the air inlets and air outlets can be any shape or size. It is also preferred, without limitation, that the inbound air or gas is directed downward at various angles, including vertically, into the fog tank or reservoir (40). According to another embodiment, the downward moving air stream may, without limitation, strike one or more surfaces that cause the inbound airflow to be redirected in various directions and angles inside of the reservoir (40). It is preferred, without limitation, that one or more redistribution surfaces are located near the bottom of the reservoir, but at least above the highest possible liquid (30) level. The fog tank or reservoir(s) (40) can be any, without limitation, size, shape, or geometry, and it can have any height of air space or volume above the liquid (30) that is located in the bottom of the reservoir (40). The liquid (30) in the bottom of the reservoir (40) can be, without limitation, any effective depth.

Figure 69:
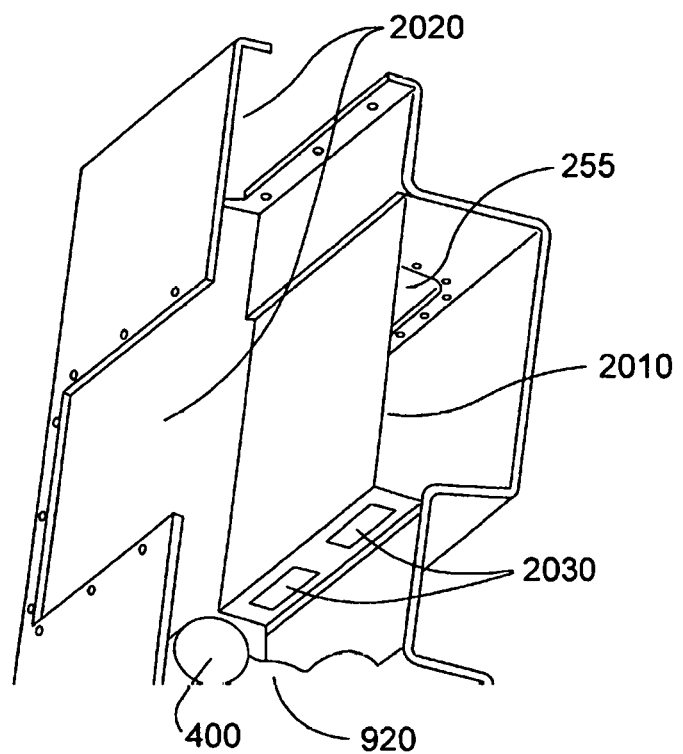
FIG. 69 is an isometric view of the tank of FIG. 56.
Figure 70:
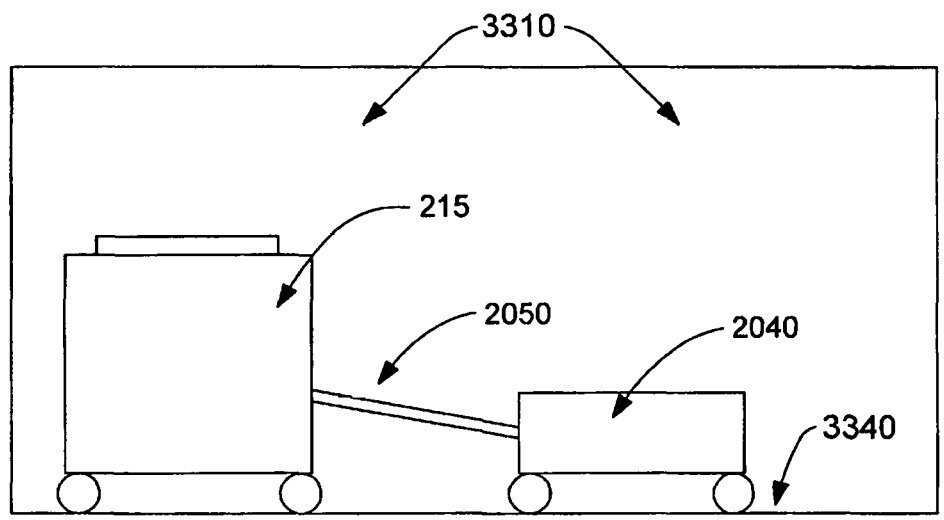
FIG. 70 is a schematic view of an embodiment of the aerosol generator including a dehumidifier of FIG. 52 in an enclosed space.
Figure 71:
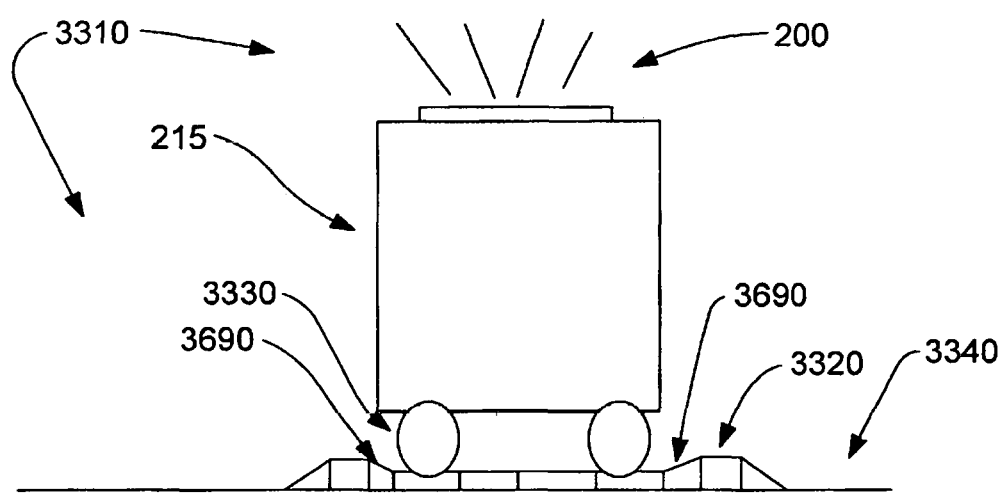
FIG. 71 is a schematic view of a first embodiment of an interface assembly used with the generator of FIG. 70.
Figure 72:
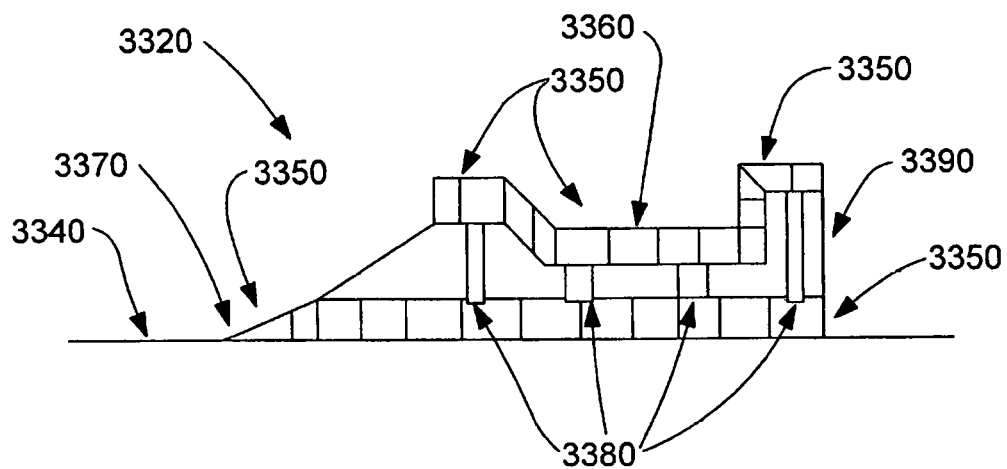
FIG. 72 is a schematic view of the interface assembly of FIG. 71.
Figure 73:
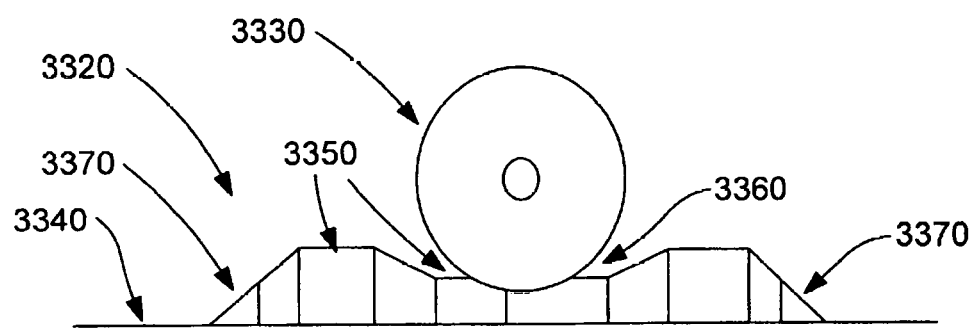
FIG. 73 is a schematic view of a wheel engaged with the interface assembly of FIG. 71.
Figure 74:
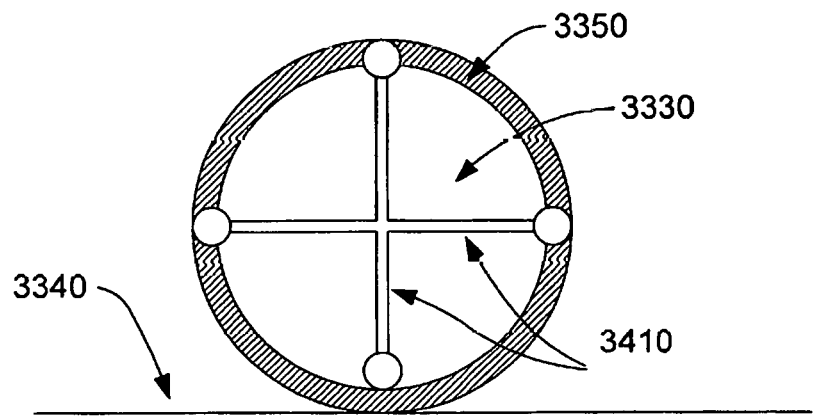
FIG. 74 is a schematic view of a second embodiment of an interface assembly used with the generator of FIG. 70.
Figure 75:
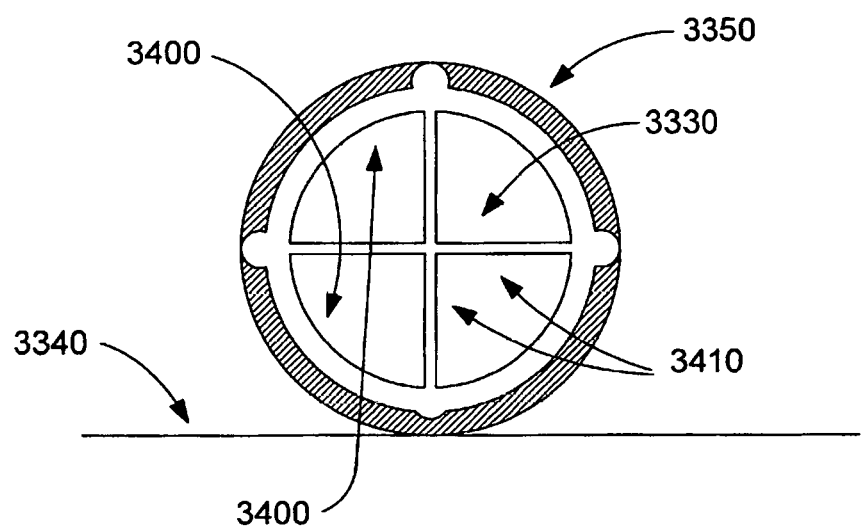
FIG. 75 is a schematic view of a third embodiment of an interface assembly used with the generator of FIG. 70.

According to an embodiment shown in FIGS. 57-58 and 69, the apparatus (215) can, without limitation, be designed and constructed so that the air entering the reservoir (40) is distributed to one or more locations inside of the reservoir (40) via means such as, but not limited to, conduit, piping, tubing, channels (2010). According to an embodiment, these means to move the air can be easily removed for cleaning. According to another embodiment, this means to move, channel, or distribute the inbound air to one or more locations throughout the fog tank or reservoir (40) can have various lengths, shapes, and geometries, and can have one or more holes or perforations (2030) of various sizes and shapes in various orientations, as best shown in FIG. 69. They can also be partially or completely enclosed. These embodiments can reduce, diminish, or eliminate, unwanted air patterns or airflow in the reservoir and/or fog tank (40) such as, but not limited to, stagnant airflow, uneven or unbalanced airflow, turbulent airflow, or vortices. It is preferred, without limitation, that the air exiting these holes or perforations (2030), is directed downward toward the liquid in the reservoir (40). It is even more preferred that the air is directed downward toward the bottom of the reservoir (40), and the bottom of the reservoir (40), or any area near the bottom of the reservoir (40), is designed so that the inbound air flow strikes a shelf (2600) (FIG. 64) or area that is not covered with liquid (30). The shelf (2600) can be canted at any angle. It is preferred, without limitation, the shelf (2600) is sloped downward at a forty-five degree angle toward the part of the reservoir (40) where the liquid (30) is held. It is very preferred that the air is directed along the wall of the tank or reservoir (40) opposite from the wall closest to the one or more orifices (170) though which the air and aerosol (20) exits the apparatus (215).

According to an embodiment, the apparatus (215) can, without limitation, be designed and constructed so that the velocity and/or volume of air exiting from the reservoir (40) or apparatus (215) can be reduced at any time during the aerosol generation and output cycle. It is preferred without limitation, this process occurs at or near the end of the aerosol generation and output cycle. It is also preferred, without limitation, that the velocity and/or volume of air or gas exiting from the reservoir (40) or apparatus (215) is reduced to at least 150 cubic feet or more per minute, and more preferred to at least 100 cubic feet or more per minute, and even more preferred that the air velocity be reduced to 10 cubic feet or more per minute. The decrease in the velocity and/or volume of air or gas and aerosol (200) exiting from the reservoir (40) or apparatus (215) can, without limitation, promote a more rapid build up of aerosol (200) in the area surrounding the apparatus.

According to an embodiment, the apparatus (215) can, without limitation, be designed and constructed so that it is connected to one or more sensor(s) (3530) or has communication with one or more sensor(s) (3530) to determine if or when an effective or sufficient amount of aerosol (200) is applied to the treated or targeted area (210). This embodiment includes configurations in which the sensor(s) (3530) may be directly or indirectly attached to the apparatus (215), or that one or more sensor(s) (3530) may be remotely located and operated in any location within the targeted area(s) (210) where the aerosol (200) may be administered. The one or more sensor(s) (3530) can be, without limitation, positioned in or at any, orientation, height, or location in the targeted area(s) (210), and communicate directly or indirectly with one or more aerosol generating apparatus(s) (215), or one or more of any remote device(s) that control one or more of any aerosol generating apparatus(s) (215), in various ways such as, but not limited to any, radio waves, sound, wire, cable, or fiber optics.

According to an embodiment in FIGS. 52-55, one or more means to dehumidify (2040) an area in which the aerosol (200) is administered can be operated, without limitation, at any time during or after one or more apparatus(s) (215) has stopped administering the aerosol (200). The dehumidification cycle time can vary for reasons including, but not limited to, the size of the targeted area being dehumidified, the amount of aerosol (200) that is deployed into the targeted area, the specific level of humidity that is desired or chosen for the dehumidification process or the targeted area.

According to an embodiment, the one or more means to dehumidify (2040) can delay starting the dehumidification process for any period of time after, without limitation, receiving a signal or command to begin the dehumidification process, receiving any humidity level information, or detecting a certain humidity level. This time delay can be impacted by inputs or factors such as, but not limited to, the size of the treated space, the number of means used to dehumidify (2040) the targeted area(s) (210), the number of aerosol generating apparatus(s) (215) in use, the temperature of the treated area, or the desired level of disinfection or efficacy of the process.

The one or more means to dehumidify (2040) can be any suitable means or apparatus(s) known to those skilled in the art. One or more means to dehumidify (2040) may also, without limitation, be included in the design and construction of one or more aerosol generating apparatus(s) (215). Without being limited, any suitable means known to those skilled in the art to remove humidity and/or any vapor(s) from the air or any environment surrounding the dehumidification apparatus (2040) may be used. The one or more means to dehumidify (2040) may also, without limitation, include or implement any catalytic technology known to those skilled in the art. The means to dehumidify can also be directly or remotely programmed or controlled, by any means known to those skilled in the art such as, but not limited to any, software, relays, timers, programmable logic circuits, or integrated circuits, and/or one or more of any remote controlling device(s) that can communicate and/or control either, or both, the dehumidification apparatus(s) and/or aerosol generator(s) (215) with any suitable wireless means, all in a manner known to those skilled in the art.

Figure 52:
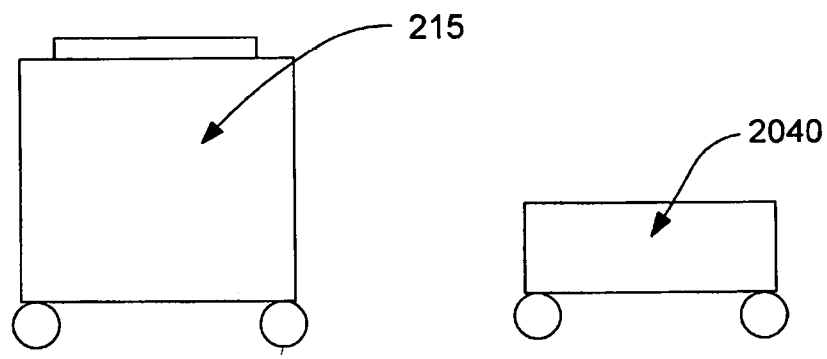
FIG. 52 is a schematic view of an aerosol generator combined with a dehumidifier.

In one embodiment shown in FIG. 52, the one or more means to dehumidify (2040) an area in which the aerosol (200) is administered is an independent apparatus that is "not" connected to the one or more aerosol generating apparatus(s) (215), and it is remotely controlled and/or programmed by one or more operator(s), all in a manner known to those skilled in the art. Without being limited, the one or more aerosol generating apparatus(s) (215) and/or the one or more means to dehumidify (2040) can be, without limitation, controlled by one or more of any aerosol generating apparatus(s) (215), and/or one or more of any suitable, digital, electronic, or analog, controller(s) such as, but not limited to, any PLC(s), remote PLC(s) (3893), remotely located PLC(s), and/or any suitable remote controlling device(s), via one or more of any suitable radio(s), all in a manner known to those skilled in the art.

Figure 53:
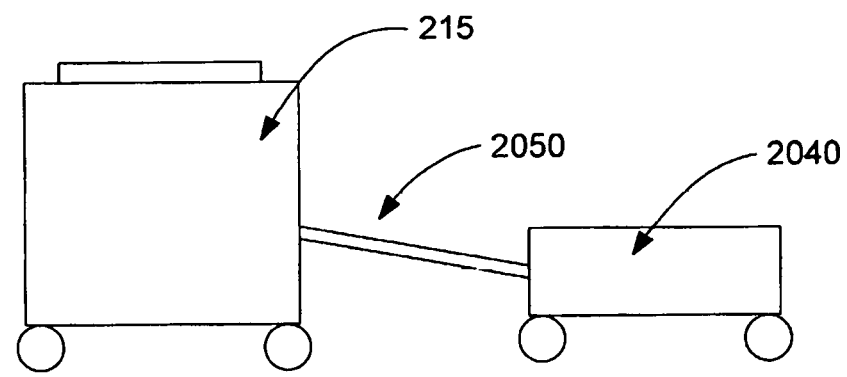
FIG. 53 is a schematic view of an aerosol generator connected to the dehumidifier.

In another embodiment shown in FIG. 53, the one or more means to dehumidify (2040) an area in which the aerosol (200) is administered, is also an independent apparatus(s), but in this particular embodiment its operation is electrically controlled by, and electrically connected to, the one or more aerosol generating apparatus(s) (215) via one or more of any suitable connection(s) (2050) known to those skilled in the art. However, the one or more means to dehumidify (2040), as well as any aerosol generating apparatus(s) (215), can still be, without limitation, controlled by one or more of any aerosol generating apparatus(s) (215), and/or one or more of any suitable, digital, electronic, or analog, controller(s) such as, but not limited to, any PLC(s), remote PLC(s) (3893), remotely located PLC(s), and/or any suitable remote controlling device(s), via one or more of any suitable radio(s), all in a manner known to those skilled in the art. Without being limited, the one or more means to dehumidify (2040), as well as any aerosol generating apparatus(s) (215), can also include two or more of any means for connecting any, power and/or communications, with any suitable socket and/or plug configuration, at any suitable and effective locations on the exterior of the device(s). It is preferred, without limitation, that at least one means for connecting any, power and/or communications, is positioned on either end of the means used for dehumidification (2040), and the connections have a socket configuration for electrical safety. This configuration can be used, without limitation, to facilitate the connection of more than one dehumidification apparatus(s) to the aerosol generator(s) (215).

In still another embodiment, the one or more means to dehumidify (2040) an area in which the aerosol (200) is administered, is also an independent apparatus(s), but in this particular embodiment its operation is controlled, either remotely and wireless and/or with any suitable wired connection, by one or more of any aerosol generating apparatus(s) (215), and/or one or more of any suitable, digital, electronic, or analog, controller(s) such as, but not limited to, any PLC(s), remote PLC(s) (3893), remotely located PLC(s), and/or any suitable remote controlling device, via one or more of any suitable radio(s), all in a manner known to those skilled in the art. However, it is electrically independent in this particular embodiment. In any of these embodiments, the one or more aerosol generating apparatus(s) (215) can, without limitation, communicate and interact with, and/or be controlled by, one or more of any suitable, digital, electronic, or analog, controller(s) such as, but not limited to, any PLC(s), remote PLC(s) (3893), remotely located PLC(s), and/or any suitable remote controlling device, via one or more of any suitable radio(s), all in a manner known to those skilled in the art.

Figure 54:
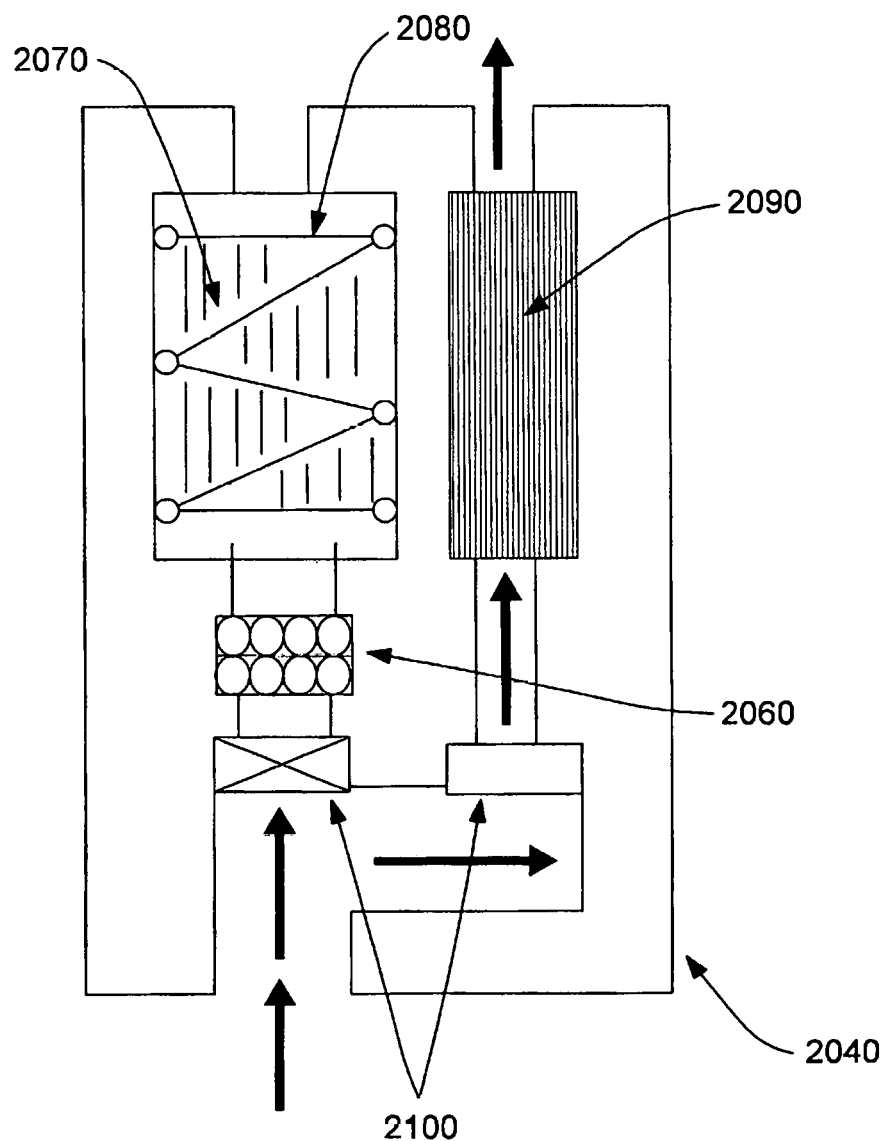
FIG. 54 is a schematic view of the dehumidifier of FIG. 52 in a first configuration.
Figure 55:
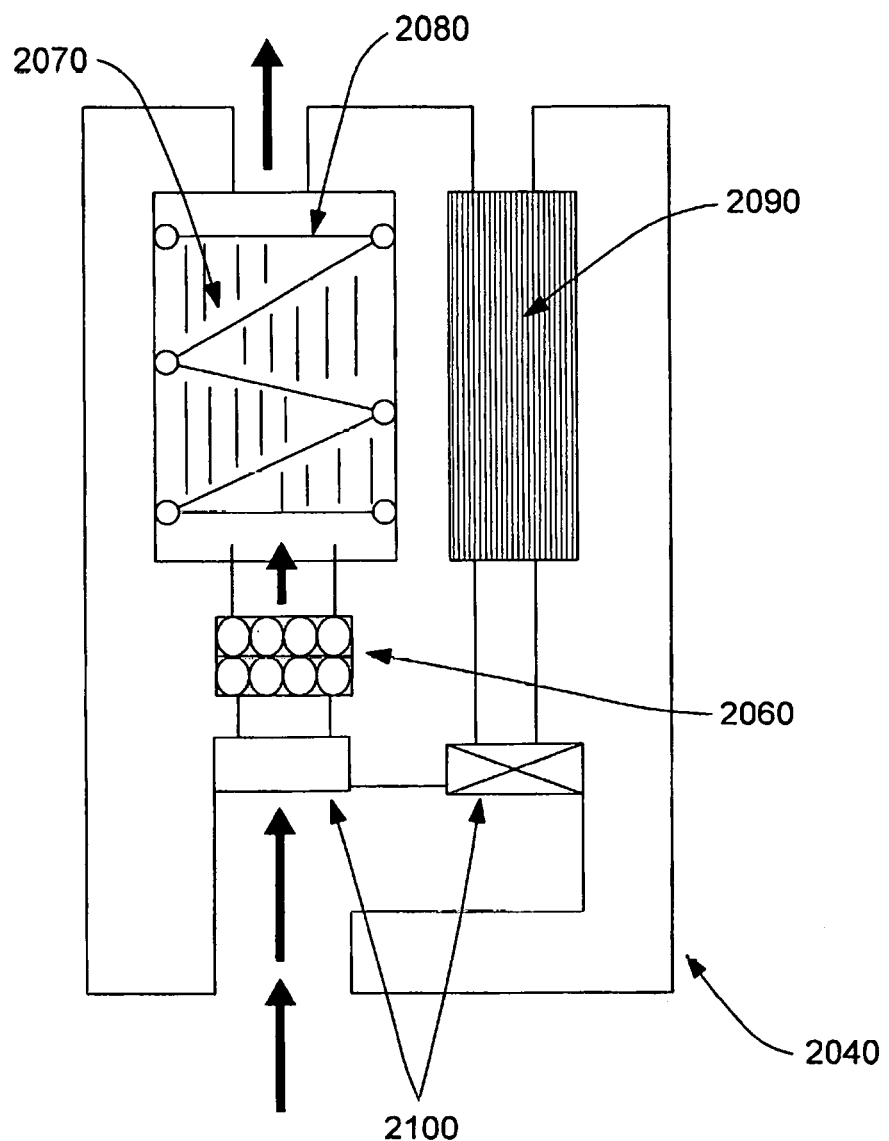
FIG. 55 is a schematic view of the dehumidifier of FIG. 52 in a second configuration.

In an embodiment shown in FIGS. 54-55, the one or more means to dehumidify (2040) an area in which the aerosol (200) is administered can contain, without limitation, one or more filter media to filter the aerosol (200) from the air during, or after it passes over the chill coils. The filter media can be any filter known in the art, but it is preferred, without limitation, that the filter media or mechanism consists of one or more separation cones (2060) that separates the aerosol (200) from the air as the air moves through the separation cone(s) (2060).

In another embodiment, the one or more means to dehumidify (2040) an area in which the aerosol (200) is administered is designed and manufactured so that one or more stainless steel filter material or metal mesh of any porosity size, number, and shape (2070) connects with, spans between, or is interwoven with the one or more chill coils (2080) of various size and shape, that are used by the means to dehumidify (2040). This construction may also, without limitation, increase the cooling efficiency of the means to dehumidify (2040) by increasing the cooled surface area.

In another embodiment, any liquid filtered from the air, or condensed by the chill coil(s) (2080) or any connecting metal filter material(s) or mesh, can without limitation, be collected in one or more collection container(s) that can also be shared with other parts of the dehumidification apparatus(s) (2040).

In another embodiment, the one or more means to dehumidify (2040) an area in which the aerosol (200) is administered can be, without limitation, designed and built so it can receive any type of suitable signal known to those skilled in the art, such as but not limited to any signal that is transmitted wireless, and/or through any wire, and this signal may cause the means to dehumidify (2040) to switch or direct the air moving through the dehumidification apparatus(s) (2040) from moving over one or more of any chill coils (2080), or any other dehumidification device(s) known to those skilled in the art, to instead flow into or through one or more of any suitable filter(s) (2090) known to those skilled in the art, that is able to effectively remove one or more of any gas(s) and/or vapor(s), and/or any chosen or selected gas(s) or vapor(s), from the air or atmosphere within the treated area(s) (210). It is preferred, without limitation, that the one more filter(s) (2090) is constructed from any suitable type of charcoal, in a manner that is known to those skilled in the art. It is more preferred, without limitation, that the one more filter(s) (2090) is constructed from one or more of any suitable type of filter media, such as, but not limited to one or more of any suitable type of charcoal or activated charcoal. It is even more preferred, without limitation, that the one more filter(s) (2090) is constructed from one or more of any suitable type of filter media, such as, but not limited to one or more of any suitable type of charcoal or activated charcoal, that can effectively remove various compounds such as, but not limited to any, hydrogen peroxide, acetic acid, and/or peroxyacetic acid (PAA), from the atmosphere within the targeted area(s) (210). Any amount of any type of filtered vapor(s) or gas(s) that are desired to be removed, can be filtered from the air or gas(s) that are moved through the filter(s). It is preferred, without limitation that at least an efficacious, effective, and/or suitable, amount of the one or more gas(s) or vapor(s) targeted for removal, are removed by the one or more filter(s) (2090).

One or more of any door(s), flap(s), covering(s), valve(s) (Hereinafter called "valve(s) (2100)), or other means known to those skilled in the art, can be, without limitation, opened and closed, at any effective and suitable time, and for any duration of time, within the design and/or construction of the dehumidification apparatus(s) (2040). The valve(s) (2100) can be opened and closed at any suitable and effective time, and consist of any, mechanical design, electro-mechanical design, pneumatic design, and/or any other suitable design(s), known to those skilled in the art. It is preferred, without limitation, that either opening and/or closing the valve(s) will cause the air or gas(s) moving through the dehumidification apparatus (2040) to move through one or more separate channel(s), tunnel(s), and/or pipe(s), that leads to one or more of any suitable filters (2090) and/or activated charcoal filter(s) (2090), and/or any other suitable means for filtering (2090) one or more of any targeted gas(s) for removal. The air and/or various gas(s) can be, without limitation, vented out of the dehumidification apparatus(s) (2040) and back into the targeted area(s) 210), after they pass through the one or more filter(s) (2090).

The atmosphere, air, and/or gas(s) from within the targeted area(s) (210) can also be, without limitation, moved through the one or more means for dehumidification (2040), and/or the one or more means for filtering (2090), at any speed, rate, and volume per minute. It is preferred, without limitation, that the atmosphere, air, and/or gas(s) within the targeted area(s) (210) are at least moved through the one or more means for dehumidification (2040), and/or the one or more means for filtering (2090), at effective and efficacious, speed, rate, and volume per minute.

Without being limited, in any of the embodiment(s), and/or in any part(s) of the present invention, the term "PLC", "PLC(s), "Controller(s)", "Micro-Controller(s)", and/or even the term "HMI(s)", can represent, infer to, reference, symbolize, and/or allude to, the use of, and/or the incorporation and use of, one or more of any, logic system(s), micro-controller(s), computer(s), programmable logic controller(s), control circuit(s), circuit(s), circuitry(s), control electronic(s), analog and/or digital control system(s), controller(s), programmable logic circuit(s) (PLC), and/or any other suitable and effective device(s), component(s), and/or system(s), known to those skilled in the art, that can at any suitable and effective time(s), control, communicate with, influence in any suitable and effective way(s), be programmed to control, execute and/or control any number of any kind of instruction(s) or operation(s), of or for any, component(s), device(s), and/or equipment(s), all in a manner known to those skilled in the art.

Without being limited, one or more of any suitable and effective source(s) of pressurized air and/or gas(s) (Hereinafter "dehumidifier blower(s)" (6210)) may be utilized in the design and construction of the one or more means for dehumidification (2040). The dehumidifier blower(s) (6210) can move any of the, air, gas(s), and/or aerosol(s) (200), into, through, or into contact with, one more part(s) or component(s) such as, but not limited to any, condensing or chill coil(s) (2080), valve(s) (2100), and/or filter(s) (2090). The source(s) of pressured air and/or gas(s) can be, without limitation, located in one or more of any suitable and effective location(s) within and/or at least connected to, the one or more means for dehumidification(s) (2040). Without being limited, the pressurized air/gas can be supplied from sources such as, but not limited to, one or more of any, fan(s), blower(s), or other suitable and effective supply of pressurized air/gas(s). The source(s) of pressured air and/or gas(s) can either push or pull any suitable and effective, quantity, volume, and/or mass, of any of the, air, gas(s), and/or aerosol(s) (200), into, through, or into contact with, one more part(s) or component(s) of the means for dehumidification (2040). Without being limited, one or more dehumidifier blower(s) (6210) can be dedicated for use with the condensing or chill coil(s) (2080), and/or another one or more dehumidifier blower(s) (6210) can also be dedicated for use with the one or more filter(s) (2090). It is preferred, without limitation, that at least one suitable and effective dehumidifier blower(s) (6210) is incorporated into the design of the means for dehumidification (2040), and the flow of any, air, gas(s), and/or aerosol(s) (200), is utilized by at least both the condensing or chill coil(s) (2080) and the one or more filter(s) (2090), at either the same and/or different times. Without being limited, various components of the means for dehumidification (2040), such as, but not limited to any, dehumidifier blower(s) (6210), valve(s) (2100), and/or condensing or chill coil(s) (2080) and any related part(s) and device(s), can be controlled by one or more of any suitable and effective PLC(s) at any suitable and effective location(s), and preferably any PLC(s) that controls and/or is a component of any means for dehumidification (2040), and more preferably any PLC(s) that controls one or more of any aerosol producing apparatus(s) (215), and even more preferably any PLC(s) that controls and/or is a component of any remote aerosol sensor(s) (5010), and very preferably any PLC(s) (6005) that controls, and/or is located in or at, and/or is a component(s) of, one or more of any, remote controlling device(s) (6010).

Without being limited, the atmosphere, air, and/or gas(s) within the targeted area(s) (210) can be moved through the one or more means for dehumidification (2040) and/or one or more means for filtering (2090) at any time. It is preferred, without limitation, that the targeted area(s) are first effectively and efficaciously dehumidified, before any atmosphere, air, and/or gas(s), from within the targeted area(s) (210), are moved through the one or more means for filtering (2090). It is more preferred, without limitation, that the targeted area(s) are effectively and efficaciously dehumidified at the same time as any atmosphere, air, and/or gas(s), within the targeted area(s) (210), are treated and/or filtered with one or more means for filtering (2090). This can be, without limitation, performed in various ways such as, but not limited to: (a) moving effective and suitable amounts of any atmosphere, air, and/or gas(s), from within the targeted area(s) (210), through both the one or means for dehumidification (2040), and the one or more means for filtering (2090), at the same time, (b) moving effective and suitable amounts of any atmosphere, air, and/or gas(s), from within the targeted area(s) (210), first through the one or means for dehumidification (2040), and then through the one or more means for filtering (2090), and/or, (c) moving effective and suitable amounts of any atmosphere, air, and/or gas(s), from within the targeted area(s) (210), first through the one or more means for filtering (2090), and then through the one or means for dehumidification (2040).

In another embodiment, the means to dehumidify (2040) an area in which the aerosol (200) is administered or deployed, can be, without limitation, designed and built so the operator(s) can program or select various options including, but not limited to, (a) any time delay between when a certain humidity level or range of humidity is detected and when the dehumidifier would commence the dehumidification process, (b) any humidity level where the means to dehumidify (2040) would stop the dehumidification process, (c) any duration of time for moving, switching, or directing the air flowing into or through any filter (2090) that is able to effectively remove any targeted gas(s) or vapor(s) from the treated area(s), (d) any duration of time that the means to dehumidify (2040) would operate and dehumidify the room.

According to an embodiment shown in FIGS. 59-63, a means to effectively or efficaciously cover various types of inbound or outbound air vents and/or any surrounding area or surfaces of the vents (2120), in the treated area can, without limitation, be used in concert with the aerosol generating apparatus (215) or any aerosol or vapor generating apparatus, and prevent or limit the movement of air, gas, aerosol (200) and vapor(s) through these vents (2120). This vent covering assembly (2300) consists of parts including, but not limited to, a means to cover the vent (2110), any material extensions (2160) that are needed to directly or indirectly attach to the cover (2110) so that it will have sufficient clearance and cover any protruding vent (2120) parts (3010), sealing material (2130) that can seal the cover (2110) to the vent (2120) or any surface(s) surrounding the vent, any one or more pole(s) (2140) which can, without limitation, be adjusted or modified for length by the operator, a means to directly or indirectly connect the pole(s) to the vent cover (2150), one or more means to directly or indirectly connect (2500) the pole(s) (2140) to the floor or any other surface (2400). This assembly of parts can be made of any mechanically, structural, and chemically suitable materials that are known to those skilled in the art for this application.

Any parts used to construct the vent covering assembly (2300) can be constructed from various materials such as, but not limited to, stainless steel, glass, polymer, polyolefin, cellulose, or even natural or manufactured fibers that are either coated or uncoated. It is preferred, without limitation, that the vent covering assembly (2300) is constructed from one or more polymers that can include, but is not limited to, PVC, polycarbonate, polypropylene, and HDPE. The materials used to construct the vent cover (2110) or extension(s) (2160) may be rigid, semi-rigid, flexible, or pliable. It is preferred, without limitation, that the vent cover (2110) and any needed extension(s) (2160) are constructed from rigid PVC. The seal material (2130) can be any material that can create an effective seal with/against any materials that it contacts. It is preferred, without limitation, that the seal material (2130) is constructed from materials such as, but not limited to, Viton, or EPDM, with a durometer of at least 10. The seal material can be, without limitation, any foam, open or closed cell material, and any shape or construction known in the art. The sealing material (2130) can also vary with variables including but not limited to its, size, shape, width, surface area, geometry, fit, thickness, density, hardness, elasticity, porosity, permeability, mechanical properties, physical properties, and other variables known to those skilled in the art. One or more strips or layers of various seal material(s) (2130) may also be utilized and can be used in various orientations, including, but not limited to, parallel to one another. It is preferred, without limitation, that the seal material consists of a single row of closed cell EPDM foam. Any of the surfaces of the vent covering assembly (2300) can, without limitation, be electrically or electrostatically charged in order to attract the "applied agent". The vent covering assembly (2300) can be designed and constructed for single or multiple uses.

According to another embodiment, the vent cover (2110) and/or its extensions (2160) can, without limitation, be constructed from, or be molded with, any material that can create an effective seal, or otherwise function as the seal, which negates the use of a separate seal material and/or seal layer (2130). This represents the vent cover (2110) in its simplest form. In this case, the vent cover (2110) and/or its extensions (2160) is designed and constructed so that it incorporates the purpose, performance, traits, attributes, and characteristics of both the seal material and/or seal layer (2130) and the vent cover (2110) and/or extensions (2160).

In another embodiment, any parts connected directly or indirectly to the means to cover the vent (2110) can be adjusted for height in order to create or maintain effective compression on any seal that is formed to effectively or efficaciously seal or cover the air or gas vents (2120). It is preferred, without limitation, that the one or more pole(s) (2140) is constructed in a manner known to those skilled in the art, so that its length can be adjusted and locked into position once sufficient or effective force is exerted onto any part of the vent covering assembly (2300) such as, but not limited to, a means to cover the vent (2110) and/or the seal material (2130).

It is preferred, without limitation, that the means to cover the vent (2110) is any shape, size, construction, or geometry that is sufficiently large enough so that the sealing means and/or seal material (2130) can effectively seal to or around any air vents (2120). It is even more preferred, without limitation, that the means to cover the vent (2110) is in the shape of a plate or bowl. This means to cover the vent (2110) can, without limitation, have one or more structural supports that are positioned in a manner known in the art to prevent any unwanted flexing of the means to cover the vent (2110) during use. The means to cover the vent (2110) can also, without limitation, have extensions (2160) directly or indirectly attached to allow the various vent cover components (2170) to effectively fit over the vent (2120) and any protruding vent parts (3010). The extensions (2160) can be made of the same materials as the means to cover the vent (2110), and have any thickness, width, length, height, geometry, or construction. The extensions (2160) can, without limitation, follow the outline of the means to cover the vent (2110).

The seal material (2130) can be attached to the vent cover (2110) or its extensions (2160) in various ways known to those skilled in the art. The seal material (2130) can be made from any compatible and suitable material. However, it is preferred, without limitation, that the seal material (2130) consists of any suitable material and design that has sufficient compression and/or compliance to form an effective seal when it is compressed or contacts between the vent cover (2110) and/or extension(s) (2160) and the vent (2120) or any surface surrounding the vent. It is even more preferred that the seal material (2130) has absorbent properties. A lip or other effective means can also be built or formed around the seal material (2130) to catch or hold any liquid if it is compressed out of the seal material (2130).

Any pole (2140) known to those skilled in the art, can be used in the present invention, but it is preferred, without limitation, that the pole (2140) has an adjustable length, and a locking means (3020) (FIG. 61) known in the art to maintain the effective or chosen pole length. Any method known to those skilled in the art can be used to incorporate a pole (2140) adjustable for length into the present invention. It is preferred, without limitation, that the pole (2140) consists of two parts, and the length of the combined poles can either gain length or loose length depending on which way the operator screws or ratchets the two pole pieces. The pole (2140) connects either directly or indirectly to the means to cover the vent (2110) and this connection can, without limitation, swivel. It is preferred, without limitation, that the pole screws into a bracket or threaded block that is directly mounted to the means to cover the vent (2110). The end of the pole that contacts the floor or other surface, can also without limitation, be adjustable for length, and have the ability to swivel. The end of the pole or support mechanism (2800) can be, without limitation, formed from, molded, coated, adhered, or covered, with any absorbent material so that the surface and/or area below the pole can be treated with any liquid. The end of the pole or support mechanism (2800) can also, without limitation, be manufactured with any material that will decrease the movement or slipping of the pole.

According to an embodiment, installation includes, but is not limited to, pressing the means to cover the vent (2110) and its accompanying seal material (2130), up against or around the vent (2110) and extending the pole until sufficient pressure is formed against or around the vent (2110), and the end of the pole (2140). Before, during, or after installation, the seals (2130) and end of the pole (2140) can be, without limitation, soaked with or saturated with any liquid consisting of any anti-pathogen, toxin, fungal, sterilization, disinfection, or sporicidal agent(s) or mixtures thereof (herein collectively "agent(s)").

Figure 63:
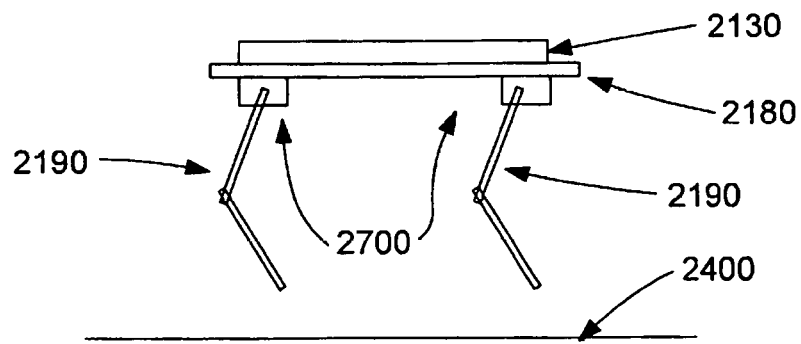
FIG. 63 is a schematic view of a fourth embodiment of a vent cover of FIG. 60.

According to an embodiment shown in FIG. 63, one or more attachment points (2700) can be added to the design of a magnetic vent cover (2180) so that a means (2190), can be attached to the vent cover to pull it from the ceiling vent without the need for a person to use a means such as, but not limited to, a ladder to reach it. This means (2190) used for pulling can include, but is not limited to, rope, cord, thread, wire, cable, twine, tube, that can be various, size, length, materials, and construction. Protruding objects (2200) of various lengths, shapes, and construction, can also, without limitation, be attached to the magnetic vent cover (2180) in various ways known in the art, for the same purposes. The protruding objects can include, but is not limited to, any dowel, pipe, or conduit, and can also be constructed from any suitable materials, and have various flexibility or rigidity. The construction of the magnetic vent cover (2180) is known to those skilled in the art, but it can, without limitation, be made by laminating a sheet of magnetic material between two or more polymer layers. The magnetic material can have any thickness, power, or strength, and the polymer coatings or laminations, can be any suitable polymer. According to another embodiment, the magnetic vent cover (2180) can, without limitation, incorporate any deformable seal material (2130), which can increase the ability of the magnetic vent cover (2180) to effectively seal the vent (2120). The seal material (2130) can without limitation, contact the vent (2120), surround the vent (2120), or contact any area near the vent (2120). The seal material (2130) can be encompassed or enclosed on one or more sides by any magnetic material (2900) of any strength. The seal material (2130) can be, without limitation, separated from the magnetic material (2900) by one or more layers of any suitable polymer of any thickness.

Figure 60:
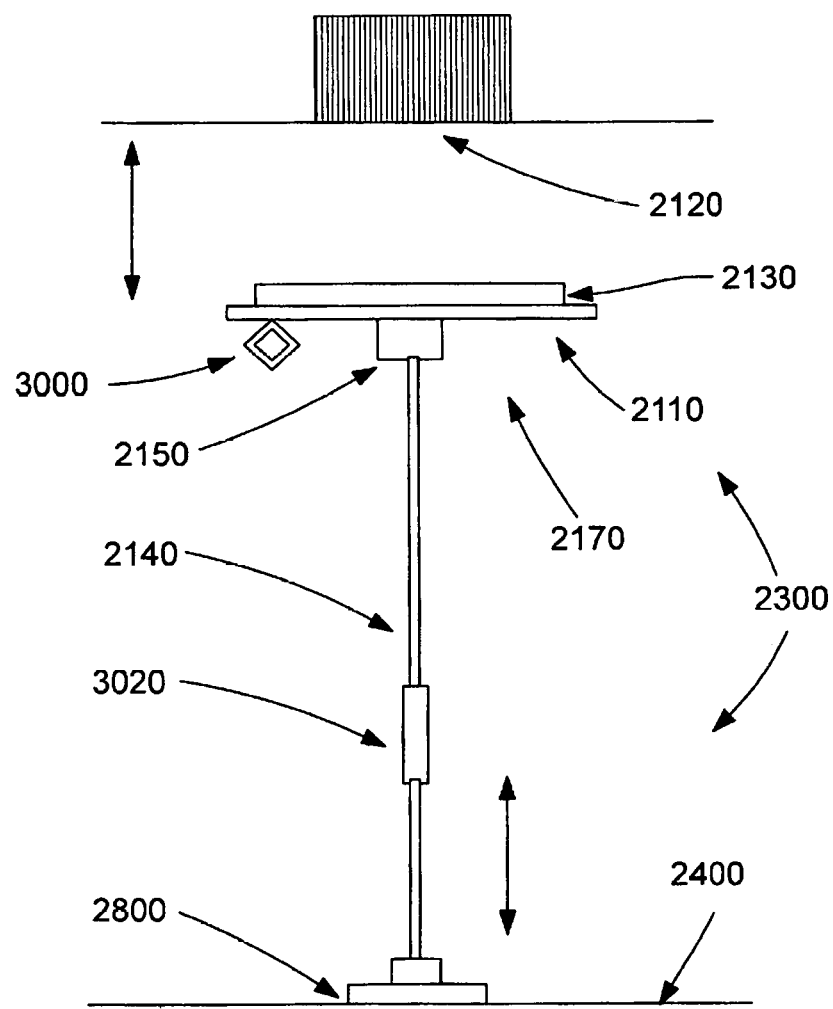
FIG. 60 is schematic view of a first embodiment of a cover engaged with the wall vent of FIG. 59.
Figure 61:
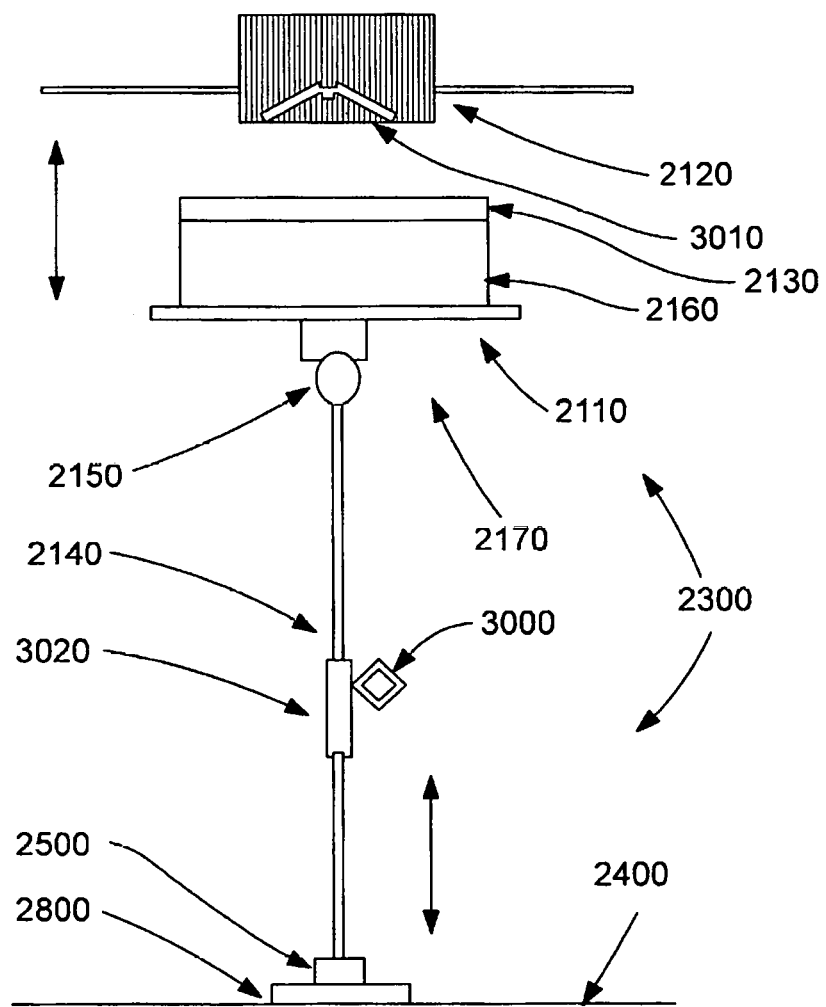
FIG. 61 is a schematic view of a second embodiment of the cover of FIG. 60.
Figure 62:
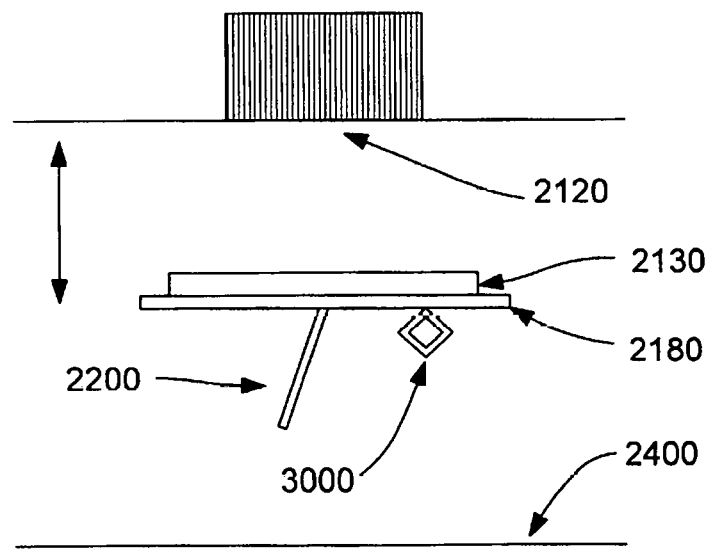
FIG. 62 is a schematic view of a third embodiment of the cover of FIG. 60.

According to an embodiment shown in FIGS. 60-61, one or more chemical contact or biological indicators (hereinafter "indicator(s)") (3000) of any size, type, or construction, may be mounted, held, hung, positioned, or placed, on any part including, but not limited to, the vent covering assembly (2300), or any part directly or indirectly connected to the vent covering assembly (2300) or magnetic vent cover (2180). It is preferred, without limitation, that the indicator (3000) is attached to a surface that faces the treated area. The vent covering assembly (2300) can be designed for the addition as well as removal of these accessories, in a manner known to those skilled in the art. The indicator (3000) provides a means for communicating or assuring that proper sanitization, detoxification, disinfection, high level disinfection, or sterilization has occurred, without limitation, on surfaces on or surrounding the vent covering assembly (2300). A detailed description of the indicator (3000) is not specifically set forth, but is known to those skilled in the art.

According to an embodiment shown in FIGS. 65-68, the "application enclosure(s)" (930) can include, without limitation, one or more wall(s) (935), of any material, that form one or more enclosed, semi-enclosed, or unenclosed area(s) (940). The one or more wall(s) (935) of the application enclosure(s) (930) may also have one or more openings or holes (herein referred to as hole(s)) (955) of any size, shape, or dimension, and the interface of these hole(s) (955) with any surface(s) (945), or any object(s) (3030), forms one or more enclosed area(s) (950) which can vary with respect to variables such as, but not limited to any, size, shape, or geometry.

According to an embodiment, the application enclosure (930) can also, without limitation, be designed and constructed so that it has one or more opening(s) or orifice(s) ("hole(s)") (955), and one or more object(s) (3030) with one or more various surfaces (945) can be positioned or inserted through these hole(s) (955), and the direct or indirect contact or interface of the object(s) (3030) with these hole(s) (955) results or causes the enclosed area(s) (950) to become, without limitation, effectively sealed. The hole(s) (955) can also be formed around one or object(s) (3030). The object(s) (3030) can, without limitation, be oriented, located, or inserted, completely through the enclosed area (950) in any orientation, through the one or more hole(s) (955). The hole(s) (955) can be any size, geometry, orientation, or in any location. The holes(s) (955) and/or any parts of the application enclosure (930) can, without limitation, be of any construction, and be adjusted by various means known in the art, to accommodate any object(s)'s attributes including, but not limited to size, width, length, shape, and/or geometry. The application enclosure (930) can also, without limitation, be designed and constructed in a manner known to those skilled in the art, so that it can be temporarily or permanently mounted, strapped, or connected to any table, bench, or other surface.

Figure 65:
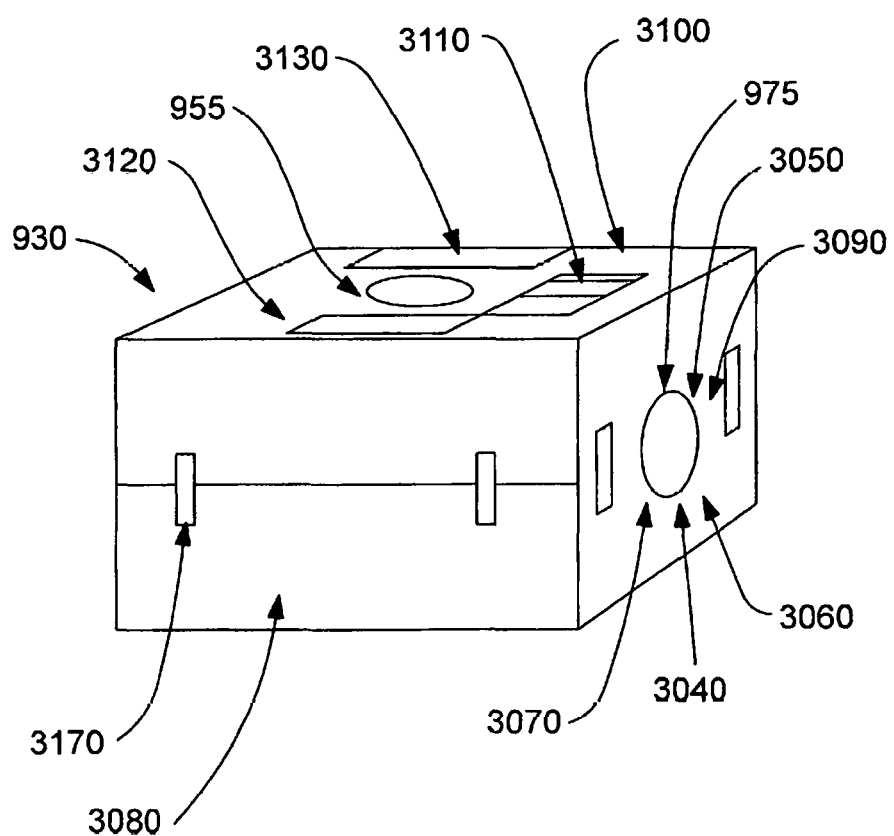
FIG. 65 is a schematic view of another alternative embodiment of the enclosure for the aerosol generator of FIG. 52.
Figure 66:
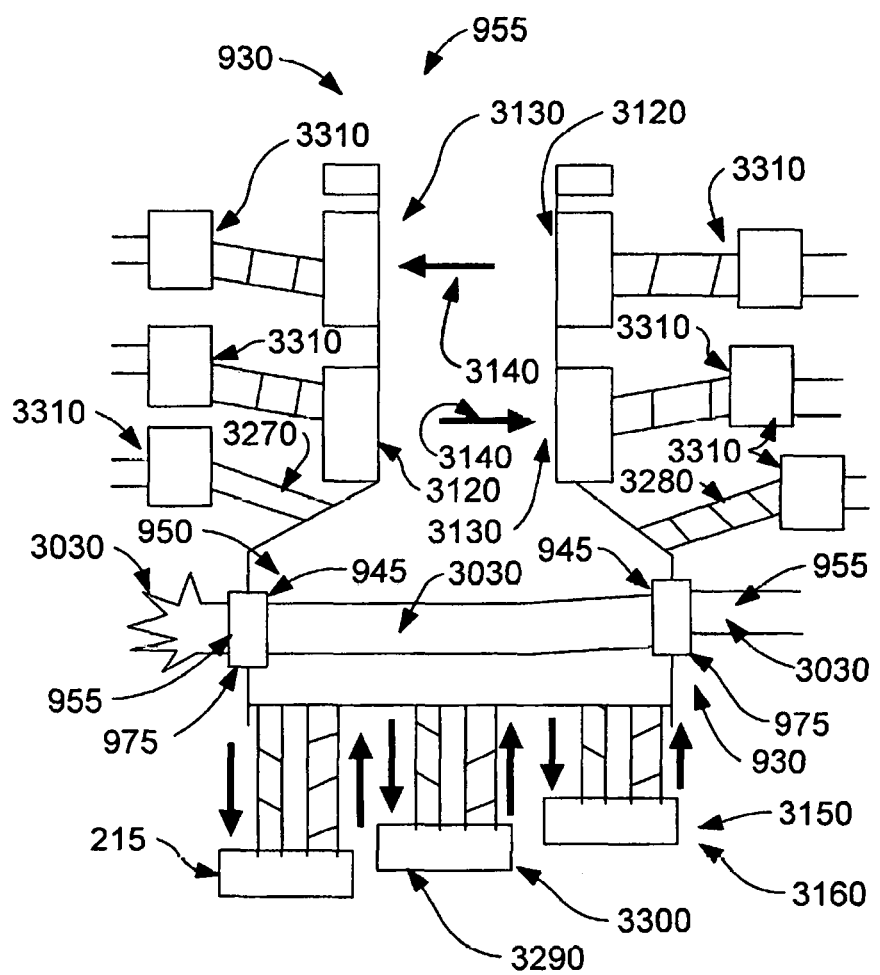
FIG. 66 is a schematic view of another alternative embodiment of the enclosure for the aerosol generator of FIG. 52.
Figure 67:
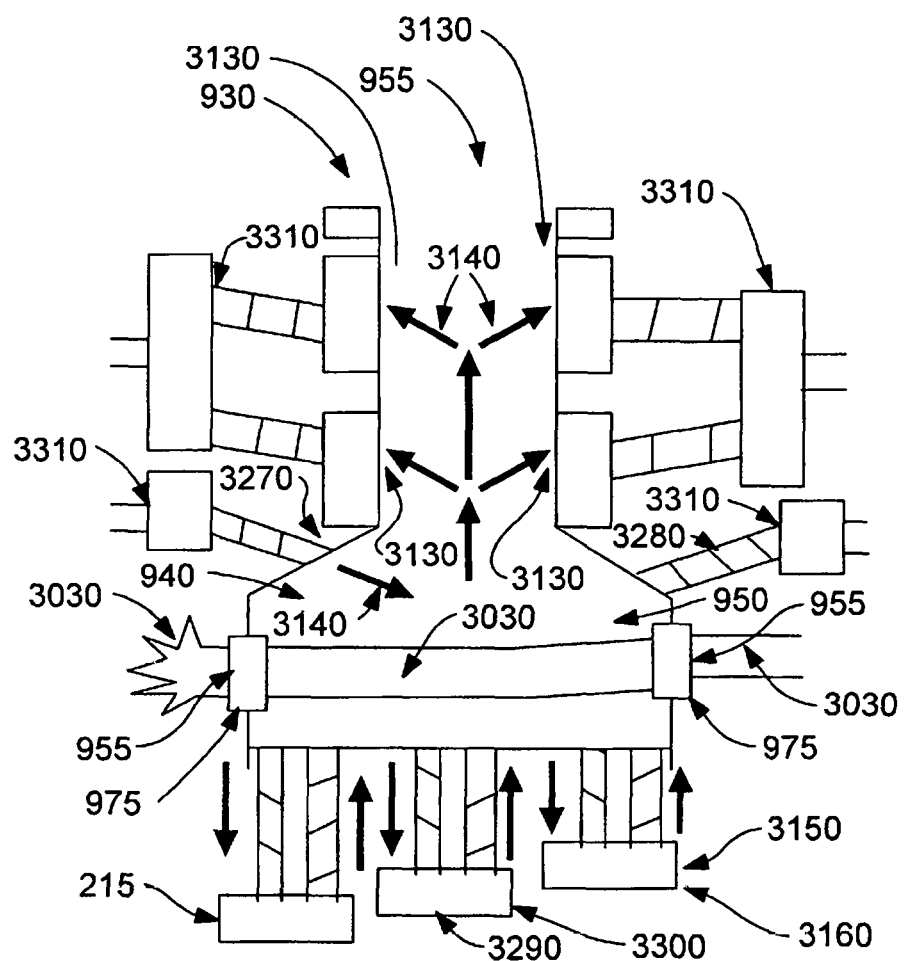
FIG. 67 is a schematic view of another alternative embodiment of the enclosure for the aerosol generator of FIG. 52.

Looking now at FIGS. 65-67, according to an embodiment, the application enclosure (930) can, without limitation, be designed and constructed so that one or more object(s) (3030) or any combination of objects (3030) can be positioned in or onto one or more section(s) (3040) of the one or more hole(s) (955) and/or their seal material (975), and the one or more opposing section(s) (3050) of each hole(s) (955) and/or their seal material (975), is then brought together by connecting the one or more component(s) (3060) that create an effectively sealed enclosed area(s) (950) when joined. It is preferred, without limitation, that this is accomplished by placing any number or combination of object(s) (3030) such as, but not limited to any legs, head, feet, hands, arms, or torso, inside or onto any part of the lower half (3070) of the section of hole(s) (955) and/or any seal material (975) directly or indirectly connected to any parts constituting the lower half (3080) of the enclosed area (950), and then enabling contact of these object(s) (3030) with any part of the upper half (3090) of the section of the hole(s) (955) and/or any seal material (975) that is directly or indirectly connected to any parts constituting the upper half (3100) of the enclosed area (950). It is preferred, without limitation, that the upper half and lower half of the enclosed area (950) are connected. It is even more preferred that upper (3100) and lower (3080) halves are able to hinge open and closed in a manner known in the art. The various application enclosure (930) parts, such as but not limited to the upper (3100) and lower (3080) halves can also, without limitation, be connected with one or more of any mechanical means (3170) known to those skilled in the art, to apply pressure to areas such as, but not limited to any seal between the upper (3100) and lower (3080) halves, and the one or more seals or interfaces between the object(s) and any part of the lower half (3070) and upper half (3090) sections, or any other sealing segments, of any hole(s) (955).

Any segments or parts of the hole(s) (955) can, without limitation, interface with the object(s) (3030) with one or more of any materials of any construction. It is preferred, without limitation, that this material is any seal forming material (975) or combination of materials (975), or any other means to form an effective seal (975), and is known to those skilled in the art. It is even more preferred, without limitation, that the seal (975) or any seal that interfaces with the object(s) (3030) can be directly or indirectly adjusted in any way, for effectiveness and fit and/or integrity, and can accommodate and effectively seal to objects (3030) of various size, shape, width, length, and geometry, and is known to those skilled in the art. The application enclosure (930) can, without limitation, seal or effectively interface with one or more of any object(s) (3030) in a manner known in the art, but it can be as simple as inserting the object(s) (3030) such as, but not limited to, any or all parts of a patient's body through any of the one or more hole(s) (955), and tightening or sealing any part connected to the object (3030) interfacing seal material (975), or interface material, that is directly or indirectly in contact with each or all of the object(s) (3030) or body part(s), to form, without limitation, an effective seal that can effectively seal the hole(s) (955). This can also be utilized, without limitation, for the hands or arms of any surgeons, nurses, technicians, or other personnel or operators, that need to access the inside of the application enclosure(s) (930) for any reason. Any pneumatic means consisting of any materials, any sealing materials (975), and construction, known to those skilled in the art, may also, without limitation, be used to effectively seal directly or indirectly around any object(s), or hand(s) or arm(s) of one or more of any personnel that interface with the application enclosure (930) in any way for any reason. One or more gloves (965) can also attach to any port(s), opening(s), or airlock(s) (960) or hole(s) (955) and be hermetically sealed to the application enclosure(s) (930). Furthermore, the gloves or gauntlets (965), and or any interface they may have with the application enclosure (930) can, without limitation, be designed in a manner known to those skilled in the art, so that they may be easily or quickly removed and replaced. It is preferred, without limitation, that the gloves or gauntlets (965) are disposable, and they can be replaced after each use of the application enclosure (930).

According to an embodiment, the application enclosure (930) can, without limitation, have one or more sources of pressurized or moving air or any gas, and these resulting flows or streams (herein referred to as "stream") of air or gas (3140) can move in various ways over, under, or across (herein referred to as "across") any door or hole (955) which personnel or robotics may use to access the inside of the application enclosure (930). The supplied air or gas stream (3140) can move, without limitation, completely or partially across any part or entirety of any door or hole (955) opening, at any angle, and at any velocity or volume. It is preferred, without limitation, that the air or gas stream is active or enabled for any door or hole (955) that is open or unsealed in any way, and the air or gas stream (3140) completely covers the door or hole (955) area and/or any area in close proximity to the door or hole (955). The one or more source(s) (3120) of the air or gas stream (3140) can be, without limitation, any size, shape, length, width, geometry, orientation, or construction, and can be positioned in any locations in various effective proximity to any door, opening, or hole (955). The air or gas can, without limitation, be directed with any form of baffles located anywhere within the application enclosure (930). It is also preferred, without limitation, that the outlet orifice for the source(s) (3120) of the air or gas stream (3140) is rectangular in shape and spans at least the width of the door or hole (955). The one or more sources (3120) of the air or gas stream (3140) can be, without limitation, located above one another, directly or indirectly opposed to one another, and separated by any distance. The one or more source(s) (3120) of the air or gas stream (3140) can also be, without limitation, perforated, and the perforations can be, without limitation, any number, size, shape, or orientation. Any air or gas that is used to form the air or gas stream (3140) can be, without limitation, filtered before being deployed or flowed, by any type of filter or filtering method (3310) including, but not limited to, a HEPA filter, all in a manner known by those skilled in the art.

It is also preferred, without limitation, that one or more door(s) or hole (955) cover(s) (Herein called "door(s)" (3110) can slide open and out of the way of the one or more human operator(s) or any robotic arms or tools, when access is needed to reach through the one or more hole(s) to work or perform any tasks anywhere inside of the enclosed area (950). The design and construction of the sliding door(s) (3110) is known to those skilled in the art. The hole(s) (955) as well as any door(s) (3110) can be any, size, width, length, depth, shape, thickness, construction, and material, and the door(s) (3110) can move via any means, and any construction, known to those skilled in the art. It is preferred without limitation that the sliding door(s) (3110) possesses sufficient attributes known in the art so that it can effectively seal the application enclosure (930) when it is closed. Any number of door(s) (3110) can be located at any location on the application enclosure (930). It is preferred, without limitation, that at least one door(s) (3110) is located on the top of the application enclosure (930). The application enclosure (930), any structures inside of the enclosed area(s) (950), and any hole(s) (955), are designed and constructed so that the hole(s) (955) are positioned or located, without limitation, at any height, distance, or location, from any objects located inside of the application enclosure (930).

According to another embodiment, an object (3030) can, without limitation, be placed completely inside the application enclosure (930), and all hole(s) (955) are either closed with door(s) (3110), or at least one hole (955) is kept open or partially open to enable personnel access into the application enclosure (930) to conduct work or tasks.

Any parts used to construct the application enclosure (930), or any door(s) (3110), can be constructed from various materials such as, but not limited to, stainless steel, glass, polymer, polyolefin, cellulose, or even natural or manufactured fibers that are either coated or uncoated. It is preferred, without limitation, that these parts or components are constructed from one or more polymers that can include, but is not limited to, PVC, polycarbonate, polypropylene, and HDPE. The application enclosure (930), or any door(s) (3110), can be, without limitation, flexible, rigid, semi-rigid, opaque, translucent, or transparent. It is preferred, without limitation, that rigid transparent materials are utilized.

According to an embodiment, one or more sources of vacuum (3130) (herein called "door vacuum") located near the door(s) (955) can be, without limitation, located anywhere in front of or opposed from the one or more outlet orifice(s) for the source(s) (3120) of the air or gas stream (3140) that can move various ways over, under, or across any door or hole (955). Any strength, velocity, volume, or amount of vacuum can, without limitation, be used. The orifice(s) for the door vacuum(s) (3130) can be, without limitation, any size, shape, length, width, geometry, orientation, or construction, and can be positioned in any locations in close proximity to any door, opening, or hole (955). It is preferred, without limitation, that the inlet orifice(s) for the door vacuum(s) (3130) can be rectangular in shape and span at least the width of the door or hole (955). The door vacuum(s) (3130) can be, without limitation, located above one another and separated by any distance, and be perforated with perforations that can be any, number, size, shape, or orientation. It is preferred, without limitation that the door vacuum(s) (3130) is active or enabled whiles the door or hole (955) is open or unsealed in any way, or one or more air or gas streams (3140) are present. Any air or gas that is pulled via vacuum can be, without limitation, filtered by any type of filter or filtering method (3310) including, but not limited to, a HEPA filter, all in a manner known by those skilled in the art.

The combination of the one or more stream(s) of air or gas (3140) moving in various ways over, under, or across any door or hole (955) and opposing door vacuum(s) (3130) can, create a synergistic effect that can, without limitation, reduce the chance of introducing contamination into the application enclosure (930) through any door or hole (955).

According to an embodiment, any positive pressure can, without limitation, be established or maintained inside of the application enclosure (930) at any time, and for any duration, or during any part of any cycle, by flowing air or any gas into the application enclosure (930). This positive pressure can, without limitation, be turned on or off at any time, and for any duration, before, during, or after any number of procedures or treatments are conducted inside of the application enclosure(s) (930). Furthermore, any or all doors (3110) can, without limitation, be opened or closed at any time and for any duration, during use of the application enclosure (930). Any positive pressure can, without limitation, be established or maintained inside of the application enclosure (930) whether any door(s) (3110) are open or closed. One or more means or outlets utilized to supply (3270) the air or gas under positive pressure can, without limitation, be located at any location within the application enclosure (930). The supplied (3270) air or gas can also, without limitation, be filtered before being deployed or flowed into the application enclosure (930), by any type of filter or filtering method (3310) including, but not limited to, a HEPA filter, all in a manner known by those skilled in the art. The air or gas can be supplied or flowed (3270) into the application enclosure (930) at any rate, speed or volume, and via means such as, but not limited to, one or more fan(s) or blower(s).

According to another embodiment, one or more of the door vacuum(s) (3130) sources can also operate while a positive pressure is established or maintained inside of the application enclosure (930). Any strength, velocity, volume, or amount of vacuum can, without limitation, be used. It is preferred, without limitation, that the door vacuum(s) (3130)

are active or enabled while any door or hole (955) is open or unsealed in any way, or one or more supplied air or gas streams (3140) are present. Any supplied air or gas stream (3140) may also, without limitation, be active near any door(s) (955) at any time while a positive pressure is established or maintained inside of the application enclosure (930). The supplied air or gas (3270) and the vacuum can, without limitation, vary in order to maintain a desired level of positive pressure inside of the application enclosure (930). This is especially important when openings such as, but not limited to, one or more door or hole(s) (955) is open or unsealed.

According to an embodiment, the application enclosure (930) can also be designed and constructed so that it has, without limitation, (a) any means to filter (3150) and/or dehumidify (3160) the atmosphere within the application enclosure to any humidity level at any time and for any duration, (b) any means to either heat (3290) or cool (3300) the atmosphere inside the application enclosure at any time and for any duration, (c) any means, located anywhere inside of the application enclosure (930), to either increase or decrease the pressure (3270) inside of the application enclosure at any time and for any duration, (d) a means to create an additional vacuum (3280) located anywhere inside of the application enclosure (930) to remove materials such as, but not limited to, any unwanted fumes, vapors or aerosols. Any air or gas that is supplied into, or pulled via vacuum inside, the application enclosure (930), can be, without limitation, filtered by any type of filter or filtering method (3310) including, but not limited to, a HEPA filter, all in a manner known by those skilled in the art. In certain circumstances, the various filters may, without limitation, be shared by similar equipment or processes, in a manner known to those skilled in the art.

According to an embodiment, the application enclosure (930) as described in the present invention, can be used in various ways including, but not limited to, the following brief description of steps, activities, and/or or procedures, that can, without limitation, be undertaken: (a) locate the object (3030) or patient's body, torso, or other parts of the body, in the application enclosure (930), (b) seal the application enclosure (930), (c) if desired or necessary, condition the atmosphere for temperature within the application enclosure (930), (d) deploy, for any time period, the aerosol and/or vapor (200) into the application enclosure (930), (e) terminate the deployment of the aerosol and/or vapor (200) once a sufficient time has passed to effectively fill the application enclosure (930), (f) expose the surfaces inside the application enclosure (930) to the aerosol and/or vapor (200) for a sufficient amount of time to achieve an efficacious outcome, (g) dehumidify, to any desired humidity range, and/or remove the remaining aerosol and/or vapor (200) from inside the application enclosure (930), (h) conduct surgery on the patient, (i) if necessary or desired, redeploy, for any time period, the aerosol and/or vapor (200) into the application enclosure (930) during surgery and remove any humidity and/or aerosol as needed, (j) complete surgery, (k) if needed or desired, terminate the surgery with a final redeployment of the aerosol and/or vapor (200), for any time period, into the application enclosure (930) (l) dehumidify, to any desired humidity range, and/or remove the remaining aerosol and/or vapor (200) from inside the application enclosure (930), (m) remove the patient from the application enclosure (930). These steps or procedures are only a small and incomplete example of the numerous combinations of various steps, activities, and/or procedures, that can take place within the application enclosure (930).

According to another embodiment, the application enclosure (930) can have various equipment located inside, such as, but not limited to any, lights, robotic apparatus(s) used for any purpose, imaging equipment, means to support or hold any objects, surgical or medical equipment or accessories, and manufacturing equipment.

Figure 68:
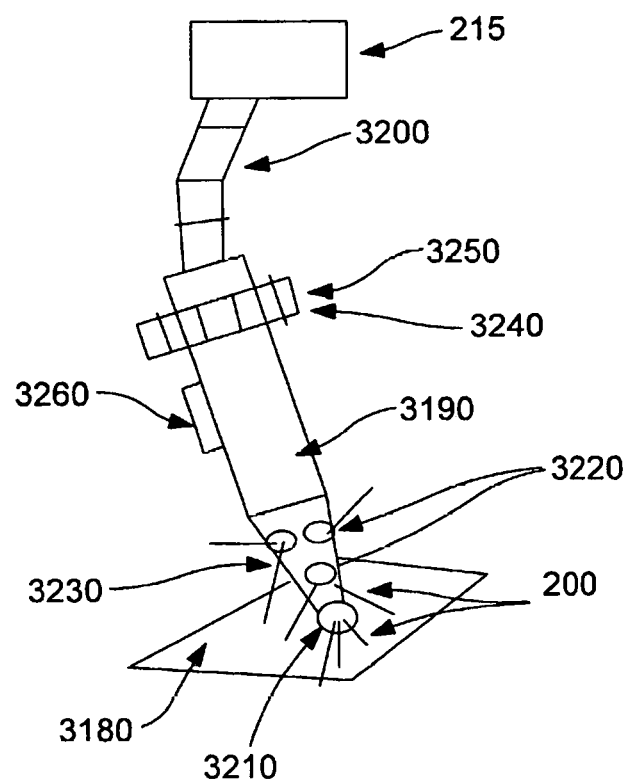
FIG. 68 is a schematic view of another alternative embodiment of the enclosure for the aerosol generator of FIG. 52.

Looking now at FIG. 68, according to an embodiment, an aerosol and/or vapor is generated by a means such as, but not limited to, the aerosol (200) generating apparatus (215) in the present invention, and the aerosol and/or vapor (200) is delivered into one or more targeted areas such as, but not limited to, any wound, any body cavity, surgical plain or surgical incision (3180). Any (200) or vapor generating means can be used in this embodiment. The aerosol and/or vapor is delivered via one or more tube, pipe, or conduit (herein called "application wand" or "wound wand") (3190) which can be any, without limitation, angle, size, length, orientation, diameter, width, or geometry. The wound wand (3190) can be connected to the aerosol (200) generating apparatus (215) in various ways knows to those skilled in the art. The wound wand (3190) can also be designed and constructed so that it can be easily connected or disconnected from any aerosol and/or vapor (200) supply line(s) (3200), and it can be effectively cleaned, sterilized, or disinfected, in a manner known to those skilled in the art. Various types of flexible pipe or tubing (3200) can, without limitation, connect to the application wand (3190) in a manner known to those skilled in the art.

It is further preferred, without limitation, that one or more perforations (3220) can be located at any location(s) on the application wand (3190). The perforations (3220) can be, without limitation, any size, pattern, shape, angle, geometry, and any orientation. The application wand (3190) can also be designed to interface with interchangeable tips (3230) that vary in attributes such as, but not limited to, length, diameter, any exit orifice (3210) attributes, number or size of perforations (3220), angle of perforations (3220). The interchangeable tips (3230) can connect to the application wand (3190) in a manner known to those skilled in the art. The exit orifice (3210) can be, without limitation, any shape, size, geometry, in order to develop an effective and efficacious device.

According to an embodiment, the application wand (3190) can, without limitation, incorporate any means anywhere on its surface which when actuated or activated (3240), controls and/or stops the flow of aerosol (200) and/or vapor that emanates from the application wand (3190) or any of its interchangeable tips (3230). These control functions can be separate or combined control interfaces. These means (3240) can, without limitation, be any mechanical/electrical means known to those skilled in the art.

According to an embodiment, any parts used to construct the application wand (3190) can be constructed from various materials such as, but not limited to, stainless steel, glass, polymer, polyolefin, cellulose, or even natural or manufactured fibers that are either coated or uncoated. It is preferred, without limitation, that the application wand (3190) is constructed from one or more polymers that can include, but is not limited to, PVC, polycarbonate, polypropylene, and HDPE. The materials used to construct the application wand (3190) may have any rigidity. Any surfaces of the application wand (3190) may have any electrical charge.

According to another embodiment, the application wand (3190) can, without limitation, incorporate any means, known to those skilled in the art, to mount or attach to, integrate, attach, or combine, either temporarily or permanently, any devices or to any devices, such as, but not limited to any, source of light, means to present or create suction, camera or any other imaging or video device, cauterization, robotic grips or hands, scalpel, means for suture application or removal, or any means for applying electrical shock or pulses.

Any, (a) liquid, (b) mixture or solids suspended in any liquid, (c) solution, (d) medication, (e) organisms, (f) anti-pathogen/toxin/fungal/sporicidal agent(s) or substance(s), (g) micro machine(s) or structure(s), (h) nano machine(s) or structure(s), may also, without limitation, be used in these embodiments.

According to an embodiment shown in FIGS. 70-73, a means (herein called "multi interface assembly") (3320) is designed and constructed to cover or at least isolate or prohibit the whole or at least a part of, one or more of any means that enable movement for the apparatus (215) or any other equipment or accessories located in the targeted or treated area (3310) such as but not limited to any wheels, tracks, rollers, or other movable means (herein collectively "wheel(s)") (3330), from having any contact with any floor or surface that they rest on (herein called "floor") (3340) in various situations such as, but not limited to, when the apparatus (215) or other equipment or accessories is moved, stopped, or held in a static or semi-static position, and the wheel(s) (3330) are in direct or indirect contact with one or more of any absorbent material(s) (3350) that can hold, contain, or absorb any liquid. The absorbent materials (3350) or any construct containing absorbent materials (3350) are either treated or pretreated in various ways known to those skilled in the art, with any liquid agent(s), so that both the wheel(s) (3330) and the floor (3340) can come in contact with the liquid agent(s). It is preferred, without limitation that the absorbent material(s) (3350) is saturated with the same liquid (30) that is generated into aerosol (200) in the present invention.

In the first part of this embodiment, the multi interface assembly (3320) can include one or more materials or parts, where the wheel(s) (3330) are moved or rolled onto or into one or more basin or indentation (herein called "basin") (3360). One or more walls or edges of any basin(s) (3360) can, without limitation, be formed of any angled material or ramps (3690), of any angle, size, construction, or length, to facilitate unhindered and easy movement of any wheel(s) (3330) into and out of the basin(s) (3360). The multi interface assembly (3320) can be made of one or more materials such as, but not limited to, stainless steel, glass, cellulose, polyolefin, paper, polymer, natural or manufactured fibers or materials, that may be coated or uncoated, or constructed with combinations of these materials, or other materials known in the art. However, any of the materials that can have any contact with the wheel(s) (3330) and any floor surface(s) (3340) shall have absorbent properties and can, without limitation, be any thickness and have any durometer. The basin(s) (3360) can, without limitation, be constructed from, or lined with, absorbent material(s) (3350) of any thickness, and it can have any dimensions, including any depth. The basin (3360) can, without limitation, have one or more directly or indirectly connecting lips or ramps (3370) of various length and angle, extending into one or more directions, to facilitate easier entry of the wheel(s) (3330) into the basin (3360), and/or onto the multi interface assembly (3320), from the floor (3340). This can, without limitation, help the operator so that they do not have to lift the apparatus to position the wheel(s) onto the absorbent material(s) (3350). The absorbent material(s) (3350) can be pretreated with one or more liquid agent(s), or the operator can moisten the absorbent material(s) (3350) with one or more liquid agent(s) in a manner known in the art, before or after the wheel(s) (3330) have had contact with the absorbent material(s) (3350). The multi interface assembly (3320) may, without limitation, also have one or more of any tube, duct, pipe, conduit, tunnel, pathway, or connection (herein called "basin tube") (3380), that connects any part of the basin (3360), or any other structure or component that directly or indirectly connects to any part of any basin (3360), with any of the absorbent material(s) (3350) that can have contact with any floor surface(s) (3340), so that any liquid or moisture may be transported, moved, or flow, at any rate or speed, from the basin (3360) to any of the absorbent material(s) (3350) contacting any floor (3340) surfaces. It is also possible, without limitation, to exclude the basin (3360), but keep one or more of any other attributes of the multi interface assembly (3320), which represents the multi interface assembly (3320) in its simplest form.

The multi interface assembly (3320) may, without limitation, also have one or more ridges (3390) of effective height that protrude vertically or on any effective angle to perform functions such as, but not limited to, prohibiting movement of the wheel(s), and maintaining the position of the wheel(s) (3330) on the absorbent material(s) (3350). The ridges (3390) may also be lined with absorbent materials (3350). The multi interface assembly (3320) may, without limitation, also have one or more handles or grip points attached or built into its design to facilitate easier handling.

According to an embodiment shown in FIGS. 74-75, the multi interface assembly (3320) may, without limitation, also include one or more removable absorbent material(s) (3350), and can be, without limitation, be directly attached to any wheel(s) (3330) and held or positioned into place with a variety of methods or combination of methods known in the art, including, but not limited to, the use of one or more pieces of elastic material (3400) around one or more edges of the absorbent material(s), and/or the use of one or more string laces or elastic bands or other material (3410) connected to the inside diameter of the absorbent material(s) assembly. This version represents the multi interface assembly (3320) in its most simple form.

According to an embodiment shown in FIG. 76, the apparatus (215) or any aerosol generator can, without limitation, be designed and constructed so that one or more filters (3420), known to those skilled in the art, can be connected to any parts of the plumbing anywhere in the design of the apparatus (215), as well as located anywhere inside of the various tanks used in the design of the apparatus (215). The filter(s) can, without limitation, be disposable and they can be designed for use in the apparatus (215), in a manner known to those skilled in the art, so that they are effective and easy to replace. In addition, all of the various devices and plumbing in the apparatus (215) such as, but not limited to any, feed tank(s) (280), reservoir(s) (40), feed tank valve(s) (300), pump(s) (130), filter(s) (3420), blower drain valve (3430) and system drain valve(s) (660), can be located and designed so that when the apparatus (215) is drained of all of the liquid agent(s) within it, it may be fully emptied of all liquid. This can, without limitation, facilitate thorough cleaning of the apparatus (215) and reduce any potential for damage resulting from any freezing liquid. Furthermore, the apparatus (215) may, without limitation, have one or more cleaning function(s) or program(s) designed into its hardware and/or system operating software so that all of the various valves in the system can simultaneously open in order to help purge or entirely drain the apparatus (215). This functionality can also, without limitation, be used to drain the various systems and plumbing of the apparatus (215) as it is being flushed and cleaned out.

Figure 76:
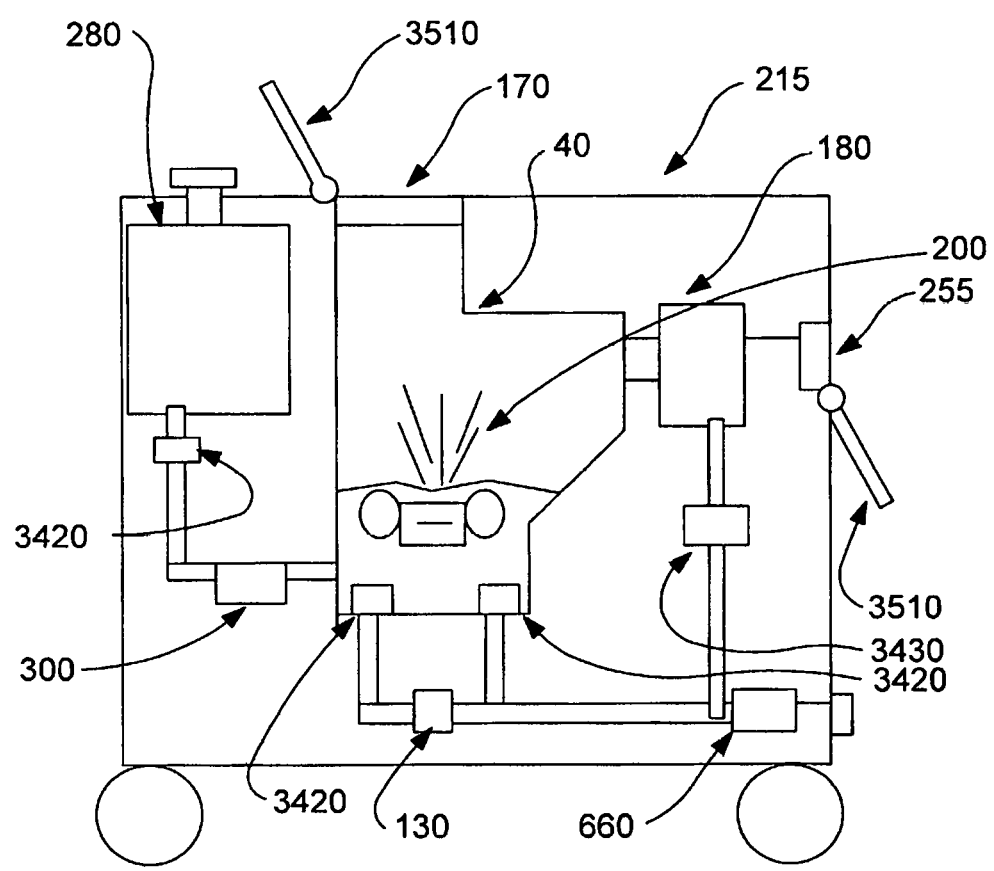
FIG. 76 is a schematic view of the generator of FIG. 70 including a number of filters.
Figure 77:
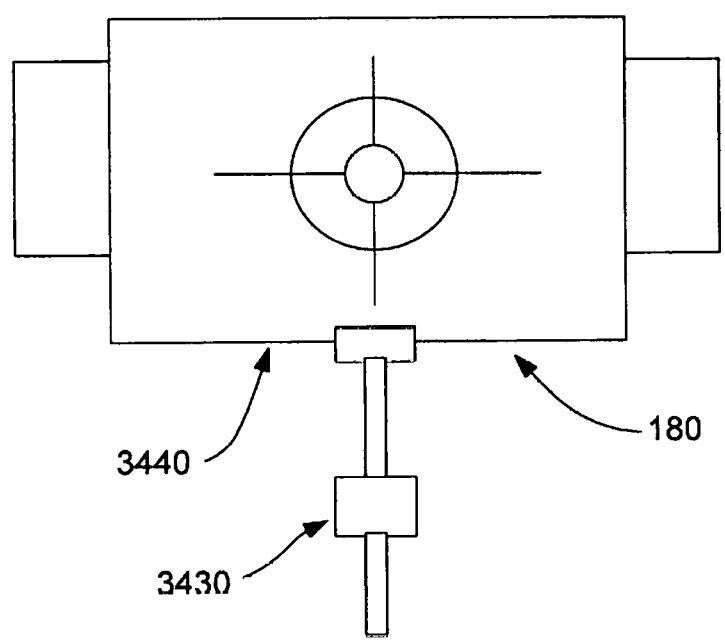
FIG. 77 is a schematic view of a blower housing for the generator of FIG. 70.

According to an embodiment shown in FIGS. 76-77, the apparatus (215) or any aerosol generator can, without limitation, be designed and constructed so that any enclosure(s), cover(s), or housing(s) (herein called "blower housing") (3440), that enclose or hold any fan, blower, or other source of pressurized air (180), including, without limitation, any attached conduit(s), pipe(s), or tubing, may be drained of any liquid that may build up in these areas during operation or cleaning of the apparatus (215). This liquid can, without limitation, be drained, in a manner known to those skilled in the art, to any tank(s), holding tank(s), drain port(s), or tank(s) and/or reservoir(s) (40) where the aerosol (200) is created. The apparatus (215) can be plumbed in various ways known to those skilled in the art, so that this liquid can be fully drained and removed from the apparatus (215) or any device. The liquid can also, without limitation, be drained back into the tank(s) or reservoir(s) (40) where the aerosol (200) is created.

Figure 78:
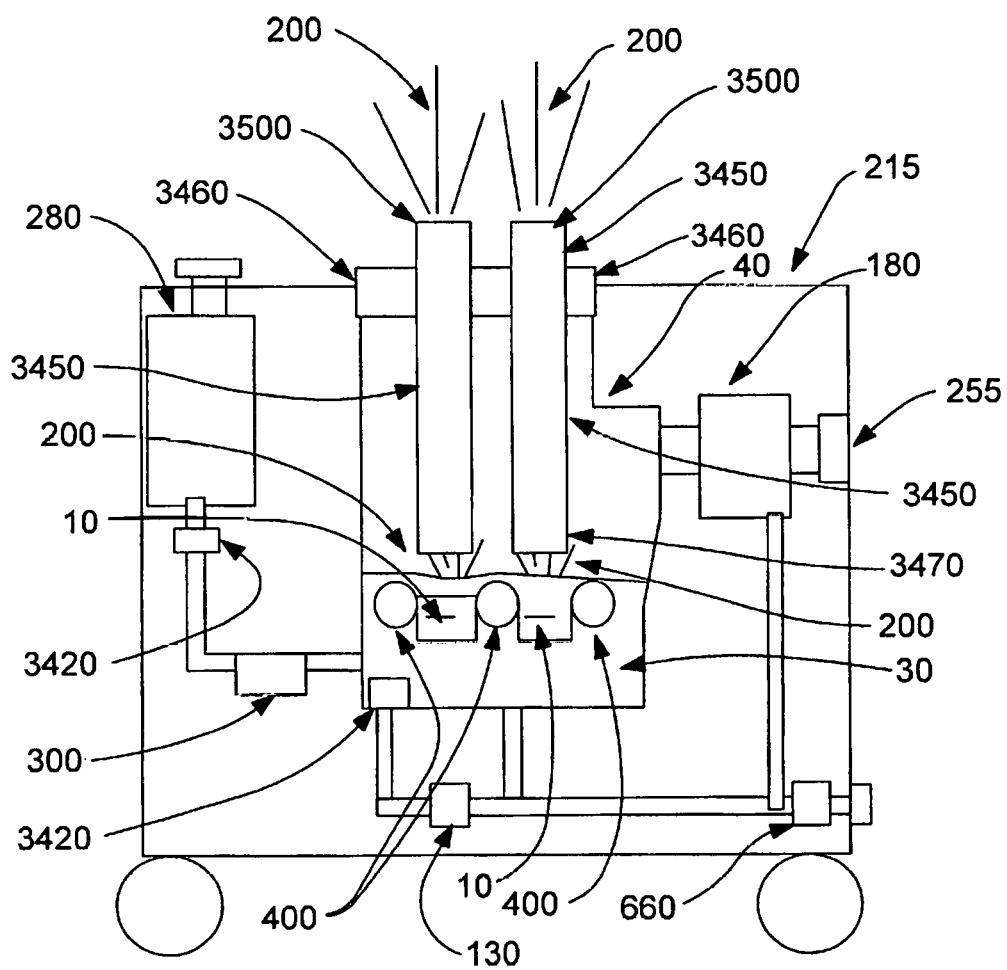
FIG. 78 is a schematic view of the generator of FIG. 70 including a first embodiment of a fog tube.
Figure 79:
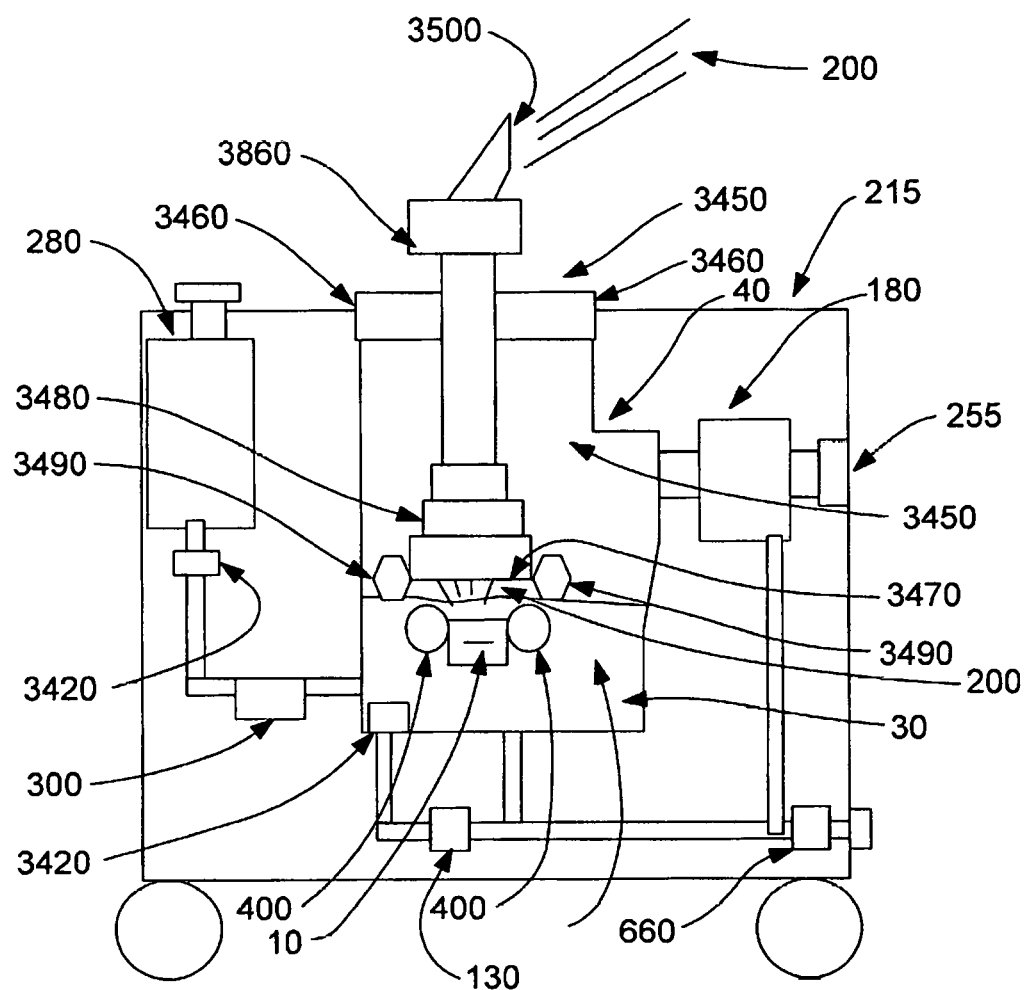
FIG. 79 is a schematic view of the generator of FIG. 70 including a second embodiment of a fog tube.

According to an embodiment shown in FIGS. 78-79, one or more of any pipe(s), tube(s), hose(s), or other enclosed or semi-enclosed means for transporting any amount of generated aerosol (herein collectively "fog tube(s)") (3450), are positioned within any tank or reservoir(s) (40) in which aerosol is created, and connect the inside of the reservoir(s) (40) with their exterior and/or the exterior of the apparatus (215). The reservoir(s) (40) are connected to one or more of any fan, blower, or other source of pressurized air (180) that can, without limitation, move any quantity of air at any rate into and through the reservoir(s). It is preferred, without limitation, that a blower (180) is used that has an output of at least 90 cubic feet/minute (cfm) or more. It is more preferred, without limitation, that a blower (180) is used that has an output of at least 150 cfm or more. It is even more preferred, without limitation, that a blower (180) is used that has an output of at least 250 cfm or more. It is very preferred, without limitation, that a blower (180) is used that has an output of at least 350 cfm or more. It is very preferred, without limitation, that a blower (180) is used that has an output of at least 450 cfm or more. In addition, the tanks or reservoir(s) (40) can be, without limitation, sealed, semi-sealed, or unsealed. It is preferred, without limitation, that the tanks or reservoir(s) (40) are sealed.

One or more of the fog tube(s) (3450) can, without limitation, connect or pass through one or more plate(s) (3460) or other structure, that can be attached to various parts of the apparatus (215) or any reservoir(s) (40). It is preferred, without limitation, that the plate(s) can be designed and constructed so that they and any attached fog tube(s) (3450) can be easily removed from the apparatus (215) or reservoir(s) (40). This can help with activities such as, but not limited to, installation, removal, and cleaning, of the plate(s) (3460) and the fog tube(s) (3450). It is preferred, without limitation, that the plate(s) (3460) and the fog tube(s) (3450) are constructed so that they form a sealed assembly when they are directly or indirectly attached to the apparatus (215) or any reservoir(s) (40).

The one or more open tube end(s) (3470) of each fog tube (3450) is positioned effectively and approximately above each transducer (10) or other source of the generated aerosol (200). However, the one or more open tube end(s) (3470) of each fog tube (3450) can also be located, without limitation, effectively and approximately to any sides, or any other angle or angled aspect, relative to each transducer (10), other source of the generated aerosol (200), or any geyser or eruption formed on the surface of any liquid (30) above any transducer (10). It is preferred, without limitation, that each open tube end(s) (3470) is horizontally angled above each geyser or eruption formed on the surface of any liquid (30) above any transducer (10), or other source of the generated aerosol (200).

In another part of this embodiment, one or more open tube end(s) (3470) can, without limitation, be positioned effectively and approximately above or near any group of one or more transducer(s) (10), or other source of the generated aerosol (200).

In another part of this embodiment, the distance that each open tube end (3470) is positioned relative to each geyser or eruption formed on the surface of any liquid (30) above any transducer (10), or other source of the generated aerosol (200), is an important part of this embodiment and the present invention. It is preferred, without limitation, that each open tube end (3470) is positioned approximately 0 to 6 inches or more from the surface of any liquid (30) above any transducer (10), or other source of the generated aerosol (200). It is more preferred, without limitation, that each open tube end (3470) is positioned approximately 0.5 to 1 inches or more from the surface of any liquid (30) above any transducer (10), or other source of the generated aerosol (200). It is even more preferred, without limitation, that each open tube end (3470) is positioned approximately 1 to 2 inches or more from the surface of any liquid (30) above any transducer (10), or other source of the generated aerosol (200). It is very preferred, without limitation, that each open tube end (3470) is positioned approximately 2 to 3 inches or more from the surface of any liquid (30) above any transducer (10), or other source of the generated aerosol (200). It is most preferred, without limitation, that each open tube end (3470) is positioned approximately 3 to 4 inches or more from the surface of any liquid (30) above any transducer (10), or other source of the generated aerosol (200). Investigation in the laboratory has found that the maximum effective distance is approximately four (4) inches from the surface of the liquid agent(s) (30) above each transducer (10), when using one or more transducer(s) (10), and after that distance the performance, effectiveness, and/or efficacious, quickly diminishes.

In another part of this embodiment, the length and/or position of the fog tube(s) (3450) can, without limitation, change inside any reservoir(s) (40) to accommodate any changing liquid (30) levels and to maintain the effective distance of any open tube end(s) (3470) to the surface of any liquid (30) above any transducer(s) (10), or other source of the generated aerosol (200). This can, without limitation, be achieved in various ways including, but not limited to, designing and constructing the fog tube(s) (3450) so they are flexible or made from one or more movable or collapsible segments (3480), and the open tube end(s) (3470) are maintained at a specific distance from the surface of any liquid (30) through the use and any direct or indirect connection of one or more of any float(s) (3490) that can float on the surface of the liquid agent(s) (30) in the reservoir(s) (40).

In another part of this embodiment, the total length of each fog tube(s) (3450) is also an important part of this embodiment and the present invention. The fog tube(s) (3450) can, without limitation, have any total length, but this length should at least be effective and efficacious. However, it is preferred, without limitation, that the fog tube(s) (3450) have a total length of approximately between six (6) and sixty (60) or more inches. It is more preferred, without limitation, that the fog tube(s) (3450) have a total length of approximately between fourteen (14) and twenty-four (24)

or more inches. It is even more preferred, without limitation, that the fog tube(s) (3450) have a total length of approximately thirty-six (36) or more inches. It is very preferred, without limitation, that the fog tube(s) (3450) have a total length of approximately forty-eight (48) or more inches.

In another part of this embodiment, the fog tube(s) (3450) can also, without limitation, have any diameter, but the diameter should at least be functional, effective, and/or efficacious. It is preferred, without limitation, that the fog tube(s) (3450) have a diameter of approximately three (3) inches. The fog tube(s) (3450) can, without limitation, be positioned in any pattern and any distance from each other. It is preferred, without limitation, that the fog tube(s) (3450) are located approximately 2.5 inches edge to edge of their outside diameter (OD) from each other in a linear row. The fog tube(s) (3450) can, without limitation, extend any length and in any direction or angle as they exit the apparatus (215) or any reservoir(s) (40). It is preferred, without limitation, that the fog tube(s) (3450) extend approximately three (3) inches vertically out of one or more reservoir(s) (40) which are connected directly or indirectly with the exterior skin of the apparatus (215).

The one or more external open tube end(s) (3500) of each fog tube (3450), located external to the apparatuses (215) or any reservoir(s) (40), can terminate in any direction or angle, which can be altered in certain embodiments as a result of the construction of the tube(s) (3450). It is preferred, without limitation, that the one or more external open tube end(s) (3500) are angled at least at a 45 degree angle, and they are pointed in a direction away from the apparatus (215). It is more preferred, that the one or more external open tube end(s) (3500) are pointing vertically. It is even more preferred, that the one or more external open tube end(s) (3500) are pointed towards the middle of the targeted or treated area (3310).

In another part of this embodiment, the fog tube(s) (3450) within the reservoir(s) (40) can, without limitation, have one or more of any bends or geometries before the open tube end(s) (3470) of any fog tube(s) (3450) are located, without limitation, effectively and approximately to any sides, above, or any other angle or angled aspect, relative to each transducer (10), other source of the generated aerosol (200), or any geyser or eruption formed on the surface of any liquid (30) above any transducer(s) (10).

In another part of this embodiment, one or more open tube end(s) (3470) can, without limitation, be configured to directly or indirectly attach to any external tubing, any dispersal implement(s), or any fixture(s) or attachment(s) used to interface with any enclosures, rooms, or other targeted areas or structures.

In another part of this embodiment, any filter (3860) can be functionally located or attached along the path of any fog tube(s) (3450), or to the one or more external open tube end(s) (3500) of each fog tube (3450). The one or more of any filter(s) (3860) can filter the output or any air/gas and/or aerosol (200) before it leaves the apparatus (215). The filter(s) can remove any quantity or any size of aerosol particles. It is preferred, without limitation, that the filter(s) (3860) remove any aerosol droplets above 5 micron or more in size. It is more preferred, without limitation, that the filter(s) (3860) remove any aerosol droplets above 3 micron or more in size. It is even more preferred, without limitation, that the filter(s) (3860) remove any aerosol droplets above 1 microns or more in size. It is very preferred, without limitation, that the filter(s) (3860) remove any aerosol droplets above 0.5 microns or more in size.

According to an embodiment shown in FIG. 76, the apparatus (215) or any aerosol generator can, without limitation, be designed and constructed so that any of its inlets or intake orifices (255), or any air outlets, exit orifices, or openings (170), can have one or means (herein called "door(s)" (3510)) to effectively cover and/or seal closed one or more of these openings. It is preferred, without limitation, that these door(s) (3510) can effectively seal to keep any liquid, gases, or vapor from escaping from the apparatus (215). It is also preferred, without limitation, that the door(s) (3510) is designed and constructed in such a way so that it can effectively be opened and closed in a manner known to those skilled in the art. It is even more preferred that the door(s) (3510) are attached either directly or indirectly to the apparatus (215) via any type of hinge known to those skilled in the art. The door(s) (3510) can be removable, or permanently attached to the apparatus (215). Any sensor known to those skilled in the art can also, without limitation, be utilized so that the apparatus cannot be operated if any of the door(s) (3510) are closed, or any of the inlets or intake orifices (255), or any air outlets, exit orifices, or openings (170), are covered in any way. The door(s) (3510) can, without limitation, be automatically opened or closed and controlled by any software, electronics, PLC (315), or HMI (320).

According to an embodiment, the apparatus (215) or any aerosol generator can, without limitation, be designed and constructed so that any software, hardware, electronics, PLC (315), or HMI (320) (herein collectively called "PLC" (315)), shall monitor, log, or record when, and/or the time between when, the apparatus (215) is fully drained of any liquid (30) in its various components. This can be monitored in various ways including, but not limited to, using any liquid level sensors known to those skilled in the art to determine when all of the various reservoir(s) (40) are empty of any liquid (30), or the PLC (315) monitoring the time that the one or more of any valve(s) such as, but not limited to, any feeder tank valve(s) (300), or any main drain valve(s) (660), are open to release the liquid (30) out the apparatus (215), and determining whether these various valves(s) are open long enough to fully drain the apparatus (215). The apparatus (215) can, without limitation, be programmed to take various actions after any liquid (30) in the apparatus (215) has expired, or reached a point of time either for the life of the liquid and/or for the time the liquid is in the apparatus (215) where the liquid (30) has expired, the liquid (30) has reached an unacceptable level of degradation, or the liquid (30) is at a point where it is near expiring, or the liquid (30) is otherwise at a point where it is at or near a point where it can lose its efficaciousness. These actions include, but are not limited to, the apparatus (215) ceasing to operate, the inability or refusal of the apparatus (215) to begin an operation cycle, the apparatus (215) notifying its operator, in various ways known to those skilled in the art, that the liquid (30) in the apparatus needs to be purged or drained in order for the apparatus (215) to resume operation either separately or in combination with one another. In addition, the apparatus (215) can be programmed so that the operator of the apparatus is only warned that the liquid (30) has or is near expiration, and the apparatus (215) does not take any further action than that. It is preferred, without limitation, that if the liquid (30) is at a point where it reaches a level of unacceptable degradation, the apparatus (215) shall not operate until all of the various valves (300) (660) in the apparatus (215) are open at least long enough to fully drain the apparatus if it was filled to capacity. The draining of the apparatus (215) can also, without limitation, take place in one or more interrupted or uninterrupted timed stages. This can, without limitation, be controlled with the use of any software or PLC (315), in a manner known by those skilled in the art.

Figure 80:
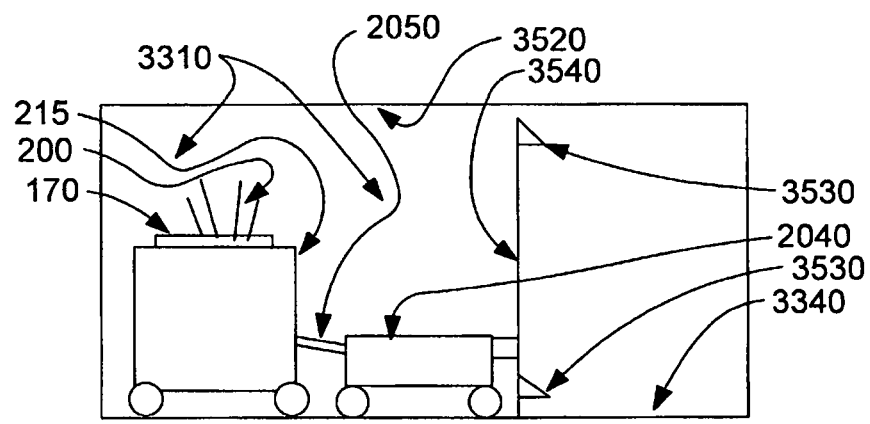
FIG. 80 is a schematic view of the generator of FIG. 70 including a first embodiment of an agent sensor.
Figure 81:
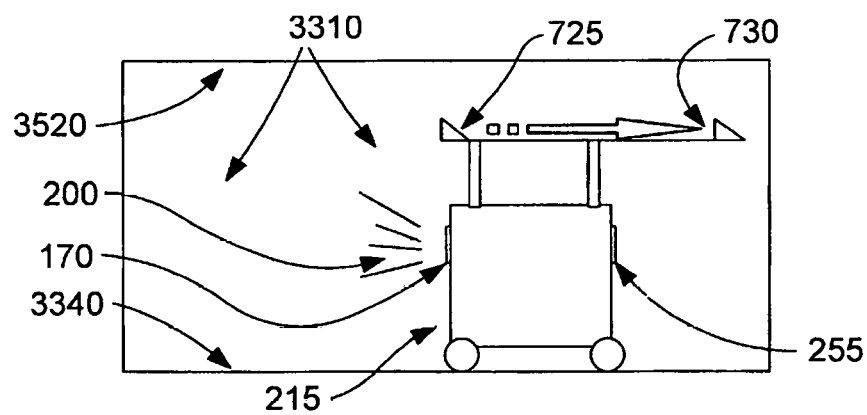
FIG. 81 is a schematic view of the generator of FIG. 70 including a second embodiment of an agent sensor.
Figure 82:
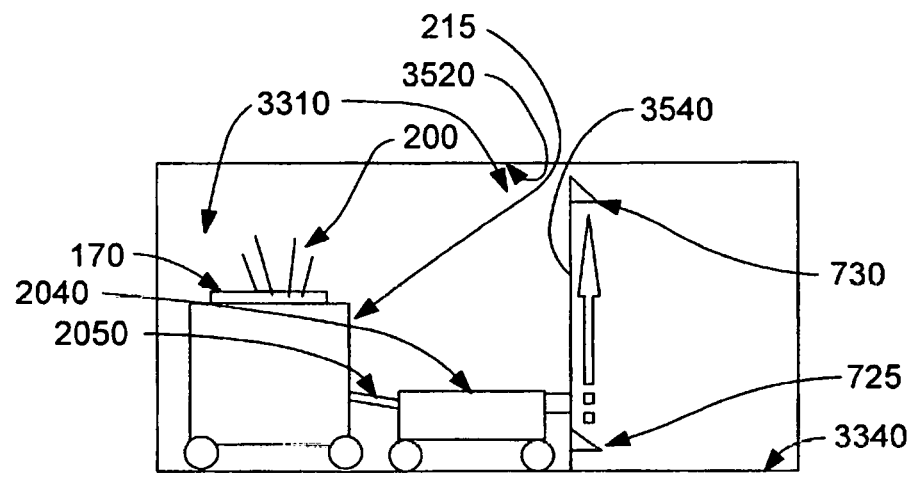
FIG. 82 is a schematic view of the generator of FIG. 70 including a third embodiment of an agent sensor.
Figure 83:
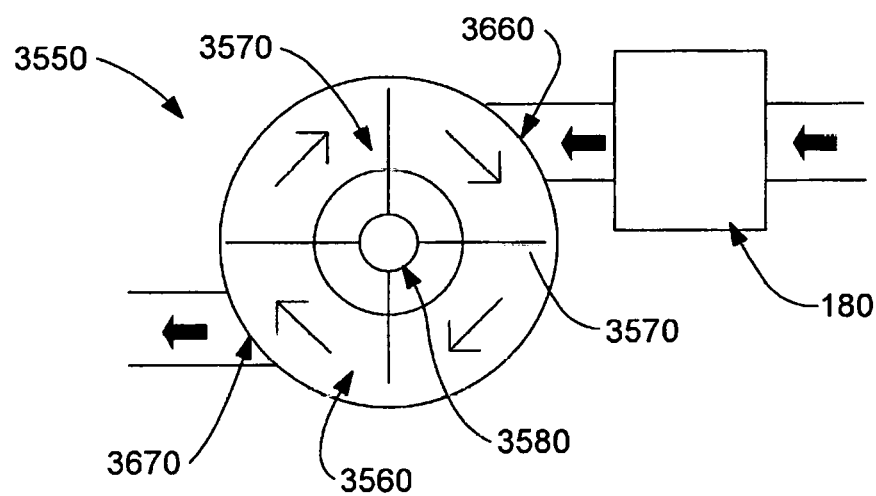
FIG. 83 is a schematic view of the generator of FIG. 70 including a first embodiment of an impaction device.
Figure 84:
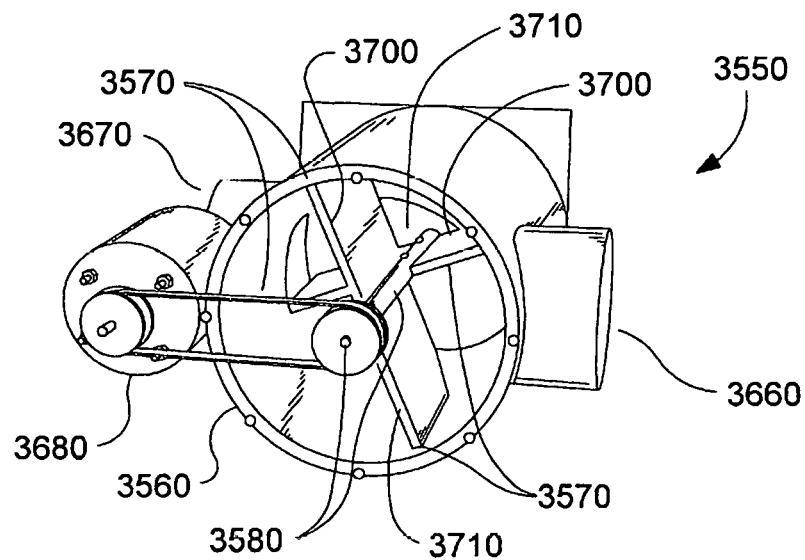
FIG. 84 is a schematic view of the generator of FIG. 70 including a second embodiment of an impaction device.
Figure 85:
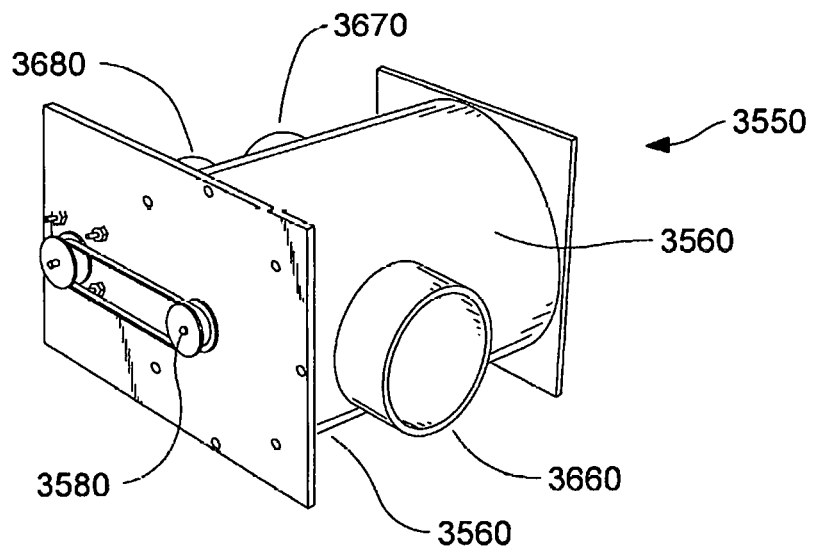
FIG. 85 is a rear view of the impaction device of FIG. 84.
Figure 86:
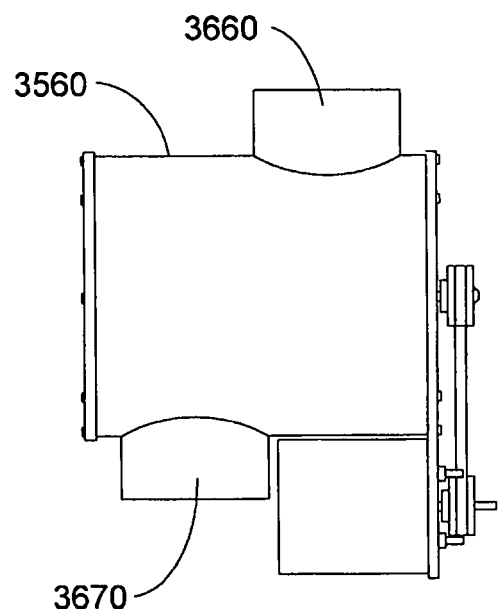
FIG. 86 is a top plan view of the impaction device of FIG. 84.
Figure 87:
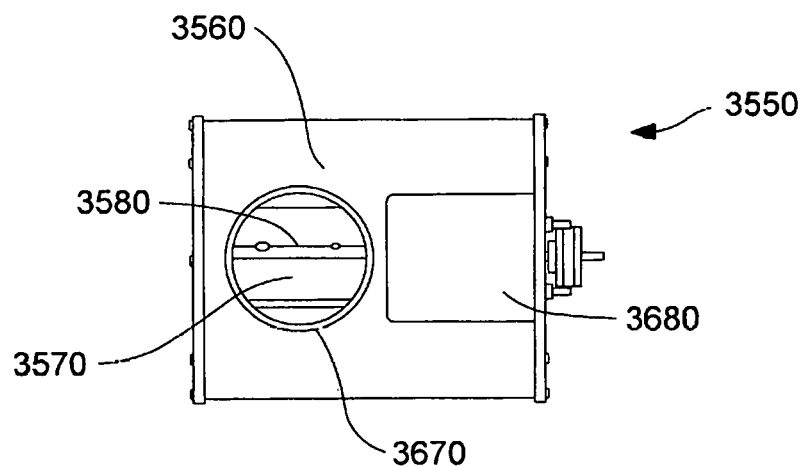
FIG. 87 is a side plan view of the impaction device of FIG. 84.
Figure 88:
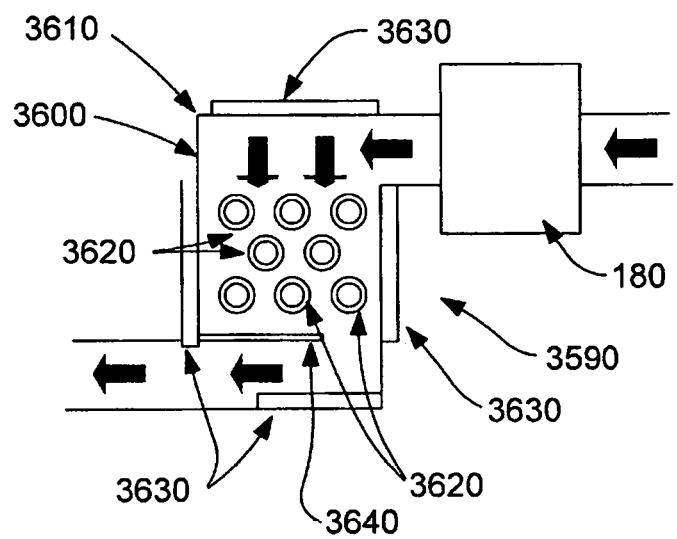
FIG. 88 is a schematic view of a first embodiment of a UV light device of the dehumidifier of FIG. 70.

According to an embodiment shown in FIGS. 80-82, the one or more of any sensor(s) (herein called "agent sensor(s)" (3530), that are utilized to determine, and/or communicate, if and/or when, an effective, efficacious, or sufficient amount of any vapor or aerosol (200) has been applied to the targeted or treated area (3310) and/or surfaces can, without limitation, be located in various or any locations or areas, and/or any combination of any number of location(s), including, but not limited to, near the ceiling(s), highest area(s), or near the highest surface(s) (herein called "ceiling" (3520), within one or more space(s) or area(s), or targeted areas (210), where the vapor or aerosol (200) is deployed. The agent sensor(s) (3530) can be or include any, without limitation, light source (725) and light sensor (730), humidity sensor, or moisture sensor, or combinations thereof.

The one or more agent sensor(s) (3530) can be located at any distance from the ceiling (3520). It is preferred, without limitation, that the agent sensor(s) (3530) are located approximately zero to thirty-six (0-36) inches from the ceiling (3520). It is even more preferred that the sensor(s) (3530) are located three to twelve (3-12) inches from the ceiling (3520). In addition, the one or more agent sensor(s) (3530) can also, without limitation, be located in various locations or areas including, but not limited to, near or approximate to any, floor(s), lowest area(s), or lowest surface(s) in the targeted or treated area (3310) (herein called "floor" (3340), within one or more space(s) or area(s) where the vapor or aerosol (200) is deployed. The one or more agent sensor(s) (3530) can also be located at any distance(s) from the floor (3340). It is preferred, without limitation, that the agent sensor(s) (3530) are located approximately zero to twenty-four (0-24) inches from the floor (3340). It is even more preferred that the sensors are located three to twelve (3-12) inches from the floor (3340).

One or more agent(s) sensor(s) (3530) can, without limitation, be located on or attached, at one or more of any height(s) and/or location(s), to one or more of any structure(s) such as, but not limited to any, stand(s), tripod(s), feet(s), pole(s), hanging apparatus(s), and/or support mechanism(s). Without being limited, the one or more agent(s) sensor(s) (3530) may also be positioned or located anywhere on any structure(s) or support mechanism(s) such as, but not limited to, one or more of any pole(s) (3540) of any length and design. Without being limited, the one or more pole(s) (3540) can also be constructed in a manner known in the art, so they can be easily adjustable for any effective length or height. It is preferred, without limitation, that the one or more sensor(s) (3530) are located at either end of one or more poles (3540) attached to one or more of any apparatus(s) (215), or one or more of any dehumidifier(s) (2040). It is more preferred, without limitation, that on each mounting structure or pole (3540) that is used, at least one light source (725) is located effectively at one end of the pole (3540) near the floor (3340), and at least one light sensor (730) is located in-line and vertically above the light source (725) effectively near the ceiling (3520), on the other end of the pole (3540). The location of the light source (725) and the light sensor (730), may also be, without limitation, reversed in this configuration. One or more agent sensor(s) (3530) can also, without limitation, directly or indirectly communicate with one or more of any digital, electronic, or analog, controller(s) such as, but not limited to any, PLC(s), located at one or more of any location(s), and/or with one or more aerosol generating apparatus(s) (215) and their HMI(s) (320) and/or PLC(s) (315), and/or with one or more of any other agent sensor(s) (3530), and/or with one or more of any remote devices and/or remote control device(s) that directly and/or indirectly communicates with and/or controls one or more of any, (a) aerosol generating apparatus(s) (215), (b) one or more agent sensor(s) (3530), (c) dehumidification device(s), (d) vent or air vent covering device(s), and/or (e) air filtration devices, in various ways such as, but not limited to any, radio, radio waves, sound, wire, cable, and/or fiber optics.

According to an embodiment, it is intended, without limitation, that the one or more of any dehumidifier(s) (2040) in the present invention is any means that can dehumidify any air, gas, or atmosphere, in the targeted area(s) (3310) using various technologies and parts such as, but not limited to, any blower (180), chiller surface(s) or chill coil(s), cooling tub(s), cooling surface(s), compressor, refrigerant, or other parts or combination of parts, known to those skilled in the art. Any humidity level can be set as the target point for the dehumidification process to meet. However, it is preferred, without limitation, that the humidity level is reduced to 70% or lower after any treatment process(s) or operational cycle(s) have are complete. It is more preferred, without limitation, that the humidity level is reduced to 50% or lower following any treatment process(s) or operational cycle(s) are complete. It is even more preferred, without limitation, that the humidity level is reduced to 40% or lower following any treatment process(s) or operational cycle(s) are complete. It is most preferred, without limitation, that the humidity level is reduced to 30% or lower following any treatment process(s) or operational cycle(s) are complete.

According to an embodiment, the one or more of any dehumidifier(s) (2040) in the present invention can be any means that can dehumidify any air, gas, or atmosphere, in the targeted area(s) (3310) using any technologies and parts known to those skilled in the art, and can transfer the dehumidified air flow to the generator (215), such as by a conduit (2050).

According to an embodiment shown in FIGS. 83-87, an enhanced impaction device (3550) improves the present art and it can, without limitation, be utilized to remove any quantity of aerosol (200) from any air or gas that is flowed through it. This impaction device (3550) consists of one or more of any housing or area, or "blade housing(s)" (3560). The blade housing(s) (3560) can, without limitation, be any size, shape, length, width, geometry, or diameter. It is preferred, without limitation, that the blade housings are at least large enough to effectively accommodate the impacting surfaces or paddles (3570). The various blade housing(s) can be, without limitation, interconnected, and they can be positioned in series or in parallel.

It is preferred, without limitation, that the blade housing(s) (3560) includes at least one inlet(s) (3660) through which air/gas and aerosol (200) enters the blade housing(s) (3560), and at least one outlet (3670) through which air/gas and aerosol (200) exits the blade housing(s) (3560). The inlet(s) (3660) and outlet(s) (3670) can, without limitation, be any size, shape, length, width, geometry, or diameter. It is preferred, without limitation, that the inlet(s) (3660) and outlet(s) (3670) are constructed from tubing that is at least four inches in diameter. The inlet(s) (3660) and outlet(s) (3670) can, without limitation, be located on or connect anywhere to, the blade housing(s) (3560). It is also preferred, without limitation, that the inlet(s) (3660) and outlet(s) (3670) are located directly in front of at least one set, cluster, or group of paddle(s) (3570), so the centerline of the inlet strikes the centerline of the shaft (3580) to which the paddle(s) (3570) are connected.

Inside the blade housing(s) (3560), one or more of any structure(s) that can act as one or more impacting surface(s) (3570) is connected to one or more of any rotating shaft or other means or source of rotation (herein called "shaft" (3580). The impacting surface(s) (3570) can be, without limitation, one or more of any paddle, blade, or cage, that can be of any design, configuration, or structure (herein called "paddles") (3570). The impacting surfaces(s) can, without limitation, be any size, and be positioned at any angle. It is preferred, without limitation, that the paddles(s) (3570) are formed of four (4) solid shapes that are approximately four (4) inches wide, and four (4) inches long, that are attached to a common shaft (3580) at ninety (90) degrees to one another. It is also preferred, without limitation, that the blade housing(s) are circular in shape.

The paddles (3570) can also be, without limitation, located in one or more independent moving group(s) (3700) including one or more paddles (3570). These independent moving group(s) (3700) of one or more paddles (3570) can be, without limitation, located in the same blade housing (3560) or any interconnected blade housing(s) (3560). Each independent moving group(s) (3700) of one or more paddles (3570) can also be, without limitation, directly or indirectly connected to their own motor (3680) and shaft (3580), or they can directly or indirectly share the same motor (3680) or shaft (3580). It is preferred, without limitation, that the one or more independent moving group(s) (3700) are connected to the same motor (3680) and the same shaft (3580). Referring to FIGS. 83-87, it is preferred, without limitation, that the air or gas and aerosol (200) mixture is moved through the inlet(s) (3660) and into the blade housing(s) (3560) where two different independent moving groups (3700) of one or more paddle(s) (3570) are located.

The paddles(s) (3570) can, without limitation, be rotated by any motor (3680), at any revolutions per minute (RPM), however it is preferred that they are at least rotated at a speed where they are effective at removing the desired or needed amount of aerosol from the air or gas that is moved through the blade housing(s) (3560). It is preferred, without limitation, that the blade housing(s) (3560) and shaft (3580) are at least effectively sealed, but it is more preferred that they are hermetically sealed in a manner known to those skilled in the art. The blade housing(s) (3560) can be, without limitation, designed to effectively interface with various means known in the art to transport air or gas, such as, but not limited to, any pipe, hose, or ducts. The blade housing(s) (3560) can be located anywhere before or after any blower, fan, or other source of pressurized air (180). The air or gas in which the aerosol (200) is carried, can be moved into the blade housing(s) (3560) at any quantity or speed. It is preferred, without limitation, that the air or gas is moved between 50 to 900 cfm. The air or gas is moved into the blade housing(s) (3560) by any blower, fan, or other source of pressurized air (180), that is either directly or indirectly connected by any effective means known in the art, such as, but not limited to, any tube, duct, pipe, conduit, or tunnel.

According to an embodiment, the one or more paddles (3570) can all, without limitation, be moved, rotated, or spun, in the same direction that is counter to any inbound flow of air or gas that is brought into the device and, into or through the blade housing(s) (3560).

According to another embodiment, the one or more paddles (3570) can all, without limitation, be moved, rotated, or spun, in the same direction as any inbound flow of air or gas that is brought into the device and, into or through the blade housing(s) (3560).

According to another embodiment, a plurality of paddles (3570) are, without limitation, moved, rotated, or spun, in any direction or pattern that is counter or opposite to the paddle (3570) that it is next to it or in close proximity to another paddle (3570).

According to another embodiment, the paddles (3570) can be, without limitation, located in one or more independent moving group(s) (3700) including one or more paddles (3570), that can be moved, rotated, or spun, in any direction or pattern that is counter or opposite to another independent moving group (3700) including one or more paddles (3570).

According another embodiment, the paddles (3570) can be, without limitation, located in one or more independent moving group(s) (3700) including one or more paddles (3570), that can be moved, rotated, or spun, in the same direction as any inbound flow of air or gas that is brought into the device and, into or through the blade housing(s) (3560).

According to another embodiment, the paddles (3570) can be, without limitation, located in one or more independent moving group(s) (3700) including one or more paddles (3570), that can be moved, rotated, or spun, in any direction or pattern that is opposite to any inbound flow of air or gas that is brought into the device and, into or through the blade housing(s) (3560).

According to a preferred embodiment, the paddles (3570) can be, without limitation, located in one or more moving group(s) (3710) including one or more paddles (3570), that can be moved, rotated, or spun, in any direction or pattern that is opposite to any inbound flow of air or gas that is brought into the device and, into or through the blade housing(s) (3560). It is preferred, without limitation, that two moving groups (3710) are utilized and attached to a shared shaft (3580), and the one or more paddles (3570) within each moving group are arranged or located so they are offset from the other moving group (3710).

According to an embodiment, any dehumidifier (2040), the apparatus (215) or any aerosol generator, or other device can, without limitation, be designed and constructed so that any blade housing(s) (3560), including, without limitation, any attached conduit(s), pipe(s), or tubing, may be drained of any liquid that may build up in these areas during operation or cleaning of the blade housing(s) (3560). This liquid can, without limitation, be drained, in a manner known to those skilled in the art, to any tanks, holding tank(s), or drain port(s), and the liquid can be fully drained and removed from any apparatus that it is installed into.

In still another part of this embodiment, this enhanced impaction device (3550) can be utilized independently as its own device, or utilized with other devices such as, but not limited to, the apparatus (215) in the present invention or any other aerosol generator(s). It can also, without limitation, be used with any dehumidifier (2040) design. The enhanced impaction device (3550) can, without limitation, be positioned anywhere in the air/gas stream in the design of any of these devices, and operated at any time by any means in order to create a means to impact aerosol particles and move aerosol particles or any coallessed particles on the impactor against the walls of the blade housing (3560). The device (3550) can also be positioned within a tortuous pathway through the device (3550) that creates a tortuous path for the air and aerosol mixture through the dehumidifier (20-40) in order to create as much dwell time within the dehumidification device (20-40) and the blade housing (3560) to increase the chance of removing aerosol from the air. It is preferred, without limitation, that the enhanced impaction device (3550) is controlled by any software, PLC (315) or HMI (320).

According to an embodiment shown in FIGS. 88-91, an enhanced ultraviolet (UV) light device (3590) can, without limitation, be designed and constructed so one or more of any geometries, sides, walls, or ceilings (herein called "enclosure walls" (3600), of any enclosure (3610) that houses one more of any UV light source(s) (3620), is lined or constructed from one or more of any mirrored surfaces or mirror(s) (3630). It is preferred, without limitation, that all of the interior enclosure walls (3640) are mirrored or constructed from mirrors. It is also preferred, without limitation, that the mirror(s) are highly efficient in their reflectivity, and they are constructed in a manner known to those skilled in the art. The basic construction of an enclosure, and the construction and use of the various UV light source(s) (3620), is known by those skilled in the art. The mirror(s) (3630) and enclosure(s) (3610) may be constructed from any chemically resistant material. Preferably, the mirror(s) (3630) and the enclosure(s) (3610) have a high chemical resistance to the liquid (30) used. It is even more preferred, that the mirror(s) (3630) are constructed from any acid and/or alkaline resistant glass such as, for example, quartz, or Type I (borosilicate glass or Pyrex) or Type II glass as defined by the United States Pharmacopoeia. It is very preferred, that the mirror(s) (3630) are constructed from materials that absorb as little of the UV light as possible.

According to an embodiment, the enclosure(s) (3610) and any source of pressurized air or gas such as, but not limited to, one or more of any fan(s) or blower(s) (180), can be designed and constructed, in a manner known to those skilled in the art, to provide and accommodate any amount of air or gas that is flowed through the enclosure at any speed and volume and with any amount of air or gas flow characteristics or turbulence. However, after testing in a laboratory, it was found that odor removal in an area treated with peroxyacetic acid (PAA), was able to be accomplished in a shorter amount of time when greater amounts of air or gas from the treated area, including, without limitation, varying amounts of aerosol, were flowed through the enclosure that housed the sources of UV light(s) (3620). It is preferred, without limitation, that air or gas from the treated area is moved through the enclosure(s) (3610) at a measurement of at least 50 cfm or more. It is more preferred, without limitation, that air or gas from the treated area is moved through the enclosure(s) (3610) at a measurement of at least 800 cfm or more. It is even more preferred, without limitation, that air or gas from the treated area is moved through the enclosure(s) (3610) at a measurement of at least 1000 cfm or more. It is very preferred, without limitation, that air or gas from the treated area is moved through the enclosure(s) (3610) at a measurement of at least 1500 cfm or more. It is most preferred, without limitation, that air or gas from the treated area is moved through the enclosure(s) (3610) at a measurement of at least 2000 cfm or more. The air or gas can, without limitation, contain any quantity of any vapor or aerosol (200) that contains any agent(s) (30). In addition, one or more of any UV light source(s) (3620) can be used and they can be packed into a space in any number density or any light output density for a given area. However, it is preferred, without limitation, that at least three (3) UV light source(s) (3620) are used. The UV light source(s) (3620) can be any UV light source known to those skilled in the art.

Figure 89:
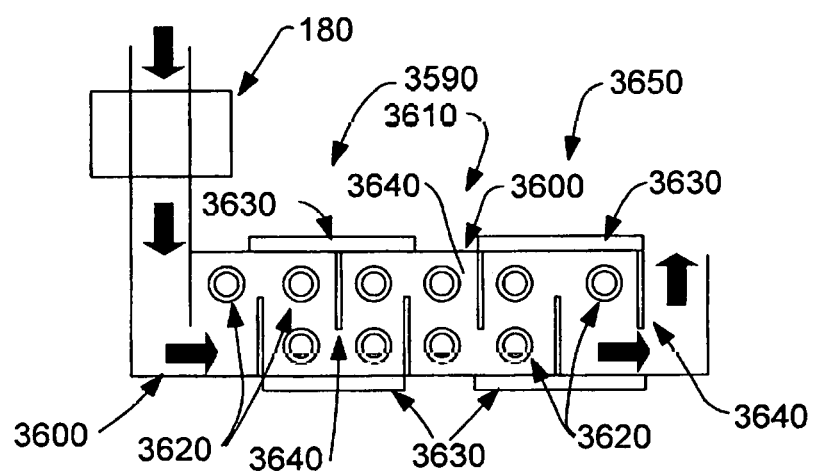
FIG. 89 is a schematic view of a second embodiment of a UV light device of the dehumidifier of FIG. 70.

According to an embodiment shown in FIG. 89, the enhanced ultraviolet (UV) light device (3620) can, without limitation, be designed and constructed so that any air or gas that is flowed into the enclosure(s) (3610), including any air or gas from any area treated with any agent(s) from any vapor or aerosol (200) generator, is moved through one or more complex maze(s), convoluted paths, complex channel(s), or tortuous path(s) (herein called "tortuous path(s)" (3650), which are mirrored on one or more walls (3600), interior walls (3640), or structures. It is preferred, without limitation, that all of the walls (3600) (3640) for this construct are made from one or more mirror(s) or mirrored surface(s). Referring to FIG. 89, this embodiment of the invention includes locating one or more UV light source(s) (3620) in various locations as well as patterns inside or in various locations within the tortuous path(s) (3650). The enclosure(s) (3610) or tortuous path(s) (3650) can be designed for any amount of air or gas at any speed, and can be any size, shape, diameter, or construct. The mirrored tortuous path(s) (3650) can, without limitation, increase the UV light exposure to the air or gas, and any aerosol (200) if it is still in the targeted area when its air or gas is processed.

Figure 90:
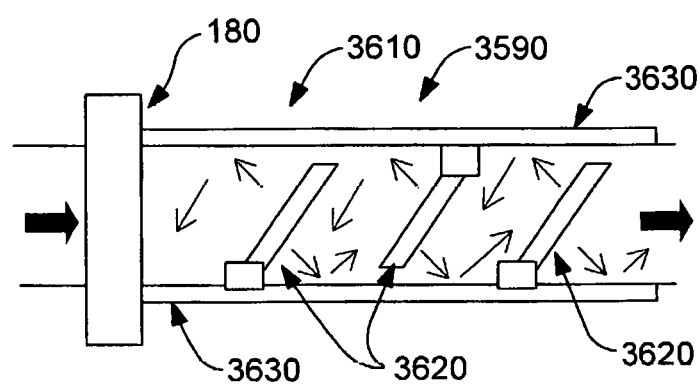
FIG. 90 is a schematic view of a third embodiment of a UV light device of the dehumidifier of FIG. 70.

According to an embodiment shown in FIG. 90, an enhanced ultraviolet (UV) light device (3590) can, without limitation, be designed and constructed so that the UV light source(s) (3620) are mounted, positioned, or located, at any angle or orientation, except 90 and 180 degrees, as well as orientated in any vertical or parallel orientation, all being respective to the direction of the air or gas flow moving through the enclosure(s) (3610). It is preferred, without limitation, that the one or more UV light source(s) (3620) are mounted, positioned, or located within the enclosure(s) (3610), at a forty-five (45) degree angle respective to the direction of the air or gas flow moving either towards or away from the UV light source(s) (3620). It is also preferred, without limitation, that this is combined with lining or constructing any enclosure walls (3600), with one or more of any mirrored surfaces or mirror(s) (3630) from which the emitted UV light can be redirected or reflected.

Figure 91:
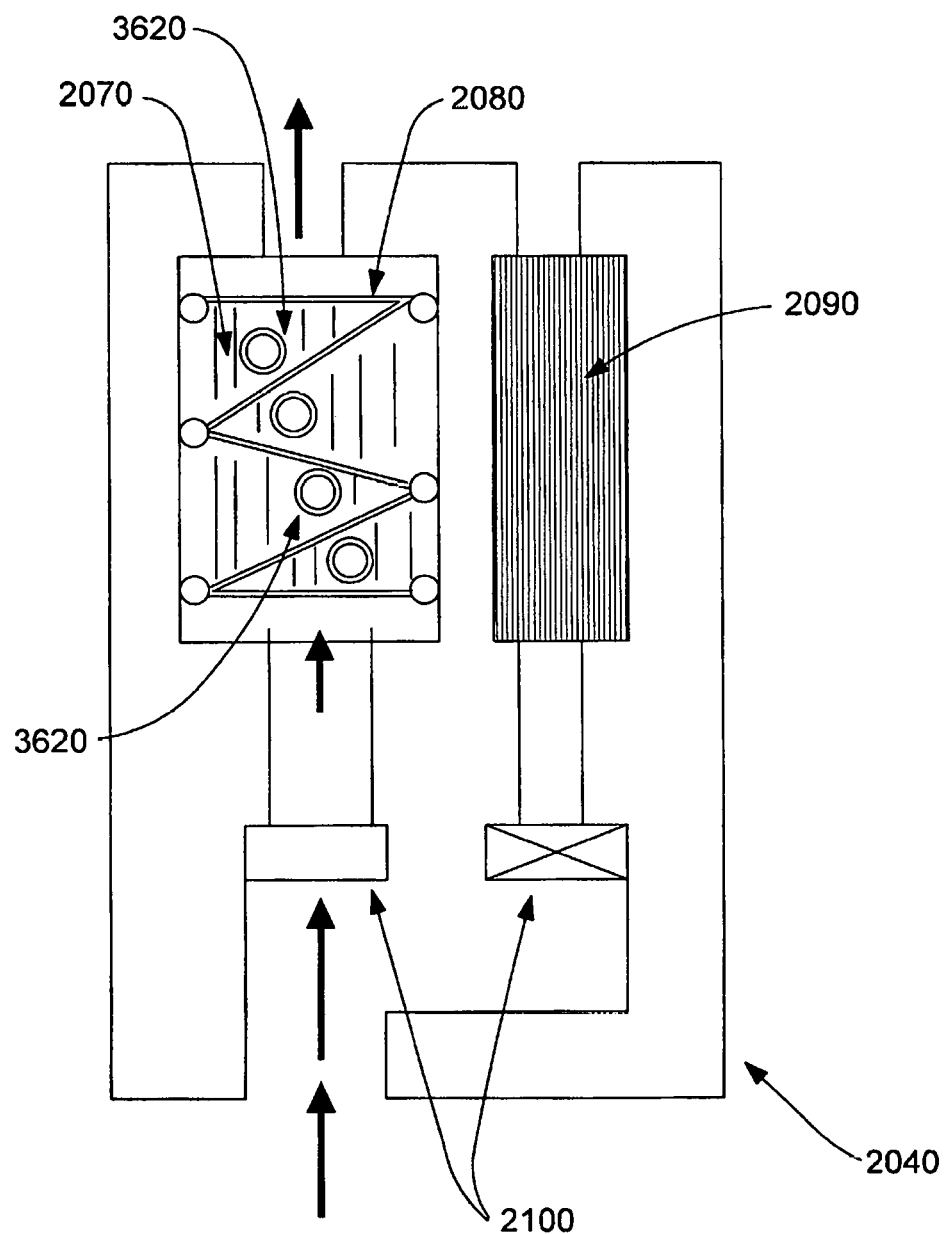
FIG. 91 is a schematic view of a fourth embodiment of a UV light device of the dehumidifier of FIG. 70.
Figure 92:
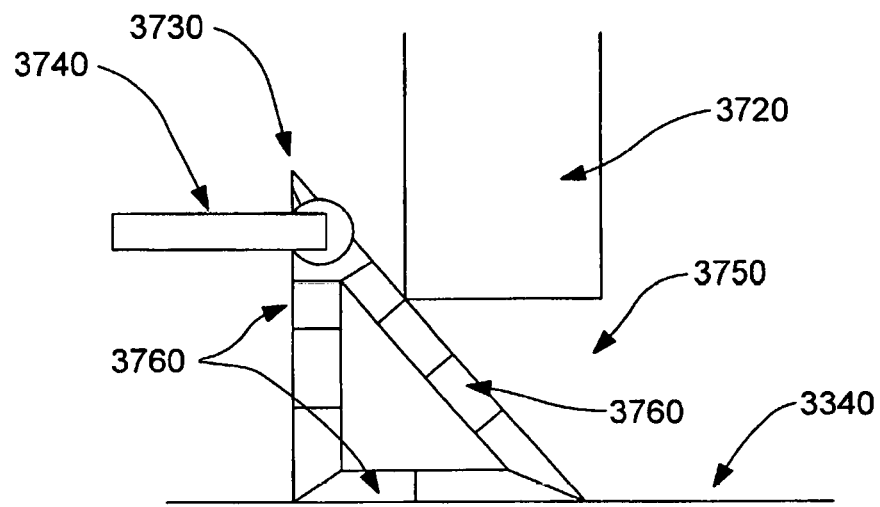
FIG. 92 is a schematic view of a first embodiment of a door seal utilized with the generator and dehumidifier of FIG. 70.
Figure 93:
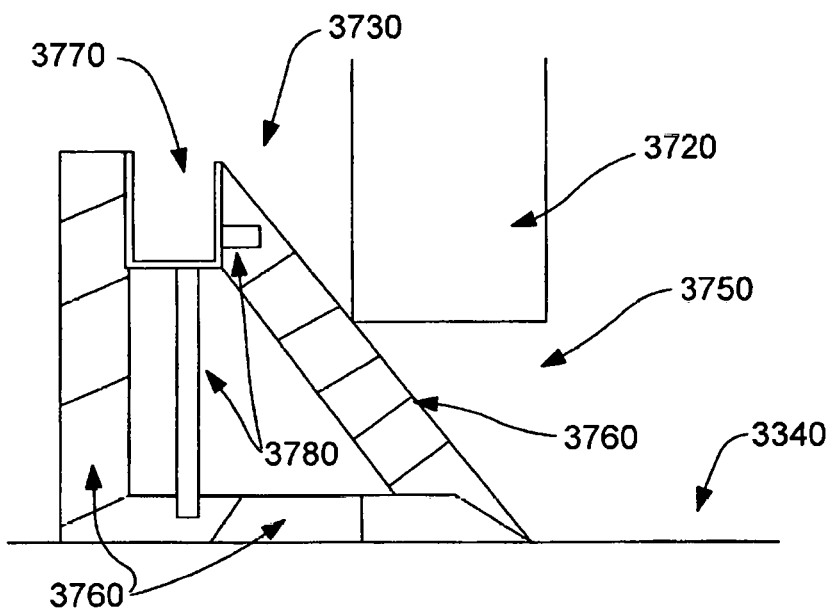
FIG. 93 is a schematic view of a second embodiment of a door seal utilized with the generator and dehumidifier of FIG. 70.
Figure 94:
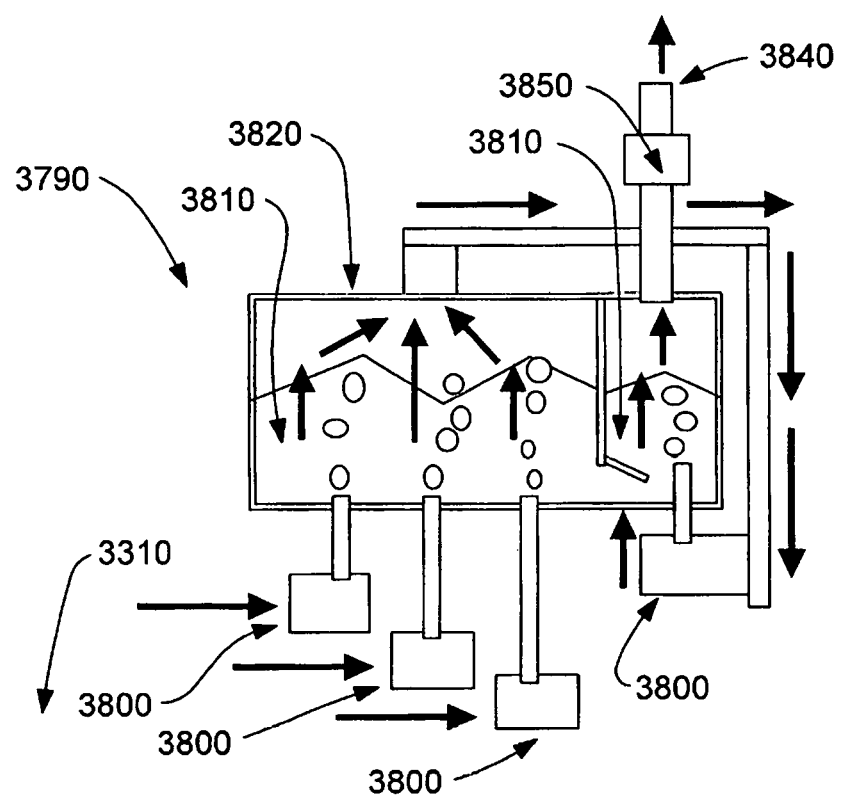
FIG. 94 is a schematic view of a deodorizing chamber utilized with the generator and dehumidifier of FIG. 70.

According to an embodiment shown in FIG. 91, according to an embodiment, any ultraviolet (UV) light device such as but not limited to the present invention and those described in U.S. Patent and U.S. application Ser. Nos. 09/855,546 and 10/671,837 to Morneault et al., and U.S. Pat. No. 7,045,096 B2 to D'Ottone, and any of their references, can, without limitation, be coupled with any dehumidification technology known to those skilled in the art. It is preferred, without limitation, that the dehumidification is achieved through the use of a dehumidifier (2040) that uses one or more cooling surface(s) or chill coil(s) (herein collectively called "chill coils" (2080)) as known by those skilled in the art. The cooling surface(s) or chill coil(s) (2080) can be, without limitation, one or more of any cooled surface(s) or cooling tube(s) that can remove humidity from the surrounding air or atmosphere, or any air or atmosphere that is moved past the chill coil(s) (2080).

Referring to FIG. 91, the cooling surfaces(s) or chill coil(s) (2080) can be located effectively near, or positioned in the same area, housing, or even enclosure(s) (3610) as the UV light source(s) (3620). It is preferred without limitation, that the UV light source(s) (3620) are positioned or located in close proximity to the chill coil(s) (2080). The air or gas can, without limitation, contain any quantity or concentration of any vapor or aerosol (200) that contains any agent(s) from the treated or targeted area(s) (3310). The air or gas stream can be dehumidified at any time, and for any duration, during any point in a treatment cycle. The chill coil(s) (2080) can, without limitation, maintain the UV light source(s) (3620), or any area in which they reside, at any temperature. It is preferred, without limitation, that the UV light source(s) (3620) are maintained during their operation, by the chill coil(s) (2080), at a temperature where they will not become frosted with moisture or ice, and this can be accomplished with various sensors and software controls known to those skilled in the art. The chill coil(s) (2080) can be operated at different times or at the same time as the UV light source(s) (3620). In addition, the chill coil(s) (2080) or any other means for dehumidification or aerosol removal, can, without limitation, operate at any time, and for any duration, during any point in a treatment cycle that is performed before the UV light source(s) (3620) are utilized. It is preferred, without limitation, that the temperature of the air or gas near the UV light source(s) (3620) is maintained between 0-70 degree Centigrade. It is even more preferred, without limitation, that the temperature of the air or gas near the UV light source(s) (3620) is maintained between 0-15 degree Centigrade. The cooling surface(s) or chill coil(s) (2080) can be maintained at any temperature, but at least at a temperature that is effective. The effective operation of any cooling surface(s) or chill coil(s) (2080) in any dehumidifier (2040) is known to those skilled in the art.

According to an embodiment, the apparatus (215) or any aerosol generator can, without limitation, be designed and constructed so that it incorporates into its design or operation, one or more UV light source(s) (3620), as well as one or more dehumidifier(s) (2040) that uses one or more chill coil(s) (2080).

According to an embodiment, any ultraviolet (UV) light device such as but not limited to the present invention and those described in U.S. Patent and U.S. application Ser. Nos. 09/855,546 and 10/671,837 to Morneault et al., and U.S. Pat. No. 7,045,096 B2 to D'Ottone, and any of their references, can, without limitation, be utilized with the apparatus (215) or any vapor or aerosol generator, that is used to treat an area with one or more aqueous agent(s) consisting of any quantity of hydrogen peroxide, or peroxyacetic acid (PAA). It is even more preferred, without limitation, that these UV light devices can be used with the apparatus (215) or any vapor or aerosol (200) generator, that is used to treat an area (3310) with one or more aqueous agent(s) including any aqueous agent(s) that are acidic. It is more preferred, without limitation, that these UV light devices can be used with the apparatus (215) or any vapor or aerosol (200) generator, that is used to treat any area (3310) with one or more aqueous agent(s) including any aqueous agent(s).

According to an embodiment, any (UV) light source device or dehumidifier (2040) can, without limitation, be designed and constructed so that any part of their design, including, but not limited to, any enclosure (3610) for any (UV) light source(s) (3620), fan or blower housing(s) (3440), or any attached conduit(s), pipe(s), or tubing, or any other components, may be drained of any liquid that may build up in these areas during operation or cleaning. This liquid can, without limitation, be drained, in a manner known to those skilled in the art, to any holding tank(s), drain port(s), or tank(s). These devices can be plumbed in various ways known to those skilled in the art, so that this liquid can be fully drained and removed from them.

According to an embodiment, the apparatus (215) or other aerosol generator can, without limitation, be designed and constructed so that any software, hardware, electronics, PLC (315), or HMI (320) (herein collectively called "PLC" (315)), can adjust the time allocated, chosen, or needed, for any step in the treatment process(s) for any targeted area(s) and/or surface(s), as well as any time between each step. This can also, without limitation, be accomplished automatically, or with any algorithm designed into any software controlling the apparatus (215) or treatment process.

Any time allocated for any step or between any step, or any timing sequence, for any part of any treatment process(s) of any targeted area(s) and/or surface(s) operation, that involves any apparatus (215) or any other associated equipment, can be adjusted, changed, or accommodated, to account for any variables or combination of variables that may impact the performance or efficacy of any treatment or process step such as, but not limited to, any volume of any treated space(s), temperature of any air or gas in the treated area(s), temperature of any surface(s) in the treated area(s) (3310), any relative humidity in the treated area(s), any dew point(s) in the treated area(s) (3310), any atmospheric pressure or any pressures in the treated area(s) (3310). These variables can be measured by, and reported to any PLC (315), via any means known to those skilled in the art.

The one or more of any time period(s) or timing sequence(s) involved with a treatment process(s) can also involve or pertain to any ancillary equipment associated with the treatment of any targeted space(s) or area(s), or the operation of the apparatus (215) such as, but not limited to, any dehumidifier (2040), or any odor removing apparatus that utilizes ultraviolet light (3620).

The PLC (315) can, without limitation, monitor, log, or report, any change to any part of any treatment process(s) including, but not limited to, any process step or between any process step, or any timing sequence(s). This information can be reported to anywhere in any format in any manner know to those skilled in the art. This information can accompany any other data relating to any successful or unsuccessful treatment process(s) or operation cycle(s) attempted.

According to an embodiment, the apparatus (215) or other aerosol generator can, without limitation, be designed and constructed so that it can conduct, operate, or execute various operational steps or sequences. One or more of the following steps can also, without limitation, be bypassed either temporarily or permanently per the desires or needs of any operator or control input. Each step can vary for any length of time for any reason known to those skilled in the art. In addition the time between each step can also vary for any length of time for any reason.

The first step is aerosol generation and deployment of the aerosol (200) into the one or more targeted area(s) (3310). This step includes, without limitation, the additional step of heating the liquid (30) that will be aerosolized, to any preset temperature. The second step is giving the deployed aerosol (200) and any vapor component(s) adequate time to effectively and efficaciously move within the targeted area(s) (3310) and contact any surfaces in the targeted area(s) (3310), all in a manner known to those skilled in the art (also known as dwell time).

The third step is dehumidification. Dehumidification can be achieved in various ways known to those skilled in the art, and with any dehumidifier (2040). Any one or more humidity level(s) can be set as the target point for the dehumidification process to meet or achieve. Dehumidification can also, without limitation, consist of operating any rotating paddles (3570) as mentioned in the present invention, and this can, without limitation, be operated with our without any other dehumidification device(s) or methodologies. The fourth step is deodorization. This is achieved by using one or more UV light source(s) (3620) as described in the present invention. The fifth step is filtering the air with one or more of any filter(s) (2070) to remove any amount of any unwanted gases or vapor. Furthermore, the aerosol generating apparatus (215) may stop all other steps and enter into or start the dehumidification step at any time for any reason. The dehumidification step may be started for reasons including, but not limited to, the apparatus (215) or operator or other input, has detected a fault with any part or operation of the apparatus (215) or any other ancillary piece of equipment, an emergency stop has been actuated, or the operator has chosen to abort or stop the function of the apparatus (215). Finally, the operator of the apparatus (215) can, without limitation, manually operate the dehumidification step or deodorization step either any time before the aerosol (200) generating apparatus (215) has started to generate and deploy any aerosol (200), or any time after the treatment process(s) or entire operational cycle is complete.

According to an embodiment shown in FIGS. 92-93, a means (herein called "door seal") (3730) is designed and constructed to cover, plug, or seal any space (herein called "door gap(s)") (3750) that can exist between any door frame or door (herein called "door") (3720) and any floor (3340) or other materials below it. The door seal (3730) can, without limitation, be friction fitted under and/or against either side of any door (3720). The door seal (3730) can, without limitation, be any length, width, height, and have any floor, doorway, or door interfacing geometries. The door seal (3730) can also be, without limitation, designed in a manner known to those skilled in the art, so that its length, width, or height, can be easily adjusted to accommodate and effectively seal with various doorway and door (3720) designs and sizes.

The door seal (3730) can, without limitation, be flexible, and have any durometer rating. It is preferred, without limitation, that the door seal (3730) has a durometer rating that allows it to be easily inserted under a door or at least effectively interfaced with one or more door gap(s) (3750). The door seal (3730) can, without limitation, be constructed from, fully covered, or at least covered on its critical interfacing surfaces, with one or more of any absorbent material(s) (3760) that can hold, contain, or absorb any liquid. Any absorbent material(s) (3760) can, without limitation, have any type, depth, length, and number, of textures or indentions, and can be any thickness or construction. The absorbent material(s) (3760) can be constructed from, without limitation, one or more materials such as, but not limited to, cellulose, paper, natural or manufactured fibers or materials, that may be coated or uncoated, or constructed with combinations of these materials, or other materials known in the art. The absorbent materials (3760) or any construct containing absorbent materials (3760) are either treated by the operator or pretreated in various ways known to those skilled in the art, with any liquid agent(s), so that the surfaces of the doorway and/or door(s) (3720) and the floor (3340) or any flooring or other materials under the door(s) (3720), can come in contact with the liquid agent(s). It is preferred, without limitation that the absorbent material(s) (3760) is saturated with the same liquid agent(s) (30) that is generated into aerosol (200) in the present invention. The door seal (3730) can also, without limitation, incorporate one or more handle(s) (3740) of various size, length, and shape, into its design to facilitate easier placement and retrieval.

According to an embodiment, the door seal (3730) can, without limitation, be designed and constructed to include one or more reservoir(s) or basin(s) (herein called "seal basin" (3770)) which can be either internally or externally located. They can be any size and shape and filled with any liquid agent(s). The seal basin(s) (3770) can also, without limitation, have one or more removable covers that can effectively directly or indirectly seal to the door seal (3730). The seal basin(s) (3770) may, without limitation, also have one or more of any tube, duct, pipe, conduit, tunnel, pathway, or connection (herein called "feed tube") (3780), that connects any part of the seal basin(s) (3770), or any other structure or component that directly or indirectly connects to any part of any seal basin(s) (3770), with any of the absorbent material(s) (3760), so that any liquid or moisture may be transported, moved, or flow, at any rate or speed, from the seal basin(s) (3770) to any of the absorbent material(s) (3760).

According to an embodiment shown in FIG. 94, a means (herein called "odor remover tank") (3790) can, without limitation, be designed and constructed so that air or gas from one or more targeted area(s) (3310) can be pumped, flowed, compressed, or moved, into and through one or more various types of liquids contained in one or more enclosed tanks or reservoirs (herein called "tank(s)") (3820). The air or gas can also, without limitation, contain any amount of any aerosol (200). The liquid(s) (herein called "neutralizer liquid(s)") (3810) held in the tank(s) (3820) can, without limitation, neutralize, degrade, or remove, any odors or vapors from the air, as well as neutralize or degrade any liquid agent(s) (30) that the aerosol (200) may contain. Any neutralizer liquid(s) (3810) can be utilized. It is preferred, without limitation, that the neutralizer liquid(s) (3810) is an aqueous solution containing any effective amount of sodium bicarbonate when the treated air or gas is from an area that is treated with an aerosol containing substances such as, but not limited to, hydrogen peroxide, or peroxyacetic acid (PAA).

It is preferred, without limitation, that one or more of any high capacity air/gas compressor(s) known to those skilled in the art, is used to move the air or gas from the treated area(s) (3310) into the neutralizer liquid(s) (3810). The air or gas can be pumped, flowed, compressed, or moved, through one or more of any adequate tube, duct, pipe, conduit, tunnel, pathway, or connection, anywhere into the neutralizer liquid(s) (3810) at any effective pressure or flow rate. The neutralizer liquid(s) (3810) can be maintained at any volume, depth, and temperature. The neutralizer liquid(s) (3810) can also, without limitation, be stirred at any time and for any duration in a manner known in the art. The air or gas may also be recirculated one or more times through the neutralizer liquid(s) (3810) before it is released from the odor remover tank (3790) out of an air outlet (3840) and back into the treated area(s) (3310) or vented into a separate area. Any air or gas can be, without limitation, processed by any effective or necessary filtering means (3850) known to those skilled in the art before it leaves any odor remover tank(s) (3790) or any connecting system of tube(s), duct(s), pipe(s), conduit(s), tunnel(s), pathway(s), or connection(s). All of the odor remover tank (3790) functions can, without limitation, be controlled directly or indirectly by any software, electronics, PLC (315), or HMI (320). The odor remover tank (3790) can be operated at anytime when it is needed or desired to remove any odors or vapor from the targeted area(s) or treated space(s) (3310). The odor remover tank (3790) device can be, without limitation, combined or operated with any aerosol (200) generating device or dehumidifier (2040).

Without being limited, and according to a preferred embodiment and with reference to FIGS. 98-102, and FIGS. 119-132, and FIGS. 139-144, a description is given, of an enhanced use of one or more remotely located or positioned sensor(s) (3530), hereinafter called "remote aerosol sensor(s)" (5010), that can be used to determine if and/or when an effective or sufficient amount of aerosol (200) is applied and/or delivered into the one or more treated or targeted area(s) (210). The remote aerosol sensor(s) (5010) can also be utilized, without limitation, to determine if and/or when an effective or sufficient amount of any aerosol (200), agent, and/or vapor, is applied and/or delivered onto one or more area(s) and/or surface(s) within the one or more treated or targeted area(s) (210). Without being limited, the remote aerosol sensor(s) (5010) can also be used with any aerosol generating means, as well as any vapor and/or gas generating apparatus(s), that deploy any generated aerosol, gas, and/or vapor, into one or more targeted area(s) (210). The remote aerosol sensor(s) (5010), and/or any of its components, can also be mounted, located, and/or used, without limitation, within, and/or incorporated into the design and construction of, any treatment chamber(s), or any other effectively sealed treatment area(s), of any apparatus that is used to treat, sanitize, disinfect, and/or sterilize, the one or more surface(s) of one or more of any object(s), with one or more of any aerosol, gas, and/or vapor. The remote aerosol sensor(s) (5010) can also be, without limitation, located, attached, connected, and/or mounted, to or at one or more of any location(s) or position(s), at one or more of any effective and suitable height(s).

Referring to FIG. 142, and without being limited, the remote aerosol sensor(s) (5010) can also be attached, directly or indirectly connected, and/or mounted, to one or more of any support structure(s) (6045), such as, but not limited to any, stand(s), tripod(s), cart(s), bracket(s), equipment(s), and/or pole(s). The support structure(s) (6045) can also be, without limitation, constructed or designed in a manner known in the art, so that they can be modified or adjusted for one or more of any effective and/or desired height(s), thereby enabling the attached or connected remote aerosol sensor(s) (5010) to be located or positioned at one or more of any effective and/or desired height(s). Without being limited, the one or more remote aerosol sensor(s) (5010), and/or their one or more support structure(s) (6045), can be located in one or more of any location(s) in one or more of any targeted or treated area(s) (210) such as, but not limited to any, chamber(s), room(s), targeted space(s) or area(s), enclosed area(s), and/or effectively sealed area(s) or space(s).

It is preferred, without limitation, that one or more remote aerosol sensor(s) (5010) are attached, or directly or indirectly connected to, any effective location(s) and/or height(s), on one or more support structure(s) (6045), and these various components are located in at least one or more effective and suitable location(s) within the targeted area(s) (210). It is more preferred, without limitation, that at least two remote aerosol sensor(s) (5010) are utilized in the targeted space(s) (210), where each remote aerosol sensor(s) (5010) is attached or directly or indirectly connected to, to its own support structure(s) (6045), and at least one remote aerosol sensor(s) (5010) and its support structure(s) (6045) (Denoted as "A") is located effectively and suitably, near, in close proximity to, or close to, one interior wall and/or corner of the room or targeted area(s) (210) and/or the aerosol or vapor generating apparatus(s) (215) that is located in the targeted area(s) (210), and at least one of another remote aerosol sensor(s) (5010) and its support structure(s) (6045) (Denoted as "B") is located at any effective and suitable location(s) across the room or targeted area(s) (210) at the furthest distance(s) possible, or the effectively furthest distance(s) possible, from the first remote aerosol sensor(s) (5010) ("A") and/or the nearest aerosol or vapor generating apparatus(s) (215).

It is even more preferred, without limitation, that at least four remote aerosol sensor(s) (5010) are utilized in the targeted space(s) (210), where at least two of the remote aerosol sensor(s) (5010) are attached or directly or indirectly connected to, the same support structure(s) (6045), and at least one of these support structure(s) (6045) and it's at least two attached remote aerosol sensor(s) (5010) (Denoted as "A") is located effectively and suitably, near, in close proximity to, or close to, one interior wall and/or corner of the room or targeted area(s) (210) and/or the aerosol or vapor generating apparatus(s) (215) that is located in the targeted area(s) (210), and at least one of another support structure(s) (6045) and it's at least two (2) attached remote aerosol sensor(s) (5010) (Denoted as "B"), is located at any effective and suitable location(s) across the room or targeted area(s) (210) at the furthest distance(s) possible, or the effectively furthest distance(s) possible, from the first remote aerosol sensor(s) (5010) ("A") and/or the nearest aerosol or vapor generating apparatus(s) (215).

It is also preferred, without limitation, that one or more of the remote aerosol sensor(s) (5010) utilized in the room or targeted area(s) (210), is located as effectively and/or possibly close to the highest point(s) or ceiling(s) (6075) of the room or targeted area(s) (210). Without being limited, one or more additional remote aerosol sensor(s) (5010) may also be located and simultaneously operated at any other suitable and effective height(s) and location(s) within the targeted area(s) (210). It is even more preferred, that if more than one remote aerosol sensor(s) (5010) is attached or directly or indirectly connected to, the same support structure(s) (6045), at least one of these remote aerosol sensor(s) (5010) is located as effectively and/or possibly close to the highest point(s) or ceiling(s) (6075) of the room or targeted area(s) (210), and at least one of another remote aerosol sensor(s) (5010) is located as effectively and/or possibly close to the lowest point(s) or floor(s) (6080) of the room or targeted area(s) (210).

The remote aerosol sensor(s) (5010) can incorporate or contain, and operate, without limitation, one or more of any sensing device(s) (5080), or any combination of various sensing device(s) (5080), at any time, such as, but not limited to any, light sensor(s) (730), temperature sensor(s) (5085), humidity or relative humidity sensor(s) (Hereinafter called "humidity sensor(s)" (5090)), dew point sensor(s) and/or hygrometer(s) (Hereinafter called dew point sensor(s) (3888)), that can capture data or conditions pertaining to the environment or atmosphere surrounding the remote aerosol sensor (5010) or in which the remote aerosol sensor(s) (5010) is located. In addition, the remote aerosol sensor(s) (5010) can incorporate or contain, and operate, without limitation, one or more of any components, support component(s), or accessory(s), related to, or work with, any sensing device(s) (5080) such as, but not limited to any, light source(s) (725) that can, without limitation, work with any light sensor(s) (730). The remote aerosol sensor(s) (5010) can also incorporate or contain, and operate, without limitation, one or more of any sensing device(s) (5080) such as, but not limited to any, sensor(s) that can sense the presence of any deposited aerosol (200) droplets and/or any deposited film of any deployed agent(s), or at least a sufficient quantity of deposited aerosol (200), that is deposited on one or more of any monitored surface(s) (Hereinafter aerosol deposit sensor(s) (3880). This particular sensor does not in any way include, or refer to, any relative humidity sensor(s), dew point sensor(s), and/or hygrometer(s), already known to those in the art. Without being limited, one or more of any, digital, electronic, or analog, controller(s) such as, but not limited to, any, PLC(s), remote PLC(s) (3893), as well as any sensing device(s) (5080), light source(s) (725), and/or any other related component(s), or any part of these various sensor(s), component(s), or any other part(s) of the remote aerosol sensor(s) (5010), that need protection from the environment or atmosphere within the targeted area(s) (210), can be suitably and effectively packaged or hermetically sealed within the one or more one or more housing(s) of the remote aerosol sensor(s) (5010).

One or more of these various sensing device(s) (5080), as well as any components, support component(s), or accessory(s), related to, or work with, any sensing device(s) (5080) can be, without limitation, located or interfaced in or on, any effective, location, position, or orientation, related to the remote aerosol sensor(s) (5010) and any of its associated parts. One or more of these various components and/or sensing device(s) (5080) can also be, without limitation, constructed or located within, under, or as a part of, one or more of any slot(s), channel(s), indentation(s), cavern(s), of any size, shape, depth, length, or complex geometry, that may connect directly or indirectly to any environment or atmosphere that interfaces with, or surrounds, the remote aerosol sensor(s) (5010). It is preferred, without limitation, that these various sensing device(s) (5080), as well as any component(s), support component(s), or accessory(s), related to, or work with, any sensing device(s) (5080) such as, but not limited to any, light source(s) (725), are located and operated in a manner so that they can effectively collect and/or report and communicate, any needed data, information, and/or condition(s), to any PLC(s), pertaining to the targeted area(s) (210).

With reference to FIGS. 98-102, and FIGS. 119-132, and FIGS. 139-144, and without being limited, any radio(s) including any transceiver(s) (6000), any of the various sensing device(s) (5080), as well as any component(s), support component(s), or accessory(s), related to, or that work with, any sensing device(s) (5080), can be electrically connected in a manner known to those skilled in the art, to one or more of any digital, electronic, or analog, controller(s), and/or control and/or sensory device(s), such as, but not limited to, any PLC(s), or any remote PLC(s) (3893). Without being limited, these one or more of any digital, electronic, or analog, controller(s), and/or control and/or sensory device(s), such as, but not limited to, any PLC(s), or any remote PLC(s) (3893), can communicate any data, information, and/or command(s) with any other PLC(s) or remotely located PLC(s) such as, but not limited to one or more of any, (a) PLC(s) that may control the sealing and/or unsealing movement(s) of one or more of any room vent or air vent covering apparatus(s) (6020) and/or vent covering assembly(s) (2300), (b) PLC(s) that may control one or more of any dehumidification and/or air filtration apparatus(s) (2040), (c) PLC(s) that may control one or more of any aerosol or vapor generating apparatus(s) (215), (d) PLC(s) that may be used to remotely control (6005) one or more of any device(s) or equipment(s), such as, but not limited to any, aerosol and/or vapor generating apparatus(s) (215), dehumidification and/or air filtration apparatus(s) (2040), and/or room vent or air vent covering apparatus(s) (6020) and/or vent covering assembly(s) (2300). Without being limited, the one or more remote aerosol sensor(s) (5010) and their one or more PLC(s) (3893), may directly and/or indirectly communicate with the one or more of any other PLC(s) that control one or more of any, device(s), independent device(s), equipment(s), apparatus(s), remote control device(s) (6010), any PLC(s) that control (6005) any remote control(s) (6010), with one or more of any suitable and effective means such as, but not limited to any, radio, transceiver, radio waves, sound, electromagnetic spectrum, wire, cable, and/or fiber optics, all in a manner known to those skilled in the art. It is preferred, without limitation, that the remote aerosol sensor(s) (5010) communicates with one or more of any suitable and effective radio(s) or transceiver(s) (6000).

Any data or information that is collected, disseminated, transmitted, and/or reported, by the one or more of any remote aerosol sensor(s) (5010), any of its PLC(s) (3893) and various sensing device(s) (5080), as well as any component(s), support component(s), or accessory(s), related to, or work with, any sensing device(s) (5080) can be, without limitation, directly or indirectly, disseminated, transmitted, reported, and/or communicated, to one or more of any, digital, electronic, or analog, controller(s) such as, but not limited to, any "programmable logic circuit(s)" hereinafter called "PLC(s)", at any, location(s) and/or at any local and/or remote location(s), at any time, and in a manner known to those skilled in the art, and can be utilized for various purposes including, but not limited to, determining if or when the targeted area(s) (210) is filled with a sufficient amount of aerosol (200) that will result in an efficacious outcome within the targeted area(s) (210) with the administered aerosol (210). These one or more PLC(s) may be, without limitation, used for any number and type of any purpose(s), and may be associated and communicate with, and/or control, in any dedicated and/or undedicated capacity or function, any number and/or combination of any device(s) and equipment(s). The one or more of these PLC(s) may also, without limitation, control, operate, and/or be located in or at, one or more of any, device(s), equipment(s), or location(s), and/or any combination of any device(s), equipment(s), or locations, such as, but not limited to any, (a) remote aerosol sensor(s) (5010), (b) aerosol generator(s) (215), (c) remote controlling device(s) (6010), (d) vent sealing device(s) (6020) and/or vent covering assembly(s) (2300), and/or (e) any dehumidification device(s) (2040) that may or may not be connected to, and/or operated with, any air filtration apparatus(s) (6040). Without being limited, any suitable and effective PLC(s) can be used in any, remote aerosol sensor(s) (5010), as well as any other device(s) and equipment(s), that is utilized in the one or more process(s) or method(s) to treat the various surfaces within the targeted area(s) (210), and they can possess and utilize any suitable and effective, design(s), software, and/or hardware. Without being limited, any of the, PLC(s), radio(s), and/or transceiver(s), utilized in any of the various device(s) and equipment(s) that are used in the one or more process(s) or method(s) utilized to treat the various surface(s) within the targeted area(s) (210), can communicate, control, and function, with any suitable and effective software, programming, and/or hardware, known to those skilled in the art.

It is preferred, without limitation, that at least one of these various PLC(s) is located in or at any, device(s), equipment(s), or locations, such as, but not limited to any, (a) remote aerosol sensor(s) (5010), (b) aerosol generator(s) (215), and/or (c) remote controlling device(s) (6010), and uses the various data, information, or conditions, that is reported and/or relayed from the one or more of any remote aerosol sensor(s) (5010) and it's various sensing device(s) (5080), to determine that the reported data, information, and/or conditions are, and/or are not, indicative or associated with the one or more treated or targeted area(s) (210) being sufficiently or efficaciously treated or filled, with the deployed or applied agent(s) and/or aerosol(s) (200) from device(s) such as, but not limited to any, aerosol generator(s) (215). It is more preferred, without limitation, that this is accomplished solely by the one or more PLC(s) (6005) that controls, and/or is located in or at, and/or is a component(s) of one or more of any, remote controlling device(s) (6010).

Without being limited, each of the one or more of any, remote aerosol sensor(s) (5010), remote controlling device(s) (6010), and any other device(s) or equipment(s), that is used in the one or more process(s) or method(s) to treat the various surface(s) within the targeted area(s) (210), can also share or report any, data, information, system data, system status, and/or anomalies, regarding any of their operation(s) and/or condition(s), to any PLC(s), at any location(s) and/or at any local and/or remote location(s), including, but not limited to, the one or more of any remote controlling device(s) (6010), that may be utilized. This can be accomplished in any manner known to those skilled in the art. It is preferred, without limitation, that each of the various, remote aerosol sensor(s) (5010), remote controlling device(s) (6010), and any other device(s) or equipment, utilized to treat the one or more surface(s) within the targeted area(s) (210), are operated by one or more of any suitable and effective PLC(s), and these various PLC(s) can also share, transmit, and/or report, any, data, information, system data, system status, and/or anomalies, regarding their operation(s) and/or condition(s), with one or more of any device(s) or equipment(s), via any suitable and effective transceiver(s) or radio(s), all in a manner known to those skilled in the art.

Without being limited, any, status(s), data(s), information(s), and/or condition(s), pertaining to and/or gathered by any, device(s) and equipment(s) utilized in the one or more process(s) or method(s) to treat the various surfaces within the targeted area(s) (210), including, but not limited to any, (a) remote aerosol sensor(s) (5010), (b) aerosol generator(s) (215), (c) vent sealing device(s) (6020) and/or vent covering assembly(s) (2300), that are located within the one or more room(s) and/or targeted area(s) (210), (d) any dehumidification device(s) (2040) that may or may not be connected to, and/or operated with, any air filtration apparatus(s) (6040), (e) mixing apparatus(s) used to mix and feed one or more of any deployable agent(s), and/or (f) apparatus(s) used to externally fill or feed any aerosol generator(s) (215), can be reported, transmitted, and/or broadcast, as well as and monitored and processed, by any PLC(s), and preferably the one or more PLC(s) that operates and controls the various remote controlling device(s) (6010). Without being limited, any, status(s), data(s), information(s), and/or condition(s), pertaining to and/or gathered by any, device(s) and equipment(s), can be reported, transmitted, or broadcast, in any effective and suitable, form, type, and/or format.

Any of the, status(s), data(s), information(s), and/or condition(s), pertaining to and/or gathered by any, device(s) and equipment(s), can be used by one or more of any of these various PLC(s), and preferably the one or more PLC(s) that operates and controls the various remote controlling device(s) (6010), for any purposes or outcomes, and preferably to cause or take any number of any actions and/or any combination of any actions, at one or more of any suitable and effective time(s), such as, but not limited to, (a) extending or modifying the operation or agent(s) deployment time of one or more of any aerosol generator(s) (215), (b) shortening or modifying the operation or agent(s) deployment time of one or more of any aerosol generator(s) (215), (c) shutting down any drive electronics (645) or amplifier(s) (230), (b) shutting down the blower(s) (180) or flow of pressurized air, (d) shutting down the apparatus(s) (215), (e) stopping the production of aerosol (200), (f) stopping the deployment of aerosol (200) into the targeted area(s) (210), (g) stopping the deployment of any agent(s) into the targeted area(s) (210), (h) activating one or more of any dehumidification device(s) (2040) (h) activating one or more of any air filtration apparatus(s) (6040), and/or (j) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210).

Without being limited, any device(s) and equipment(s) utilized in the one or more process(s) or method(s) to treat the various surfaces within one or more of any targeted area(s) (210), including the remote controlling device(s) (6010), can also be programmed and configured, so that they can be assigned to one or more of any, zone(s), area(s), group(s), subset(s), frequency(s), and/or operating area(s), at any time, and in one or more of any location(s) or targeted area(s) (210). One or more of any device(s) and equipment(s) can also be, without limitation, assigned to, or be controlled by, one or more specific remote controlling device(s) (6010). This can all be accomplished by any suitable and effective, software and/or hardware means. For example, and without limitation, each piece of any equipment or device(s) that is utilized, can have one or more of any, suitable and effective selection hardware and/or software switch(s) and/or software interface(s), that can be used to assign one or more of any equipment or device(s), to one or more of any, zone(s), area(s), group(s), subset(s), frequency(s), and/or operating area(s).

Furthermore, and without limitation, the one or more remote controlling device(s) (6010) can communicate with the one or more these pieces of equipment or device(s) that is assigned to one or more of these, zone(s), area(s), group(s), subset(s), frequency(s), and/or operating area(s), by embedding or including one or more unique identifier(s), code(s), and/or command(s), that is assigned to or used only with one or more of these various zone(s), area(s), group(s), subset(s), frequency(s), and/or operating area(s), in any of the transmissions, signals, and/or communications made by the remote controlling device(s) (6010). For example, and without limitation, the PLC(s) located within or connected to the remote controlling device(s) (6010) can send one or more command(s) at any suitable and effective time(s), via one or more of any connected radio(s) and/or transceiver(s) (6030), to all of the various aerosol generator(s) (215) that are assigned to two separate groups for example, respectfully Zone 1 and Zone 2, to shut down and stop deploying aerosol (200) into their individually assigned targeted areas (210), where each of these assigned targeted areas (210) can share the same space and/or be located in completely separate space(s) or targeted area(s) (210). Without being limited, after those one or more command(s) are sent or transmitted, and/or the various equipment and device(s) in Zone 1 and Zone 2 acknowledge their receipt and the successful execution of those command(s), one or more of any additional command(s) can also be sent by the remote controlling device(s) (6010), to the dehumidification device(s) (2040), air filtration apparatus(s) (6040), and vent sealing device(s) (6020) and/or vent covering assembly(s) (2300), in Zone 1 and Zone 2, where the reception of these command(s) or signals(s) by these various devices can result in one or more of any activity(s) such as, but not limited to: (a) the activation of one or more of any dehumidification device(s) (2040) (b) the activation one or more of any air filtration apparatus(s) (6040), and/or (c) the activation, opening, and/or unsealing, of one or more of any vent sealing device(s) (6020) and/or vent covering assembly(s) (2300) interfaced with the various air vent(s), air inlet(s), air outlet(s), or room vent(s) (6025).

Without being limited, one or more of any device(s) or equipment(s) operating in the same targeted area(s) (210), can also be assigned to the same or even different, zone(s), area(s), group(s), subset(s), frequency(s), and/or operating area(s), at any time. Without being limited, one or more of any, zone(s), area(s), group(s), subset(s), frequency(s), and/or operating area(s), may be assigned to and/or created in, one or more of any location(s) or targeted area(s) (210). Without being limited, the same area(s), group(s), subset(s), frequency(s), and/or operating area(s), may also be, assigned or created in, and utilized within, one or more location(s) or targeted area(s) (210).

It is also preferred, without limitation, that the one or more remote controlling device(s) (6010) communicates with and/or controls all of the various device(s) and equipment(s) that are used in the one or more process(s) or method(s) utilized to treat the various surface(s) within the targeted area(s) (210) such as, but not limited to any, (a) remote aerosol sensor(s) (5010), (b) aerosol generator(s) (215), (c) vent sealing device(s) (6020) and/or vent covering assembly(s) (2300), that are located within the one or more room(s) and/or targeted area(s) (210), (d) any dehumidification device(s) (2040) that may or may not be connected to, and/or operated with, any air filtration apparatus(s) (6040), (e) mixing apparatus(s) used to mix and feed one or more of any deployable agent(s), and/or (f) apparatus(s) used to externally fill or feed any aerosol generator(s) (215). Without being limited, the one or more of any remote controlling device(s) (6010) can communicate with and/or control all of these various device(s) and equipment(s) with one or more of any suitable and effective means such as, but not limited to any, radio, transceiver, radio waves, sound, electromagnetic spectrum, wire, cable, and/or fiber optics, all in a manner known to those skilled in the art. It is also preferred, without limitation, that the remote controlling device(s) (6010) communicates, controls, and/or sends commands, to any device(s) or equipment(s) with one or more of any suitable and effective radio(s) and/or transceiver(s) (6030), and these various device(s) and equipment(s) that are used in the one or more process(s) or method(s) to treat the various surfaces within the targeted area(s) (210) also have one or more of any suitable and effective radio(s) and/or transceiver(s). It is also preferred, without limitation, that each of the various device(s) and equipment(s) that is used in the one or more process(s) or method(s) to treat the various surface(s) within the targeted area(s) (210) also has one or more of any, suitable and effective PLC(s) that can control and operate these device(s) and equipment(s), as well as any suitable radio(s) or transceiver(s) that can communicate with these PLC(s) in addition to any other device(s) or equipment and their PLC(s).

The remote controlling device(s) (6010) can also have, without limitation, one or more of any antenna(s) (6065) that can work with the one or more radio(s) and/or transceiver(s) (6030). The remote controlling device(s) (6010) can also have, without limitation, one or more of any suitable and effective human machine interface(s) or HMI's (6070). It is preferred, without limitation, that the human machine interface(s) (6070) is any suitable and effective touch screens known to those skilled in the art. Without being limited, the one or more PLC(s) (6005) that are, associated with, located within, operate, and/or control, the remote controlling device(s) (6010), can communicate with and/or be connected to one or more of any of the various part(s) and component(s) of the remote controlling device(s) (6010), in a manner known to those skilled in the art, such as, but not limited to any, (a) human machine interface(s) or HMI's (6070), (b) PLC(s) (6005), (c) radio(s) and/or transceiver(s) (6030), and/or (d) antenna(s) (6065).

Without being limited, if or when any of these various PLC(s), and more preferably the PLC(s) (6005) that control and/or are located in or at one or more of any remote controlling device(s) (6010), determine that that the data or conditions reported by the one or more remote aerosol sensor(s) (5010), are indicative or associated with the one or more treated or targeted area(s) (210) being sufficiently or efficaciously treated or filled with the deployed or applied agent(s) and/or aerosol(s) (200), the one or more of any PLC(s) in any one or more location(s), can cause or take any number of any actions and/or any combination of any actions, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s) (6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210) (j) shutting down any equipment(s) or device(s) that support the function and/or operation of any aerosol generator(s) (215).

Without being limited, any desired and/or effective, humidity level(s), aerosol (200) concentration level(s), aerosol (200) density level(s), vapor concentration level(s), vapor density level(s), that are reached or attained within the targeted area(s) (210) after deployment of the aerosol(s) (200), can be sustained or maintained, for any effective and suitable amount of time(s) within the targeted area(s), until the aerosol (200) containing atmosphere(s) within the targeted area(s) (210) undergoes or is subjected to one or more of any activity(s) and/or any combination of activity(s), such as, but not limited to being, purged, replaced, processed, filtered, dehumidified, and/or conditioned, with any suitable and effective method(s), equipment(s), device(s), and/or in any suitable and effective manner(s).

Without being limited, the time between stopping any supply or deployment of any aerosol(s) (200) and/or any gas(s), into the targeted area(s) (210), and starting any suitable and effective dehumidification process(s) to dehumidify the atmosphere(s) within the targeted area(s), can be any amount(s) or duration(s) of time that is suitable, efficacious, and/or desirable. It is preferred, without limitation, that the time between stopping any supply or deployment of any aerosol(s) (200) and/or any gas(s), into the targeted area(s) (210), and starting any suitable and effective dehumidification process(s) to dehumidify the atmosphere(s) within the targeted area(s), is at least one minute or more. It is more preferred, without limitation, that the time between stopping any supply or deployment of any aerosol (200) and/or any gas(s), into the targeted area(s) (210), and starting any suitable and effective dehumidification process(s) to dehumidify the atmosphere(s) within the targeted area(s), is less than thirty minutes. It is even more preferred, without limitation, that the time between stopping any supply or deployment of any aerosol (200) and/or any gas(s), into the targeted area(s) (210), and starting any suitable and effective dehumidification process(s) to dehumidify the atmosphere(s) within the targeted area(s), is less than twenty minutes. It is very preferred, without limitation, that the time between stopping any supply or deployment of any aerosol(s) (200) and/or any gas(s), into the targeted area(s) (210), and starting any suitable and effective dehumidification process(s) to dehumidify the atmosphere(s) within the targeted area(s), is between three and fifteen minutes. It is extremely preferred, without limitation, that the time between stopping any supply or deployment of any aerosol(s) (200) and/or any gas(s), into the targeted area(s) (210), and starting any suitable and effective dehumidification process(s) to dehumidify the atmosphere(s) within the targeted area(s), is between five and ten minutes.

Without being limited, the time between stopping any supply or deployment of any aerosol(s) (200) and/or any gas(s), into the targeted area(s) (210), and activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), can be any amount(s) or duration(s) of time that is suitable, efficacious, and/or desirable. It is preferred, without limitation, that the time between stopping any supply or deployment of any aerosol(s) (200) and/or any gas(s), into the targeted area(s) (210), and activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), is at least one minute or more. It is more preferred, without limitation, that the time between stopping any supply or deployment of any aerosol(s) (200) and/or any gas(s), into the targeted area(s) (210), and activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), is less than thirty minutes. It is even more preferred, without limitation, that the time between stopping any supply or deployment of any aerosol(s) (200) and/or any gas(s), into the targeted area(s) (210), and activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), is less than twenty minutes. It is very preferred, without limitation, that the time between stopping any supply or deployment of any aerosol(s) (200) and/or any gas(s), into the targeted area(s) (210), and activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), is between two and fifteen minutes. It is extremely preferred, without limitation, that the time between stopping any supply or deployment of any aerosol(s) (200) and/or any gas(s), into the targeted area(s) (210), and activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), is between five and ten minutes.

Without being limited, the activation, opening, actuating, and/or unsealing, of the one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), can also be postponed until the one or more of any, dehumidification device(s) (2040) and/or air filtration apparatus(s) (6040), that are treating or processing the atmosphere(s) within the targeted area(s) (210) have reached one or more of any criteria(s) and/or condition(s) such as, but not limited to, (a) the one or more dehumidification device(s) (2040) have reduced the humidity or relative humidity level(s) in the one or more targeted area(s) (210), down to one or more of any, point(s), level(s), or range(s), that is suitable, efficacious, and/or desirable, and/or (b) the one or more air filtration apparatus(s) (6040) have reduced one or more of any substance(s) such as, but not limited to any, vapor(s), dust(s), gas(s), and/or odor(s), in the one or more targeted area(s) (210), down to one or more of any, point(s), level(s), value(s), or range(s), that is suitable, efficacious, and/or desirable.

Without being limited, the one or more dehumidification device(s) (2040) and/or air filtration apparatus(s) (6040) can also operate for any, suitable, efficacious, and/or desirable, amount of time(s), after the activation, opening, actuating, and/or unsealing, of one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210).

It is also preferred, without limitation, that the one or more vent sealing device(s) (6020) and/or vent covering assembly(s) (2300) that are utilized, may include elements of and/or are the various automated vent sealing device(s) or vent covering device(s) described in U.S. Pat. No. 8,196,604 and U.S. patent application Ser. No. 13/494,824 to Ricciardi et al. Without being limited, these vent sealing device(s) (6020) and/or vent covering assembly(s) (2300) can be utilized to, cover, inhibit, retard, stop, and/or control, the flow of any air and/or gas(s) through one or more of any, inlet vent(s), outlet vent(s), air vent(s), air inlet(s), air outlet(s), or room vent(s) (Hereinafter called room vent(s) (6025)), at any time.

It is also preferred, without limitation, that these various automated vent sealing device(s) (6020) and/or vent covering assembly(s) (2300) include one or more of any, PLC(s) (6060), radio(s) or transceiver(s) (6055), elevation stand(s)/tripod(s) or support pole(s) (2140), in their design, as well as any, hardware or design elements, known in the art, so that they can be controlled by one or more of any suitable or effective device(s) such as, but not limited to any, remote controlling device(s) (6010), via any suitable and effective, direct wire or cable control(s), and/or any suitable or effective wireless means, known to those skilled in the art. It is preferred, without limitation, that the various vent sealing device(s) (6020) and/or vent covering assembly(s) (2300) are in communication with, and/or are controlled by, one or more of any suitable and effective, local and/or connected PLC(s) (6060).

Without being limited, the one or more local and/or connected PLC(s) (6060) can communicate with one or more of any suitable and effective device(s) involved in any process(s) or step(s) to treat the surface(s) within the treated area(s) (210), preferably the remote controlling device(s) (6010), and preferably via one or more of any transceiver(s) (6055). Also, without being limited, the one or more local and/or connected PLC(s) (6060) can receive and/or send any, data, condition(s), status(s), and/or command(s), at any time(s), to or from, one or more of any suitable and effective device(s) involved in any process(s) or step(s) to treat the surface(s) within the treated area(s) (210), preferably the remote controlling device(s) (6010), and preferably via one or more of any transceiver(s) (6055). For example, and without being limited, the local and/or connected PLC(s) (6060) can receive one or more of any command(s) at any suitable and effective time(s), such as, but not limited to the, command to seal, command to unseal, command to move up, command to move down, command to open, and/or command to close, from one or more of any suitable and effective device(s) that are involved in any process(s) or step(s) to treat the surface(s) within the targeted area(s) (210), preferably the remote controlling device(s) (6010). Without being limited, the local and/or connected PLC(s) (6060) can communicate any information such as, but not limited to any, condition(s), and/or status(s), that are related to the automated vent sealing device(s) (6020) and/or vent covering assembly(s) (2300), to one or more of any suitable and effective device(s) involved in any process(s) or step(s) to treat the surface(s) within the treated area(s) (210), preferably the remote controlling device(s) (6010), and preferably via one or more of any transceiver(s) (6055).

Without being limited, the elevation stand(s) or support pole(s) (2140), to which the vent covering assembly(s) (2300) can be directly or indirectly connected, can be adjusted for any number of suitable and effective height(s) at any time.

Without being limited, the, activation, actuation, opening, operation, and/or unsealing, of these various vent sealing device(s) (6020) and/or vent covering assembly(s) (2300) enables sufficient, effective, and/or suitable amounts, of air and/or gas(s) to pass through the one or more room vent(s) (6025), and into and/or through, the one or more room(s), enclosed area(s), or targeted area(s) (210). It is preferred, without limitation, that the automated sealing device(s) (6020) and/or vent covering assembly(s) (2300) are attached to one or more of any effective and suitable, mechanical, motorized, and/or hydraulic means (6050) that can cause the one or more vent covering assembly(s) (2300) to unseal, open, move away from, and/or unseal from, the one or more room vent(s) (6025) when the means (6050) is activated, actuated, and/or operated. It is also preferred, without limitation, that the action of activating, opening, actuating, operating, and/or unsealing, the one or more of any vent sealing device(s) (6020) and/or vent covering assembly(s) (2300), and their one or more of any sealing or covering material(s) (2130), is achieved by one or more of any suitable and effective mechanical, motorized, and/or hydraulic means that is controlled by one or more of any suitable and effective PLC(s) that directly and/or indirectly communicates with any remote aerosol sensor(s) (5010) and/or any remote controlling device(s) (6010).

The remote aerosol sensor(s) (5010) can be, without limitation, constructed and/or configured with or without one or more aerosol deposit sensor(s) (3880). It is preferred, without limitation, that the remote aerosol sensor(s) (5010) incorporates at least one or more aerosol deposit sensor(s) (3880) in its design or construction. If the remote aerosol sensor(s) (5010) device is constructed and/or configured with one or more aerosol deposit sensor(s) (3880), certain configurations are preferable more than others, but this does not in any way limit the scope in which the remote aerosol sensor(s) (5010) can be configured, constructed, and/or utilized. It is preferred, without limitation, that the remote aerosol sensor(s) (5010), incorporates at least one or more of any, aerosol deposit sensor(s) (3880). It is more preferred, without limitation, that the remote aerosol sensor(s) (5010), incorporates at least one or more of any, aerosol deposit sensor(s) (3880), and temperature sensor(s) (5085). It is even more preferred, without limitation, that the remote aerosol sensor(s) (5010), incorporates at least one or more of any, aerosol deposit sensor(s) (3880), temperature sensor(s) (5085), and relative humidity sensor(s) (5090). It is very preferred, without limitation, that the remote aerosol sensor(s) (5010), incorporates at least one or more of any, aerosol deposit sensor(s) (3880), temperature sensor(s) (5085), light source(s) (725), light sensor(s) (730). It is extremely preferred, without limitation, that the remote aerosol sensor(s) (5010), incorporates at least one or more of any, aerosol deposit sensor(s) (3880), temperature sensor(s) (5085), light source(s) (725), light sensor(s) (730), humidity sensor(s) (5090), and/or dew point sensor(s) (3888).

However, if the remote aerosol sensor(s) (5010) device is constructed and/or configured without utilizing one or more aerosol deposit sensor(s) (3880), certain configurations are preferable more than others, but this does not in any way limit the scope in which the remote aerosol sensor(s) (5010) can be configured, constructed, and/or utilized. It is preferred, without limitation, that the remote aerosol sensor(s) (5010), that are devoid of one or more aerosol deposit sensor(s) (3880), have at least one or more of any, light source(s) (725) and light sensor(s) (730). It is more preferred, without limitation, that the remote aerosol sensor(s) (5010), that are devoid of one or more aerosol deposit sensor(s) (3880), have at least one or more of any, light source(s) (725) and light sensor(s) (730), and temperature sensor(s) (5085). It is even more preferred, without limitation, that the remote aerosol sensor(s) (5010), that are devoid of one or more aerosol deposit sensor(s) (3880), have at least one or more of any, light source(s) (725), light sensor(s) (730), and relative humidity sensor(s) (5090). It is very preferred, without limitation, that the remote aerosol sensor(s) (5010), that are devoid of one or more aerosol deposit sensor(s) (3880), have at least one or more of any, light source(s) (725), light sensor(s) (730), temperature sensor(s) (5085), humidity sensor(s) (5090), and/or dew point sensor(s) (3888).

The use of two or more of any sensing device(s) (5080) together such as, but not limited to any, humidity sensor (5090), and light sensor (730), can be, without limitation, helpful in situations where at least one sensor, or even more than one sensor, for example the light sensor (730) and/or the humidity sensor (5090), may be reporting inaccurate, conflicting, and/or erroneous data. In this case, any one or more of any digital, electronic, or analog, controller(s) such as, but not limited to, any PLC(s), and preferably any PLC(s) that controls and/or is a component of any device(s) and/or equipment(s) that is utilized in the one or more process(s) or method(s) to treat the various surfaces within the targeted area(s) (210), and more preferably, any PLC(s) that controls one or more of any aerosol producing apparatus(s) (215), and even more preferably any PLC(s) (6005) that controls, and/or is located in or at, and/or is a component(s) of, one or more of any, remote controlling device(s) (6010), can, without limitation, be notified of this event or situation, and either ignore the one or more remote aerosol sensor(s) (5010) that have any problem(s), conflict(s), conflicting data, and/or error(s), and/or cause or take any number of any actions and/or any combination of actions, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s) (6040) (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210) and/or (j) ignoring one or more of any erroneous, conflicting, and/or problematic sensor(s) and any of their data, for any amount of time, depending on various criteria, logic, or operating conditions, that may be established or encountered. This can, without limitation, happen in any possible circumstances, such as, but not limited to, (a) the humidity sensor (5090) reports accurate data supporting the presence of an efficacious amount of aerosol (200) within the targeted area(s) (210), but the light sensor (730) incorrectly reports the absence of an efficacious amount of aerosol (200) within the targeted area(s) (210), (b) the light sensor (730) reports accurate data supporting the presence of an efficacious amount of aerosol (200) within the targeted area(s) (210), but the humidity sensor (5090) incorrectly reports the absence of an efficacious amount of aerosol (200) within the targeted area(s) (210), (c) both the light sensor (730) and the humidity sensor (5090) fail to report that there is an efficacious amount of aerosol (200) within the targeted area(s) (210). Without being limited, the use of two or more of any other sensing devices (5080) such as, but not limited to any, aerosol deposit sensor(s) (3880), light sensor(s) (730), temperature sensor(s) (5085), humidity sensor(s) (5090), and dew point sensor(s) (3888), may also be helpful in situations where one or more sensors, may be reporting inaccurate, conflicting, and/or erroneous data, and can result in similar outcomes or actions.

One or more of any digital, electronic, or analog, controller(s) such as, but not limited to, any PLC(s), and preferably any PLC(s) that controls and/or is a component of any device(s) and/or equipment(s) that is utilized in the one or more process(s) or method(s) to treat the various surfaces within the targeted area(s) (210), and more preferably, any PLC(s) that controls one or more of any aerosol producing apparatus(s) (215), and even more preferably any PLC(s) (6005) that controls, and/or is located in or at, and/or is a component(s) of, one or more of any, remote controlling device(s) (6010), can be, without limitation, programmed or configured to accommodate or compensate for one or more of any variable(s), at any time, such as, but not limited to any, (a) temperature, (b) humidity, (c) dew point (d) density of deployed aerosol (200), (e) size of deployed aerosol (200), (f) atmospheric pressure within the targeted area(s) (210), (g) size(s) or volume(s) of any targeted area(s) (210), and/or (h) amount of deposited aerosol (200) sensed by any aerosol deposit sensor(s) (3880) at any time, by adjusting, or either extending or shortening, the total amount of time that the one or more aerosol generating apparatus(s) (215) deploy aerosol (200) into the one or more targeted area(s) (210). Any modifications that may be made to the time that the one or more aerosol generating apparatus(s) (215) deploy aerosol (200) can, without limitation, be made at any time before or during the deployment of any aerosol (200), by any PLC(s) at any suitable and effective location(s), and preferably any PLC(s) (6005) that controls, and/or is located in or at, and/or is a component(s) of, one or more of any, remote controlling device(s) (6010). Any modifications to the deployment time can also be, without limitation, impacted, influenced, or affected, by any data or information collected or reported, at any time, from the one or more of any sensing device(s) (5080).

Various operational variables such as, but not limited to, the temperature of the atmosphere within any part of the targeted area(s) can have, without limitation, an effect on the outcome of the treatment for the targeted area(s) (210). This may be, without limitation, found in harsh or extreme environments. For example, and without being limited, any elevated temperatures in one or more targeted area(s) (210) may, without limitation, increase the need for longer aerosol (200) deployment times by the one or more aerosol generating apparatus(s) (215), in order to achieve the desired or efficacious results. Any detected temperature(s) within the targeted area (210) can also, without limitation, result in any extended time for aerosol (200) deployment from any initially chosen or calculated treatment time that was decided before the treatment cycle for the targeted area(s) (210) began. Any detected temperature(s) within the targeted area (210) can also, without limitation, result in any shortening of the time needed for aerosol (200) deployment from any initially chosen or calculated treatment time for a given volume of the targeted area(s) (210).

The humidity sensor(s) (5090) can, without limitation, have various capabilities and attributes such as, but not limited to, (a) the ability to sense and report any humidity level, relative humidity, and/or airborne moisture level, (Hereinafter called "humidity"), (b) without being limited, the ability to sense and report any, dew point(s) and/or dew point data or level(s), (c) have any suitable and effective sensitivity, and/or (d) have the ability to be controlled and/or communicate with one or more of any digital, electronic, or analog, controller(s) such as, but not limited to, any PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(s) or method(s) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010). The humidity sensor(s) (5090) can, without limitation, indicate or communicate to any of these directly or indirectly connected, digital, electronic, or analog, controller(s) such as, but not limited to, any PLC(s) at any location(s), any, dew point(s), and/or moisture, relative humidity, and/or humidity level(s) or data, it collects, which can be accomplished in a manner known to those skilled in the art. It is preferred, without limitation, that the one or more of any remote and/or directly connected, digital, electronic, or analog, controller(s) such as, but not limited to, any PLC(s) at any location(s), is indicated, communicated, and/or receives, any information about the status of any, humidity level(s), dew point(s), relative humidity, or data, that is detected in the targeted area(s) (210), in various ways such as, but not limited to, receiving any, signal, electrical signal, electrical value or intensity of any electrical signal, or lack of any electrical signal(s) from the humidity sensor(s) (5090). This communication can result in one or more of any actions and/or any combination of any actions, at one or more of any suitable and effective time(s), such as, but not limited to: (a) extending or modifying the operation or agent(s) deployment time of one or more of any aerosol generator(s) (215), (b) shortening or modifying the operation or agent(s) deployment time of one or more of any aerosol generator(s) (215), (c) shutting down any drive electronics (645) or amplifier(s) (230), (b) shutting down the blower(s) (180) or flow of pressurized air, (d) shutting down the apparatus(s) (215), (e) stopping the production of aerosol (200), (f) stopping the deployment of aerosol (200) into the targeted area(s) (210), (g) stopping the deployment of any agent(s) into the targeted area(s) (210), (h) activating one or more of any dehumidification device(s) (2040) (h) activating one or more of any air filtration apparatus(s) (6040), and/or (j) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210). Without being limited, any effective humidity sensor(s) (5090), known in the art, may be utilized in the present invention. The humidity sensor(s) (5090) can, without limitation, be positioned in any suitable and effective, location(s), direction(s), angle(s), orientation(s), configuration(s), and/or position(s).

An effective or sufficient amount of administered aerosol (200) within the targeted area(s) (210) can be indicated, without limitation, by any detected, moisture, relative humidity, and/or humidity, data, levels, and/or percentages, (hereinafter called "humidity level(s)). It can also be, without limitation, indicated by one or more of any detected, dew point(s), and/or dew point data or level(s). These various humidity level(s), dew point(s), and/or relative humidity level(s), can be, without limitation, sustained for any effective amount of time, but preferably at least any effective and/or efficacious amount of time, before one or more of any actions and/or any combination of any actions, are taken, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s) (6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210). Without being limited, the effective, sufficient amount, or specified quantity, of administered aerosol (200) into the targeted area(s) (210) and any associated, dew point(s), and/or humidity level(s) or data, can also vary for any intended or unintended reasons or designs, before one or more of any actions and/or any combination of any actions, are taken, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s) (6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210).

The humidity level(s) and/or humidity data within the targeted area(s) (210), can without limitation, rise from any humidity level(s) or data that is detected before any aerosol (200) or vapor(s) is deployed into the targeted area(s) (210), and then reach any other humidity level(s) or data, preferably rising to between about 70-100 percent relative humidity or humidity level(s), and more preferably rising to between about 80-100 percent relative humidity or humidity level(s), and even more preferably rising to between about 84-100 percent relative humidity or humidity level(s), and very preferably rising to between about 85-99 percent relative humidity or humidity level(s), when the targeted area(s) (210) is completely full of aerosol (200) and has reached any quantity, output, density, and/or concentration, of aerosol (200) that is suitable or effective, and/or results in or obtains a level of efficaciousness on the targeted surface(s) that is desired within the targeted area(s) (210).

Without being limited, once any threshold level(s) or targeted humidity data, and/or dew point(s), within the targeted area(s) (210), is reached and/or detected, and preferably once any of the, efficacious, suitable, desired, needed, and/or targeted, humidity level(s) and/or humidity data within the targeted area(s) (210), is reached and/or detected, during one or more of any situation(s) or activity(s) including, but not limited to, during any deployment of any aerosol (200) or vapor(s) into the targeted area(s) (210), one or more of any actions and/or any combination of any actions, at one or more of any suitable and effective time(s), can be taken or executed, such as, but not limited to: (a) extending or modifying the operation or agent(s) deployment time of one or more of any aerosol generator(s) (215), (b) shortening or modifying the operation or agent(s) deployment time of one or more of any aerosol generator(s) (215), (c) shutting down any drive electronics (645) or amplifier(s) (230), (b) shutting down the blower(s) (180) or flow of pressurized air, (d) shutting down the apparatus(s) (215), (e) stopping the production of aerosol (200), (f) stopping the deployment of aerosol (200) into the targeted area(s) (210), (g) stopping the deployment of any agent(s) into the targeted area(s) (210), (h) activating one or more of any dehumidification device(s) (2040) (h) activating one or more of any air filtration apparatus(s) (6040), and/or (j) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210).

In addition, and without limitation, the dew point(s), humidity level(s), and/or humidity data, that is detected before any aerosol (200) or vapor is deployed into the targeted area(s) (210), can potentially effect the total amount of time that is necessary to reach a quantity, output, density, and/or concentration, of aerosol (200) within the targeted area(s) (210), that is effective or gives a level of efficaciousness that is desired. For example, and without limitation, the less humidity that is detected before any aerosol (200) or vapor is deployed into the targeted area(s) (210), typically the longer amount of time it may take to reach a quantity, output, density, and/or concentration, of aerosol (200) within the targeted area(s) (210) that is effective or gives a level of efficaciousness that is desired. Conversely, and without limitation, typically, the more humidity that is detected before any aerosol (200) or vapor is deployed into the targeted area(s) (210), the shorter the amount of time it may take to reach a quantity or concentration of aerosol (200) within the targeted area(s) (210) that is effective or gives a level of efficaciousness that is desired.

For any given temperature, dew point, and/or humidity level, the total amount of time that is needed to expose the various surfaces(s) within the targeted area(s) (210) to the aerosol (200) may also, without limitation, vary, and can include any amount of time between after the deployment of any aerosol (200) into the targeted area(s) (210) has stopped, and the targeted area(s) (210)s are then evacuated of any aerosol (200) and/or vapor in one or more ways, or combination of ways, including, but not limited to, allowing fresh ventilation air to flow through the targeted area(s) (210), operating one or more of any effective dehumidification equipment within the targeted area(s) (210), flowing the atmosphere within the targeted area(s) (210) through one or more of any adequate filter(s) and/or charcoal activated filter(s).

Without being limited, after the one or more apparatus(s) (215) are shut down and/or the deployment of any aerosol(s) (200) into the one or more targeted area(s) (210) has stopped or been terminated, the one or more of any dehumidification device(s) (2040) and/or air filtration apparatus(s) (6040), that process or treat the atmosphere(s) within the targeted area(s) (210), and/or may be located within the targeted area(s) (210), may be activated. However, and without limitation, the dehumidification device(s) (2040) and/or air filtration apparatus(s) (6040), may also be activated at any, or any other, suitable and effective time(s). The dehumidification device(s) (2040) and/or air filtration apparatus(s) (6040), may also, without limitation, operate for any, suitable, efficacious, and/or desirable, amount or length of time(s), after the activation, opening, actuating, and/or unsealing, of one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210).

The one or more of any dehumidification device(s) (2040) may be, without limitation, operated for any, suitable, efficacious, and/or desirable, amount or length of time(s). It is preferred, without limitation, that the dehumidification device(s) (2040) is operated at least long enough to reduce the humidity or relative humidity level(s) in the one or more targeted area(s) (210), to one or more of any, point(s), level(s), or range(s), that is suitable, efficacious, and/or desirable. It is more preferred, without limitation, that the dehumidification device(s) (2040) is operated at least long enough to reduce the humidity or relative humidity level(s) in the one or more targeted area(s) (210), to one or more of any, point(s), level(s), or range(s), that is at least close to or even below the humidity or relative humidity, point(s), level(s), or range(s), that were present in the one or more targeted area(s) (210) before any aerosol(s) (200) was deployed into these area(s), location(s), or space(s) (210).

Without being limited, the one or more of any air filtration apparatus(s) (6040) may also be, without limitation, operated for any, suitable, efficacious, and/or desirable, amount or length of time(s). It is also preferred, without limitation, that the air filtration apparatus(s) (6040) is operated at least long enough to reduce one or more of any substance(s) such as, but not limited to any, vapor(s), dust(s), gas(s), and/or odor(s), in the one or more targeted area(s) (210), down to one or more of any, point(s), level(s), value(s), or range(s), that is suitable, efficacious, and/or desirable. It is also more preferred, without limitation, that the air filtration apparatus(s) (6040) is operated at least long enough to reduce one or more of any substance(s) such as, but not limited to any, vapor(s), dust(s), gas(s), and/or odor(s), in the one or more targeted area(s) (210), to one or more of any, point(s), level(s), value(s), or range(s), that is at least close to or even below the point(s), level(s), value(s), or range(s), of any, vapor(s), dust(s), gas(s), and/or odor(s), that were present in the one or more targeted area(s) (210) before any aerosol(s) (200) was deployed into these area(s), location(s), or space(s) (210).

Referring to FIG. 142, and without being limited, one or more of any independent device(s) (Hereinafter called toxicity detector(s) (6205)) that are known to those skilled in the art and used to sense, detect, and/or report, one or more of any airborne, matter, substance(s), material(s), or agent(s), such as, but not limited to one or more of any, chemical(s), gas(s), molecule(s), biological particle(s), virus(s), and/or bacteria(s), at any time(s), can communicate, in any suitable and effective ways known to those skilled in the art, and preferably with any suitable and effective transceiver(s), with one or more of any, device(s), and equipment(s), as well as any PLC(s) that controls and/or is a component of any device(s) and/or equipment(s) that is utilized in the one or more process(s) to treat the various surfaces within the targeted area(s) (210), and preferably, any PLC(s) that controls one or more of any aerosol producing apparatus(s) (215), and more preferably any PLC(s) (6005) that controls, and/or is located in or at, and/or is a component(s) of, one or more of any, remote controlling device(s) (6010). The toxicity detector(s) (6205) can also, without limitation, be incorporated into the design and construction of various device(s) and equipment(s) such as, but not limited to any, remote aerosol sensor(s) (5010), and/or aerosol producing apparatus(s) (215).

Without being limited, if the toxicity detector(s) (6205) detects one or more of any airborne, matter, substance(s), material(s), or agent(s), and these detected and/or analyzed substance(s) meets one or more of any, criteria, thresholds, and/or established ranges, especially that indicate that the targeted area(s) (210) is filled with any, matter, material(s), or agent(s), such as, but not limited to one or more of any, chemical(s), gas(s), biological particle(s), virus(s), and/or bacteria(s), to render the area(s) contaminated and/or dangerous, the one or more of any, device(s), equipment, as well as any PLC(s) that controls and/or is a component of any device(s) and/or equipment(s) that is utilized in the one or more process(s) to treat the various surfaces within the targeted area(s) (210), and preferably, any PLC(s) that controls one or more of any aerosol producing apparatus(s) (215), and more preferably any PLC(s) (6005) that controls, and/or is located in or at, and/or is a component(s) of, one or more of any, remote controlling device(s) (6010), can take or cause any number of any actions and/or any combination of any actions, at one or more of any suitable and effective time(s), such as, but not limited to: (a) activating any drive electronics (645) or amplifier(s) (230), (b) activating the blower(s) (180) or flow of pressurized air, (c) activating the apparatus(s) (215), (d) activating or starting the production of aerosol (200), (e) starting and continuing the deployment of any aerosol(s) (200) into the targeted area(s) (210), (f) starting the deployment of any agent(s) into the targeted area(s) (210), (g) activating, closing, actuating, and/or sealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), and rendering them closed or sealed, and/or (h) closing and sealing any automated, door(s), window(s), or the like, that access the targeted area(s) (210), where the aerosol(s) (200) or agent(s) that are emitted or delivered from the aerosol generating apparatus(s) (215) are comprised of one or more substance(s) or agent(s) that can decontaminate these space(s) and/or neutralize any of the detected and/or analyzed sub stance(s).

It is preferred, without limitation, that the aerosol(s) (200) or agent(s) that are used to treat the space(s) and surface(s) within the targeted area(s) (210), are emitted or delivered from the aerosol generating apparatus(s) (215) into the one or more targeted area(s) (210) until these space(s) and surface(s) are effectively and suitably treated and/or decontaminated. Without being limited, the one or more toxicity detector(s) (6205) can also monitor and report the progress or status(s) of the one or more treatment(s) of the one or more targeted area(s) (210) to any, equipment(s), device(s), and/or PLC(s) in any location(s).

It is also preferred, without limitation, that when the toxicity detector(s) (6205) in the targeted area(s) (210) have confirmed that all of the one or more targeted area(s) (210) are suitably and effectively treated and/or decontaminated, and all of the various sensing device(s) (5080) that are part of the remote aerosol sensor(s) (5010) confirm that there is a sufficient and effective amount of aerosol(s) within the treated area(s) (210), the one or more of any, device(s), equipment, as well as any PLC(s) that controls and/or is a component of any device(s) and/or equipment(s) that is utilized in the one or more process(es) to treat the various surfaces within the targeted area(s) (210), and preferably, any PLC(s) that controls one or more of any aerosol producing apparatus(s) (215), and more preferably any PLC(s) (6005) that controls, and/or is located in or at, and/or is a component(s) of, one or more of any, remote controlling device(s) (6010), can take or cause any number of any actions and/or any combination of any actions, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s) (6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210).

Without being limited, the one or more remote controlling device(s) (6010) can also be programmed in a manner known in the art, so that the one or more of any dehumidification device(s) (2040) and/or air filtration apparatus(s) (6040) cannot be turned off or shut down, and/or cannot be easily turned off or shut down through one or more software choice(s) or option(s) via any manner known to those in the art, until the level(s), data, and/or concentration(s), of any targeted, vapor(s), dust(s), gas(s), and/or odor(s), within the atmosphere(s) of the one or more targeted area(s), have at least reached, or are even below, one or more of any threshold(s), point(s), level(s), or range(s), that is suitable, efficacious, and/or desirable.

Without being limited, the one or more remote controlling device(s) (6010) can also be programmed, in a manner known in the art, so that it can communicate with one or more of any, sound(s), graphical user interface(s), and/or light(s) of any color, at any time(s), if and/or when the level(s) and/or concentration(s) of any targeted, vapor(s), dust(s), gas(s), and/or odor(s), within the atmosphere(s) of the one or more targeted area(s), have at least reached, or are even below, one or more of any threshold(s), point(s), level(s), or range(s), that is suitable, efficacious, and/or desirable.

The one or more light source(s) (725) and light sensor(s) (730) can be directly or indirectly connected, or they can be placed or positioned independent from one another. The distance between the light source(s) (725) and light sensor(s) (730) can be any distance, but should be at least any suitable or effective distance. It is preferred, without limitation, that the light source(s) (725) and light sensor(s) (730) are separated by a distance of one (1) foot or less. It is more preferred, without limitation, that the light source(s) (725) and light sensor(s) (730) are at separated by a distance between zero to one (1) foot or more. It is even more preferred, without limitation, that the light source(s) (725) and light sensor(s) (730) are separated by a distance between zero and twenty-four inches or more. It is very preferred, without limitation, that the light source(s) (725) and light sensor(s) (730) are separated by a distance between zero to four (4) feet or more. Without being limited, one or more of any effective source(s) of light or light source(s) (725), and one or more of any effective means for sensing any, presence, absence, and/or any change, in light or the amount of light, or light sensor(s) (730), known to those skilled in the art, may be utilized in the present invention. The light source(s) (725) can have, without limitation, any: (a) intensity(s), (b) brightness(s), (c) period(s), (d) frequency(s), (e) type of light(s), (f) wavelength(s), and (g) power(s). Without being limited, the light sensor(s) (730) can have any sensitivity, and sense light with various attributes including, but not limited to any: (a) light intensity(s), (b) light brightness(s), (c) period(s) of light, (d) frequency(s) of light, (e) type of light(s), (f) power(s), (g) presence or absence of light, and/or (h) wavelength(s) of light. It is preferred, without limitation that the one or more of any light source(s) (725) and light sensor(s) (730), that are utilized, have attributes that are at least suitable for their intended application. Each remote aerosol sensor(s) (5010) can, without limitation, consist of at least one or more of any effective laser(s), of any power or class type, for a light source(s) (725), and at least one or more of any photoelectric sensor(s), of any type and sensitivity (730), for a light sensor(s) (730). The one or more light source(s) (725) and one or more light sensor(s) (730) that are utilized can be, without limitation, configured or positioned so that the light sensor(s) (730) receives light in various ways including, but not limited to, directly from one or more light source(s) (725), indirectly from one or more light source(s) (725), from any reflected light that is generated from one or more light sources(s) (725). Any light that is reflected back to the one or more light sensor(s) after being generated by one or more of any light source(s) (725) may reflect off of one or more of any surface(s) or substance(s) including, but not limited to any, aerosol (200), and/or one or more reflecting surface(s) or mirrored surface(s) (hereinafter called "reflector(s)" (5030)). The aerosol (200) may be of any effective, concentration, density, and size. Without being limited, the light source(s) (725) and light sensor(s) (730) may be positioned in one or more of any effective, direction(s), angle(s), orientation(s), configuration(s), and/or position(s). If light from one or more reflected surface(s) or reflector(s) (5030) is utilized, the one or more surface(s) or reflector(s) (5030) from which the light is reflected back to the light sensor(s) (730) can be, without limitation, positioned at one or more of any effective, distance(s), and orientation(s) or angle(s), from the one or more light sensor(s) (730) and one or more light source(s) (725). The reflective surface(s) or reflector(s) (5030) may be, without limitation, any suitable and effective, size(s) and shape(s).

The emitted light or energy, or light source(s) (725) can have, without limitation, one or more of any traits or attributes including, but not limited to, any: (a) intensity(s), (b) brightness(s), (c) period(s), (d) frequency(s), (e) type of light(s), (f) wavelength(s), and (g) power(s). Without being limited, any suitable and effective light source(s) (725) known to those skilled in the art, can be utilized. The one or more light source(s) (725) and light sensor(s) (730) can, without limitation, be controlled and/or communicate with one or more of any digital, electronic, or analog, controller(s) such as, but not limited to, any PLC(s) at any location(s). The means to sense the light (730) can, without limitation, vary widely in its sensitivity and ability to sense any kind of light consisting of any traits or attributes of light including, but not limited to, any: (a) light intensity(s), (b) light brightness(s), (c) period(s) of light, (d) frequency(s) of light, (e) type of light(s), (f) power(s), (g) presence or absence of light, and/or (h) wavelength(s) of light. Any suitable and effective light sensor(s) (730) known to those skilled in the art, can be, without limitation, utilized.

Without being limited, the means to sense the light (730) can also have various capabilities known in the art, including, without limitation, the ability to have any adjustable sensitivity and trigger level(s), and/or the ability to communicate with one or more of any digital, electronic, or analog, controller(s) such as, but not limited to, any PLC(s) at any location(s), and/or any other suitable components, that can also have any adjustable sensitivity and trigger level(s). The light sensor(s) (730) can, without limitation, indicate to or communicate with one or more of any digital, electronic, or analog, controller(s) such as, but not limited to, any PLC(s) at any location(s), if or when it either receives or ceases to receive any trait or attribute pertaining to any light such as, but not limited to, any desired or set level of light stimulus or light intensity. Without being limited, the light sensor(s) (730) can also, indicate to or communicate with, one or more of any digital, electronic, or analog, controller(s) such as, but not limited to, any PLC(s) at any location(s), by way of sending or communicating with, one or more of any, power level(s), voltage(s), signal(s), and/or amperage(s), to communicate any information pertaining to any light that is detected such as, but not limited to, the presence or absence of any light, and/or any, level, intensity, and/or power, of any light, all in a manner known to those skilled in the art.

Without being limited, if or when these one or more of any PLC(s), and preferably the remote PLC(s) (3893) located in or associated with the remote aerosol sensor(s) (5010), and more preferably the PLC(s) (6005) that control and/or are located in or at one or more of any remote controlling device(s) (6010), determine that that the data or conditions reported by one or more of any sensing device(s) that are in or are a part of the (5080) remote aerosol sensor(s) (5010), and preferably by all of the various sensing device(s) (5080) utilized in the remote aerosol sensor(s) (5010), indicate or report that the one or more treated or targeted area(s) (210) is sufficiently, effectively, and/or efficaciously, treated or filled with the deployed or applied agent(s) and/or aerosol(s) (200), the one or more of any PLC(s) in any one or more location(s), can cause or take any number of any actions and/or any combination of any actions, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s) (6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210).

Without being limited, any signal(s) or electrical output from the one or more light sensor(s) (730) can also be amplified by any suitable and effective means for signal or electrical amplification, before the signal(s) or electrical output is received by one or more of any PLC(s) or remote PLC (3893). With reference to FIGS. 119-132 and FIG. 143, and without being limited, a description of a means used to amplify any electrical output or signal(s) from any of the light sensor(s) (730) that may be utilized, is given. Without being limited, one part of the light sensor(s) (730) is connected to a positive DC voltage V+ and another part of the light sensor(s) (730) is connected to an input of any suitable and effective amplifier(s) (6195). Without being limited, an output of the amplifier (6195) is connected to one end of the current sensing resistor (6200) and to any suitable and effective input of the microprocessor or PLC(s) (3893), preferably to the analog input of the microprocessor or PLC(s) (3893). The other end of the current sensing resistor (6200) is connected to ground. Without being limited, any, amplifier (6195), current sensing resistor (6200), and microprocessor or PLC(s) (3893), may be utilized. It is preferred, without limitation, that the amplifier (6195), current sensing resistor (6200), and microprocessor or PLC(s) (3893), are at least suitable and effective. Without being limited, any signal(s) sent by the light sensor(s) (730) produces or allows for any suitable and effective current to flow, preferably a current of at least 0.5 micro-amp.

Without being limited, the one or more amplifier(s) (6195) can amplify one or more electrical characteristics or attributes, that are reported or sent from one or more of any light sensor(s) (730) or any related component(s), such as, but not limited to any, voltage(s), amperage(s), and/or electrical current(s), and at least a sensor voltage(s), sensor amperage(s), and/or sensor current(s), is generated at the output of the amplifier (6195) with the current sensing resistor (6200). Without being limited, the at least sensor voltage(s), sensor amperage(s), and/or sensor current(s), that is either amplified, not amplified, and is received by the microprocessor or PLC(s) (3893), is compared with any, value(s), information, and/or data, stored in the firmware and/or software of the microprocessor or PLC(s) (3893). Without being limited, if the one or more of any, data, information, electrical voltage, amperage, electrical current, and/or signal(s), reported to the microprocessor or PLC(s) (3893) by the light sensor(s) (730), meets one or more of any criteria that indicates that the targeted area(s) is effectively, sufficiently, and/or efficaciously filled with aerosol(s) (200), the microprocessor or PLC(s) (3893) will send one or more of any, signal(s), command(s), information, and/or data, preferably via the one or more transceiver(s) (6000), that will result in or cause any number of any actions and/or any combination of any actions, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s) (6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210).

Without limitation, an effective or sufficient amount of administered aerosol (200) into one or more targeted area(s) (210) can be indicated by its causing any, disruption, diminishment, decrease, or cessation, of the light that is emitted from the light source(s) (725), before it reaches any light sensor(s) (730). Without being limited, the effective or suitable, amount, density, concentration, and/or specified quantity, of administered aerosol (200) into any targeted area(s) (210) can vary for any intended or unintended reasons or designs, and the trigger or sensitivity levels for the light sensor(s) (730) can be, without limitation, varied, calibrated, and/or adjusted, for any amount, degree, or level, of light disruption, that can be sensed for each or any situation and/or any level(s), concentration(s), and/or density(s), of any aerosol(s) that is equated with an efficacious outcome.

Without being limited, the effective, efficacious, and/or sufficient, amount of aerosol(s) within the one or more targeted area(s) (210), can result in any, density and/or concentration(s), of any aerosol(s) in these space(s) (210), and this can relate or correspond to one or more of any value(s) or data(s) related to any light or lack of light, that is sensed at any time, by the one or more light sensor(s) (730), such as, but not limited to any, (a) light intensity(s), (b) light brightness(s), (c) period(s) of light, (d) frequency(s) of light, (e) type of light(s), (f) power(s), (g) presence or absence of light, and/or (h) wavelength(s) of light.

Also, without being limited, the one or more of any concentration(s) and/or density(s) of various aerosol(s) can vary within the targeted area(s) (210) for any intended or unintended reason(s) or design, and the trigger or sensitivity levels of the light sensor(s) (730) can be, without limitation, varied, calibrated, or adjusted, for one or more of any value(s) or data(s) related to any light or lack of light, that is sensed at any time, by the one or more light sensor(s) (730), such as, but not limited to any, (a) light intensity(s), (b) light brightness(s), (c) period(s) of light, (d) frequency(s) of light, (e) type of light(s), (f) power(s), (g) presence or absence of light, and/or (h) wavelength(s) of light, that correspond with or indicate condition(s) that are indicative of the one or more targeted area(s) (210) being filled with an amount of aerosol (200) that is effective, efficacious, sufficient, and/or desired.

One or more remote aerosol sensor(s) (5010), as well as any of its components, including, but not limited to any, temperature sensor(s) (5085), humidity sensor(s) (5090), light source(s) (725), light sensor(s) (730), dew point sensor(s) (3888), and aerosol deposit sensor(s) (3880), can be, without limitation, controlled and/or communicate directly or indirectly with one or more of any, digital, electronic, or analog, controller(s) such as, but not limited to, any PLC(s) at any location(s), and communicate any data, information, status(s), and/or condition(s). The one or more remote aerosol sensor(s) (5010) can also, without limitation, communicate directly or indirectly with one or more of any equipment(s) or device(s) such as, but not limited to any, aerosol generating apparatus(s) (215), and/or one or more of any remote controlling device(s) (6010), in various ways such as, but not limited to any, radio, radio waves, sound, wire, cable, or fiber optics, and communicate any, data, information, status(s), and/or condition(s). Without being limited, any information or data reported by the remote aerosol sensor(s) (5010) to any equipment or device(s), such as, but not limited to, one or more of any, aerosol generating apparatus(s) (215), and/or remote controlling device(s) (6010), can be used by one or more of any of these devices or equipment, to modify and/or control any, operating attributes, variables, or activities, such as, but not limited to any, (a) aerosol deploy time(s) within or into the targeted area(s) (210), (b) dwell time(s) before dehumidification of the atmosphere within the targeted area(s) (210), (c) dwell time(s) before filtering the atmosphere within the targeted area(s) (210), (d) pause in any operation(s) within or affecting the targeted area(s) (210), (e) dehumidification time(s) for the atmosphere within the targeted area(s) (210), (f) filtering time(s) for the atmosphere within the targeted area(s) (210), (g) stoppage of any equipment and/or device(s) within or affecting the targeted area(s) (210) (h) deodorization time(s) for the atmosphere within the targeted area(s) (210) (i) ventilation time(s) of the targeted area(s) (210) by activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), all in order to achieve an outcome in the targeted area(s) (210) that is efficacious, desired, and/or effective.

Any data, information, status, and/or condition(s), reported or communicated by one or more of any remote aerosol sensor(s) (5010) to any, suitable and effective PLC(s) at any suitable and effective location(s), any PLC(s) at any local and/or remote location(s), and/or any equipment(s) or device(s), such as, but not limited to, one or more of any, aerosol generating apparatus(s) (215), and/or remote controlling device(s) (6010), can also be used, without limitation, by any of these, component(s), equipment(s), and/or device(s), to take or execute one or more of any actions and/or any combination of any actions, at one or more of any suitable and effective time(s), such as, but not limited to: (a) extending or modifying the operation or agent(s) deployment time of one or more of any aerosol generator(s) (215), (b) shortening or modifying the operation or agent(s) deployment time of one or more of any aerosol generator(s) (215), (c) shutting down any drive electronics (645) or amplifier(s) (230), (b) shutting down the blower(s) (180) or flow of pressurized air, (d) shutting down the apparatus(s) (215), (e) stopping the production of aerosol (200), (f) stopping the deployment of aerosol (200) into the targeted area(s) (210), (g) stopping the deployment of any agent(s) into the targeted area(s) (210), (h) activating one or more of any dehumidification device(s) (2040) (i) activating one or more of any air filtration apparatus(s) (6040), and/or (j) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210).

Referring to FIGS. 98-102, and FIGS. 119-132, and FIGS. 139-144, it is preferred, without limitation, that each remote aerosol sensor (5010), contains at least one or more of any, digital, electronic, or analog, controller(s) such as, but not limited to, any PLC(s) (Hereinafter called "remote PLC(s)" (3893). It is more preferred, without limitation, that at least one or more suitable and effective remote PLC (3893) is utilized in the design of the remote aerosol sensor(s) (5010). It is also preferred, without limitation, that each remote aerosol sensor(s) (5010) communicates directly or indirectly via one or more of any suitable radio(s), with one or more of any, suitable and effective PLC(s) at any suitable and effective location(s), and/or any PLC(s) at any local and/or remote location(s), equipment and device(s) and their PLC(s), aerosol generating apparatus(s) (215), and/or any remote controlling device(s) (6010). However, the remote aerosol sensor(s) (5010) can also, without limitation, communicate with one or more of any, PLC(s), equipment, device(s), aerosol generating apparatus(s) (215), and/or any remote controlling device(s) (6010), with other means known to those skilled in the art, such as, but not limited to any, sound, fiber optics, or wires, all in a manner known to those skilled in the art.

The location or position of each remote aerosol sensor(s) (5010) within the targeted area(s) (210) can, without limitation, impact the accuracy of the true progress and actual efficaciousness of the treatment within the targeted area(s). One or more of any remote aerosol sensor(s) (5010) may be, without limitation, located at one or more of any location(s) and orientation(s) within the one or more targeted area(s) (210). It is preferred, without limitation, that at least one or more remote aerosol sensor(s) (5010) and/or sensing device(s) (5080) is positioned as close to the highest ceiling surface(s) or at least a higher ceiling surface(s) (Hereinafter called "highest ceiling surface(s)" or "ceiling surface(s)" (5005)), as possible, and is also located as far away from the aerosol generator (215) as possible. This is especially useful in situations where, without limitation, the aerosol (200) fills the targeted area (210) from the floor(s) (5000) to the ceiling(s) (5005). Without being limited, in situations where the targeted area(s) (210) are alternatively filled with aerosol (200) from the ceiling(s) (5005) to the floor(s) (5000), it is preferred, without limitation, that at least one or more remote aerosol sensor(s) (5010) and/or sensing device(s) (5080) is positioned as close to the lowest floor surface(s) or at least a lower floor surface(s) (Hereinafter called "lowest floor surface(s)" or "floor surfaces(s)" (5000)), as possible, and is also located as far away from the aerosol generator (215) as possible.

However, it is more preferred, without limitation, that no matter how the targeted area(s) (210) is filled, and/or initially filled, with any one or more of any aerosol (200), the one or more of any remote aerosol sensor(s) (5010) and its various component(s), is positioned or located in one or more or a plurality of any location(s) such as, but not limited to, (a) near the floor(s) or lowest point(s) within the targeted area(s) (210), and (b) near the ceiling(s) or highest point(s) within the targeted area(s) (210), and (c) any location(s) or positions(s) that are located half way between the floor(s) or lowest point(s) within the targeted area(s) (210) and the ceiling(s) or highest point(s) within the targeted area(s) (210), and (d) any suitable and effective location(s) within the targeted area(s) (210) that are near the aerosol generator(s) (215), and (e) any suitable and effective location(s) within the targeted area(s) (210) that are located as far away from the one or more aerosol generator(s) (215) as possible, and (f) any suitable and effective location(s) near the floor(s) or lowest point(s) within the targeted area(s) (210), that are located as far away from the one or more aerosol generator(s) (215) as possible, and (g) any suitable and effective location(s) near the ceiling(s) or highest point(s) within the targeted area(s) (210), that are located as far away from the one or more aerosol generator(s) (215) as possible.

The one or more of any sensing device(s) (5080), as well as one or more of any light source(s) (725), can be, without limitation, effectively positioned or located within one or more exterior facing cavity(s) or orifice(s) (hereinafter called "sensor cavity(s)" (5070). The sensor cavity(s) (5070) can be any effective, size, shape, or design, and have one or more openings of any size and shape. The sensor cavity(s) (5070) can also, without limitation, connect with or be, one or more of any suitable tunnel(s), or conduit(s). Without being limited, the sensor cavity(s) (5070) can also protrude fully through one or more of any parts(s) of the remote aerosol sensor(s) (5010) and/or its housing(s). It is preferred, without limitation, that the various attributes of the sensor cavity(s) (5070), and any other related component(s), are at least suitable and effective. It is also preferred, without limitation, that any of the one or more sensing device(s) (5080), or even the one or more light source(s) (725), located within the sensor cavity(s) (5070), are protected from any damage by covering or protecting the one or more openings of the sensor cavity(s) (5070) with one or more structure(s) or object(s) such as, but not limited to any protective and suitable, bar(s), cover(s), grate(s), grill(s), or screen(s), (hereinafter called "protective cover(s)" (5075)). The protective cover(s) (5075) can be, without limitation, any suitable and effective thickness, porosity, density, width, design, and construction, to allow the various sensing device(s) (5080) to effectively operate, as well for any light source(s) (725) to emit any effective light, and/or any light sensor(s) (730) to effectively sense any of the generated light, but still all interact with and/or sense the environment or atmosphere that surrounds the remote aerosol sensor(s) (5010), in an effective and efficacious way. It is preferred, without limitation, that the various attributes of the one or more of any sensor cavity(s) (5070), and any protective cover(s) (5075) that are utilized, are at least suitable and effective, especially with regards to the various one or more of any sensing device(s) (5080), or even the one or more light source(s) (725), that may be utilized. Any light source(s) (725) and/or light sensor(s) (730) may also, without limitation, be protected with, or located behind, one or more of any suitable and effective protective cover(s) (5075) such as, but not limited to any, window(s), that would protect these various components from any environment(s) that surrounds the remote aerosol sensor(s) (5010). It is preferred, without limitation, that the various cover(s) (5075) suitably and effectively interface with the housing(s) of the remote aerosol sensor(s) (5010).

Without being limited, the one or more of any sensing device(s) (5080) can have various capabilities and attributes including, but not limited to any, sensitivity, and/or trigger level(s). The sufficient, efficacious, and/or effective, amount of aerosol(s) (200) in the enclosed space or targeted area(s) (210), can be, without limitation, any, amount of aerosol, density of aerosol, and/or concentration of aerosol. Without being limited, to guarantee, maintain, and/or assure, that the remote aerosol sensor(s) (5010) and any of its part(s) or component(s), including but not limited to any, microprocessor or PLC(s) (3893), and/or any sensing device(s) (5080) such as, but not limited to any, light sensor(s) (730), relative humidity sensor(s) (5090), dew point sensor(s) (3888), and/or aerosol deposit sensor(s) (3880), are all able to accurately and effectively indicate when the targeted area(s) are filled with a sufficient, efficacious, and/or effective, amount of aerosol (200), one or more of these component(s), including but not limited to any pertaining software and/or firmware, may need to be calibrated, updated, and/or adjusted, for one or more of any, operational scenarios, operating characteristics or attributes, and/or environmental factors, including, but not limited to any, (a) size of the aerosol(s) that is being sensed, (b) characteristics of the light within the targeted area(s) (210), (c) chemical or molecular characteristics of the aerosol(s), (d) temperature of the atmosphere within the targeted area(s) (210), (e) density or concentration of the aerosol(s), (f) physical characteristics of the aerosol(s), (g) sizes of the targeted area(s) (210), (h) volume of the atmosphere(s) within the targeted area(s) (210), and/or height(s) of the targeted area(s) (210).

The one or more of any sensing device(s) (5080) can also have, without limitation, the capability or functionality, to be controlled and/or communicate with one or more of any digital, electronic, or analog, controller(s) such as, but not limited to, any suitable and effective PLC(s) at any suitable and effective location(s), and/or any PLC(s) at any local and/or remote location(s). It is preferred, without limitation, that the various components of the remote aerosol sensor(s) (5010) communicate with at least one or more of any suitable and effective PLC(s) that is incorporated into the design of the remote aerosol sensor(s) (5010). It is more preferred, without limitation, that the various components of the remote aerosol sensor(s) (5010) directly or indirectly communicate with at least one or more of any PLC(s) that is incorporated into the design of the remote aerosol sensor(s) (5010), as well as one or more of any other PLC(s), at any time(s), that are a part of and/or control, various device(s) and equipment(s) that are used in the one or more process(es) utilized to treat the various surface(s) within the targeted area(s) (210) such as, but not limited to any, (a) remote controlling device(s) (6010), (b) aerosol generator(s) (215), (c) vent sealing device(s) (6020) and/or vent covering assembly(s) (2300), that are located within the one or more room(s) and/or targeted area(s) (210), (d) any dehumidification device(s) (2040) that may or may not be connected to, and/or operated with, any air filtration apparatus(s) (6040), (e) mixing apparatus(s) used to mix and feed one or more of any deployable agent(s), and/or (f) apparatus(s) used to externally fill or feed any aerosol generator(s) (215).

Any data or information that is collected and reported by any sensing devices (5080), or any other components of the remote aerosol sensor(s) (5010), to any suitable and effective PLC(s) at any suitable and effective location(s), and/or any PLC(s) at any local and/or remote location(s) can, without limitation, result in one or more of any action(s), and/or any number and/or combination of any actions, at one or more of any suitable and effective time(s), to take place or transpire, such as, but not limited to: (a) extending or modifying the operation or agent(s) deployment time of one or more of any aerosol generator(s) (215), (b) shortening or modifying the operation or agent(s) deployment time of one or more of any aerosol generator(s) (215), (c) shutting down any drive electronics (645) or amplifier(s) (230), (b) shutting down the blower(s) (180) or flow of pressurized air, (d) shutting down the apparatus(s) (215), (e) stopping the production of aerosol (200), (f) stopping the deployment of aerosol (200) into the targeted area(s) (210), (g) stopping the deployment of any agent(s) into the targeted area(s) (210), (h) activating one or more of any dehumidification device(s) (2040) (i) activating one or more of any air filtration apparatus(s) (6040), and/or (j) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210).

In addition, any data or information that is collected and reported by any sensing devices (5080), or any other components of the remote aerosol sensor(s) (5010), to any suitable and effective PLC(s) at any suitable and effective location(s), and/or any PLC(s) at any local and/or remote location(s) can, without limitation, result in one or more of any delay of any suitable and effective amount of time(s) before one or more of any action(s), and/or any number and/or combination of any actions, at one or more of any suitable and effective time(s), take place or transpire, such as, but not limited to: (a) extending or modifying the operation or agent(s) deployment time of one or more of any aerosol generator(s) (215), (b) shortening or modifying the operation or agent(s) deployment time of one or more of any aerosol generator(s) (215), (c) shutting down any drive electronics (645) or amplifier(s) (230), (b) shutting down the blower(s) (180) or flow of pressurized air, (d) shutting down the apparatus(s) (215), (e) stopping the production of aerosol (200), (f) stopping the deployment of aerosol (200) into the targeted area(s) (210), (g) stopping the deployment of any agent(s) into the targeted area(s) (210), (h) activating one or more of any dehumidification device(s) (2040) (i) activating one or more of any air filtration apparatus(s) (6040), and/or (j) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210).

It is preferred, without limitation, that any, data, reported data, information, and/or any signal(s) from one or more of any remote aerosol sensor(s) (5010) that is located the furthest distance(s) within the targeted area(s) (210), from the one or more aerosol generating apparatus(s) (215), is utilized to determine the timing, completion, and/or execution, of one or more of any action(s), and/or any number and/or combination of any actions, at one or more of any suitable and effective time(s), to take place or transpire, such as, but not limited to: (a) extending or modifying the operation or agent(s) deployment time of one or more of any aerosol generator(s) (215), (b) shortening or modifying the operation or agent(s) deployment time of one or more of any aerosol generator(s) (215), (c) shutting down any drive electronics (645) or amplifier(s) (230), (b) shutting down the blower(s) (180) or flow of pressurized air, (d) shutting down the apparatus(s) (215), (e) stopping the production of aerosol (200), (f) stopping the deployment of aerosol (200) into the targeted area(s) (210), (g) stopping the deployment of any agent(s) into the targeted area(s) (210), (h) activating one or more of any dehumidification device(s) (2040) (i) activating one or more of any air filtration apparatus(s) (6040), (j) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), (k) determining if any time delay is needed before either shutting down the one or more of any apparatus(s) (215) and/or stopping the application or deployment of any aerosol (200) into the targeted area(s) (210), and/or (l) calculating or determining any time delay that may be needed for an efficacious or successful outcome from the deployment of the aerosol (200), before either shutting down the one or more of any aerosol generating apparatus(s) (215) and/or stopping the application or deployment of any aerosol (200) into the targeted area(s) (210).

Without being limited, instead of using any time delay(s) as previously mentioned, any digital, electronic, or analog, controller(s) such as, but not limited to, any PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(s) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010), can, without limitation, solely refer to or utilize any data or information from any one or more remote aerosol sensor(s) (5010) that reports or communicates any data that has not significantly differed, and/or has had the least amount of differing data, from any of it's data that was reported before or just prior to any aerosol (200) or vapor that is deployed into the targeted area(s) (210), in order to determine if or when an efficacious or sufficient amount of aerosol (200) is present in the entire targeted area(s) (210), so that one or more of any actions and/or any combination of any actions, at one or more of any suitable and effective time(s), can be taken or executed, such as, but not limited to: (a) extending or modifying the operation or agent(s) deployment time of one or more of any aerosol generator(s) (215), (b) shortening or modifying the operation or agent(s) deployment time of one or more of any aerosol generator(s) (215), (c) shutting down any drive electronics (645) or amplifier(s) (230), (b) shutting down the blower(s) (180) or flow of pressurized air, (d) shutting down the apparatus(s) (215), (e) stopping the production of aerosol (200), (f) stopping the deployment of aerosol (200) into the targeted area(s) (210), (g) stopping the deployment of any agent(s) into the targeted area(s) (210), (h) activating one or more of any dehumidification device(s) (2040) (i) activating one or more of any air filtration apparatus(s) (6040), and/or (j) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210).

It is preferred, without limitation, that the information or data from the last remote aerosol sensor(s) (5010) that reports any information or data, or any number of any combination(s) of any information or data, such as, but not limited to any, (a) the lowest humidity level(s), (b) sensing with any relative humidity sensor(s) (5090), any humidity related data or humidity level(s) that is below one or more of any established threshold(s) for any humidity data or level(s), (c) sensing with any relative humidity sensor(s) (5090), any humidity related data or humidity level(s) that is above one or more of any established threshold(s) for any humidity data or level(s), (d) highest temperature(s), (e) sensing with any light sensor(s) (730), any absence of light from any light source(s) (725), (f) sensing with any light sensor(s) (730), any presence of light from any light source (s) (725), (g) sensing with any light light sensor(s) (730), the weakest presence of light from any light source(s) (725), (h) sensing with any light sensor(s) (730), the strongest presence of light from any light source(s) (725), (i) sensing with any light sensor(s) (730), any light that is below one or more of any established threshold of any light presence from any light source(s) (725), (j) sensing with any light sensor(s) (730), any light that is above one or more of any established threshold of any light presence from any light source(s) (725), (k) the absence of any signal, current, and/or amperage from any aerosol deposit sensor(s) (3880), (l) the absence of any significant signal, current, and/or amperage from any aerosol deposit sensor(s) (3880), (m) sensing the lowest signal, current, and/or amperage from any aerosol deposit sensor(s) (3880), is utilized by one or more of any PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(s) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010), to determine if or when an efficacious or sufficient amount of aerosol (200) is present in all of the targeted area(s) (210) so that one or more of any actions and/or any combination of any actions, at one or more of any suitable and effective time(s), can be taken or executed, such as, but not limited to: (a) extending or modifying the operation or agent(s) deployment time of one or more of any aerosol generator(s) (215), (b) shortening or modifying the operation or agent(s) deployment time of one or more of any aerosol generator(s) (215), (c) shutting down any drive electronics (645) or amplifier(s) (230), (b) shutting down the blower(s) (180) or flow of pressurized air, (d) shutting down the apparatus(s) (215), (e) stopping the production of aerosol (200), (f) stopping the deployment of aerosol (200) into the targeted area(s) (210), (g) stopping the deployment of any agent(s) into the targeted area(s) (210), (h) activating one or more of any dehumidification device(s) (2040) (i) activating one or more of any air filtration apparatus(s) (6040), and/or (j) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210).

This referencing of certain remote aerosol sensor(s) (5010) within the targeted area(s) (210), by any PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(es) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010), based on certain criteria for any of their reported data value(s) or information, or after comparing any of their reported data or information with any of the reported data from one or more of any other remote aerosol sensor(s) (5010), and/or utilizing any time extensions to accommodate for variables such as, but not limited to any, (a) temperature(s), (b) humidity level(s), (c) deposited aerosol status(s) reported by any aerosol deposit sensor(s) (3880), (d) light detection status(s) reported by any light sensor(s) (730), all in order to effectively manage and control the efficacious operation of various equipment(s) and device(s) such as, but not limited to any, aerosol generating apparatus(s) (215), vent sealing device(s) (6020) and/or vent covering assembly(s) (2300), and/or dehumidification device(s) (2040), within the same targeted area(s) (210), can be, without limitation, utilized to compensate for one or more of any circumstances such as, but not limited to, (a) any elevated temperature anomalies that may be detected in one or more location(s) within the targeted area(s) (210), or (b) where one or more remote aerosol sensor(s) (5010) within the targeted area(s) (210) may be immersed within the deployed aerosol (200) and reporting the presence of an efficacious amount of aerosol (200), or conditions to indicate an efficacious amount of aerosol (200) is present, while one or more additional remote aerosol sensor(s) (5010) report either the absence or insufficient amount of deployed aerosol (200) within the targeted area(s) (210) because they are positioned in locations of the targeted area(s) (210) that have not been filled, or not adequately filled, with the deployed aerosol (200). Without being limited, it is important to note that depending on how the various, PLC(s), light sensor(s) (730), and/or light source(s) (725) are positioned, located, utilized, and/or programmed, the presence of an efficacious or sufficient amount of aerosol (200) in the targeted area(s) (210), can be indicated by various situations or conditions including, but not limited to: (a) the detection of a certain or sufficient amount of light or one or more of any variables pertaining to light, typically and without limitation, because a certain amount of light emitted by the light source(s) (725) that is indicative of the targeted area(s) (210) being filled with an efficacious or effective amount of aerosol(s) (200), has reflected off the aerosol(s) (200) in these spaces and has been detected by the light sensor(s) (730) and/or (b) the failure to detect a certain or sufficient amount of light or one or more of any variables pertaining to light, because the deployed aerosol(s) (200) has blocked the transmission or passage of light from the light source(s) (725) to the light sensor(s) (730).

It is preferred, without limitation, that all of the light sensor(s) (730) located in all of the various remote aerosol sensor(s) (5010) positioned within the targeted area(s) (210), must report to any one or more PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(es) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010), the presence of an efficacious or sufficient amount of aerosol (200) before the production and/or deployment of any aerosol(s) (200) into the targeted area(s) (210) can be terminated.

It is more preferred, without limitation, that before the production and/or deployment of aerosol (200) into the targeted area(s) (210) is terminated, various attributes or conditions must be met such as, but not limited to, (a) all humidity sensor(s) (5090) that are utilized within the targeted area(s) (210) must report a humidity level that is preferably at least between about 70-100 percent relative humidity or humidity level(s), and more preferably between about 80-100 percent relative humidity or humidity level(s), and even more preferably between about 84-100 percent relative humidity or humidity level(s), and very preferably between about 85-99 percent relative humidity or humidity level(s), when the targeted area(s) (210) is completely full of aerosol (200) and has reached any quantity, output, density, and/or concentration, of aerosol (200) that is suitable or effective, and (b) any light sensor(s) (730) that are also utilized in the targeted area(s) (210) must also report the presence of an efficacious or sufficient amount of deployed aerosol(s) (200) within the targeted area(s) (210), where all of this data and information is reported to any one or more PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(es) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010).

It is even more preferred, without limitation, that before the production and/or deployment of aerosol (200) into the targeted area(s) (210) is terminated, various attributes or conditions must be met such as, but not limited to, (a) all of the aerosol deposit sensor(s) (3880) that are utilized within the targeted area(s) (210) must report the presence of an efficacious or sufficient amount of deployed aerosol(s) (200) within the targeted area(s) (210), and (b) all humidity sensor(s) (5090) that are utilized within the targeted area(s) (210) must report a humidity level that is preferably at least between about 70-100 percent relative humidity or humidity level(s), and more preferably between about 80-100 percent relative humidity or humidity level(s), and even more preferably between about 84-99 percent relative humidity or humidity level(s), and very preferably between and including about 85-100 percent relative humidity or humidity level(s), when the targeted area(s) (210) is completely full of aerosol (200) and has reached any quantity, output, density, and/or concentration, of aerosol (200) that is suitable or effective, and (c) any light sensor(s) (730) that are also utilized in the targeted area(s) (210) must also report or indicate the presence of an efficacious or sufficient amount of deployed aerosol(s) (200) within the targeted area(s) (210), where all of this data and information is reported to any one or more PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(es) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010).

Without being limited, the one or more of any aerosol producing apparatus(s) (215) may also operate and/or deploy any aerosol(s) (200) into the targeted area(s) (210), for any number of any extra or additional duration(s) or amount(s) of, time(s), and/or cycle time(s), that are additional to or beyond, the original operating time(s) or aerosol (200) deployment time(s) or cycle(s), that were selected, chosen, or determined, by any means, for the initial or originally planned operating time(s) or cycle(s) that the aerosol producing apparatus(s) (215) was programmed, planned, or selected, to run.

This extended time for deploying any agent(s) and/or aerosol(s) into the one or more targeted area(s) (210) can transpire or be utilized, without being limited, for one or more reasons such as, but not limited to, (a) one or more of any, error(s), malfunction(s), and/or conflicting data, that may be associated with and/or reported by, one or more of any remote aerosol sensor(s) (5010) and/or sensing device(s) (5080), at any time, that are positioned in one or more of any location(s) in one or more of any targeted area(s) (210), at any time(s), (b) the failure to reach, detect, and/or attain, one or more of, and/or any number of any combination(s) of, and/or even all of, various detectable condition(s), at one or more of any location(s) in one or more of any targeted area(s) (210), by the one or more remote aerosol sensor(s) (5010) and it's one or more of any sensing device(s) (5080), at any time(s), such as, but not limited to, any desired, sufficient, efficacious, and/or effective, (a) humidity level(s), (b) temperature(s), (c) aerosol (200) concentration level(s), (d) aerosol (200) density level(s), and/or (e) amount(s) of aerosol (200) that is deposited onto the one or more aerosol deposit sensor(s) (3880) and/or any other surface(s) of the remote aerosol sensor(s) (5010).

Without being limited, this extended time for deploying any agent(s) and/or aerosol(s) into the one or more targeted area(s) (210) may happen, transpire, or be utilized, at one or more of any suitable and effective time(s), to make certain or assure that the one or more treated or targeted area(s) (210) are sufficiently or efficaciously treated or filled with the deployed or applied agent(s) and/or aerosol(s) (200). It is preferred, without limitation, that these additional durations or amounts of aerosol (200) deployment time(s) or operation time(s) for the aerosol producing apparatus(s) (215), are at least suitable and effective. If any extra or additional aerosol (200) deployment time(s) or cycle time(s) are utilized, it is preferred, without limitation, that this additional time(s) or cycle time(s) is at least less than or equal to the original aerosol (200) deployment time(s) or operation cycle time(s) that were selected, chosen, utilized, and/or determined, by any means. If any extra or additional aerosol (200) deployment time(s) or cycle time(s) are utilized, it is more preferred, without limitation, that this additional aerosol deployment time(s) or cycle time(s) is at least one minute or more. If any extra or additional aerosol (200) deployment time(s) or cycle time(s) are utilized, it is even more preferred, without limitation, that this additional aerosol deployment time(s) or cycle time(s) is at least sixty minutes or less. If any extra or additional aerosol (200) deployment time(s) or cycle time(s) are utilized, it is very preferred, without limitation, that this additional aerosol deployment time(s) or cycle time(s) is less than thirty minutes. If any extra or additional aerosol (200) deployment time(s) or cycle time(s) are utilized, it is extremely preferred, without limitation, that this additional aerosol deployment time(s) or cycle time(s) is between about five to twenty minutes.

According to an embodiment, and according to FIGS. 98-102, the remote aerosol sensor(s) (5010) can incorporate and utilize one or more of any light source(s) (725) in combination with one or more of any light sensor(s) (730), all in one or more of any of its various possible configurations. In the first aspect, one or more light source(s) (725) can be, without limitation, effectively located opposite to one or more light sensor(s) (730). It is preferred, without limitation, that the one or more light source(s) (725) can be, without limitation, directly or indirectly connected to, or located within, one or more housing(s) of the remote aerosol sensor(s) (5010), and the one or more light sensor(s) (730) is externally located to the one or more light source(s) (725) at any effective distance, and effectively faces or approximately faces, the light source(s) (725). It is also preferred, without limitation, that the light sensor(s) (730) is positioned, located, or attached to, one or more mounting extension(s) (5035). The mounting extension(s) (5035) can be, without limitation, designed and constructed, and directly or indirectly attach to the remote aerosol sensor(s) (5010), all in any manner known to those skilled in the art. The mounting extension(s) (5035) can be, without limitation, permanently positioned or located. The mounting extension(s) (5035) and/or the light sensor(s) (730) can also be, without limitation, moved in any way into any suitable position or into any suitable length and/or height, to effectively position the light sensor(s) (730), all in a manner known to those skilled in the art. It is preferred, without limitation, that the mounting extension(s) (5035) can be designed and constructed in a manner known in the art, so it can be, without limitation, extended, retracted, or telescope, to any effective length. In addition, the mounting extension(s) (5035) can also, without limitation, be designed and constructed in a manner known in the art, so it can move and lock into one or more of any effective location(s), position(s), or place(s) when needed or desired. It is preferred, without limitation, that the light sensor(s) (730) can be repeatedly moved to the same approximate, location, orientation, and/or distance, each time that it is moved. The light source(s) (725) and light sensor(s) (730) can also, without limitation, switch places or locations, which discloses this first aspect in an alternative form.

In the second aspect, one or more of both the light source(s) (725) and light sensor(s) (730) can be, without limitation, effectively located opposite to one or more of any reflecting surface(s), mirrored surface(s), or reflector(s) (5030). It is preferred, without limitation, that the light source(s) (725), light sensor(s) (730), and reflector(s) (5030), are all positioned at effective angle(s) and/or locations so that the various components may work effectively together to determine if or when an efficacious or sufficient amount of aerosol (200) is present in the targeted area(s) (210). The various components may also, without limitation, be positioned at any effective height relative to one another. It is preferred, without limitation, that the one or more of both the light source(s) (725) and light sensor(s) (730) can be, without limitation, directly or indirectly connected to, or located anywhere effectively within, one or more housing(s) of the remote aerosol sensor(s) (5010), and one or more reflector(s) (5030) is externally located to the remote aerosol sensor(s) (5010) at any effective distance, and effectively faces or approximately faces the light source(s) (725) and light sensor(s) (730). It is preferred, without limitation, that the reflector(s) (5030) is positioned and angled sufficiently so that a sufficient amount of light from the light source(s) (725) is effectively reflected back into the light sensor(s) (730).

The distance between both the light source(s) (725) and light sensor(s) (730), and the reflector(s) (5030), can be, without limitation, any distance, but should be at least an effective distance. The distance between both the light source(s) (725) and light sensor(s) (730), and the reflector(s) (5030), can be, without limitation, separated by a distance of one (1) foot or less. However, it is preferred, without limitation, that the distance between both the light source(s) (725) and light sensor(s) (730), and the reflector(s) (5030), is at least one (1) foot or more. It is more preferred, without limitation, that the distance between both the light source(s) (725) and light sensor(s) (730), and the reflector(s) (5030), is at least two (2) feet or more. It is even more preferred, without limitation, that the distance between both the light source(s) (725) and light sensor(s) (730), and the reflector(s) (5030), is at least four (4) feet or more.

It is preferred, without limitation, that both the light source(s) (725) and light sensor(s) (730) can be, without limitation, directly or indirectly connected to, or located within, one or more housing(s) of the remote aerosol sensor(s) (5010), and the one or more reflector(s) (5030) is externally located to both the light source(s) (725) and light sensor(s) (730), at any effective distance, and faces or approximately faces, both the light source(s) (725) and light sensor(s) (730). It is also preferred, without limitation, that the reflector(s) (5030) is positioned, located, or attached to, one or more mounting extension(s) (5035). The mounting extension(s) (5035) can be, without limitation, designed and constructed, and directly or indirectly attach to the remote aerosol sensor(s) (5010), all in any manner known to those skilled in the art. The mounting extension(s) (5035) can be, without limitation, permanently positioned or located. The mounting extension(s) (5035) and/or the reflector(s) (5030) can also be, without limitation, moved in any way into any suitable position or into any suitable length and/or height, to effectively position the reflector(s) (5030), all in a manner known to those skilled in the art. It is preferred, without limitation, that the mounting extension(s) (5035) can be designed and constructed in a manner known in the art, so it can be, without limitation, extended, retracted, or telescope, to any effective length. In addition, the mounting extension(s) (5035) can also, without limitation, be designed and constructed in a manner known in the art, so it can move and lock into an effective location or place when needed or desired. It is preferred, without limitation, that the reflector(s) (5030) can be repeatedly moved to the same approximate, location, orientation, and/or distance, each time that it is moved. Both the light source(s) (725) and light sensor(s) (730), and reflector(s) (5030), can also, without limitation, switch places or locations, which discloses this first aspect in an alternative form.

In the third aspect, one or more of both the light source(s) (725) and light sensor(s) (730) can be, without limitation, effectively located in the same area and pointed in the same direction and monitor one or more of any sized part and/or area(s) of the targeted area(s) (210). Without being limited, the arrangement of the light source(s) (725) and light sensor(s) (730) in this manner, can form or construct the basis for the one or more of any reflective aerosol detector(s) (6095) that can be integrated into or included in the design of the remote aerosol sensor(s) (5010), as further described below. It is preferred, without limitation, that the light source(s) (725) and light sensor(s) (730), are all positioned at effective angle(s) and/or locations so that the various components may work effectively together to determine if or when an efficacious or sufficient amount of aerosol (200) is present in the targeted area(s) (210). The various components may also, without limitation, be positioned at any effective height relative to one another. It is preferred, without limitation, that the one or more of both the light source(s) (725) and light sensor(s) (730) can be, without limitation, directly or indirectly connected to, or located anywhere effectively within, one or more housing(s) of the remote aerosol sensor(s) (5010). It is preferred, without limitation, that both the light source(s) (725) and light sensor(s) (730) are configured so that a sufficient amount of light that emanates from the light source(s) (725) is reflected off of any aerosol (200) that may be present in the targeted area(s) (210) and back to the light sensor(s) (730) where this reflected light is sensed by the light sensor(s) (730).

Without being limited, the effective, efficacious, and/or sufficient, amount of aerosol(s) within the one or more targeted area(s) (210), can result in any, density and/or concentration(s), of any aerosol(s) in these space(s) (210), and this can relate or correspond to one or more of any value(s) or data(s) related to any light sensed, at any time, by the one or more light sensor(s) (730), such as, but not limited to any, (a) light intensity(s), (b) light brightness(s), (c) period(s) of light, (d) frequency(s) of light, (e) type of light(s), (f) presence or absence of light, and/or (g) wavelength(s) of light.

Also, without being limited, the one or more of any concentration(s) and/or density(s) of various aerosol(s) can vary within the targeted area(s) (210) for any intended or unintended reason(s) or design, and the trigger or sensitivity levels of the light sensor(s) (730) can be, without limitation, varied, calibrated, or adjusted, for one or more of any value(s) or data(s) related to any reflected light sensed at any time, by the one or more light sensor(s) (730), such as, but not limited to any, (a) light intensity(s), (b) light brightness(s), (c) period(s) of light, (d) frequency(s) of light, (e) type of light(s), (f) presence or absence of light, and/or (g) wavelength(s) of light, that correspond with or indicate condition(s) that are indicative of the one or more targeted area(s) (210) being filled with an amount of aerosol (200) that is effective, efficacious, sufficient, and/or desired.

Any transmitted, data, information, and/or signal(s), regarding any reflected light that is collected and communicated from the light sensor(s) (730), can be used by any one or more PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(s) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010), to determine if or when an efficacious or sufficient amount of aerosol (200) is present in the entire targeted area(s) (210), so that the production and/or deployment of aerosol (200) into the targeted area(s) (210) can be terminated. It is preferred, without limitation, that both the light source(s) (725) and light sensor(s) (730) are positioned and angled sufficiently so that a sufficient amount of light from the light source(s) (725) is effectively reflected back into the light sensor(s) (730). The light source(s) (725) and light sensor(s) (730) can be separated by any effective distance.

With reference to FIGS. 98-102, and FIGS. 119-132, and FIGS. 139-143, and without being limited, any, data, information, signal(s), sensor voltage, sensor amperage, electrical signal(s), and/or sensor current, that is reported or sent by any light sensor(s) (730) and any associated component(s), can also be amplified, with any suitable and effective means for amplification (6195), including the amplification means shown in FIG. 143, and described later when the more preferred description of the remote aerosol sensor(s) (5010) is given, before it is received by any part(s) or component(s) such as, but not limited to any, sensor(s) (3897), and/or one or more of any PLC(s), and preferably any PLC(s) (3893) that controls and/or is a component of any remote aerosol sensor(s) (5010).

Without being limited, the sensing circuit that is shown in FIG. 143, can amplify the small, and/or any, electrical current, amperage, and/or electrical voltage, changes, that may be reported by any light sensor(s) (730) so that the one or more of any suitable and effective sensor(s) (3897), and/or one or more of any PLC(s), and preferably any PLC(s) (3893) that controls and/or is a component of any remote aerosol sensor(s) (5010), can see larger changes, and/or be able to effectively detect any changes, in any, signal(s), sensor voltage, sensor amperage, electrical signal(s), and/or sensor current, that is reported or sent by any light sensor(s) (730) and any associated component(s).

Without limitation, any suitable and effective, current(s), voltage(s), and/or amperage(s), can be used to communicate or indicate, from any, light sensor(s) (730), device(s), component(s), sensing device(s) (5080), and/or means to amplify any signal(s) (6195), to any suitable and effective, sensor(s) (3897), and/or one or more of any PLC(s), and preferably any PLC(s) (3893) that controls and/or is a component of any remote aerosol sensor(s) (5010), any one or more condition(s) or environment(s) that the one or more sensing device(s) (5080) and/or light sensor(s) (730), are experiencing.

Without being limited, any suitable and effective, power level(s) data, information, signal(s), voltage(s), sensor voltage(s), amperage(s), sensor amperage(s), electrical signal(s), and/or sensor current(s), can be reported, sent, communicated, and/or shared, by any light sensor(s) (730) and any associated component(s), with or to any part(s) or component(s) such as, but not limited to any, sensor(s) (3897), and/or one or more of any PLC(s), and preferably any PLC(s) (3893) that controls and/or is a component of any remote aerosol sensor(s) (5010).

It is preferred, without limitation, that a voltage between 0-24 Volts or more, and more preferred, without limitation, that a voltage less than or about 24 Volts, and even more preferred, without limitation, that a voltage between 0-15 Volts, and very preferred, without limitation, that a voltage between 1-6 Volts, and extremely preferred, without limitation, that a voltage between 4-6 Volts, is used to communicate with or send electrical signal(s) to, the one or more sensor(s) (3897), and/or one or more of any PLC(s), and preferably any PLC(s) (3893) that controls and/or is a component of any remote aerosol sensor(s) (5010), from the various light sensor(s) (730). In addition, and without limitation, it is preferred, that an amperage between 0-20 Amps or more, and more preferred, that an amperage less than or about 20 Amps, and even more preferred an amperage between 0 to 1.0 Amps, and very preferred an amperage of 0.5 nA or greater Amps, and extremely preferred an amperage between about 0.5 nA to 1.0 Amps, is also utilized to communicate with or send electrical signal(s) to, the one or more sensor(s) (3897), and/or one or more of any PLC(s), and preferably any PLC(s) (3893) that controls and/or is a component of any remote aerosol sensor(s) (5010), from the various light sensor(s) (730).

The output of the means for amplification (6195) can be, without being limited, communicated to or fed into any suitable and effective comparator, known to those skilled in the art, directly and/or indirectly, and compared to any set reference(s), and/or it can be communicated to or fed into one or more analog input(s) of any suitable and effective micro-controller(s) or PLC(s), and any comparison(s), computation(s), and/or analysis, can be done in any firmware and/or software, all in a manner known to those skilled in the art. Any suitable and effective means can be used to monitor the aforementioned voltage(s) and/or make any decision(s) and/or cause various action(s) to result, by processing the communicated voltage(s). It is preferred, without limitation, that this means for monitoring is at least one or more of any suitable and effective devices(s) that can communicate with one or more of any PLC(s), and more preferably this means for monitoring is one or more of any suitable and effective PLC(s) at any suitable and effective location(s), and even more preferably this means for monitoring is one or more of any PLC(s) that controls and/or is a component of any remote aerosol sensor(s) (5010).

Without being limited, any, data, information, signal(s), sensor voltage(s), sensor amperage(s), and/or sensor current(s), that is reported or sent, and/or not reported or sent, by any light sensor(s) (730) and any associated component(s), and received by any microprocessor(s) or PLC(s) (3893), may be reported at any time(s) via any suitable and effective means known to those skilled in the art, including, but not limited to any, transceiver(s) (6000), to one or more of any PLC(s) at any suitable and effective location(s), and preferably any PLC(s) that controls and/or is a component of any device(s) and/or equipment(s) that is utilized in the one or more process(s) to treat the various surfaces within the targeted area(s) (210), and more preferably, any PLC(s) that controls one or more of any aerosol producing apparatus(s) (215), and even more preferably any PLC(s) (6005) that controls, and/or is located in or at, and/or is a component(s) of, one or more of any, remote controlling device(s) (6010).

However, it is preferred, without limitation, that any sensor voltage, sensor amperage, and/or sensor current, that is reported or sent, and/or not reported or sent, by any light sensor(s) (730) and any associated component(s), and that is received by the microprocessor(s) or PLC(s) (3893), is compared with any value(s) or data stored in any firmware and/or software of the microprocessor(s) or PLC(s) (3893). Furthermore, and without being limited, if any reported sensor voltage, sensor amperage, and/or sensor current, meets any one or more criteria or condition(s), that indicates that the targeted area(s) are effectively, suitably, and/or efficaciously filled with aerosol (200), the microprocessor(s) or PLC(s) (3893) will send one or more of any, signal(s), command(s), information, and/or data, preferably via the one or more transceiver(s) (6000), that can result in or cause any number of any actions and/or any combination of any actions, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s)

(6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), because a sufficient, efficacious, and/or effective, amount of aerosol (200) is present or contained in the enclosed space or targeted area(s) (210) being treated.

Without being limited, the presence of an effective or sufficient amount(s) of administered aerosol(s) (200) within one or more targeted area(s) (210) can be indicated by their interaction with the light that is emitted by any light source(s) (725), and any effect(s) that this may have on what is sensed by any light sensor(s) (730). This interaction of the deployed aerosol(s) (200) in the targeted area(s) (210) with any light that is emitted by any light source(s) (725), and is then received by any light sensor(s) (730), can cause the light sensor(s) (730) to emit, send, and/or communicate, any, current(s), voltage(s), and/or amperage(s), and/or any change in any, current(s), voltage(s), and/or amperage(s), to one or more of any PLC(s), and more preferably one or more of any suitable and effective PLC(s) at any suitable and effective location(s), and even more preferably one or more of any PLC(s) that controls and/or is a component of any remote aerosol sensor(s) (5010), at any time(s).

In one possible situation, and without limitation, as more aerosol(s) (200) are deployed into the targeted area(s) (210), the light sensor(s) (730) sense more light that is emitted by the light source(s) (725) and that is reflected by these aerosol(s) (200). The light sensor(s) (730) can report these one or more situation(s), status(s), and/or level(s), of any sensed light, to one or more of any PLC(s), and more preferably one or more of any suitable and effective PLC(s) at any suitable and effective location(s), and even more preferably one or more of any PLC(s) that controls and/or is a component of any remote aerosol sensor(s) (5010). The light sensor(s) (730) can report any sensed, aerosol concentration(s), aerosol density(s), and/or any suitable, effective, and/or efficacious amount(s), of any aerosol(s), via one or more of any status(s) or level(s) and/or one or more of any change(s) in any, status(s) or level(s), of any electrical, current(s), voltage(s), and/or amperage(s), that can be reported by the light sensor(s) (730) to one or more of any PLC(s), and more preferably one or more of any suitable and effective PLC(s) at any suitable and effective location(s), and even more preferably one or more of any PLC(s) that controls and/or is a component of any remote aerosol sensor(s) (5010). It is preferred, without limitation, that in this configuration the light sensor(s) (730) report or communicate increasing status(s) or level(s), of any electrical, current(s), voltage(s), and/or amperage(s), to any PLC(s), as more light is reflected by the increasing amount(s) of aerosol(s) (200) back to the one more light sensor(s) (730).

Without being limited, any, data, information, sensor voltage, sensor amperage, and/or sensor current, that is reported or sent by any light sensor(s) (730), and/or any associated component(s), and that is received by the microprocessor(s) or PLC(s) (3893), where the light sensor(s) (730) receive light that is emitted by the light source(s) (725) and this light has reflected off of the aerosol(s) (200), is compared with any value(s) or data stored in the firmware and/or software of the microprocessor(s) or PLC(s) (3893). Furthermore, and without being limited, if any of this reported, data, information, sensor voltage, sensor amperage, and/or sensor current, is above any stored value or data, and/or meets any criteria, that indicates that the targeted area(s) are effectively, suitably, and/or efficaciously filled with aerosol (200), the microprocessor(s) or PLC(s) (3893) will send one or more of any, signal(s), command(s), information, and/or data, preferably via the one or more transceiver(s) (6000), that can result in or cause any number of any actions and/or any combination of any actions, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s) (6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), because a sufficient, efficacious, and/or effective, amount of aerosol (200) is present or contained in the enclosed space or targeted area(s) (210) being treated. These same processes and action(s) described can also apply to any other digital, electronic, or analog, controller(s) such as, but not limited to any, PLC(s) at any suitable and effective location(s), PLC(s) that controls and/or is a component of any device(s) and/or equipment(s) that is utilized in the one or more process(s) or method(s) to treat the various surfaces within the targeted area(s) (210), PLC(s) that controls one or more of any aerosol producing apparatus(s) (215), PLC(s) (6005) that controls, and/or is located in or at, and/or is a component(s) of, one or more of any, remote controlling device(s) (6010). It is preferable that the light sensor (730) outputs an electrical signal, which is proportional to the intensity of light detected.

In another possible situation, and without limitation, as more aerosol(s) (200) are deployed into the targeted area(s) (210), the light sensor(s) (730) sense less light that is emitted by the light source(s) (725), as more aerosol(s) (200) that are deployed into the targeted area(s) (210) block this emitted light. The light sensor(s) (730) can report these one or more situation(s), status(s), and/or level(s), of any sensed light and/or blocked light, to one or more of any PLC(s), and more preferably one or more of any suitable and effective PLC(s) at any suitable and effective location(s), and even more preferably one or more of any PLC(s) that controls and/or is a component of any remote aerosol sensor(s) (5010). The light sensor(s) (730) can report any sensed, aerosol concentration(s), aerosol density(s), and/or any suitable, effective, and/or efficacious amount(s), of any aerosol(s), via one or more of any status(s) or level(s) and/or one or more of any change(s) in any, status(s) or level(s), of any electrical, current(s), voltage(s), and/or amperage(s), that can be reported by the light sensor(s) (730) to one or more of any PLC(s), and more preferably one or more of any suitable and effective PLC(s) at any suitable and effective location(s), and even more preferably one or more of any PLC(s) that controls and/or is a component of any remote aerosol sensor(s) (5010). It is preferred, without limitation, that in this configuration the light sensor(s) (730) report or communicate decreasing status(s) or level(s), of any electrical, current(s), voltage(s), and/or amperage(s), to any PLC(s), as more light is blocked by the aerosol(s) (200) from reaching the one or more light sensor(s) (730). The light sensor(s) (730) can also, without limitation, cease reporting or communicating any electrical, current(s), voltage(s), and/or amperage(s), to any PLC(s), when suitable, effective, and/or efficacious, amount(s), density(s), and/or concentration(s), of aerosol(s) (200) is present in the targeted area(s) (210), and the light that is emitted from the light source(s) (725) is blocked by the aerosol(s) (200) from reaching the one or more light sensor(s) (730).

Without being limited, any, data, information, sensor voltage, sensor amperage, and/or sensor current, that is reported or sent by any light sensor(s) (730), and/or any associated component(s), and that is received by the microprocessor(s) or PLC(s) (3893), where the light sensor(s) (730) may, or may not, receive light that is emitted by the light source(s) (725) because the aerosol(s) (200) may interfere with, diminish, and/or even block, the passage of light from the light source(s) (725) to the light sensor(s) (730), is compared with any value(s) or data stored in the firmware and/or software of the microprocessor(s) or PLC(s) (3893). Furthermore, and without being limited, if any of this reported, data, information, sensor voltage, sensor amperage, and/or sensor current, is below any stored value or data, and/or meets any criteria, that indicates that the targeted area(s) are effectively, suitably, and/or efficaciously filled with aerosol (200), the microprocessor(s) or PLC(s) (3893) will send one or more of any, signal(s), command(s), information, and/or data, preferably via the one or more transceiver(s) (6000), that can result in or cause any number of any actions and/or any combination of any actions, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s) (6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), because a sufficient, efficacious, and/or effective, amount of aerosol (200) is present or contained in the enclosed space or targeted area(s) (210) being treated. These same processes and action(s) described can also apply to any other digital, electronic, or analog, controller(s) such as, but not limited to any, PLC(s) at any suitable and effective location(s), PLC(s) that controls and/or is a component of any device(s) and/or equipment(s) that is utilized in the one or more process(s) or method(s) to treat the various surfaces within the targeted area(s) (210), PLC(s) that controls one or more of any aerosol producing apparatus(s) (215), PLC(s) (6005) that controls, and/or is located in or at, and/or is a component(s) of, one or more of any, remote controlling device(s) (6010). It is preferable that the light sensor (730) outputs an electrical signal, which is proportional to the intensity of light detected.

Without being limited, any, information, data, and/or electrical, current(s), voltage(s), and/or amperage(s), all of which can be represented by any, suitable and effective value(s), and are communicated or reported by the light sensor(s) (730), can be communicated or sent to, and detected, monitored, and/or analyzed, by one or more of any PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(s) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010). The PLC(s) can then utilize and/or compare the data that is communicated or reported from the light sensor(s) (730), at any time(s), to determine if a suitable, effective, and/or efficacious, amount of aerosol(s) (200) is present within the targeted area(s) (210).

Without being limited, the aerosol(s) (200) can be deployed into the targeted area(s) (210) at any suitable and effective, density(s), concentration(s), and/or quantity(s), in order to be, suitable, effective, and/or efficacious. Also, without being limited, the light sensor(s) (730), and/or any other devices such as, but not limited to any, suitable and effective PLC(s) at any suitable and effective location(s), and/or any PLC(s) at any local and/or remote location(s), and preferably any PLC(s) that controls and/or is a component of any remote aerosol sensor(s) (5010), can be calibrated, programmed, and/or adjusted, to indicate or recognize any, quantity(s), degree(s), condition(s), value(s), change(s), status(s), and/or level(s), of any light(s) emitted by the light source(s) (725) and received by the light sensor(s) (730), that indicates that a suitable, effective, and/or efficacious, quantity(s), level(s), concentration(s), and/or density(s), of any aerosol(s) (200), is present in the targeted area(s) (210). The quantity(s), degree(s), condition(s), value(s), change(s), status(s), and/or level(s), of any light(s) emitted by the light source(s) (725) and received by the light sensor(s) (730), that indicates that a suitable, effective, and/or efficacious, quantity(s), level(s), concentration(s), and/or density(s), of any aerosol(s) (200), is present in the targeted area(s) (210), can be communicated by the light sensor(s) (730) to any PLC(s) in any suitable and effective location(s), using any suitable and effective, current(s), voltage(s), and/or amperage(s), and/or any other suitable and effective means known to those skilled in the art.

Without being limited, the sensing circuit that is shown in FIG. 143, can also be utilized to amplify any electrical, current, voltage, and/or amperage, changes that may be reported by any light sensor(s) (730), so that the one or more of any suitable and effective sensor(s) (3897), and/or one or more of any PLC(s), and preferably any PLC(s) (3893) that controls and/or is a component of any remote aerosol sensor(s) (5010), can see larger changes, and/or be able to effectively detect any changes, in any, signal(s), sensor voltage(s), sensor amperage(s), electrical signal(s), and/or sensor current(s), that is reported or sent by any light sensor(s) (730) and/or any associated component(s) at any time(s).

With reference to FIG. 100 and FIGS. 139-144, and without limitation, a preferred description of the remote aerosol sensor(s) (5010) that incorporates one or more of any reflective aerosol detector(s) (6095) is given, where the reflective aerosol detector(s) (6095) consists of various parts including, but not limited to, one or more of any, light source(s) (725) and light sensor(s) (730), where the light sensor(s) (730) monitors or senses any light that was emitted from the light source(s) (725) and has reflected off of any aerosol(s) (200) that are deployed within the targeted area(s) (210). It is preferred, without limitation, that the light source(s) (725) is at least one of any suitable and effective infrared (IR) light emitter(s). It is also preferred, without limitation, that the light sensor(s) (730) is at least one of any suitable and effective infrared (IR) light detector(s). The light source(s) (725) and light sensor(s) (730) can be, without limitation, located in any suitable and effective location(s). The light source(s) (725) and light sensor(s) (730) can also be, without limitation, located as, joined, combined, or separate, components in one or more of any suitable and effective location(s). It is preferred, without limitation, that the light source(s) (725) and light sensor(s) (730) are suitably and effectively located in any common or shared enclosure or housing.

The light source(s) (725) and light sensor(s) (730) can be, without limitation, located or positioned in any proximity to one another, or distance of separation between the components, that is suitable and effective, preferably with a distance of separation that is less than six feet, more preferably with a distance of separation, which is between zero inches to thirty-six inches, even more preferably with a distance of separation that is between zero inches to twelve inches, very preferably with a distance of separation that is between zero inches to two inches, and extremely preferably with a distance of separation that is between 0.01 inches to one inch.

The light source(s) (725) and light sensor(s) (730) can be configured or positioned in any one or more of any angle(s). It is preferred, without limitation, that if the light source(s) (725) and light sensor(s) (730) are in any angled position(s), they are at least angled in any suitable and effective angle(s) towards one another. It is preferred, without limitation, that the light source(s) (725) and light sensor(s) (730) are positioned so that they are at least facing or pointing in the same direction. It is even more preferred, without limitation, that the light source(s) (725) and light sensor(s) (730) are positioned so that they are at least facing or pointing in the same direction outward and away from the remote aerosol sensor(s) (5010). The remote aerosol sensor(s) (5010) and/or the light source(s) (725) and light sensor(s) (730) can face any one or more place(s) or area(s) within the targeted area(s). It is preferred, without limitation, that the remote aerosol sensor(s) (5010) and/or the light source(s) (725) and light sensor(s) (730) are located or positioned so that they face out into any of the, room(s), space(s), and/or targeted area(s) (210).

The light source(s) (725) is energized with any suitable and effective, voltage, amperage, and current, causing the device to emit any suitable and effective light, and any suitable and effective characteristics of light, preferably, and without limitation, light that is in the infrared (IR) light spectrum. Without being limited, the light source(s) (725) emits light, at any suitable and effective time(s) and for any suitable and effective duration(s) and intensity(s), toward any aerosol (200) that is in any suitable and effective proximity in the atmosphere to the light source(s) (725). Light that is emitted by the light source(s) (725) is reflected back to the light sensor(s) (730) by any aerosol (200) droplets that may be present. The light sensor(s) (730) is directly or indirectly connected to, and can communicate with, all in a manner known to those skilled in the art, one or more of any suitable and effective PLC(s) at any suitable and effective location(s), and/or any PLC(s) at any local and/or remote location(s), and preferably any PLC(s) (3893) that controls and/or is a component of any remote aerosol sensor(s) (5010).

According to another embodiment, and according to FIGS. 98-102, the remote aerosol sensor(s) (5010) can also, without limitation, incorporate and utilize at least one or more, layer or window (Hereinafter called "aerosol deposit window(s)" (3890)) anywhere in front of the one or more of any light sensor(s) (730), and/or between one or more of any light source(s) (725) and one or more of any light sensor(s) (730), all in various possible configurations. The one or more aerosol deposit window(s) (3890) can be, without limitation, located or positioned at any suitable distance(s), location(s), and position(s) from the one or more of any light source(s) (725), and/or light sensor(s) (730), including, but not limited to, being located in any suitable location(s) within the atmosphere of the targeted area(s) (210). The one or more aerosol deposit window(s) (3890) can also be, without limitation, located or positioned as an independent component any distance from, and/or between, the one or more of any light source(s) (725) and light sensor(s) (730). Without being limited, the one or more aerosol deposit window(s) (3890) can be suitably connected, positioned, located, or attached, indirectly or directly on or to, one or more of any mounting extension(s) (5035) that may be used. It is preferred, without limitation, that the aerosol deposit window(s) (3890) is at least located or positioned at an effective distance(s) from the light source(s) (725) and/or light sensor(s) (730). It is also preferred, without limitation, that the one or more aerosol deposit window(s) (3890) is at least suitably located anywhere within the line of site between and/or in front of any of the light source(s) (725) and/or any light sensor(s) (730).

Without being limited, the one or more aerosol deposit window(s) (3890) can be used to determine, or at least help determine, if an effective or efficacious amount of aerosol (200) has been deposited on the various surface(s) within the targeted area(s) (210), as the aerosol (200) that is deployed into the targeted area(s) (210) can be deposited onto one or more sides of the aerosol deposit window(s) (3890), and the one or more light sensor(s) (730) can sense or detect any change in the light that passes through the aerosol deposit window(s) (3890) as a result of the deposited aerosol (200), or any film or deposition coating that conglomerates on the aerosol deposit window(s) (3890). The light sensor(s) (730) can, without limitation, communicate with, and/or indicate or report to, one or more PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(s) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010), if or when it either receives or ceases to receive any trait or attribute pertaining to light such as, but not limited to, any level of light, power of light, and/or light intensity. The communication can be accomplished in various ways known in the art. This communication can result in or cause, any number of any actions and/or any combination of any actions, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s)

(2040) (h) activating one or more of any air filtration apparatus(s) (6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210).

Without being limited, the one or more aerosol deposit window(s) (3890), as well as the one or more of any light source(s) (725) and/or light sensor(s) (730), can be located in any suitable orientation, angle, or direction. One or more sides of the one or more aerosol deposit window(s) (3890) can also be, without limitation, exposed to the environment or atmosphere within the targeted area(s) (210). It is preferred, without limitation, that at least one side of the one or more aerosol deposit window(s) (3890) is exposed to the environment or atmosphere within the targeted area(s) (210). The aerosol deposit window(s) (3890) can be, without limitation, positioned, interfaced with, or located at or on, any suitable location(s), within, within any side of, or anywhere outside of, the remote aerosol sensor(s) (5010) and/or the housing(s) of the remote aerosol sensor(s) (5010). The aerosol deposit window(s) (3890) can also be, without limitation, located in or more separate compartments within the remote aerosol sensor(s) (5010), with one or more of any light source(s) (725) and/or light sensor(s) (730). It is preferred, without limitation, that if one or more aerosol deposit window(s) (3890) is utilized, it is located or positioned within, or interfaced with, the one or more housing(s) of the remote aerosol sensor(s) (5010). It is more preferred, without limitation, that if one or more aerosol deposit window(s) (3890) is utilized, it is located or positioned within, or interfaced with, the one or more housing(s) of the remote aerosol sensor(s) (5010), and at least one suitable light sensor(s) (730) is effectively positioned behind the aerosol deposit window(s) (3890). It is even more preferred, without limitation, that if one or more aerosol deposit window(s) (3890) is utilized, it is located or positioned within, or interfaced with, the one or more housing(s) of the remote aerosol sensor(s) (5010), and at least one suitable light sensor(s) (730) is effectively positioned behind the aerosol deposit window(s) (3890), and one or more light source(s) (725) is effectively positioned to effectively interact with the aerosol deposit window(s) (3890) and the light sensor(s) (730).

The aerosol deposit window(s) (3890) can be, without limitation, manufactured or constructed from any suitable material. The aerosol deposit window(s) (3890) can also be, without limitation, manufactured or constructed from any suitable light transmitting material and have any effective amount of light transmission. It is preferred, without limitation that the aerosol deposit window(s) (3890) is at least suitably clear, transparent, and/or translucent. It is also preferred, without limitation, that the aerosol deposit window(s) (3890) are constructed from any suitable glass and/or plastic. It is more preferred, without limitation, that the aerosol deposit window(s) (3890) is constructed from any suitable glass and/or plastic. It is even more preferred, without limitation, that the aerosol deposit window(s) (3890) is constructed from any suitable glass or plastic that is clear or transparent. The aerosol deposit window(s) (3890) can be any suitable thickness, size, and shape.

Any surface(s) of the aerosol deposit window(s) (3890) can also have, without limitation, any suitable surface treatment(s) known to those skilled in the art. The various surface(s) of the aerosol deposit window(s) (3890) can have, without limitation, any suitable surface tension and/or wettability. It is preferred, without limitation, that at least the various surface(s) of the aerosol deposit window(s) (3890) that interact with the atmosphere or environment within the targeted area(s) (210) have a sufficient and suitable material property(s), surface tension, and/or wettability, that can allow the aerosol deposit window(s) (3890) to indicate or cause a result that is detectable by any light sensor(s) (730), that an efficacious and effective amount of aerosol (200) is deployed into the targeted area(s) (210). It is more preferred, without limitation, that the various surface(s) of the aerosol deposit window(s) (3890) that interact with the atmosphere or environment within the targeted area(s) (210) have at least a material property(s), surface tension, and/or wettability, that can cause at least a suitable and effective amount of the aerosol (200) that is deposited on the surface(s) to remain in various forms or shapes such as, but not limited to any, beaded form, partial beaded form, droplet form, partial droplet form, convex shape, and/or partially shape, but at least in a shape of form that can allow the aerosol deposit window(s) (3890) to indicate or cause a result that is detectable by any light sensor(s) (730), that an efficacious and effective amount of aerosol (200) is deployed into the targeted area(s) (210). The various material(s), surface(s), and/or surface treatment(s), of the aerosol deposit window(s) (3890) can be, without limitation, engineered and tailored, in a manner known to those skilled in the art, for any agent(s) that any deployed aerosol (200) may consist of and be deposited on the aerosol deposit window(s) (3890). The aerosol deposit window(s) may also, without limitation, be used with any agent that is deployed into the targeted area(s) (210) in a vapor form.

The aerosol deposit window(s) (3890) can also be, without limitation, heated and/or cooled to any suitable temperature, at any time, and for any duration of time, depending on the operating environment that the remote aerosol sensor(s) (5010) is operating within, and/or the result(s) or effect(s) that are desired. The aerosol deposit window(s) (3890) can be heated with one or more of any suitable heating means (Hereinafter called "deposit window heater(s)" (3884)), and/or cooled with one or more of any suitable cooling means (Hereinafter called "deposit window cooler(s)" (3891)), all known to those skilled in the art. The aerosol deposit window(s) (3890) can be heated and/or cooled at any effective and suitable time, for any effective and suitable duration, and to one or more of any effective temperature(s) or temperature range(s). It is preferred, without limitation, that if the aerosol deposit window(s) (3890) is heated or cooled, this is accomplished with one or more of any suitable device(s) known to those skilled in the art such as, but not limited to any, thermoelectric cooler (TEC), peltier device, or peltier heat pump, that can heat or cool the aerosol deposit window(s) (3890) directly and/or indirectly. The one or more means or devices used for heating and/or cooling the aerosol deposit window(s) (3890) can be, without limitation, controlled and/or communicate with one or more of any digital, electronic, or analog, controller(s) such as, but not limited to, any PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(s) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010). Without being limited, the aerosol deposit window(s) (3890) can be heated and/or cooled directly or indirectly with any means known to those skilled in the art, such as, but not limited to any, conduction, or heating or cooling with any cooled or heated, air, atmosphere, or gas, that contacts the aerosol deposit window(s) (3890).

According to an embodiment, the remote aerosol sensor(s) (5010) can be located in various ways in one or more of any suitable location(s) within the targeted area(s) (210). It is preferred, without limitation, that the remote aerosol sensor(s) (5010) has one or more feet or support(s) structures (5040) that can support the remote aerosol sensor(s) (5010) when it is placed on any suitable surface(s) within the targeted area(s) (210). The remote aerosol sensor(s) (5010) may also have, without limitation, one or more suspension points (5015) of any size and design, from which the remote aerosol sensor(s) (5010) can be suspending in the atmosphere in the targeted area(s) (210) with one or more of any suitable material(s) or object(s) such as, but not limited to any, rope, chain, wire, bracket, or string, (Hereinafter called "suspension material(s)" (5110)) that can be constructed from any suitable material. The remote aerosol sensor(s) (5010) may also have, without limitation, one or more permanent or temporary wall or surface mounting hardware or bracket(s) (Hereinafter called "mounting hardware") (5012). The surface mounting hardware (5012) can be any size or shape, and constructed in a manner known in the art. The remote aerosol sensor(s) (5010) may also, without limitation, be designed and constructed so that it may be removably attached either directly or indirectly to any part of the apparatus (215).

According to an embodiment, and according to FIGS. 98-102 and FIGS. 119-132 and FIGS. 139-144, it is preferred, without limitation, that the remote aerosol sensor(s) (5010) incorporates and utilizes at least one or more of any aerosol deposit sensor(s) (3880), all in any of its various possible configurations. It is preferred, without limitation, that the aerosol deposit sensor(s) (3880) can be the primary sensor(s), and/or one of the various primary sensor(s), within the remote aerosol sensor(s) (5010) that can be used by the one or more of any digital, electronic, or analog, controller(s) such as, but not limited to, any PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(es) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010), to make decisions regarding certain actions or outcomes, or take various actions or combination of actions, such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s) (6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210).

The aerosol deposit sensor(s) (3880) can be, without limitation, any suitable and effective, size, shape, thickness, and geometry. Without being limited, the one or more aerosol deposit sensor(s) (3880) can be located or interfaced in or on any suitable and effective, location(s), angle(s), position(s), and/or orientation(s), in any effective manner known to those skilled in the art. It is preferred, without limitation, that the aerosol deposit sensor(s) (3880) is located in any, angled and/or vertical position(s). It is more preferred, without limitation, that the aerosol deposit sensor(s) (3880) is mounted on any exterior side(s) of the remote aerosol sensor(s) (5010). The aerosol deposit sensor(s) (3880), or at least the one or more aerosol (200) contact surface(s) (3898), can be directly or indirectly exposed to, or have direct or indirect contact with, the atmosphere or environment within the one or more targeted area(s) (210). Indirect exposure to, or indirect contact with, the atmosphere or environment within the one or more targeted area(s) (210), can include, without limitation, positioning the aerosol deposit sensor(s) (3880) and/or its contact surface(s) (3898) in one or more of any area(s) or space(s) such as, but not limited to any, enclosed area(s), and/or semi-enclosed area(s), where direct contact may be difficult with the aerosol (200) that may be present within the targeted area(s) (210), and moving any sampled gas(s) and/or aerosol (210) from these areas to the aerosol deposit sensor(s) (3880), or at least the one or more aerosol (200) contact surface(s) (3898), via one or more of any sources of pressurized air such as, but not limited to any, fan, blower, or pump, via one or more of any conduit(s), hose(s), pipe(s), and tunnel(s). It is preferred, without limitation, that the one or more aerosol deposit sensor(s) (3880), and/or its aerosol (200) contact surface(s) (3898), at least have direct contact with the atmosphere or environment within the targeted area(s). It is more preferred, without limitation, that the one or more remote aerosol sensor(s) (5010) and/or its aerosol (200) contact surface(s) (3898), face out towards one or more of any area(s) or space(s) within the targeted area(s) (210).

Referring to FIGS. 98-102 and FIGS. 119-132, and FIGS. 139-144, and without being limited, the aerosol deposit sensor(s) (3880) can include, at least one or more aerosol (200) contact surface(s) (3898), consisting of at least one or more non-conductive material(s) (Hereinafter called "insulator material(s) (3882)) that is exposed to the atmosphere within the targeted area(s) (210), and this contact surface(s) (3898) is suitably connected to at least two or more conductors (3881) that are connected to at least one or more suitable sensor(s) (3897), and/or one or more of any digital, electronic, or analog, controller(s) such as, but not limited to, any PLC(s), or remote PLC(s) (3893), that can monitor and/or report various data such as, but not limited to, (a) the presence or absence of any electrical signal(s) that may be established between the at least two or more electrodes that are being utilized, (b) any amount of conductivity that may be established between the at least two or more electrodes that are being utilized, (c) any amount of electrical current that may be established between the at least two or more electrodes that are being utilized, and/or (d) any change in any electrical, current, amperage, voltage, and/or any other electrical characteristics or attributes that would indicate the completion of a circuit, as a result of any contact of the contact surface(s) (3898) with a sufficient amount of aerosol (200).

Without being limited, and referring to FIGS. 98-102 and FIGS. 119-132, the aerosol deposit sensor(s) (3880) is constructed so that little to no conductivity may exist, and little to no amount of current will pass, between the two or more conductors (3881), until a sufficient and effective amount of aerosol (200) is deposited onto the one or more aerosol deposit sensor(s) (3880), and more specifically the one or more contact surface(s) (3898), causing a sufficient and effective deposition of aerosol (200) (Hereinafter called "deposited aerosol" or "deposited aerosol droplets" (3883)), and/or liquid film (3899) to form, on the contact surface(s) (3898) and sufficiently connecting the two or more electrodes or conductors (Hereinafter called "conductor(s)" (3881)) electrically and completing one or more electrical circuit(s). It is preferred, without limitation that the various components of the aerosol deposit sensor(s) (3880), such as, but not limited to, the contact surface(s) (3898), insulator material(s) (3882), conductors (3881), are all designed and constructed so that a sufficient, and/or significantly strong enough, electrical connection is established between the two or more conductors (3881) to create an electrical circuit that can be detected, monitored, and/or communicated, by one or more of any conductivity sensor(s) (3897), and/or any one or more PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(es) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010), to indicate or significantly indicate when a sufficient and efficacious amount of aerosol (200) is deployed into the one or more targeted area(s) (210).

The light sensor(s) (730) and/or aerosol deposit sensor(s) (3880) can also include, without limitation, any suitable and effective means known to those skilled in the art, to monitor, sense, and/or communicate, various inputs such as, but not limited, to, (a) the presence or absence of any electrical signal(s) that may be established between the at least two or more electrodes that are being utilized, (b) any amount of conductivity that may be established between the at least two or more electrodes that are being utilized, and/or (c) any amount of electrical current that may be established between the at least two or more electrodes that are being utilized, and/or (d) any status(es) or change(s) in any, electrical, current, amperage, voltage, and/or any other electrical characteristics or attributes that would indicate the completion of a circuit, as a result of any contact of the contact surface(s) (3898) with a sufficient amount of aerosol (200), (e) any status(es) or change(s) in any, electrical, current, amperage, voltage, and/or any other electrical characteristics or attributes that would be sent or communicated by the one or more light sensor(s) (730) indicating that the targeted area(s) (210) is filled with an effective or sufficient amount(s) of aerosol(s) (200). Without being limited, this means can include any "conductivity sensor(s)" (3897), that can be used to monitor or sense various inputs or data pertaining to the aerosol deposit sensor(s) (3880) and/or light sensor(s) (730), such as, but not limited to any, (a) electrical signal(s), (b) presence of conductivity, (c) presence or absence of electrical current, (d) amount of conductivity, (e) amount of electrical current, (f) amount of voltage (g) amount of voltage change, (h) current, (i) current change, (j) amperage, and/or (k) amperage change, (l) presence or absence of electrical voltage, and/or (m) presence or absence of electrical amperage.

Without being limited, this means can also include, but is not limited to, one or more of any suitable, digital, electronic, or analog, controller(s) such as, but not limited to any, one or more PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(es) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010).

Without being limited, the conductivity sensor(s) (3897) can also directly or indirectly connect to and communicate with any one or more PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(es) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010), and all in a manner known to those skilled in the art. The conductivity sensor(s) (3897) may also include, without limitation, any suitable and effective, voltage, amperage, and/or current sensor(s), known to those skilled in the art. The one or more conductivity sensor(s) (3897) and/or one or more of any suitable, digital, electronic, or analog, controller(s) such as, but not limited to any, suitable and effective PLC(s) at any suitable and effective location(s), and/or any PLC(s) at any local and/or remote location(s), and preferably any PLC(s) that controls and/or is a component of any remote aerosol sensor(s) (5010), can be placed in one or more of any suitable location(s) or position(s) such as, but not limited to, between each conductor (3881) that is utilized, and the one or more of any PLC(s) or remote PLC(s) that are utilized, as well as effectively near or on the various conductor(s) (3881) that are utilized.

It is preferred, without limitation, that this conductivity sensor(s) (3897) is any suitable and effective sensor that can monitor and communicate the presence and/or absence of any current. This type of sensor(s) (3897) can also, without limitation, report the presence or absence of current, change in current, and/or the amount of current that is being sensed. It is preferred, without limitation, that any, amperage, voltage, and/or amount of current that may flow between the at least two or more conductors (3881), is monitored and/or reported by one or more of, any conductivity sensor(s) (3897), and/or any suitable and effective PLC(s) at any suitable and effective location(s), and/or any PLC(s) at any local and/or remote location(s), and preferably any PLC(s) that controls and/or is a component of any remote aerosol sensor(s) (5010).

However, it is more preferred, without limitation, that any electrically related data or information pertaining to, but not limited to any, voltage, current, and/or amperage, and/or any change in these various electrical characteristics or attributes, that is related to, pertains to, or describes, any, electrical condition(s), effect(s), status(s), and/or activity(s), of the at least two or more conductors (3881), the aerosol deposit sensor(s) (3880), and/or the light sensor(s) (730), is monitored, analyzed, and/or reported, by one or more of, any suitable and effective PLC(s) at any suitable and effective location(s), and/or any PLC(s) at any local and/or remote location(s), and preferably any PLC(s) that controls and/or is a component of any remote aerosol sensor(s) (5010). The at least one or more conductivity sensor(s) (3897) can also be, without limitation, incorporated into the design of one or more of any digital, electronic, or analog, controller(s) such as, but not limited to, any suitable and effective PLC(s) at any suitable and effective location(s), and/or any PLC(s) at any local and/or remote location(s), and preferably any PLC(s) that controls and/or is a component of any remote aerosol sensor(s) (5010).

Referring to FIG. 127 and FIGS. 140-141 and FIG. 143, and without being limited, one or more of any suitable means to amplify any, electrical signal(s), amperage(s), voltage(s), current(s), and/or electrical power, or any suitable and effective amplifier(s) (3887) known to those skilled in the art, may also be utilized to boost and/or amplify any needed electrical signal(s) and/or electrical characteristics or attributes such as, but not limited to any, voltage, amperage, and/or current, before any electrical related information, status, data, value(s), and/or signal(s), is communicated, conducted, or transmitted, from any of the various sensing device(s) (5080), including, but not limited to any, light sensor(s) (730), and/or any aerosol deposit sensor(s) (3880), to various locations such as, but not limited to, the one or more conductivity sensor(s) (3897), and/or one or more of any PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(s) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010). Any electrical, signal(s), output(s), characteristic(s), and/or attribute(s), such as, but not limited to any, voltage(s), amperage(s), and/or current(s), that are emitted or sent from and/or transmitted through, one or more of any sensing device(s) (5080), may be amplified to one or more of any suitable and effective level(s) or value(s), before they are sent or transmitted to one or more of any location(s) such as, but not limited to, the one or more conductivity sensor(s) (3897), and/or one or more of any PLC(s) at any suitable and effective location(s), and preferably any PLC(s) that controls and/or is a component of any remote aerosol sensor(s) (5010).

The presence of the aerosol (200), or deposited aerosol (3883), on the contact surface(s) (3898) can create, without limitation, one or more liquid film(s) (3899) on the various surface(s) of the contact surface(s) (3898) depending on various conditions. The aerosol(s) (200) and the resulting liquid film(s) (3899), and/or deposited aerosol (3883) droplets, can, without limitation, consist of one or more of any suitable and effective liquid(s) with one or more of any suitable and effective, polarity(s), ion content(s), number of ion(s), ion(s) content, charge(s), ionic content(s), mineral content(s), metal and/or metallic content(s), and/or no charge(s) or neutral charge(s). Without being limited, the aerosol(s) (200) and the resulting liquid film(s) (3899), and/or deposited aerosol (3883) droplets, can also have any suitable and effective, polarity(s), ion content(s), number of ion(s), charge(s), mineral content(s), metallic content(s), and/or no charge(s) or neutral charge(s). It is preferred, without limitation, that various characteristics and attributes of the aerosol(s) (200) and the resulting liquid film(s) (3899), and/or deposited aerosol (3883) droplets, such as, but not limited to any suitable and effective, polarity(s), ion content(s), number of ion(s), charge(s), mineral content(s), metallic content(s), and/or no charge(s) or neutral charge(s), is at least effective, efficacious, and suitable. It is also preferred, without limitation, that the deposited aerosol(s) (200) and liquid(s) is at least effectively and suitably, electrically conductive when used with the aerosol deposit sensor(s) (3880). It is more preferred, without limitation, that the deposited liquid(s) is at least any suitable aqueous solution, and is effectively and suitably electrically conductive.

The aerosol (200) that is deposited on the contact surface(s) (3898), and any liquid film (3899) that may result on the contact surface(s) (3898), can also be any and without limitation, thickness, width, density, uniformity, cohesiveness, volume, and/or mass. It is preferred, without limitation, that the aerosol(s) (200) that is deposited on the contact surface(s) (3898), and/or any liquid film(s) (3899) is at least an effective and sufficient, thickness, width, density, uniformity, cohesiveness, volume, and/or mass, so that one or more sufficient and effective electrical circuit(s), or electrical connection(s) between the various conductor(s) (3881), can be established, as well as detected and monitored by one or more of any, conductivity sensor(s) (3897), and/or any suitable and effective PLC(s) at any suitable and effective location(s), and/or any PLC(s) at any local and/or remote location(s), and preferably any PLC(s) that controls and/or is a component of any remote aerosol sensor(s) (5010), indicating or significantly indicating when a sufficient and efficacious amount of aerosol (200) is deployed into the one or more targeted area(s) (210). It is preferred, without limitation, that full effectiveness and efficacy of the aerosol deployment within the targeted area(s) (210), is achieved with as thin of, any aerosol (200) deposit(s), any film(s) of deposited aerosol (3883), and/or any deposited liquid layer(s) (3899), from the deployed aerosol(s) (200) contacting the contact surface(s) (3898), as well as any other surfaces within the targeted area(s) (210), as possible. However, one or more of any or certain application(s) may also, without limitation, require thicker of any, aerosol (200) deposit(s), film(s) of deposited aerosol(s) (3883), and/or deposited liquid layer(s) (3899), from the deployed aerosol(s) (200) contacting the contact surface(s) (3898) and the various surfaces within the targeted area(s) (210).

Referring to FIGS. 98-102 and FIGS. 119-132, and without being limited, the aerosol deposit sensor(s) (3880) can have at least one or more insulator material(s) (3882) that is located or positioned between two or more electrodes or conductors (3881). Without being limited, the one or more contact surface(s) (3898), with which the aerosol (200) in the targeted area(s) (210) contacts, is constructed, or at least partially and suitably constructed, from the one or more insulator material(s) (3882). The various contact surface(s) (3898) can be, without limitation, constructed in a manner so that a sufficient amount of insulator material(s) (3882) is utilized to electrically insulate the various electrodes or conductors (3881), but still allow the aerosol (200) that is deposited to electrically connect the two or more electrodes or conductors (3881) when a sufficient amount of aerosol (200) to have an efficacious or desired effect within the targeted area(s) has interacted with the contact surface(s) (3898).

The insulator material(s) (3882) can be, without limitation, any suitable, length, width, thickness, shape, and geometry. The insulator material(s) (3882) can also be, without limitation, constructed from one or more of any suitable material(s) such as, but not limited to any, glass, polymer, or any other suitable and effective materials known in the art, that have suitable and effective electrical insulating properties. It is preferred, without limitation, that the insulator material(s) (3882) are non-conductive. It is more preferred, without limitation, that the insulator material(s) (3882) are at least non-conductive enough so that the aerosol deposit sensor(s) (3880) may properly function. It is even more preferred, without being limited, that the insulator material(s) (3882) are at least sufficiently non-conductive so that the one or more of any suitable, digital, electronic, or analog, controller(s) such as, but not limited to any, suitable and effective PLC(s) at any suitable and effective location(s), and/or any PLC(s) at any local and/or remote location(s), and preferably any PLC(s) that controls and/or is a component of any remote aerosol sensor(s) (5010), or even any conductivity sensor(s) (3897), may be able to effectively and accurately determine, and/or communicate, report, or relay, when an effective or sufficient amount of aerosol (200) has contacted the aerosol deposit sensor(s) (3880) and indicate when a sufficient, effective, and efficacious amount of aerosol (200) is deployed into the one or more targeted area(s) (210).

Figure 122:
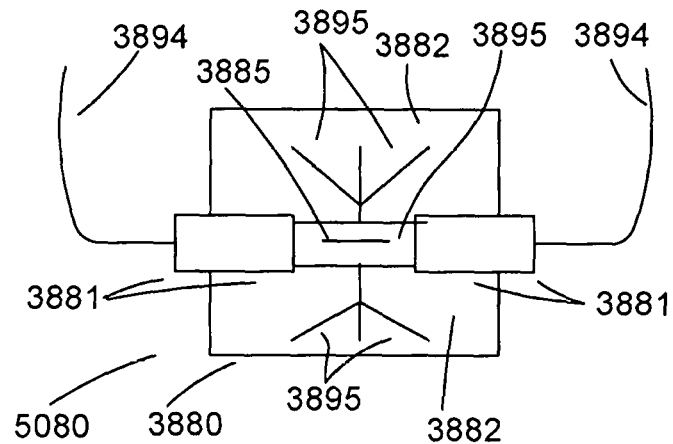
Figure 123:
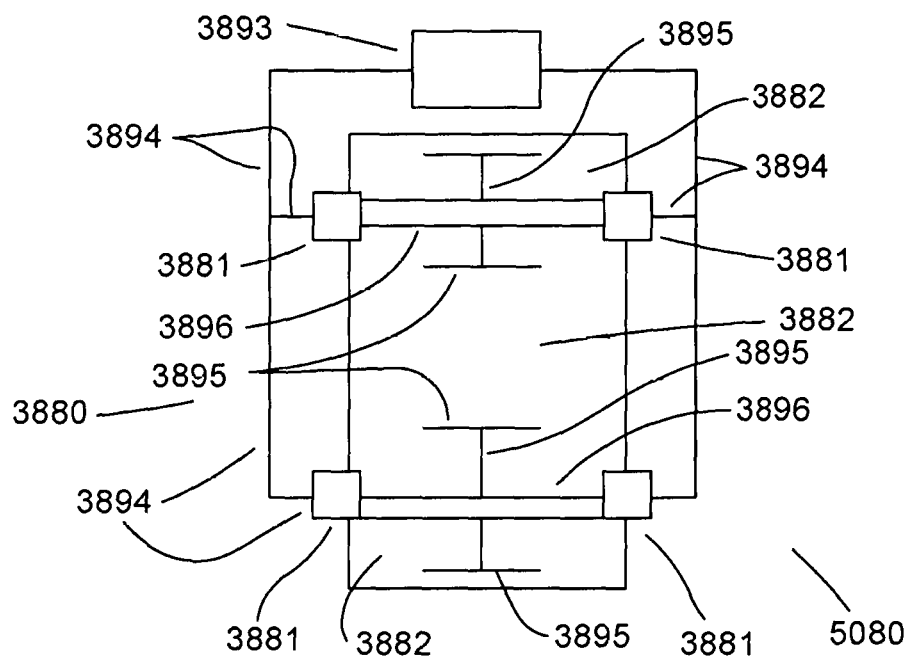

Referring to FIGS. 122-123, the various contact surface(s) (3898) and/or insulator material(s) (3882) can have, without limitation, one or more trough(s), groove(s), cut(s), and/or channels (Hereinafter called "channel(s)" (3895). These channel(s) (3895) can be any, without limitation, length, width or depth. The one or more channel(s) (3895) can also be, without limitation, located or positioned in one or more of any pattern(s) or orientation(s). The one or more channel(s) (3895) can also be, without limitation, connected, partially connected, or not connected. It is preferred, without limitation, that the various channel(s) (3895) interconnect. It is also preferred, without limitation, that if any channel(s) (3895) are utilized, at least one or more channel(s) (3895) within the insulator material(s) (3882) and/or the various contact surface(s) (3898) connect the two or more electrodes or conductors (3881) together with the channel(s) (3895). Without being limited the channel(s) (3895) can help divert any substantial amount of liquid or aerosol droplet(s) (200) that is deposited on the contact surface(s) (3898), to the various electrodes or conductors (3881). This can be, without limitation, used for various purposes including process safety and/or quality control of the process, as a greater amount of channeled liquid in the channel(s) (3895) can increase the chance for completing the electrical connection between at least two or more of the electrodes or conductors (3881) signifying that a sufficient and efficacious amount of aerosol (200) is deployed into the one or more targeted area(s) (210). The one or more insulator material(s) (3882) and/or the various contact surface(s) (3898) can also be, without limitation, canted or angled at any angle toward one or more of any channel(s) (3895). It is preferred, without limitation, that the one or more insulator material(s) (3882) and/or the various contact surface(s) (3898) are at least effectively canted or angled toward one or more of any channel(s) (3895). It is more preferred, without limitation, that the one or more insulator material(s) (3882) and/or the various contact surface(s) (3898) are at least effectively canted or angled toward at least one or more channel(s) (3895) that connects at least two or more electrodes or conductors (3881) that when electrically connected, their electrical connection can accurately and effectively signify that a sufficient and efficacious amount of aerosol (200) is deployed into the one or more targeted area(s) (210).

Figure 119:
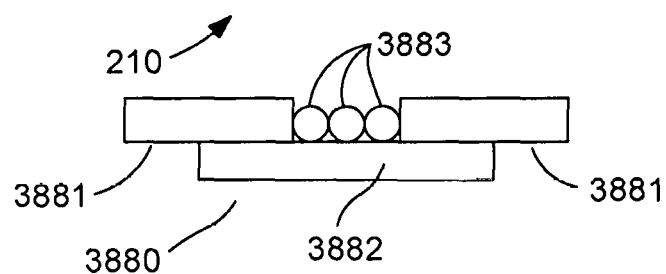
Figure 120:
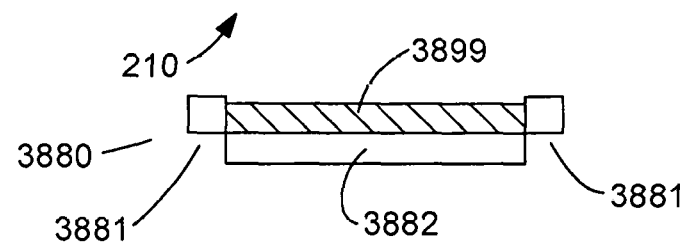
Figure 121:
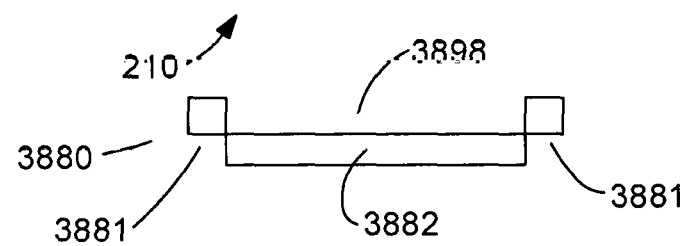

Referring to FIGS. 119-121, and without being limited, side views of the aerosol deposit sensor(s) (3880) are given. Without being limited, FIGS. 119-121, show a few of the various possible results if the aerosol (200) that is in the targeted area(s) (210), makes contact with the "contact surface(s)" (3898). The deposited aerosol (3883) and liquid, on the contact surface(s) (3898) can, without limitation, take one or more of any forms such as, but not limited to, a uniform covering of numerous deposited aerosol droplets (3883), a non-uniform covering of numerous deposited aerosol droplets (3883), a uniform film (3899) of deposited liquid, a non-uniform film (3899) of deposited liquid, and/or any combinations of these forms, all depending on one or more variables known to those skilled in the art. Any surface(s) of the aerosol deposit sensor(s) (3880), and more specifically, the contact surface(s) (3898), can also have, without limitation, any suitable and effective surface treatment(s) known to those skilled in the art. This can be used, without limitation, to modify the behavior of the deposited aerosol (200) and liquid on the one or more contact surface(s) (3898). The various surface(s) of the aerosol deposit sensor(s) (3880), and more specifically, the contact surface(s) (3898), can have, without limitation, any suitable and effective surface tension and/or wettability.

It is preferred, without limitation, that at least the various surface(s) of the aerosol deposit sensor(s) (3880), and more specifically, the contact surface(s) (3898), that interact with the atmosphere or environment within the targeted area(s) (210) have a sufficient, effective, and suitable material property, surface tension, and/or wettability, that can allow the aerosol deposit sensor(s) (3880) to interact with deposited aerosol (200) and liquid in a manner to indicate or cause a result that is detectable by any, conductivity sensor(s) (3897), and/or any suitable and effective PLC(s) at any suitable and effective location(s), and/or any PLC(s) at any local and/or remote location(s), and preferably any PLC(s) that controls and/or is a component of any remote aerosol sensor(s) (5010), when an efficacious and effective amount of aerosol (200) is deployed into the targeted area(s) (210). It is more preferred, without limitation, that at least the various surface(s) of the aerosol deposit sensor(s) (3880), and more specifically, the contact surface(s) (3898), that interact with the atmosphere or environment within the targeted area(s) (210) have a sufficient and suitable material property, surface tension, and/or wettability, that can allow and/or help promote at least a sufficient quantity of deposited aerosol (200) and liquid to effectively interact with the at least two or more conductors (3881) in a manner to indicate or cause a result that is detectable by any, conductivity sensor(s) (3897), and/or any suitable and effective PLC(s) at any suitable and effective location(s), and/or any PLC(s) at any local and/or remote location(s), and preferably any PLC(s) that controls and/or is a component of any remote aerosol sensor(s) (5010), when an efficacious and effective amount of aerosol (200) is deployed into the targeted area(s) (210).

The various material(s), surface(s), and/or surface treatment(s), of the aerosol deposit sensor(s) (3880), and more specifically, the contact surface(s) (3898), can be, without limitation, engineered and tailored, in a manner known to those skilled in the art, for any agent(s) that may be contained in any deployed aerosol (200) and deposited on the contact surface(s) (3898) of the aerosol deposit sensor(s) (3880). The aerosol deposit sensor(s) (3880), and more specifically, the contact surface(s) (3898) may also, without limitation, be used with any agent that is deployed into the targeted area(s) (210) in any vapor form.

Referring to FIGS. 119-132, and without being limited, the aerosol deposit sensor(s) (3880) can have at least two or more electrodes or conductors (3881) that are effectively and electrically separated or isolated with one or more suitable insulator material(s) (3882). The various electrodes or conductors (3881) can be, without limitation, positioned any distance from one another. It is preferred, without limitation, that the electrodes or conductors (3881) are at least located at one or more of any suitable and effective distance(s) from one another. It is more preferred, without limitation, that the various electrodes or conductors (3881) are at least separated from each other at a distance that can effectively and accurately indicate when a sufficient and efficacious amount of aerosol (200) is not only deployed into the one or more targeted area(s) (210), but also deposited onto the contact surface(s) (3898). The electrodes or conductors (3881) can be, without limitation, constructed from, and/or effectively include in their construction, one or more of any suitable and effective material(s), known to those skilled in the art, that are electrically conductive. It is preferred, without limitation, that the electrodes and conductors (3881) are constructed from any suitable and effective stainless steel.

Without being limited, the various electrodes or conductors (3881) can have any attributes and characteristics, such as, but not limited to any suitable and effective, length, width, height, shape, and/or geometry. Without being limited, the one or more electrodes or conductors (3881) can also consist of one or more pieces or components. It is preferred, without limitation, that these one or more pieces or components are electrically connected. These pieces or components cans also, without limitation, branch out in one or more directions, with one or more branches. The various electrodes or conductors (3881) can have or utilize, without limitation, any amount of surface area exposed to any contact surface(s) (3898) and/or insulator material(s) (3882). It is preferred, without limitation, that at least an effective amount of surface area is exposed to any contact surface(s) (3898) and/or insulator material(s) (3882), and any aerosol(s) (200) or liquid(s) that is deposited on these surfaces.

The two or more electrodes or conductors (3881) can also, without limitation, interface with the various contact surface(s) (3898) and/or insulator material(s) (3882), in various ways including, but not limited to any suitable, orientation, angle, geometry, and/or location. The two or more electrodes or conductors (3881) can also, without limitation, be located or positioned anywhere on or within the surface of any contact surface(s) (3898) and/or insulator material(s) (3882), in any suitable location(s). Without being limited, the two or more electrodes or conductors (3881) can also be, without limitation, located or positioned at any suitable and effective, depth(s), height(s), and/or angle(s), within the surface of any contact surface(s) (3898) and/or insulator material(s) (3882). It is preferred, without limitation that if the two or more electrodes or conductors (3881) are positioned or located within the contact surface(s) (3898) and/or insulator material(s) (3882), at least a sufficient amount of the surface(s) of the electrodes or conductors (3881) is effectively exposed to any aerosol (200) or liquid that is deposited on these surfaces, so that any, suitable and effective PLC(s) at any suitable and effective location(s), and/or any PLC(s) at any local and/or remote location(s), and preferably any PLC(s) that controls and/or is a component of any remote aerosol sensor(s) (5010), and/or any conductivity sensor(s) (3897), may be able to effectively and accurately determine when a sufficient and efficacious amount of aerosol (200) is not only deployed into the one or more targeted area(s) (210), but also deposited onto the contact surface(s) (3898).

With reference to FIGS. 98-102 and FIGS. 119-132, and FIGS. 139-144, and without limitation, a preferred description of the aerosol deposit sensor(s) (3880) is given. Without being limited, the one or more conductors (3881) and any other conductive component(s) such as, but not limited to any, conductive path(s) (3885), utilized in the design and construction of the aerosol deposit sensor(s) (3880), can be separated by any suitable and effective distance(s). It is preferred, without limitation, that at least the one or more of any conductors (3881) including any conductive path(s) (3885), are separated by a distance between and including zero to twenty-four inches or more. It is more preferred, without limitation that at least the one or more of any conductors (3881) including any conductive path(s) (3885), are separated by a distance of at least 0.005 inches or more. It is even more preferred, without limitation that the one or more of any conductors (3881) including any conductive path(s) (3885), are separated by a distance between zero to six inches. It is very preferred, without limitation, that the one or more of any conductors (3881) including any conductive path(s) (3885), are separated by a distance that is twelve inches or less.

In addition, and without being limited, the one or more of any insulator material(s) (3882) can separate any conductors (3881) as well as any other conductive component(s) such as, but not limited to any, conductive path(s) (3885), that are all utilized in the design and construction of the aerosol deposit sensor(s) (3880), by any suitable and effective distance(s). It is preferred, without limitation, that the one or more of any insulator material(s) (3882) separates any conductors (3881) as well as any other conductive component(s) such as, but not limited to any, conductive path(s) (3885), that are all utilized in the design and construction of the aerosol deposit sensor(s) (3880), by a distance between and including zero to twenty-four inches or more. It is more preferred, without limitation, that the one or more of any insulator material(s) (3882) separates any conductors (3881) as well as any other conductive component(s) such as, but not limited to any, conductive path(s) (3885), that are all utilized in the design and construction of the aerosol deposit sensor(s) (3880), by a distance of at least 0.005 inches or more. It is even more preferred, without limitation, that the one or more of any insulator material(s) (3882) separates any conductors (3881) as well as any other conductive component(s) such as, but not limited to any, conductive path(s) (3885), that are all utilized in the design and construction of the aerosol deposit sensor(s) (3880), by a distance between zero to six inches. It is very preferred, without limitation, that the one or more of any insulator material(s) (3882) separates any conductors (3881) as well as any other conductive component(s) such as, but not limited to any, conductive path(s) (3885), that are all utilized in the design and construction of the aerosol deposit sensor(s) (3880), by a distance that is twelve inches or less.

The aerosol deposit sensor(s) (3880) can, without limitation, vary widely in its sensitivity and ability to sense any kind of any deposited aerosol(s) (200) in the targeted area(s)

(210). Without being limited, the aerosol deposit sensor(s) (3880) can also have various capabilities known in the art, including, without limitation, the ability to have any adjustable sensitivity and trigger level(s), and/or the ability to communicate with one or more of any digital, electronic, or analog, controller(s) such as, but not limited to, any PLC(s) at any location(s), and/or any other suitable components, that can also have any adjustable sensitivity and trigger level(s). The aerosol deposit sensor(s) (3880) can, without limitation, indicate to or communicate with one or more of any digital, electronic, or analog, controller(s) such as, but not limited to, any PLC(s) at any location(s), if or when it either receives or ceases to receive any trait or attribute pertaining to any deposited aerosol(s) (200) at any time(s), such as, but not limited to, any desired or set level of electrical characteristics or attributes, such as, but not limited to any, amperage(s), current(s), and/or voltage(s). Without being limited, the aerosol deposit sensor(s) (3880) can also, indicate to or communicate with, one or more of any digital, electronic, or analog, controller(s) such as, but not limited to, any PLC(s) at any location(s), by way of sending or communicating with, one or more of any, power level(s), voltage(s), data(s), information(s), electrical signal(s), current(s), signal(s), and/or amperage(s), to communicate any information pertaining to any aerosol(s) (200) that is detected such as, but not limited to, (a) the presence or absence of any aerosol(s) (200) on the aerosol deposit sensor(s) (3880), and/or any, (b) persistence of any deposited aerosol(s) (200) on the aerosol deposit sensor(s) (3880), (c) amount of any deposited aerosol(s) (200) on the aerosol deposit sensor(s) (3880), (d) completeness of coverage of any deposited aerosol(s) (200) on the aerosol deposit sensor(s) (3880), (e) percentage or degree of any aerosol (200) coverage on the aerosol deposit sensor(s) (3880).

Without being limited, any signal(s) or electrical output from the one or more aerosol deposit sensor(s) (3880) can also be amplified by any suitable and effective means for signal or electrical amplification (Hereinafter called "amplifier" (3887)), before the signal(s) or electrical output is received by one or more of any, PLC(s) or remote PLC (3893). With reference to FIGS. 119-132 and FIG. 141, and without being limited, a description of a means used to amplify the electrical output or signal(s) from any of the aerosol deposit sensor(s) (3880) that may be utilized, is given. Without being limited, one part of the aerosol deposit sensor(s) (3880) is connected to a positive DC voltage V+ and another part of the aerosol deposit sensor(s) (3880) is connected to an input of the amplifier (3887). Without being limited, an output of the amplifier (3887) is connected to one end of the current sensing resistor (6180) and to any suitable and effective input of the microprocessor or PLC(s) (3893), preferably to the analog input of the microprocessor or PLC(s) (3893). The other end of the current sensing resistor (6180) is connected to ground. Without being limited, any suitable and effective number of any suitable and effective, amplifier(s) (3887), current sensing resistor(s) (6180), and microprocessor or PLC(s) (3893), may be utilized. It is preferred, without limitation, that the amplifier (3887), current sensing resistor (6180), and microprocessor or PLC(s) (3893), are at least suitable and effective. Without being limited, any signal(s) sent by the aerosol deposit sensor(s) (3880) produces or allows for any suitable and effective current to flow, preferably a current of at least 0.5 microamp.

Without being limited, the amplifier (3887) can amplify one or more electrical characteristics or attributes, such as, but not limited to any, voltage, amperage, and electrical current, and at least a sensor voltage, sensor amperage, and/or sensor current, is generated at the output of the amplifier (3887) with the current sensing resistor (6180). Without being limited, the at least sensor voltage, sensor amperage, and/or sensor current, that is received by the microprocessor or PLC(s) (3893), is compared with any value(s) or data stored in the firmware and/or software of the microprocessor or PLC(s) (3893). Without being limited, if the one or more of any, data, information, electrical voltage, amperage, electrical current, and/or signal(s), reported to the microprocessor or PLC(s) (3893) by the aerosol deposit sensor(s) (3880) and/or any related component(s), meets one or more of any criteria that indicates that the targeted area(s) (210) is effectively, sufficiently, and/or efficaciously filled with aerosol(s) (200), the microprocessor or PLC(s) (3893) will send one or more of any, signal(s), command(s), information, and/or data, preferably via the one or more transceiver(s) (6000), that will result in or cause any number of any actions and/or any combination of any actions, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s) (6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210).

Without limitation, an effective or sufficient amount of administered aerosol (200) into one or more targeted area(s) (210) in this embodiment is indicated by its causing any, current to flow, and/or any change in any, voltage, current, and/or amperage, all of which can be represented by any, data, information, or value(s), and can be detected, monitored, and/or analyzed, by one or more of any PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(es) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010). Without being limited, the effective or suitable, amount, density, concentration, and/or specified quantity, of administered aerosol (200) into any targeted area(s) (210) can vary for any intended or unintended reasons or designs, and the trigger or sensitivity levels for the, aerosol deposit sensor(s) (3880) and/or any other devices such as, but not limited to any, suitable and effective PLC(s) at any suitable and effective location(s), and/or any PLC(s) at any local and/or remote location(s), and preferably any PLC(s) that controls and/or is a component of any remote aerosol sensor(s) (5010), can be, without limitation, varied, calibrated, and/or adjusted, for any amount, degree, or level, of aerosol (200) that is deposited onto the one or more surface(s) of the aerosol deposit sensor(s) (3880), that can be sensed for each or any situation and/or any level(s), concentration(s), and/or density(s), of any aerosol(s) (200) that is equated with an efficacious outcome.

Without being limited, the effective, efficacious, and/or sufficient, amount of aerosol(s) (200) within the one or more targeted area(s) (210), can result in any, density(s), and/or concentration(s), of any aerosol(s) in these space(s) (210), and this can relate or correspond to one or more of any suitable and effective, value(s), information(s), signal(s), electrical signal(s), data(s), and/or electrical characteristic(s), that is sensed, communicated, connected, enabled, and/or created, at any time, by the one or more aerosol deposit sensor(s) (3880), such as, but not limited to any, (a) current(s), (b) amperage(s), and/or (c) voltage(s), that can be communicated or sent to the one or more of any suitable and effective, sensor(s) (3897), and/or any PLC(s), and preferably one or more of any PLC(s) (3893) that controls and/or is a component of any remote aerosol sensor(s) (5010).

Also, without being limited, the aerosol deposit sensor(s) (3880), and/or any other devices such as, but not limited to any, suitable and effective PLC(s) at any suitable and effective location(s), and/or any PLC(s) at any local and/or remote location(s), and preferably any PLC(s) that controls and/or is a component of any remote aerosol sensor(s) (5010), can be calibrated, programmed, and/or adjusted, to indicate, acknowledge, and/or recognize any, amount(s) and/or thickness(s) of any deposited aerosol(s) (200) and any related electrical, voltage(s), amperage(s), and/or current(s), that may flow through and/or be transmitted by the aerosol deposit sensor(s) (3880), that indicates that a suitable, effective, and/or efficacious, quantity(s), level(s), concentration(s), and/or density(s), of any aerosol(s) (200), is present in the targeted area(s) (210). Without being limited, any suitable and effective electrical, voltage(s), amperage(s), and/or current(s), that may flow through, and/or be transmitted by, the aerosol deposit sensor(s) (3880), can indicate that a suitable, effective, and/or efficacious, quantity(s), level(s), concentration(s), and/or density(s), of any aerosol(s) (200), is present in the targeted area(s) (210), and can be communicated by the aerosol deposit sensor(s) (3880) to any PLC(s) in any suitable and effective location(s), using any suitable and effective, current(s), voltage(s), and/or amperage(s), and/or any other suitable and effective means known to those skilled in the art.

Also, without being limited, the one or more of any concentration(s) and/or density(s) of various aerosol(s) can vary within the targeted area(s) (210) for any intended or unintended reason(s) or design, and the trigger or sensitivity levels of the, aerosol deposit sensor(s) (3880) and/or any other devices such as, but not limited to any, suitable and effective PLC(s) at any suitable and effective location(s), and/or any PLC(s) at any local and/or remote location(s), and preferably any PLC(s) that controls and/or is a component of any remote aerosol sensor(s) (5010), can be, without limitation, varied, calibrated, or adjusted, for one or more of any value(s) or data(s) related to any amount of deposited aerosol (200) on the surface(s) of the aerosol deposit sensor(s) (3880), such as, but not limited to any, (a) current(s), (b) amperage(s), (c) voltage(s), that is sensed at any time, by the one or more aerosol deposit sensor(s) (3880) and/or any other devices such as, but not limited to any, suitable and effective PLC(s) at any suitable and effective location(s), and/or any PLC(s) at any local and/or remote location(s), and preferably any PLC(s) that controls and/or is a component of any remote aerosol sensor(s) (5010), and correspond with or indicate condition(s) that are indicative of the one or more targeted area(s) (210) being filled with an amount of aerosol (200) that is effective, efficacious, sufficient, and/or desired.

Without being limited, any, data, information, signal(s), sensor voltage, sensor amperage, electrical signal(s), and/or sensor current(s), that is reported or sent by any aerosol deposit sensor(s) (3880) and any associated component(s), can also be amplified, with any suitable and effective means for amplification, including the amplification means shown in FIG. 141, and described later when the more preferred description of the remote aerosol sensor(s) (5010) is given, before it is received by any part(s) or component(s) such as, but not limited to any, sensor(s) (3897), and/or one or more of any PLC(s), and preferably any PLC(s) (3893) that controls and/or is a component of any remote aerosol sensor(s) (5010).

Without being limited, the sensing circuit that is shown in FIG. 141, can amplify the small, and/or any, electrical current, amperage, and/or electrical voltage, changes, that may be reported by any aerosol deposit sensor(s) (3880) so that the one or more of any suitable and effective sensor(s) (3897), and/or one or more of any PLC(s), and preferably any PLC(s) (3893) that controls and/or is a component of any remote aerosol sensor(s) (5010), can see larger changes, and/or be able to effectively detect any changes, in any, signal(s), sensor voltage, sensor amperage, electrical signal(s), and/or sensor current, that is reported or sent by any aerosol deposit sensor(s) (3880) and any associated component(s).

Without being limited, any suitable and effective, data, information, signal(s), voltage, sensor voltage, amperage, sensor amperage, electrical signal(s), and/or sensor current, can be reported, sent, communicated, and/or shared, by any aerosol deposit sensor(s) (3880) and any associated component(s), with or to any part(s) or component(s) such as, but not limited to any, sensor(s) (3897), and/or one or more of any PLC(s), and preferably any PLC(s) (3893) that controls and/or is a component of any remote aerosol sensor(s) (5010). Also, without being limited, any, suitable, effective, and/or usable, current(s), voltage(s), and/or amperage(s), may flow through or across the various conductors (3881) at any, suitable, effective, and/or usable time(s), and for any, suitable, effective, and/or usable, duration(s) of time(s). It is preferred, without limitation, that a voltage between 0-24 volts or more, and more preferred, without limitation, that a voltage less than or about 24 Volts, and even more preferred, without limitation, a voltage between 0-15 Volts, and very preferred, without limitation, a voltage between 1-6 Volts, and extremely preferred, without limitation, a voltage between 4-6 Volts, is used to communicate with or send electrical signal(s) to, the one or more sensor(s) (3897), and/or one or more of any PLC(s), and preferably any PLC(s) (3893) that controls and/or is a component of any remote aerosol sensor(s) (5010), from the various aerosol deposit sensor(s) (3880). In addition, and without limitation, it is also preferred, that an amperage between 0-20 Amp or more, more preferred, that an amperage less than 20 Amp, and even more preferred an amperage between 0 to 1.0 Amp, and very preferred an amperage of 0.5 nA or greater Amps, and extremely preferred an amperage between 0.5 nA to 1.0 Amps, is also utilized to communicate with or send electrical signal(s) to, the one or more sensor(s) (3897), and/or one or more of any PLC(s), and preferably any PLC(s) (3893) that controls and/or is a component of any remote aerosol sensor(s) (5010), from the various aerosol deposit sensor(s) (3880).

Without limitation, any suitable and effective, current(s), voltage(s), and/or amperage(s), can be used to communicate or indicate, from any, aerosol deposit sensor(s) (3880), device(s), component(s), sensing device(s) (5080), and/or means to amplify any signal(s) (3887), to any suitable and effective, sensor(s) (3897), and/or one or more of any PLC(s), and preferably any PLC(s) (3893) that controls and/or is a component of any remote aerosol sensor(s) (5010), any one or more condition(s) or environment(s) that the one or more sensing device(s) (5080) and/or surface(s) of the aerosol deposit sensor(s) (3880), are experiencing.

Without limitation, the current(s) that are sensed, at any suitable and effective time(s), by the one or more sensor(s) (3897), and/or one or more of any PLC(s), and preferably any PLC(s) (3893) that controls and/or is a component of any remote aerosol sensor(s) (5010), and pertain to, are related to, and/or are attributed to, any aerosol deposit sensor(s) (3880) that are in any dry or close to dry condition(s), can have any suitable and effective amperage(s), preferably, the current can have any amperage less than or about 20 Amp, more preferably, the current can have any amperage between 0 to 1.0 Amp, even more preferably the current can have an amperage less than about 100 nA, very preferably the current can have an amperage less than about 10 nA, extremely preferably the current can have an amperage less than about 1 nA.

Without limitation, the current(s) that are sensed by the one or more sensor(s) (3897), and/or one or more of any PLC(s), and preferably any PLC(s) (3893) that controls and/or is a component of any remote aerosol sensor(s) (5010), that pertains to, are related to, and/or are attributed to, any aerosol deposit sensor(s) (3880) that has a sufficient, effective, and/or efficacious amount, of aerosol(s) (200) deposited on the surface(s) at least between the at least two conductors (3881) of the aerosol deposit sensor(s) (3880) that produces, enables, or allows for, any suitable and effective current to flow, can have any suitable and effective amperage(s), preferably, the current can have any amperage less than or about 20 Amp, more preferably, the current can have any amperage between about 0 to 1.0 Amp or greater, even more preferably the current can have an amperage greater than about 0.5 micro-Amp, very preferably the current can have an amperage greater than about 10 micro-Amp, extremely preferably the current can have an amperage greater than about 100 micro-Amp.

Without being limited, any, data, information, signal(s), sensor voltage, sensor amperage, and/or sensor current, that is reported or sent by any aerosol deposit sensor(s) (3880) and any associated component(s), and received by any microprocessor(s) or PLC(s) (3893), may be reported at any time(s) via any suitable and effective means known to those skilled in the art, including, but not limited to any, transceiver(s) (6000), to one or more of any PLC(s) at any suitable and effective location(s), and preferably any PLC(s) that controls and/or is a component of any device(s) and/or equipment(s) that is utilized in the one or more process(es) to treat the various surfaces within the targeted area(s) (210), and more preferably, any PLC(s) that controls one or more of any aerosol producing apparatus(s) (215), and even more preferably any PLC(s) (6005) that controls, and/or is located in or at, and/or is a component(s) of, one or more of any, remote controlling device(s) (6010).

However, it is preferred, without limitation, that any sensor voltage, sensor amperage, and/or sensor current, that is reported or sent by any aerosol deposit sensor(s) (3880) and any associated component(s), and that is received by the microprocessor(s) or PLC(s) (3893), is compared with any value(s) or data stored in any firmware and/or software of the microprocessor(s) or PLC(s) (3893). Furthermore, and without being limited, if any reported sensor voltage, sensor amperage, and/or sensor current, meets any one or more criteria or condition(s), that indicates that the targeted area(s) (210) are effectively, suitably, and/or efficaciously filled with aerosol (200), the microprocessor(s) or PLC(s) (3893) will send one or more of any, signal(s), command(s), information, and/or data, preferably via the one or more transceiver(s) (6000), that can result in or cause any number of any actions and/or any combination of any actions, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s) (6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), because a sufficient, efficacious, and/or effective, amount of aerosol (200) is present or contained in the enclosed space or targeted area(s) (210) being treated.

Figure 127:
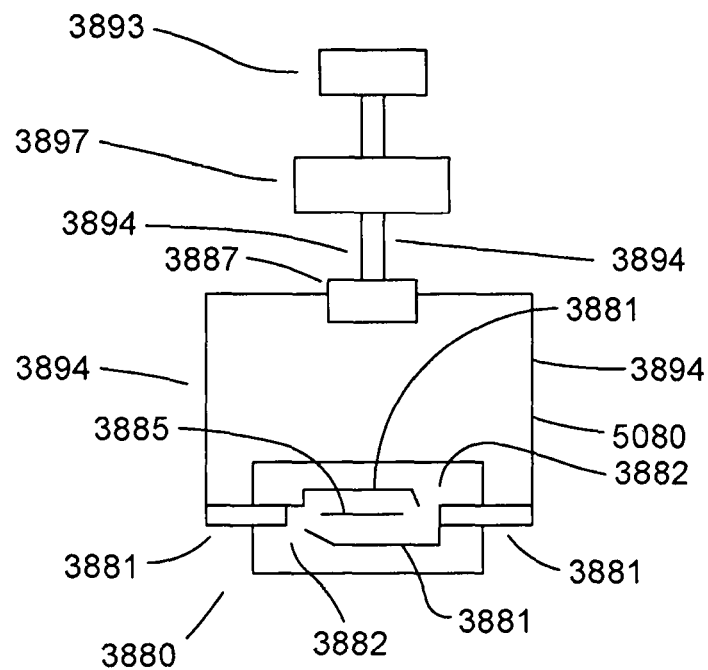
Figure 128:
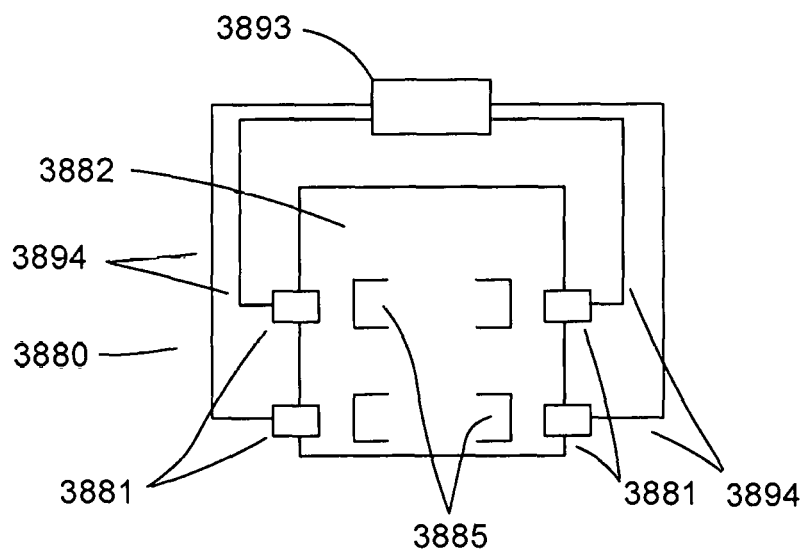
Figure 129:
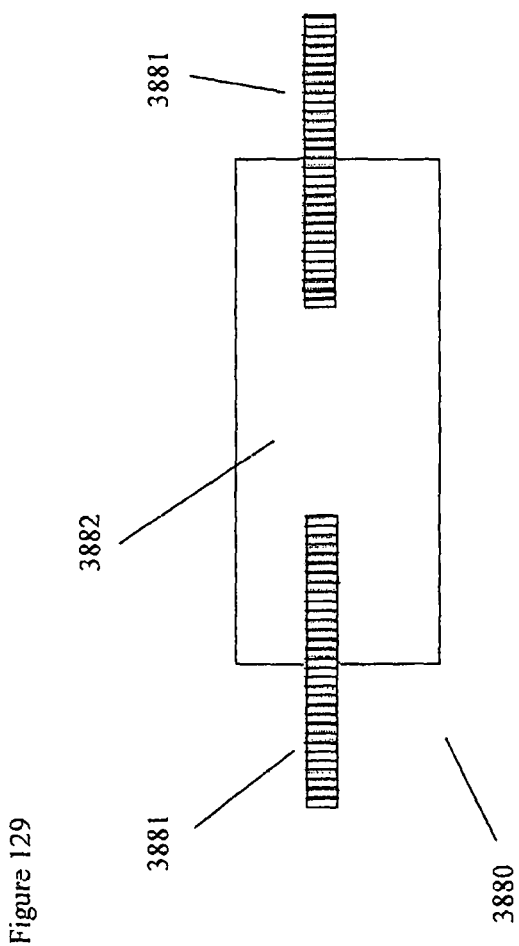

Referring to FIGS. 127-128, and without being limited, one or more electrodes or conductors (3881), and/or any other suitable conductive material(s) (Hereinafter called "conductive path(s)" (3885)), may also be located in one or more of any effective and suitable way(s) and/or location(s), or various combinations thereof, such as, but not limited to, (a) within or partially within, (b) effectively isolated, within or partially within, (c) partially on and/or within, (d) effectively isolated, and partially on and/or within, (e) on the surface of, (f) effectively isolated, and on the surface of, (g) embedded on and/or within, (h) effectively isolated, and embedded on and/or within, (i) partially embedded on and/or within, (j) effectively isolated, and partially embedded on and/or within, (k) fully and/or partially embedded on and/or within, and effectively exposed to the surface of, (l) effectively isolated, and fully and/or partially embedded on and/or within, and effectively exposed to the surface of, the one or more insulator material(s) (3882).

Alternatively, and without being limited, one or more insulator material(s) (3882) may also be located in one or more of any effective and suitable way(s) and/or location(s), or various combinations thereof, such as, but not limited to, (a) within or partially within, (b) effectively isolated, within or partially within, (c) partially on and/or within, (d) effectively isolated, and partially on and/or within, (e) on the surface of, (f) effectively isolated, and on the surface of, (g) embedded on and/or within, (h) effectively isolated, and embedded on and/or within, (i) partially embedded on and/or within, (j) effectively isolated, and partially embedded on and/or within, (k) fully and/or partially embedded on and/or within, and effectively exposed to the surface of, (l) effectively isolated, and fully and/or partially embedded on and/or within, and effectively exposed to the surface of, the one or more of any suitable conductive material(s) or effectively sized conductive path(s) (3885) that is suitably and effectively connected to at least two or more electrodes or conductors (3881).

These conductive path(s) (3885) can be, without limitation, either electrically isolated and merely serve as a partial and/or non-partial conductive path(s) across the insulator material(s) (3882), and/or they can also connect with one or more of any, conductivity sensor(s) (3897), and/or any suitable and effective PLC(s) at any suitable and effective location(s), and/or any PLC(s) at any local and/or remote location(s), and preferably any PLC(s) that controls and/or is a component of any remote aerosol sensor(s) (5010), and be utilized to indicate when a sufficient and efficacious amount of aerosol (200) is not only deployed into the one or more targeted area(s) (210), but also deposited onto the contact surface(s) (3898). It is preferred, without limitation, that the conductive path(s) (3885) are electrically isolated and merely serve as a partial and/or non-partial conductive path(s) across the insulator material(s) (3882) with which they are directly and/or indirectly interfaced with. Without being limited, and referring to FIG. 122, one or more conductive path(s) (3885) can also be directly or indirectly positioned or interfaced with, and/or located on or within, the one or more channel(s) (3895) that may be utilized.

The one or more materials such as, but not limited to the, conductive path(s) (3885), electrodes or conductors (3881), and/or insulator material(s) (3882) can be, without limitation, interfaced with each other in various ways known to those skilled in the art, such as, but not limited to, (a) embedding one or more of these material(s), partially or completely, into the other one or more of these material(s) (ie: one or more conductive path(s) (3885) are completely or partially embedded into the one or more insulator material(s) (3882), or vice versa), (b) printing or marking one or more of these material(s) into or onto the other one or more of these material(s) (ie: one or more conductive path(s) (3885) are printed into or onto one or more insulator material(s) (3882), or vice versa). Any amount of the conductive path(s) (3885), electrodes or conductors (3881), and insulator material(s) (3882) may be utilized. It is preferred, without limitation, that at least a suitable and effective amount of the one or more conductive path(s) (3885), electrodes or conductors (3881), and/or insulator material(s) (3882), are utilized. It is more preferred, without limitation, that at least a suitable and effective amount of the one or more conductive path(s) (3885), electrodes or conductors (3881), and/or insulator material(s) (3882), are utilized and exposed to the environment within the targeted area(s) (210).

Figure 124:
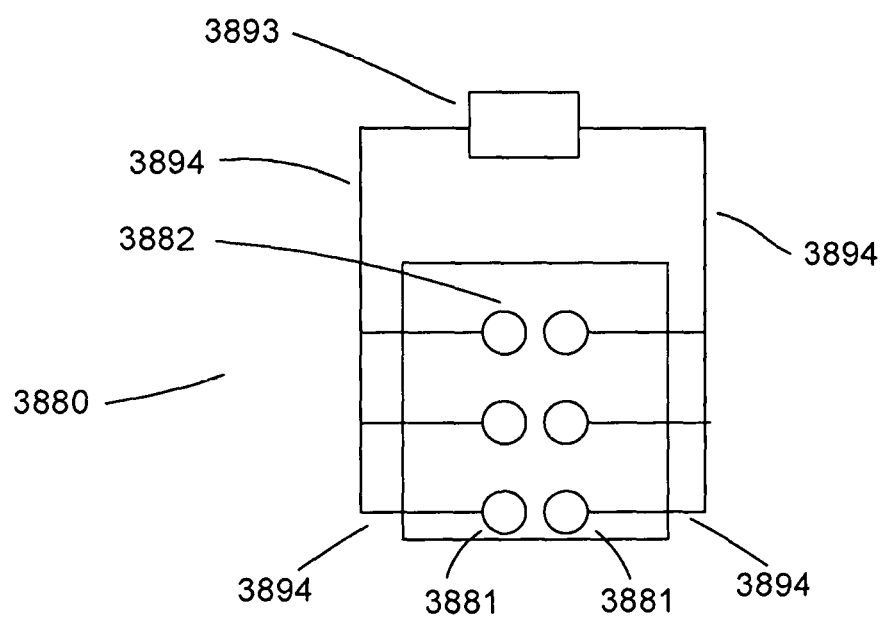
Figure 125:
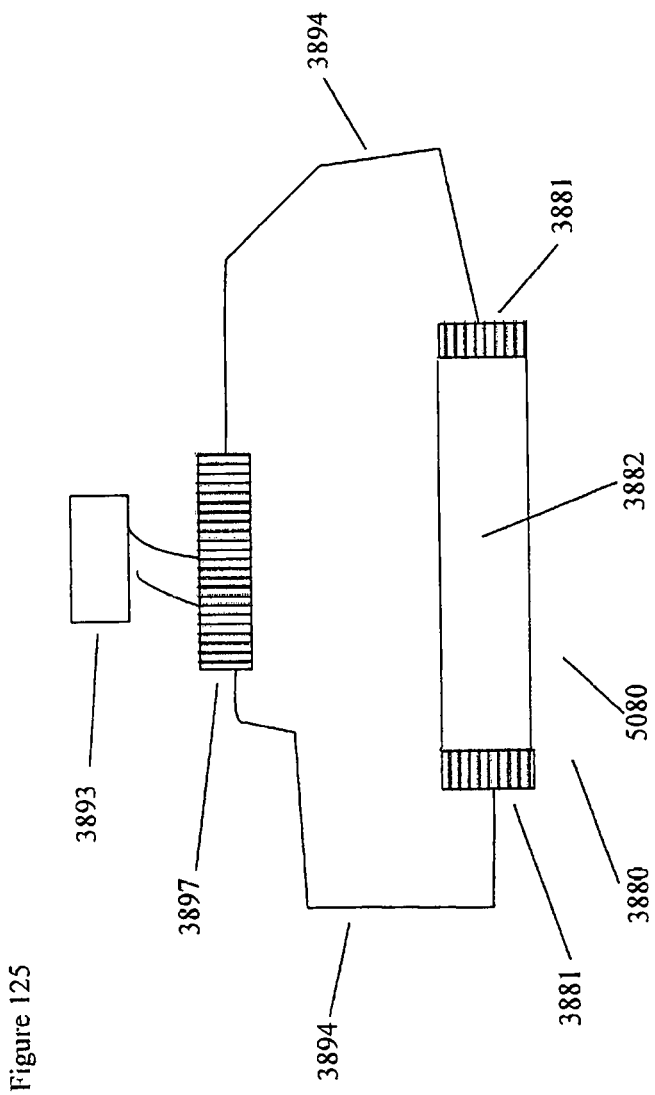
Figure 126:
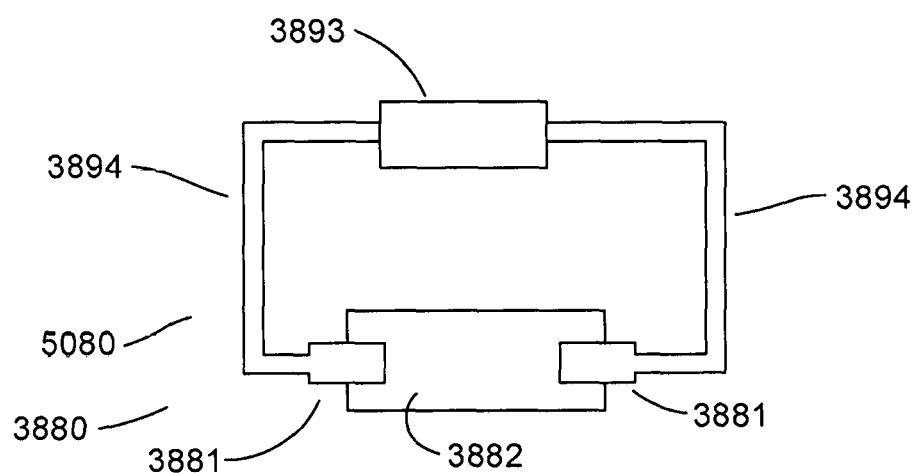

Referring to FIGS. 119-132, and without being limited, at least two or more electrodes or conductors (3881) are connected to at least one or more of any suitable, digital, electronic, or analog, controller(s) such as, but not limited to any, conductivity sensor(s) (3897), and/or any suitable and effective PLC(s) at any suitable and effective location(s), and/or any PLC(s) at any local and/or remote location(s), and preferably any PLC(s) that controls and/or is a component of any remote aerosol sensor(s) (5010). Any number of electrodes or conductors (3881) can be, without limitation, used with each aerosol deposit sensor(s) (3880) and contact surface(s) (3898) that are used. It is preferred, without limitation, that at least two or more electrodes or conductors (3881) are used with each aerosol deposit sensor(s) (3880) and contact surface(s) (3898), and they are suitably and effectively wired or cabled, with one or more of any suitable wires or cables (Hereinafter called "wire(s)" (3894)), to one or more of any, conductivity sensor(s) (3897), and/or any suitable and effective PLC(s) at any suitable and effective location(s), and/or any PLC(s) at any local and/or remote location(s), and preferably any PLC(s) that controls and/or is a component of any remote aerosol sensor(s) (5010). Without being limited, the various electrodes or conductors (3881) that are used with each aerosol deposit sensor(s) (3880) and contact surface(s) (3898), may also be suitably and effectively wired or cabled, with one or more of any suitable and effective wire(s) (3894), and connect to one or more of any suitable and effective amplifier(s) (3887) known to those skilled in the art, before any direct or indirect connection is made with the various electrodes or conductors (3881) to any, conductivity sensor(s) (3897), and/or any suitable and effective PLC(s) at any suitable and effective location(s), and/or any PLC(s) at any local and/or remote location(s), and/or preferably any PLC(s) that controls and/or is a component of any remote aerosol sensor(s) (5010). Referring to FIGS. 123-124, and FIG. 128, and without being limited, more than two electrodes or conductors (3881) can share the same circuit or connection(s) to one or more of any PLC(s), conductivity sensor(s) (3897), and/or remote PLC(s) (3893), on either side of the insulator material(s) that keeps the electrical circuit(s) from being completed.

The electrodes or conductors (3881) can be, without limitation, configured and wired according to any effective electrical design(s) that allows the aerosol deposit sensor(s) (3880) to perform effectively and accurately. The electrodes or conductors (3881) can also be, without limitation, configured and wired to establish one or more of any suitable and effective electrical circuit(s) of any complexity, including, but not limited to any, circuit(s) that is configured in parallel and/or series. The electrodes or conductors (3881), insulator material(s), and contact surface(s) (3898), can be, without limitation, configured and wired so that current may flow between any of the two or more electrodes or conductors (3881) in order to complete one or more circuit(s) and indicate when a sufficient and efficacious amount of aerosol (200) is not only deployed into the one or more targeted area(s) (210), but also deposited onto the contact surface(s) (3898).

Any suitable and effective, amperage, current, and voltage, may flow through the electrodes or conductors (3881) and any other connected wiring and/or related systems at any time. It is preferred, without limitation, that the current that is used to flow between the various electrodes or conductors (3881), is any current that would typically be measured in units of microamp or milliamp, by those skilled in the art. It is also preferred, without limitation, that at least a safe amount of current is utilized. One or more of any guards or protective structures can also, without limitation, be used to guard, cover, and/or protect one or more of any components such as, but not limited to, the aerosol deposit sensor(s) (3880), the contact surface(s) (3898), and/or the electrodes or conductors (3881). The one or more guard(s), cover(s), and/or protective structure(s), that are utilized, can also have, without limitation, any suitable number and size of any, grates, perforations, and/or holes. It is preferred, without limitation, that if any guard(s), cover(s), and/or protective structure(s), are utilized, they are at least sufficiently and effectively designed to allow an effective and representative amount of aerosol (200) from the targeted area(s) (210) to access the aerosol deposit sensor(s) (3880), and more specifically, the contact surface(s) (3898).

Without being limited, and referring to FIGS. 119-132, and FIGS. 139-144, another example of the aerosol deposit sensor(s) (3880) is given. Without being limited, and in this example, one or more of any circuit(s) (6215) and/or one or more of any potential circuit(s) (6215), established and/or utilized in the design of the aerosol deposit sensor(s) (3880), can apply any suitable and effective, voltage, preferably a stable voltage, across one or more of any part(s) of the two or more of any conductors (3881). It is preferred, without limitation, that the conductors are constructed and arranged to form one or more of any suitable and effective, grid(s) and/or pattern(s), of conductor(s). The various conductor(s) (3881) can, without limitation, suitably and effectively, interlock, loosely interlock, oppose each other, and/or interrelate to each other. It is preferred, without limitation, that various conductor(s) (3881) are suitably and effectively spaced so that they do not touch and/or are suitably and effectively isolated electrically.

It is preferred, without limitation, that each side, representing each potential, of the circuit(s) (6215) that are a part of the aerosol deposit sensor(s) (3880), connects to one or more of its own conductors (3881), and these conductors (3881) are interlocking and/or partially interlocking in their design, all without touching, where the deposited aerosol(s) (200) and/or vapor(s) are able to form the electrical connection(s) between each side of the electrical circuit(s) (6215) and allow any suitable and effective amount(s) of electrical current(s) to flow.

Referring to FIG. 141, and without being limited, the one or more of any circuit(s) (6215) that are formed by the various conductor(s) (3881) can be, active, completed, and/or formed, at any suitable and effective time(s), and for any suitable and effective duration(s). The one or more of any circuit(s) (6215) can also be, without limitation, open, partially open, and/or partially closed, at any suitable and effective time(s) and for any suitable and effective duration(s), before any deployed aerosol(s) (200), vapor(s), and/or agents(s) are deployed into the targeted area(s) (210) and onto the aerosol deposit sensor(s) (3880).

Without being limited, the one or more circuit(s) (6215) that are formed by the various conductor(s) (3881), can be, open, and/or have any suitable and effective, impedance, high impedance, or very high impedance, when the various surface(s) of the aerosol deposit sensor(s) (3880) are at least dry, preferably effectively and suitably dry, and more preferably, close to, at, and/or about, any suitable and effective dry condition(s).

It is preferred, without limitation, that the one or more circuit(s) (6215) that are formed by the various conductor(s) (3881) are at least suitably and effectively open, before any aerosol(s) (200) and/or vapor(s) are deployed into the one or more targeted area(s) (210) and/or deposited onto the various surfaces of the aerosol deposit sensor(s) (3880). The one or more circuit(s) (6215) that are formed by the various conductor(s) (3881) can have, without limitation, any suitable and effective, impedance and conductivity, at any time(s). It is preferred, without limitation that the one or more circuit(s) (6215) that are formed by the various conductor(s) (3881) are high impedance (low conductivity), and more preferably very high impedance (low conductivity), before any aerosol(s) (200) and/or vapor(s) are deposited onto the aerosol deposit sensor(s) (3880).

It is also preferred, without limitation that the one or more circuit(s) (6215) that are formed by the various conductor(s) (3881) are not only suitably and effectively open, but they are also high impedance (low conductivity), and more preferably they are not only suitably and effectively open, but they are also very high impedance (low conductivity), before any aerosol (200) and/or vapor(s) are deposited onto the aerosol deposit sensor(s) (3880).

Also, without limitation, during the operation of the aerosol deposit sensor(s) (3880) when various surfaces such as, but not limited to any of its, insulator material(s) (3882), conductor(s) (3881), and/or any other surface(s) of the aerosol deposit sensor(s) (3880), are in any suitable and effective dry state(s) and/or in or about any suitable and effective dry condition(s), it is preferred, without limitation, that there is no, or effectively no, amount(s) of current(s), that flows between and/or through the various conductor(s) (3881) and/or the one or more of any circuit(s) (6215) that are formed by the various conductor(s) (3881).

However, it is more preferred, without limitation, that when various surfaces of the aerosol deposit sensor(s) (3880) such as, but not limited to any, insulator material(s) (3882), conductor(s) (3881), and/or any other surface(s) of the aerosol deposit sensor(s) (3880), are in any dry state(s) and/or in or about any suitable and effective dry condition(s), at least only suitable and effective amount(s) of electrical current(s), preferable any effectively small or even minuscule amount(s) of electrical current(s), flows between and/or through the various conductor(s) (3881) and/or the one or more of any circuit(s) (6215) that are formed by the various conductor(s) (3881).

Many different electrically insulating material(s) can be used to construct various components of the aerosol deposit sensor(s) (3880), such as, but not limited to any, suitable and effective electrical insulator material(s) (3882) that interface with any electrical conductor(s) (3881), and the various electrical insulator material(s) that can be used are all known to those skilled in the art. Many of these electrical insulator material(s), may not be "perfect" or otherwise "theoretically perfect" electrical insulators, but they can still be effective and usable. Without being limited, the incorporation and use of the types of electrical insulating materials that are "less than perfect" or "less than theoretically perfect" to construct the aerosol deposit sensor(s) (3880), are actually preferred for use in this example.

Without limitation, during the operation of the aerosol deposit sensor(s) (3880) with these "less than perfect" electrical insulators and/or insulator material(s) (3882), there can be small or minuscule amount(s), of electrical current(s), preferably at least electrical current(s) that are suitable and effective, that flows through the various conductor(s) (3881) and/or the one or more of any circuit(s) (6215) that are formed by the various conductor(s) (3881), due to any leakage(s) through and/or across, the one or more of any electrical insulating material(s) that are used in the design and construction of the aerosol deposit sensor(s) (3880). This leakage can be, without limitation, any suitable and effective amount(s) of electrical, amperage(s), current(s), and/or voltage(s).

This is actually, without limitation, preferred since it establishes, condition(s), status(s), or situation(s), where the various surfaces of the aerosol deposit sensor(s) (3880) such as, but not limited to any, insulator material(s) (3882), conductor(s) (3881), and/or any other surface(s) of the aerosol deposit sensor(s) (3880), are in any suitable and effective dry state(s), and/or in or about any suitable and effective dry condition(s), and yet they are on the edge of conducting electrical current(s) between and/or through the various conductor(s) (3881) and/or the one or more of any circuit(s) (6215) that are formed by the various conductor(s) (3881), where the deposited aerosol(s) (200) and/or vapor(s) can then initiate and/or increase, and/or easily initiate and/or increase, the flow of electrical current(s) between and/or through the various conductor(s) (3881) and/or the one or more of any circuit(s) (6215).

Also, in this particular example, and without being limited, as the droplets of aerosol (200) begin to be deposited and/or any vapor(s) condense, on the surface(s) of the aerosol deposit sensor(s) (3880), preferably on the one or more grid(s) of conductors (3881), they will start to make one or more connection(s) between the conductors (3881), thus connecting or completing the circuit(s) (6215), in the design of the aerosol deposit sensor(s) (3880), and thus increasing the conductivity of the aerosol deposit sensor(s) (3880) and allowing more electrical current(s) to flow as more droplets of aerosol (200) are deposited and/or more of any vapor(s) condense, on the surface(s) of the aerosol deposit sensor(s) (3880). Typically, and without limitation, this electrical current will continue to increase and then stabilize to any suitable and effective value(s) or range of value(s), once the aerosol deposit sensor(s) (3880) are, suitably, effectively, efficaciously, and/or fully, covered or coated with any agent(s) or aerosol(s) (200) that are deployed into and are present in the targeted area(s) (210). Without being limited, this current flow(s) can be sensed by monitoring the voltage(s) across any suitable and effective precision current sensing resistor(s) (6180), known to those skilled in the art, that is preferably connected in series between the aerosol deposit sensor(s) (3880) and its conductor(s) (3881), and ground.

Without being limited, the voltage(s) would then be amplified, with one or more of any suitable and effective amplification means (3887) known to those skilled in the art, to one or more of any, effective, suitable, and/or usable, level(s) or value(s), such that the amplified voltage(s) fall within one or more of any suitable and effective range(s) of output(s) over the sensed current range(s), such as, but not limited to, preferably between about 0 to 24 Volts or more, more preferably between about 0 to 12 Volts, and even more preferably between about 0 to 8 Volts, and very preferably between about 0-5 Volts.

The output of the means for amplification (3887) can be, without being limited, communicated to or fed into any suitable and effective comparator, known to those skilled in the art, directly and/or indirectly, and compared to any set reference(s), and/or it can be communicated to or fed into one or more analog input(s) of any suitable and effective micro-controller(s) or PLC(s), and any comparison(s), computation(s), and/or analysis, can be done in any firmware and/or software, all in a manner known to those skilled in the art. Any suitable and effective means can be used to monitor the aforementioned voltage(s) and/or make any decision(s) and/or cause various action(s) to result, by processing the communicated voltage(s). It is preferred, without limitation, that this means for monitoring is at least one or more of any suitable and effective devices(s) that can communicate with one or more of any PLC(s), and more preferably this means for monitoring is one or more of any suitable and effective PLC(s) at any suitable and effective location(s), and even more preferably this means for monitoring is one or more of any PLC(s) that controls and/or is a component of any remote aerosol sensor(s) (5010).

Referring to FIG. 142, and without being limited, during the deployment of any aerosol(s) (200) into the targeted area(s) (210), one or more of any suitable and effective source(s) of pressurized air and/or gas(s) may be utilized within the one or more targeted area(s) (210) to facilitate, help, and/or accelerate, the movement and/or dispersion of the aerosol(s) (200) within the targeted area(s) (210). Without being limited, any equipment, device(s), and/or their various source(s) of the pressurized air and/or gas(s) that are used to, facilitate, help, and/or accelerate, the movement and/or dispersion of the aerosol(s) (200) within the targeted area(s) (210), can be monitored and/or controlled by one or more of any PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(s) to treat the various surfaces within the targeted area(s) (210), and even more preferably any PLC(s) that controls one or more of any aerosol producing apparatus(s) (215), and very preferably any PLC(s) (6005) that controls, and/or is located in or at, and/or is a component(s) of, one or more of any, remote controlling device(s) (6010).

The one or more of any source(s) of the pressurized air and/or gas(s), that are used to facilitate, help, and/or accelerate, the movement and/or dispersion of the aerosol(s) (200) within the targeted area(s) (210) can be, without limitation, located in one or more of any suitable and effective location(s) within the targeted area(s) (210). Without being limited, the pressurized air and/or gas(s) can be supplied from any suitable and effective source(s) such as, but not limited to, one or more of any, fan(s), blower(s), and/or other suitable and effective supply of pressurized air and/or gas(s). Without being limited, the source(s) of pressurized air and/or gas(s) can be provided by one or more of any suitable and effective device(s). The source(s) of pressurized air and/or gas(s) can also, without being limited, be incorporated into the design and construction of any remote aerosol sensor(s) (5010). The source(s) of pressurized air and/or gas(s) can either push or pull any suitable and effective quantity of air or gas(s), and/or aerosol(s) (200), to one or more of any, location(s) or area(s), within the targeted areas(s) (210), at any suitable and effective rate(s) or speed(s). The output from the source(s) of pressurized air and/or gas(s) can be directed or pointed at any suitable and effective angle(s), orientation(s), and/or position(s).

It is preferred, without limitation, that during the deployment of aerosol(s) (200) into the targeted area(s) (210), at least the one or more aerosol producing apparatus(s) (215), and/or the one or more means to dehumidify (2040), can be utilized as the source(s) of the pressurized air and/or gas(s), to facilitate, help, and/or accelerate, the movement and/or dispersion of the aerosol(s) (200) within the targeted area(s) (210). When used in this capacity, and without limitation, the one or more aerosol producing apparatus(s) (215) can suspend or stop the production of aerosol(s) (200) for any suitable and effective amount of time, but still operate one or more source(s) of its pressurized air or gas(s) such as, but not limited to, one or more of any, blower(s) or fan(s) (180) that are used in the design and construction of the aerosol producing apparatus(s) (215). When also used in this capacity, and without being limited, the one or more means to dehumidify (2040) can operate the one or more source(s) of its pressurized air such as, but not limited to, one or more of any, dehumidifier blower(s) (6210), preferably with the various condensing or chill coil(s) (2080) and any related part(s) and device(s) turned off or disabled, and more preferably where the various, air, gas(s), and/or aerosol(s) (200) from the targeted area(s) (210) are prevented from flowing through, and/or coming in any contact with, any filter(s) (2090), and the various condensing or chill coil(s) (2080) and any related part(s) and device(s) are turned off or disabled, and even more preferably, where the one or more valve(s) (2100) are positioned or utilized so that any, air, gas(s), and/or aerosol(s) from the targeted area(s) (210) are kept from flowing through, and/or coming in any contact with, any filter(s) (2090), and the various condensing or chill coil(s) (2080) and any related part(s) and device(s) are turned off or disabled.

Without being limited, any of the source(s) of the pressurized air and/or gas(s), that are used to facilitate, help, and/or accelerate, the movement and/or dispersion of the aerosol(s) (200) within the targeted area(s) (210), can be operated, at any suitable and effective time(s), for any suitable and effective number of times, and for any suitable and effective duration(s) of time, all during the various treatment cycle(s) or regimen(s) that are used to treat the targeted area(s) (210) with any aerosol(s) (200).

Also, without being limited, the one or more source(s) of the pressurized air and/or gas(s), that are used to facilitate, help, and/or accelerate, the movement and/or dispersion of the aerosol(s) (200) within the targeted area(s) (210), can start their first operation or operational cycle(s), at any suitable and effective time(s), preferably between about zero to 30 minutes after the deployment of aerosol (200) into the targeted area(s) (210) has started, more preferably between about one to ten minutes after the deployment of aerosol (200) into the targeted area(s) (210) has started, even more preferably between about one to five minutes after the deployment of aerosol (200) into the targeted area(s) (210) has started, and very preferably about four minutes or less after the deployment of aerosol (200) into the targeted area(s) (210) has started.

Without being limited, during the treatment of the targeted area(s) (210), the one or more source(s) of the pressurized air and/or gas(s), that are used to facilitate, help, and/or accelerate, the movement and/or dispersion of the aerosol(s) (200) within the targeted area(s) (210), can be operated preferably for a length of time between about zero to 30 minutes, more preferably for a length of time between about one to ten minutes, even more preferably for a length of time between about two to six minutes, and very preferably for a length of time of about five minutes or less.

Also, without being limited, during one or more of any steps taken during the treatment of the targeted area(s) (210) by the aerosol producing apparatus(s) (215), the one or more source(s) of the pressurized air and/or gas(s), that are used to facilitate, help, and/or accelerate, the movement and/or dispersion of the aerosol(s) (200) within the targeted area(s) (210), can start or restart their operation or operational cycle(s), preferably between about every zero to 30 minutes after the termination or stoppage of the last or previous operation of the one or more source(s) of the pressurized air and/or gas(s), more preferably between about every one to ten minutes after the termination or stoppage of the last or previous operation of the one or more source(s) of the pressurized air and/or gas(s), even more preferably between about every two to six minutes after the termination or stoppage of the last or previous operation of the one or more source(s) of the pressurized air and/or gas(s), and very preferably about every five minutes or less after the termination or stoppage of the last or previous operation of the one or more source(s) of the pressurized air and/or gas(s).

Without being limited, the operation of the one or more source(s) of the pressurized air and/or gas(s), that are used to facilitate, help, and/or accelerate, the movement and/or dispersion of the aerosol(s) (200) within the targeted area(s) (210), may be stopped at any time by any suitable and effective PLC(s) at any suitable and effective location(s), and/or any PLC(s) at any local and/or remote location(s), and preferably any PLC(s) that controls and/or is a component of any remote aerosol sensor(s) (5010), and more preferably any PLC(s) (6005) that controls, and/or is located in or at, and/or is a component(s) of, one or more of any, remote controlling device(s) (6010). For example, and without being limited, the operation of these one or more source(s) of the pressurized air and/or gas(s), may be terminated for one or more reasons including, but not limited to, an effective or efficacious amount of aerosol (200) has been deployed into the targeted area(s) (210), the deployment of aerosol (200) into the targeted area(s) (200) has permanently stopped, one or more of any dwell time(s) has started after the deployment of aerosol (200) into the targeted area(s) (210) has stopped, the dwell time(s) have expired, one or more of any dehumidification device(s) (6015) and/or air filtration apparatus(s) (6040) started their operation, there was an emergency shut down of all of the various device(s), equipment(s), and/or component(s), within the targeted area(s) (210).

With reference to FIGS. 95-97, FIGS. 103-118, and FIGS. 133-138, and according to an embodiment an optimized and miniaturized aerosol generator (3800) is described, which optimizes and enhances the design of the aerosol producing apparatus (215) that was previously disclosed. Without being limited, it was discovered that the aerosol generating device (215) design possessed certain limitations that needed further improvement(s) such as, but not limited to: (a) the overall design was too large for certain applications, and needed to be more compact, (b) it took an unacceptable amount of time for the liquid (30) in any and/or all of the reservoir(s) (40) and/or feed tank(s) (280) to heat up to an effective or sufficient temperature either before and/or during the deployment of aerosol (200), and (c) the size of the air space(s) above the transducers (10) in the tank(s) or reservoir(s) (40) in which they are located, was sufficiently large enough and/or had sufficient geometries to allow for an undesired amount of turbulent air flow and/or one or more vortices to be generated, where it can be reasonable to assume that aerosol (200) conglomeration could thus transpire, which is typically not desired, causing larger aerosol (200) droplets to be generated and dispersed. The present invention addresses these issues, as well as other various additional improvements to the design of the aerosol generating device (215) and the optimized and miniaturized aerosol generator (3800). Without being limited, the result is a smaller more compact optimized and miniaturized aerosol generator (3800) and apparatus (215) that is able to produce an aerosol (200) that not only appears thicker, but the aerosol (200) also visually looks lighter and has a longer persistence time, which is a good indicator that a thicker cloud of smaller aerosol (200) droplets are being created. The optimized and miniaturized aerosol generator (3800) can be, without limitation, viewed as either a subcomponent of the aerosol generating device (215), or as a separate independent device.

In one aspect, the tank(s), pressurized enclosure(s), or otherwise reservoir(s) (40), in which the one or more transducer(s) (10) are located, as well as the means for monitoring and controlling the liquid level in the reservoir(s) (40), is redesigned to have multiple performance enhancing changes.

First, and referring to FIGS. 95-97, FIGS. 103-108, and FIGS. 133-137, one or more airflow outlet(s) (4015) can be, without limitation, positioned near or approximately above one or more transducers(s) (10). More specifically, one or more airflow outlet(s) (4015) can be located, without limitation, approximately centered and directly above each transducer (10). It is preferred, without limitation, that the one or more airflow outlet(s) (4015) and/or one or more air outlet pipe(s) (4025), are suitably and effectively centered above, below, and/or around, the one or more transducer(s) (10) and/or the direction of their emitted energy or ultrasonic output or signal. It is even more preferred, without limitation, that the one or more surfaces and/or materials of the airflow outlet(s) (4015), air outlet pipe(s) (4025), or any other parts and components located within the reservoir(s) (40), are suitably and effectively located so that they are not damaged by the energy, ultrasonic output, or signal(s), that is emitted, radiated, and/or transmitted, by the one or more transducer(s) (10). Without being limited, this can be important when utilizing transducer(s) (10) such as, but not limited to those described in the present invention, due to their power and the length of the field of energy, ultrasonic output, or signal(s), that they can emit, radiate, and/or transmit. The one or more airflow outlet(s) (4015) can also be, without limitation, positioned at any angle or orientation. However, it is preferred, without limitation, that the airflow outlet(s) (4015) are positioned so that each orifice is approximately horizontal with the surface of the liquid (30) within the reservoir (40). The one or more airflow outlet(s) (4015) can also be, without limitation, positioned effectively close to, level with, or approximately flush with, the one or more reservoir ceiling(s) (4055) within the reservoir(s) (40). The airflow outlet(s) (4015) can be positioned at any effective height above the transducer(s) (10).

However, to take advantage of the improvements in this invention, the one or more airflow outlet(s) (4015) should be, without limitation, located within a certain height range or gap (denoted in FIG. 103 by distance "A") above any liquid (30) that covers the transducer(s) as follows. It is preferred, without limitation, that at least one or more airflow outlet(s) (4015) is positioned between 0.04 inches to 12.0 inches above the surface of the liquid that is above each aerosol (200) producing transducer (10). It is more preferred, without limitation, that at least one or more airflow outlet(s) (4015) is positioned between 0.04 inches to 3.0 inches above the surface of the liquid that is above each aerosol (200) producing transducer (10). It is even more preferred, without limitation, that at least one or more airflow outlet(s) (4015) is positioned between 0.04 inches to 1.5 inches above the surface of the liquid that is above each aerosol (200) producing transducer (10). It is very preferred, without limitation, that at least one or more airflow outlet(s) (4015) is positioned between 0.05 inches to 1.0 inches above the surface of the liquid that is above each aerosol (200) producing transducer (10). It is extremely preferred, without limitation, that at least one or more airflow outlet(s) (4015) is positioned between 0.06 inches to 0.08 inches above the surface of the liquid that is above each aerosol (200) producing transducer (10). Without being limited, the use of at least one or more airflow outlet(s) (4015) located above each transducer (10), can also be utilized to increase performance. It is preferred, without limitation, that only one airflow outlet(s) (4015), having an effective diameter, is located approximately above each transducer (10).

The liquid (30) should also be maintained at least at an effective depth above the transducers (10) located within the reservoir(s) (40). It is preferred, without limitation that the depth of the liquid (30) is maintained at a depth between 0.25 inches to 8 inches above the transducer(s) (10). It is even more preferred, without limitation that the depth of the liquid (30) is maintained at a depth between 0.5 inches to 5 inches above the transducer(s) (10). It is even more preferred, without limitation that the depth of the liquid (30) is maintained at a depth between approximately 1.25 inches to 1.32 inches above the transducer(s) (10). It is very preferred, without limitation that the depth of the liquid (30) is maintained at a depth of approximately 1.28 inches above the transducer(s) (10). Without being limited, it is important that the liquid (30) depth above the transducer(s) is maintained as constant as possible, especially with the more shallow liquid (30) depths above the transducer(s) (10).

Second, the design of the optimized and miniaturized aerosol generator (3800) and aerosol generating device (215) can be, without limitation, enhanced by special placement of the airflow outlet(s) (4015) respective to the geyser (4045) of raised liquid (30) and any associated aerosol plume (4050) that the transducer generates above the surface of the liquid (30). Referring to FIGS. 103-106, including FIGS. 106-A and 106-B, FIGS. 107-108, and FIGS. 133-137, the geyser (4045) of raised liquid (30) and any associated aerosol plume (4050) that the transducer(s) (10) generates above the surface of the liquid (30) can be located anywhere below the airflow outlet(s) (4015). However, for optimum performance, it is preferred, without limitation, that at least an effective portion of the geyser(s) (4045) of raised liquid (30) and any associated aerosol plume(s) (4050) is located within and/or below the airflow outlet(s) (4015), or otherwise within and/or below the one or more air outlet pipe(s) (4025). It is preferred, without limitation, that at least 0.5 percent or more of the geyser(s) (4045) of raised liquid (30) and any associated aerosol plume(s) (4050) that the transducer generates above the surface of the liquid is located within or below the airflow outlet(s) (4015) or otherwise within the one or more air outlet pipe(s) (4025). It is more preferred, without limitation, that at least 7 percent or more of the geyser(s) (4045) of raised liquid (30) and any associated aerosol plume(s) (4050) that the transducer(s) generates above the surface of the liquid is located within or below the airflow outlet(s) (4015) or otherwise within the one or more air outlet pipe(s) (4025). It is even more preferred, without limitation, that at least 75 percent or more of the geyser(s) (4045) of raised liquid (30) and any associated aerosol plume(s) (4050) that the transducer(s) generates above the surface of the liquid is located within or below the airflow outlet(s) (4015) or otherwise within the one or more air outlet pipe(s) (4025). It is very preferred, without limitation, that at least 90 percent or more of the geyser(s) (4045) of raised liquid (30) and any associated aerosol plume(s) (4050) that the transducer(s) generates above the surface of the liquid is located within or below the airflow outlet(s) (4015) or otherwise within the one or more air outlet pipe(s) (4025). It is extremely preferred, without limitation, that at least 98 percent or more of the geyser(s) (4045) of raised liquid (30) and any associated aerosol plume(s) (4050) that the transducer(s) generates above the surface of the liquid is located within or below the airflow outlet(s) (4015) or otherwise within the one or more air outlet pipe(s) (4025).

Any effective number of geyser(s) (4045) of raised liquid (30) and any associated aerosol plume(s) (4050) that the one or more transducer(s) generates above the surface of the liquid can be, without limitation, located within and/or below the one or more airflow outlet(s) (4015) and/or the one or more air outlet pipe(s) (4025). It is preferred, without limitation, that the one or more airflow outlet(s) (4015), and/or one or more air outlet pipe(s) (4025), are suitably and approximately centered above, below, and/or around, the one or more geyser(s) (4045) of raised liquid (30) and any associated aerosol plume(s) (4050), and/or the transducer(s) (10). One or more of any airflow outlet(s) (4015) and/or air outlet pipe(s) (4025), can be, without limitation, allocated to or effectively function with, one or more of any geyser(s) (4045) of raised liquid (30) and any associated aerosol plume(s) (4050), and/or one or more of any transducer(s) (10).

Without being limited, at least an effective number of geyser(s) (4045) of raised liquid (30) and any associated aerosol plume(s) (4050) can be located within and/or below the airflow outlet(s) (4015) or otherwise within the one or more air outlet pipe(s) (4025). It is preferred, without limitation, that at least one or more geyser(s) (4045) of raised liquid (30) and any associated aerosol plume(s) (4050) that the one or more transducer(s) generates above the surface of the liquid (30) can be located within and/or below the one or more airflow outlet(s) (4015) and/or within the one or more air outlet pipe(s) (4025). However, it is more preferred, without limitation, that only one geyser (4045) of raised liquid (30) and any associated aerosol plume(s) (4050), generated by only one transducer, is generated above the surface of the liquid (30), and is located within and/or below only one airflow outlet (4015) or otherwise within only one air outlet pipe (4025).

Referring to FIGS. 95-97, FIGS. 103-109, FIGS. 111-112, and FIGS. 117A-117B, and without limitation, the one or more airflow outlet(s) (4015) can also be connected to one or more of any suitable conduit, hose, or pipe (Herein called air outlet pipe(s) (4025)). These pipe(s) may also, without limitation, connect with one or more of any other air outlet pipe(s) (4025) at any location. The airflow outlet(s) (4015) and air outlet pipe(s) (4025) may, without limitation, have any diameter or any change in diameter at any location. The shape and diameter of the airflow outlet(s) (4015) and air outlet pipe(s) (4025) should at least be, without limitation, any effective shape and diameter. It is preferred, without limitation, that the diameter of the airflow outlet(s) (4015) and/or air outlet pipe(s) (4025) is between 0.5 inches to 6 inches or more. It is more preferred, without limitation, that the diameter of the airflow outlet(s) (4015) and/or air outlet pipe(s) (4025) is between 1.75 inches to 4 inches. It is even more preferred, without limitation, that the diameter of the airflow outlet(s) (4015) and/or air outlet pipe(s) (4025) is between 2 inches to 3 inches.

The air outlet pipe(s) (4025) may also, without limitation, extend any distance into the reservoir(s) (40) in order to position the airflow outlet(s) (4015) into any location within the reservoir(s) (40), and more preferably position the airflow outlet(s) (4015) into any preferred distance from the surface of the liquid (30) as previously mentioned. The air outlet pipes(s) (4025) can also be, without limitation, any effective and efficacious length and terminate with one or more exhaust outlet(s) (4060) from which the generated aerosol (200) is deployed into the targeted area(s) (210). Without being limited, any, filter, screen or mesh material, and/or grate material, may be located or positioned within the design of the airflow outlet(s) (4015) and/or the air outlet pipes(s) (4025). The exhaust outlet(s) (4060) can also, without limitation, incorporate one or more of any design enhancements such as, but not limited to one or more of any, filter(s), screen or mesh material(s), or grate material(s). The exhaust outlet(s) (4060) may also, without limitation, interface with one or more of any attachment port(s), socket(s), plug(s), and/or component(s), whose design and construction is known to those skilled in the art, so that it may connect with one or more of any accessories known in the art, and/or one or more of any other delivery pipe(s), hose(s), or conduit(s). The exhaust outlet(s) (4060) can also, without limitation, be any size or shape. It is preferred, without limitation, that the air outlet pipes(s) (4025) are a total length between 0.25 inches to 30 inches or more. It is more preferred, without limitation, that the air outlet pipes(s) (4025) are a total length between 1 inches to 14 inches. It is even more preferred, without limitation, that the air outlet pipes(s) (4025) are a total length between 3 inches to 12 inches. It is very preferred, without limitation, that the air outlet pipes(s) (4025) are a total length between 12 inches to 26 inches.

Figure 105:
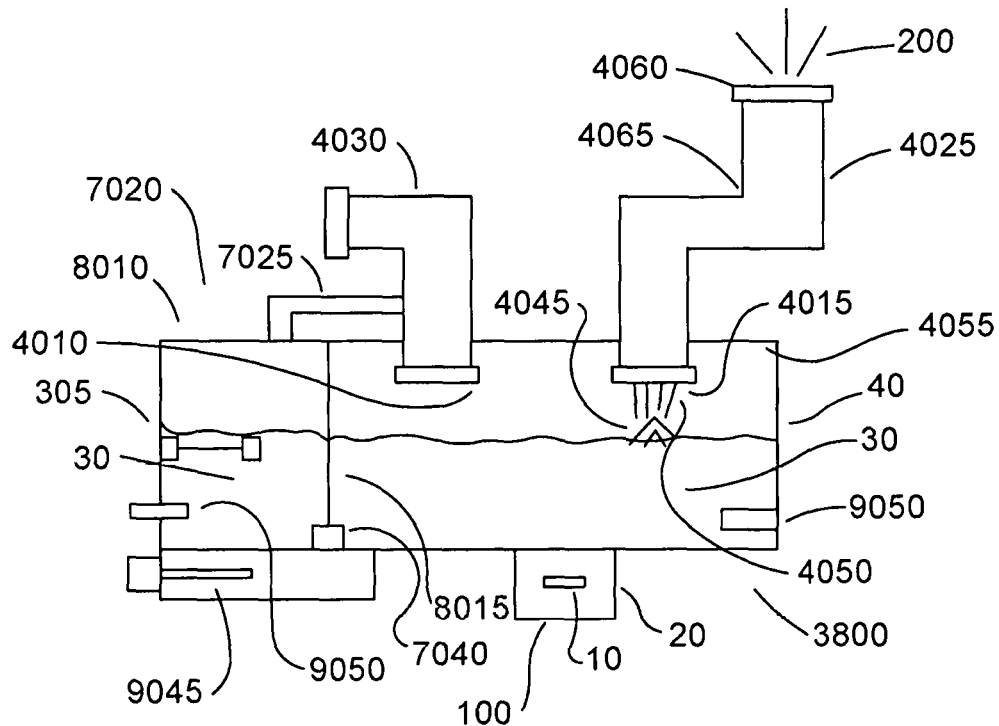
FIG. 105 is a schematic view of an optimized and miniaturized aerosol generator, showing a float chamber and an aerosol chamber according to the present invention.

Third, and referring to FIG. 103 and FIG. 105, the design of the optimized and miniaturized aerosol generator (3800) and aerosol generating device (215) can also, without limitation, be enhanced by incorporating one or more of any geometry changes or bend(s) (Hereinafter called "bend(s)" (4065)), of any suitable angle or shape, in any locations of one or more of any air outlet pipes(s) (4025), between the airflow outlet(s) (4015) and before any exhaust outlet(s) (4060). The geometry changes or bend(s) (4065) can be used for various purposes including, but not limited to, minimizing or eradicating larger droplets of liquid (30) that may be splashed or ejected from the geyser (4045) and/or aerosol plume (4050) and have entered the air outlet pipes(s) (4025). It is preferred, without limitation, one or more bends (4065) between 30 to 90 degree is utilized before the exhaust outlet(s) (4060). It is more preferred, without limitation, one or more bends (4065) between 30 to 180 degree is utilized before the exhaust outlet(s) (4060). It is even more preferred, without limitation, that one or more bends (4065) between 90 degree and 180 degree, is utilized before the exhaust outlet(s) (4060). It is very preferred, without limitation, that at least two 90 degree bends (4065) are utilized before the exhaust outlet(s) (4060). Without being limited, the air outlet pipes(s) (4025) can also, without limitation, have any length between the various bend(s) (4065) if they are utilized. It is preferred, without limitation, that the air outlet pipes(s) (4025) terminate in about a vertical orientation, however they may be positioned in and terminate at any suitable angle. The air outlet pipes(s) (4025) may also, without limitation, terminate at any suitable location within, on, or outside of, the aerosol producing apparatus (215).

Referring to FIGS. 95-97, FIGS. 103-108, and FIG. 117-A to 117-B and without being limited, one or more air outlet pipes(s) (4025) may also terminate within or into one or more of any shared outlet(s) or common outlet(s) (hereinafter called "shared outlet(s)" (9080)). The one or more shared outlet(s) (9080) can be, without limitation, positioned in various locations such as, but not limited to, inside, outside, partially inside, the one or more housing(s) of the aerosol generating apparatus (215). It is preferred, without limitation, that the shared outlet(s) (9080) are located within the housing of the aerosol generating apparatus (215). Without being limited, the one or more shared outlet(s) (9080) can have one or more drain(s) that can be plumbed to one or more of any suitable location(s) including, but not limited to, any catch pan or catch container. The one or more shared outlet(s) (9080) may also have, without limitation, one or more opening(s) or orifice(s) (Herein after called "shared outlet opening(s)" (9086). The one or more shared outlet(s) (9080), as well as the one or more shared outlet opening(s) (9086), may be, without limitation, any, shape, geometry, length, width, height, and/or depth. It is preferred, without limitation, that the dimensions and sizes of the one or more shared outlet(s) (9080), as well as the one or more shared outlet opening(s) (9086), are at least suitable and effective. The one or more shared outlet(s) (9080), shared outlet opening(s) (9086), and/or exhaust outlet(s) (4060), can be, without limitation, located in one or more of any effective and suitable location(s).

Without being limited, the one or more shared outlet(s) (9080), shared outlet opening(s) (9086), and/or exhaust outlet(s) (4060), can incorporate one or more of any design enhancements such as, but not limited to any, filter(s), screen or mesh material(s), or grate material(s). Without being limited, one or more shared outlet(s) (9080), shared outlet opening(s) (9086), and/or one or more exhaust outlet(s) (4060) can also suitably and effectively interface, with one or more of any attachment port(s), socket(s), plug(s), and/or component(s), whose design and construction is known to those skilled in the art, so that the shared outlet(s) (9080), shared outlet opening(s) (9086), and/or one or more exhaust outlet(s) (4060), may suitably connect, and effectively function, with one or more of any accessories known in the art, and/or one or more of any other delivery pipe(s), hose(s), plug(s), and/or conduit(s).

Fourth, and referring to FIGS. 104-108, the design of the optimized and miniaturized aerosol generator (3800) and aerosol generating device (215) can be enhanced by the positioning of one or more inbound airflow inlet(s) (4010) that supply air/gas flow into or inside the one or more tank(s) or reservoir(s) (40) in which the transducer(s) (10) are located. One or more inbound airflow inlet(s) (4010) may be used to supply the moving or pressurized air or gas, to the reservoir(s) (40) in which the transducer(s) (10) are located, but it is preferred, without limitation, that one inbound airflow inlet(s) (4010) is utilized. Referring to FIGS. 95-97, and FIGS. 103-108, the one or more inbound airflow inlet(s) (4010) can be, without limitation, positioned anywhere, and at any angle and orientation, within the reservoir(s) (40). However, it is preferred, without limitation, that the inbound airflow inlet(s) (4010) are located not only at any effective location above the liquid (30) and/or effectively near the one or more transducers(s) (10) within the reservoir(s) (40), but their output is also directed downward toward the liquid (30) within the reservoir(s) (40). The one or more inbound airflow inlet(s) (4010) can also be, without limitation, positioned effectively close to, level with, or approximately flush with, the one or more reservoir ceiling(s) (4055) within the reservoir(s) (40). It is also preferred, without limitation, that the inbound airflow inlet(s) (4010) are positioned so that each orifice of the airflow inlet(s) (4010) is approximately horizontal with the surface of the liquid (30) within the reservoir (40). The one or more inbound airflow inlet(s) (4010) can also be, without limitation, positioned at any effective distance from the one or more airflow outlet(s) (4015) and/or transducer(s) (10). More specifically, it is preferred, without limitation, that the one or more inbound airflow inlet(s) (4010) are located, approximately above the liquid (30) and between or amongst the one or more airflow outlets (4015) which are located approximately above the one or more transducer(s) (10). It is more preferred, without limitation, that the one or more inbound airflow inlet(s) (4010) are located effectively next to the one or more airflow outlets (4015). It is even more preferred, without limitation, that one inbound airflow inlet (4010) is located effectively between two airflow outlets (4015). It is very preferred, without limitation, that one inbound airflow inlet (4010) is located effectively and centered between two airflow outlets (4015).

The inbound airflow inlet(s) (4010) can be, without limitation, located at any distance above the surface of the liquid (30) that covers the transducer(s) (10) or the surface of the liquid (30) within the reservoir(s) (40). It is preferred, without limitation, that the inbound airflow inlet(s) (4010) are at least located at an effective distance from the surface of the liquid (30). However, to take advantage of the improvements in this invention, the one or more inbound airflow inlet(s) (4010) should be, without limitation, located within a certain height range or gap (denoted in FIG. 103 by distance "B") above any liquid (30) that covers the transducer(s) as follows. It is preferred, without limitation, that at least one or more inbound airflow inlet(s) (4010) is positioned between 0.04 inches to 12 inches above the surface of the liquid that is above each aerosol (200) producing transducer (10). It is more preferred, without limitation, that at least one or more inbound airflow inlet(s) (4010) is positioned between 0.04 inches to 3.0 inches above the surface of the liquid that is above each aerosol (200) producing transducer (10). It is even more preferred, without limitation, that at least one or more inbound airflow inlet(s) (4010) is positioned between 0.04 inches to 1.5 inches above the surface of the liquid that is above each aerosol (200) producing transducer (10). It is very preferred, without limitation, that at least one or more inbound airflow inlet(s) (4010) is positioned between 0.05 inches to 1.0 inches above the surface of the liquid that is above each aerosol (200) producing transducer (10). It is extremely preferred, without limitation, that at least one or more inbound airflow inlet(s) (4010) is positioned between 0.06 inches to 0.08 inches above the surface of the liquid that is above each aerosol (200) producing transducer (10). Without being limited, the use of at least one or more inbound airflow inlet(s) (4010) located approximately between two airflow outlets (4015), each having an effective diameter, can also be utilized to increase performance. It is preferred, without limitation, that only one inbound airflow inlet (4010), having an effective diameter, is located approximately between two airflow outlets (4015).

More than one inbound airflow inlet(s) (4010) can also, without limitation, be positioned within the reservoir(s) (40) in a manner so that the delivered air or gas is more evenly distributed or supplied to the airflow outlet(s) (4015). This can, without limitation, help to increase the efficiency and performance of the apparatus (215). The inbound airflow inlet(s) (4010) can be positioned in any effective angle or orientation. However, it is preferred, without limitation that at least two inbound airflow inlet(s) (4010) are located opposite to one another within the reservoir(s) (40). It is even more preferred, without limitation, that at least two pairs of inbound airflow inlet(s) (4010) are located opposite to one another within the reservoir(s) (40). It is very preferred, without limitation, that at least one pair of inbound airflow inlet(s) (4010) are located opposite to one another respective to each airflow outlet(s) (4015). It is extremely preferred, without limitation, that at least two pairs of inbound airflow inlet(s) (4010) are located opposite to one another respective to each airflow outlet(s) (4015). The use of one or more baffles or other structures may also, without limitation, be used within the reservoir (40) to increase the efficiency of the air flow, as well as reduce any turbulence or vortices, as the air or gas flows from the inbound airflow inlet(s) (4010) to the airflow outlet(s) (4015).

Without being limited, the gap or amount of space (distance "A"), at the preferred distances previously mentioned, between the surface of the liquid (30) and the one or more airflow outlet(s) (4015), can establish increased air velocities not only near the airflow outlet(s) (4015), but also near the geyser(s) (4045) and aerosol plume(s) (4050), that can be similar to a venturi-like effect, that helps to more effectively capture and move the generated aerosol (200) out of the tank or reservoir (40), and into the targeted area(s) (210) while minimizing the chance for aerosol (200) coalescence in the process. It is preferred, without limitation, that the air/gas within the reservoir(s) (40) flows uniformly through the airflow outlet(s) (4015) and into the air outlet pipe(s) (4025). It is also preferred, without limitation, that this air/gas flow, and/or venturi-like effect, is uniformly experienced all the way around the geyser(s) (4045) and aerosol plume(s) (4050) for greater performance and efficiency. It is desired, without limitation, that the airflow outlet(s) (4015) are as close to the liquid (30) surface as effectively and efficaciously as possible, for increased performance and desired effect on the process. However, care needs to be taken, because if the airflow outlet(s) (4015) are too low to the surface of the liquid (30) undesired effects can result such as, but not limited to, the liquid (30) can be pushed and/or pulled up through the airflow outlet(s) (4015), or the air/gas within the reservoir(s) (40) will be unable to escape. Without being limited, the net effect of these improvements is an aerosol (200) output that not only appears visually thicker and of increased quantity, but also appears lighter and more wispy, which is typically indicative of an aerosol (200) consisting of smaller droplets. These improvements have not been seen with previous designs known in the art.

Referring to FIGS. 95-97, FIGS. 103-109, and FIGS. 117A-117B, and without limitation, the one or more inbound airflow inlet(s) (4010) can also be connected to one or more of any suitable conduit, hose, or pipe (Herein called air inlet pipe(s) (4030)). These pipe(s) may also, without limitation, connect with one or more of any other air inlet pipe(s) (4030) at one or more of any suitable location(s). The inbound airflow inlet(s) (4010) and air inlet pipe(s) (4030) may, without limitation, have any diameter or any change in diameter at any location(s). The shape and diameter of the inbound airflow inlet(s) (4010) and air inlet pipe(s) (4030) should at least be, without limitation, any effective shape and diameter. It is preferred, without limitation, the diameter of the inbound airflow inlet(s) (4010) and/or air inlet pipe(s) (4030) is between 0.5 inches to 6 inches or more. It is more preferred, without limitation, that the diameter of the inbound airflow inlet(s) (4010) and/or air inlet pipe(s) (4030) is between 0.75 inches to 4 inches. It is even more preferred, without limitation, that the diameter of the inbound airflow inlet(s) (4010) and/or air inlet pipe(s) (4030) is between 1.5 inches to 3 inches. The air inlet pipe(s) (4030) may also, without limitation, extend any distance into the reservoir(s) (40) in order to position the inbound airflow inlet(s) (4010) into any location within the reservoir(s) (40), and more preferably position the inbound airflow inlet(s) (4010) into any preferred distance from the surface of the liquid (30) as previously mentioned. The air inlet pipe(s) (4030) can also be, without limitation, any effective and efficacious length.

Figure 106A:
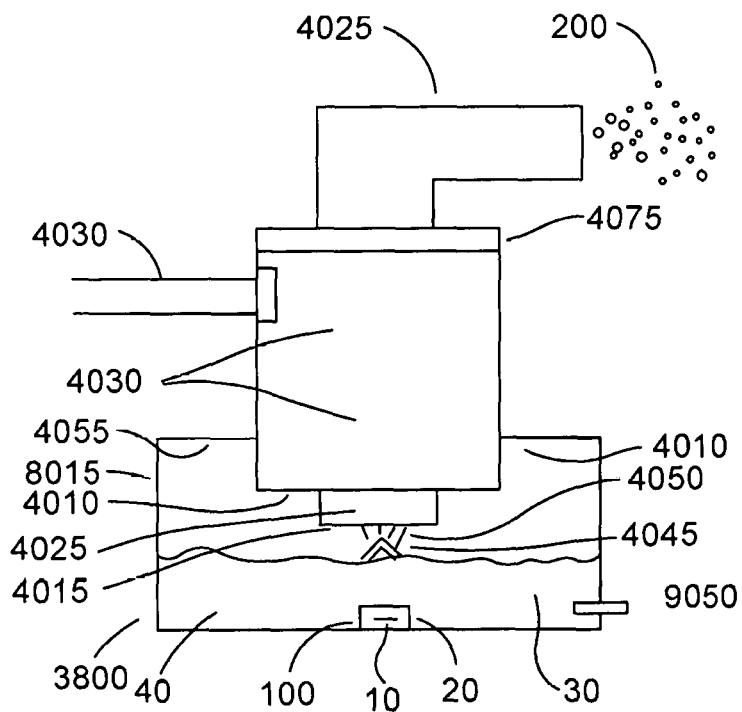
FIG. 106-A is a schematic view of an optimized and miniaturized aerosol generator, showing an air outlet pipes located within an air inlet pipe, according to the present invention.
Figure 106B:
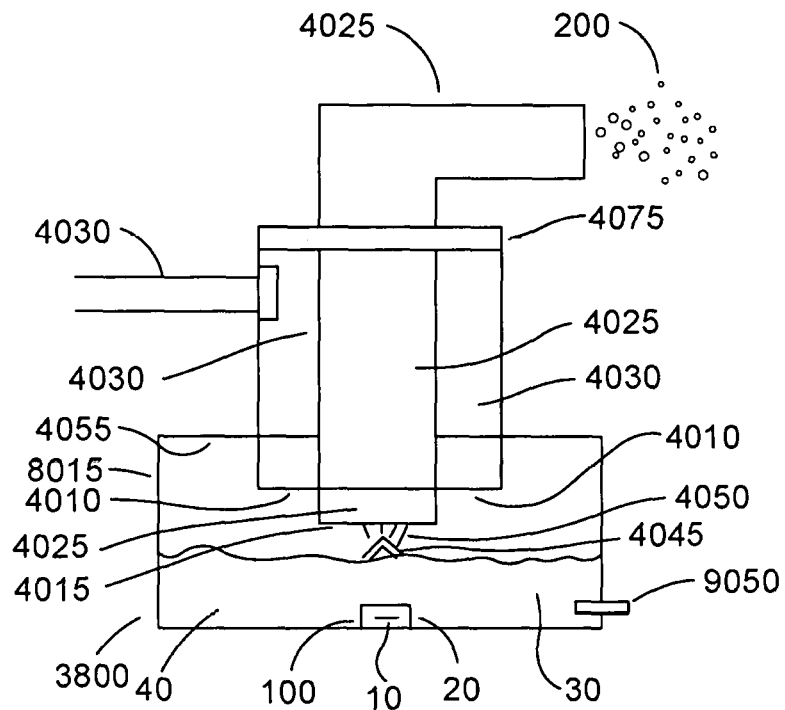
Figure 109:
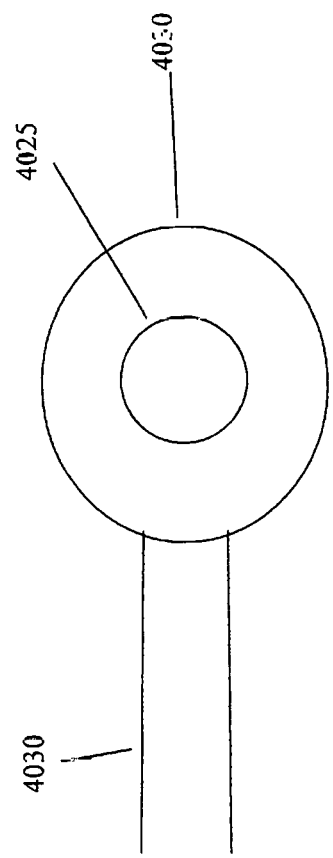
FIG. 109 is an interior schematic top view of an air outlet pipes located within an air inlet pipe of an optimized and miniaturized aerosol generator according to the present invention.

Referring to FIGS. 106-109, including FIGS. 106-A and 106-B, and FIG. 134, and without being limited, where FIGS. 106-109 is an interior view that shows the presence of one or more air outlet pipes(s) (4025) positioned within the one or more air inlet pipe(s) (4030), and FIG. 109 being a top view shows the presence of the one or more air outlet pipes(s) (4025) positioned within the one or more air inlet pipe(s) (4030). It is preferred, without limitation, that only one air outlet pipe (4025) is located within one air inlet pipe (4030) in this configuration. Any suitable sealing device, design, or material (Herein called "air inlet top seal" (4075)), can be, without limitation, used to effectively, or at least suitably, seal, cover, or interface with, the air inlet pipe(s) (4030), so that the air/gas that is flowed through the air inlet pipe(s) (4030) cannot escape. It is preferred, without limitation, that the air inlet top seal also effectively, or at least suitably, seals, covers, or interfaces with, the air outlet pipes(s) (4025), so that the air/gas that is flowed through the air inlet pipe(s) (4030) cannot escape.

Referring to FIGS. 105-109, and without being limited, the air inlet pipe(s) (4030) and inbound airflow inlet(s) (4010) can extend any distance past the air outlet pipes(s) (4025) and/or the airflow outlet(s) (4015). Without being limited, the air inlet pipe(s) (4030) and inbound airflow inlet(s) (4010) can extend any effective and efficacious distance past the air outlet pipes(s) (4025) and/or the airflow outlet(s) (4015). It is preferred, without limitation, that the inbound airflow inlet(s) (4010) extend between 0 to 12 or more inches past the airflow outlet(s) (4015). It is more preferred, without limitation, that the inbound airflow inlet(s) (4010) extend between 0 to 12 inches past the airflow outlet(s) (4015). It is even more preferred, without limitation, that the inbound airflow inlet(s) (4010) extend at least between 0 to 2 inches past the airflow outlet(s) (4015). It is very preferred, without limitation, that the inbound airflow inlet(s) (4010) extend between 0 to 1 inches past the airflow outlet(s) (4015). It is extremely preferred, without limitation, that the inbound airflow inlet(s) (4010) extend between 0 to 0.5 inches past the airflow outlet(s) (4015).

Alternatively, and without limitation, the air outlet pipes(s) (4025) and the airflow outlet(s) (4015) can extend any distance past the air inlet pipe(s) (4030) and/or inbound airflow inlet(s) (4010). Without being limited, the air outlet pipes(s) (4025) and the airflow outlet(s) (4015) can extend any effective and efficacious distance past the air inlet pipe(s) (4030) and/or inbound airflow inlet(s) (4010). It is preferred, without limitation, that the airflow outlet(s) (4015) extend between 0 to 12 or more inches past the inbound airflow inlet(s) (4010). It is more preferred, without limitation, that the airflow outlet(s) (4015) extend between 0 to 12 inches past the inbound airflow inlet(s) (4010). It is even more preferred, without limitation, that the airflow outlet(s) (4015) extend at least between 0 to 2 inches past the inbound airflow inlet(s) (4010). It is very preferred, without limitation, that the airflow outlet(s) (4015) extend between 0 to 1 inches past the inbound airflow inlet(s) (4010). It is extremely preferred, without limitation, that the airflow outlet(s) (4015) extend between 0 to 0.5 inches past the inbound airflow inlet(s) (4010).

Referring to FIGS. 103-106B, and FIG. 108, and without being limited, it is important to note that a suitable and effective air gap, space, or distance, should be present between the top surface of the liquid (30) within the reservoir(s) (40), and a bottom of the air inlet pipe(s) (4030), inbound airflow inlet(s) (4010), air outlet pipe(s) (4025), and/or airflow outlet(s) (4015), to allow at least an effective quantity of air/gas to pass through the reservoir(s) (40) with at least an effective velocity, in order for the optimized and miniaturized aerosol generator(s) (3800) to either function and/or function with at least an effective level of performance.

Figure 107:
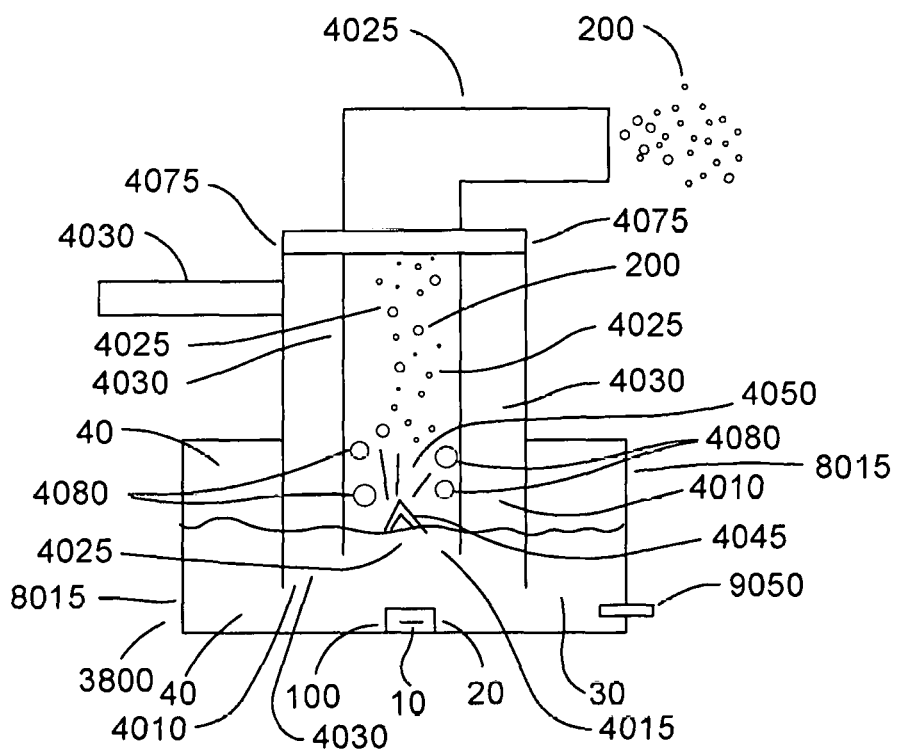
FIG. 107 is a schematic view of an optimized and miniaturized aerosol generator, showing an air outlet pipes located within an air inlet pipe and where the air inlet pipe the air outlet pipe are located effectively within the liquid in the reservoir according to the present invention.
Figure 108:
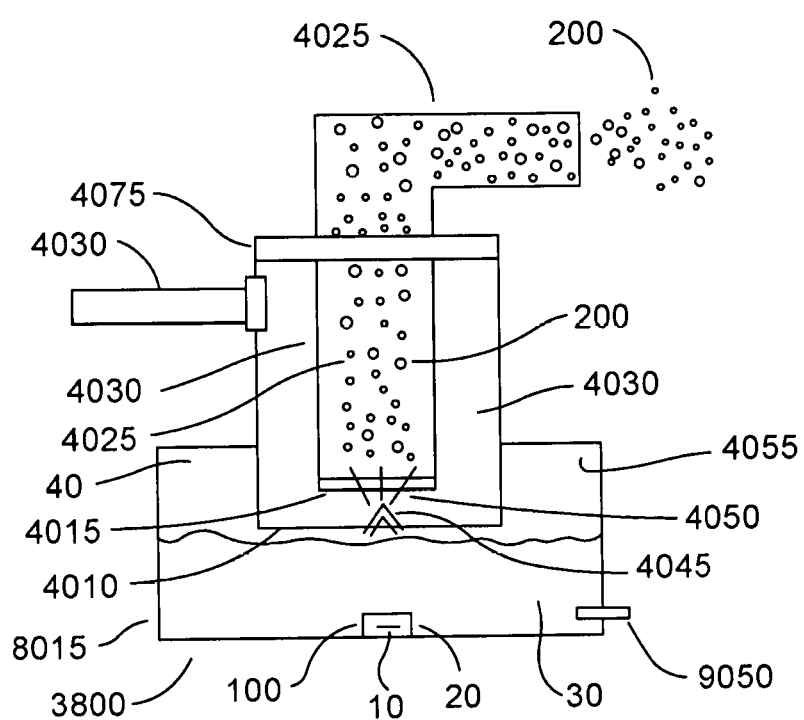
FIG. 108 is a schematic view of an optimized and miniaturized aerosol generator, showing the air outlet pipes(s) located within the air inlet pipe(s), and the airflow outlet located higher than the inbound airflow inlet according to the present invention.

Referring to FIG. 107, the one or more air inlet pipe(s) (4030), inbound airflow inlet(s) (4010), air outlet pipe(s) (4025), and/or airflow outlet(s) (4015), can, without limitation, extend any distance into the liquid (30) within the reservoir(s) (40). It is preferred, without limitation that this distance is at least an effective distance. Various combinations of these various components effectively extending into the liquid (30) can be utilized such as, but not limited to, (a) the one or more air inlet pipe(s) (4030) and/or inbound airflow inlet(s) (4010) are effectively located within or immersed in the liquid (30), while the one or more air outlet pipe(s) (4025) and/or airflow outlet(s) (4015) are effectively positioned outside of or above the liquid (30), (b) the one or more air outlet pipe(s) (4025) and/or airflow outlet(s) (4015) are effectively located within or immersed in the liquid (30), while the one or more air inlet pipe(s) (4030) and/or inbound airflow inlet(s) (4010) are effectively positioned outside of or above the liquid (30), (c) the one or more air outlet pipe(s) (4025), airflow outlet(s) (4015), air inlet pipe(s) (4030), and/or inbound airflow inlet(s) (4010), are effectively located within or immersed in the liquid (30). It is preferred, without limitation, that the one or more air inlet pipe(s) (4030) and/or inbound airflow inlet(s) (4010) are effectively located within or immersed in the liquid (30), while the one or more air outlet pipe(s) (4025) and/or airflow outlet(s) (4015) are effectively positioned outside of or above the liquid (30).

The air outlet pipes(s) (4025) can be, without limitation, perforated in one or more of any suitable and effective location(s), with one or more air flow holes (4080) of any effective shape(s) and size(s), at any effective distance(s), especially above the liquid (30). These air flow hole(s) (4080) can help facilitate an effective flow of air or gas from the air inlet pipe(s) (4030) to the air outlet pipes(s) (4025) in order to remove the generated aerosol (200) out of the reservoir(s) (40) and/or the air outlet pipes(s) (4025). The air flow holes are formed through a side wall of outlet pipe (4025).

It is also preferred, without limitation, that the one or more air inlet pipe(s) (4030), inbound airflow inlet(s) (4010), air outlet pipe(s) (4025), and/or airflow outlet(s) (4015), are effectively, suitably, and approximately centered above, below, and/or around, the one or more geyser(s) (4045) of raised liquid (30) and any associated aerosol plume(s) (4050), and/or the transducer(s) (10). It is also even more preferred, without limitation, that the one or more surfaces and/or materials of parts and components such as, but not limited to, the air inlet pipe(s) (4030), inbound airflow inlet(s) (4010), air outlet pipe(s) (4025), and/or airflow outlet(s) (4015), are suitably and effectively located so that they are not damaged by the energy, ultrasonic output, or signal, that is emitted, radiated, and/or transmitted, by the one or more transducer(s) (10). Without being limited, and as previously mentioned, this can be important when utilizing transducer(s) (10) described in the present invention due to their power and the length of the field of energy, ultrasonic output, or signal, that they can emit, radiate, and/or transmit. One or more of any air inlet pipe(s) (4030), inbound airflow inlet(s) (4010), air outlet pipe(s) (4025), and/or airflow outlet(s) (4015), can be, without limitation, allocated to or effectively function with, one or more of any geyser(s) (4045) of raised liquid (30) and any associated aerosol plume(s) (4050), and/or one or more of any transducer(s) (10).

Referring to FIGS. 103-108, and without being limited, the air inlet pipe(s) (4030) and inbound airflow inlet(s) (4010), as well as the air outlet pipes(s) (4025) and the airflow outlet(s) (4015), can have, without limitation, one or more opening(s), of any, size(s), shape(s), and geometry(s), at one or more of any location(s). It is preferred, without limitation, that the number of opening(s) for these location(s) and/or structures, as well as their size(s), shape(s), geometry(s), position(s), and location(s), are at least effective and efficacious. It is also preferred, without limitation, that the one or more, air inlet pipe(s) (4030), inbound airflow inlet(s) (4010), air outlet pipes(s) (4025), and airflow outlet(s) (4015), are suitably and effectively positioned. Without being limited, at least one air outlet pipes(s) (4025), and airflow outlet(s) (4015), can be centered above and/or around at least one, transducer (10), transducer housing (20), and/or transducer assembly (100). The at least one, air inlet pipe(s) (4030), inbound airflow inlet(s) (4010), air outlet pipes(s) (4025), and airflow outlet(s) (4015), can also be, without limitation, centered above and/or around at least one, transducer (10), transducer housing (20), and/or transducer assembly (100) in various effective configurations and distances. It is preferred, without limitation, that the one or more, air inlet pipe(s) (4030), inbound airflow inlet(s) (4010), air outlet pipes(s) (4025), and airflow outlet(s) (4015), are not only suitably and effectively positioned and spaced from each other and the transducer(s) (10), but they do not adversely interfere with, or adversely effect the performance of, the one or more transducer(s) (10) that are utilized.

Figure 117A:
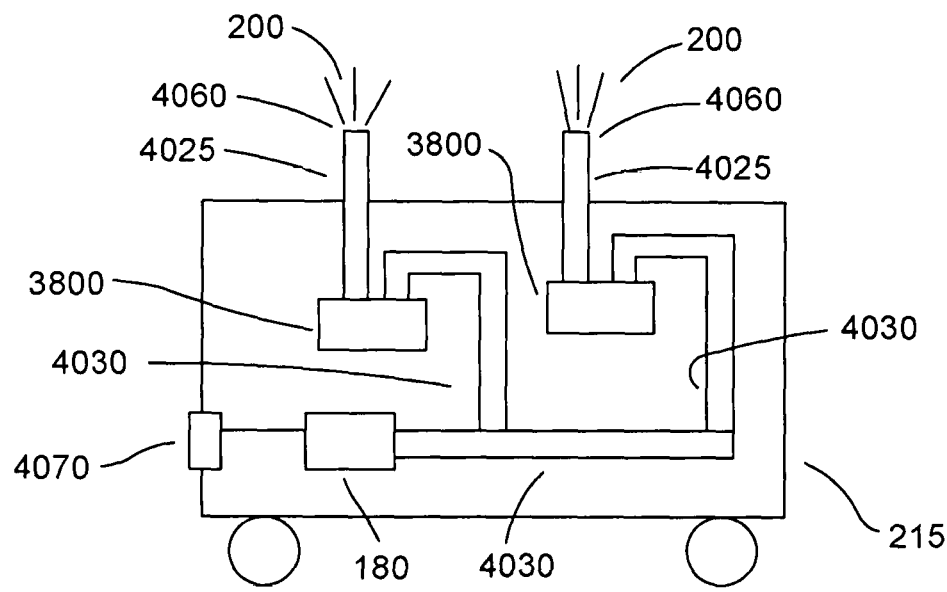
FIG. 117-A is a schematic view of an optimized and miniaturized aerosol generating connected to a shared fan according to the present invention.
Figure 117B:
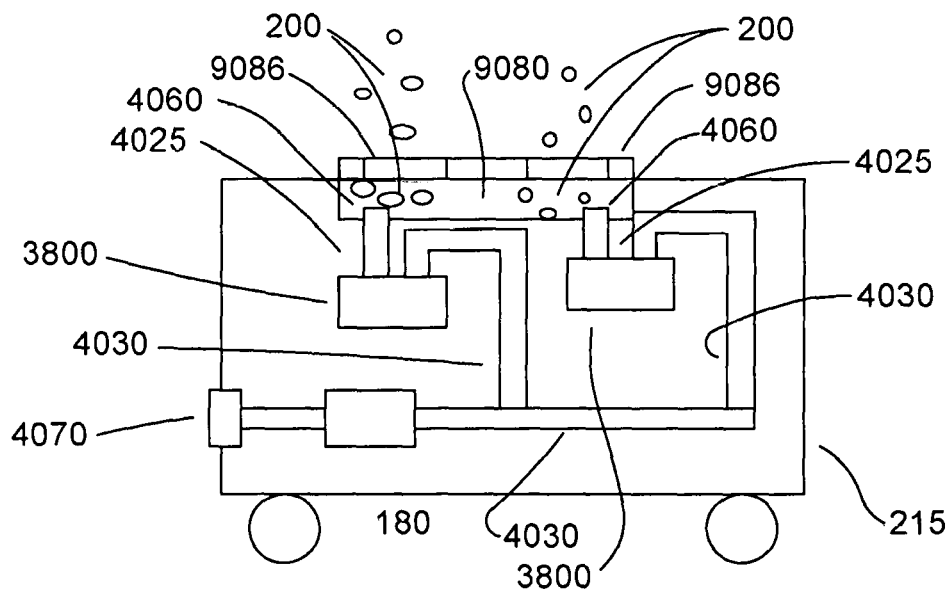

Referring to FIGS. 117A-117B, the one or more air inlet pipe(s) (4030) can, without limitation, be suitably connected to, one or more of any, blower(s), fan(s), or any other effective or suitable source(s) of any pressurized air or gas(s) (180). Each optimized and miniaturized aerosol generator(s) (3800) can be, without limitation, solely connected to, or even share, one or more blower(s), fan(s), or any other effective or suitable source(s) of any pressurized air or gas(s) (180). It is preferred, without limitation, that the various optimized and miniaturized aerosol generator(s) (3800) are connected to at least one of any suitable fan(s) or blower(s) (180). It is more preferred, without limitation, that the various optimized and miniaturized aerosol generator(s) (3800) used in the aerosol generating apparatus (215) are all connected to, and share the airflow from, one or more of any, blower(s), fan(s), or any other effective or suitable source(s) of any pressurized air or gas(s) (180). It is even more preferred, without limitation, that the various optimized and miniaturized aerosol generator(s) (3800) used in the aerosol generating apparatus (215) are all connected to, and share the airflow from, exactly one of any suitable, blower or fan (180). Without being limited, the one or more of any, blower(s), fan(s), or any other effective and suitable source(s) of any pressurized air or gas(s) (180), can connect in any suitable and effective way know in the art, to one or more of any air/gas entry point(s) (4070) located at one or more of any suitable and effective location(s) such as, but not limited to, inside, outside, on the exterior surface of, and/or or within, the apparatus(s) (215).

Any quantity and velocity of air or any gas may be supplied to the reservoir(s) (40) for any length of time by the source(s) of pressurized air or gas(s) that is utilized. However, it is preferred, without limitation, that a blower (180) of effective size and output is utilized. It is preferred, without limitation that the source of pressurized air or gas or blower (180) is able to provide air or gas to the reservoir at measurement of between approximately 3-2000 or more cubic feet per minute (cfm). It is more preferred, without limitation that the source of pressurized air or gas or blower (180), is able to provide air or gas to the reservoir at measurement of between approximately 3-500 cubic feet per minute (cfm). It is more preferred, without limitation that the source of pressurized air or gas or blower (180), is able to provide air or gas to the reservoir at measurement of between approximately 10-100 cubic feet per minute (cfm). It is more preferred, without limitation that the source of pressurized air or gas or blower (180), is able to provide air or gas to the reservoir at measurement of between approximately 20-40 cubic feet per minute (cfm).

Also, referring to FIGS. 117A-117B, the one or more entry points or inlet(s) (Herein called "air entry point(s)" (4070)) where the air or gas enters the air inlet pipe(s) (4030) may also, without limitation, be located at any suitable and effective location anywhere on or inside the aerosol (200) producing apparatus (215). The one or more air entry point(s) (4070) can, without limitation, incorporate one or more of any design enhancements such as, but not limited to any, filter, screen or mesh material, and/or grate material. The air entry point(s) (4070) may also, without limitation, interface with one or more of any attachment port(s) or attachment component(s) whose design and construction is known to those skilled in the art, so that it may connect with one or more of any accessories and/or any other delivery pipe(s), hose(s), or conduit(s). The air entry point(s) (4070) can also, without limitation, be any size or shape.

Fifth, and referring to FIGS. 95-97, and FIGS. 103-108, the design of the optimized and miniaturized aerosol generator (3800) and aerosol generating device (215) can be enhanced, without limitation, by reducing the amount of space between the one or more reservoir ceiling(s) (4055) and the liquid (30) within the reservoir(s) (40). In addition, this enhancement can also, without limitation, be aided by reducing the total amount of air/gas volume, above the liquid (30) and inside of the reservoir(s) (40). Desired attributes such as, but not limited to, a faster air/gas flow, or increased volume of air/gas, supplied to the air outlet pipes(s) (4025) and/or the airflow outlet(s) (4015), can be, without limitation, established by creating a small gap between the surface of the liquid (30) and/or limiting the amount of space within the reservoir(s) (40). This can also, without limitation, help to establish a stronger venturi-like effect that reduces aerosol dwell time, decreases the chance for unwanted vortices, and increases aerosol (200) output from the apparatus. The airflow outlet(s) (4015) and inbound airflow inlet(s) (4010) can be, without limitation, positioned at any effective distance from the one or more reservoir ceiling(s) (4055) inside of the reservoir(s) (40), however it is preferred, without limitation, that the airflow outlet(s) (4015) and inbound airflow inlet(s) (4010) are positioned so that they are flush with the reservoir ceiling(s) (4055).

Without being limited, the one or more reservoir ceiling(s) (4055) can consist of one or more components. It is preferred, without limitation that the one or more reservoir ceiling(s) (4055) consists of one component and it is made from one piece of suitable material. The one or more reservoir ceiling(s) (4055) can be positioned, without limitation, at one or more of any angle(s), geometry(s), orientation(s), and/or distance(s) above the liquid (30) within the reservoir(s) (40). It is preferred, without limitation, that the one or more reservoir ceiling(s) (4055) is positioned at an effective, angle(s), geometry(s), orientation(s), and/or distance(s) above the liquid (30) within the reservoir(s) (40), as well as the transducer(s) (10). It is also preferred, without limitation, that the reservoir ceiling(s) (4055) is positioned so that it is approximately horizontal with the surface of the liquid (30) within the reservoir (40). The one or more reservoir ceiling(s) (4055) can also be, without limitation, positioned effectively close to, level with, or approximately flush with, one or more of any parts or components within the reservoir(s) (40) such as, but not limited to any, airflow outlet(s) (4015), and/or inbound airflow inlet(s) (4010).

However, to take advantage of the improvements in this invention, the one or more reservoir ceiling(s) (4055) should be, without limitation, located within a certain height range or gap (denoted in FIG. 103 by distance "C") above any liquid (30) that covers the transducer(s) as follows. It is preferred, without limitation, that the reservoir ceiling(s) (4055) is positioned between 0.04 inches to 12.0 inches above the surface of the liquid that is above each aerosol (200) producing transducer (10). It is more preferred, without limitation, that the reservoir ceiling(s) (4055) is positioned between 0.04 inches to 3.0 inches above the surface of the liquid that is above each aerosol (200) producing transducer (10). It is even more preferred, without limitation, that the reservoir ceiling(s) (4055) is positioned between 0.04 inches to 1.5 inches above the surface of the liquid that is above each aerosol (200) producing transducer (10). It is very preferred, without limitation, that the reservoir ceiling(s) (4055) is positioned between 0.05 inches to 1.0 inches above the surface of the liquid that is above each aerosol (200) producing transducer (10). It is extremely preferred, without limitation, that the reservoir ceiling(s) (4055) is positioned between 0.06 inches to 0.08 inches above the surface of the liquid that is above each aerosol (200) producing transducer (10).

Sixth, and referring to FIGS. 95-97, FIGS. 103-108 to FIGS. 114-116, and FIGS. 117A-117B, the design of the optimized and miniaturized aerosol generator (3800) and aerosol generating device (215) can be enhanced, without limitation, by improving the way that the liquid (30) is heated before it is converted into an aerosol (200) by the transducer(s) (10). The prior art has described heating the liquid before it is aerosolized. For example, this is described in (col. 4, line 4-8) of U.S. Pat. No. 4,366,125 (Kodera et al., 1980), which is incorporated herein by reference in its entirety, including any references cited therein, where heating the liquid is described in the following quote: "The germacidal liquid (19) is held in an upper basin (25), the bottom of which is immersed in the warm water (18) in the lower basin (21). The upper basin (25) is supplied with the germacidal liquid from a tank and through a heating element (both not shown) and an inlet pipe (24).". Another example is described in (col. 8, line 9-12) of U.S. Pat. No. 5,878,355 (Berg et al. 1996), and (col. 8, line 15-18) of U.S. Pat. No. 6,102,992 (Berg et al. 1998), which is incorporated herein by reference in its entirety, including any references cited therein, where heating the liquid is described in the following quote: "Referring back to FIG. 2, it is preferred that the overflow reservoir include a heating element (72) for heating the capture liquid before generating an aerosol."

However, the current art as currently described has proven to be ineffective and not enabling for maintaining the needed effective and efficacious liquid (30) temperatures, in the reservoir in which multiple transducer(s) (10) are located, for aerosol generation between 80 to 150 degree Fahrenheit or more, and more so for liquid (30) temperatures between 85 to 150 degree Fahrenheit, and even more so for liquid (30) temperatures between 90 to 150 degree Fahrenheit, and very much so for liquid (30) temperatures between 95 to 128 degree Fahrenheit. This is, without limitation, due to various interacting variables such as, but not limited to, (a) the amount of liquid (30) in the reservoir (40) in which the transducer(s) (10) are located, (b) the temperature to which the liquid (30) is initially heated for the aerosol (200) production to begin, (c) the heat loss due to the amount of air flowing over the surface of the liquid (30) above the transducer(s) (10), (d) the heat lost due to any air temperature variation that may be encountered between the inside of the reservoir(s) (40) and the environment outside of the apparatus (215), (e) the number of transducers (10) that are required for effective operation of the apparatus (215) and the resulting amperage required, (f) the minimum effective temperature of the liquid (30) above the transducer(s) (10), (g) the total amperage available to the entire apparatus (215), and (h) the amount of liquid (30) removed from the reservoir(s) (40) in the form of any aerosol (200).

Without being limited, these variables must be considered, or the aerosol (200) generating apparatus (215) may not be a successful product in the market place, especially if at least two to four, but preferably at least six or more transducers, are needed for acceptable performance. The prior art failed to mention these various issues and their effect on sufficiently heating the liquid (30) and the resulting amperage availability problems. However, and without being limited, an improved apparatus (215) utilizing the various enhancements, including, but not limited to, operating at least one, but preferably two, and even more preferably three, of the new optimized and miniaturized aerosol generators (3800), can successfully operate for extended periods of time with at least a 20 amp 115 VAC rated single commercial power source. It is important to remember, without limitation, that in order to meet electrical safety standards in the United States, especially for a mobile apparatus (215), an apparatus can only utilize power from one electrical source, which further complicates the amperage availability dilemma for heating and maximizing the number of transducer(s) that can be effectively and efficaciously operated.

First, one problem with depending on a large volume reservoir (40), or even combining a large reservoir with a secondary reservoir as described in Berg et al. 1996 & 1998), to supply the liquid (30) used for covering the transducer(s) (10), is that the more liquid that is used to fill these places, the longer it takes to initially warm that liquid (30) to at least the minimum operating temperature, and the more amperage it then takes to sustain the established or necessary operating liquid (30) temperature(s) once the transducer(s) (10) are operating and air is flowing over the transducers to remove the aerosol (200).

Heat can be lost from the liquid (30) above the transducer(s) (10), in various ways including, but not limited to, (a) heat lost to the air flowing over the liquid covering the transducer(s) (10), (b) heat conducted to any materials surrounding the liquid (30), (c) heat lost as large ejected droplets that cooled in the air and/or on surfaces, fall back into the liquid surrounding the transducer(s) (10), or (d) heat lost as the heated liquid (30) is removed from the reservoir(s) (40), in aerosol (200) form.

Without being limited, it was observed in the laboratory that once the transducer(s) are producing aerosol (200), amperage availability for heating the liquid (30) becomes scarce due to the large amounts of amperage that is necessary to produce the aerosol (200). The more aerosol (200) that is needed or desired to be produced, means more transducers (10) are needed to be operated, and this increases the total amount of amperage that is needed by the apparatus (215). The result is that this severely reduces or even eliminates the amount of amperage available to heat the liquid (30) while the transducer(s) are operated. This is, without limitation, especially a problem when operating at least two to four, but preferably at least six or more transducers, in the apparatus (215), since operating the transducers requires a large majority of the available amperage. These issues are especially relevant, without limitation, for operating scenarios where the liquid (30) must be kept at high operating temperatures for the entire time the transducer(s) (10) are producing aerosol (200) and multiple transducers are operated.

Over heating the liquid (30) and using the heated liquid (30) as a way to store and use the heat over time may, without limitation, work in certain applications. However this also has inherent problems in situations including, but not limited to, (a) the liquid is thermally sensitive and over heating the liquid to a sufficient temperature to store a sufficient amount of heat will degrade the chemical(s) in the liquid (30), and/or (b) the amount of stored heat in the liquid (30) is insufficient to provide an adequate operating liquid temperature for the duration of a full aerosol (200) generation and deploy cycle. Both of these situations have been witnessed in the laboratory.

Another problem related to (Kodera et al., 1980) is that they were silent with respect to maintaining the germicidal liquid in the reservoir with the transducer at an effective temperature or within an effective temperature range during the full operating cycle. When considering the various variables that can cool a liquid in a reservoir, it is reasonable to determine that only the "warm water" (Kodera et al., 1980) circulated under the reservoir in which the transducer is located would not be sufficient alone, even when combined with the heated liquid that would replenish the tank, to keep the germicidal liquid at a constant temperature. This is especially relevant given the notoriously small amounts of liquid, and thus small amounts of additional inputted heat, that are utilized to replenish the liquid covering the ultrasonic transducers over a given amount of time. In addition, (Kodera et al., 1980) was silent with respect to utilizing a thermocouple to control the liquid temperature, which meant that their apparatus was most likely designed for a steady state environment, and not one where operating variables could change necessitating more heat being applied to maintain a constant liquid temperature in the aerosolized liquid. The lower bath was only described as being "warm" and in cases where the heat may be removed faster from the whole system than heat is being added, the germicidal liquid above the transducers can not be expected to remain close to the same temperature and the reproducibility of the system would be lost.

Referring to FIGS. 95-97, FIGS. 103-108, and FIGS. 114-117B, and without limitation, maintaining the liquid (30) temperature surrounding the transducer(s) (10) at the desired or needed temperature(s) or temperature range(s), is also impacted by various variables such as, but not limited to, (a) the number of transducers being operated in each optimized and miniaturized aerosol generator (3800), (b) the number of optimized and miniaturized aerosol generator(s) (3800) being operated in each apparatus (215), (c) the total volume of the liquid (30) in the reservoir(s) (40) in which the transducer(s) (10) are located, and any other liquid (30) directly connected to this liquid (30) in areas such as, but not limited to any liquid sensor compartment(s) (8010), (d) the minimum temperature and/or the temperature range(s) that the liquid (30) must be held while generating the aerosol (200), (e) the amount of wattage allocated to each heater element that heats the liquid (30) in each reservoir(s) (40) in which the transducer(s) (10) are located, (f) allocation or method of allocation of amperage between all heater element(s) to maintain the temperature of the liquid (30), and (g) the amount of aerosol (200) that is generated and deployed per unit of time.

Any number of transducer(s) (10) may be located within the reservoir(s) (40) of the optimized and miniaturized aerosol generator (3800) and/or aerosol generating device (215). It is preferred, without limitation, that the number of transducer(s) (10) is at least effective and sufficient. However, and without being limited, the more transducer(s) (10) that are located within the reservoir(s) (40), the harder it is to keep the liquid at the desired or needed temperature(s), for reasons including, but not limited to, (a) more liquid (30) is needed to effectively and sufficiently cover the transducer(s) (10), and (b) the more transducer(s) that are located within the reservoir(s) (40), typically the more air that is needed to circulate through the reservoir(s) to effectively remove the aerosol (200) that is generated to avoid conglomeration of the generated aerosol within the reservoir(s) (40). It is preferred, without limitation, that at least one transducer(s) (10) is located in the reservoir(s) (40). It is more preferred, without limitation, that two or more transducer(s) (10) are located in the reservoir(s) (40). It is even more preferred, without limitation, that two transducers (10) are located in the reservoir(s) (40). It is very preferred, without limitation, that between one to two transducer(s) (10) are located in the reservoir(s) (40). This can, without limitation, help to increase the performance of the optimized and miniaturized aerosol generator(s) (3800) and/or apparatus (215).

Any number of optimized and miniaturized aerosol generator(s) (3800) may be located within the aerosol generating device (215). It is preferred, without limitation, that the number of optimized and miniaturized aerosol generator(s) (3800) is at least effective and sufficient. However, and without being limited, this number is typically dictated by considerations such as, but not limited to, the intended market and/or purpose of the apparatus (215), as well as the total amount of amperage available to the apparatus (215). It is not uncommon to have each apparatus (215) limited to 20 amps of available power due to various safety regulations and standards encountered in the market place. It is preferred, without limitation, that each aerosol (200) generating apparatus (215) includes at least one optimized and miniaturized aerosol generator(s) (3800). It is more preferred, without limitation, that each aerosol (200) generating apparatus (215) includes two or more optimized and miniaturized aerosol generator(s) (3800). It is even more preferred, without limitation, that each aerosol (200) generating apparatus (215) includes three optimized and miniaturized aerosol generator(s) (3800). It is very preferred, without limitation, that each aerosol (200) generating apparatus (215) includes three or more optimized and miniaturized aerosol generator(s) (3800).

Any volume of liquid (30) may be utilized in the reservoir(s) (40) in which the transducer(s) (10) are located, as well as any other connecting areas such as, but not limited to any liquid sensor compartment(s) (8010). It is preferred, without limitation, that the volume of liquid (30) is at least effective and a sufficient volume. However, and without being limited, in order to obtain maximum performance, it is preferred, without limitation, that the liquid (30) capacity of the reservoir(s) (40) in which the transducer(s) (10) are located, is as small as possible while still enabling an effective and sufficient amount of liquid (30) to cover the transducer(s) (10) while they are operating. In addition, and without being limited, as more liquid (30) surrounds the transducer(s) (10) various costs are associated such as, but not limited to, (a) it will take longer to heat the liquid (30) in the reservoir(s) (40) to at least the minimum accepted temperature(s) or within the accepted temperature range(s) when starting the apparatus (215), (b) more amperage will be required by the one or more heating elements to not only preheat the liquid (30) to at least the minimum accepted temperature(s) or within the accepted temperature range(s), but also maintain the liquid (30) at those temperature(s).

Without being limited, the total volume of the liquid (30) in the reservoir(s) (40) in which the transducer(s) (10) are located, and any other liquid (30) directly connected to this liquid (30) in areas such as, but not limited to any, liquid sensor compartment(s) (8010), can range from about 0.05 liter to about 15 liters or more, preferably between about 0.1 liters to at least 2 liters or more, more preferably between about 0.1 liter to about 1 liter, even more preferably about 0.1 liters to about 0.8 liter, and very preferably about 0.1 to about 0.6 liter.

Referring to FIGS. 95-97, and FIGS. 103 and 113, and without being limited, the liquid sensor compartment(s) (8010) can be located in any effective and suitable location(s). It is preferred, without limitation, that the liquid sensor compartment(s) (8010) are located along the length of the reservoir(s) (40) in which the transducer(s) (10) are located. It is also preferred, without limitation, that the length of the liquid sensor compartment(s) (8010) is controlled or influenced by the length of the reservoir(s) (40) in which the transducer(s) (10) are located. The liquid sensor compartment(s) (8010) can have any effective and suitable length(s), width(s), and/or diameter(s). Without being limited, the width of the liquid sensor compartment(s) (8010) can range from about 0.25 inches to about 4 inches or more, preferably between about 0.25 inches to at least about 2.0 inches, more preferably between about 0.5 inches to about 1.75 inches, even more preferably about 1.0 inches to about 1.5 inches, and very preferably about 1.25 inches. Without being limited, the volume of the liquid (30) within the liquid sensor compartment(s) (8010) can range from about 0.01 liter to about 15 liters or more, preferably between about 0.01 liter to at least 2 liters or more, more preferably between about 0.04 liter to about 1 liter, even more preferably about 0.05 liters to about 0.5 liter, very preferably about 0.1 to about 0.5 liter, and extremely preferred about 0.18 liter.

Referring to FIGS. 103-108, and FIGS. 133-138, and without being limited, the reservoir(s) (40) in which the transducer(s) (10) are located can also have any effective and suitable length(s), width(s), and/or diameter(s). Without being limited, the width of these one or more reservoir(s) (40) can range from about 0.5 inches to about 4.5 inches or more, preferably between about 1 inch to at least about 4 inches, more preferably between about 1 inch to about 3 inches, even more preferably about 1.5 inches to about 2.75 inches, very preferably about 2.5 inches.

Referring to FIGS. 133-138, and without being limited, the reservoir(s) (40), or the various areas or parts of the reservoir(s) (40), in which the transducer(s) (10) are located, can also be separated into, or designated as, one or more area(s), segment(s), or zone(s) (Hereinafter called reservoir building segment(s) (9091)) which are designated for one or more of any function(s) or activity(s), or one or more of any combination(s) of any function(s) or activity(s), such as, but not limited to, one or more area(s) where the airflow inlet(s) (4010) are located (Hereinafter called air inlet zone(s) (9093)), one or more area(s) where the airflow outlet(s) (4015) are located (Hereinafter called air outlet zone(s) (9094)), and/or one or more area(s) where the transducer(s) and/or their corresponding geyser(s) (4045) of raised liquid (30) are located (Hereinafter called aerosol production zone(s) (9092)).

The reservoir building segment(s) (9091) can have any width and length. It is preferred, without limitation, that the width and length of the reservoir building segment(s) (9091) is at least suitable and effective. Without being limited, the length, width, and/or diameter of each of the one or more reservoir building segment(s) (9091) can range from about 0.5 inches to about 4.5 inches or more, preferably between about 1 inch to at least about 4 inches, more preferably between about 1 inch to about 3 inches, even more preferably about 1.5 inches to about 2.75 inches, very preferably about 2.5 inches. Also without being limited, the volume of each of the one or more reservoir building segment(s) (9091) can range from about 0.01 liter to about 15 liters or more, preferably between about 0.01 liter to at least 2 liters or more, more preferably between about 0.04 liter to about 1 liter, even more preferably about 0.05 liters to about 0.5 liter, very preferably about 0.1 to about 0.5 liter, and extremely preferred about 0.1 liter.

The volume of liquid (30) in one or more of any reservoir building segment(s) (9091) can also, without being limited, range from about 0.0 liters to about 0.5 liters or less. Without being limited, the one or more reservoir building segment(s) (9091) can contain or hold limited amounts of liquid (30), or little to no liquid (30), in situations such as, but not limited to, the one or more reservoir building segment(s) (9091) are only designed and constructed to accommodate or interface with one or more of various parts and components such as, but not limited to, the air inlet pipe(s) (4030), inbound airflow inlet(s) (4010), air outlet pipes(s) (4025), and/or the airflow outlet(s) (4015), and contain or hold small amounts of liquid (30), contain or hold little to no liquid (30), and/or not contain or hold any liquid (30).

Referring to FIG. 138, and without being limited, the one or more reservoir building segment(s) (9091) can be designed and constructed to have one or more shelve(s), structure(s), or island(s), of material (Hereinafter called "reservoir shelve(s)" (9096)) that can rise out of the liquid (30) in the reservoir(s) (40), or be located within the liquid (30) within the reservoir(s) (40). The one or more reservoir shelve(s) (9096) can be, without limitation, located in any effective and suitable location(s) within the reservoir(s) (40). The reservoir shelves (9096) may be, without limitation, located in one or more of any locations such as, but not limited to, under each inlet pipe(s) (4030) and/or inbound airflow inlet(s) (4010).

Without being limited, the reservoir shelve(s) (9096) can be any height, length, and/or width, and can be constructed from one or more of any suitable and effective material(s). It is preferred, without limitation, that the various dimensions of the reservoir shelves(s) (9096) are at least effective and suitable. It is more preferred, without limitation, that the reservoir shelve(s) (9096) are at least high enough to so that they rise out of the highest point of the liquid (30) within the reservoir(s) (40) and/or their top surface(s) (9097) are not submerged under the liquid (30) in the reservoir(s) (40).

Without being limited, the reservoir shelves(s) (9096) can serve various functions such as, but not limited to, reduce the amount of liquid (30) located within the reservoir(s) (40) and/or the one or more reservoir building segment(s) (9091), (b) limit the amount of liquid (30) that may be directly exposed to the air/gas that flows out of the airflow inlet(s) (4010), (c) deflect or redirect the air/gas that flows into the reservoir, into one or more of any other parts or areas within the reservoir(s) (40). It is preferred, without limitation, that if the reservoir shelve(s) (9096) are used, they are positioned under the each inlet pipe(s) (4030) and/or inbound airflow inlet(s) (4010), and their length and width approximately matches the inside area of the inlet pipe(s) (4030) and/or inbound airflow inlet(s) (4010) that are centered above them.

Without being limited, one or more feature(s) or structure(s) such as, but not limited to any, channel(s), tunnel(s), conduit(s), and/or groove(s) (Hereinafter called "reservoir connection(s)" (9095)) can be also utilized with the reservoir shelve(s) (9096), and enable the liquid (30) within the reservoir(s) (40) to flow or connect between the one or more of any reservoir building segment(s) (9091) or other parts of the reservoir(s) (40). The one or more reservoir connection(s) (9095) can be, without limitation, used to connect all of the liquid within the reservoir(s) (40) and also help to effectively drain all of the liquid in the reservoir(s) when needed.

One or more reservoir connection(s) (9095) can be, without limitation, located in one or more of any effective and suitable location(s) within, between, or through, the reservoir shelves(s) (9096). It is preferred, without limitation, that if a reservoir connection(s) (9095) is needed, it is utilized in the form of any effective and suitably sized groove(s) or channel(s). The reservoir connection(s) (9095) can be, without limitation, any effective and suitable length, width and height. It is preferred, without limitation, that the reservoir connection(s) (9095) are at least constructed so that an effective and suitable amount of liquid (30) is able to flow or move within the reservoir(s) (40) as needed, as well as cover the transducer(s) (10) with a sufficient and effective amount of liquid (30). It is also preferred, without limitation, that the bottom surface(s) of the reservoir connection(s) (9095) are at least flush with, or at least approximately even with, the various bottom surfaces or floor(s) of the reservoir(s) (40).

Referring to FIGS. 133-138, any effective and suitable number of these various reservoir building segment(s) (9091) can be, without limitation, assembled together in any suitable and effective, order, design, pattern, and/or format, in order to form one or more of any effective operating reservoir(s) (40) and/or component(s) of the optimized and miniaturized aerosol generator(s) (3800). Any effective and suitable height(s), depth(s), length(s), width(s), and/or diameter(s), may be used for these reservoir building segment(s) (9091). Without being limited, one or more of any reservoir building segment(s) may also have one or more different dimension(s), than one or more of any other reservoir building segment(s) (9091) that are utilized. It is preferred, without limitation, that all of the utilized reservoir building segment(s) (9091) have similar dimensions.

Referring to FIGS. 133-134, and without being limited, the reservoir(s) (40) in which the transducer(s) (10) are located, can be formed and organized, as well as condensed, combined, or concentrated, so that all of the various parts, components, function(s), and/or activity(s), that are related to, or interface with or within, the reservoir(s) (40), such as, but not limited to, the area(s) where the airflow inlet(s) (4010) are located, the area(s) where the airflow outlet(s) (4015) are located, and/or the area(s) where the transducer(s) and/or their corresponding geyser(s) (4045) of raised liquid (30) are located, can all be located within or interface with the same, or around the same, area(s) of the reservoir(s) (40). More specifically, and without being limited, the various zones such as, but not limited to, the air inlet zone(s) (9093), air outlet zone(s) (9094), and aerosol production zone(s) (9092), can all be located within, or interfaced to, the same reservoir building segment (9091).

Without being limited, in this simple and compact form, the width of these reservoir(s) (40) can range from about 0.5 inches to about 4.5 inches or more, preferably between about 1 inch to at least about 4 inches, more preferably between about 1 inch to about 3 inches, even more preferably about 1.5 inches to about 2.75 inches, and very preferably about 2.5 inches. Also without being limited, in this simple and compact form, the length of these reservoir(s) (40) can range from about 0.5 inches to about 4.5 inches or more, preferably between about 1 inch to at least about 4 inches, more preferably between about 1 inch to about 3 inches, even more preferably about 1.5 inches to about 2.75 inches, and very preferably about 2.5 inches. Also without being limited, in this simple and compact form, the volume of the liquid (30) in these reservoir(s) (40) can range from about 0.01 liter to about 15 liters or more, preferably between about 0.01 liter to at least 2 liters or more, more preferably between about 0.04 liter to about 1 liter, even more preferably about 0.05 liters to about 0.5 liter, very preferably about 0.1 to about 0.5 liter, and extremely preferred about 0.1 liter.

Referring to FIGS. 133 and 134, and without limitation, the one or more airflow outlet(s) (4015), and/or the one or more air outlet pipe(s) (4025), are suitably and effectively centered above, below, and/or around, the one or more transducer(s) (10) and/or the direction of their emitted energy or ultrasonic output or signal, within the reservoir(s)

(40) in which the transducer(s) (10) are located. Also referring to FIG. 133, and without limitation, the one or more airflow inlet(s) (4010) and/or air inlet pipe(s) (4030) can be positioned within, or interfaced with, the reservoir(s) (40), in one or more of any suitable and effective locations. Also, referring to FIG. 134, and without limitation, the one or more airflow outlet(s) (4015) and/or one or more air outlet pipe(s) (4025), can be effectively and suitably positioned within the one or more airflow inlet(s) (4010) and/or air inlet pipe(s) (4030), and suitably and effectively centered above, below, and/or around, the one or more transducer(s) (10) and/or the direction of their emitted energy or ultrasonic output or signal, within the reservoir(s) (40) in which the transducer(s) (10) are located.

Referring to FIG. 136, and without being limited, the reservoir(s) (40) in which the transducer(s) (10) are located can be formed and organized so that one area of the reservoir(s) (40) is dedicated to the air inlet zone(s) (9093), and the other area is dedicated to both the aerosol production zone(s) (9092) and the air outlet zone(s) (9094). More specifically, and without being limited, the one or more airflow outlet(s) (4015) and/or one or more air outlet pipe(s) (4025), can be suitably and effectively centered above, below, and/or around, the one or more transducer(s) (10) and/or the direction of their emitted energy or ultrasonic output or signal, within the reservoir(s) (40), and the one or more airflow inlet(s) (4010) and/or air inlet pipe(s) (4030) can be effectively and suitably positioned in one or more different area(s) or location(s) within, or interfaced with, the same reservoir(s) (40).

Without being limited, in this form or organization of the reservoir (40), where two reservoir building segment(s) (9091) are utilized, the width of these reservoir(s) (40) the width of these reservoir(s) (40) can range from about 0.5 inches to about 4.5 inches or more, preferably between about 1 inch to at least about 4 inches, more preferably between about 1 inch to about 3 inches, even more preferably about 1.5 inches to about 2.75 inches, and very preferably about 2.5 inches. Also, without being limited, the length of these reservoir(s) (40) can range from about 1 inch to about 9 inches or more, preferably between about 2 inches to at least about 8 inches, more preferably between about 2 inches to about 6 inches, even more preferably about 3 inches to about 5.5 inches, and very preferably about 5 inches. Also, without being limited, in this reservoir form, the volume of the liquid (30) in these reservoir(s) (40) can range from about 0.01 liter to about 15 liters or more, preferably between about 0.01 liter to at least 2 liters or more, more preferably between about 0.04 liter to about 1 liter, even more preferably about 0.05 liters to about 0.5 liter, very preferably about 0.1 to about 0.5 liter, and extremely preferred about 0.2 liter.

Referring to FIG. 137, and without being limited, the reservoir(s) (40) in which the transducer(s) (10) are located can be formed and organized so that one area of the reservoir(s) (40) is dedicated to the air inlet zone(s) (9093), and two different or distinct areas are dedicated to both the aerosol production zone(s) (9092) and the air outlet zone(s) (9094). More specifically, and without being limited, one or more airflow outlet(s) (4015) and/or one or more air outlet pipe(s) (4025), can be suitably and effectively centered above, below, and/or around, each of the one or more transducer(s) (10) and/or the direction of their emitted energy or ultrasonic output or signal, within the reservoir(s) (40), and the one or more airflow inlet(s) (4010) and/or air inlet pipe(s) (4030) can be effectively and suitably positioned in one or more different area(s) or location(s) within, or interfaced with, the same reservoir(s) (40). It is preferred, without limitation, that the one or more airflow inlet(s) (4010) and/or air inlet pipe(s) (4030) are located between each of the transducer(s) (10) and their respective airflow outlet(s) (4015) and/or one or more air outlet pipe(s) (4025). It is even more preferred, without limitation, that two separate transducers (10) are utilized within a reservoir (40), and each transducer (10) has its own dedicated airflow outlet (4015) and air outlet pipe (4025).

Without being limited, in this form or organization of the reservoir (40), where three reservoir building segment(s) (9091) are utilized, the width of these reservoir(s) (40) can range from about 0.5 inches to about 4.5 inches or more, preferably between about 1 inch to at least about 4 inches, more preferably between about 1 inch to about 3 inches, even more preferably about 1.5 inches to about 2.75 inches, and very preferably about 2.5 inches. Also without being limited, the length of these reservoir(s) (40) can range from about 1.5 inches to about 13.5 inches or more, preferably between about 3 inches to at least about 12 inches, more preferably between about 3 inches to about 9 inches, even more preferably about 4.5 inches to about 8.25 inches, and very preferably about 7.75 inches. Also, without being limited, in this simple and compact form, the volume of the liquid (30) in these reservoir(s) (40) can range from about 0.01 liter to about 15 liters or more, preferably between about 0.01 liter to at least 2 liters or more, more preferably between about 0.04 liter to about 1 liter, even more preferably about 0.05 liters to about 0.5 liter, very preferably about 0.1 to about 0.5 liter, and extremely preferred about 0.3 liter.

Without being limited, suitable and effective length and/or width dimensions can also be used for the reservoir(s) (40) in which the transducer(s) (10) are located, and at least suitable and effective reservoir (40) dimensions should be utilized to accommodate the various size(s) and number(s) of the various parts and components that are utilized such as, but not limited to, the transducer(s) (10), air inlet pipe(s) (4030), inbound airflow inlet(s) (4010), air outlet pipes(s) (4025), and/or the airflow outlet(s) (4015).

It is important that a sufficient and effective amount, depth, and/or height, of liquid (30) is maintained above the face or energy radiating side of the one or more transducer(s) (10) that is in contact with the liquid (30) within the reservoir(s) (40) of the optimized and miniaturized aerosol generator(s) (3800), at least while they are operating and receiving power. This can, without limitation, prevent damage to the transducer(s) (10). Any sufficient and effective amount, depth, and/or height, of liquid (30) may be utilized and maintained above the face or energy radiating side of the one or more transducer(s) (10) that is in contact with the liquid (30) within the reservoir(s) (40) of the optimized and miniaturized aerosol generator(s) (3800). It is preferred, without limitation, that the depth, and/or height, of the liquid (30) that is utilized or maintained above the transducer(s) (10) is between about 0.25 inches to about 8.0 inches. It is more preferred, without limitation, that the depth, and/or height, of the liquid (30) that is utilized or maintained above the transducer(s) (10) is between about 0.25 inches to about 5.0 inches. It is even more preferred, without limitation, that the depth, and/or height, of the liquid (30) that is utilized or maintained above the transducer(s) (10) is between about 0.25 inches to about 2.0 inches. It is very preferred, without limitation, that the depth, and/or height, of the liquid (30) that is utilized or maintained above the transducer(s) (10) is between about 0.5 inches to about 2.0 inches. It is extremely preferred, without limitation, that the depth, and/or height, of the liquid (30) that is utilized or maintained above the transducer(s) (10) is between about 1.0 inches to about 1.5 inches. It may also be, without limitation, possible to operate the optimized and miniaturized aerosol generator(s) (3800) by utilizing or maintaining a liquid (30) depth, and/or height, above the transducer(s) (10), that is below 0.25 inches if lower power(s) and/or frequency(s) are utilized to operate the transducer(s) (10).

Without being limited, the transducer(s) (10) within the optimized and miniaturized aerosol generator(s) (3800) can be operated at any suitable and/or effective frequency. It is preferred, without limitation, that the transducer(s) (10) are operated at any frequency between about 0.025 MHz to about 10 MHz or higher. It is more preferred, without limitation, that the transducer(s) (10) are operated at any frequency between about 0.5 MHz to about 4 MHz. It is even more preferred, without limitation, that the transducer(s) (10) are operated at any frequency between about 0.5 MHz to about 3.0 MHz. It is very preferred, without limitation, that the transducer(s) (10) are operated at any frequency between about 1.0 MHz to about 3.0 MHz. It is extremely preferred, without limitation, that the transducer(s) (10) are operated at any frequency between about 1.2 MHz to about 2.5 MHz.

Without being limited, the transducer(s) (10) within the optimized and miniaturized aerosol generator(s) (3800) may also be operated at any suitable and/or effective power. It is preferred, without limitation, that the transducer(s) (10) are operated at any suitable and effective power or peak to peak voltage, between about 20 (Vp-p) to about 300 volts peak to peak (Vp-p). It is more preferred, without limitation, that the transducer(s) (10) are operated at any suitable and effective power or peak to peak voltage, between about 50 (Vp-p) to about 300 volts peak to peak (Vp-p). It is even more preferred, without limitation, that the transducer(s) (10) are operated at any suitable and effective power or peak to peak voltage, between about 75 (Vp-p) to about 300 volts peak to peak (Vp-p). It is very preferred, without limitation, that the transducer(s) (10) are operated at any suitable and effective power or peak to peak voltage, between about 100 (Vp-p) to about 260 volts peak to peak (Vp-p). It is extremely preferred, without limitation, that the transducer(s) (10) are operated at any suitable and effective power or peak to peak voltage, between about 190 (Vp-p) to about 230 volts peak to peak (Vp-p).

Any effective and suitable aerosol (200) producing transducer(s) known to those skilled in the art may be, without limitation, utilized or included in the design of the optimized and miniaturized aerosol generator(s) (3800). However, it is preferred, without limitation that the transducer(s) (10) that are utilized, are constructed in a manner described in this document and are at least protected with a suitable and effective protective barrier. Without being limited, the transducer(s) (10) may be operated with one or more of any suitable and/or effective combination(s) of power and frequency. It is preferred, without being limited, the transducer(s) (10) are be operated at a frequency between about 1.0 MHz to about 3.0 MHz, and at a suitable and effective power or peak to peak voltage, between about 100 (Vp-p) to about 260 volts peak to peak (Vp-p). The transducer(s) (10) may also have a diameter or width of various lengths. It is preferred, without limitation, that the transducer(s) (10) at least have a diameter or width that is suitable and effective. Without being limited, the diameter or width of the transducer(s) (10) can range from about 0.25 inches to about 3 inches or more, preferably between about 0.5 inches to at least about 2.5 inches, more preferably between about 0.75 inches to about 2 inches, and even more preferably about 1 inch.

Any liquid (30) temperature or range of temperatures may be utilized in the reservoir(s) (40) in which the transducer(s) (10) are located, as well as any other connecting areas such as, but not limited to any liquid sensor compartment(s) (8010). Without being limited, the effective operating temperature of the liquid (30) may also vary depending upon parameters and attributes such as, but not limited to, the desired aerosol (200) output volume, the type of liquid (30) used, and the surface tension of the liquid (30). It is preferred, without limitation, that the temperature, or range of temperatures, of the liquid (30) that at least surrounds and/or covers the transducer(s), is at least effective, efficacious, and sufficient, and this temperature(s) is at least maintained while the one or more transducer(s) is producing aerosol (200). It is also preferred, without limitation, that at least the liquid (30) that surrounds and/or covers the transducer(s) (10), is preheated to any effective or desired temperature or range of temperatures, before the transducer(s) start to produce aerosol (200). The temperature of the liquid (30) above the transducer(s) (10) may also, without limitation, start to drop to any temperature, and more preferably to any effective temperature, after aerosol (200) generation has started and/or finished. It is preferred, without limitation, that if the temperature of the liquid (30) above the transducer(s) (10) drops during an aerosol (200) generation cycle, it at least drops within an effective, efficacious, and/or desired temperature range. It is preferred, without limitation, that at least the liquid (30) that surrounds and/or covers the transducer(s) (10), is kept at a temperature of at least 80 degree Fahrenheit or more. It is more preferred, without limitation, that at least the liquid (30) that surrounds and/or covers the transducer(s) (10), is kept at a temperature between 80 to 150 degree Fahrenheit or more. It is even more preferred, without limitation, that at least the liquid (30) that surrounds and/or covers the transducer(s) (10), is kept at a temperature between 90 to 150 degree Fahrenheit. It is very preferred, without limitation, that at least the liquid (30) that surrounds and/or covers the transducer(s) (10), is kept at a temperature between 90 to 130 degree Fahrenheit.

Referring to FIGS. 95-97, FIGS. 103-108, the temperature of the liquid (30) that surrounds and/or covers the transducer(s) (10), or any other liquid used within the apparatus (215), can be, without limitation, monitored by one or more of any liquid temperature sensing device(s) (Hereinafter called temperature sensor(s) (9050)) such as, but not limited to any, thermocouple(s), or RTD(s). The temperature sensor(s) (9050) can communicate with one or more of any digital, electronic, or analog, controller(s), such as, but not limited to, any PLC(s). Without being limited, the one or more of any digital, electronic, or analog, controller(s), such as, but not limited to, any PLC(s), can control, one or more of any liquid heating source(s) (9045) used in any suitable or desirable locations. It is preferred, without limitation, that one or more of any suitable heat source(s) are at least located in, or at least directly or indirectly interfaced with the liquid (30) that surrounds and/or covers the transducer(s) (10), or the reservoir(s) (40) in which the transducer(s) (10) are located. It is more preferred, without limitation, that at least one or more heating source(s) (9045) is interfaced with the bottom of the reservoir (40) in which the transducer(s) (10) are located. It is even more preferred, without limitation, that only one suitable heating source (9045) is utilized to increase the performance of the apparatus (215). The one or more heating source(s) (9045) can be, without any limitation, any suitable heat source, or combination of any suitable heat sources, known in the art, that is or has any, watt density, design, and power. Without being limited, the one or more heating source(s) (9045) can directly and/or indirectly heat any liquid(s) used to make or mix the liquid (30) that is utilized, any of the mixed liquid (30) before it enters the reservoir(s) (40), the liquid (30) in the reservoir(s) (40) in which the transducer(s) are located (10), and/or any other liquid (30) in one or more of any, tank(s), reservoir(s), compartment(s), and/or container(s), using any suitable and effective means known to those skilled in the art.

Without being limited, the one or more heating source(s) (9045) can be located at or in one or more of any suitable location(s) such as, but not limited to, within any reservoir(s) (40) in which the one or more transducer(s) (10) are located, within one or more of any walls or floor(s) of any reservoir(s) (40), attached to the exterior of one or more of any walls or floors of the reservoir(s) (40). It is preferred, without limitation, that the heating source (9045) that is utilized is any suitable heating element or cartridge type heater (Hereinafter called "heating element" (9045)). It is also preferred, without limitation, that the heating element (9045) is inserted into, and sufficiently interfaces with, a suitable hole that is centered and located within the bottom of each reservoir (40) material, and heats the liquid (30) in the reservoir(s) in which the transducer(s) (10) are located. The heat source(s) (9045) can be any suitable size or length, but it is preferred, without limitation, that the heat source(s) (9045) or heating element (3856) is at least large and/or long enough to also heat the liquid (30) in the one or more liquid sensor compartment(s) (8010). The reservoir(s) (40), or any other tank(s), reservoir(s), or compartment(s), can be constructed from any suitable material. It is preferred, without limitation, that at least the bottom of the reservoir(s) (40) is constructed from stainless steel. It is more preferred, without limitation, that the bottom of both the reservoir(s) (40) and the liquid sensor compartment(s) (8010) are constructed from stainless steel. It is even more preferred, without limitation, that the bottom of both the reservoir(s) (40) that the transducer(s) (10) are located in, and the liquid sensor compartment(s) (8010), are constructed from the same piece of material.

The one or more heating source(s) (9045) in the one or more aerosol (200) generating apparatus (215) can be, without limitation, operated at any time, for any duration, and in one or more of any operational combination(s). It is preferred, without limitation, that the heating source(s) (9045) are at least operated for any effective time, duration, and/or operational combination(s). The one or more heating source(s) (9045) can also have, or be rated for, any power or wattage. It is preferred, without limitation, that the heating source(s) (9045) have a power or wattage rating between 25 watts to 2000 watts or more. It is more preferred, without limitation, that the heating source(s) (9045) have a power or wattage rating between 25 watts to at least 1600 watts. It is even more preferred, without limitation, that the heating source(s) (9045) have a power or wattage rating between 250 watts to 1500 watts. It is very preferred, without limitation, that each heating source (9045) has a power or wattage rating between 300 watts to 700 watts.

It has been found that depending on the number of transducers (10) that are operated in the aerosol generating apparatus (215), the availability of sufficient power or amperage to the aerosol generator(s) (3800) and/or aerosol (200) generating apparatus (215) can, without limitation, at least impact the ability of the heating source(s) (9045) to effectively or suitably maintain the temperature of the liquid (30) that surrounds or covers the transducer(s) (10), at the needed or desired temperature(s) or within the needed or desired temperature range(s). This can be, without limitation, especially problematic when it is desired to operate as many transducer(s) (10) as possible, and produce as much aerosol (200) as possible, for any desired period of time, while still preserving enough power or amperage to maintain the temperature of the liquid (30) that surrounds and covers the transducer(s) (10), at the needed or desired temperature(s) or within the needed or desired temperature range(s).

Without being limited, one way to maximize the number of transducers (10) that are operating in the aerosol (200) generating apparatus (215) and also simultaneously maintain the liquid (30) above and/or surrounding the transducer(s) (10) at or within the desired or needed temperature(s) or temperature range(s), is to reallocate, and/or consolidate and allocate, the available power or amperage for any heating, to one or more heating source(s) (9045), and then cycling this power from one or more dedicated heating source(s) (9045) to another one or more dedicated heating source(s) (9045) as needed. Without being limited, this can be accomplished by controlling the power that is supplied to the more than one or plurality of heating source(s) (9045) via one or more of any digital, electronic, or analog, controller(s) such as, but not limited to, any PLC(s), as well as any other electrical components known to those skilled in the art, and cycling a sufficient amount of power between the various heating source(s) (9045) when it is needed.

Any amount of power or amperage can be, without limitation, cycled between or amongst the various heating source(s) (9045) at any time and for any duration of time. It is preferred, without limitation, that the available power or amperage for the heating source(s) (9045) is at least cycled between or amongst the one or more heating source(s) (9045) that are responsible for heating the liquid (30) in each reservoir(s) (40) in which the transducer(s) (10) are located. It is also preferred, without limitation, that at least an effective amount of power or amperage is cycled between or amongst the various heating source(s) (9045). Any available power or amperage that can be allocated to the various heating source(s) (9045) can be, without limitation, cycled amongst one or more of any of the heating source(s) (9045) at any time associated with the apparatus (215). It is preferred, without limitation, that any available power or amperage is dedicated to only one heating source (9045) at a time, and more preferably at least one heating source(s) (9045) that is located in, or interfaced with, each optimized and miniaturized aerosol generator (3800). This power or amperage can also be, without limitation, allocated to more than one heating source(s) (9045) at the same time, if sufficient power or amperage is available. Sufficient power or amperage may not always, without limitation, need to be cycled, allocated, and/or consolidated, between or amongst the various heating source(s) (9045) for reasons including, but not limited to, the optimized and miniaturized aerosol generator(s) (3800) is not generating aerosol (200), but the apparatus (215) is operational, and the power or amperage that would typically be used to generate aerosol (200) is all, or at least sufficiently, allocated by the one or more of any digital, electronic, or analog, controller(s) such as, but not limited to, any PLC(s), to at least all of the various heating source(s) (9045) responsible for heating the liquid (30) in all of the different reservoir(s) (40) in which the transducer(s) (10) are located.

Without being limited, at least a sufficient amount of power is cycled between or amongst the various heating source(s) (9045) for any effective and efficacious amount of time. It is preferred, without limitation, that at least a sufficient amount of power or amperage is allocated to at least one or more heating source(s) (9045) between 1 second or less to 5 minutes or more, before being allocated to one or more different heating source(s) (9045). It is more preferred, without limitation, that at least a sufficient amount of power or amperage is allocated to at least one or more heating source(s) (9045) between 0.1 seconds to 4 minutes, before being allocated to one or more different heating source(s) (9045). It is even more preferred, without limitation, that at least a sufficient amount of power or amperage is allocated to at least one or more heating source(s) (9045) for at least 10 seconds to 60 seconds, before being allocated to one or more different heating source(s) (9045). It is very preferred, without limitation, that at least a sufficient amount of power or amperage is allocated to at least one or more heating source(s) (9045) for at least 15 seconds to 40 seconds, before being allocated to one or more different heating source(s) (9045).

The power or amperage provided to the various heating source(s) (9045) can be, without limitation, cycled between or amongst the various heating source(s) (9045) any number of times per any time period. It is preferred, without limitation, that the power or amperage provided to the various heating source(s) (9045) is cycled between or amongst the various heating source(s) (9045) for any effective and efficacious number of times per any effective and efficacious time period. It is more preferred, without limitation, that the temperature of the liquid (30), above and/or surrounding the transducer(s) (10), and/or within the reservoir(s) (40) in which the transducer(s) are located, determines exactly where or to which heating source(s) (9045), the power or amperage is allocated or cycled between or amongst the various heating source(s) (9045). Any liquid (30) temperature can, without limitation, determine which heating source(s) (9045) are allocated sufficient power or amperage. However, it is preferred, without limitation, that the coldest liquid (30), and more preferably the coldest one or more reservoir(s) (40) in which the transducer(s) (10) are located, determines exactly where or to which one or more heating source(s) (9045), the power or amperage is allocated or cycled between or amongst the various heating source(s) (9045).

For example, and without limitation, one or more of any PLC(s) can sense and determine which liquid (30) within three different reservoirs (40) in which the transducer(s) (10) are located, of three different optimized and miniaturized aerosol generator(s) (3800) located within an aerosol generating apparatus (215), has the coldest temperature, and then allocate the available power or amperage to the heating source (9045) that is responsible for heating that coldest liquid (30) until it reaches the needed or desired temperature(s), or is within the needed or desired temperature range(s). Once this liquid (30) is sufficiently heated, the one or more PLC(s) can then repeat the process and sense and determine again which liquid (30) within those three different reservoirs (40), in which the transducer(s) are located, has the newest coldest temperature, and then reallocate the available power or amperage to the heating source (9045) that is responsible for heating that coldest liquid (30) until it too reaches the needed or desired temperature(s), or is within the needed or desired temperature range(s). Without being limited, this process can be, without limitation, repeated as needed for any number of times or cycles, or it can be utilized until various situations take place such as, but not limited to, (a) the apparatus (215) and/or optimized and miniaturized aerosol generator (s) (3800) is shut down, (b) the optimized and miniaturized aerosol generator(s) (3800) are not generating aerosol (200), but the apparatus (215) is still operational, and the power or amperage that would typically be used to generate aerosol (200) is all, or at least sufficiently, allocated by the one or more of any digital, electronic, or analog, controller(s) such as, but not limited to, any PLC(s), to all of the various heating source(s) (9045) responsible for heating the liquid (30) in all of the different reservoir(s) (40) in which the transducer(s) (10) are located, (c) the one or more of any digital, electronic, or analog, controller(s) such as, but not limited to, any PLC(s), has shut down all of the one or more optimized and miniaturized aerosol generator(s) (3800) so they are not generating aerosol (200), but the apparatus (215) is still operational, and the power or amperage that would typically be used to generate aerosol (200) is all, or at least sufficiently, allocated to one or more of any dehumidifier(s) (2040) and/or suitable deodorization filter(s) (2090).

Figure 95:
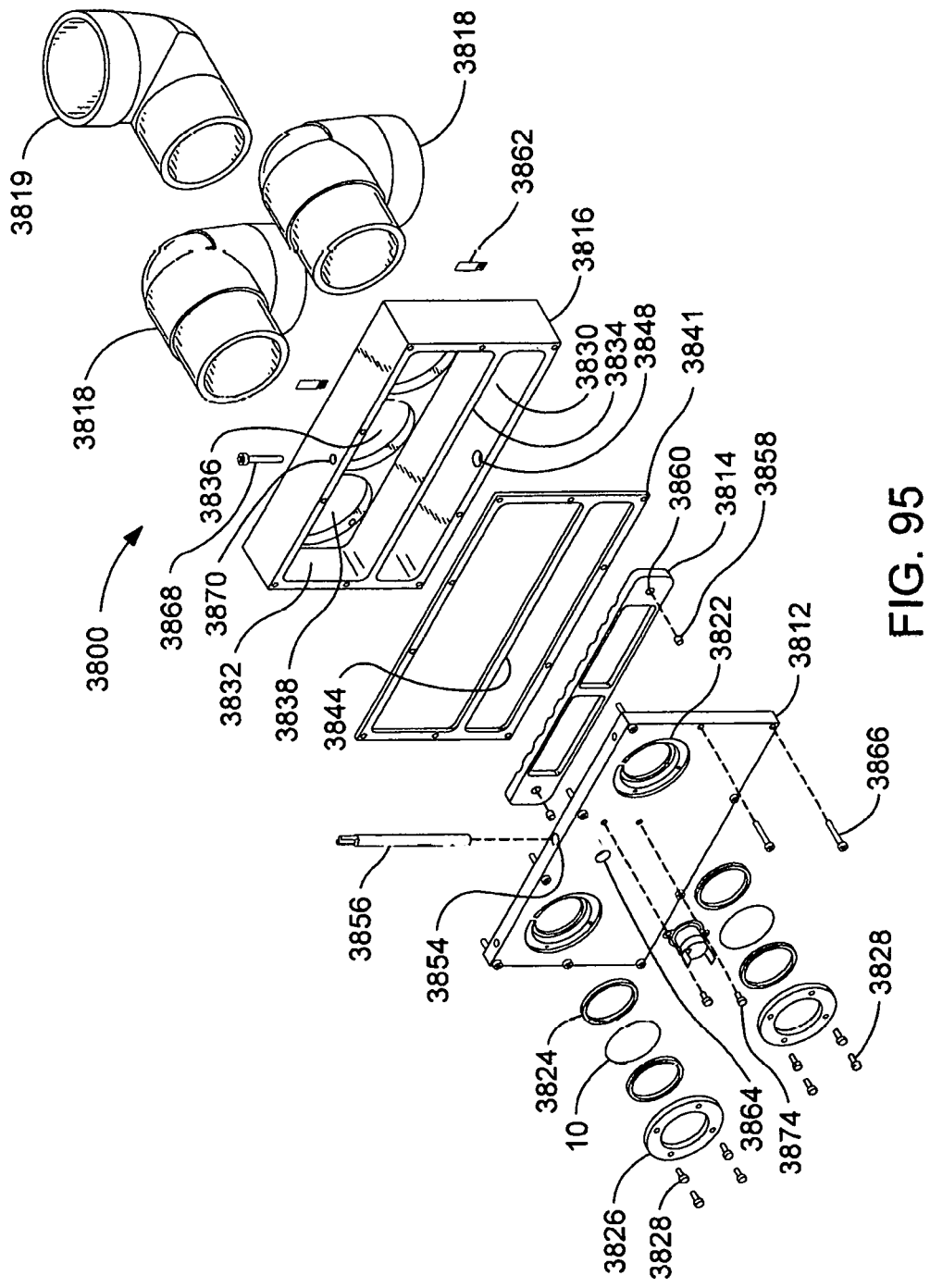
FIG. 95 is an exploded perspective view of a optimized and miniaturized aerosol generator.
Figure 96:
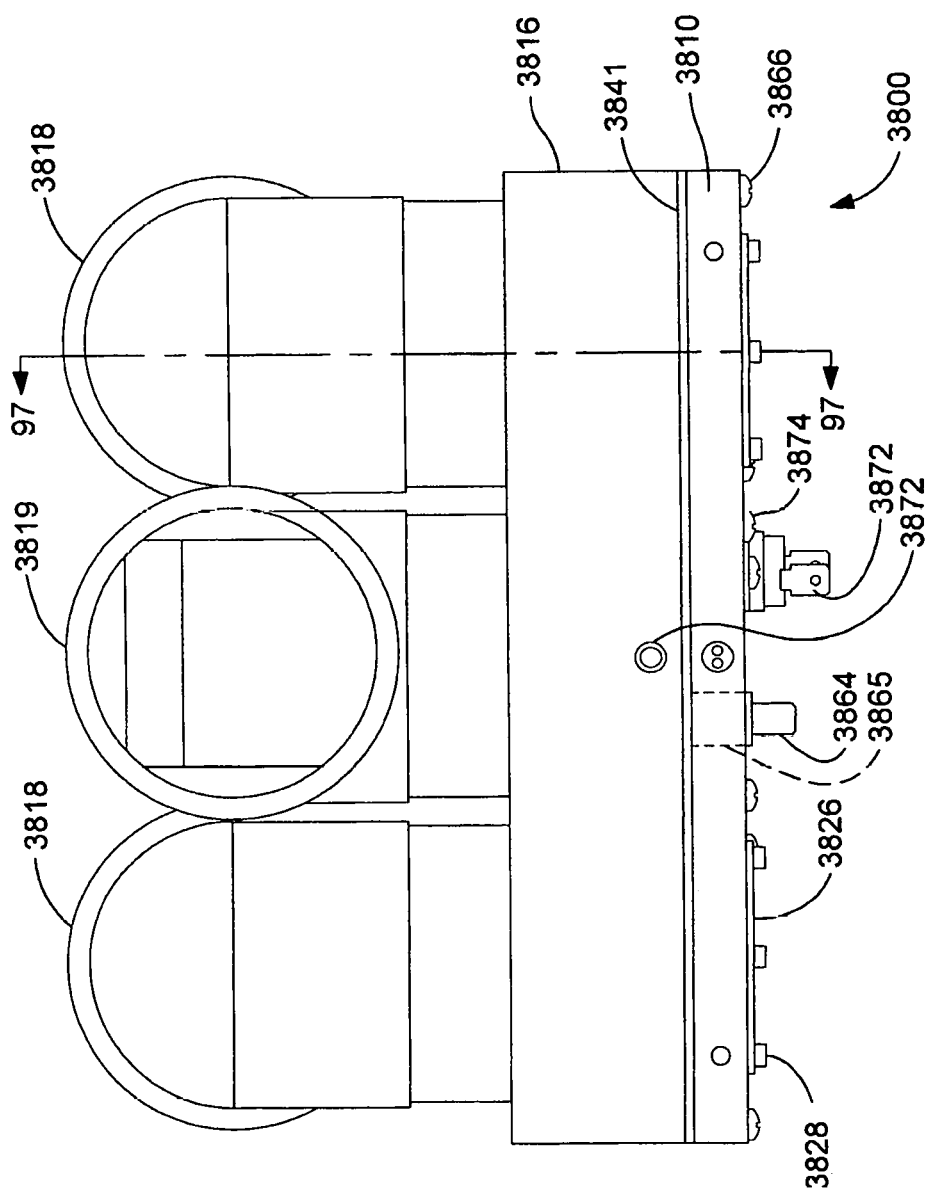
FIG. 96 is a side view of a optimized and miniaturized aerosol generator.
Figure 97:
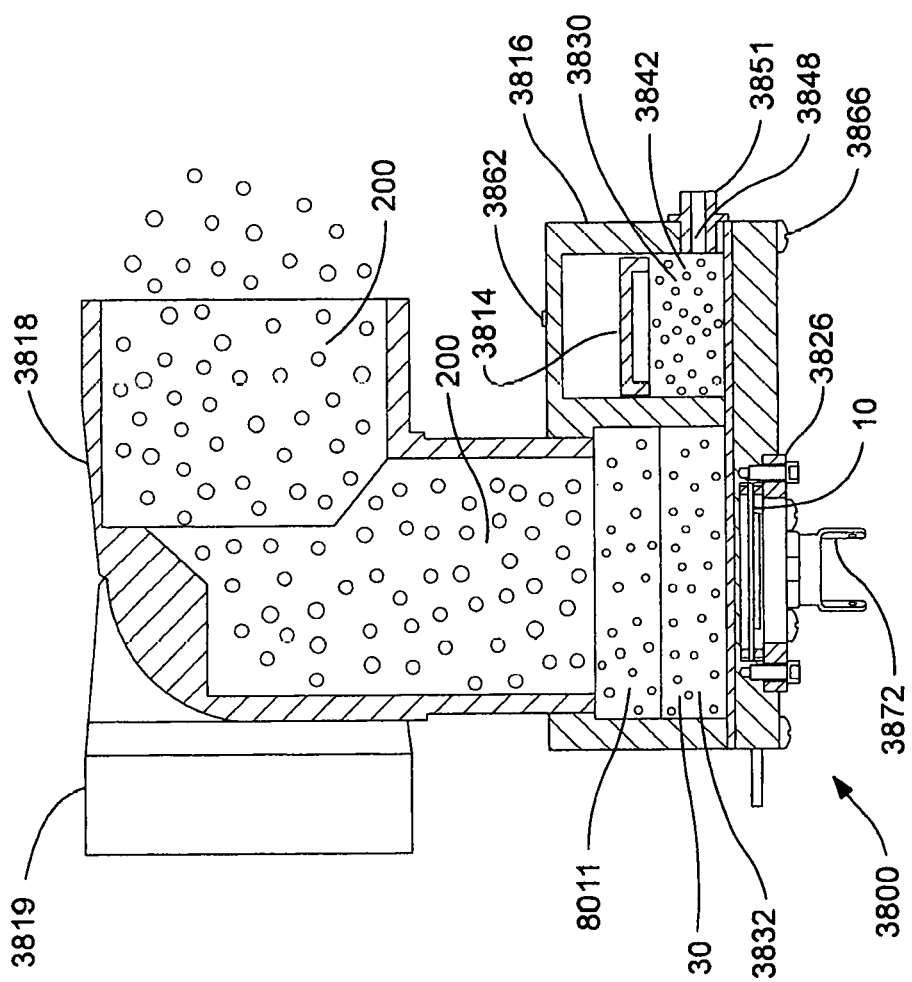
FIG. 97 is a cross sectional view of a optimized and miniaturized aerosol generator cut through FIG. 96.
Figure 98:
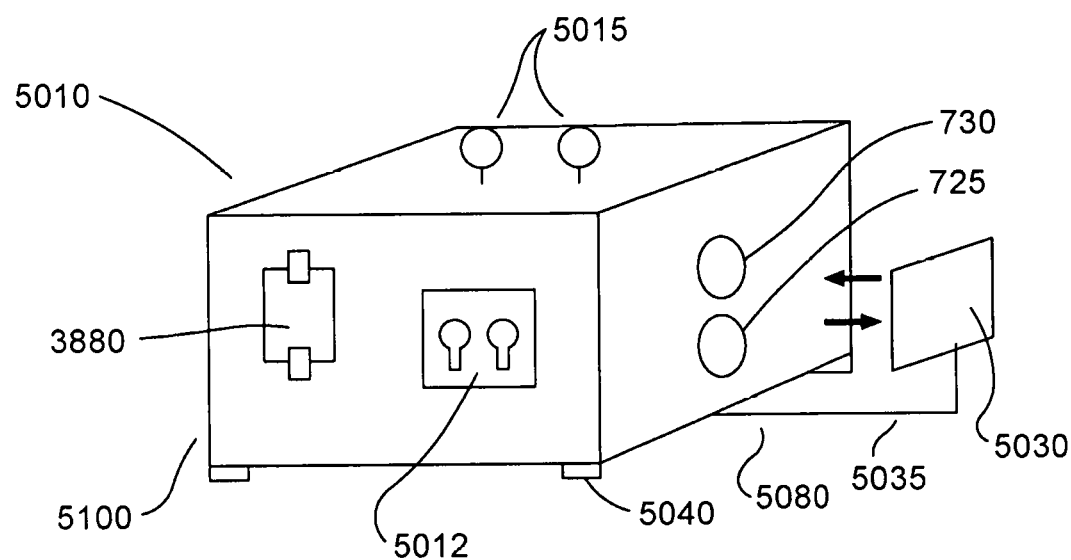
FIG. 98 is a perspective view of a remote aerosol sensor to remotely sense the environment within an area targeted for aerosol deployment according to the present invention.
Figure 99:
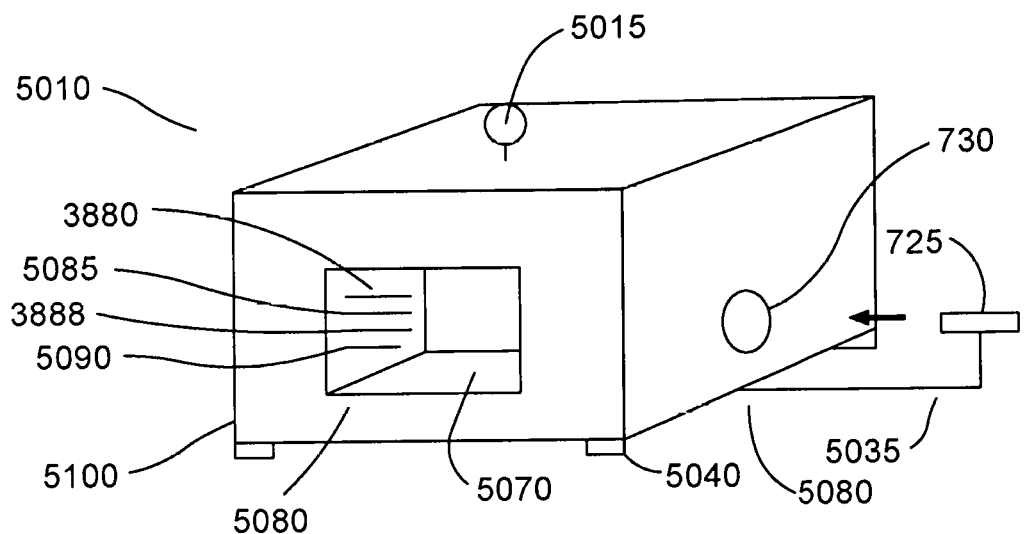
FIG. 99 is a perspective view of a remote aerosol sensor with a sensor cavity to remotely sense the environment within an area targeted for aerosol deployment, according to the present invention.
Figure 100:
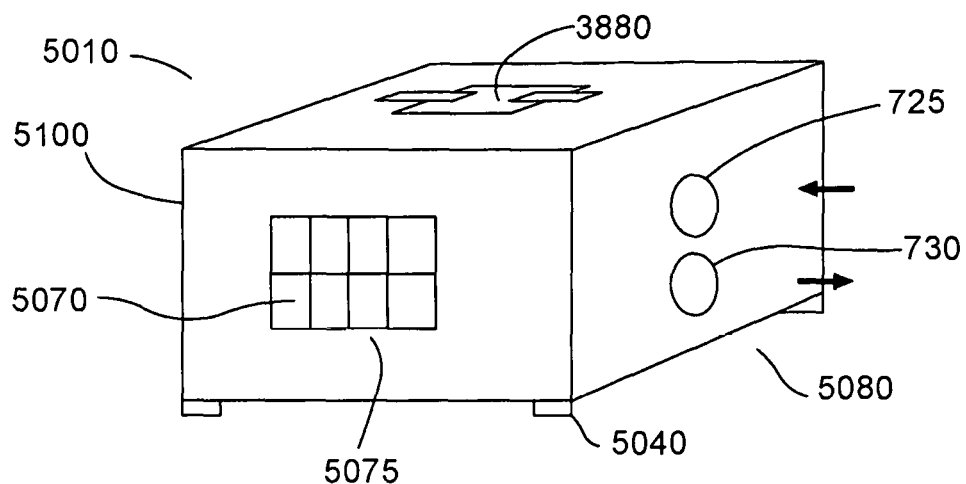
FIG. 100 is a perspective view of a remote aerosol sensor with an aerosol deposit sensor to remotely sense the environment within an area targeted for aerosol deployment according to the present invention.
Figure 101:
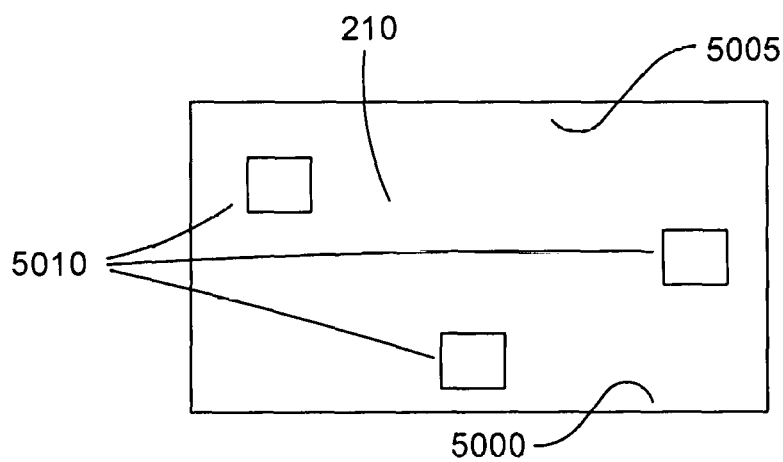
FIG. 101 is a schematic view of one or more targeted area(s) in which one or more remote aerosol sensor(s) are located in various locations in an enclosed area, according to the present invention.
Figure 102:
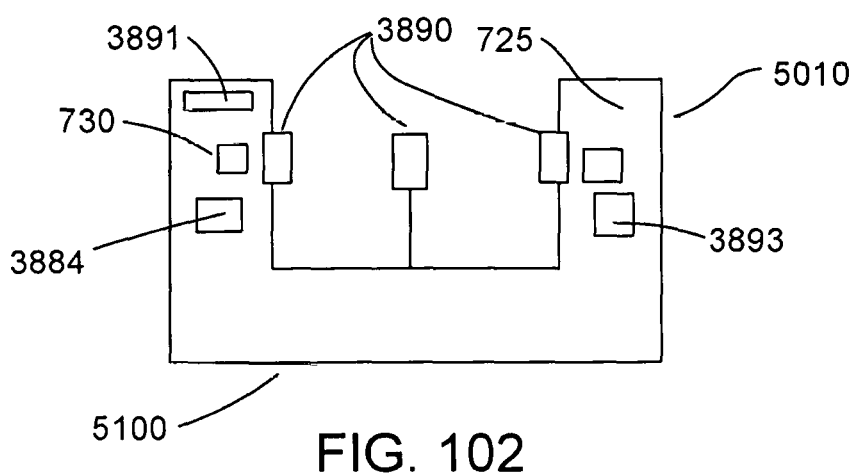
FIG. 102 is a schematic view of an embodiment of various parts and components of a means to remotely sense the environment within an area targeted for aerosol deployment according to the present invention.
Figure 118:
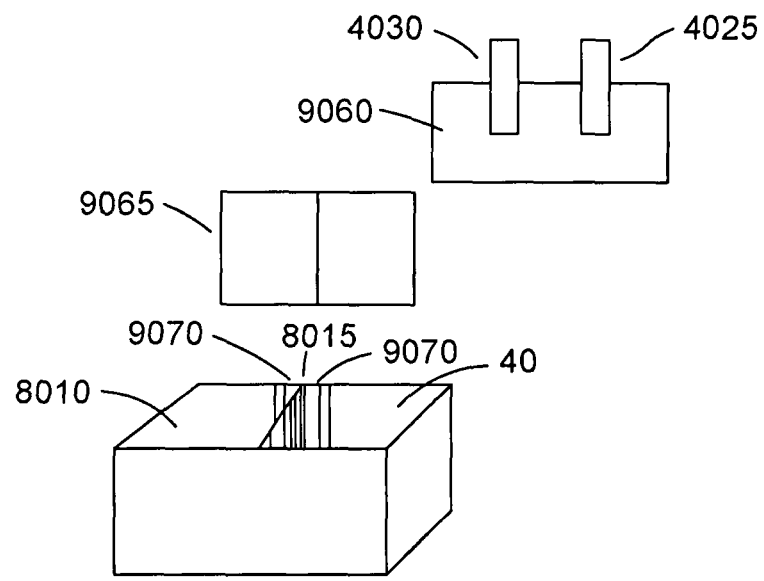

Referring to FIGS. 95-97, FIGS. 103-108, FIGS. 111-112, and FIG. 118, the reservoir(s) (40) in which the transducer(s) (10) are located, including, but not limited to any, liquid sensor compartment(s) (8010), can be constructed from one or more of any suitable components or materials. It is preferred, without limitation, that the reservoir(s) (40) and the liquid sensor compartment(s) (8010) at least share a common floor or base (Hereinafter called "transducer plate" (3812)). It is preferred, without limitation, that the transducer plate (3812) is at least constructed from any suitable grade of stainless steel. The transducer plate (3812) can also be any suitable thickness. It is preferred, without limitation, that the transducer plate (3812) is at least a suitable thickness to work effectively with any suitable heating source(s) (9045) that may be interfaced with it, as well as accommodate any interfaced transducer(s) (10). Referring to FIGS. 95-97, various components are, without limitation, utilized to construct and seal the walls and floor, of the reservoir(s) (40) in which the transducer(s) (10) are located, and the liquid sensor compartment(s) (8010). Referring to FIG. 118, and without being limited, in a more simple aspect, any or all of the outer wall(s) and/or floor(s) of the reservoir(s) (40) in which the transducer(s) (10) are located, and the liquid sensor compartment(s) (8010), can be, without limitation, constructed from the same material or manufactured to function as one component. This can be accomplished in any suitable manner known to those skilled in the art such as, but not limited to any, injection molding, thermo-molding, or even plastic welding the various wall and floor components together. Without being limited, one or more separate roof(s) or ceiling(s) component(s) (Hereinafter "removable cover" (9060)) can then be, without limitation, interfaced with one or more of any components such as, but not limited to any, air inlet pipe(s) (4030), airflow inlet(s) (4010), air outlet pipe(s) (4025), airflow outlet(s) (4015), or any other component(s), and then be connected or interfaced with one or more of any suitable seal(s) or gasket(s) (9065), to the various walls of the reservoir(s) (40) and/or liquid sensor compartment(s) (8010). In this more simple aspect, the one or more wall(s), structure(s), or barrier(s) (Hereinafter called "separation wall(s)" (8015)), that forms or establishes at least one or more suitable, barrier(s), complete barrier(s), and/or partial barrier(s), between the liquid sensor compartment(s) (8010) and the reservoir(s) (40) can also be, without limitation, constructed from any number of independent part(s) and can slide in and out for repair, replacement, or cleaning, via one or more of any suitable grooves, tracks, or indentations (Hereinafter called "tracks" (9070). It is preferred, without limitation, that only one wall or separation wall(s) (8015) would separate the liquid sensor compartment(s) (8010) from the reservoir(s) (40) in which the transducer(s) (10) are located, and they would slide in and out via one or more tracks or indentations (9070) that would be present between the liquid sensor compartment(s) (8010) and reservoir(s) (40) at any suitable location where the wall(s) or barrier(s) would be positioned.

Seventh, and referring to FIGS. 95-97, FIGS. 103 and 105, and FIGS. 111-112, the design of the optimized and miniaturized aerosol generator (3800) and aerosol generating device (215) can be enhanced, without limitation, by improving how the liquid (30) depth above the transducer(s) (10) is maintained within the reservoir(s) (40). The use of one or more of any suitable liquid level sensor(s) (305) located anywhere within the reservoir(s) (40) in which the transducer(s) is located, is known in the art. However, it has been found that the environment within the reservoir(s) (40) in which the transducer(s) (10) are located, can be turbulent due to influences such as, but not limited to any, liquid (30) wave action inherent to this environment. The wave action can be, without limitation, especially disruptive to gathering effectively accurate liquid (30) level or liquid (30) depth readings, especially in smaller and more compact reservoir(s) (40) in which the transducer(s) (10) are located. This is especially true with respect to the various improvements just described in the current invention. Accurate liquid level and/or depth readings are important for reasons including, but not limited to, maintaining an effective and/or sufficient amount of liquid (30) above the transducer(s) (10) within the reservoir(s) (40). This liquid (30) wave action, and more specifically, any wave action on the surface of the liquid (30), can be created from sources such as, but not limited to, any liquid (30) turbulence created as a result of operating the transducer(s) (10), any ejected droplets of liquid (30) returning back to the liquid (30) in the reservoir(s) (40), or any air flow within the reservoir(s) (40).

Referring to FIGS. 95-97, FIGS. 103 and 105, and FIGS. 111-112, it has been found that the turbulence within the reservoir(s) (40) can be avoided by positioning one or more of any suitable liquid level sensor(s) (305) known in the art within, without limitation, one or more protected areas or compartments (hereinafter called "liquid sensor compartment(s)" (8010)), thereby effectively isolating or protecting them from any adverse wave effects experienced within the reservoir(s) (40) in which the transducer(s) (10) are located. It is preferred, without limitation, that one or more, and more preferably only one, liquid sensor compartment(s) (8010) is suitably and effectively interfaced with the reservoir(s) (40) in which the transducer(s) (10) are located. One or more suitable liquid level sensor(s) (305) known in the art may also, without limitation, be utilized within the reservoir(s) (40) in which the transducer(s) (10) are located as well. It is preferred, without limitation, that the liquid level sensor compartment(s) (8010) are effectively connected to the reservoir(s) (40) in which the transducer(s) (10) are located, so that the liquid level experienced in the reservoir(s) (40) is also effectively and sufficiently reflected or experienced within the liquid level sensor compartment(s) (8010). The liquid level sensor compartment(s) (8010) can be, without limitation, directly or indirectly connected in any various effective ways to the reservoir(s) (40) in which the transducer(s) (10) are located. The liquid level sensor compartment(s) (8010) can be located, without limitation, within the reservoir(s) (40), or located anywhere outside of the reservoir(s) (40). It is preferred, without limitation, that the one or more liquid level sensor compartment(s) (8010) are at least, suitably and effectively, separated, completely separated, and/or partially separated, from the one or more reservoir(s) (40) by one or more of any suitable wall(s), barrier(s), structure(s), or otherwise separation wall(s) (8015) of any effective thickness and height. It is more preferred, without limitation, that the one or more liquid level sensor compartment(s) (8010) are suitably and effectively separated from the one or more reservoir(s) (40) by one or more of any suitable wall(s), barrier(s), structure(s), or otherwise separation wall(s) (8015) of any effective thickness and height, and the only connection with the reservoir(s) (40) is through one or more of any reservoir connection orifice(s) (7040). It is further preferred, without limitation, that the liquid level sensor compartment(s) (8010) is effectively sealed to prevent the escape of various things such as, but not limited to any, water vapor, aerosol, or any gases(s) or vapor(s) from the agent or liquid (30).

The reservoir(s) (40) and liquid level sensor compartment(s) (8010) can be, without limitation, sufficiently and effectively connected at any effective distance beneath the surface of the liquid (30) in the reservoir(s) (40) and/or the liquid level sensor compartment(s) (8010), so that any adverse effects such as, but not limited to, any undesired amount of, liquid (30) turbulence, air turbulence, or liquid (30) wave action, is either not experienced within the liquid level sensor compartment(s) (8010) or at least not experienced enough to significantly impact or have a detrimental effect on the accuracy of any means used to measure the depth or volume of the liquid (30) in these areas. More specifically, the reservoir(s) (40) in which the transducer(s) (10) are located and the liquid level sensor compartment(s) (8010) can be, without limitation, suitably connected with one or more of any, opening, tunnel, conduit, pipe, shaft, or orifice (hereinafter called "reservoir connection orifice" (7040)). The reservoir connection orifice(s) (7040) can be, without limitation, any effective shape, size, geometry, or length. It is preferred, without limitation, that the reservoir connection orifice(s) (7040) is between 0.10 inch to 2.0 inches or more in diameter. It is more preferred, without limitation, that the reservoir connection orifice(s) (7040) is between 0.10 inch to 1.5 inch in diameter. It is even more preferred, without limitation, that the reservoir connection orifice(s) (7040) is between 0.10 inch to 1.25 inch in diameter. It is very preferred, without limitation, that the reservoir connection orifice(s) (7040) is between 0.120 inch to 1.0 inch in diameter. The reservoir connection orifice(s) (7040) can also be, without limitation, located at one or more locations within the liquid level sensor compartment(s) (8010) and/or the reservoir(s) (40).

The liquid level sensor compartment(s) (8010) can be, without limitation, any sized tank, compartment, or reservoir, and can hold any effective or desired amount of liquid. It is preferred, without limitation, that the liquid level sensor compartment(s) (8010) holds approximately 0.1 liter to 15 liters or more of liquid (30). It is more preferred, without limitation, that the liquid level sensor compartment(s) (8010) holds approximately 0.1 liter to at least 2 liters of liquid (30). It is even more preferred, without limitation, that the liquid level sensor compartment(s) (8010) holds approximately 0.1 liter to 1 liter of liquid (30). It is very preferred, without limitation, that the liquid level sensor compartment(s) (8010) holds approximately 0.1 liter to 0.5 liter of liquid (30). One or more of any liquid level sensor(s) (305) known to those skilled to in the art, can be, without limitation, utilized within the liquid level sensor compartment(s) (8010) to communicate and/or help maintain any suitable or desired liquid (30) volume, liquid (30) level, or depth of liquid (30).

It is preferred, without limitation, that the liquid level sensor compartment(s) (8010) is separated from the reservoir(s) (40) in which the transducer(s) (10) are located, by at least one or more separation wall(s) (8015) and connected with at least one or more reservoir connection orifice(s) (7040). It is also preferred, without limitation, that at least part of the reservoir connection orifice(s) (7040) interfaces with the bottom surface or floor of the reservoir(s) (40) and liquid level sensor compartment(s) (8010). It is also preferred, without limitation, that both the reservoir(s) (40) and the liquid level sensor compartment(s) (8010) share a common base plate, floor, or bottom. However, the various reservoir(s) (40) and liquid level sensor compartment(s) (8010) may also, without limitation, be completely independent. Referring to FIG. 118, the reservoir(s) (40) and the liquid level sensor compartment(s) (8010) may also be, without limitation, constructed out of the same piece of material, or at least the various side-walls and floor components are sufficiently welded or bonded together, which could eliminate the need for any bottom sealing gasket(s) (3841) as shown in FIGS. 95-96. Referring to FIGS. 95-96, it is preferred, without limitation, that the reservoir(s) (40) in which the transducer(s) (10) are located and the liquid level sensor compartment(s) (8010) are constructed from at least two different components, the transducer plate (3812) and the fluid container (3816), separated by one or more gasket(s) or sealing gasket (3841).

With reference to FIG. 96, one or more drains (3865) may also, without limitation, be located in one or more of any suitable location(s) such as, but not limited to, the reservoir(s) (40) in which the transducer(s) (10) are located, and the liquid level sensor compartment(s) (8010). One or more drainage grooves or troughs of any suitable depth, shape, length, and width, may also, without limitation, be positioned anywhere on the bottom or floor(s) of the various reservoir(s) (40) and/or liquid level sensor compartment(s) (8010) and connect with the one or more drain(s) (655), and help with draining the liquid (30). However, it is preferred, without limitation, that at least one or more drain(s) (655) is located in the reservoir(s) (40) and the one or more drainage grooves or troughs connect not only with one another, but also connect the various areas within both the reservoir(s) (40) and liquid level sensor compartment(s) (8010) to the at least one or more drain(s) (655).

Referring to FIGS. 95-97, FIG. 103, FIG. 105, FIG. 110, FIG. 113, and FIG. 118, an improved liquid level sensor (7020) is described that may be, without limitation, utilized to determine any, liquid level, liquid volume, or liquid depth, of any kind of liquid, in one or more of any tank(s), reservoir(s), or container(s), including, but not limited to, the reservoir(s) (40) in which the transducer(s) (10) are located and/or the liquid level sensor compartment(s) (8010). Without being limited, this improved sensor improves the art by offering an alternative for remotely sensing any liquid depth, liquid volume, or liquid level, especially in areas experiencing high electrical noise or electrical interference. It is preferred, without limitation, that at least one or more improved liquid level sensor(s) (7020) is utilized to determine the liquid level, liquid volume, or liquid depth, of any liquid (30) that may be present in at least the liquid level sensor compartment(s) (8010). However, one or more of any other suitable means known in the art may also, without limitation, be utilized to determine the volume or depth of the liquid that is either in the reservoir(s) (40) in which the transducer(s) (10) are located, and/or in the liquid level sensor compartment(s) (8010).

Figure 103:
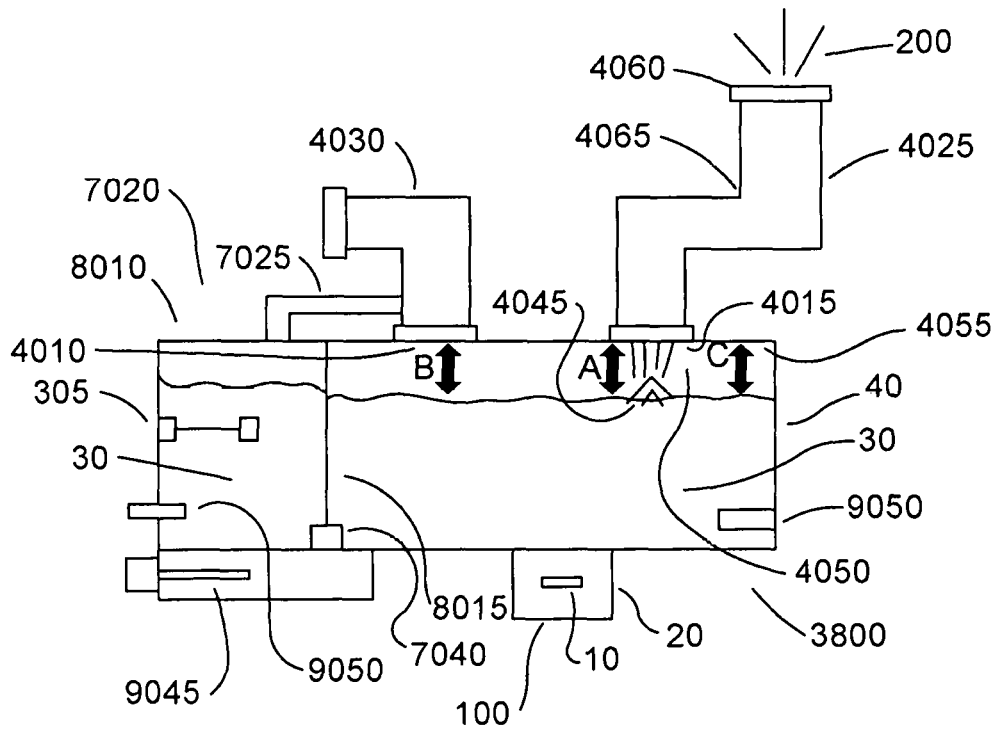
FIG. 103 is a schematic view of an optimized and miniaturized aerosol generator according to the present invention.
Figure 104:
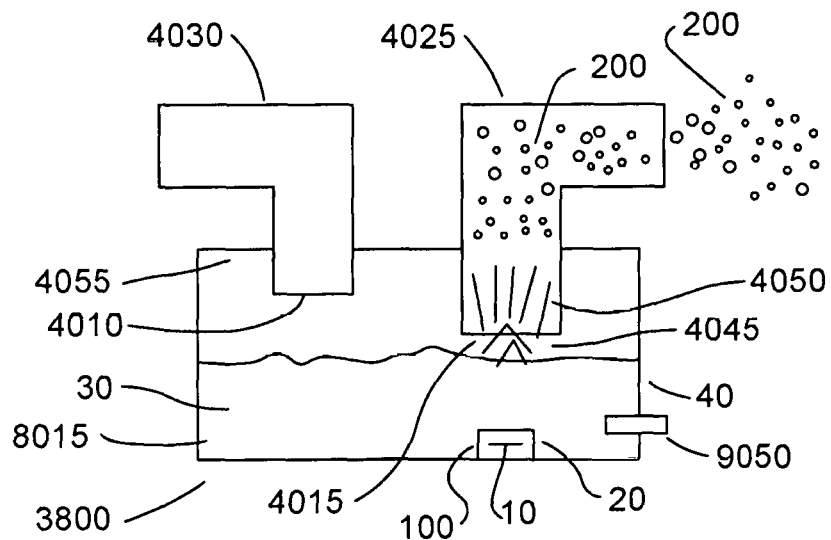
FIG. 104 is a schematic view of an optimized and miniaturized aerosol generator, showing an air outlet pipes position directly over a transducer according to the present invention.

Referring to FIGS. 95-97, FIG. 103, FIG. 105, FIG. 110, FIG. 113, and FIG. 118, and without being limited, the improved liquid level sensor (7020) includes various components. First, it includes one or more float(s) (3814) that can have, without limitation, any effective size, shape, thickness, or material construction. It is preferred, without limitation, that one or more float(s) (3814), and more preferably only one float (3814), is positioned in each liquid sensor compartment (8010). The one or more float(s) (3814) may be, without limitation, located in any suitable reservoir(s), tank(s), or container(s), and float on, or be suitably suspended within, any liquid contained within these spaces. It is preferred, without limitation, that the one or more float(s) (3814) are located inside of the liquid level sensor compartment(s) (8010). It is also preferred, without limitation, that the float(s) (3814) are made from a polymer material that effectively floats in water, or any other liquid that the float(s) (3814) may be located in. With reference to FIG. 103, the air space above the liquid (30) within the liquid level sensor compartment(s) (8010), or any suitable reservoir(s), tank(s), or container(s), can also be, without limitation, plumbed or effectively connected with one or more of any suitable, tube(s), conduit, pipe(s), or duct(s) (Hereinafter called "vent pipe(s)" (7025), to one or more of any suitable and effective location(s). The vent pipe(s) (7025) can be used for purposes such as, but not limited to, enabling a sufficient flow of air/gas in or out of the liquid level sensor compartment(s) (8010), or any other tank(s), reservoir(s), or container(s), as the liquid (30) depth fluctuates, in order to prevent the float(s) (3814) from locking into one or more various position(s). It is preferred, without limitation, that any suitably sized vent pipe(s) (7025) are connected to either the air inlet pipe(s) (4030) or the air outlet pipe(s) (4025).

Figure 110:
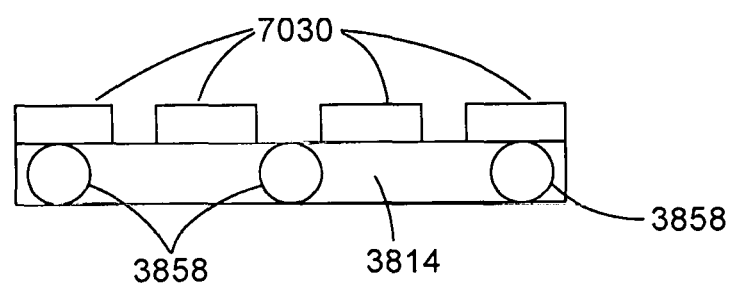
FIG. 110 is a schematic view of a level float of an optimized and miniaturized aerosol generator according to the present invention.
Figure 113:
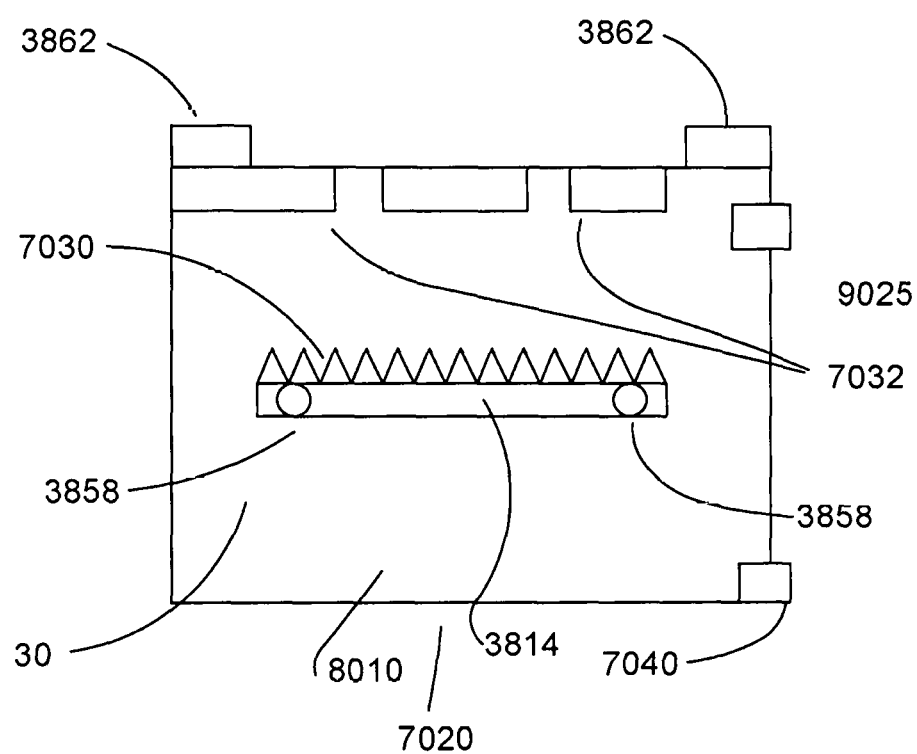
FIG. 113 is a schematic view of a liquid level sensor compartment of an optimized and miniaturized aerosol generator, according to the present invention.

Referring to FIGS. 95 and 113, and without being limited, the float(s) (3814) can have one or more pockets or indentions (Hereinafter called "air pocket(s)" (3815) of any suitable depth, height, geometry, size, and shape, located under, on top of, and/or within, the float(s) (3814), to offer various functions such as, but not limited to, decrease the mass of the float(s) (3814), and create one or more air pockets, that can all aid in float (3814) buoyancy. Referring to FIG. 110 and FIG. 113, the float(s) (3814) can have, without limitation, one or more of any connecting or non-connecting, protrusions, grooves, pockets, indentations, or sufficient texture (Hereinafter called "texture" (7030)), located at the top surface(s) of the float(s) (3814) that can prevent vacuum or suction from occurring that may otherwise result in the float(s) (3814) sticking to the top of the liquid level sensor compartment(s) (8010), or any other tank(s), reservoir(s), or container(s), if the liquid level fluctuates to a sufficient maximum depth for this to occur. The roof or interior surface of the liquid level sensor compartment(s) (8010), or any other tank(s), reservoir(s), or container(s), may also have one or more of any connecting or non-connecting, protrusions, grooves, pockets, indentations, or sufficient texture (Hereinafter called "roof texture" (7032)), to fulfill the same purpose as the texture (7030) on the float(s) (3814). It is preferred, without limitation, that if any protrusions, grooves, pockets, indentations, or sufficient texture (7030), are utilized, they are configured or constructed in a manner so that the float(s) (3814) can remain level on or within, any liquid contained in any of the tank(s), reservoir(s), or container(s), including, but not limited to, the reservoir(s) (40) in which the transducer(s) (10) are located, and the float(s) (3814) don't stick or get affixed to their roof(s).

The one or more float(s) (3814) can also directly or indirectly interface with or include, without limitation, one or more magnet(s) (3858) of any effective strength. The one or more magnet(s) (3858) can be, without limitation, located or directly or indirectly interfaced anywhere, on, within, or around, the one or more float(s) (3814). It is preferred, without limitation, that the magnet(s) (3858) are located within the float (3814), or at least sealed within the float (3814) or the float material, and are protected from the liquid (30) in various ways known to those skilled in the art. The magnet(s) (3858) can also, without limitation, be effectively encapsulated with any suitable protective material, of any suitable thickness.

The magnet(s) (3858) can be, without limitation, interfaced or located in, on, or within, any effective, location, position, or orientation, of the float(s) (3814). It is preferred, without limitation, that at least two or more magnet(s) (3858) are utilized with each float (3814), and each magnet (3858) is at least located in a machined hole located at either end of each float (3814), and effectively sealed into the float (3814). It is also preferred, without limitation, that each magnet(s) (3858) is paired with at least one or more hall effect sensor(s)" (3862).

One or more hall effect sensor(s) (3862) may be, without limitation, placed in any suitable location, and in any suitable proximity, to the magnet(s) (3858). The one or more hall effect sensor(s) (3862) may also be, without limitation, located at any depth or height within, or more preferably outside of, the various tanks(s), reservoir(s), or container(s). It is preferred, without limitation, that any wall or ceiling material(s) used to construct the various tank(s), reservoir(s), or container(s), and/or any structure(s), component(s), or means used to cover the various tank(s), reservoir(s), or container(s), are at least effectively compatible with the hall effect sensor(s) (3862) and magnet(s) (3858) that are utilized.

The one or more hall effect sensor(s) (3862) may also, without limitation, interact or function with one or more magnet(s) (3858). The one or more float(s) (3814) and magnet(s) (3858) can, without limitation, move any distance to or from the hall effect sensor(s) (3862) at any time, and be within any proximity to the one or more hall effect sensor(s) (3862). It is preferred, without limitation, that the one or more float(s) (3814) and magnet(s) (3858) at least move within an effective distance of, or range within, the one or more hall effect sensor(s) (3862). Without being limited one or more of any, float(s) (3814), magnet(s) (3858), and/or hall effect sensor(s) (3862), can be positioned at any distance, or move any distance, at any time, respective to one another. Any type of hall effect sensor(s) (3862) may be, without limitation, utilized and may have any sensitivity and accuracy. It is preferred, without limitation, that the sensitivity and accuracy of the hall effect sensor(s) (3862) is at least effective. It is also preferred, without limitation, that the one or more hall effect sensor(s) (3862) are effectively located outside of the one or more of any reservoir(s), tank(s), or container(s). It is more preferred, without limitation, that the hall effect sensor(s) (3862) are effectively located outside of the liquid level sensor compartment(s) (8010). It is even more preferred, without limitation, that the hall effect sensor(s) (3862) are suitably positioned and effectively located on top of the one or more of any, reservoir(s), tank(s), container(s), or area(s), including, but not limited to, the liquid level sensor compartment(s) (8010).

Without being limited, the voltage output from these sensor(s) (3862) is proportional to the distance of the various magnet(s) (3858), and this in turn can be interpreted by one or more of any digital, electronic, or analog, controller(s) such as, but not limited to, any PLC(s), as the liquid (30) depth. Any voltage, and/or voltage change, reported by the hall effect sensor(s) (3862) can be interpreted as any liquid depth and/or liquid level. It is preferred, without limitation, that the voltage output from the hall effect sensor(s) (3862) is proportional to the magnetic flux density that is sensed by the hall effect sensor(s) (3862), and the closer the magnet(s) is to the sensor(s) (3862), the more voltage output is generated by the sensor(s) (3862) and communicated to one or more of any digital, electronic, or analog, controller(s) such as, but not limited to, any PLC(s). Using more than one pairs of magnet(s) (3858) and hall effect sensor(s) (3862) can offer, without limitation, greater redundancy. It is preferred, without limitation, that the lowest voltage signal reported is equated with, or is assigned, the priority for any decision or logic choice made to fill the various reservoir(s) (40), tank(s), reservoir(s), or container(s).

When used with the new optimized and miniaturized aerosol generator (3800), it is preferred, without limitation, that the various parts such as, but not limited to, the float(s) (3814), magnet(s) (3858), hall effect sensor(s) (3862), and digital, electronic, or analog, controller(s) such as, but not limited to, any PLC(s), are constructed and configured so that if the liquid (30) level in the reservoir(s) (40) in which the transducer(s) (10) are located, and/or the liquid level sensor compartment(s) (8010), drops below, or even rises above, one or more of any set point(s), liquid depth(s), or range of liquid depth(s), that is established, one or more of any digital, electronic, or analog, controller(s) such as, but not limited to, any PLC(s), can cause the apparatus (215), and/or optimized and miniaturized aerosol generator (3800), and/or one more of any of its components, to shut down and/or enter a fault or error mode.

It is also preferred, without limitation, that the various parts such as, but not limited to, the float(s) (3814), magnet(s) (3858), hall effect sensor(s) (3862), and digital, electronic, or analog, controller(s) such as, but not limited to, any PLC(s), are constructed and configured so that if the liquid (30) level in the reservoir(s) (40) in which the transducer(s) (10) are located, and/or the liquid level sensor compartment(s) (8010), drops below, or rises above, one or more of any set point(s), liquid depth(s), or range of liquid depth(s), that is established, one or more of any digital, electronic, or analog, controller(s) such as, but not limited to, any PLC(s), can cause or make the logic choice to either fill the various reservoir(s) (40), tank(s), reservoir(s), or container(s), or stop any filling activity.

Any suitable hall effect sensor(s) (3862) can, without limitation, be utilized. However, it is preferred, without limitation, that hall effect sensor(s) (3862) with higher resolution are utilized in order to obtain more exact liquid (30) level data, and liquid (30) level control over the transducer(s) (10). This manner of supplying liquid (30) to the reservoir(s) (40) in which the transducer(s) (10) are located, or any other chamber(s), compartments, or tank(s) connected to the reservoir(s) (40), can be, without limitation, utilized in the design and construction of the new optimized and miniaturized aerosol generator (3800).

Another improvement to the design of the optimized and miniaturized aerosol generator (3800) and aerosol generating device (215), includes, without limitation, changing how the agent, in liquid concentrate form or concentrated liquid (Hereinafter called "concentrated agent liquid", "liquid agent in concentrated form", "concentrated agent", "liquid concentrate", or the like, (9005)), is mixed with one or more of any other suitable liquid(s) such as, but not limited to, any kind or type of water (Hereinafter called "dilution liquid(s)" (9010)), before it is supplied to any reservoir(s) (40), or any other chamber(s) or tank(s) connected to the reservoir(s)

Figure 111:
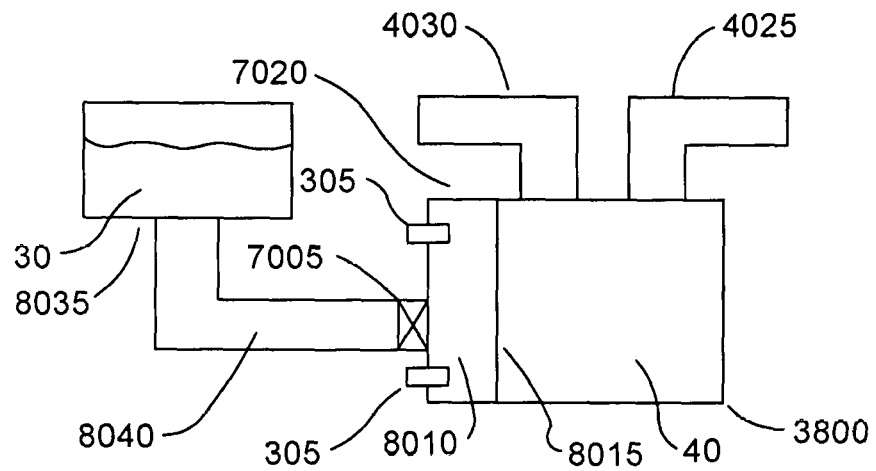
FIG. 111 is a schematic view of a feed tank with pre-mixed liquid connected to an optimized and miniaturized aerosol generator via according to the present invention.
Figure 112:
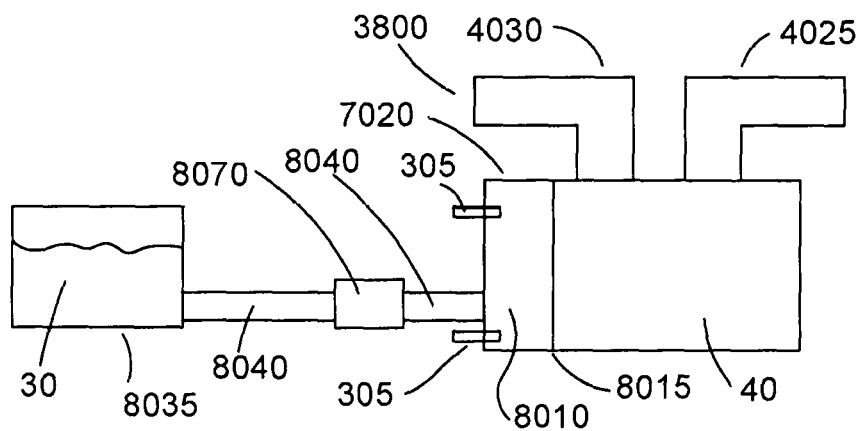
FIG. 112 is a schematic view of a feed tank and pump connected to an optimized and miniaturized aerosol generator according to the present invention.

(40). Referring to FIG. 111 and FIG. 112, traditionally, the liquid (30) is typically diluted or premixed from a concentrated liquid (9005) outside of the apparatus (215), and it is then deposited into one or more feed tank(s) (8035) of various sizes, that supply agent liquid (30) via one or more of any suitable, pipe(s), hose(s), tube(s), or conduit (Hereinafter called "supply tube(s) (8040)), to the reservoir(s) (40) in which the transducer(s) (10) are located, as it is needed. The mixed liquid (30) can be, without limitation, supplied to the reservoir(s) (40) in which the transducer(s) (10) are located, or any other connecting reservoir(s), in various ways such as, but not limited to, via any gravity feed system(s), or the liquid (30) can be pumped directly into the reservoir(s) (40) with any suitable pump (8070), all of which is known to those skilled in the art. The supply of this liquid (30) is typically, without limitation, controlled by one or more of any sufficient reservoir valve(s) (7005), and/or one or more of any sufficient pump(s) (8070), which is in turn controlled by one or more digital, electronic, or analog, controller(s) such as, but not limited to, any PLC(s). This manner of supplying liquid (30) to the reservoir(s) (40) in which the transducer(s) (10) are located, or any other chamber(s), compartment(s), or tank(s) connected to the reservoir(s) (40), can be, without limitation, utilized with one or more of the new optimized and miniaturized aerosol generator(s) (3800) or any of the new enhancements that are disclosed. However, this means for supplying liquid (30) to the various reservoir(s) (40) can be, without limitation, problematic for reasons including, but not limited to, the amount of time that is needed to preheat the one or more feed tank(s) (8035) may be too excessive for certain customers, and certain mixed liquids (30) may have a finite shelf life once they are mixed and may not be completely used before they have expired or experienced an unacceptable level of degradation.

Figure 114:
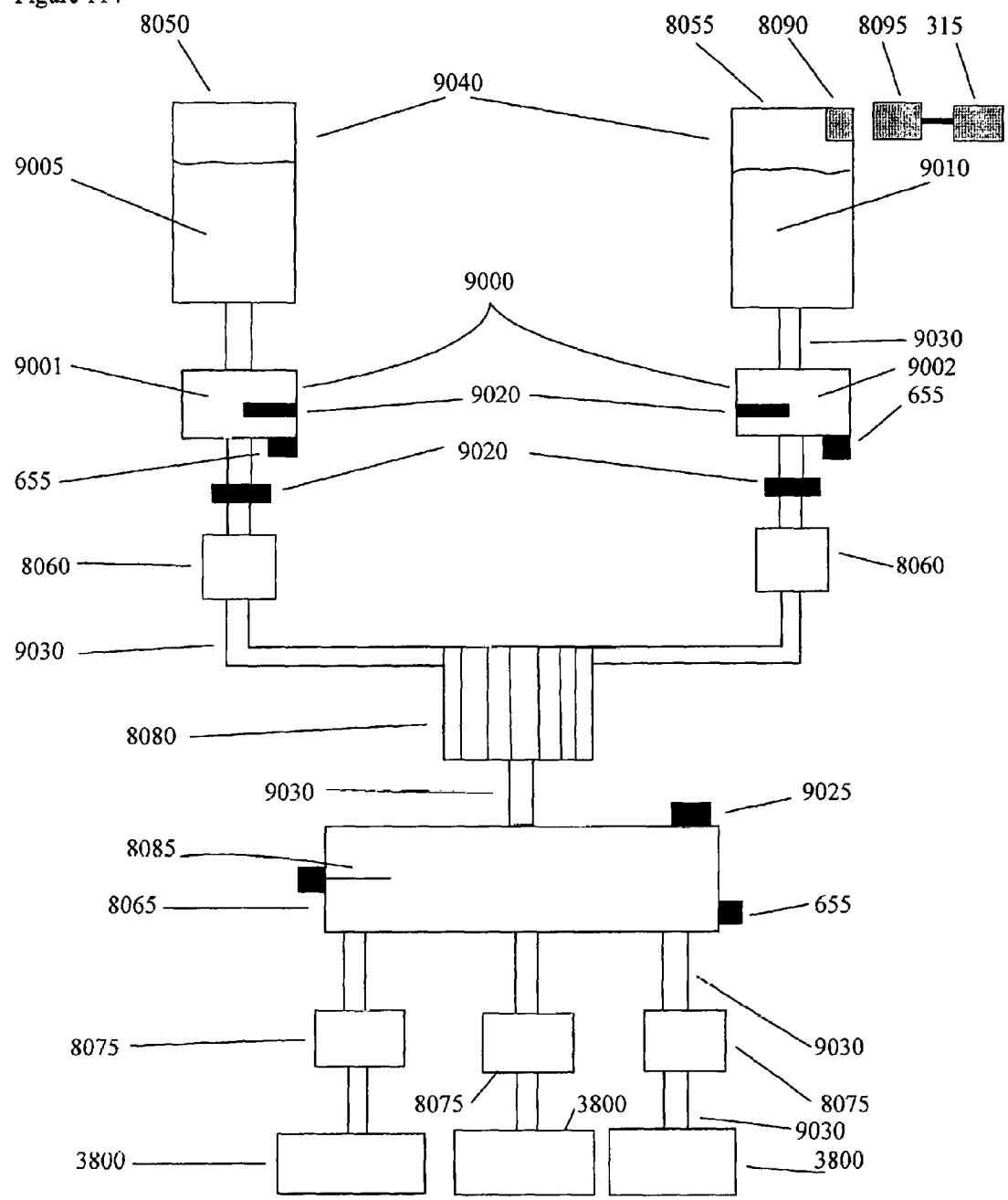
FIG. 114 is a schematic view of two pre-mix reservoirs feeding a mixing apparatus for supplying liquid to a plurality of optimized and miniaturized aerosol generators all according to the present invention.
Figure 115:
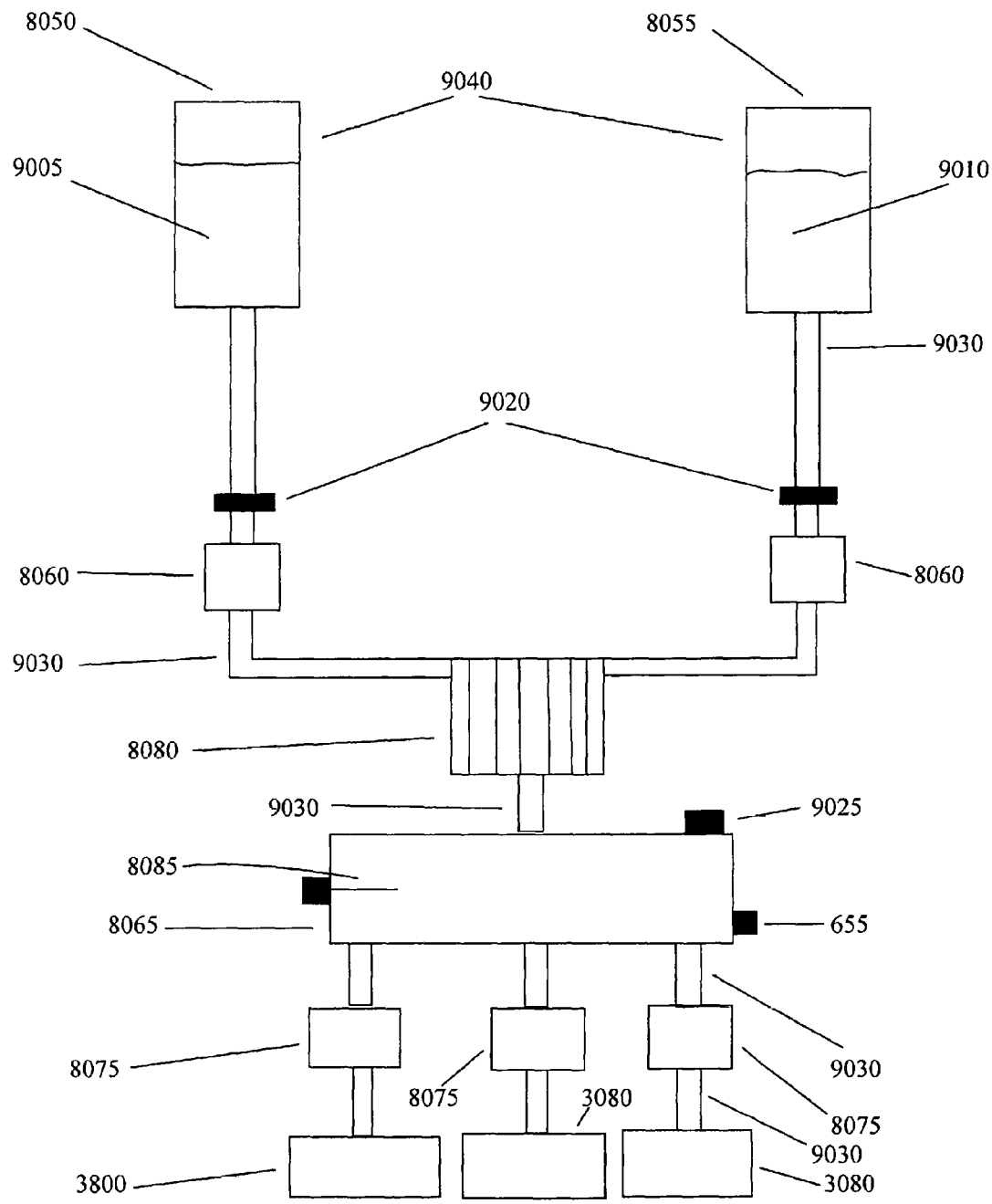
FIG. 115 is a schematic view of a mixing apparatus for supplying liquid to a plurality of optimized and miniaturized aerosol generators according to the present invention.

Referring to FIGS. 114-115, it is preferred, without limitation, that a new and improved means is utilized for mixing a liquid agent in concentrate form(s) (9005) with one or more liquid(s) such as, but not limited to, any kind or type of water, before it is supplied to any reservoir(s) (40), or one or more of any other connecting tank(s), reservoir(s), or compartment(s), as the mixed liquid (30) end product. This new and improved means can offer, without limitation, various advantages including, but not limited to, (a) enabling small amounts of mixed liquid (30) to be presented to the reservoir(s) (40) in which the transducer(s) (10) are located on demand, or when needed, (b) providing small amounts of liquid (30) that is mixed with suitable or acceptable accuracy and repeatability, (c) providing a more efficient supply and use of liquid concentrate and mixed liquid (30) for at least one or more aerosol (200) deployment cycle(s), (d) providing a design that is more compact and space saving.

This new means consists of various attributes. Referring to FIGS. 114-115, the first attribute, is the source of the liquid (30). It is preferred, without limitation, that the agent liquid (30) that fills the reservoir(s) (40), is sourced from one or more of any suitable agent liquid(s) that is in any suitable concentrated form(s) (9005), and is then mixed with one or more of any suitable liquid(s), or dilution liquid(s) (9010), such as, but not limited to, any water. The one or more source(s) of the concentrated agent liquid(s) (9005), (Hereinafter called "liquid concentrate source(s)" (8050)), can be, without limitation, one or more of any suitable, container(s), reservoir(s), tank(s), carboy(s), bottle(s), suitable package(s), or cartridge(s), of any suitable design, size, and construction, that directly or indirectly interfaces with the apparatus(s) (215) or any hardware or components connected to the apparatus(s) (215) and/or the optimized and miniaturized aerosol generator(s) (3800), and contains and supplies the concentrated agent, or agent liquid, in any concentrated, or suitably concentrated, form (9005). Without being limited, one or more of any concentrated agent liquid(s) (9005) can be utilized. These concentrated agent liquid(s) (9005) can then be, without limitation, mixed or diluted to any suitable and efficacious percentage(s) or parts per million in solution, as shown later. Without being limited, the concentrated agent liquid(s) (9005) can also be one or more of any liquid, chemical, solution, compound, and/or any other suitable liquid, that is desired or needed to be diluted to any amount(s) or any percentage(s), by the one or more of any dilution liquid(s) (9010). It is preferred, without limitation, that the concentrated agent liquid(s) (9005) is at least diluted with the dilution liquid(s) (9010), to one or more of any effective and/or suitable amount(s) or percentage(s). It is also preferred, without limitation that the concentrated agent liquid(s) (9005) consists of at least peroxyacetic acid (PAA) in any suitable concentrate form. It is more preferred, without limitation, that the concentrated agent liquid(s) (9005) includes a peroxyacetic acid concentrate having the following ingredients: (a) 4.5% of Peroxyacetic acid (PAA), (b) 22% of hydrogen peroxide, 9% of Acetic acid, (c) 64.5% of Distilled water, and (d) 73.5% of Inert ingredients.

The liquid concentrate source(s) (8050) can be, without limitation, fixed component(s), and/or releasably secured, and attach or interface anywhere to any suitable part of the apparatus(s) (215), and/or the optimized and miniaturized aerosol generator(s) (3800), all in a manner known in the art. In addition, any one or more parts of the liquid concentrate source(s) (8050) can, without limitation, interface with one or more of any suitable sleeves or receptacle(s) connected to or are a part of the apparatus(s) (215), in a manner known in the art. It is preferred, without limitation, that the liquid concentrate source(s) (8050) are at least one single or multi use container(s), or bottle(s), that interface with at least one or more receptacle(s) connected to or are a part of the apparatus(s) (215), and/or the optimized and miniaturized aerosol generator(s) (3800). This type of container(s) or bottle(s) can be, without limitation, designed and constructed in a manner known to those skilled in the art. However, a fixed liquid concentrate source(s) (8050), in the form of one or more of any suitably sized reservoir(s), tank(s), container(s), that are directly or indirectly connected or plumbed to any reservoir(s) (40), may also, without limitation, be utilized, and have one or more of any resealable closure(s) that is of any suitable size and construction. It is preferred, without limitation, that this type of liquid concentrate source(s) (8050) is easily refillable by the operator of the aerosol generating apparatus (215).

The one or more liquid concentrate source(s) (8050) and/or one or more dilution liquid source(s) (8055), can also be, without limitation, marked or tagged in any suitable location with one or more of any, identifier, marking, code, RFID chip or tag, barcode, symbol code, symbol, or image (Hereinafter called "identification code(s)" (8090)). The identification code(s) (8090) can be, without limitation, unique or non-unique. The identification code(s) (8090) utilized can be, without limitation, any optical or radio frequency machine-readable representation of data. It is preferred, without limitation, that the identification code(s) (8090) utilized, are in the form of any barcode, and each barcode is unique for each bottle, package, container, or liquid concentrate source (8050). It is also preferred, without limitation, that the identification code(s) (8090) are at least located approximately on or effectively near the area of the spout, drain, outlet, or neck, of the package(s) or container(s), where the liquid concentrate would leave the liquid concentrate source(s) (8050).

The identification code(s) (8090) can contain, communicate, or relate to, without limitation, one or more of any relevant information or data known to those skilled in the art including, but not limited to, date of product manufacture, date of product expiration, lot number, and part number. It is preferred, without limitation that the identification code(s) (8090) at least contain information related to the specific lot number or production batch number that the liquid concentrate source (8050) belongs to. It is more preferred, without limitation, that the identification code(s) (8090) at least contain information related to the specific lot number or production batch number that the liquid concentrate source (8050) belongs to, and a unique part number. It is even more preferred, without limitation, that the identification code(s) (8090) at least contain information related to the specific lot number or production batch number that the liquid concentrate source (8050) belongs to, a unique part number, and the date of manufacture. It is very preferred, without limitation that the identification code(s) (8090) at least contain information related to the specific lot number or production batch number that the liquid concentrate source (8050) belongs to, a unique part number, the date of manufacture, and the product expiration date.

The identification code(s) (8090) can be, without limitation, detected and deciphered by one or more of any suitable identification code reading device (8095) known to those skilled in the art. The identification code reading device (8095) can, report, communicate, or signal, with one or more of any digital, electronic, or analog, controller(s) such as, but not limited to, any PLC(s) (315). Without being limited, the one or more of any digital, electronic, or analog, controller(s) such as, but not limited to, any PLC(s) (315), can utilize any of the reported information from the identification code reading device(s) (8095), and be programmed to execute various outcomes or actions such as, but not limited to: (a) limit the number of times the apparatus(s) (215) and/or the optimized and miniaturized aerosol generator(s) (3800), can be operated with one or more of, a specific identification code(s) (8090), a certain lot number(s) or production batch number(s), or a certain part or product number(s) or product identification data, and (b) prevent the apparatus(s) (215) and/or the optimized and miniaturized aerosol generator(s) (3800) from being operated with a liquid concentrate source (8050) whose liquid contents (9005) have expired.

Referring to FIGS. 114-115, the second attribute for this new means, is the one or more source(s), of the one or more of any suitable dilution liquid(s) (9010) (hereinafter called "dilution liquid source(s)" (8055)), that is mixed with the liquid concentrate (9005). It is preferred, without limitation, that the dilution liquid(s) (9010) is any effective kind or type of water. The dilution liquid source(s) (8055) can be, without limitation, one or more of any suitable, container(s), reservoir(s), tank(s), carboy(s), bottle(s), suitable package(s), or cartridge(s), of any design, size, and construction, that directly or indirectly interfaces with the apparatus(s) (215) or any hardware or components connected to the apparatus(s) (215) and/or the optimized and miniaturized aerosol generator(s) (3800), and contains and supplies one or more of any suitable dilution liquid(s) (9010). The dilution liquid source(s) (8055) can be, without limitation, fixed component(s), and/or releasably secured, and attach or interface anywhere to any suitable part of the apparatus(s) (215), and/or the optimized and miniaturized aerosol generator(s) (3800), all in a manner known in the art. In addition, any one or more parts of the dilution liquid source(s) (8055) can, without limitation, interface with one or more of any suitable sleeves or receptacle(s) connected to or are a part of the apparatus(s) (215), in a manner known in the art.

It is preferred, without limitation, that the dilution liquid source(s) (8055) are fixed container(s), tanks(s), or reservoir(s) that connect to or are a part of the apparatus(s) (215), and/or the optimized and miniaturized aerosol generator(s) (3800). However, the dilution liquid source(s) (8055) may also, without limitation, be any single or multi use container(s), or bottle(s), that interface with at least one or more receptacle(s) connected to or are a part of the apparatus(s) (215), and/or the optimized and miniaturized aerosol generator(s) (3800). This type of container(s) or bottle(s) can be, without limitation, designed and constructed in a manner known to those skilled in the art. The dilution liquid source(s) (8055) can also be, without limitation, marked or tagged in any suitable and effective location with one or more of any, identifier, marking, code, RFID chip or tag, barcode, symbol code, symbol, image, or identification code(s) (8090).

Referring to FIGS. 114-115, and without being limited, in order for this new means to work effectively and efficaciously, at least a sufficient and/or desired amounts of both the concentrated agent liquid (9005) and dilution liquid (9010) must be available and supplied when needed. If either, or both, of the concentrated agent liquid (9005) and/or dilution liquid (9010) are unavailable for mixing, the final liquid (30) that is presented, if any, to the reservoir(s) (40) may be, without being limited, not mixed to the required or desired concentration, or even not presented at all to the reservoir(s) (40).

Various means known to those skilled in the art may, without limitation, be utilized to monitor and report any availability, quantity, absence, presence, and/or supply, of these various liquids, especially before being mixed. For example, one or more of any sensors known to those skilled in the art, that are used to directly or indirectly sense the presence, absence, volume, flow rate, and/or liquid level, of any, liquid, flow of any liquid, or liquid level (Hereinafter called "liquid detector(s)" (9020)), may be, without limitation, utilized or located anywhere inside and/or outside of one more of any of the following locations including, but not limited to, (a) the liquid concentrate source(s) (8050), (b) the dilution liquid source(s) (8055), (c) any pre-mix reservoir(s) (9000) that may be used such as, but not limited to, any, concentrate pre-mix reservoir(s) (9001) and/or dilution liquid premix reservoir(s) (9002), (d) mixed liquid buffer tank(s) (8065), (e) any reservoir(s) (40), compartment(s), and/or container(s) located within or associated with the optimized and miniaturized aerosol generator(s) (3800), (f) one or more of any other additional tank(s), reservoir(s), or container(s) of any size, that may be used for any purpose, (g) any location(s) along any suitable tube(s), conduit(s), pipe(s), or hose(s) (Hereinafter called supply pipe(s) (9030)) that may be used to connect the various components together such as, but not limited to, the liquid concentrate source(s) (8050) and dilution liquid source(s) (8055), to the one or more mixing apparatus(s) (8080), and eventually to the optimized and miniaturized aerosol generator(s) (3800), and/or (h) one or more of any additional tank(s), reservoir(s), or container(s) of any size and used for any purpose, that may be connected anywhere between the liquid concentrate source(s) (8050) and/or the dilution liquid source(s)

(8055), and the one or more mixing apparatus(s) (8080) and/or the optimized and miniaturized aerosol generator(s) (3800).

The liquid detector(s) (9020) can include, without limitation, one or more of any devices such as, but not limited to any, transducer(s), and/or photo interrupter(s), and any other related parts or components. The liquid detector(s) (9020) can, without limitation, communicate any data with, and/or be controlled by, one or more of any digital, electronic, or analog, controller(s) such as, but not limited to, any PLC(s). It is preferred, without limitation, that if any of these liquid detector(s) (9020) sense and report one or more of the various liquid conditions including, but not limited to, the absence of any liquid, the absence of any liquid flow, insufficient liquid presence or depth, and/or insufficient liquid flow, when these conditions are undesirable or will lead to an outcome that is not efficacious, the liquid detector(s) (9020), may communicate these conditions or information to one or more of any digital, electronic, or analog, controller(s) such as, but not limited to, any PLC(s), that will then cause the apparatus (215), and/or optimized and miniaturized aerosol generator (3800), and/or one more of any of its components, to shut down and/or enter a fault or error mode. The liquid detector(s) (9020) can have, without limitation, any suitable and effective sensitivity and/or any trigger levels.

Without being limited, one or more of any tank(s), reservoir(s), or container(s) (Hereinafter called pre-mix reservoir(s) (9000)), consisting of any suitable size, shape, and construction, can also be located or suitably connected or plumbed between the one or more mixing apparatus(s) (8080) and the one or more of any liquid concentrate source(s) (8050) (Hereinafter called "concentrate pre-mix reservoir(s)" (9001)), and/or between the one or more mixing apparatus(s) (8080) and the one or more dilution liquid source(s) (8055) (Hereinafter called "dilution liquid premix reservoir(s)" (9002)). Any amount of liquid from the liquid concentrate source(s) (8050) and/or dilution liquid source(s) (8055) may, without limitation, flow at any rate, flow with and/or without any restrictions, or even be pumped into these pre-mix reservoir(s) (9000) at any time. Without being limited, if the pre-mix reservoir(s) (9000) are utilized, at least an effective and suitable amount of liquid is moved or flowed, with or without the assistance of one or more of any suitable pump(s), into the various pre-mix reservoir(s) (9000). In place of any reliance on one or more of any pump(s), any suitable gravity feed system or configuration can also be, without limitation, established and utilized, as known to those skilled in the art, to flow any liquids as needed in this invention. Without being limited, the flow of any liquids into the various pre-mix reservoir(s) (9000), or any other locations, can be controlled by one or more of any digital, electronic, or analog, controller(s) such as, but not limited to, any PLC(s), that can control any pumps and/or valves that may be used.

One or more of any suitable pump(s) and/or valve(s) may also be, without limitation, positioned or located between the one or more liquid concentrate source(s) (8050) and the one or more concentrate pre-mix reservoir(s) (9001), and/or the one or more dilution liquid source(s) (8055) and the one or more dilution liquid premix reservoir(s) (9002). Without being limited, if any of these pump(s) and/or valve(s) are utilized, they can be actuated, started, stopped, opened, and/or closed, at any time and for any duration of time, and can be controlled, without limitation, by one or more of any digital, electronic, or analog, controller(s) such as, but not limited to, any PLC(s). It is preferred, without limitation, that each liquid type is designated one or more of its own pre-mix reservoir(s) (9000). For example, and without being limited, the concentrated agent liquid (9005) can flow, with or without being pumped with any suitable pump(s), from the liquid concentrate source(s) (8050) to the concentrate pre-mix reservoir(s) (9001), and/or the dilution liquid (9010) can flow, with or without being pumped with any suitable pump(s), from the dilution liquid source(s) (8055) to the one or more dilution liquid premix reservoir(s) (9002).

However, it is preferred, without limitation, that if the pre-mix reservoir(s) (9000) are utilized, the various liquids can freely flow without being pumped, and freely fill at least the various concentrate pre-mix reservoir(s) (9001) from the liquid concentrate source(s), and/or freely fill the dilution liquid premix reservoir(s) (9002) from the dilution liquid source(s) (8055). It is more preferred, without limitation, that that if the pre-mix reservoir(s) (9000) are utilized, at least one pre-mix reservoir(s) (9000) of suitable size, is suitably connected or plumbed to the liquid concentrate source(s) (8050), and when one or more concentrate source(s) (8050) that at least holds a sufficient or effective amount of liquid, is interfaced with the apparatus (215), and/or directly or indirectly connected to the pre-mix reservoir(s) (9000), all of the liquid contents, or at least a suitable or an effective amount of the liquid in the liquid concentrate source(s) (8050), freely flows into at least one pre-mix reservoir(s) (9000), and more specifically into at least one concentrate pre-mix reservoir(s) (9001).

The one or more of any pre-mix reservoir(s) (9000) can also, without limitation, interface with or possess one or more of any suitable liquid level sensor(s) (305) such as, but not limited to, any float switch(s), infrared liquid level sensor(s), and/or the improved liquid level sensor(s) described later that includes parts such as, but not limited to, suitable float(s) (3814), magnet(s) (3858), and hall effect sensor(s) (3862). These one or more of any suitable liquid level sensor(s) (305), can also, without limitation, be used to detect and communicate the depth, liquid level, and/or volume of the liquid (30) within any pre-mix reservoir(s) (9000). Any other suitable liquid level sensor(s) (305) known in the art, may also be used. This data can be, without limitation, communicated to any one or more of any digital, electronic, or analog, controller(s) such as, but not limited to, any PLC(s), and result in various actions such as, but not limited to, (a) cause concentrated agent liquid (9005) to either move, or stop movement, from the liquid concentrate source(s) (8050) through any valve(s) and/or pump(s), if any are utilized, to the concentrate pre-mix reservoir(s) (9001) when its liquid level(s) reaches any certain depths and/or liquid levels, (b) cause dilution liquid (9010) to either move, or stop movement, from the dilution liquid source(s) (8055) through any valve(s) and/or pump(s), if any are utilized, to the dilution liquid premix reservoir(s) (9002) when its liquid level(s) reaches any certain depth(s) and/or liquid level(s), (c) stop the flow of any liquid, if possible and/or desired, into the pre-mix reservoir(s) (9000), (d) cause the apparatus (215), and/or optimized and miniaturized aerosol generator (3800), and/or one more of any of its components, to shut down and/or enter a fault or error mode, when the depth or level of liquid in the one or more pre-mix reservoir(s) (9000) reaches one or more of any minimum and/or maximum depth(s) or liquid level(s). The one or more of any pre-mix reservoir(s) (9000) can also have, without limitation, one or more suitable drain(s) in any suitable location, that can be manually controlled and/or automated. The drain(s) can be, without being limited, plumbed to one or more of any suitable location(s) including, but not limited to, any catch pan or catch container.

The one or more of any digital, electronic, or analog, controller(s) such as, but not limited to, any PLC(s), can also, without limitation, use any data reported pertaining to the amount of liquid, or volume of liquid, that is available in one or more of any liquid source(s) such as, but not limited to, the liquid concentrate source(s) (8050), dilution liquid source(s) (8055), concentrate pre-mix reservoir(s) (9001), dilution liquid premix reservoir(s) (9002), and/or feed tank(s) (8035) filled with any pre-mixed liquid, and communicate to the operator various information such as, but not limited to, (a) the total amount of aerosol (200) deployment time that is available or remaining, (b) the amount or volume of liquid concentrate (9005) available, (c) the amount or volume of dilution liquid (9010) available, and/or (d) the total amount of cubic feet or cubic meters that is available, or remaining, for treatment by the aerosol generating apparatus(s) (215). Without being limited, the machine operator may also be warned if they choose to deploy aerosol (200) for a specific or even range of aerosol deployment time, and the one or more of any digital, electronic, or analog, controller(s) such as, but not limited to, any PLC(s), determines that an insufficient amount of any needed liquid(s) is available.

The one or more of any digital, electronic, or analog, controller(s) such as, but not limited to, any PLC(s), can also, without limitation, monitor, determine, and/or calculate, the amount of liquid concentrate (9005) and/or dilution liquid (9010) that is pumped from one or more of any liquid source(s) such as, but not limited to, the liquid concentrate source(s) (8050), dilution liquid source(s) (8055), concentrate pre-mix reservoir(s) (9001), and/or dilution liquid premix reservoir(s) (9002), to the one or more mixing apparatus(s) (8080) by the one or more of any pumps, and preferably by the one or more stepper motor driven peristaltic pump(s) (8060) and/or any other similar performing pump(s) known to those skilled in the art. Without being limited, by keeping track of when one or more new liquid concentrate source(s) (8050) and/or dilution liquid source(s) (8055), of a known quantity or volume, or approximate quantity or volume, and more preferably any information gathered by reading any number of identification code(s) (8090) that may be present on any liquid concentrate source(s) (8050) and/or dilution liquid source(s) (8055) that are interfaced with the apparatus (215), in addition to any data or information such as, but not limited to, the number of pumping cycles, number of pump revolutions, any operation time or operation cycle(s) time, and/or the quantity or volume of liquid that is pumped, by one or more of any pump(s) (8060), the one or more of any digital, electronic, or analog, controller(s) such as, but not limited to, any PLC(s), can calculate and/or determine various data, information, or outcomes. This data, information, or outcomes can then be communicated in any manner known to those skilled in the art, to the one or more operator(s) of the apparatus(s) (215) such as, but not limited to, (a) the total amount of aerosol (200) deployment time that is available or remaining, (b) the amount or volume of liquid concentrate (9005) available, (c) the amount or volume of dilution liquid (9010) available, and/or (d) the total amount of cubic feet or cubic meters of treatable space that is available or remaining. Without being limited, the operator may also be warned if they choose to deploy aerosol (200) for a specific or even range of aerosol deployment time, and the one or more of any digital, electronic, or analog, controller(s) such as, but not limited to, any PLC(s), determines that an insufficient amount of one or more of any necessary liquid(s) is available.

It is also preferred, without limitation, that at least one or more liquid detector(s) (9020) is located anywhere along the paths of either, and/or both, the concentrated agent liquid (9005) and dilution liquid (9010) before they are mixed together. It is further preferred, without limitation, that the liquid detector(s) (9020) is any suitable "photo interrupter" known to those skilled in the art. The photo interrupter(s) may be, without limitation, positioned either on or suitably and effectively close to the supply pipe(s) (9030) that are utilized. It is also preferred, without limitation, that the supply pipe(s) (9030) are at least constructed from an effectively clear or transparent polymer. Without being limited, the "photo interrupter" typically consists of at least one or more infrared light emitter(s) that is positioned on one side of the supply pipe (9030), and at least one or more infrared light detector(s) that is positioned across from the emitter(s) on the other side of the supply pipe(s) (9030), all in a manner known to those skilled in the art. Without being limited, if the liquid detector(s) (9020) detects the absence, and/or lack of sufficient flow, of the concentrated agent liquid(s) (9005) and/or dilution liquid(s) (9010) when the various liquid(s) is needed and should be present, at least in sufficient quantity(s), this condition, data, and/or information, can be communicated to one or more of any digital, electronic, or analog, controller(s) such as, but not limited to, any PLC(s), that can then cause the apparatus (215), and/or optimized and miniaturized aerosol generator (3800), and/or one more of any of its components, to take any one or more action(s), such as, but not limited to, shut down and/or enter a fault or error mode.

The various liquid conditions described including, but not limited to, the absence of any liquid, the absence of any liquid flow, insufficient liquid presence or depth, and/or insufficient liquid flow, may also have, without limitation, various unexpected causes including, but not limited to, any one or more obstruction(s) caused by any foreign object debris caught in any components such as, but not limited to any, tube(s), hose(s), conduit(s), tank(s), reservoir(s) and/or container(s). One or more of any suitable filter(s) may be, without limitation, positioned anywhere inside and/or between one or more location(s) such as, but not limited to, the liquid concentrate source(s) (8050) and/or dilution liquid source(s) (8055), and reservoir(s) (40), to aid in preventing any blockage(s) that could occur in one or more of any component(s) and/or location(s), that connect the liquid concentrate source(s) (8050) and dilution liquid source(s) (8055) to the reservoir(s) (40) in which the transducer(s) (10) are located. One or more of any suitable filter(s) may also be, without limitation, positioned at any suitable location(s) inside of the various liquid concentrate source(s) (8050) and/or dilution liquid source(s) (8055).

Figure 116:
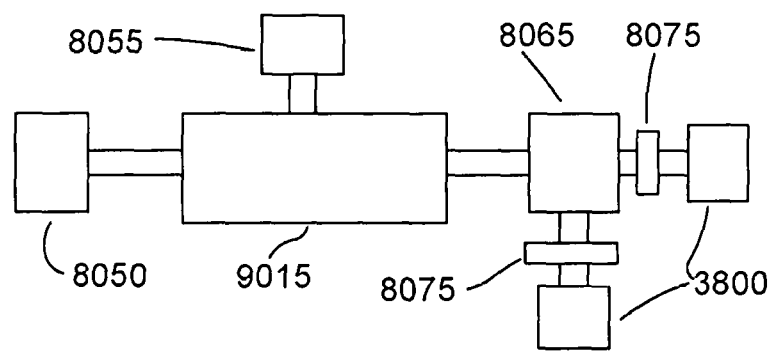
FIG. 116 is a schematic view of a system for mixing concentrated liquid agent for an optimized and miniaturized aerosol generator according to the present invention.

The third attribute for the new and improved means for mixing the liquid (30) from its concentrated form, is the manner in which the liquid concentrate (9005), and the liquid or dilution liquid(s) (9010) used to dilute the concentrate, is actually mixed. Referring to FIG. 116, and without being limited, the concentrated agent liquid (9005) and the dilution liquid (9010) can be mixed with any traditional means known to those skilled in the art, such as, but not limited to, any venturi or venturi-like mixing system (9015). These types of systems typically include, without limitation, pumping and moving the dilution liquid (9010), such as, but not limited to any water, under pressure, and one or more venturi-like mechanism(s) in the mixing device (9015) pulls the concentrated agent liquid (9005) out of its container(s) and mixes it with the flow of the moving dilution liquid (9010) or water. The mix ratio can be modified, without limitation, in various ways known to those skilled in the art, including but not limited to, changing the venturi size or the various venturi or venturi-like dynamics.

However, and without being limited, the traditional means of mixing the various liquids was found to be undesirable for use with the optimized and miniaturized aerosol generator(s) (3800), and the new and improved means for creating the mixed liquid (30) from a more concentrated liquid form, since these traditional mixing means were found to have various undesired attributes such as, but not limited to, (a) a flow output rate and quantity that was too large, (b) a design that did not offer the finite control that is needed when pumping and mixing the small amounts of the concentrated agent liquid (9005) and dilution liquid (9010) that is needed, especially when considering the reduced rate of liquid (30) that is supplied to and required by the optimized and miniaturized aerosol generator(s) (3800). This may be, without limitation, overcome in various ways including, but not limited to, using one or more larger mixed liquid buffer tank(s) (8065) from which the various reservoir(s) (40) can be fed from, but this then defeats the space savings gained, and increases the amount of mixed liquid (30) that may need to be thrown out from time to time by the operator after it has expired.

Referring to FIGS. 114-115, a preferred means is shown for mixing the liquid (30) from the liquid concentrate source(s) (8050) and dilution liquid source(s) (8055). It is preferred, without limitation, that the concentrated agent liquid (9005) is pumped from one or more liquid concentrate source(s) (8050) into one or more mixing apparatus(s) (8080), and the dilution liquid (9010) is pumped from one or more dilution liquid source(s) (8055) into the same one or more mixing apparatus(s) (8080) that the concentrated agent liquid (9005) also enters. It is also preferred, without limitation, that the liquid from each liquid concentrate source(s) (8050), and dilution liquid source(s) (8055), is pumped or moved with at least one or more pump(s) (8060) that is dedicated to each tank, reservoir, or container, and/or at least one or more tank(s), reservoir(s), or container(s) that hold the same liquid(s). Any suitable and effective pump(s) and associated pumping components known to those skilled in the art can be, without limitation, utilized. It is preferred, without limitation, that one or more pump(s) (8060) which are able to supply at least a suitable and effective quantity of any liquid(s), at the needed flow rate(s), are utilized. Without being limited, any suitable pump(s) (8060) can also be combined, and/or function with, one or more of any suitable part(s) and/or component(s), in any suitable and effective location(s), that can restrict, reduce, diminish, and/or control, the flow of the pumped liquid to the desired or needed flow rate(s), all in a manner known to those skilled in the art. However, it is preferred, without limitation, that each pump is a suitable peristaltic pump. It is even more preferred, without limitation, that the liquid moved from the liquid concentrate source(s) (8050) and dilution liquid source(s) (8055) is pumped with its own stepper motor driven peristaltic pump (8060). The stepper motor driven peristaltic pumps (8060) can be expensive, but they offer advantages such as, but not limited to, the ability to precisely control the pump rates and/or flow rate of the liquid that is moved out of each liquid concentrate source (8050) and/or dilution liquid source(s) (8055).

The use of more than one stepper motor driven peristaltic pumps (8060) that is designated to each liquid type, also offers, without limitation, additional advantages such as, but not limited to, the ability to control the ratio in which the liquids are pumped from the liquid concentrate source(s) (8050) and dilution liquid source(s) (8055). This can be accomplished, without limitation, by changing the number of pumping operations that are conducted per unit of time for each tank or reservoir such as, but not limited to, the liquid concentrate source(s) (8050) and dilution liquid source(s) (8055). Any ratio of pumping from the various tanks or reservoirs such as, but not limited to the liquid concentrate source(s) (8050) and dilution liquid source(s) (8055) may be utilized. It is preferred, without limitation, that the stepper motor driven peristaltic pumps (8060) are configured, programmed, and/or timed, so that the liquid that is pumped from one liquid concentrate source (8050) is pumped only one (1) time for every twenty-five (25) times that liquid is pumped from one dilution liquid source (8055), assuming that the output of the stepper motor driven peristaltic pumps (8060) that are utilized, is approximately identical, or at least effectively similar. It is more preferred, without limitation, that the stepper motor driven peristaltic pumps (8060) are configured, programmed, and/or timed, so that one (1) unit of any measure of liquid is pumped or flowed from one liquid concentrate source (8050) for every twenty-five (25) units of any measure of liquid that is pumped or flowed from one dilution liquid source (8055).

The stepper motor driven peristaltic pumps (8060) can also be, without limitation, configured, programmed, and/or controlled, at any time by one or more of any digital, electronic, or analog, controller(s) such as, but not limited to, any PLC(s), so that the ratio(s) of any liquid mixing can change, even during the deployment of any aerosol (200) by the optimized and miniaturized aerosol generator(s) (3800). It is preferred, without limitation, that this is achieved by either slowing down or speeding up the stepper motor of each stepper motor driven peristaltic pumps (8060) that are used, which either decreases or increases the pumping rate or liquid flow rate of each pump (8060). The stepper motor can be controlled by one or more of any digital, electronic, or analog, controller(s) such as, but not limited to, any PLC(s). Without being limited, the stepper motor driven peristaltic pumps (8060), or any other pumps that may be used, may be controlled and/or communicate with one or more of any digital, electronic, or analog, controller(s) such as, but not limited to, any PLC(s), all in a manner known to those skilled in the art.

Without being limited, any combination of any number of different types of feed reservoir(s) (9040) containing any suitable types of liquids, may be utilized together, with any pumping ratio or flow rate from any of the feed reservoir(s) (9040), and feed into one or more of any mixing apparatus(s) (8080), at any time. It is preferred, without limitation, that each liquid concentrate source (8050) is paired with only one dilution liquid source (8055) and they both feed into at least one or more mixing apparatus(s) (8080) where the pumped liquids are suitably mixed. It is preferred, without limitation, that at least effective pumping ratio(s) or flow rate(s) from any of the feed reservoir(s) (9040) are utilized.

The one or more mixing apparatus(s) (8080), can be any suitable means, known to those skilled in the art, to effectively mix two or more liquids together. The mixing apparatus(s) (8080) can accept, without limitation, one or more of any fluid source inputs, and have one or more fluid outputs, after the various inputted liquids are suitably and effectively mixed. It is preferred, without limitation, that the mixing apparatus(s) (8080) utilized is any "in-line mixer". It is more preferred, without limitation, that the "in-line mixer"

is a "static in-line mixer", whereby the various fluids are mixed as they are joined in at least one or more common space(s) and are mixed by traveling through one or more of any suitable and effective turbulent path(s). Without being limited, one or more of any suitable and effective "in-line mixer(s)" and/or "static in-line mixer(s)" known to those skilled in the art, may be utilized. Any suitable "in-line mixer" can, without limitation, be used that can achieve an effective mixture of the concentrated agent liquid (9005) and dilution liquid (9010). It is preferred, without limitation, that one or more mixing apparatus(s) (8080), is suitably and effectively connected to one or more liquid concentrate source(s) (8050) and one or more dilution liquid source(s) (8055). It is more preferred, without limitation, that one or more mixing apparatus(s) (8080), in the form of any "static in-line mixer", is suitably and effectively connected to one or more liquid concentrate source(s) (8050) and one or more dilution liquid source(s) (8055). It is even more preferred, without limitation, that only one mixing apparatus(s) (8080), in the form of any "static in-line mixer", is connected to both a liquid concentrate source (8050) and a dilution liquid source (8055). It is very preferred, without limitation, that one or more mixing apparatus(s) (8080), at least in the form of any "static in-line mixer", is not only connected to at least one or more stepper motor driven peristaltic pump(s) (8060) that is suitably connected to at least one or more liquid concentrate source(s) (8050), but is also suitably connected to at least one or more stepper motor driven peristaltic pump(s) (8060) that is suitably connected to at least one or more dilution liquid source(s) (8055).

The fourth attribute for the new and improved means for mixing the liquid (30) from its concentrated form, or deriving the aerosolized liquid (30), is the manner and/or locations in which the mixed liquid is allocated after it has been mixed. Traditionally, the mixed liquid (30) can be, without limitation, premixed and it is supplied to the reservoir(s) (40) in which the transducer(s) (10) are located via one or more feed tank(s) (280). Alternatively, after the liquid from the liquid concentrate source(s) (8050) and dilution liquid source(s) (8055) is mixed, it can be, without limitation, moved, flowed, and/or pumped, directly into the reservoir(s) (40) in which the transducer(s) (10) are located. Without being limited, this was found to be undesirable when operating and supplying mixed liquid (30) to more than one optimized and miniaturized aerosol generator(s) (3800), for reasons including, but not limited to, one or more of the optimized and miniaturized aerosol generator(s) (3800) can have a different, significantly different, and/or effectively different liquid (30) consumption rate. This can be, without limitation, especially critical for the optimized and miniaturized aerosol generator(s) (3800) because of the limited or small amount of liquid that can be intentionally designed to be utilized within the, optimized and miniaturized aerosol generator(s) (3800), and/or apparatus (215). Depending on variables such as, but not limited to, the number of transducer(s) (10) that are used, and the amount of aerosol (200) output per transducer(s) (10), this can, without limitation, cause one or more reservoir(s) (40) of various optimized and miniaturized aerosol generators (3800), to experience one or more of various conditions such as, but not limited to being, over filled, and/or under filled.

Referring to FIGS. 114-115, and without limitation, a preferred means is shown for supplying mixed liquid (30) to the one or more reservoir(s) (40) in which the transducer(s) (10) are located, and more preferably to the liquid sensor compartment(s) (8010). It is preferred, without limitation, that before the mixed liquid (30) is moved, flowed, and/or pumped, into the liquid sensor compartment(s) (8010), and/or the one or more reservoir(s) (40) in which the transducer(s) (10) are located, it is first deposited into one or more holding tank(s), reservoir(s), or container(s) (Hereinafter called mixed liquid buffer tank(s) (8065)). It is also preferred, without limitation, that at least one or more mixed liquid buffer tank(s) (8065) is assigned to, connected to, or utilized for, each optimized and miniaturized aerosol generator(s) (3800). It is more preferred, without limitation, that only one mixed liquid buffer tank (8065) is allocated to supply the one or more optimized and miniaturized aerosol generator(s) (3800) that are utilized in each aerosol generating apparatus (215).

The mixed liquid buffer tank(s) (8065) can be any suitable size, shape, and construction. It is preferred, without limitation, that the mixed liquid buffer tank(s) (8065) have a capacity between at least 0-2 liters or more. It is more preferred, without limitation, that the mixed liquid buffer tank(s) (8065) have a capacity between 0-1 liters or more. It is even more preferred, without limitation, that the mixed liquid buffer tank(s) (8065) have a capacity between 0.25-0.5 liters. It is very preferred, without limitation, that the mixed liquid buffer tank(s) (8065) have a capacity between at least 0.1-0.25 liters.

Without being limited, the mixed liquid buffer tank(s) (8065), and/or one or more of any other reservoir(s), tank(s), compartment(s), and container(s) used in the present invention, can be sufficiently and effectively vented when needed, with one or more of any suitable vent(s) (9025) located in any suitable and effective location(s), all in a manner known to those skilled in the art. The one or more of any, feed reservoir(s) (9040) and/or pre-mix reservoir(s) (9000), may also be, without being limited, suitably and effectively vented in a manner known to those skilled in the art. One or more of any hose(s), tube(s), or pipe(s), may be, without limitation, used to connect to one or more of any vent(s) (9025) and vent the mixed liquid buffer tank(s) (8065), or any other tank(s), container(s), compartment(s), and/or reservoir(s), to one or more of any suitable and effective location(s). It is preferred, without limitation, that at least one or more of any suitable hose(s), tube(s), pipe(s), or conduit(s) is utilized. It is also preferred, without limitation, that the mixed liquid buffer tank(s) (8065) is suitably and effectively vented and it is suitably connected to one or more of any air inlet pipe(s) (4030) or air outlet pipe(s) (4025), or any other suitable location(s) located within the apparatus(s) (215) and/or on the exterior of the apparatus(s) (215). Without being limited, the one or more of any hose(s), tube(s), or pipe(s), or conduit(s), utilized for venting the mixed liquid buffer tank(s) (8065) can be used for purposes such as, but not limited to, provide a suitable means for any gas(s) or vapor(s) to escape, enabling a sufficient flow of air/gas in or out of the mixed liquid buffer tank(s) (8065), or any other tank(s), reservoir(s), or container(s), especially during any pumping activities. Without being limited, the mixed liquid buffer tank(s) (8065), or any other tank(s), reservoir(s), or container(s), that are utilized, can also have, without limitation, one or more of any suitable drain(s) (655) in any suitable location, that can be manually controlled and/or automated. The drain(s) (655) can be, without being limited, plumbed to any suitable location(s) including, but not limited to, one or more of any catch pan(s) or catch container(s).

One or more of any suitable liquid level sensor(s) (305) such as, but not limited to, any float switch(s), infrared liquid level sensor(s), and/or the improved liquid level sensor(s) previously described that consists of suitable float(s) (3814), magnet(s) (3858), and hall effect sensor(s) (3862), can also, without limitation, be used to detect and communicate the depth, liquid level, or volume of the liquid (30) within the mixed liquid buffer tank(s) (8065). Any other suitable liquid level, depth, or volume, sensors known in the art, may also be used. This data can be, without limitation, communicated to one or more of any digital, electronic, or analog, controller(s) such as, but not limited to, any PLC(s), and result in various actions such as, but not limited to, (a) cause more mixed liquid (30) to be generated and fill the mixed liquid buffer tank(s) (8065) when its liquid (30) level reaches a certain depth and/or liquid level, (b) cause the flow of the generated mixed liquid (30) to stop filling the mixed liquid buffer tank(s) (8065) when its liquid (30) level reaches a certain depth and/or liquid level, (c) cause the apparatus (215), and/or optimized and miniaturized aerosol generator (3800), and/or one more of any of its components, to shut down and/or enter a fault or error mode, when the depth or level of liquid (30) in the mixed liquid buffer tank(s) (8065) reaches one or more of any minimum or maximum depth(s) or liquid level(s).

Once the mixed liquid (30) is in the mixed liquid buffer tank(s) (8065), any amount of this liquid (30) can be, without limitation, moved or flowed with any valve control, and/or pumped, into the liquid sensor compartment(s) (8010), or the one or more reservoir(s) (40) in which the transducer(s) (10) are located, at any time when needed, at any suitable flow rate, and for any suitable duration of time. Referring to FIGS. 114-115, and FIG. 116, it is preferred, without limitation, that any suitable amount of the mixed liquid (30) that is in the mixed liquid buffer tank(s) (8065) can be pumped into the liquid sensor compartment(s) (8010) and/or any reservoir(s) (40) in which the transducer(s) (10) are located, or any other reservoir(s) connected to these reservoir(s) (40), with at least one or more of any suitable pump(s) (Hereinafter called "feed pump(s)" (8075)). It more preferred, without limitation, that each optimized and miniaturized aerosol generator(s) (3800) is connected to only one feed pump (8075), and the various feed pump(s) (8075) that are connected to each optimized and miniaturized aerosol generator(s) (3800) all source their mixed liquid (30) from at least one or more common or shared mixed liquid buffer tank(s) (8065). It is also preferred, without limitation, that each feed pump (8075) that is utilized, is controlled, and/or communicates with, one or more of any digital, electronic, or analog, controller(s) such as, but not limited to, any PLC(s), all in a manner known to those skilled in the art.

Any number of any suitable feed pump(s) (8075) can be, without limitation, utilized. However, it is preferred, without limitation, that each feed pump (8075) utilized is any suitable peristaltic pump. It is even more preferred, without limitation, that these feed pump(s) (8075) are gear motor driven, and they cycle on and off when needed, at a fixed speed that adequately fulfills and replenishes the liquid (30) needs of the optimized and miniaturized aerosol generator(s) (3800) as it generates aerosol (200).

Any suitable tube(s), conduit(s), pipe(s), conduit(s), or hose(s), or otherwise supply pipe(s) (9030), may be, without limitation, utilized to connect the various feed reservoir(s) (9040) such as, but not limited to, the liquid concentrate source(s) (8050) and dilution liquid source(s) (8055) to the various components, and ultimately to the reservoir(s) (40) located within the optimized and miniaturized aerosol generator(s) (3800). It is preferred, without limitation, that the various tube(s), conduit(s), pipe(s), conduit(s), or hose(s), or otherwise supply pipe(s) (9030), are any suitably clear and flexible tubing.

One or more of any suitable pH sensors (8085) known in the art, may also be, without limitation, positioned or effectively interfaced anywhere within and/or between the liquid concentrate source(s) (8050) and/or dilution liquid source(s) (8055), and the reservoir(s) (40) in which the transducer(s) (10) are located. It is preferred, without limitation, that at least one or more pH sensor(s) is suitably located within each mixed liquid buffer tank(s) (8065) that are utilized. The pH sensor(s) can, without limitation, sense any pH range. However, it is preferred, without limitation, that the pH sensor(s) at least accurately sense a pH in the range between 2-8. It is more preferred, without limitation, that the pH sensor(s) at least accurately sense a pH in the range between 1-10.

The pH sensors (8085) can communicate with one or more of any digital, electronic, or analog, controller(s) such as, but not limited to, any PLC(s). Without being limited, if the pH is not within a specified or expected range at any time, the one or more of any digital, electronic, or analog, controller(s) such as, but not limited to, any PLC(s), can cause various outcomes to happen such as, but not limited to (a) change the mix ratios that are used with the various liquids that are mixed, or (b) cause the apparatus (215), and/or optimized and miniaturized aerosol generator(s) (3800), and/or one more of any of its components, to shut down and/or enter a fault or error mode.

Referring to FIGS. 95-97, and FIGS. 103-118, and without being limited, any components directly or indirectly connected to, or interfaced with, the optimized and miniaturized aerosol generator (3800) can be positioned in any suitable location or orientation. In addition, one or more of any optimized and miniaturized aerosol generator(s) (3800) may be, without limitation, utilized within the design and construction of any aerosol (200) generating apparatus(s) (215). The one or more optimized and miniaturized aerosol generator(s) (3800) may be incorporated in any suitable or effective way into the design and construction of the aerosol generating apparatus(s) (215). It is preferred, without limitation, that at least one or more optimized and miniaturized aerosol generator(s) (3800) is incorporated into the design of the aerosol generating apparatus (215). It is more preferred, without limitation, that at least two to three optimized and miniaturized aerosol generator(s) (3800) are incorporated into the design of the aerosol generating apparatus (215). It is even more preferred, without limitation, that at least three or more optimized and miniaturized aerosol generator(s) (3800) are incorporated into the design of the aerosol generating apparatus (215).

Without being limited, and according to a preferred embodiment and with reference to FIGS. 95-97, an even more specific description of the optimized and miniaturized aerosol generator (3800) is given. The optimized and miniaturized aerosol generator (3800) preferably includes the transducer plate (3812), the at least one transducer (10), the level float (3814), the fluid container (3816), at least one aerosol output member (3818) and an air input member (3819). At least one transducer counterbore (3822) is formed through a bottom of the transducer plate (3810). Without being limited, each side of the transducer (10), and more preferably, the protective barrier (not shown) that is interfaced with the transducer (10), is sandwiched between at least two polymer rings (3824).

Without being limited, at least one of these polymer sealing rings (3824) may be used in this particular assembly, but this can diminish safety and quality, and therefore at least two polymer rings (3824) are suggested to be utilized. It is preferred, without limitation, that the polymer rings (3824) are constructed from one or more of any suitable and effective polymer consisting of any suitable and effective hardness. It is more preferred, without limitation, that the polymer rings (3824) are constructed from one or more of any suitable and effective material(s), or any combination of material(s), such as, but not limited to any, Butyl, Teflon, PTFE, Nitrile, Neoprene, and/or Viton. Without being limited, the aerosolized liquid (30) can include one or more of various chemical agents that can necessitate that different polymer rings (3824), of various construction, may need to be utilized for chemical compatibility, as known to those skilled in the art. Any suitable and effective construction techniques and polymer ring (3824) design(s), can also be, without limitation, utilized.

Each transducer (10), and/or any transducer assembly, is retained in the counterbore (3822) with at least one retaining ring (3826). The retaining ring (3826) is secured in the counterbore (3822) with at least two ring fasteners (3828). The fluid container (3816) includes a float chamber (3830) and an aerosol chamber (3832). A middle rib (3834) separates the float chamber (3830) and the aerosol chamber (3832). An input hole (3836) is formed through a top of the fluid container (3816) to receive the air input member (3819). At least one output hole (3838) is formed through a top of the fluid container (3816) to receive the at least one aerosol output member (3818). The two output holes (3838) are preferably formed adjacent the air input hole (3836). The sum of the surface areas of the air input hole (3836) and the two aerosol output holes (3838) take-up at least 50% of a surface area of a top of the aerosol chamber (3832).

A sealing gasket (3841) is preferably placed between a top of the transducer plate (3812) and a bottom of the fluid container (3816) to prevent leakage of aerosol solution (30) in the float chamber (3830) and the aerosol chamber (3832). At least one solution passage (3844) is preferably cut through a middle rib (3846) of the sealing gasket (3841). The level float (3814) is contained in the float chamber (3830). The aerosol solution (30) is pumped into the float chamber (3830) through a solution input port (3848). A pipe nipple (3851) or the like of a supply pipe or hose is threaded into the solution input port (3848). The aerosol solution (30) flows through the at least one solution passage (3844) into the aerosol chamber (3832). Air is pumped into the aerosol chamber (3832) through the air input member (3819) from an air blower, such as the blower (180) shown FIG. 6 or FIG. 117-A and FIG. 117-B. However, any suitable air-blowing device may be used. One or more transducer driver(s) (not shown), or any suitable electronics and components known to those skilled in the art, and as previously disclosed, that are needed for effectively operating the one or more transducer(s) such as, but not limited to one or more of any suitable, variable frequency oscillator(s) or signal generator(s), and power amplifier(s), is used to operate the at least one transducer(s) (10). The at least one transducer(s) (10) vibrates and produces an aerosol (200) from the aerosol solution (30), which exits the at least one aerosol output member (3818). The transducer plate (3812) is preferably fabricated from a metal, such as 316 stainless steel for heat conducting purposes. At least one heater bore (3854) is formed through the transducer plate (3812) to receive at least one heater element (3856). The heater element (3856) heats the transducer plate (3812), which heats the aerosol solution (30) in the float and aerosol chambers.

A magnet (3858) is secured in a magnet hole (3860) formed through each end of the level float (3814). A pair of hall effect sensors (3862) or the like are attached to a top of the fluid container (3816). The pair of hall effect sensors (3862) detect a height of the level float (3814) in the float chamber (3830). The pair of hall effect sensors (3862) can be, without limitation, connected to any suitable A/C converter and/or an electronic controller, such as the electronic controller (315) shown in FIG. 10 and FIG. 114, which determines an average voltage signal of the two hall effect sensors (3862). If the height of the level float (3814) is too low, the electronic controller sends a signal to a supply pump, such as the supply pump (8075) shown in FIG. 114. The supply pump shown in FIG. 114 pumps the aerosol solution (30) through the solution input port (3848) from one or more of any reservoir(s), tank(s), and/or mixed liquid buffer tank(s) (8065). A drain valve (3864) can be without limitation, opened by the electronic controller to drain the float and aerosol chambers of the aerosol solution (30), when the optimized and miniaturized aerosol generator (3800) is turned off. The drain valve (3864) is connected to the reservoir. The drain valve (3864) is threaded into a drain hole (3865) formed through the transducer plate (3810) and located below a middle of the aerosol chamber (3832). A plurality of container fasteners (3866) are used to secure the transducer plate (3810) and the sealing gasket (3841) to a bottom of the fluid container (3816). A heat sensor (3868) is threaded into a sensor hole (3870) in a side wall of the aerosol chamber (3832). The heat sensor (3868) monitors a temperature of the aerosol liquid (30) in the aerosol chamber (3832). The heat sensor (3668) is connected to the electronic controller. If a temperature of the aerosol liquid (30) becomes too hot, the electronic controller will activate a power cutoff switch (3872), which cuts power to every electrical component in the optimized and miniaturized aerosol generator (3800). The cutoff switch (3872) may also be operated by a manual control. The cutoff switch (3872) is preferably attached to a bottom of the transducer plate (3810) with at least two fasteners (3874).

Without being limited, by operating the optimized and miniaturized aerosol generator(s) (3800) with the various attributes and configurations such as, but not limited to, those related to the temperature of the liquid (30) that is aerosolized, the frequency that the transducer(s) (10) are operated at, the power or volts peak to peak that the transducer(s) are operated at, and the various design and construction characteristics of the optimized and miniaturized aerosol generator(s) (3800) the result can be, the production and deployment of an aerosol (200) where the average particle size may range from less than one micron to about 10 microns, preferably less than about 5 microns, more preferably less than one micron, and even more preferably about 0.68 microns. In addition, and without limitation, the output of the optimized and miniaturized aerosol generator(s) (3800), or the amount of aerosolized liquid (30) that is generated and then deployed into the targeted area(s) (210), can range from 10 to 2,500 milliliters (mL) or more, preferably between 500 to at least 2,500 milliliters (mL), more preferably between 800 to 2,500 milliliters (mL) or more, and even more preferably between 1,100 to 2,500 milliliters (mL) or more. Without being limited, the optimized and miniaturized aerosol generator(s) (3800) improves the art by enabling a very dense cloud of extremely small aerosol particles to be continuously generated within a steady range of efficacious temperature, all within at least one small aerosol generation reservoir and aerosol generating apparatus.

With reference to FIGS. 119-132, and FIGS. 139-144 and without limitation, a more preferred description of the remote aerosol sensor(s) (5010) is given. The remote aerosol sensor (5010) preferably, and without limitation, includes a circuit board (6100), a transceiver (6000), an aerosol deposit sensor (3880), a first housing half (6105), and a second housing half (6110). Without being limited, the one or more transceiver(s) (6000) enables wireless communication between the microprocessor or PLC(s) (3893) and any of their connected circuit board(s) (6100), and any PLC(s) at any suitable and effective location(s), preferably any PLC(s) that controls and/or is a component of any device(s) and/or equipment(s) that is utilized in the one or more process(s) to treat the various surfaces within the targeted area(s) (210), and more preferably, any PLC(s) that controls one or more of any aerosol producing apparatus(s) (215), and even more preferably any PLC(s) (6005) that controls, and/or is located in or at, and/or is a component(s) of, one or more of any, remote controlling device(s) (6010).

The circuit board (6100) preferably, and without limitation, includes a microprocessor or PLC(s) (3893), at least one light source(s) (725), at least one light sensor (730), at least one relative humidity sensor(s) (5090), and at least one temperature sensor(s) (5085). Any suitable and effective circuit board(s) may be utilized. Without being limited, the circuit board(s) (6100) is powered, preferably by at least one battery (6140), and more preferably by at least two batteries (6140). It is preferred, without limitation, that the battery(s) (6140) are rechargeable. It is also preferred, without limitation, that the remote aerosol sensor(s) (5010) is designed and constructed, and has the capabilities, all in a manner known to those skilled in the art, so that it can suitably and effectively recharge the battery(s) (6140). The remote aerosol sensor(s) (5010) can be interfaced with one or more of any suitable and effective exterior power source(s), in one or more of any suitable and effective manner, to provide sufficient and effective power, to recharge the battery(s) (6140), and/or operate the remote aerosol sensor(s) (5010), all in a manner known to those skilled in the art. At least one voltage regulator (6145) is preferably, and without limitation, used to regulate voltage from the at least one battery (6140). The at least one battery (6140) is preferably, and without limitation, rechargeable with at least one battery charge circuit (6150). The voltage of the at least one battery (6140) is preferably, and without limitation, monitored with at least one battery monitor (6155). The battery monitor (6155) indicates, with any indicator known to those skilled in the art, that the at least one battery (6140) needs to be charged, because of a low voltage or power condition. A program connector (6160) allows the microprocessor or PLC(s) (3893) to be updated with any programming changes. Without being limited, the first and second housing halves (6105) and (6110), are preferably, and without limitation, attached or connected to each other with at least one, but more preferably at least two fasteners (6165). When the first and second housing halves (6105) and (6110), are attached to each other. At least one relative humidity sensor(s) (5090) is attached to the circuit board(s) (6100). At least one humidity access opening(s) (6170) is formed through a front of the first housing half (6105) to allow aerosol (200) to communicate or interact with the relative humidity sensor(s) (5090). It is preferred, without limitation, that at least one humidity access opening (6170) of suitable and effective size is positioned or located in front of or effectively near each relative humidity sensor(s) (5090) that is utilized.

The temperature sensor(s) (5085) and the relative humidity sensor(s) (5090) is suitably and effectively connected to the one or more microprocessor or PLC(s) (3893) in a manner known to those skilled in the art. Without being limited, any, data, information, signal(s), sensor voltage, sensor amperage, and/or sensor current, that is reported or sent by any temperature sensor(s) (5085), and/or relative humidity sensor(s) (5090), and any associated component(s), and received by any microprocessor(s) or PLC(s) (3893), may be reported at any time(s) via any suitable and effective means known to those skilled in the art, including, but not limited to any, transceiver(s) (6000), to one or more of any PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(s) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010).

However, it is preferred, without limitation, that any, data, information, signal(s), sensor voltage, sensor amperage, and/or sensor current, that is reported or sent by any temperature sensor(s) (5085), and/or the relative humidity sensor(s) (5090), and any associated component(s), and that is received by the microprocessor(s) or PLC(s) (3893), is compared with any value(s) or data stored in the firmware and/or software of the microprocessor(s) or PLC(s) (3893). Furthermore, and without being limited, if any reported data, information, signal(s), sensor voltage, sensor amperage, and/or sensor current, meets any criteria that indicates that the targeted area(s) are effectively, suitably, and/or efficaciously filled with aerosol (200), the microprocessor(s) or PLC(s) (3893) will send one or more of any, signal(s), command(s), information, and/or data, preferably via the one or more transceiver(s) (6000), that can result in or cause any number of any actions and/or any combination of any actions, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s) (6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), because a sufficient, efficacious, and/or effective, amount of aerosol (200) is present or contained in the enclosed space or targeted area(s) (210) being treated. These same processes and action(s) described can also apply to any other digital, electronic, or analog, controller(s) such as, but not limited to any, PLC(s) at any suitable and effective location(s), PLC(s) that controls and/or is a component of any device(s) and/or equipment(s) that is utilized in the one or more process(s) or method(s) to treat the various surfaces within the targeted area(s) (210), PLC(s) that controls one or more of any aerosol producing apparatus(s) (215), PLC(s) (6005) that controls, and/or is located in or at, and/or is a component(s) of, one or more of any, remote controlling device(s) (6010).

Without being limited, if the relative humidity recorded or sensed within the targeted area(s) (210) has a value preferably of at least 70 or more, and more preferably of at least 80 or more, and even more preferably of 84 or more, and very preferably between and including 85 to 100, and extremely preferably any value between and including 95 to 100, the microprocessor or PLC(s) (3893) will send one or more of any, signal(s), command(s), information, and/or data, preferably via the one or more transceiver(s) (6000), that can result in or cause any number of any actions and/or any combination of any actions, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s) (6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), because a sufficient, efficacious, and/or effective, amount of aerosol (200) is present or contained in the enclosed space or targeted area(s) (210) being treated.

One or more aerosol deposit sensor(s) (3880) is preferably, and without limitation, attached to a rear of the second housing half (6110). However, one or more aerosol deposit sensor(s) (3880) may also be, without limitation, located on one or more of any other side(s) of the remote aerosol sensor(s) (5010) including, but not limited to any, top, side(s), front, and/or bottom, of the device. The aerosol deposit sensor(s) (3880) is preferably, and without limitation, connected to at least one amplifier (3887) and at least one current sensing resistor (6180). However, referring to FIG. 144, and without limitation, the aerosol deposit sensor(s) (3880) can also be, without being limited, directly connected to any microprocessor or PLC(s) (3893) without being connected to any amplifier(s) (3887) and/or any current sensing resistor(s) (6180).

With reference to FIGS. 119-132 and FIGS. 139-144, and without being limited, a description of the aerosol deposit sensor (3880) is given for the more preferred version of the remote aerosol sensor(s) (5010), as well as a description of a means used to amplify any electrical output, data, and/or signal(s) from the aerosol deposit sensor (3880). Without being limited, the aerosol deposit sensor (3880) includes at least two or more conductors (3881). Without being limited, one of the at least two conductors (3881) is connected to a positive DC voltage V+ and another one of the two conductors (3881) is connected to an input of the amplifier (3887). Without being limited, an output of the amplifier (3887) is connected to one end of the current sensing resistor (6180) and to any suitable and effective input of the microprocessor or PLC(s) (3893), preferably to the analog input of the microprocessor or PLC(s) (3893). The other end of the current sensing resistor (6180) is connected to ground. Without being limited, any number of any, amplifier (3887), current sensing resistor (6180), and microprocessor or PLC(s) (3893), may be utilized. It is preferred, without limitation, that the amplifier (3887), current sensing resistor (6180), and microprocessor or PLC(s) (3893), are at least suitable and effective. Alternatively, and without being limited, one or more aerosol deposit sensor(s) (3880) may also communicate with, or be connected to, the one or more microprocessor or PLC(s) (3893), without using any means that can be used to amplify the electrical output or signal(s) from the aerosol deposit sensor(s) (3880) before they reach the microprocessor(s) or PLC(s) (3893).

Without being limited, the aerosol (200) deposited between the at least two conductors (3881) of the aerosol deposit sensor(s) (3880), produces or allows for any suitable and effective electrical current to flow. Without being limited, this current and any associated electrical characteristics or attributes such as, but not limited to any, current, amperage, and/or voltage, is reported to, sent to, shared with, or communicated with, the one or more of any microprocessor(s) or PLC(s) (3893). Without being limited, the aerosol deposited between the at least two conductors produces or allows for an electrical current to flow of at least 0.5 micro-amp, preferably an amperage between 0-20 Amp or more, more preferably an amperage less than or about 20 Amp, and even more preferably an amperage between 0 to 1.0 Amp, and very preferably an amperage of 0.5 nA or greater, and extremely preferably an amperage between 0.5 nA to 1.0 Amp. Also, without being limited, the aerosol deposited between the at least two conductors produces or allows for an electrical current to flow with at least a suitable and effective voltage, preferably a voltage between 0-24 volts or more, and more preferably a voltage less than 24 Volts, and even more preferably a voltage between 0-15 Volts, and very preferably a voltage between 1-6 Volts, and extremely preferably a voltage between 4-6 Volts.

Without being limited, the amplifier (3887) can amplify the electrical current, amperage, and/or voltage, and a sensor voltage, sensor amperage, and/or sensor current is generated at the output of the amplifier (3887) with the current sensing resistor (6180).

Without being limited, any, data, information, signal(s), sensor voltage, sensor amperage, and/or sensor current, that is reported or sent by any aerosol deposit sensor (3880) and any associated component(s), and received by any microprocessor(s) or PLC(s) (3893), may be reported at any time(s) via any suitable and effective means known to those skilled in the art, including, but not limited to any, transceiver(s) (6000), to one or more of any PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(s) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010).

However, it is preferred, without limitation, that any sensor voltage, sensor amperage, and/or sensor current, that is reported or sent by any aerosol deposit sensor (3880) and any associated component(s), and that is received by the microprocessor(s) or PLC(s) (3893), is compared with any value(s) or data stored in the firmware and/or software of the microprocessor(s) or PLC(s) (3893). Furthermore, and without being limited, if any reported sensor voltage, sensor amperage, and/or sensor current, is above any stored value or data, and/or meets any criteria, that indicates that the targeted area(s) are effectively, suitably, and/or efficaciously filled with aerosol (200), the microprocessor(s) or PLC(s) (3893) will send one or more of any, signal(s), command(s), information, and/or data, preferably via the one or more transceiver(s) (6000), that can result in or cause any number of any actions and/or any combination of any actions, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s) (6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), because a sufficient, efficacious, and/or effective, amount of aerosol (200) is present or contained in the enclosed space or targeted area(s) (210) being treated. These same processes and action(s) described can also apply to any other digital, electronic, or analog, controller(s) such as, but not limited to any, PLC(s) at any suitable and effective location(s), PLC(s) that controls and/or is a component of any device(s) and/or equipment(s) that is utilized in the one or more process(s) or method(s) to treat the various surfaces within the targeted area(s) (210), PLC(s) that controls one or more of any aerosol producing apparatus(s) (215), PLC(s) (6005) that controls, and/or is located in or at, and/or is a component(s) of, one or more of any, remote controlling device(s) (6010).

With reference to FIGS. 119-132 and FIGS. 139-144, and without being limited, a description of the light source(s) (725) and the light sensor(s) (730) is given for the more preferred version of the remote aerosol sensor(s) (5010), as well as a description of a means that can be used to amplify the electrical output or signal(s) from the light sensor(s) (730) before they reach the microprocessor(s) or PLC(s) (3893). Without being limited, the one or more light source(s) (725) and the one or more light sensor(s) (730) are attached, without limitation, to the circuit board (6100). A first light source access opening (6185) is formed through the front of the first housing half (6105) to allow the emission of light by one or more light source(s) (725). A second light sensor access opening (6190) is formed through the front of the first housing half (6105) to allow reflected light to be sensed by the one or more light sensor (730). Without being limited, the light source(s) (725) and light sensor(s) (730) may also share one or more of the same light sensor access opening(s) (6185), (6190). However, it is preferred, without limitation, that at least one dedicated light source access opening(s) (6185), and at least one dedicated light sensor access opening(s) (6190), all of suitable and effective, size(s), shape(s), angle(s), orientation(s), and/or location(s), is positioned or located in front of, and/or suitably and effectively positioned near, each respective, light source(s) (725) and light sensor(s) (730), that is utilized.

Without being limited, a sufficient, efficacious, and/or effective, amount of aerosol (200) in the enclosed space or targeted area(s) (210) will cause light emitted from the light source(s) (725) to be reflected off of the aerosol (200) in the targeted area(s) (210), and sensed by the light sensor(s) (730). Without being limited, the light sensor(s) (730) will then send one or more of any data, information, electrical current, signal(s), and/or electrical signal(s), to the microprocessor or PLC(s) (3893).

Without being limited, any, data, information, signal(s), sensor voltage, sensor amperage, sensor current, and/or electrical signal(s), that is reported or sent by any light sensor(s) (730) and any associated component(s), can also be amplified, with any suitable and effective means for amplification, including the amplification means shown in FIGS. 140 and 143, before it is received by the microprocessor(s) or PLC(s) (3893). Without being limited, and in this configuration, one part of the light sensor(s) (730) can be connected to a positive DC voltage V+, and another part of the light sensor(s) (730) can be connected to an input of the amplifier (6195). Without being limited, an output of the amplifier (6195) is connected to one end of the current sensing resistor (6200) and to any suitable and effective input of the microprocessor(s) or PLC(s) (3893), preferably to the analog input of the microprocessor or PLC(s) (3893). The other end of the current sensing resistor (6200) is connected to ground. Without being limited, any number of any, amplifier (6195), current sensing resistor (6200), and microprocessor or PLC(s) (3893), may be utilized. It is preferred, without limitation, that the amplifier (6195), current sensing resistor (6200), and microprocessor or PLC(s) (3893), are at least suitable and effective.

Without being limited, the light that is reflected off of the aerosol(s) (200) in the targeted area(s) (210) and sensed by the light sensor(s) (730), results in or causes, the light sensor(s) (730) to produce, send, or allow, for any suitable and effective electrical current, to flow, or depending on the configuration of the hardware used, the reduction or cessation of any electrical current. Without being limited, this current and any associated electrical characteristics is reported to, sent to, shared with, or communicated with, the one or more of any microprocessor(s) or PLC(s) (3893). It is preferred, without limitation, that when an efficacious, effective, and/or suitable amount of aerosol(s) (200) is present in the targeted area(s), the light sensor(s) (730) produce, send, or allow, for a current to flow, of at least 0.5 micro-amp. Without being limited, the amplifier (6195) can amplify the electrical current, amperage, and/or voltage, and a sensor voltage, sensor amperage, and/or sensor current is generated at the output of the amplifier (6195) with the current sensing resistor (6200).

Without being limited, any, data, information, signal(s), sensor voltage, sensor amperage, and/or sensor current, that is reported or sent by any light sensor(s) (730) and any associated component(s), and received by any microprocessor(s) or PLC(s) (3893), may be reported at any time(s) via any suitable and effective means known to those skilled in the art, including, but not limited to any, transceiver(s) (6000), to one or more of any PLC(s) at any suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(s) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010).

However, it is preferred, without limitation, that any sensor voltage, sensor amperage, and/or sensor current, that is reported or sent by any light sensor(s) (730) and any associated component(s), and that is received by the microprocessor(s) or PLC(s) (3893), is compared with any value(s) or data stored in the firmware and/or software of the microprocessor(s) or PLC(s) (3893). Furthermore, and without being limited, if any reported sensor voltage, sensor amperage, and/or sensor current, is above the stored value or data, and/or meets any criteria that indicates that the targeted area(s) are effectively, suitably, and/or efficaciously filled with aerosol (200), the microprocessor(s) or PLC(s) (3893) will send one or more of any, signal(s), command(s), information, and/or data, preferably via the one or more transceiver(s) (6000), that can result in or cause any number of any actions and/or any combination of any actions, at one or more of any suitable and effective time(s), such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol (200), (e) stopping the deployment of aerosol (200) into the targeted area(s) (210), (f) stopping the deployment of any agent(s) into the targeted area(s) (210), (g) activating one or more of any dehumidification device(s) (2040) (h) activating one or more of any air filtration apparatus(s) (6040), and/or (i) activating, opening, actuating, and/or unsealing, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210), because a sufficient, efficacious, and/or effective, amount of aerosol (200) is present or contained in the enclosed space or targeted area(s) (210) being treated. These same processes and action(s) described can also apply to any other digital, electronic, or analog, controller(s) such as, but not limited to any, PLC(s) at any suitable and effective location(s), PLC(s) that controls and/or is a component of any device(s) and/or equipment(s) that is utilized in the one or more process(s) or method(s) to treat the various surfaces within the targeted area(s) (210), PLC(s) that controls one or more of any aerosol producing apparatus(s) (215), PLC(s) (6005) that controls, and/or is located in or at, and/or is a component(s) of, one or more of any, remote controlling device(s) (6010).

Without being limited, an example of a preferred process to treat the surface(s) within the one or more treated area(s) includes the following sequential steps:

a) Determine the volume(s) of the targeted area(s) (210) and input and/or communicate these value(s) to one or more PLC(s) at any, suitable and effective location(s), and preferably any PLC(s) that controls and/or is a component of any remote aerosol sensor(s) (5010), and more preferably any PLC(s) that controls and/or is a component of any device(s) and/or equipment(s) that is utilized in the one or more process(s) to treat the various surfaces within the targeted area(s) (210), and even more preferably, any PLC(s) that controls one or more of any aerosol producing apparatus(s) (215), and very preferably any PLC(s) (6005) that controls, and/or is located in or at, and/or is a component(s) of, one or more of any, remote controlling device(s) (6010). Without being limited, one or more of any other parameters that can effect the cycle(s) or process(s) that are needed or desired to treat the surface(s) within the targeted area(s) can also be inputted and/or communicated, with or to any, suitable and effective PLC(s), such as, but not limited to any, agent deployment time(s) for any aerosol producing apparatus(s) (215), dwell time(s) before the aerosol(s) and/or humidity is removed from the targeted area(s) (210), dehumidification time(s), and/or air filtration time(s). It is preferred, without limitation, that any information or data that is inputted or communicated to any PLC(s) or micro-controller(s), and/or remote controlling device(s) (6010), by the human operator(s), is done so using one or more of any suitable and effective human machine interface(s) (HMI(s)) (6070), all in a manner known to those skilled in the art.

b) Suitably and effectively, setup, position, and/or activate, one or more of various apparatus(s) within the targeted area(s), such as, but not limited to any, aerosol producing apparatus(s) (215) and/or vapor producing apparatus(s), remote aerosol sensor(s) (5010), means to dehumidify (2040), vent sealing device(s) (6020), vent covering assembly(s) (2300), and/or air filtration apparatus(s) (6040). Without being limited, one or more of any, aerosol producing apparatus(s) (215) and/or vapor producing apparatus(s), remote aerosol sensor(s) (5010), means to dehumidify (2040), vent sealing device(s) (6020), vent covering assembly(s) (2300), and/or air filtration apparatus(s) (6040), can be suitably and effectively located in any, location(s), position(s), space(s), and/or area(s) (210), that may, or may not be, connected to one another.

These various device(s) that are used in the process(s) to treat the surface(s) within the targeted area(s) (210), may also, without limitation, connect to one another, in any suitable and effective manner known to those skilled in the art, for various purposes such as, but not limited to, (a) sharing and/or supplying any power, (b) establishing communications for control of, and/or any feedback from, the various apparatus(s), and/or (c) establishing communications so that various device(s) can report or communicate their status(s) or condition(s). It is preferred, without limitation, that all of these various device(s) are able to communicate with one another, and/or at least with the remote controlling device(s) (6010), via any suitable and effective wireless means.

Without being limited, all of the various device(s) that are used in any of the steps(s) or process(s) to treat the surface(s) within the targeted area(s) (210), can incorporate one or more of any suitable and effective PLC(s) or micro-controller(s) in their designs. Also, without being limited, these PLC(s) or micro-controller(s) can also connect to, and communicate and function with, one or more of any suitable and effective transceiver(s), that can also be incorporated into the construction of these various device(s), all in a manner known to those skilled in the art. These PLC(s) or micro-controller(s) can also, without limitation, communicate and function with, any transceiver(s) and PLC(s) or micro-controller(s), that are a part of any other device(s) that are used in any of the steps(s) or process(s) to treat the surface(s) within the targeted area(s) (210), all in a manner known to those skilled in the art.

For example, and without being limited, the one or more of any, means to dehumidify (2040), and/or the air filtration apparatus(s) (6040), may include one or more of any suitable and effective PLC(s) or micro-controller(s) (6230), that can connect to and communicate with one or more of any suitable and effective transceiver(s) (6235). These PLC(s) or micro-controller(s) (6230) can also control various function(s) of these device(s).

In another example, and without being limited, the one or more of any, aerosol producing apparatus(s) (215) and/or vapor producing apparatus(s), may also include one or more of any suitable and effective PLC(s) or micro-controller(s) (6220), that can connect to and communicate with one or more of any suitable and effective transceiver(s) (6225). These PLC(s) or micro-controller(s) (6220) can also control various function(s) of these device(s).

Without being limited, all of the various device(s) that are used to treat the surface(s) within the targeted area(s) (210), such as, but not limited to any, aerosol producing apparatus(s) (215) and/or vapor producing apparatus(s), remote aerosol sensor(s) (5010), means to dehumidify (2040), vent sealing device(s) (6020), vent covering assembly(s) (2300), air filtration apparatus(s) (6040), and/or remote controlling device(s) (6010), may communicate any, data, status(s), condition(s), logic, logic sequence(s), and/or command(s), at any suitable and effective time(s), to one or more of any device(s) that are used in any of the steps(s) or process(s) to treat the surface(s) within the targeted area(s) (210). One or more of any of these device(s), may also control, one or more of any other of these device(s), at any suitable and effective time(s). Without being limited, one or more of any device(s) other than the remote controlling device(s) (6010), may control one or more of any process(s) or step(s) to treat the surface(s) within the targeted area(s) (210), at one or more of any suitable and effective time(s).

However, and without being limited, one or more, and preferably all, of the various device(s) used or that take part in any process(s) or step(s) to treat the surface(s) within the targeted area(s) (210), such as, but not limited to any, aerosol producing apparatus(s) (215) and/or vapor producing apparatus(s), remote aerosol sensor(s) (5010), means to dehumidify (2040), vent sealing device(s) (6020), vent covering assembly(s) (2300), and/or air filtration apparatus(s) (6040), can communicate with and are controlled by, the one or more of any suitable and effective remote controlling device(s) (6010).

It is also preferred, without limitation, that the operator is able to monitor, edit any operational parameter(s) for, and/or control, when necessary or desired, any of the apparatus(s) used or involved in any process(s), to treat the surface(s) within the targeted area(s) (210), from any suitable and effective location(s), preferably from outside of the targeted area(s) (210) via the one or more of any remote controlling device(s) (6010).

c) Suitably and effectively, setup, establish, and/or activate, the one or more of any vent sealing device(s) (6020) and/or vent covering assembly(s) (2300) within the targeted area(s) (210), and effectively interface these device(s) with the various air/gas vent(s), air inlet(s), air outlet(s), and/or room vent(s) (6025) that are within the targeted area(s) (210).

d) Suitably and effectively position and activate one or more remote aerosol sensor(s) (5010) in the one or more targeted area(s) (210). It is preferred, without limitation, that at least one remote aerosol sensor(s) (5010) is positioned as far as possible, and as high as possible, within the one or more treated space(s) or targeted area(s) (210), from the one or more aerosol generator(s) (215). It is also preferred, without limitation, that at least one remote aerosol sensor(s) (5010) is positioned as far as, and as low as, possible, within the one or more treated space(s) or targeted area(s) (210), from the one or more aerosol generator(s) (215). It is also preferred, without limitation, that one or more remote aerosol sensor(s) (5010) are located at these various location(s) that may surround the one or more aerosol generator(s) (215).

e) The one or more remote aerosol sensor(s) (5010) communicates various data pertaining to the one or more targeted area(s) (210), such as, but not limited to any, humidity level(s), relative humidity level(s), dew point(s), deposited aerosol status(s), and/or temperature(s), to any suitable and effective PLC(s) at any suitable and effective location(s), and/or any PLC(s) at any local and/or remote location(s), and preferably the PLC(s) (6005) that controls, and/or is located in or at, and/or is a component(s) of, one or more of any, remote controlling device(s) (6010).

f) The one or more of any PLC(s), and preferably the PLC(s) (6005) that controls, and/or is located in or at, and/or is a component(s) of, one or more of any, remote controlling device(s) (6010) uses the reported and/or inputted data to determine the minimum and/or maximum aerosol (200) deployment time(s) for each respective targeted area(s). This can include using any data tables that can associate the various reported or inputted data value(s), with any, suitable, effective, and/or efficacious, outcome(s). In addition the various inputted data or inputted data value(s) can be used with one or more of any suitable and effective algorithm(s) to calculate one or more of any suitable and effective operational attributes relative to the communicated data, such as, but not limited to any, aerosol (200) deployment time(s), dwell time(s), moment(s) or timing schedule(s) to open or unseal the one or more of any vent sealing device(s) (6020) and/or vent covering assembly(s) (2300) that are interfaced with the various air vent(s), air inlet(s), air outlet(s), or room vent(s) (6025), and/or dehumidification/ deodorization time(s), dehumidification time(s), and/or air filtration time(s).

g) Deploy aerosol (200) and/or vapor, into the targeted area(s) (210) using the one or more of any suitable and effective vapor and/or aerosol producing apparatus(s) (215). The command that is given to start the deployment of the aerosol(s) (200) and/or vapor, into the targeted area(s) (210) can be sent from one or more of any PLC(s) and transceiver(s) at any, suitable and effective location(s), preferably any suitable and effective, transceiver(s), HMI(s), and/or PLC(s) (6005) that controls, and/or is located in or at, and/or is a component(s) of, one or more of any, remote controlling device(s) (6010).

h) Deploy aerosol (200) and/or vapor into the targeted area(s) (210) until at least one, but preferably all, of the one or more remote aerosol sensor(s) (5010) positioned within the targeted area(s) (210), report or indicate that the targeted area(s) (210) are filled with any, suitable, effective, and/or efficacious, amount(s) of aerosol(s) (200), and/or the maximum amount of allowable time(s) to treat the volume(s) of the targeted area(s) (210) has been fully utilized. It is preferred, without limitation, that at least the following criteria are reported by the one or more of any sensor(s), and preferably all of the sensor(s) or sensing device(s) (5080) that are a part of the one or more remote aerosol sensor(s) (5010) such as, but not limited to: (a) The relative humidity sensor(s) (5090) report relative humidity data that indicates that an effective, suitable, and/or efficacious, amount(s) of aerosol(s) (200) has filled the targeted area(s), (b) The light sensor(s) (730) report data that indicates that an effective, suitable, and/or efficacious, amount(s) of aerosol(s) (200) has filled the targeted area(s), (c) The aerosol deposit sensor(s) (3880) report data that indicates that an effective, suitable, and/or efficacious, amount(s) of aerosol(s) (200) has filled the targeted area(s) and/or contacted its sensing surface(s), all before the deployment or administration of the aerosol(s) (200) into the one or more targeted area(s) (210) is permanently stopped or terminated.

i) Stop the deployment of the aerosol(s) (200) into the targeted area(s). Without being limited, one or more of any suitable and effective device(s) can determine when to give, and to give, one or more of any command(s), to stop the deployment of any aerosol(s) (200), as well as determine, and/or give, any other command(s) at any time(s), regarding any other processing step(s) or activity(s) to treat the surface(s) within the targeted area(s) (210). It is preferred, without limitation, that the remote controlling device(s) (6010), determines and/or executes each of the various step(s) and/or activity(s), that is taken for all of the various, processing step(s), process activity(s), and process cycle(s), and/or executes and monitors any other activity(s) or step(s) that may be needed, in order to effectively complete all of the various step(s), activity(s), and/or any other process(s), that are needed to suitably or effectively treat the surface(s) within the targeted area(s) (210).

j) Allow the targeted area(s) to sit and dwell, with limited and/or no processing activities, for any, suitable, effective, and/or efficacious amount of time(s). This allows the deployed aerosol(s) (200) to have additional time to move within, disperse within, and/or interact with, various surface(s) and/or atmosphere(s) within the targeted area(s) (210).

k) End the dwell time.

l) Dehumidify, and/or deodorize, the targeted area(s) (210) for any, suitable, effective, and/or efficacious amount(s) of time(s), with one or more of any, means to dehumidify (2040), filter(s) (2090), and/or air filtration apparatus(s) (6040). The targeted area(s) (210) can be dehumidified to any, suitable, effective, and/or efficacious, humidity or relative humidity level or value(s). The targeted area(s) (210) can also be deodorized to any, suitable, effective, and/or efficacious, level(s) or threshold(s) of any, gas(s), molecule(s), and/or vapor(s). It is preferred, without limitation, that the targeted area(s) (210) are at least dehumidified to a relative humidity level(s) or value(s) that is close or approximate to, and/or below, the humidity level(s) or relative humidity level(s) or value(s) that were recorded or sensed before the aerosol producing apparatus(s) (215) deployed aerosol(s) (200) into the targeted area(s) (210). It is more preferred, without limitation, that the targeted area(s) (210) are dehumidified until one or more, or preferably even all, of the following criteria are reported by the one or more sensor(s) that are a part of the one or more remote aerosol sensor(s) (5010) in the targeted area(s) (210) such as, but not limited to: (a) The relative humidity sensor(s) (5090) report relative humidity data that indicates that the relative humidity in the targeted area(s), is close or approximate to, and/or below, the humidity level(s) or relative humidity level(s) or value(s) that was recorded or sensed before the aerosol(s) (200) was deployed into the targeted area(s) (210). The relative humidity within the targeted area(s) (210) can also be reduced to any other level that is desired by the machine operator, (b) The light sensor(s) (730) report data that indicates that the targeted area(s) are devoid, and/or sufficiently and/or effectively clear, of the deployed aerosol(s) (200), and/or (c) The aerosol deposit sensor(s) (3880) report data that indicates that the aerosol(s) (200) that were deposited onto the aerosol deposit sensor(s) (3880) have sufficiently and/or effectively dissipated or dried.

m) Activate, open, actuate, and/or unseal, one or more of any vent sealing device(s) (6020) and/or vent covering assembly(s) (2300) interfaced with the various air vent(s), air inlet(s), air outlet(s), or room vent(s) (6025), that are located inside the one or more room(s), enclosed area(s), or targeted area(s) (210). However, and without being limited, the vent sealing device(s) (6020) and/or vent covering assembly(s) (2300) can also be activated, opened, actuated, and/or unsealed, at any other suitable or effective time(s). For example, and without being limited, the vent sealing device(s) (6020) and/or vent covering assembly(s) (2300) can be activated, opened, actuated, and/or unsealed, at any suitable and effective time(s) after the deployment of the aerosol(s) (200) into the targeted area(s) has stopped. It is preferred, without limitation, that the vent sealing device(s) (6020) and/or vent covering assembly(s) (2300) are activated, opened, actuated, and/or unsealed, at any suitable and effective time(s) during any dehumidification and/or deodorization activities or processes.

n) The dehumidification and/or deodorization activities or processes can also continue to run or operate until the operator manually turns these various systems off.

Without being limited, the remote aerosol sensor(s) (5010) offers various advantages to the traditional process of treating the one or more surface(s) and/or atmosphere(s) within the one or more targeted area(s) (210) with any deployed aerosol(s) and/or gas(s). For example, and without being limited, the use of the remote aerosol sensor(s) (5010) can eliminate or reduce the complexity of, and/or increase the repeatability, efficacy, and/or accuracy of, the treatment process(s) used to treat the various surface(s) and/or atmosphere(s) within the targeted area(s). Without being limited, this is especially important, when one or more of any variable(s) can have an effect or impact on, and/or can diminish the outcome(s) of, any treatment cycle(s) performed within the targeted area(s) by any, aerosol and/or vapor producing apparatus(s) (215), such as, but not limited to any, atmospheric temperature(s), relative humidity(s), dew point(s), volume(s) of the targeted area(s) (210), size or volume of object(s) within the targeted area(s) (210) (which can reduce the actual volume within a targeted area(s) (210)), and/or the characteristics and/or attributes of the various material(s) within the targeted area(s) (210).

In another more detailed example, and without being limited, after the aerosol producing apparatus(s) (215) has initially deployed aerosol (200) into the targeted area(s) (210), one or more cloud(s) of aerosol (200) typically and initially forms or is suspended around or in the general vicinity of the aerosol producing apparatus(s) (215) before the rest of the targeted area(s) begins to fill, and/or are efficaciously filled, with aerosol (200). It was found, without being limited, that the one or more of various sensing devices that were located close to or on the aerosol producing apparatus(s) (215) and used to measure the efficacy or progress of the treatment of the targeted area(s) (210), could give false reports indicating that all of the surface(s) or volume(s) within the targeted area(s) (210) were fully or efficaciously treated, when this was actually not the case. Without being limited, by remotely monitoring the one or more of any remote location(s) relative to the aerosol producing apparatus(s) (215), with one or more of the remote aerosol sensor(s) (5010), and preferably at one or more location(s) that are the furthest possible from the aerosol producing apparatus(s) (215), and more preferably at one or more location(s) that is not only located at the furthest possible location(s) from the aerosol producing apparatus(s) (215), but at least at one or more location(s) that is located effectively or suitably near or at the highest ceiling(s) or space(s) in the targeted area(s) (210), and even more preferably, at one or more location(s) that is not only located at the furthest possible location(s) from the aerosol producing apparatus(s) (215), but at least at one or more location(s) that is located effectively or suitably near or at the highest, ceiling(s), location(s), and/or space(s), in the targeted area(s) (210), and/or one or more location(s) that is located effectively or suitably near or at the lowest, floor(s), location(s), and/or space(s), in the targeted area(s) (210), the operator and/or the one or more of any suitable and effective PLC(s) at any suitable and effective location(s), that are in charge of, controls, and/or monitors, the treatment process(s) within the targeted area(s) (210), can monitor the real and actual progress, effectiveness, and efficacy, of the treatment process(s), and preferably in one or more of area(s) of the targeted area(s) (210), that can be representative of the overall progress or status for the treatment of the entire targeted area(s) (210).

The present invention includes apparatuses and methods related to the generation, extraction, and delivery or application of an aerosol (200) of liquid (30) that is created with ultrasound or piezoelectric transducers (10), for a wide range of uses including but not limited to: (a) the sanitization, disinfection, high-level disinfection, or sterilization of one or more areas and the surfaces in those areas, (b) the delivery of other types of liquid (30) in the form of an aerosol (200) for various purposes, such as, but not limited to, the application of pesticides, fungicides, moisture, fuel, chemical neutralizers, medication, fertilizer, and/or any other suitable particles, to one or more areas and surfaces within those area(s). The attributes of the area or treated area (9212) to which the aerosol (200) is delivered or applied can vary and can include, but is not limited to any: spaces that are open, enclosed, semi-enclosed, unsealed, sealed, or partially sealed. It is preferred, without limitation, that the area in which the aerosol (200) is administered in the present invention is enclosed and effectively sealed to prevent the leakage of the aerosol (200) from the enclosed and/or treated area (9212).

Referring initially to FIGS. 145-146, FIG. 155, and FIGS. 157-161, any suitable aerosol generating machine (9196) and/or the aerosol generating apparatus (9101), can be operated either outside, partially inside and partially outside, or within, any area in which the aerosol (200) is deployed or administered. It is preferred, without limitation, that at least one aerosol generating apparatus (9101) is located within and/or is a component or part of, the aerosol generating machine (9196).

With reference now to the drawings, and particularly to FIG. 145, there is shown a perspective view of an aerosol generation apparatus (9101). With reference to FIGS. 145-149, FIG. 152, and FIG. 154, the aerosol generation apparatus (9101) preferably includes an aerosol generation case (9110), a case cover plate (9112), at least one outlet pipe (9114), at least one air feed manifold (9116), at least one ultrasonic transducer (10), at least one transducer power supply (9120) and at least one microprocessor based controller (9122). Without being limited, the aerosol generation case (9110) preferably includes at least one of any effective, fluid reservoir (9124) and transducer chamber (9128). Without limitation, the transducer chamber (9128) can also have any suitable sump and/or a lower fluid supply reservoir (Herein called "Transducer Fluid Supply Chamber") (9126) that can be heated with one or more of any suitable heating element (9188). It is preferred, without limitation, that the transducer fluid supply chamber (9126) is connected to the transducer chamber (9128), and more preferably, it is an open basin or sump where liquid (30) can freely flow and/or circulate between: (a) any part of any area(s) where the one or more transducer(s) (10) are located, (b) any part of any area(s) where the one or more heater element(s) (9188) is located, and/or (c) any other areas within the transducer chamber (9128) and/or transducer fluid supply chamber (9126). Referring to FIGS. 152-153, and without limitation, it is preferred that the floor (9198) of the transducer chamber (9128) is rounded or has a gentle convex curvature as it transitions from the one or more area(s) where the transducers (10) are located, down to the transducer fluid supply chamber (9126). Without being limited, the fluid supply chamber (9126), fluid reservoir (9124), and transducer chamber (9128), can be any effective size(s), length(s), height(s), width(s), depth(s), shape(s), geometry(s), complex geometry(s), and/or volume(s).

Preferably, and without limitation, the fluid reservoir (9124) is formed adjacent one side of the aerosol generation case (9110) and the transducer chamber (9128) is formed adjacent an opposing side of the aerosol generation case (9110). The transducer fluid supply chamber (9126) is formed in the transducer chamber (9128) and below a bottom of the transducer chamber (9128). A fluid passage (9130) is formed through a bottom of the fluid reservoir (9124) to substantially a bottom of the transducer fluid supply chamber (9126), such that the fluid flows, preferably downward, from the fluid reservoir (9124) to the transducer fluid supply chamber (9126). The case cover plate (9112) is preferably attached to a top of the aerosol generation case (9110) with a plurality of fasteners (9132).

Each outlet pipe (9114) preferably includes at least one outer base tube (9134), at least one inner tube (9136) and at least one exhaust tube (9140). It is preferred, without limitation, that the aerosol generation apparatus (9101) and/or the outlet pipe (9114), and any of their parts and components, such as, but not limited to any, base tube portion (9146), outer base tube (9134), inner tube (9136), transition tube (9156), and/or exhaust tube (9140), have at least any effective height(s), length(s), and/or width(s), to effectively, encircle, enclose, and/or accommodate, at least an effective portion or part of the one or more of any geyser(s) (4045), and more preferably the entire geyser(s) (4045) and any generated aerosol plume(s) (4050).

It also preferred, without limitation, that any pipe(s), conduit(s), hose(s), and/or tube(s) (9216), that encircle, enclose, and/or accommodate, the one or more of any geyser(s) (4045) and plume(s) (4050), are at least located or positioned at or about any effective vertical orientation, preferably at a 90 degree angle, from the aerosol hole(s) (9154), and do not bend, or at least not significantly bend, until they are at least any suitable and effective distance above any geyser(s) (4045) and/or any generated plume(s) (4050).

The outer base tube (9134) preferably includes an inlet base portion (9142) and an outlet base portion (9144). The inlet base portions (9142) includes a base tube portion (9146), a conical tube portion (9148) and a body tube portion (9150)(9151). The base tube portion (9146) extends from a smaller outer perimeter end of the conical input portion (9148) and the body tube portion (9150)(9151) extends from an opposing end of the conical tube portion (9148).

The outlet base portion (9144) includes a body tube portion (9151) a conical tube portion (9153), an inner tube receiver end (9155) and an exhaust tube receiver (9157). A larger end of the conical tube portion (9153) extends from body tube portion (9151) and the inner tube receiver end (9155) extends from a smaller outer perimeter end of the conical tube portion (9153). The inner tube receiver end (9155) is sized to receive an outer perimeter of the inner tube (9136). The exhaust tube receiver (9157) extends from a top of the inner tube receiver end (9155). The exhaust tube receiver (9157) is sized to receiver an outer perimeter of the exhaust tube (9140).

A top of the inner tube (9136) is concentrically attached to, and preferably effectively sealed to, the inner tube receiver end (9155). With reference to FIG. 167, it is preferred, without limitation, that the air/gas that enters the inner air chamber (9152) is only allowed to exit the inner air chamber (9152) by way of the one or more air outlet gap(s) (9229).

Without limitation, the inner tube receiver end (9155) connects effectively with, and is preferably hermetically sealed to the outer base tube (9134), inner tube (9136), and/or the transition tube (9156), forming an air tight flow path so that air/gas and any aerosol can pass effectively from the transducer chamber (9128) through the base tube portion (9146) into the expansion area (9255) and then through the inner tube (9136) through the inner tube receiver end (9155) and finally into the transition tube (9156) and exhaust tube (9140), all without leaking or escaping from the system of sealed parts.

An inner air chamber (9152) is formed between an outer surface of the inner tube (9136) and an inner surface of the body tube portions (9150)(9151) of the inlet and outlet base portions (9142), (9144). The body tube portions (9150) (9151) of the inlet and outlet base portions (9142), (9144), and inner tube receiver end (9155), are attached to each other with adhesive, sonic welding or any other suitable process. Without limitation, one or more of any suitable aerosol hole(s) (9154) is formed through a top of the case cover plate (9112) concentric with, and/or encompassing, at least one or more transducer(s) (10), but preferably and without limitation, concentric with each ultrasonic transducer (10). The ultrasonic transducer (10) is preferably any effective piezoelectric transducer. The base tube portion (9146) of the inlet base portion (9142) is attached to the case cover plate (9112), concentric with the aerosol hole (9154).

The exhaust tube (9140) is suitably secured to the inner tube receiver end (9155) which is suitably connected to the inner tube (9136). Without being limited, the outer wall surface of the inner tube (9136) facing the inside wall surface of the outer base tube (9134), the inside wall surface of the outlet base portion (9144) facing the outer wall surface of the inner tube (9136) and/or alternatively the inside wall surface of the outer base tube (9134) facing the outside wall surface of the inner tube (9136), are also suitably connected and suitably sealed to the inner tube receiver end (9155) forming a sealed dead end at the top of the inner air chamber (9152) preventing any passage of any air/gas and aerosol through or into this area and/or to other parts of the aerosol generator (9101). It is preferred, without limitation, that this forces the air/gas that is introduced into the inner air chamber (9152) via the exhaust supply hole (9168), down and into the expansion area (9255) and ultimately into the inner tube (9136) where it can flow into the inner tube receiver end (9155), the transition tube (9156), the exhaust tube (9140), the inclined tube (9158), and finally the outlet tube (9160), preferably effectively moving and/or carrying the generated aerosol (200) with the airflow as it exits the aerosol generation apparatus (9101).

The at least one exhaust tube (9140) preferably includes at least one, transition tube (9156), inclined tube (9158), and outlet tube (9160). Preferably, and without limitation, one end of the inclined tube (9158) extends from the transition tube (9156) at an acute angle "A" to a horizontal plane. The outlet tube (9160) extends upward from an opposing end of the inclined tube (9158). The inclined tube (9158) is inclined to force any liquid condensate or any liquid droplets that can form and/or appear, to roll back into the transducer chamber (9128).

The at least one air feed manifold (9116) includes, without limitation, at least one, inlet manifold (9162) and supply manifold (9164). The inlet manifold (9162) includes, without limitation, at least one of any suitable, inlet tube (9163), chamber tube end (9165), supply tube outlet (9167), transducer chamber supply tube (9257), air connector tube (9173), and inlet tube outlet (9265). The inlet tube (9163) preferably, and without limitation, receives air from any suitable air pump (not shown).

Without limitation, the chamber supply tube (9257) connects either directly or indirectly with the transducer chamber (9128) and the air pump (180), and/or any other suitable components that may connect with these various parts. The chamber tube end (9165) supplies air/gas to the transducer chamber (9128). With reference to FIG. 156, the air/gas supplied by the chamber tube end (9165) flows through the plate hole (9260) into the transducer chamber (9128). A distal end of the inlet tube (9163) is directly or indirectly connected to one or more of any suitable air pump, source of air/gas flow, and/or pressurized source of air/gas (9178).

The supply tube outlet (9167) supplies air to the supply manifold (9164). The supply manifold (9164) includes, without limitation, at least one of any, supply tube inlet end (9169), exhaust supply tube (9166), exhaust hole supply tube (9259), and preferably two supply tube ends (9171). The supply inlet tube end (9169) receives air from the supply tube outlet (9167) through an air connector tube (9173). Without limitation, the supply tube ends (9171) can supply air/gas to at least an interior of each of the two outer base tubes (9134) through at least one exhaust supply hole (9168) effectively located in each outer base tube (9134). The exhaust hole supply tube (9259) can include, without limitation, one or more of any parts and components such as, but not limited to, any other suitable connecting pipe(s), hose(s), and/or conduit, that can directly or indirectly connect or interconnect with at least one or more of any exhaust supply hole (9168) and/or suitable air pump(s) (9178).

At least one plate hole (9260) is formed through a top of the at least one case cover plate (9112) over substantially a center of the transducer fluid supply chamber (9126). A distal end of the chamber supply tube (9257) and/or chamber tube end (9165) is concentrically secured over and/or to this opening or hole (Herein called "Plate Hole") (9260) in the case cover plate (9112). Without being limited, the plate hole (9260) may be any effective size and shape, and can be located at one or more of any effective location(s) entering the transducer chamber (9128). It is preferred, without limitation, that the plate hole (9260) is approximately centered in or to the transducer chamber (9128), and it is positioned approximately between the two transducers (10) in or to the transducer chamber (9128). The air/gas that flows from the chamber supply tube (9257) and/or chamber tube end (9165), and through the plate hole (9260), can be diverted, directed, and/or diffused in one or more of any directions inside of the transducer chamber (9128), using any effective means known to those skilled in the art, from the one or more of any locations the air/gas enters the transducer chamber (9128).

For example, and without being limited, and referring to FIG. 153, one or more of any structure, ramp, and/or plate (Herein called "deflector plate") (9202), having one or more parts of any effective size, shape, length, width, height, volume, angle, and/or geometry, can be located at one or more of any effective location(s) under the one or more plate hole(s) (9260). It is preferred, without limitation, that if a deflector plate is used, it can be positioned using one or more of any effective brackets or support structure(s) (Herein called "deflector bracket(s)") (9203) connecting to one or more of any suitable locations in the transducer chamber (9128), case cover plate (9112), and/or plate hole(s) (9260).

The deflector plate (9202) can move or redirect any flow of any air/gas entering the transducer chamber (9128) to any direction, location, and/or area(s) within the transducer chamber (28). It is preferred, without limitation, that the deflector plate (9202) at least directs an effective amount of the air/gas flow entering the transducer chamber (9128) to, or at least in the direction of, the one or more aerosol hole(s) (9154).

An exhaust supply hole (9168) is formed through the wall of the outlet pipe (9114) approximately near the outlet base portion (9144), and accesses the inner air chamber (9152). Without being limited, various parts such as, but not limited to any, base tube portion(s (9146), tube(s) (9216), outlet pipe(s) (9114), and/or exhaust tube(s) (9140) can be preferably concentrically secured, and more preferably their distal ends, over the aerosol hole(s) (9154). A vent hole (9253) is formed through the case cover plate (9112) over the fluid reservoir (9124). A vent tube (9170) is secured to the vent hole (9253) with a hose nipple (9172) or the like. The vent tube (9170) can, without limitation, prevent vacuum lock from developing in the fluid reservoir (9124). At least one transducer counter bore (9174) is formed in a bottom of each transducer chamber (9128) to receive at least one ultrasonic transducer (10) and/or transducer assembly (9232). Each ultrasonic transducer (10) is preferably, and without limitation, located in any effective transducer assembly (9232) and effectively secured in the transducer counterbore (9174). The transducer (10) can also be secured in the transducer counterbore (9174) in any suitable manner known to those skilled in the art. Without being limited, the one or more transducer(s) (10) may be located, coupled, mounted on and/or in, at any effective locations in any suitable tank or reservoir (9128), or otherwise positioned within or to any suitable tank or reservoir (9128) with any suitable transducer holding, sealing, housing, and/or mounting device(s) or assembly(s), all in a manner known to those skilled in the art. The transducer chamber(s) (9128) can be any effective height(s), length(s), width(s), geometry(s), depth(s), design(s) and/or shape(s), all in a manner known to those skilled in the art.

According to FIG. 146, and FIGS. 168-169, and without limitation, a transducer assembly (9232), can include various parts and components including, but not limited to one or more of any, housing(s) (9233), transducer(s) (10), seal(s), top insert ring(s) (9235), bottom insert ring(s), clamping mechanism(s) (not shown), transducer(s) (10) that is coupled with any protective barrier(s) (60) that faces any liquid (30), any suitable bonding substance or adhesive (70) to effectively bond or connect the transducer(s) (10) to the protective barrier(s) (60), Upper Seal (9236), Lower Seal (9237), retaining screws or bolts (9230), bulkhead or floor seal (9245), and/or outer o-ring seal (9231). Without limitation, the one or more transducer(s) (10) can be, enclosed or packaged in, assembled with, or coupled with, any suitable and effective, transducer assembly(s) (9232) and housing(s) (9233). Without being limited, the transducer assemblies (9232) and/or housing(s) (9233) can include one or more of any effective means to hold and/or seal with any number of components such as, but not limited to any, transducer(s) (10), means for sealing, and/or means for clamping or exerting any suitable force one or more of any components of the transducer assembly (9232). In one example, and without limitation, the various parts of the transducer assembly (9232) can be effectively bolted and/or screwed together with one or more of any suitable parts such as, but not limited to any, seals, bolts, and/or screws. In another example, and without limitation, the one or more parts of the transducer assembly (9232) including, but not limited to any, top insert ring, upper seal, lower seal, transducer (10), and/or any transducer (10) that is suitably interfaced with any suitable protective barrier (60), and housing (9233), can be pressed together with any amount of effective pressure, all in a manner known to those skilled in the art.

Without limitation, it can also be assumed that when one or more of any transducer (10) is mentioned or incorporated in the present invention, it can also include one or more of any suitable transducer assembly (9232) either described in the present invention, and/or known to those skilled in the art.

According to an embodiment, the transducer assembly (9232) may include any effective combination of any hermetically or non-hermetically sealed or unsealed housing(s) (9233) and any suitable transducer(s) (10), and/or any effective combination of at least one housing (9233), at least one o-ring or suitable seal(s), at least one transducer (10), and at least one top insert ring (9235) that is suitably sealed or unsealed, and/or any other hermetically or non-hermetically sealed or unsealed means to hold, hold-fast, secure, and/or protect any transducer(s) (10), that is either interfaced with any suitable part(s) of the transducer chamber (9128) or any other tank(s), or mounted to or in any suitable part(s) of the transducer chamber (9128), or positioned within any suitable part(s) of the transducer chamber (9128), or preferably coupled or attached to the bottom wall of a transducer chamber(s) (9128).

Without being limited, one or more of any transducer(s) (10), transducer assemblies (9232), and/or any suitable housing(s) (9233) and any other effective parts, that may hold or contain any transducer(s) (10), may also be effectively located within and/or interfaced with, one or more of any suitable, tank(s) or reservoir(s), acoustically connected tank(s), and/or acoustically coupled tank(s), such as, but not limited to those taught in U.S. Pat. No. 3,561,444 (Boucher et al.), and/or the like, that directly or indirectly connect with any reservoir(s) or chamber(s) where any geyser(s) (4045) may form and aerosol (200) is generated. Without limitation, any component(s) such as, but not limited to, any aerosol hole(s) (9154), pipe(s) (9216), and/or outlet pipe(s) (9114) may suitably and effectively interface or connect with any reservoir(s) where any geyser(s) (4045) and ultrasonically produced aerosol may form.

According to an embodiment, and without limitation, it is preferred that the transducer(s) (10) used in the present invention, are at least similar in form, function, and assembly with various parts, to those described in U.S. Pat. No. 7,641,130 (Ricciardi et al.), and the face of the transducer(s) can be protected by any suitable and effective barrier(s).

According to an embodiment, and without limitation, one or more of any effective sealed interface or seal can be located between any suitable part(s) or component(s) related to the transducer (10), to seal against any liquid intrusion, such as, but not limited to any, protective barrier (60), tank floor (9198) or any other suitable mounting surface for the transducer assembly (9232), top insert ring (9235), transducer (10), housing (9233), and/or any other suitable means to hold, seal, secure to, hold-fast, secure, and/or protect, the transducer(s) (10).

According to an embodiment, and without limitation, one or more of any effective sealed interface or seal can exist between any part or component, where needed, of the aerosol generation apparatus (9101) such as, but not limited to any, protective barrier (60), seals (not shown), transducer (10), top insert ring (9235), tank floor (9198), housing (9233), and/or any other suitable means to hold, seal, holdfast, secure, and/or protect, the transducer(s) (10).

Without limitation, any transducer (10) or any other connected part(s) to the transducer (10), can be effectively mounted into and/or to any suitable transducer assembly (9232) and/or housing (9233), preferably in a manner that at least prohibits any liquid (30) leakage out of the transducer chamber (9128) or any liquid to leak and damage any part of any transducer (10) or its connecting components, and provides effective operation of the transducer (10), all in a manner known to those skilled in the art.

In a preferred embodiment, and according to FIG. 169, and without limitation, at least one of any suitable seal and/or O-ring seal, is effectively located under or below any suitable part of any transducer (10) (Herein called "Lower Seal") (9237) effectively sealing the transducer (10) to the housing (9233), preferably to at least a bottom of any suitable recess (Herein called "Housing Recess") (9239) within the housing (9233) and effectively sealing the transducer (10) to at least the housing (9233).

Also, and without limitation, at least one of any suitable seal and/or O-ring seal, is effectively located on top of or over any suitable part of any transducer (10) (Herein called "Upper Seal") (9236) effectively sealing the transducer (10) to at least any suitable top insert ring (9235).

In a more preferred embodiment, and according to FIG. 168, and without limitation, at least one of any effective lower seal (9237), is effectively located under any suitable part of any protective barrier (60) such as, but not limited to any glass, that is effectively interfaced and/or connected with any transducer (10), effectively sealing the protective barrier (60) to the housing (9233), preferably to at least a bottom of any suitable housing recess (9239) within the housing (9233) and effectively sealing the protective barrier (60) to at least the housing (9233).

Also, and without limitation, at least one of any effective upper seal (9236), is effectively located on top of or over any suitable part of any protective barrier (60), effectively sealing the protective barrier (60) to at least any suitable top insert ring (9235).

According to FIGS. 168-169, and without limitation, the top insert ring (9235) can exert any effective mechanical pressure on and/or to the various parts of the transducer assembly (9232), when it is effectively located into place within and/or to the housing (9233), causing one or more of any effective seal(s) to form with any parts and components of the transducer assembly (9232) and/or aerosol generation apparatus (9101), such as, but not limited to any, transducer (10), seals (not shown), protective barrier (60), top insert ring (9235), upper seal (9236), lower seal (9237), housing (9233), tank floor (9198), bottom chamber plate (9137), bulkhead seal (9245), and any other part(s) of the housing (9233) and/or transducer assembly (9232). Any amount of mechanical pressure, preferably an effective amount, can be exerted on and/or to, one or more parts and components such as, but not limited to any, transducer (10), seals (not shown), protective barrier (60), top insert ring (9235), upper seal (9236), lower seal (9237), housing (9233), tank floor (9198), bottom chamber plate (9137), bulkhead seal (9245), and any other part(s) of the aerosol generation apparatus (9101), housing (9233), and/or transducer assembly (9232), by parts and components including, but not limited to any, top inset ring (9235), all in a manner known to those skilled in the art. The transducer assembly (9232) can interface, hold, and/or seal with, one or more of any transducer(s) (10).

According to FIGS. 168-169, and without limitation, one or more of any suitable seal(s) and/or o-ring(s) may also be effectively located at one or more of any effective location(s), such as, but not limited to, under any suitable groove and/or outside lip near and/or about the outer circumference of the top insert ring (9235) (Herein called "Outer O-ring Seal") (9231).

According to FIGS. 168-169, and without limitation, one or more of any suitable seals and/or o-rings may also be effectively located in order to effectively seal and/or mount any transducer assembly(s) (9232) to one or more of any suitable surface(s) such as, but not limited to any, tank floor (9198), and/or bottom chamber plate (9137). It is preferred, without limitation, that one or more of any suitable seal(s) and/or o-ring(s) is effectively located under or within one or more of any suitable groove(s), lip(s), and/or outside lip(s), near and/or about the outer circumference of the housing (9233) (Herein called "Bulkhead Seal(s)") (9245).

Without being limited, one or more of any part(s) of the present invention may also be used and/or adapted to remove any aerosol from any other transducer related aerosol generation apparatuses known in the art, and/or one or more of any of its parts, components and configurations, such as, but not limited to, the apparatus and its various components and configurations taught in U.S. Pat. No. 3,561,444 (Boucher et al.). In this particular application, and without limitation, any suitable case cover plate (9112) or the like, or at least any suitable sealing roof or lid, from or similar to the present invention, could be suitably and effectively modified, located, positioned over, interfaced with, and/or connected to, any suitable and effective location(s) of or within the basin and/or reservoir where the one or more geyser(s) (4045) are located. In addition, and without limitation, any of the various suitable components of the aerosol generation apparatus (9101) in the present invention such as, but not limited to any, aerosol hole(s) (9154), tube(s) (9216), base tube portion(s) (9146), outlet pipe(s) (9114), and/or any other parts of the aerosol generation apparatus (9101), can be suitably and effectively directly or indirectly connected, to any reservoir and/or positioned over any one or more geyser(s) (4045).

Without being limited, a power amplifier (9176) supplies the at least one ultrasonic transducer (18) with electrical power. Any suitable transducer (10), transducer design, assembly of transducer related parts, and transducer housing(s) and/or mounting fixture(s), may be used in the present invention. Also without being limited, the transducer(s) (10) can be made of any suitable piezoelectric material, preferably a lead-zirconate-titanate (PZT) material, and more preferably lead-zirconate-titanate-four (PZT-4). It is also preferred, without limitation, that the transducer(s) (10) is coated with any suitable conductive coating (not shown) that enables an electrical signal to energize or drive the transducer(s) (10) causing it to emit any pressure and/or energy of any desired character.

Without limitation, the power amplifier (9176) can also include one or more of any suitable oscillator or powered oscillator. Without being limited, it is preferable to supply the ultrasonic transducer (10) with at least any suitable voltage and wattage, and more preferably and without limitation, any voltage between 20 to 300 volts peak to peak and wattage between 1 to 600 watts. Without limitation, the one or more transducer(s) (10), can be operated at any suitable and effective frequency, preferably at a frequency range between about 0.025 MHz to about 10 MHz or higher, more preferably between about 0.5 MHz to about 2.5 MHz, and even more preferably between about 1.2 MHz and about 2.2 MHz. Any effective wattage can be supplied to each ultrasonic transducer(s) (10). It is preferred, without limitation, that the wattage supplied to each ultrasonic transducer (10) is between 120 to 450 watts. It is more preferred, without limitation, that the wattage supplied to each ultrasonic transducer (10) is between 110 to 600 watts. It is even more preferred, without limitation, that the wattage supplied to each ultrasonic transducer (10) is between 90 to 500 watts. It is very preferred, without limitation, that the wattage supplied to each ultrasonic transducer (10) is between 75 to 550 watts. It is extremely preferred, without limitation, that the wattage supplied to each ultrasonic transducer (10) is between 51 to 600 watts.

Referring to FIGS. 149-151, FIG. 154, and FIG. 156, and without limitation, one or more of any suitable and effective means known to those skilled in the art, can be used to determine one or more of any depths of the liquid (30) in the transducer chamber(s) (9128) and/or fluid reservoir(s) (9124), from one or more of any direct or indirect location(s). It is preferred, without limitation, that the liquid level sensor (9180) locations are at least effective. It is more preferred, without limitation, that at least one suitable liquid level sensing device (9180) is at least located at any suitable proximity to, and/or is effectively connected to, and senses the liquid (30) level in, at least one of any effective fluid reservoir(s) (9124) that is effectively separated from the at least one of any effective transducer chamber (9128). The fluid reservoir(s) (9124) and transducer chamber(s) (9128) can be any effective, size(s), length(s), width(s), depth(s), shape(s), geometry(s), complex geometry(s), and/or volume(s). It is preferred, without limitation, that the fluid reservoir(s) (9124) holds less liquid than the transducer chamber (9128).

Without being limited, the fluid reservoir(s) (9124) is suitably connected to the transducer chamber (9128), so the liquid (30) can flow and/or be connected between the fluid reservoir(s) (9124) and the transducer chamber (9128), in such a way so that the liquid (30) level that is sensed or recorded in the fluid reservoir(s) (9124) is at least approximate to, and preferably close to, and more preferably an exact representation of, the liquid (30) level or depth in the transducer chamber(s) (9128), and even more preferably the height or depth of the liquid over the transducer(s) (10).

The fluid reservoir(s) (9124) and the transducer chamber (9128) are preferably, and without limitation, connected via one or more of any effective opening(s), conduit(s), tube(s), pipe(s), or the like (Herein called "Fluid Passage(s)") (9130). The one or more of any effective fluid passage inlet(s) (9211) and fluid passage outlet(s) (9210), connected to the one or more fluid passage(s) (9130) can be any effective size(s), length(s), width(s), depth(s), shape(s), geometry(s), complex geometry(s), and/or volume(s). The fluid passage outlet(s) (9210) can be located at one or more of any effective location(s) within and/or to the transducer chamber(s) (9128).

It is preferred, without limitation, that the fluid passage inlet(s) (9211), fluid passage outlet(s) (9210), and fluid passage(s) (9130), are designed and located effectively, so that at least a liquid (30) level inside of the fluid reservoir(s) (9124) is an effectively accurate representation of the liquid (30) level within the transducer chamber (9128) and/or above the transducer(s) (10), to provide effective operation of the aerosol generation apparatus (9101) and/or the aerosol generating machine (9196).

It is more preferred, without limitation, that the fluid passage inlet(s) (9211), fluid passage outlet(s) (9210), and fluid passage(s) (9130), are designed and located so the liquid level inside of the fluid reservoir(s) (9124), where at least one of the liquid level sensor(s) (9180) are located, is not disrupted, disturbed, or changed, by any wave action or surface waves present in the transducer chamber (9128) during operation of the transducer(s) (10), in such a manner, way, amount, and/or intensity, that may cause the liquid level sensor(s) (9180) to provide inaccurate data and/or enough inaccuracy in the liquid level(s) that is sensed or recorded, to cause ineffective operation of the aerosol generation apparatus (9101) and/or the aerosol generating machine (9196). It is also preferred, without limitation, that the fluid reservoir(s) (9124) is located at any effective position and/or height above any sump in the transducer chamber (9128) and/or the transducer fluid supply chamber (9126).

Without limitation, at least one of any effective heater element(s) or any other effective means for heating liquid (Herein called "Heater Element") (9188), can be located in one or more of any effective location(s) within the transducer chamber (9128). At least one of any effective heater element (9188), can also be located in one or more of any effective location(s) of any parts and components including, but not limited to any, transducer fluid supply chamber (9126), and/or one or more of any tanks (not shown) that supply any liquid to the transducer chamber (9128) and/or transducer fluid supply chamber (9126).

It is preferred, without limitation, that at least one fluid passage (9130) is effectively connected to, the fluid reservoir(s). It is more preferred, without limitation, that at least one fluid passage (9130) is effectively connected to, and oriented downward from, the fluid reservoir(s) (9124) and effectively connects with the transducer chamber (9128), and preferably connects effectively with any sump in the transducer chamber (9128) and/or the transducer fluid supply chamber (9126). It also is preferred, without limitation, that the liquid in the transducer chamber (9128) is effectively heated in and/or near, any sump in the transducer chamber (9128) and/or the transducer fluid supply chamber (9126).

It is preferred, without limitation, that the opening (Herein called "Fluid Passage Opening") (9210) for the fluid passage (9130) is located at least close or near the heater element (9188), and more preferably just below and centered to the heater element (9188).

With reference to FIG. 156, at least one liquid level sensor hole(s) (9214) is formed through the case cover plate (9112) over the fluid reservoir (9124) at one or more of any effective location(s). At least one liquid level sensor(s) (9180) is effectively attached to a top of the case cover plate (9112) over the at least one liquid level sensor hole(s) (9214) to determine at least one fluid or liquid (30) level(s) or height(s) in or at location(s) such as, but not limited to any, fluid reservoir (9124), transducer chamber(s) (9128), and/or above the one or more transducer(s) (10).

It is preferred, without limitation, that at least two liquid level sensor(s) (9180) are positioned approximately at either end of the fluid reservoir (9124). It more preferred, without limitation, that these at least two liquid level sensor(s) (9180) are positioned approximately at either end of the fluid reservoir (9124), and at least one additional liquid level sensor(s) (9180) is located approximately in the middle of the fluid reservoir (9124). It is also preferred, without limitation, that if a liquid level sensor(s) (9180) is positioned approximately in the middle of the fluid reservoir (9124), it is dedicated at least to the control of the flow of liquid (30) into the fluid reservoir (9124) and the connected transducer chamber (9128), and starting and stopping the flow of liquid into these locations as needed, to maintain at least any suitable depth(s) or level(s) of liquid (30) over and/or above the transducer(s) (10). It is preferred, without limitation, that at least any suitable and effective liquid (30) level(s) or depth(s) is maintained above the one or more transducer(s) (10). It is more preferred, without limitation, that a liquid (30) depth is maintained approximately between 0.25 and 2.0 inches above the face of the transducer(s) (10), and even more preferably about 1.25 inches above the face of the transducer(s) (10), as disclosed in U.S. Pat. No. 7,641,130 (Ricciardi et al.), which is incorporated herein by reference in its entirety, including any references cited therein.

It is also preferred, without limitation, that any liquid level sensors (9180) can sense and report multiple liquid (30) levels. Any suitable and effective liquid level sensor(s) (9180) can be used in the present invention. It is preferred, without limitation, that the liquid level sensor(s) (9180) are conductivity based liquid level sensors, where the sensors (9180) have one or more of any suitable conductive probe(s), electrode(s), rod(s), or pin(s) (Herein called "Sensor Pin(s)") (9191), that protrude downward into the tank and/or reservoir (9124) at different lengths to sense different liquid (30) levels, and a circuit is completed when the sensor pin(s) (9191) are in contact with any conductive liquid (30). Without being limited, the conductivity type of liquid level sensor (9180) preferably also uses at least one or more conductive probe(s), electrode(s), rod(s), or pin(s), used as a reference (Herein called "Reference Pin(s)") (9181) that extends to any effective length into the liquid (30) in the fluid reservoir (9124) for effective electrical function of the liquid level sensor (9180), all in a manner known to those skilled in the art.

Without being limited, the liquid level sensor(s) (9180) can report its status and/or liquid (30) levels to any suitable device(s) known to those skilled in the art, such as, but not limited to any microprocessor bases controller (9122), that controls the aerosol generating apparatus (9101) and/or the aerosol generating machine (9196) so any actions can be taken when needed such as, but not limited to, (a) starting and stopping the flow of a liquid and filling or stopping the filling, of the fluid reservoir (9124) and/or the connected transducer chamber (9128) when the liquid level(s) in these locations is at any desired and/or specified heights and/or depths, and (b) sensing any liquid (30) level(s) and/or depth(s) at preset liquid (30) level(s) in the fluid reservoir (9124) and the connected transducer chamber (9128) and shutting down the aerosol generation device (9101) and/or aerosol generating machine (9196), if any liquid (30) level(s) reaches any level(s) or depth(s) that is determined to be too high or too low for safe and/or effective function of the aerosol generating machine (9196) or apparatus(s) (9101).

The liquid level sensor(s) (9180) can sense any liquid (30) height, depth, or level in one or more of any locations such as, but not limited to any, fluid reservoir (9124), and/or connected transducer chamber (9128). It is preferred, without limitation, that the liquid level sensor(s) (9180) can sense at least one of the following liquid (30) levels that can result in the following preferred actions for any aerosol (200) generating apparatus (9101) and/or aerosol (200) generating machine (9196): (a) Emergency machine stop—High liquid level, (b) Emergency machine stop—Low liquid level, (c) Liquid feed on—low liquid level, (d) Liquid feed off—high liquid level. It is preferred, without limitation, that any liquid (30) feeding to the fluid reservoir (9124) and/or transducer chamber (9128), is at least any effective rate for suitable function and performance of any aerosol generating apparatus (9101) and/or aerosol generating machine (9196).

Without being limited, any liquid (30) levels can be monitored, detected, maintained, and/or established, by one or more of any liquid level sensor(s) (9180) at any location(s), for any purposes such as, but not limited to: (a) maintaining the effective operation of the aerosol generation apparatus (9101), (b) maintaining the effective operation of the aerosol generating machine (9196), (c) maintaining effective control of the filling and stoppage of filling of any liquid to or within the fluid reservoir (9124) and/or the transducer chamber (9128), (d) maintaining the effective and safe operation of the transducer(s) (10), by maintaining an effective liquid (30) level above the transducer(s) (10), (e) maintaining an effective and safe level of liquid above and/or around any heater element(s) (9188) that may be used in any tank(s) and/or reservoirs (9124)(9128).

Without being limited, an even more detailed description of the preferred liquid level sensor(s) (9180) can be described as follows. At least one liquid level sensor (9180) is attached to a top of the case cover plate (9112) over at least one liquid level sensor hole (9214) to determine at least one fluid (30) level in the fluid reservoir (9124) and/or transducer chamber (9128). With reference to FIG. 150 and FIG. 154, and without limitation, the liquid level sensor (9180) preferably includes at least one reference pin (9181), a first pin (9183), a second pin (9185), a first comparator (9187) and a second comparator (9189). Without limitation, the sensor pin(s) (9191) can include the first pin (9183) and the second pin (9185). If necessary, more than two pins may be used. The reference pin (9181) is connected to a positive terminal of the first and second comparators (9187), (9189) through a voltage divider. The first pin (9183) is connected to a negative terminal of the first comparator (9187). The second pin (9185) is connected to a negative terminal of the second comparator (9187). Normally, the first and second comparators (9187), (9189) output a voltage low or zero to the microprocessor based controller (9122). When a level of the disinfectant level rises to the level of the first pin (9183), current flows from the first pin (9183) to the reference pin (9181), which causes the voltage at the negative terminal to be lower than at the positive terminal. The first comparator (9187) outputs a voltage high (Vcc) to show the level has reached at least to a bottom of the first pin (9183). If the disinfectant level rises to at least a bottom of the second pin (9185), the second comparator (9189) will output a voltage high (Vcc).

Without being limited, a tube nipple (9182) is preferably threaded through a side wall of the fluid reservoir (9124). One end of a fill tube (9184) is secured to the tube nipple (9182) and a distal end of the fill tube is attached to an output of any suitable liquid valve (9186) and an input of the liquid valve is attached to a tank of fluid (not shown). One or more of any suitable liquid pump may also take the place of the liquid valve (9186).

Without limitation, at least one heater element (9188) is threaded through a side wall of the transducer fluid supply chamber (9126), preferably near the bottom thereof. At least one supply chamber thermocouple (9190) is threaded through a side wall of the transducer fluid supply chamber (9126). One or more of any suitable temperature sensor(s) or temperature sensing device(s) (Herein called "Thermocouple") (9190), can be used in one or more of any locations within any tank(s) or reservoir(s) such as, but not limited to any, transducer chamber (9128), transducer fluid supply chamber (9126), and/or fluid reservoir (9124). Without being limited, at least one transducer thermocouple (9192) is also threaded through a side wall of the transducer chamber (9128).

The at least one microprocessor based controller (9122) is preferably used to monitor, power, and/or control, various components, such as, but not limited to, those described in the following description. The fluid reservoir (9124) is preferably filled with liquid (30) through at least one of any suitable liquid valve (9186). Without being limited the one or more of any liquid valve(s) (9186) can also feed any liquid at any time into the transducer chamber (9128) or any other connected location(s). The liquid (30) is preferably gravity fed to the liquid valve (9186) from any suitable supply tank or reservoir. Without limitation, the liquid (30) is heated by the at least one heater element (9188) to a preferable temperature of at least above 80 degree F., a more preferable temperature between 90° F.-150° F., and very preferable about 110° degree F., but any other effective temperature(s) may also be used at any times. The temperature of the liquid (30) is measured at least with the supply chamber thermocouple (9190) and/or the transducer thermocouple (9192).

The at least one ultrasonic transducer (10) is at least powered by any effective power amplifier (9176). An aerosol (200) is generated by vibration and/or or any effective activation of the ultrasonic transducer (10) forming an aerosol (200) from the liquid (30) above the transducer (10) that is supplied in the transducer chamber (9128). Air/gas is pumped or flowed into the transducer chamber (9128). Air/gas is also pumped or flowed into at least one inner air chamber(s) (9152) that can be, without limitation, formed between the outer base tube (9134) and the inner tube (9136), through the one or more of any exhaust supply hole(s) (9168). The air/gas pumped or flowed into the transducer chamber (9128) pushes or otherwise moves or flows the aerosol (200) generated by the vibration of the at least one ultrasonic transducer(s) (10) through the outlet pipe (9114), and air/gas that is pumped, moved, and and/or flowed, into the inner air chamber (9152) provides at least a second source of effective air/gas pressure and/or movement or flow of air/gas, that contributes in moving the aerosol (200) through the outlet pipe (9114).

With reference to FIGS. 145-171C, and without limitation, the following embodiments can be used to further describe the current invention. According to FIGS. 145-146, FIGS. 152-154, FIG. 156, and FIGS. 157-161, and according to an embodiment, and without limitation, one or more of any suitable source(s) of pressurized air/gas(s) or flow of air/gas(s) can be located or provided at one or more of any suitable location(s) effectively near or along any part of any ultrasonically created liquid surface disturbance, geyser (4045), aerosol plume (4050), stream of aerosol (200) and/or moving cloud(s) of aerosol (200), at any suitable location(s) outside of, but still connected to the interior space(s) of, the tank(s) and/or reservoir(s) where the ultrasonically created liquid surface disturbance(s) and/or aerosol is generated (Herein called "Transducer Chamber(s)") (9128), in order to move and/or assist in moving the aerosol (200) into any location(s) such as, but not limited to, the one or more of any treated area(s) (9212). Without being limited, the ultrasonically created liquid (30) surface disturbance(s) can include, but is not limited to any, geyser, liquid nipple, resultant aerosol plume (4050) and/or any other raised liquid or liquid feature (Herein called "Geyser(s)") (4045) that can be created by one or more of any transducer(s) (10) on or above any surface (Herein called "Liquid Surface") (9241) of any liquid (30) in any transducer chamber(s) (9128).

It is preferred, without limitation, that at least one source of pressurized air/gas is also supplied to the transducer chamber(s) (9128) at least in a manner as previously described in the present invention, and/or at least in a manner known to those skilled in the art, to assist in removing the aerosol (200) from the transducer chamber(s) (9128). However, referring to FIG. 157 and FIG. 160, and without being limited, in various aspects of the present invention, the transducer chamber(s) (9128) can also not be supplied with a source, and/or its own source and/or dedicated source, of pressurized air/gas. It is preferred, without limitation, that at least an effective supply of air/gas is supplied to the transducer chamber(s) (9128) via one or more of any suitable chamber supply tube (9257) and/or chamber tube end (9165) and its one or more of any suitable openings, or otherwise any plate hole(s) (9260) that can open into the transducer chamber(s) (9128). The plate hole(s) (9260) can be located at one or more of any suitable and effective locations to and/or within the transducer chamber(s) (9128). Without being limited, the one or more plate hole(s) (9260) can have any effective features, attributes, and/or design characteristics such as, but not limited to any, size, length, shape, width, height, length, diameter, hole or opening count, location(s) within the transducer chamber (9128), plunge depth into the transducer chamber (9128), and/or geometry. Without being limited, the plate hole(s) (9260) can also have any suitable and effective length, and can extend any suitable and effective length and/or positions into or within the transducer chamber (9128).

It is preferred, without limitation, that the one or more, of any effective openings for any pipe(s) or conduit(s) supplying any, source(s) of any pressurized air/gas(s) and/or source(s) of any flow(s) of air/gas(s), that moves, and/or helps to move the aerosol (200), such as, but not limited to any, exhaust supply hole(s) (9168), is located at one or more of any effective locations such as, but not limited to, within, along, inside of, outside of, through, and/or to, one or more of any suitable conduit(s), tube(s), hose(s), pipe(s), chamber(s), aerosol hole(s) (9154), base tube portion(s) (9146), inner tube(s) (9136), cavity(s), and/or any other suitable enclosed or semi-enclosed means for transporting any amount of generated aerosol (104), (Herein called "Tube(s)") (9216), preferably after the aerosol(s) (200) and/or geyser(s) (4045) has left the one or more tank(s) or transducer chamber(s) (9128) where the ultrasonically created liquid surface disturbance(s) and/or aerosol (200) is generated.

Without limitation, the base tube portion (9146), tube(s) (9216), and/or any other parts of the outlet pipe (9114), can also, without limitation, extend to any suitable and effective distance(s) into the transducer chamber(s) (9128). The tube(s) (9216) can also directly and/or indirectly connect with and/or include, one or more of any additional and suitable, conduit(s), tube(s), hose(s), pipe(s), chamber(s), cavity(s), and/or any other suitable enclosed or semi-enclosed means for effectively transporting any effective, amount, volume, velocity, flow rate, and/or pressure, of any air/gas(s) and/or generated aerosol (200), such as, but not limited to any, outlet pipe(s) (9114) and/or any of its various parts and component(s), and/or outlet tube(s) (9160). Without limitation, the tube(s) (9216) can also include various parts such as, but not limited to any, transition tube(s) (9156), exhaust tube(s) (9140), base tube portion(s) (9146), inner tube(s) (9136), transition tube(s) (9156), and/or outlet pipe(s) (9114).

The tube(s) (9216) can be supplied with any effective flow of air/gas(s) from one or more any exhaust supply hole(s) (9168) that are effectively located anywhere, on, inside of, or within the walls of, the tube(s) (9216). It is preferred, without limitation, that this effective flow of air/gas(s) also includes and can be adjusted for any effective variables and characteristics such as, but not limited to any, amount, volume, velocity, flow rate, and/or pressure, of any air/gas(s) and/or any aerosol density or volume. The exhaust supply hole(s) (9168) can connect with one or more of any suitable and effective connecting pipe(s), hose(s), tube(s) conduit(s), and/or any other effective means for effectively transporting any air/gas(s) to the exhaust supply hole(s) (9168) (Herein called Air/Gas Supply Tube(s) (9228). The air/gas supply tube(s) (9228), can suitably connect with one or more of any suitable air pump(s) (180). Without being limited, the air/gas supply tube(s) (9228) can also include any, exhaust hole supply tube(s) (9259), and/or supply tube end(s) (9171). Without limitation, the air/gas supply tube(s) (9228), can be any, size, shape, width, height, length, diameter, design, and/or geometry. It is preferred, without limitation, that the air/gas supply tube(s) (9228) are at least located and positioned suitably and effectively. Referring to FIGS. 157-161 and FIGS. 158-159, and without limitation, the at least one, but preferably at least an effective quantity, of the exhaust supply hole(s) (9168) and any connecting tubing and/or pipes such as but not limited to any air/gas supply tube(s) (9228), are suitably interfaced with the at least one tube(s) (9216), and the exhaust supply hole(s) (9168) are located as close to the liquid (30) surface as possible so that they are effective.

Without being limited, the aerosol (200), geyser(s) (4045), and/or plume(s) (4050), can be considered as having left the transducer chamber(s) (9128), (a) preferably, once the aerosol (104), geyser(s) (4045), and/or plume(s) (4050), have left any space or volume within the transducer chamber(s) (9128), where being inside any portion of any tube(s) (9216) that is still located inside of any interior space or volume within the transducer chamber(s) (9128) is considered being inside of the transducer chamber(s) (9128), (b) more preferably, once the aerosol (200), geyser(s) (4045), and/or plume(s) (4050), have left the transducer chamber(s) (9128), via one or more of any, outlet pipe(s) (9114), extension(s) of any base tube portion(s) (9146), aerosol hole(s) (9154), and/or any other similar and effective opening(s), (c) even more preferably, once the aerosol (200), geyser(s) (4045), and/or plume(s) (4050), have moved past and/or through one or more of any threshold(s), opening(s), mouth(s), and/or orifice(s), of or connected to any parts of the aerosol generating apparatus (9101) that allows the geyser(s) (4045), plume(s) (4050), and/or aerosol (200), to leave the transducer chamber (9128) such as, but not limited to any, outlet pipe(s) (9114), extension(s) of any base tube portion(s) (9146), aerosol hole(s) (9154), tube(s) (9216), and/or outlet orifice(s) (9218), where any, part, portion, and/or entirety, of these one or more component(s) or feature(s), is located at one or more of any effective location(s) inside and/or outside of any transducer chamber(s) (9128), (d) very preferably, once the aerosol (200), geyser(s) (4045), and/or plume(s) (4050) have moved past and/or through one or more of any threshold(s), opening(s), mouth(s), and/or orifice(s), of or connected to any parts of the aerosol generating apparatus (9101), that are preferably positioned or located at one or more of any effective angle(s), more preferably positioned or located at one or more of any effective angle(s) at and/or between about zero to ninety degrees, even more preferably positioned or located at any horizontal orientation, and very preferably positioned or located at any orientation that is at least about parallel to any liquid (30) surface in the transducer chamber (9128) above the transducer(s) (10), that allows the geyser(s) (4045), plume(s) (4050), and/or aerosol (200) to effectively leave the transducer chamber (9128) such as, but not limited to any, outlet pipe(s) (9114), extension(s) of any base tube portion(s) (9146), aerosol hole(s) (9154), tube(s) (9216), air flow holes (4080), and/or outlet orifice(s) (9218), where any, part, portion, and/or entirety, of these one or more component(s) or feature(s), is located at one or more of any effective location(s) inside and/or outside of any transducer chamber(s) (9128), (e) extremely preferably, in various circumstances, such as, but not limited to, when the generated aerosol(s) (200), plume(s) (4050), and/or geyser(s) (4045), have moved past and/or through one or more of any, threshold(s), opening(s), mouth(s), and/or orifice(s) (Herein called "Outlet Orifice(s)") (9218), of or connected to, any tube(s) (9216), and/or any other various parts of the aerosol generating apparatus (9101), at any one or more of any effective location(s), that allows the geyser(s) (4045), plume(s) (4050), and/or aerosol (200), to leave the transducer chamber (9128) such as, but not limited to any, outlet pipe(s) (9114), extension(s) of any base tube portion(s) (9146), tube(s) (9216), and/or aerosol hole(s) (9154).

Without limitation, any effective amount, volume, velocity, flow rate, and/or pressure, of any air/gas can flow into the outlet orifice(s) (9218) and/or through any location(s) inside of the tube(s) (9216). Without being limited, the one or more parts of the aerosol generating apparatus (9101), that the air/gas and/or aerosol must pass through in order to leave any transducer chamber(s) (9128), such as, but not limited to any, outlet orifice(s) (9218), aerosol hole(s) (9154), and/or tube(s) (9216), can have any effective attributes or design characteristics such as, but not limited to any, size, shape, width, height, length, diameter, hole or opening count, and/or geometry.

Referring to FIGS. 152-154 and FIGS. 157-161, and without limitation, the tube(s) (9216), can have any effective length. It is preferred, without limitation, that the length of the tube(s) (9216) is at least effective and efficacious. However, it is preferred, without limitation, that the tube(s) (9216) have a total length of approximately between one and sixty or more inches. It is more preferred, without limitation, that the tube(s) (9216) have a total length of approximately between four and 20 or more inches. It is even more preferred, without limitation, that the tube(s) (9216) have a total length between about 6 and 12 or more inches. It is very preferred, without limitation, that the tube(s) (9216) have a total length between about 7 to 12 inches.

Referring to FIGS. 152-154 and FIGS. 157-161, and without limitation, the tube(s) (9216), can have any effective diameter. It is preferred, without limitation, that the diameter of the tube(s) (9216) is at least effective and efficacious. However, it is preferred, without limitation, that the tube(s) (9216) have a total diameter of approximately between 0.25 inch and twenty or more inches. However, it is preferred, without limitation, that the tube(s) (9216) have a diameter of approximately between one inch and 10 or more inches. It is more preferred, without limitation, that the tube(s) (9216) have a diameter of between about two inch and six inches. It is even more preferred, without limitation, that the tube(s) (9216) have a diameter of and/or between about three inches and four inches.

Without being limited, the diameter of the various pipe(s), tube(s), conduit(s), and/or any other structure(s), that any, geyser(s) (4045), plume(s) (4050), and/or aerosol (200), travel through, such as, but not limited to any, aerosol hole(s) (9154), base tube portion(s) (9146), tube(s) (9216), expansion area(s) (9255), and/or inner tube(s) (9136), is at least large enough to effectively, encompass, encircle, and/or surround, the one or more of any, geyser(s) (4045), plume(s) (4050), and/or aerosol (200), that is generated, and preferably large enough so that the aerosol (200) that is generated and flowed into the one or more treated area(s) (9212) is at least, efficacious and/or effective, and has any, volume, density, and/or average droplet size, that is at least efficacious and/or effective. Without being limited, there can be any distance between any part of any geyser(s) (4045) and/or plume(s) (4050), and any inner wall surface of any pipe(s), tube(s), conduit(s), and/or any other structure(s), that any, geyser(s) (4045), plume(s) (4050), and/or aerosol (200), can travel through, and it is preferred, without limitation that this distance(s) is at least effective. Also, without being limited, any reference to any diameter in the current invention can include, but is not limited to any, inside diameter, and/or outside diameter, and preferably it is any inside surface diameter.

Referring to FIGS. 157-158, FIGS. 160-161, and FIGS. 162-165, and without being limited, the exhaust supply hole(s) (9168) can be any effective, shape, diameter, size, geometry, width, length, and/or height. Any effective amount, volume, velocity, flow rate, and/or pressure, of any air/gas can flow out of the exhaust supply hole(s) (9168). The exhaust supply hole(s) (9168) can also be orientated at one or more of any effective angles and directions. For example, and referring to FIGS. 163-164, without limitation, the exhaust supply hole(s) (9168) can be located and oriented so that the outbound air/gas stream that flows from the exhaust supply hole(s) (9168), can form one or more of any effective angular and/or circular motion of air/gas within the tube(s) (9216). In another example, and referring to FIG. 165, and without limitation, the exhaust supply hole(s) (9168) can also be located and oriented so that the outbound air/gas stream that flows from the exhaust supply hole(s) (9168), can point their output of any air/gas(s) upward within the tube(s) (9216). It is preferred, without limitation, that the exhaust supply holes (9168) are horizontally mounted and point inward toward a center of the tube(s) (9216).

Referring to FIGS. 145-146 and FIGS. 166-167, it is preferred, without limitation, that the inbound air/gas flow enters the one or more inner air chamber(s) (9152) from at least one horizontally positioned exhaust supply hole(s) (9168), and the air/gas flow is able to effectively flow downward within the one or more inner air chamber(s) (9152) toward the expansion area (9255) and/or flow at least at a suitable distance(s), preferably completely down and around the exterior of the one or more inner tube(s) (9136) and within the inner air chamber (9152). It is preferred, without limitation, that the air/gas leaves the inner air chamber(s) (9152), and then enters the expansion area(s) (9255), and then enters the inner tube (9136), where the air/gas and aerosol (200) eventually makes its way to the outlet tube (9160), and then out of the aerosol generation apparatus (9101).

Without limitation, any effective distribution of the flow of any air/gas, introduced via the exhaust supply hole(s) (9168), can be presented, at any one or more of any location(s) within and/or into, the tube(s) (9216), around the inner tube(s) (9136), and/or toward any expansion area(s) (9152). It is preferred, without limitation, that this flow of air/gas is at least an evenly distributed flow of air/gas, from one or more of any directions and/or angles, that is introduced and flowed into locations such as, but not limited to any, tube(s) (9216), base tube portion(s) (9146), aerosol hole(s) (9154), and inner air chamber(s) (9152).

Without being limited, any part of any, expansion area(s) (9255), aerosol hole(s) (9154), and any other connected parts of any outlet pipe(s) (9114), tube(s) (9216), and/or aerosol generating apparatus (9101), can be designed for any effective, amount, volume, velocity, flow rate, and/or pressure, of any air/gas flow. Also, without being limited any part of any, expansion area(s) (9255), aerosol hole(s) (9154), tube(s) (9216), inner tube(s) (9136), inner tube receiver end(s) (9155), exhaust tube receiver(s) (9157), transition tube(s) (9156), exhaust tube(s) (9140), and/or any other connected parts of the outlet pipe (9114), and/or aerosol generating apparatus (9101), can be designed for any effective amount of radial and/or vertical expansion of any one or more part(s) of any geyser(s) (4045) and/or aerosol (200) that is generated or created.

Alternatively, and without limitation, the expansion area(s) (9255) does not have to be designed for and/or have any amount, and/or any significant amount, of dimension changes, relative to any other connected tube(s) (9216) such as, but not limited to any, base tube portion(s) (9146) and inner tube(s) (9136), to accommodate any radial and/or vertical expansion of one or more of any part(s) of the geyser(s) (4045) and/or aerosol (200) that is generated.

It is preferred, without limitation, that any, expansion area(s) (9255), tube(s) (9216), and/or any other suitable parts and components of the aerosol generation apparatus (9101), at least have any effective size, geometry, volume, dimensions, and any other various characteristics, so that at least an effective amount of generated aerosol (200) is able to be removed from any part of the geyser(s) (4045) and/or aerosol plume (4050), as well as from any one or more areas of the aerosol generating apparatus (9101) such as, but not limited to any, transducer chamber(s) (9128), aerosol hole(s) (9154), base tube portion(s) (9146), pipe(s) (9216), and inner tube(s) (9136), including the aerosol generating apparatus (9101) itself. The one or more expansion area(s) (9255) can be located at any effective distance(s) from the surface (9241) of the liquid (30) where the geyser(s) (4045) are created. It is preferred, without limitation, that the expansion area(s) (9255) are at least effectively located.

Without limitation, the expansion area(s) (9255) can have any effective, size, shape, width, volume, height, length, diameter, hole or opening count, and/or geometry. Also, without being limited, one or more of any suitable and effective, exhaust supply hole(s) (9168), base tube portion(s) (9146), and inner tube(s) (9136), may directly or indirectly interface and/or connect effectively with the expansion area(s) (9255).

With reference to FIGS. 157-161 and FIG. 166, and according to an embodiment, and without limitation, the one or more of any effective parts of any tube(s) (9216), and/or any suitable open end(s) of any, tube(s) (9216) and/or base tube portion(s) (9146), including any outlet orifice(s) (9218), can, without limitation, be located effectively and approximately at any effective distance above, around, and/or near, one or more of any, and/or one or more of any group(s) of any, transducer(s) (10) and/or the geyser(s) (4045) and aerosol they produce. Without being limited, the open end(s) and/or outlet orifice(s) (9218), and/or at least an effective portion of the open end(s) and/or outlet orifice(s) (9218), of the one or more of any tube(s) (9216) and/or base tube portion(s) (9146), are effectively located, above, around, to encompass, and/or to encircle, at any depth, height, and/or length, of the one or more of any geyser(s) (4045) and/or accompanying aerosol plumes (4050), and/or aerosol (200) that are generated from or off the geyser(s) (4045) that are generated from the operation of the ultrasonic transducer(s) (10). Also, without being limited, any part of and/or preferably the whole of the open end(s) and/or "Outlet Orifice(s)" (9218), of the one or more of any tube(s) (9216) and/or base tube portion(s) (9146), can extend to any effective height or length above the surface of the liquid (30) in the transducer chamber(s) (9128).

It is preferred, without limitation, that the one or more of any, open tube (9216) end(s) and/or one or more of any outlet orifice(s) (9218), is positioned between about 0.1 to 6 inches or more from the surface of any liquid (30) above any one or more transducer(s) (10). It is more preferred, without limitation, that the open tube end(s) and/or outlet orifice(s) (9218), is positioned between about 0.25 to 2 inches or more from the surface of any liquid (30) above one or more of any transducer(s) (10). It is even more preferred, without limitation, that the open tube end(s) and/or outlet orifice(s) (9218), is positioned between about 0.5 to 3 inches or more from the surface of any liquid (30) above any one or more transducer(s) (10). It is very preferred, without limitation, that the open tube end(s) and/or outlet orifice(s) (9218), is positioned between about 0.5 to about 4 inches or more from the surface of any liquid (30) above any one or more transducer(s) (10). It is most preferred, without limitation, that the open tube end(s) and/or outlet orifice(s) (9218), is positioned between about 0.20 to about 1 inch from the surface of any liquid (30) above one or more of any transducer(s) (10).

Without limitation, it is preferred, that the open end(s) of any tube(s) (9216) and/or base tube portion(s) (9146), including the outlet orifice(s) (9218), are at least effectively centered over the one or more transducer(s) (10) and/or the geyser(s) (4045) they produce, and it is more preferred, that only one tube (9216), base tube portion (9146), and/or outlet orifice (9218) is at least effectively and concentrically centered above and/or around each transducer (10) and/or the geyser(s) (4045) it creates. Without being limited, the one or more of any tube(s) (9216), base tube portion(s) (9146), and/or outlet orifice(s) (9218) can, without limitation, suitably connect or pass through, preferably in an effectively sealed manner, the one or more of any, suitable covers for the transducer chamber(s) (9128), and/or case cover plate(s) (9112).

Without being limited, any open ends of the one or more of any tube(s) (9216), base tube portion(s) (9146), and/or outlet orifice(s) (9218), inside of and/or approximate to, the one or more transducer chamber(s) (9128), can also be located effectively and approximate to any sides, or any other angle or angled aspect, relative to each transducer (10) and/or any generated geyser(s) (4045). It is preferred, without limitation, that any openings to any one or more of any tube(s) (9216), base tube portion(s) (9146), and/or outlet orifice(s) (9218), are horizontally positioned above each geyser(s) (4045).

With reference to FIGS. 145-146, FIG. 149, FIGS. 152-153, FIGS. 157-161, and FIG. 166, and without limitation, one or more of any fan, blower, air pump, and/or any other effective and suitable source of any pressurized air/gas (Herein called "Air Pump") (180) can, without limitation, move and/or supply any air/gas and/or aerosol (200) at any effective, amount, volume, velocity, flow rate, and/or pressure, into, through, and/or out of, one or more of any parts of the aerosol generation apparatus (9101), such as but not limited to any, inlet tube(s) (9163), chamber supply tube (9257), chamber tube end (9165), exhaust supply tube(s) (9166), exhaust hole supply tube (9259), supply tube end(s) (9171), exhaust supply hole(s) (9168), inner air chamber(s) (9152), expansion area(s) (9255), transducer chamber(s) (9128), air/gas supply tube(s) (9228), supply manifold (9164), air feed manifold (9116), inlet manifold (9162), air outlet gap (9229), aerosol hole (9154), and plate hole(s) (9260).

It is preferred, without limitation, that at least one effective air pump(s) (180) is connected to one or more of any effective location(s) and/or component(s) of the aerosol generating apparatus(s) (9101), and the air pump(s) (180) has an output of at least 3 cubic feet per minute (cfm) or more. It is more preferred, without limitation, that at least one air pump(s) (180) is connected and used that has an output of at least 80 cfm or more. It is even more preferred, without limitation, that at least one air pump(s) (180) is connected and used that has an output of at least 100 cfm or more. It is very preferred, without limitation, that at least one air pump(s) (180) is connected and used that supplies air/gas at a measurement between about 50 to 650 or more feet per minute (fpm). It is extremely preferred, without limitation, that at least one air pump(s) (180) is connected and used that has an air/gas output measurement of about 350 to 500 feet per minute (fpm). In addition, the tanks or reservoir(s) (9128) in which the transducer(s) (10) are located, can be, without limitation, sealed, semi-sealed, or unsealed. It is preferred, without limitation, that the tanks or reservoir(s) (9128) in which the transducer(s) (10) are located, are effectively sealed.

With reference to FIGS. 145-146, it is preferred, without limitation, that at least one air pump(s) (180) is connected to at least one inlet tube(s) (9163), which effectively directly or indirectly connects with at least one chamber supply tube (9257) and/or chamber tube end (9165), where the chamber supply tube (9257) and/or the inlet tube (9163) can also, and preferably, suitably connect either directly or indirectly at one or more of any effective location(s) with at least one inlet manifold(s) (9162), in addition to the transducer chamber(s) (9128). The vertical air connector tube(s) (9173) can be positioned at one or more of any effective angle(s) and/or effective location(s). It is preferred, without limitation, that the air connector tube(s) (9173) is at least positioned about or at a vertical angle and has at least an effective length. Without being limited, the at least one vertical air connector tube(s) (9173) connects directly or indirectly with the at least one exhaust supply tube(s) (9166) and/or exhaust hole supply tube (9259), preferably at or about the midpoint(s) of the exhaust supply tube(s) (9166), where the ends of the exhaust supply tube(s) (9166) and/or exhaust hole supply tube (9259), preferably connects directly or indirectly with at least one exhaust supply hole(s) (9168) that connects with the at least one inner air chamber(s) (9152).

In a preferred aspect of the present invention, and without limitation, at least one, but more preferably only one, exhaust supply tube (9166) and supply tube inlet end (9169) suitably directly or indirectly connects with at least one, but more preferably only one, vertical air connector tube(s) (9173), where the at least one, but more preferably only one, exhaust supply tube (9166) splits and connects with at least two, but more preferably two separate, opposing and equal sides of identical pipe pieces or exhaust hole supply tube (9259). Furthermore, and without limitation, where one end of each exhaust hole supply tube (9259), suitably connects with at least one, but more preferably only one, outlet pipe (9114) via at least one, but more preferably only one, exhaust supply hole (9168), and where each of these at least one, but more preferably two, outlet pipes (9114) suitably connects to at least one, but more preferably only one, common or shared transducer chamber (9128). In addition, and without limitation, at least one, but more preferable only one, chamber supply tube (9257) connects directly or indirectly with at least one, but preferably only one, transducer chamber (9128), where the more than one aforementioned outlet pipes (9114) are both suitably connected to this same transducer chamber (9128) that directly or indirectly interfaces with at least one, but preferably only two, transducers (10).

With reference to FIGS. 145-146, FIG. 149, FIG. 154, FIGS. 157-161, and FIG. 166, and without limitation, the roof and/or the under side of the case cover plate (9112), that faces and/or covers the liquid (30) in the transducer chamber (9128) (Herein called "Chamber Roof") (9227), can be any effective distance or height (Herein called "Chamber Air Gap") (9266) above the surface of the liquid (30). Without being limited, the chamber air gap (9266) can be adjusted for any variables such as, but not limited to any, amount, volume, velocity, flow rate, and/or pressure, of any air/gas(s) and/or aerosol (200), that can pass or move through one or more of any location(s) such as, but not limited to any, transducer chamber(s) (9128), base tube portion(s) (9146), expansion area(s) (9255), inner tube (9136), exhaust tube (9140), and/or outlet tube (9160).

Without being limited, the chamber air gap (9266) can also be adjusted to any effective height to effectively accommodate any liquid (30) surface disturbance within the transducer chamber (9128), caused by various sources, such as, but not limited to any, transducer(s) (10) and/or geyser(s) (4045). It is preferred, without limitation, that the chamber roof (9227) is at least as effectively close as possible to the surface of the liquid (30) in the transducer chamber (9128) as possible.

It is preferred, without limitation, that the chamber roof (9227), is positioned at least at a distance between about 0.1 to 6 inches or more from the surface of any liquid (30) above any transducer (10). It is more preferred, without limitation, that the chamber roof (9227), is positioned between about 0.25 to 2 inches or more from the surface of any liquid (30) above any transducer (10). It is even more preferred, without limitation, that the chamber roof (9227), is positioned between about 0.5 to 3 inches or more from the surface of any liquid (30) above any transducer (10). It is very preferred, without limitation, that the chamber roof (9227), is positioned between about 0.5 to about 4 inches or more from the surface of any liquid (30) above any transducer (10). It is most preferred, without limitation, that the chamber roof (9227), is positioned between about 0.20 to about 1 inch from the surface of any liquid (30) above any transducer (10).

With reference to FIGS. 145-146, FIG. 149, FIGS. 157-161, and FIG. 166, and without limitation, the one or more flow(s) of any air/gas(s) from the one or more air pump(s) (180) can vary in one or more of any of its attributes or characteristics such as, but not limited to any, volume, amount, velocity, flow rate, and/or pressure, at one or more of any locations of the aerosol generating apparatus (9101). It is preferred, without limitation, that the flow of the air/gas(s) that flows into and/or through, any transducer chamber(s) (9128) is effectively different in one or more of any of its attributes or characteristics such as, but not limited to any of its, volume, amount, velocity, flow rate, and/or pressure, than the flow of the air/gas(s) that flows into and/or through, any inner air chamber(s) (9152). It is more preferred, without limitation, that the flow of the air/gas(s) that flows through at least one or more of any location(s) of the chamber supply tube (9257) and/or chamber tube end (9165), on the side of the traducer chamber(s) (9128) but still past the inlet manifold (9162) and/or the supply tube outlet (9167), is effectively different in one or more of any of its attributes or characteristics such as, but not limited to any of its, volume, amount, velocity, flow rate, and/or pressure, than the flow of the air/gas(s) that flows through any part(s) of the exhaust supply tube(s) (9166), exhaust hole supply tube (9259), and/or supply manifold (9164). It is even more preferred, without limitation, that the flow of the air/gas(s) that flows into and/or through, any plate hole(s) (9260), or any other suitable source(s) of air/gas(s) into the transducer chamber(s) (9128), is different in one or more of any of its attributes or characteristics such as, but not limited to any of its, volume, amount, velocity, flow rate, and/or pressure, than the flow of the air/gas(s) that flows near, into, and/or through, any exhaust supply hole(s) (9168).

Without being limited, the exhaust supply hole(s) (9168) and the plate hole(s) (9260) can also be independently supplied by the same or even different air pumps (180). However, it is preferred, without limitation, that the exhaust supply hole(s) (9168) and the plate hole(s) (9260) are supplied by the same air pump(s) (180) via any suitably connected system of any effective, pipe, hose, and/or conduit. It is also preferred, without limitation, that the flow of air/gas(s) from this shared air pump(s) (180) is split so that any effective amount, volume, velocity, flow rate, and/or pressure, of any air/gas(s) from the shared air pump(s) (180) flows to the transducer chamber(s) (9128), and another effective amount, volume, velocity, flow rate, and/or pressure, of any air/gas(s) from the shared air pump(s) (9178) flows to the air manifold(s) (9116), and more preferably to the one or more exhaust supply hole(s) (9168). Any effective ratio(s) or proportion(s) of the amount, volume, velocity, flow rate, and/or pressure, of any air/gas(s) from the one or more air pump(s) (180), can be diverted to the various parts and locations of the aerosol generation apparatus (9101). Without limitation, it is preferred that between about 5 to 95 percent, and it is more preferred that between about 40 to 80 percent, and it is even more preferred that between about 51 to 80 percent, and it is very preferred that between about 70 to 80 percent, and it is extremely preferred that about 75 percent, of the portion, amount, volume, velocity, flow rate, and/or pressure, of any air/gas(s) from the one or more, and preferably at least one common air pump(s) (180), is allocated to the exhaust supply hole(s) (9168) and/or the air manifold(s) (9116), and, it is preferred that between about 5 to 95 percent, and it is more preferred that between about 20 to 60 percent, and it is even more preferred that between about 20 to 49 percent, and it is very preferred that between about 20 to 30 percent, and it is extremely preferred that about 25 percent, of the other and/or remaining portion, amount, volume, velocity, flow rate, and/or pressure, of any air/gas(s) from the one or more, and preferably at least one common air pump(s) (180), is allocated to the plate hole(s) (9260) and/or transducer chamber(s) (9128).

With reference to FIGS. 145-146, FIG. 149, FIGS. 157-161, and FIG. 166, and without limitation, more than one of any pressure or atmospheric pressure values, can also be present and/or maintained within one or more of any, locations, parts, and/or areas, of the aerosol generation apparatus (9101) during its operation. It is preferred, without limitation, that these pressure(s) or atmospheric pressure(s) are at least effective. It is also preferred, without limitation, that these more than one pressure(s) or atmospheric pressure(s) are generated by at least an effective flow of any air/gas(s) through the one or more of any, locations, parts, and/or areas, of the aerosol generation apparatus (9101) during its operation.

It is also preferred, without limitation that at least two different pressure(s) or atmospheric pressure(s) are present and/or maintained within the one or more of any, locations, parts, and/or areas, of the aerosol generation apparatus (9101) during its operation. It is preferred, without limitation, that these at least two different pressures or atmospheric pressures are at least effective. It is also preferred, without limitation, that these different pressures or atmospheric pressures assist in effective removal of the aerosol (200) that is produced within the aerosol generation apparatus (9101).

Without limitation, one or more of any effective pressure(s) or atmospheric pressure differentials can occur in or between any, locations, parts, and/or areas, of the aerosol generation apparatus (9101) during its operation, such as, but not limited to any: (a) transducer chamber (9128) and the expansion area (9255), (b) transducer chamber (9128) and the air outlet gap (9229), (c) expansion area (9255) and the air outlet gap (9229), (d) expansion area (9255) and the inner air chamber (9152), (e) plate hole (9260) and the exhaust supply hole (9168), (f) transducer chamber (9128) and the inner air chamber (9152).

With reference to FIGS. 145-146, FIG. 149, FIGS. 157-161, and FIG. 166, and without limitation, more than one value for any air/gas characteristic(s) or flow attribute(s) such as, but not limited to any air/gas, air/gas velocity, air/gas volume, and/or air/gas flow rate, (Herein called "Air/gas Flow Attribute Value(s)"), can be present and/or maintained within one or more of any, locations, parts, and/or areas, of the aerosol generation apparatus (9101) during its operation. It is preferred, without limitation, that these more than one air/gas flow attribute value(s) are at least effective. It is also preferred, without limitation, that these more than one air/gas flow attribute value(s) are generated by at least an effective flow of any air/gas(s) through the one or more of any, locations, parts, and/or areas, of the aerosol generation apparatus (9101) during its operation.

It is also preferred, without limitation that at least two different air/gas flow attribute value(s) are present and/or maintained within the one or more of any, locations, parts, and/or areas, of the aerosol generation apparatus (9101) during its operation. It is preferred, without limitation, that these at least two air/gas flow attribute value(s) are at least effective. It is also preferred, without limitation, that these different air/gas flow attribute value(s) assist in effective removal of the aerosol (200) that is produced within the aerosol generation apparatus (9101).

Without limitation, any effective air/gas flow attribute value difference(s) or differential(s) can occur in or between any, locations, parts, and/or areas, of the aerosol generation apparatus (9101) during its operation, such as, but not limited to any: (a) transducer chamber (9128) and the expansion area (9255), (b) transducer chamber (9128) and the air outlet gap (9229), (c) expansion area (9255) and the air outlet gap (9229), (d) expansion area (9255) and the inner air chamber (9152), (e) plate hole (9260) and the exhaust supply hole (9168), (f) transducer chamber (9128) and the inner air chamber (9152).

It is preferred, without limitation that at least two different and effective air/gas flow attribute values are present and/or maintained within the one or more of any, locations, parts, and/or areas, of the aerosol generation apparatus (9101) during its operation, so that an effective amount of aerosol (200) that is produced, is able to be effectively removed from the aerosol generation apparatus (9101) and deployed into the treated area(s) (9212). For example, it is preferred, without limitation, that the air/gas flow attribute value(s), such as, but not limited to any, air/gas velocity (ie: meters per second), that are maintained and/or recorded at or within the inner air chamber (9152) and/or exhaust supply hole(s) (9168), are effectively larger than the air/gas flow attribute value(s), such as, but not limited to any, air/gas velocity (ie: meters per second), that are maintained and/or recorded at or within the transducer chamber (9128), plate hole (9260), and/or base tube portion (9146). This can, without limitation, prevent any air/gas and/or aerosol (200) from moving from location(s) such as, but not limited to, the transducer chamber (9128) and/or expansion area (9255), into locations such as, but not limited to any, inner air chamber (9152) and/or exhaust supply hole(s) (9168).

In a fifth aspect of this embodiment, and without limitation, the flow of any air/gas that is supplied to any tank(s) and/or reservoir(s) (9128), where the ultrasonically created liquid surface disturbance(s) (4045) is generated, can be balanced, put into any proportion, and/or put into any ratio, preferably at least effectively, with the flow of any air/gas that is supplied to the one or more additional source(s) of pressurized air/gas(s) or flow of air/gas(s), along the path of the evacuated, moving, evacuating, and/or extracted, aerosol, after it has left the tank and/or reservoir (9128) where the ultrasonically created liquid surface disturbance (4045) is generated.

These various flows of air/gas can be adjusted for various attributes including, but not limited to any, height of the geyser (4045), any pipe diameters, volume of the air outlet gap (9229), air/gas velocity (ie: meters per second), air/gas volume (ie: cubic feet per minute), location(s), interior dimensions of any components any of the air/gas flows through, and the volume, concentration, and/or density, of any aerosol (200) that is created. Without being limited, it is preferred that these various sources and/or flows of any air/gas are adjusted for any effective aerosol output from the aerosol generating apparatus, and even more preferred for maximum effective aerosol output.

Various means known to those skilled in the art can be used to control the flow of any air/gas(s) into various part(s) and or location(s) of the aerosol generation apparatus (9101). For example, and without being limited, various pipe(s), hose(s), tube(s) conduit(s), and/or any other effective means for effectively transporting any air/gas(s), can have any effective attribute(s) that can help to control or influence the amount, volume, velocity, flow rate, and/or pressure, of any air/gas(s) as it flows to or through various locations, such as, but not limited to any effective, length, width, shape, geometry, bending angle, and/or diameter. It is preferred, without limitation, that the various means that the air/gas(s) flows through from the air pump(s) (180) to the transducer chamber(s) (9128) and the inner air chamber(s) (9152), such as, but not limited to any, chamber supply tube (9257), and exhaust manifold (9116), are made from one or more of any suitable and effective pipe(s) or tubing(s) that has an inside diameter of at least between 0.25 inch to 1.25 inches.

It is preferred, without limitation, that any tubing and/or pipes that supplies any air/gas to the transducer chamber (9128) has an inside diameter of about one inch. It is also preferred, without limitation, that tubing or pipes that supplies the air/gas to the one or more exhaust supply hole(s) (9168) has an inside diameter of about one inch. It is preferred, without limitation, that various parts such as, but not limited to any supply manifold (9164), air feed manifold (9116), inlet manifold (9162), exhaust supply hole(s) (9168), plate hole(s) (9260), inlet tube(s) (9163), inlet tube outlet(s) (9265), chamber supply tube (9257) and/or chamber tube end (9165), have similar diameter(s) and/or dimension(s) that is about the diameter of any connecting pipe(s), hose(s), or other means that supply the air/gas(s), and more preferably have an inside diameter of about one inch.

The transducer chamber (9128) can have any attributes such as, but not limited to any effective, size(s), shape(s), volume(s), depth(s), and/or geometry(s). Without limitation the transducer chamber (9128) is at least effective in its design. The transducer chamber (9128) can have any effective length and width. It is preferred, without limitation, that the transducer chamber (9128) at least has a length between about 0.25 to 12 inches or more, and more preferably a length between about 6 to 9 inches. It is also preferred, without limitation, that the transducer chamber (9128) at least has a width between about 0.25 to 12 inches or more, and more preferably a width between about 1 to 5 inches.

The transducer chamber (9128) can hold any liquid volume. It is preferred, without limitation, that the liquid volume that the transducer chamber(s) (9128) holds, is at least effective. Without being limited, the transducer chamber(s) (9128) can be one or more of any suitable reservoir(s) or tank(s) where one or more geyser(s) (4045) and aerosol (200) are created within.

The one or more aerosol hole(s) (9154) can have any attributes such as, but not limited to any effective, size(s), shape(s), volume(s), depth(s), and/or geometry(s). It is preferred, without limitation that two aerosol holes (9154) are used. It is also preferred, without limitation, that the aerosol hole(s) (9154) are about two inches in diameter. It is preferred, without limitation, that the base tube portion (9146) is about two inches in diameter. It is preferred, without limitation, that the inside of the outlet pipe (9114) expands from about two inches at the base tube portion (9146) to about four inches at the body tube portion (9150) (9151), and back down to two inches diameter space within or at the inner tube receiver end (9155) component and/or outlet base portion (9144). It is also preferred, without limitation, that the inner tube is about three inches in diameter and suitably connects and seals with the inner tube receiver end (9155). It is preferred, without limitation, that the transition tube (9156), exhaust tube (9140), and outlet tube (9160), are about two inches in diameter.

Referring to FIG. 166, and without limitation, the flow of any air/gas(s) into the one or more parts of the aerosol generating apparatus (9101), can also be controlled by one or more of any suitable and effective valves (Herein called "Air Control Valve(s)") (9226). The air control valve(s) (9226) can be located at any location, preferably at least any effective location. The air control valve(s) (9226) can be any type of valve such as, but not limited to any, ball valve, and/or butterfly valve. The air control valve(s) (9226) can also be constructed from any suitable materials. Without being limited, any suitable barrier, semi-barrier, impediment, and/or partial obstruction, to the flow of any air/gas(s), can be located at one or more of any location(s), and also take the place of and/or act as any air control valve(s) (9226). It is preferred, without limitation, that if one or more of any air control valve(s) (9226) are used in the design of the aerosol generation apparatus (9101), then at least one valve is effectively positioned to cause at least an effective amount, volume, velocity, flow rate, and/or pressure, of the air/gas(s) to be provided by the air pump (180) to the air manifold (9116) and/or transducer chamber (9128).

With reference to FIGS. 145-146, FIG. 149, FIGS. 157-161, and FIG. 166, and without limitation, and according to an embodiment, the preferred form of the present invention can be further defined by various aspects such as, but not limited to any effective, measurements, dimensions, and/or configuration of any parts of the aerosol generation apparatus (9101), in order to increase and/or maximize the performance of the present invention.

In one aspect, and referring to FIGS. 145-171C, and without limitation, the various parts and components of the aerosol generator apparatus (9101), such as, but not limited to one or more of any, air pump (180), pipe (9216), air manifold (9116), inlet manifold (9162), supply manifold (9164), outlet basin portion (9144), body tube portion (9151), conical tube portion (9153), inner tube receiver end (9155), exhaust tube receiver (9157), supply tube inlet end (9169), supply tube end (9171), exhaust supply tube (9166), exhaust hole supply tube (9259), inlet tube (9163), chamber tube end (9165), supply tube outlet (9167), chamber supply tube (9257), air connector tube (9173), inlet tube outlet (9265), outlet pipe (9114), air/gas supply tube (9228), exhaust supply hole (9168), inner air chamber (9152), fluid supply chamber (9126), transducer chamber (9128), depth of liquid (30) in the transducer chamber (9128), chamber air gap (9266), aerosol hole (9154), base tube portion (9146), conical tube (9148), expansion area (9255), body tube portion (9150)(9151), outer base tube (9134), inner tube (9136), outlet base portion (9144), inner tube receiver end (9155), transition tube (9156), exhaust tube (9140), outlet tube (9160), transducer assembly (9232), outlet orifice (9218), plate hole (9260), and air outlet gap (9229), ultrasonic transducer (10), transducer assembly (9232) power amplifier (9176), and signal generator (not shown), can have any suitable and effective, features, attributes, and/or design characteristics, such as, but not limited to any, ratio, number, size ratio, size, shape, geometry, depth, angle, diameter, hole or opening count, structure, volume, frequency, scale, power, height, length, width, velocity, flow rate, output, and/or proportion, of any part(s) and component(s), preferably and without limitation, to create, attain, control, accommodate, and/or maintain, any effective, performance criteria, output, attributes, performance, characteristics, and/or variables, for the effective function of the aerosol generating apparatus (9101), such as, but not limited to, (a) the size of the transducer(s) (10) that are operated, (b) the number of transducer(s) (10) that are operated, (c) the aerosol output from the transducer(s) (10), (d) the height of the geyser(s) (4045) and any aerosol plume(s) (4050) that are generated, (e) the power the transducer(s) (10) are operated at, (f) the maximum production of any aerosol (200), (g) the frequency(s) the transducer(s) (10) are operated at, (h) the size of the geyser(s) (106) and any aerosol plume(s) (4050) that are generated, (i) the production of any effective aerosol output (200), (j) creating and/or maintaining any effective, amount, volume, velocity, flow rate, and/or pressure, of any air/gas(s) through the one or more of any, or even all of, the part(s) of the aerosol generating apparatus (l), (k) the effective and/or efficient removal of any generated aerosol (200) from within any part of the aerosol generation apparatus (9101) and the effective dispersal of that aerosol (200) into any targeted area(s) (9212).

In another aspect, and referring to FIGS. 145-171C, and without being limited, the aerosol generation apparatus (9101) can be designed and constructed for use with one or more of any geyser(s) (4045) and accompanying plume(s) (4050) having any effective size, width, volume of liquid, volume of aerosol (200), concentration of aerosol (200), and/or height. It is preferred, without limitation that the height of the plume (4050) is between about 0.25 to 15 inches. It is more preferred, without limitation that the height of the plume (4050) is between about 1 to 10 inches. It is even more preferred, without limitation that the height of the plume (4050) is between about 3 to 10 inches. It is very preferred, without limitation that the height of the plume (4050) is between about 4 to 10 inches.

In still another aspect, and referring to FIGS. 145-146, FIG. 149, FIG. 163, and FIG. 167, and without limitation, the various design features and other attributes of the outlet pipe (9114) are important to the improved function of the aerosol generation apparatus (9101).

In one part, and without limitation, the number of exhaust supply hole(s) (9168) that connect with the inner air chamber (9152) is important. Any effective number of exhaust supply hole(s) (9168) may connect with the inner air chamber (9152) and/or tube(s) (9216) at any suitable and effective location(s). It is preferred, without limitation, that at least one exhaust supply hole(s) (9168) effectively connects with the inner air chamber (9152). Laboratory testing with the current configuration of the aerosol generating apparatus (9101) was conducted and showed a reduced aerosol (200) output when operating with two exhaust supply holes (9168) interfaced with the inner air chamber (9152), when compared with operating with only one exhaust supply hole (9168) interfaced with the inner air chamber (9152). Therefore, it is more preferred, without limitation, that only one exhaust supply hole(s) (9168) effectively connects with the inner air chamber (9152).

In a second part, and without limitation, the location of the exhaust supply hole(s) (9168) can also be important. Without limitation, the exhaust supply hole(s) (9168) can be located in one or more of any suitable and effective locations with respect to the outlet pipe(s) (9114), and more specifically the outer base tube(s) (9134). It is preferred, without limitation, that at least one exhaust supply hole(s) (9168) is located between about 0.05 to 15 inches from the base of the base tube portion (9146) and/or the chamber roof (9227). It is more preferred, without limitation, that at least one exhaust supply hole(s) (9168) is located between about 1 to 10 inches from the base of the base tube portion (9146) and/or the chamber roof (9227). It is even more preferred, without limitation, that at least one exhaust supply hole(s) (9168) is located between about 4 to 8 inches from the base of the base tube portion (9146) and/or the chamber roof (9227). It is very preferred, without limitation, that at least one exhaust supply hole(s) (9168) is located between about 4.5 to 6.5 inches from the base of the base tube portion (9146) and/or the chamber roof (9227). It is extremely preferred, without limitation, that the at least one exhaust supply hole(s) (9168) is at least located as suitably and effectively close to the inner tube receiver end (9155) as possible.

In a third part, and without limitation, the design and construction of an inner air chamber (9152) is important. Without limitation, the inner air chamber (9152) can have any effective, volume, area, height, width, length, and/or diameter. Referring to FIG. 146 and FIG. 163, and without limitation, the total area of the inner air chamber (9152), when looking at the outlet pipe (9114) and inner air chamber (9152) from a top perspective, is at least effective, and more preferably effective when it is compared to the total area of all of the exhaust supply hole(s) (9168) that may connect with the inner air chamber (9152). Referring to FIG. 163, it is preferred, without limitation, that the total area of the inner air chamber (9152), looking at the outlet pipe (9114) and inner air chamber (9152) from a top perspective, is at least the total area of the one or more exhaust supply hole(s) (9168) that may connect with the inner air chamber (9152). Referring to FIG. 163, and denoted by (A2), it is preferred, without limitation, that the total area of the inner air chamber (9152), looking at the outlet pipe (9114) and inner air chamber (9152) from a top perspective, can be between at least 1.10 to 5 times the area of the one or more exhaust supply hole(s) (9168) that may connect with the inner air chamber (9152). Referring to FIG. 163, and denoted by (A2), it is more preferred, without limitation, that the total area of the inner air chamber (9152), looking at the outlet pipe (9114) and inner air chamber (9152) from a top perspective, can be between at least 1.5 to 2.5 times the area of the one or more exhaust supply hole(s) (9168) that may connect with the inner air chamber (9152).

In a fourth part, and referring to FIG. 167, and without limitation, the width, distance, and/or size of the space or gap (Herein called "Air outlet gap") (9229), or otherwise the distance from the inner tube (9136) and the body tube portion (9150)(9151) that forms the inner air chamber (9152), can be any effective size or distance. It is preferred, without limitation, that the air outlet gap (9229) is about 0.10 inch to about 2 inches or more in length. It is more preferred, without limitation, that this the air outlet gap (9229) is between about 0.10 inch to about 0.50 inch in length.

In a fifth part, and referring to FIG. 167, and without limitation, the inner wall of the air outlet gap (9229) or otherwise the distance around the inner tube (9136) that forms the inner surface of the air chamber (9152) can be any effective size, circumference, or distance. It is preferred, without limitation, that the outside diameter of the inner tube (9136) is between about 0.25 to about 10 inches or more. It is more preferred, without limitation, that the outside diameter of the inner tube (9136) is between about 2 inches to about 3.5 inches. It is even more preferred, without limitation, that the outside diameter of the inner tube (9136) is between about 3 inches to about 3.25 inches. Without limitation, the one or more of any air outlet gap(s) (9229) can be any distance, preferably at least an effective distance, from the surface (9241) of the liquid (30) where the one or more geyser(s) (4045) is formed. It is preferred, without limitation, that the one or more of any air outlet gap(s) (9229) is at least suitability located as close to the surface (9241) of the liquid (30) where the one or more geyser(s) (4045) is formed, as effectively as possible.

In a sixth part, and referring to FIGS. 171A, 171B and 171C, and without limitation, there can be any effective difference in the diameter and/or width (denoted by A4) between any one or more pipe(s) (9216) that are used to convey any air/gas(s) and aerosol (200).

Referring to FIG. 171A, and without limitation, one or more of any pipe(s) or tube(s) (9216), preferably the inner tube (9136), that is closer to the outlet tube (9160), can be smaller in width or diameter than the one or more of any pipe(s) (9216), preferably the base tube portion (9146), that is closer to the transducer chamber (9128).

Referring to FIG. 171B, and without limitation, one or more of any pipe(s) or tube(s) (9216), preferably the inner tube (9136), that is closer to the outlet tube (9160), can be the same size in width or diameter than the one or more of any pipe(s) (9216), preferably the base tube portion (9146), that is closer to the transducer chamber (9128).

Referring to FIG. 171C, and without limitation, one or more of any pipe(s) or tube(s) (9216), preferably the inner tube (9136), that is closer to the outlet tube (9160), is larger in width or diameter than the one or more of any pipe(s) (9216), preferably the base tube portion (9146), that is closer to the transducer chamber (9128). It is preferred, without limitation, that the inner tube (9136), in the present invention, is larger in width or diameter than the base tube portion (9146).

In a seventh part, and without limitation, the inner tube (9136) can be any effective size within the body tube portion (9150)(9151). Further, and without limitation, the length of the inner tube (9136) and/or the depth or the distance of extension of the inner tube (9136) within the body tube portion (9150)(9151), can be any length, depth, and/or distance. It is preferred, without limitation, that the inner tube (9136) has a length and/or extends down from the inner tube receiver end (9155) with a distance, length, or height that is at least effective. It is more preferred, without limitation, that the inner tube (9136) has a length and/or extends down from the inner tube receiver end (9155) with a length or distance of between about 0.25 to 14 inches or more. It is even more preferred, without limitation, that the inner tube (9136) has a length and/or extends down from the inner tube receiver end (9155) with a length or distance of between about 3 to 8 inches. It is very preferred, without limitation, that the inner tube (9136) has a length and/or extends down from the inner tube receiver end (9155) with a length or distance of between about 3.75 to 6.5 inches.

In a eighth part, and without limitation, the aerosol hole(s) (9154) and base tube portion(s) (9146) can have any inside diameter. It is preferred, without limitation, that the inside diameter of the aerosol hole(s) (9154) and base tube portion(s) (9146) is at least effective. It is also preferred, without limitation, that the inside diameter of the diameter of the aerosol hole(s) (9154) and/or base tube portion(s) (9146) is at least between 0.25 to 24 inches or more. It is more preferred, without limitation, that the inside diameter of the diameter of the aerosol hole(s) (9154) and/or base tube portion(s) (9146) is between 2 to 4 inches. It is even more preferred, without limitation, that the inside diameter of the diameter of the aerosol hole(s) (9154) and/or base tube portion(s) (9146) is about 2 inches.

In an ninth part, and without limitation, the base tube portion(s) (9146) can be any length and/or height. It is preferred, without limitation, that the length and/or height of the base tube portion(s) (9146) is at least effective. It is also preferred, without limitation, that the length and/or height of the base tube portion(s) (9146) is at least between 0.25 to 5 inches or more. It more preferred, without limitation, that the length and/or height of the base tube portion(s) (9146) is at least between 0.25 to 3 inches. It is even more preferred, without limitation, that the length and/or height of the base tube portion(s) (9146) is about 2 inches.

In a tenth part, and without limitation, the body tube portion(s) (9150)(9151) and/or any connections to the base tube portion(s) (9146) can have any inside diameter. It is preferred, without limitation, that the inside diameter of the body tube portion(s) (9150)(9151) and/or any connections to the base tube portion(s) (9146), is at least effective. It is also preferred, without limitation, that the inside diameter of the body tube portion(s) (9150)(9151) and/or any connections to the base tube portion(s) (9146), is at least between 0.25 to 25 or more inches. It is more preferred, without limitation, that the inside diameter of the body tube portion(s) (9150)(9151) and/or any connections to the base tube portion(s) (9146), is between 2 to 6 inches. It is even more preferred, without limitation, that the inside diameter of only the body tube portion(s) (9150)(9151), is about 4 inches.

In an eleventh part, and without limitation, the inner tube(s) (9136) can have any inside diameter. It is preferred, without limitation, that the inside diameter of the inner tube(s) (9136) is at least effective. It is also preferred, without limitation, that the inside diameter of the diameter of the inner tube(s) (9136) is at least between 0.25 to 24 or more inches. It is more preferred, without limitation, that the inside diameter of the diameter of the inner tube(s) (9136) is between 2 to 4 inches. It is even more preferred, without limitation, that the inside diameter of the diameter of the inner tube(s) (9136) is about 3 inches.

In a twelfth part, and without limitation, the expansion chamber(s) or area(s) (9255) can be any, size, shape, volume size, length, width, diameter, geometry and/or height, preferably that is effective. It is preferred, without limitation, that the expansion chamber(s) or area(s) (9255) at least has a height, length, and/or distance between about 0.01 inch to about 6 inches or more. It is more preferred, without limitation, that the expansion chamber(s) or area(s) (9255) has a height, length, and/or distance between about 0.01 inch to about 2 inches. It is even more preferred, without limitation, that the expansion chamber(s) or area(s) (9255) has a height, length, and/or distance between about 0.25 inch to about 1 inch.

In a thirteenth part, and without limitation, the inside diameter of the aerosol hole (9154), base tube portion (9146) and/or the inner tube (9136) can be any effective size, shape, and diameter. It is preferred, without limitation, that all of these components are about circular in shape. It is also preferred, without limitation, that the aerosol hole (9154) and base tube portion (9146) have about the same diameters. Without limitation, the diameters of the aerosol hole(s) (9154) and/or the base tube portion(s) (9146) can transition into one or more of any effective diameters of the inner tube(s) (9136), body tube portion(s) (9150)(9151), and/or any other tube(s) (9216).

In a fourteenth part, and without limitation, there can be any difference between the inside diameter of the base tube portion(s) (9146) and the inside diameter of the inner tube(s) (9136). It is preferred, without limitation, that if there is a difference between the inside diameter of the base tube portion(s) (9146) and the inside diameter of the inner tube(s) (9136) it is at least effective. It is more preferred, without limitation, that if there is a the difference between the inside diameter of the base tube portion(s) (9146) and the inside diameter of the inner tube(s) (9136), it is between about 0.10 to 4 inches or more, preferably with the diameter of the base tube portion(s) (9146) being smaller than the diameter of the inner tube(s) (9136). It is even more preferred, without limitation, that if there is a difference between the inside diameter of the base tube portion(s) (9146) and the inside diameter of the inner tube(s) (9136), it is between about 0.5 to 2 inches, preferably with the diameter of the base tube portion(s) (9146) being smaller than the diameter of the inner tube(s) (9136). It is very preferred, without limitation, that if there is a difference between the inside diameter of the base tube portion(s) (9146) and the inside diameter of the inner tube(s) (9136), it is about 1 inch, preferably with the diameter of the base tube portion(s) (9146) being smaller than the diameter of the inner tube(s) (9136).

In a fifteenth part, and referring to FIG. 146 and FIG. 167, and without limitation, the one or more locations where the air/gas(s) leaves any "inner air chamber" (9152) and enters the expansion chamber(s) or area(s) (9255) (Herein called "Air Outlet Gap") (9229) is also important. The air outlet gap (9229) can be any, number, size, shape, volume size, length, width, diameter, geometry, and/or height, preferably that is effective. It is preferred, without limitation, that the air outlet gap (9229) is any effective, space, distance, hole, and/or gap, preferably uninterrupted and/or not impeded by one or more of any structures, between any part of a bottom rim and/or a lower circumference or edge of the inner tube(s) (9136) and a surface and/or a wall surface of the conical tube (9148). Alternatively, and without limitation, the air outlet gap (9229) is any, space, distance, hole, and/or gap, preferably uninterrupted and/or not impeded by one or more of any structures, between any part of a bottom rim and/or a lower circumference or edge of the inner tube(s) (9136) and a body tube portion (9150) (9151) and/or any other wall or other surface or structure that connects to a body tube portion (9150) (9151). It is preferred, without limitation, that the distance that forms the air outlet gap (9229) is between about 0.01 inch to 6 inches or more. It is more preferred, without limitation, that the distance that forms the air outlet gap (9229) is between about 5 inch to 6 inches. It is even more preferred, without limitation, that the distance that forms the air outlet gap (9229) is between about 0.5 inch to 1.5 inches. It is very preferred, without limitation, that the distance that forms the air outlet gap (9229) is between about 0.01 inch to 1 inch.

According to an embodiment, and with reference to FIG. 146, FIGS. 157-161, FIG. 165, and FIG. 166, and without limitation, there can be one or more of any change(s) in any, amount(s), volume(s), velocity(s), flow rate(s), and/or pressure(s), of any air/gas(s), within any part of the aerosol generation apparatus (9101). It is preferred, without limitation, that any change(s) in any, amount(s), volume(s), velocity(s), flow rate(s), and/or pressure(s), of any air/gas(s), within any part of the aerosol generation apparatus (9101) is at least effective. Without being limited, any effective air/gas(s), pressure(s), atmospheric pressure(s), flow pressure(s), amount(s), volume(s) of flow(s), air/gas rate of flow(s), and/or velocity of flow(s), including any differences or differential(s) of these values, can exist or be maintained at and/or between one, or more of any location(s) of the aerosol generation apparatus (9101), such as, but not limited to any: (a) transducer chamber (9128) and expansion area(s) (9255), (b) transducer chamber (9128) and tube(s) (9216), (c) transducer chamber (9128) and inner air chamber(s) (9152), (d) transducer chamber (9128) and inner tube(s) (9136), (e) transducer chamber (9128) and exhaust supply hole(s) (9168), (f) expansion area(s) (9255) and tube(s) (9216), (g) expansion area(s) (9255) and inner air chamber(s) (9152), (h) expansion area(s) (9255) and inner tube(s) (9136), (i) inner air chamber(s) (9152) and inner tube(s) (9136), (j) inner air chamber(s) (9152) and tube(s) (9216), (k) plate hole (9260) and aerosol hole (9154), (l) plate hole (9260) and exhaust supply hole (9168), (m) aerosol hole (9154) and exhaust supply hole (9168), (n) plate hole (9260) and outlet tube (9160), (o) inner air chamber(s) (9152) and outlet tube (9160), (p) exhaust hole supply tube (9259) and chamber supply tube (9257), (q) base tube portion(s) (9146) and expansion area(s) (9255), and/or (r) base tube portion(s) (9146) and inner air chamber(s) (9152), and it preferred, without limitation, that it or they are at least effective, it is more preferred without limitation, that it or they are at least effective so that any air/gas(s) and/or aerosol (200) does not flow from one or more of location(s) such as, but not limited to any, transducer chamber(s) (9128) against any flow and/or intended flow of any air/gas and into one or more locations such as, but not limited to any, inner air chamber(s) (9152) and/or exhaust supply hole(s) (9168), and more preferably it or they are at least effective so that at least an effective amount of aerosol (200) is removed and/or deployed from the aerosol generation apparatus (9101).

According to an embodiment, and with reference to FIG. 148 and FIG. 170, and without limitation, at least one transducer chamber shield (9135) can also be effectively positioned in or at one or more of any effective location(s) inside the transducer chamber (9128). The transducer chamber shield (9135) can include one or more of any components such as, but not limited to any, bottom chamber plate (9137), top chamber plate (9139), and/or chamber wall sleeve (9141). Without being limited, one or more of any parts or components of the transducer chamber shield (9135) can be used and/or located, preferably effectively, within the transducer chamber (9128). Also, and without limitation, any of the one or more of any components of the transducer chamber shield (9135), can be independent in their design and/or function. Without being limited, one or more of the various parts and components of the transducer chamber shield (9135), can also be suitable connected. Without limitation, any part of the transducer chamber shield (9135) can also, and without limitation, have any effective, features, attributes, and/or design characteristics such as, but not limited to any, size, slope, arch, shape, width, height, length, diameter, hole or opening count, and/or geometry.

It is preferred, without limitation, that the transducer chamber shield (9135) includes at least one of any suitable chamber wall sleeve (9141). The various parts of the transducer chamber shield (9135) such as, but not limited to any, bottom chamber plate (9137), top chamber plate (9139), and chamber wall sleeve (9141), are preferably fabricated from any suitable stainless steel, but any other suitable materials may also be used. It is preferred, without limitation, that any suitable and effective distance is maintained between the one or more parts and components of the transducer chamber shield (9135), such as but not limited to any, bottom chamber plate (9137), top chamber plate (9139), and/or chamber wall sleeve (9141), and any surface(s) of the transducer chamber (9128).

Without limitation, the transducer chamber shield (9135) can protect the one or more of any, walls and/or surfaces, of the transducer chamber (9128), from being damaged from the energy and/or acoustic energy output from the at least one ultrasonic transducers (10). Without limitation, the energy and/or acoustic energy can melt and/or damage the aerosol generation case (9110), and/or any other parts of any tank(s) or reservoirs such as, but not limited to any, transducer chamber (9128), that are fabricated from a plastic material. Without limitation, the use of at least one or more of any effective chamber wall sleeve(s) (9141), can also assist with creating, attaining, and/or maintaining, one or more of any effective and/or desired temperature(s) and/or thermal performance(s) or action(s), for any liquid (30) within any transducer chamber(s) (9128) and/or during operation of one or more of any transducer(s) (10) such as, but not limited to any, (a) heating of any liquid (30) in the transducer chamber(s) (9128) with any suitable heater element(s) (9188) to one or more of any effective, established, and/or needed, liquid (30) temperature(s), (b) decreasing any time(s) that is required to heat any liquid (30) in the transducer chamber(s) (9128) with any suitable heater element(s) (9188) to any effective, established, and/or needed, liquid (30) temperature(s), and/or (c) extending any time between one or more of any liquid (30) heating event(s) and/or temperature(s) where the liquid in the transducer chamber (9128) needs to be reheated by any effective heater element(s) (9188) or any other suitable means for heating the liquid (30), to maintain, attain, and/or reach any, effective, established, and/or needed, liquid temperature(s) (30), and preferably limiting the number of times any heater element(s) (9188) needs to be used, energized, or powered, to maintain any effective, established, and/or needed, liquid (30) temperature(s) in the transducer chamber(s) (9128).

Without limitation, the at least one ultrasonic transducer (10) can also be suitably attached to a top surface of the bottom chamber plate (9137), all in a manner known to those skilled in the art. Referring to FIG. 170, and without being limited, the top surface of the bottom chamber plate (9137) can also include one or more of any protruding structure(s) (9242) on or to which the one or more transducer(s) (10) can be suitably attached or mounted. The protruding structures (9242) can also have any effective, features, attributes, and/or design characteristics such as, but not limited to any, size, slope, arch, shape, width, height, length, diameter, hole or opening count, and/or geometry.

It is preferred, without limitation, that the protruding structures (9242) are at least effectively flat on top, and they rise between about 0.25 to 6 inches or more, from the bottom or floor of the transducer chamber (9128) surrounding and/or immediately surrounding the transducer(s) (10) and/or the protruding structures (9242). Without limitation, the protruding structures (9242) can also be effectively rounded and/or sloped at one or more of any location(s), to assist with any liquid runoff.

Without being limited, the bottom chamber plate (9137) can be placed or located on or near a bottom of any transducer chamber (9128) and/or it can be located at any effective distance from the bottom of any transducer chamber (9128). The bottom chamber plate (9137) can also, without limitation, have one or more of any effective, spacer(s), feet(s), and/or support(s) (Herein called "Shield Feet") (9268), on which the bottom chamber plate (9137) and/or the transducer chamber shield (9135), can suitably rest.

Without being limited, the bottom chamber plate (9137) and/or any one or more of any of its parts and components, can also be designed and intended as a removable insert for the transducer chamber (9128). At least one of any suitability sized hole (not shown) can be formed through the bottom chamber plate (9137), and can serve any purposes such as, but not limited to, allowing any ultrasonic energy to be directed through the bottom chamber plate (9137) to the surface (9241) of the liquid (30). However, and without being limited, the bottom chamber plate (9137) can also, preferably form at least an effective part of the floor of the transducer chamber (9128). Without limitation, at least one of any suitably sized hole (not shown) can also be formed through the bottom chamber plate (9137), and can preferably provide any effective clearance for at least any electrical wires extending from the at least one ultrasonic transducer (10) and/or any part of any transducer assembly (9232). Without being limited, one or more of any bottom chamber plate(s) (9137) can also suitably seal to any one or more suitable location(s) on the bottom or floor of a transducer chamber (9128).

Without limitation, the chamber wall sleeve (9141) can be a separate component, and/or it can suitably connect with the bottom chamber plate (9137). Without limitation, the chamber wall sleeve (9141) can be placed on top of the bottom chamber plate (9137) and/or the floor or bottom of the transducer chamber (9128). Without limitation, at least one of any suitability sized hole(s) (not shown) can also be formed through the chamber wall sleeve (9141), at one or more of any effective location(s), and can serve purposes such as, but not limited to, allowing any, air/gas(s), and/or liquid(s), to pass through the hole(s).

Without being limited, any part of the transducer chamber shield (9135), can also have one or more of any effective, hole(s), open arch(s), and/or perforation(s) (not shown), for purposes including, but not limited to any, draining and/or transferring of any liquid, and/or to serve as any suitable location where one or more of any suitable sensing device(s) may pass through.

Without limitation, any suitable top chamber plate (9139) can also be used, and it can be located at any suitable location within the transducer chamber (9128) in any suitable manner, preferably it can effectively connect with and/or be placed on top of the chamber wall sleeve (9141). Without limitation, at least one of any suitability sized aerosol pass hole (9143) can be formed through the top chamber plate (9139), and can serve purposes such as, but not limited to, allowing any, air/gas(s), geyser(s) (4045) and/or ultrasonic energy, to pass through the hole(s) and/or effectively out of the transducer chamber (9128).

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

We claim:

1. An ultrasonic aerosol generation apparatus comprising:
   a transducer tank includes a transducer chamber, said transducer chamber is capable of containing a liquid;
   at least one ultrasonic transducer is located in said transducer chamber;
   at least one outlet pipe includes an outer base tube and an inner tube, said inner tube is located inside said outer base tube, a top of said inner tube is attached to an inside surface of said outer base tube, an inner air chamber is formed between said inner tube and said outer base tube, said outer base tube includes a bottom outer perimeter which is less than a middle outer perimeter thereof;
   at least one exhaust supply tube is connected to a source of positive air flow, said at least one exhaust supply tube communicates with said inner air chamber, wherein the positive air flow flows through said inner air chamber and carries aerosol generated by said at least one ultrasonic transducer from a liquid contained in said transducer chamber through said inner tube to extract and move the aerosol.

2. The ultrasonic aerosol generation apparatus of claim 1, further comprising:
   a microprocessor based controller controlling power supplied to said at least one transducer.

3. The ultrasonic aerosol generation apparatus of claim 1, further comprising:
   a level sensor for detecting a level of the liquid in said transducer chamber.

4. The ultrasonic aerosol generation apparatus of claim 1, further comprising:
   a heater element for heating the liquid in said transducer chamber.

5. The ultrasonic aerosol generation apparatus of claim 1 wherein:
   at least one thermocouple is located in said transducer chamber.

6. The ultrasonic aerosol generation apparatus of claim 1 wherein:
   a transducer supply chamber is formed below a bottom of said transducer chamber.

7. The ultrasonic aerosol generation apparatus of claim 6, further comprising:
   a liquid valve for controlling a flow of a liquid from said transducer supply chamber to said transducer chamber.

8. An ultrasonic aerosol generation apparatus comprising:
   a transducer tank includes a transducer chamber, said transducer chamber is capable of containing a liquid;

at least one ultrasonic transducer is located in said transducer chamber;

at least one tube is located over said at least one ultrasonic transducer chamber; and at least two air supply tubes are connected to at least one source of positive air flow, said at least two air supply tubes communicate with said at least one tube, wherein the positive air flow carries aerosol generated by said at least one ultrasonic transducer from a liquid contained in said transducer chamber through said at least one tube, the positive air flow flows through said at least one tube to extract the aerosol.

9. The ultrasonic aerosol generation apparatus of claim 8, further comprising:

a microprocessor based controller controlling power supplied to said at least one transducer.

10. The ultrasonic aerosol generation apparatus of claim 8, further comprising:

a level sensor for detecting a level of the liquid in said transducer chamber.

11. The ultrasonic aerosol generation apparatus of claim 8, further comprising:

a heater element for heating the liquid in said transducer chamber.

12. The ultrasonic aerosol generation apparatus of claim 8 wherein:

at least one thermocouple is located in said transducer chamber.

13. The ultrasonic aerosol generation apparatus of claim 8 wherein:

a transducer supply chamber is formed below a bottom of said transducer chamber.

14. The ultrasonic aerosol generation apparatus of claim 13, further comprising:

a liquid valve for controlling a flow of a liquid from said transducer supply chamber to said transducer chamber.

* * * * *